United States Patent
Son et al.

(10) Patent No.: US 12,043,627 B2
(45) Date of Patent: Jul. 23, 2024

(54) COMPOUND AND COLOR CONVERSION FILM COMPRISING SAME

(71) Applicant: LG CHEM, LTD., Seoul (KR)

(72) Inventors: Seonkyoung Son, Daejeon (KR); Seongmi Cho, Daejeon (KR); Hoyong Lee, Daejeon (KR); Cheol Jun Song, Daejeon (KR)

(73) Assignee: LG CHEM, LTD., Seoul (KR)

( * ) Notice: Subject to any disclaimer, the term of this patent is extended or adjusted under 35 U.S.C. 154(b) by 987 days.

(21) Appl. No.: 16/971,420

(22) PCT Filed: Nov. 8, 2019

(86) PCT No.: PCT/KR2019/015160
§ 371 (c)(1),
(2) Date: Aug. 20, 2020

(87) PCT Pub. No.: WO2020/105918
PCT Pub. Date: May 28, 2020

(65) Prior Publication Data
US 2021/0002294 A1    Jan. 7, 2021

(30) Foreign Application Priority Data
Nov. 19, 2018 (KR) .................. 10-2018-0142552

(51) Int. Cl.
*C07D 495/04* (2006.01)
*C08K 5/45* (2006.01)
*F21V 8/00* (2006.01)

(52) U.S. Cl.
CPC .............. *C07D 495/04* (2013.01); *C08K 5/45* (2013.01); *G02B 6/005* (2013.01)

(58) Field of Classification Search
CPC .................................................. C07D 495/04
See application file for complete search history.

(56) References Cited

U.S. PATENT DOCUMENTS

| | | | |
|---|---|---|---|
| 6,337,536 | B1 | 1/2002 | Matsubara et al. |
| 2005/0136287 | A1 | 6/2005 | Bae et al. |
| 2009/0057613 | A1 | 3/2009 | Yamamoto et al. |
| 2018/0282276 | A1 | 10/2018 | Mun et al. |

FOREIGN PATENT DOCUMENTS

| | | |
|---|---|---|
| CN | 1863890 A | 11/2006 |
| CN | 102617834 A | 8/2012 |
| JP | 2008-226505 A | 9/2008 |
| JP | 2016-079291 A | 5/2016 |
| KR | 10-2000-0011622 A | 2/2000 |

OTHER PUBLICATIONS

International Search Report issued for International Application No. PCT/KR2019/015160 on Feb. 20, 2020, 7 bages.

(Continued)

*Primary Examiner* — Alexander C Kollias
(74) *Attorney, Agent, or Firm* — ROTHWELL, FIGG, ERNST & MANBECK, P.C.

(57) ABSTRACT

The present specification relates to a compound represented by Formula 1, and a color conversion film, a backlight unit, and a display device each including the compound.

19 Claims, 1 Drawing Sheet

(56) References Cited

OTHER PUBLICATIONS

Mak et al., "Optically tunable intramolecular charge transfer dyes for vacuum deposited bulk heterojunction solar cells", Nanotechnology, 19 (2008) 424008, 8 pages.
Céron-Carrasco et al., "Spectral signatures of thieno[3,4-b]pyrazines: Theoretical interpretations and design of improved structures", Dyes and Pigments 99 (2013) 972-978.
Velusamy et al, "Dibenzo[f,h]thieno[3,4-b]quinoxaline-Based Small Molecules for Efficient Bulk-Heterojunction Solar Cells", Org. Lett., vol. 11, No. 21, 2009, 4898-4901.
Huang et al., "A ternary cascade structure enhances the efficiency of polymer solar cells", J. Mater. Chem., 2010, 20, 2820-2825.
Kolay et al., "Synthesis and optical properties of fused aromatic thienopyrazine based π-conjugated polymers", Smart Mater. Struct. 20 (2011) 075013, 6 pages.
Wang et al., "Highly π-extended polymers based on phenanthropyrazine: Synthesis, characterization, theoretical calculation and photovoltaic properties", Polymer 54 (2013) 6191-6199.

[Figure 1]
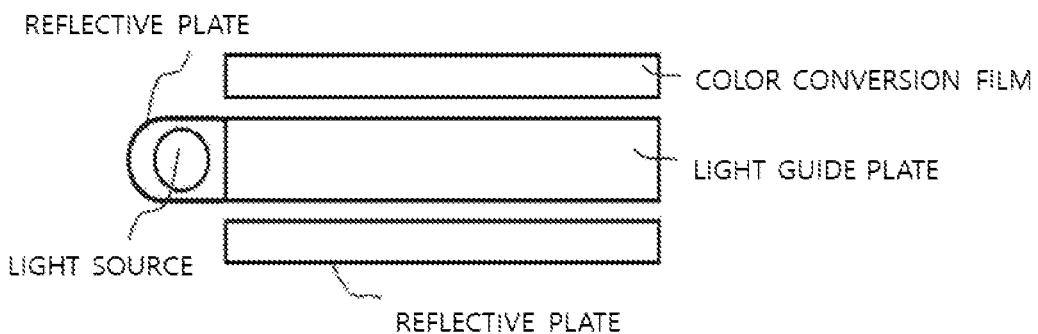
[Figure 2]
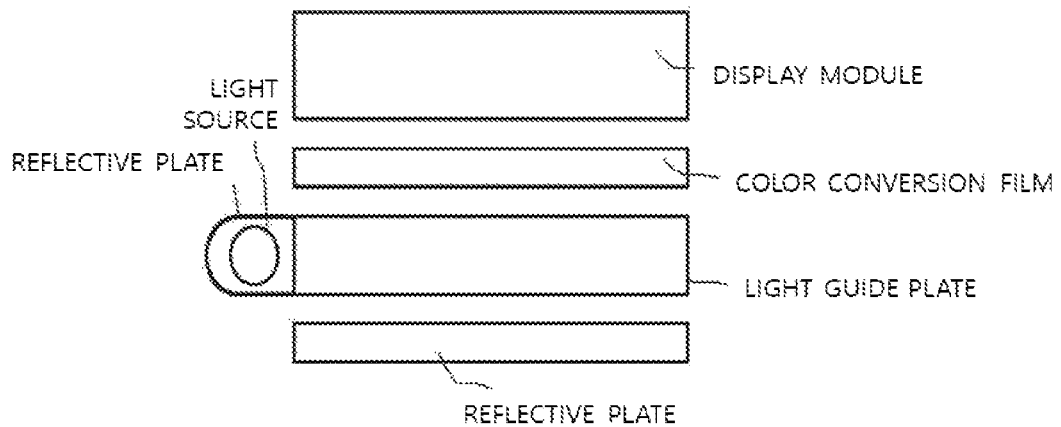

COMPOUND AND COLOR CONVERSION FILM COMPRISING SAME

TECHNICAL FIELD

The present specification relates to a compound, and a color conversion film, a backlight unit, and a display device each including the compound.

This application is a 35 U.S.C. 371 National Phase Entry Application from PCT/KR2019/015160 filed on Nov. 8, 2019, designating the United States, which claims priority to and the benefit of Korean Patent Application No. 10-2018-0142552 filed in the Korean Intellectual Property Office on Nov. 19, 2018, the entire contents of which are incorporated herein by reference.

BACKGROUND OF THE INVENTION

The existing light emitting diodes (LEDs) are obtained by mixing a green phosphor and a red phosphor with a blue light emitting diode or mixing a yellow phosphor and a blue-green phosphor with a UV light emission light emitting diode. However, in this method, it is difficult to control colors, and accordingly, the color rendering is not good. Therefore, the color gamut deteriorates.

In order to overcome the deterioration in the color gamut and reduce the production costs, methods of implementing green and red colors have been recently attempted by using a method of producing a quantum dot in the form of a film and combining the same with a blue LED. However, cadmium-based quantum dots have safety problems, and the other quantum dots have much lower efficiency than that of the cadmium-based quantum dots. Further, quantum dots have low stability against oxygen and water, and have a disadvantage in that the performance thereof significantly deteriorates when the quantum dots are aggregated. In addition, when quantum dots are produced, it is difficult to constantly maintain the size thereof, and thus, the production cost is high.

BRIEF DESCRIPTION OF THE INVENTION

The present specification provides a compound, and a color conversion film, a backlight unit, and a display device each including the compound.

An exemplary embodiment of the present specification provides a compound represented by the following Formula 1.

[Formula 1]

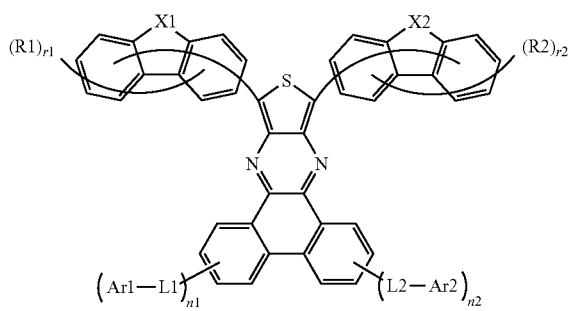

In Formula 1,

X1 and X2 are the same as or different from each other, and are each independently N(A1); C(A2)(A3); O; or S, L1 and L2 are the same as or different from each other, and are each independently a direct bond; —O—; a substituted or unsubstituted arylene group; or a substituted or unsubstituted heteroarylene group, Ar1 and Ar2 are the same as or different from each other, and are each independently hydrogen; deuterium; a halogen group; a nitrile group; —C(=O)ORa; a substituted or unsubstituted alkyl group; a substituted or unsubstituted haloalkyl group; a substituted or unsubstituted alkoxy group; a substituted or unsubstituted aryloxy group; a substituted or unsubstituted alkenyl group; a substituted or unsubstituted aryl group; or a substituted or unsubstituted heterocyclic group, or adjacent groups are bonded to each other to form a substituted or unsubstituted ring, Ra is hydrogen; deuterium; or a substituted or unsubstituted alkyl group, R1 and R2 are the same as or different from each other, and are each independently hydrogen; deuterium; a halogen group; a nitrile group; a substituted or unsubstituted alkyl group; a substituted or unsubstituted aryl group; or a substituted or unsubstituted heterocyclic group, or adjacent groups are bonded to each other to form a substituted or unsubstituted ring, A1 to A3 are the same as or different from each other, and are each independently one substituent selected from the group consisting of hydrogen; deuterium; a halogen group; a nitrile group; a substituted or unsubstituted alkyl group; a substituted or unsubstituted alkoxy group; a substituted or unsubstituted aryloxy group; a substituted or unsubstituted alkenyl group; a substituted or unsubstituted aryl group; and a substituted or unsubstituted heterocyclic group or a substituent to which two or more groups selected from the group are linked, or adjacent substituents are bonded to each other to form a substituted or unsubstituted ring, r1 and r2 are the same as or different from each other, and are each independently an integer from 0 to 7, when r1 is 2 or higher, a plurality of R1's are the same as or different from each other, when r2 is 2 or higher, a plurality of R2's are the same as or different from each other, n1 and n2 are the same as or different from each other, and are each independently an integer from 0 to 4, when n1 is 2 or higher, a plurality of L1-Ar1's are the same as or different from each other, and when n2 is 2 or higher, a plurality of L2-Ar2's are the same as or different from each other.

Another exemplary embodiment of the present specification provides a color conversion film including: a resin matrix; and the compound represented by Formula 1, which is dispersed in the resin matrix.

Still another exemplary embodiment of the present specification provides a backlight unit including the color conversion film.

Yet another exemplary embodiment of the present specification provides a display device including the backlight unit.

Advantageous Effects

By using the compound described in the present specification as a fluorescent material of a color conversion film, it is possible to provide a color conversion film which has excellent brightness and color gamut and excellent quantum efficiency.

BRIEF DESCRIPTION OF DRAWINGS

FIG. 1 is a schematic view in which a color conversion film according to an exemplary embodiment of the present specification is applied to a backlight.

FIG. 2 is a schematic view exemplifying a structure of a display device according to an exemplary embodiment of the present specification.

DETAILED DESCRIPTION OF THE INVENTION

Hereinafter, the present specification will be described in more detail.

An exemplary embodiment of the present specification provides the compound represented by Formula 1.

The compound represented by Formula 1 has a structure in which a tricyclic aryl group or a tricyclic heteroaryl group is substituted with dibenzo[f,h]thieno[3,4-b]quinoxaline. The compound of the present invention, which is a material having a large stokes shift at an absorption peak and an emission peak, may suppress a phenomenon in which fluorescence is quenched by itself. Further, the compound of the present invention may act as a stronger acceptor than the benzothiadiazole (BTD) structure conventionally used as an acceptor material, and in the D (donor)-A (acceptor)-D (donor) structure, the effect of the compound of the present invention is better than that of benzothiadiazole. Specifically, the compound of the present invention may facilitate the wavelength adjustment of a molecule in a long wavelength region by moving the absorption and emission peaks to the long wavelength region compared to benzothiadiazole. A compound synthesized in the present invention has fluorescence from orange to red.

When one part "includes" one constituent element in the present specification, unless otherwise specifically described, this does not mean that another constituent element is excluded, but means that another constituent element may be further included.

When one member is disposed "on" another member in the present specification, this includes not only a case where the one member is brought into contact with another member, but also a case where still another member is present between the two members.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a cyano group; a nitrile group; a nitro group; a carboxyl group (—COOH); an ester group; a hydroxyl group; an alkyl group; a haloalkyl group; a cycloalkyl group; an alkoxy group; an aryloxy group; an alkenyl group; an aryl group; and a heterocyclic group, being substituted with a substituent to which two or more substituents among the exemplified substituents are linked, or having no substituent. For example, "the substituent to which two or more substituents are linked" may be a biphenyl group. That is, the biphenyl group may also be an aryl group, and may be interpreted as a substituent to which two phenyl groups are linked. Another example of "the substituent to which two or more substituents are linked" may be an ethenylphenyl group. The ethenylphenyl group is interpreted as a substituent in which an ethenyl group and a phenyl group are linked.

In an exemplary embodiment of the present specification, the "substituted or unsubstituted" means being substituted with one or two or more substituents selected from the group consisting of deuterium; a halogen group; a cyano group; a nitrile group; a nitro group; a carboxyl group (—COOH); an ester group having 1 to 10 carbon atoms; a hydroxyl group; an alkyl group having 1 to 10 carbon atoms; a haloalkyl group having 1 to 10 carbon atoms; a cycloalkyl group having 3 to 30 carbon atoms; an alkoxy group having 1 to 10 carbon atoms; an aryloxy group having 6 to 30 carbon atoms; an alkenyl group having 2 to 10 carbon atoms; an aryl group having 6 to 30 carbon atoms; and a heterocyclic group having 2 to 30 carbon atoms, being substituted with a substituent to which two or more substituents among the exemplified substituents are linked, or having no substituent.

In the present specification, the fact that two or more substituents are linked indicates that hydrogen of any one substituent is linked to another substituent. For example, an isopropyl group and a phenyl group may be linked to each other to become a substituent of

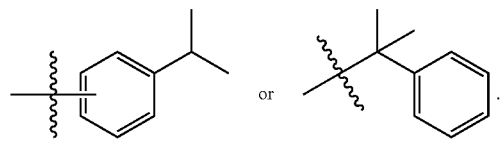

In the present specification, the case where three substituents are linked to one another includes not only a case where (Substituent 1)-(Substituent 2)-(Substituent 3) are consecutively linked to one another, but also a case where (Substituent 2) and (Substituent 3) are linked to (Substituent 1). For example, two phenyl groups and an isopropyl group may be linked to each other to become a substituent of

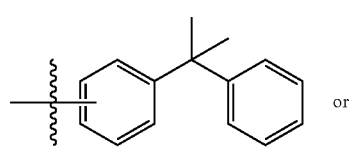

or

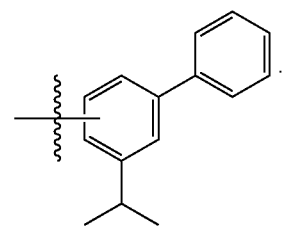

The same also applies to the case where four or more substituents are linked to each other.

In the present specification, * or

means a moiety bonded to another substituent or a bonding portion.

In the present specification, a halogen group may be fluorine, chlorine, bromine or iodine.

In the present specification, an ester group may be —C(=O)OR$_{105}$, or —OC(=O)R$_{106}$, and R$_{105}$ and R$_{106}$ are the same as or different from each other, and are each independently hydrogen, a substituted or unsubstituted alkyl group, a substituted or unsubstituted alkenyl group, a substituted or unsubstituted aryl group, or a substituted or unsubstituted heterocyclic group, but are not limited thereto. Specifically, R$_{105}$ and R$_{106}$ are the same as or different from each other, and are each independently an alkyl group having 1 to 25 carbon atoms; an alkenyl group having 2 to 25 carbon atoms; an aryl group having 6 to 30 carbon atoms; or a heterocyclic group having 2 to 30 carbon atoms. In an exemplary embodiment of the present specification, R$_{105}$ and R$_{106}$ are the same as or different from each other, and are each independently an alkyl group having 1 to 10 carbon atoms; an alkenyl group having 1 to 10 carbon atoms; an aryl group having 6 to 20 carbon atoms; or a heterocyclic group having 2 to 20 carbon atoms.

In the present specification, an alkyl group may be straight-chained or branched, and the number of carbon atoms thereof is not particularly limited, but is preferably 1 to 30; 1 to 20; 1 to 10; or 1 to 5. Specific examples thereof include methyl, ethyl, propyl, n-propyl, isopropyl, butyl, n-butyl, isobutyl, tert-butyl, sec-butyl, 1-methylbutyl, 1-ethylbutyl, pentyl, n-pentyl, isopentyl, neopentyl, tert-pentyl, hexyl, n-hexyl, 1-methylpentyl, 2-methylpentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, isohexyl, 4-methylhexyl, 5-methylhexyl, and the like, but are not limited thereto.

In the present specification, a cycloalkyl group is not particularly limited, but has preferably 3 to 30 carbon atoms; 3 to 20 carbon atoms; 3 to 10 carbon atoms; or 3 to 6 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, a haloalkyl group may be straight-chained or branched, and refers to a group in which hydrogen of the above-described alkyl group is substituted with one or two or more halogen groups. The number of carbon atoms thereof is not particularly limited, but is preferably 1 to 30; 1 to 20; 1 to 10; or 1 to 5. The description on the above-described alkyl group may be applied to the alkyl group. Specific examples of the haloalkyl group include a fluoromethyl group, a difluoromethyl group, a trifluoromethyl group, a chloromethyl group, a dichloromethyl group, a trichloromethyl group, a bromomethyl group, a dibromomethyl group, a tribromomethyl group, and the like, but are not limited thereto.

In the present specification, an alkoxy group, which is a group in which an alkyl group is linked to an oxygen atom, may be straight-chained, branched, or cyclic. The number of carbon atoms thereof is not particularly limited, but is preferably 1 to 30; 1 to 20; 1 to 10; or 1 to 5. Specific examples thereof include methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, an alkenyl group may be straight-chained or branched, and the number of carbon atoms thereof is not particularly limited, but is preferably 2 to 30; 2 to 20; 2 to 10; or 2 to 5. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, an aryl group means a monovalent aromatic hydrocarbon or a monovalent group of an aromatic hydrocarbon derivative. In the present specification, an aromatic hydrocarbon means a compound in which pi electrons are completely conjugated and containing a planar ring, and a group derived from an aromatic hydrocarbon means a structure in which an aromatic hydrocarbon or a cyclic aliphatic hydrocarbon is fused with an aromatic hydrocarbon. Further, in the present specification, an aryl group intends to include a monovalent group in which two or more aromatic hydrocarbons or derivatives of an aromatic hydrocarbon are linked to each other. The aryl group is not particularly limited, but preferably has 6 to 50 carbon atoms; 6 to 30 carbon atoms; 6 to 25 carbon atoms; 6 to 20 carbon atoms; 6 to 18 carbon atoms; or 6 to 13 carbon atoms, and the aryl group may be monocyclic or polycyclic. Specific examples of the monocyclic aryl group include a phenyl group, a biphenyl group, a terphenyl group, and the like, but are not limited thereto. Specific examples of the polycyclic aryl group include a naphthyl group, an anthracenyl group, a phenanthryl group, a triphenyl group, a pyrenyl group, a perylenyl group, a chrysenyl group, a fluorenyl group, and the like, but are not limited thereto.

In the present specification, the fluorenyl group may be substituted, and adjacent substituents may be bonded to each other to form a substituted or unsubstituted ring.

In the present specification, when it is said that a fluorenyl group may be substituted, the substituted fluorenyl group includes all the compounds in which substituents of a pentagonal ring of fluorene are spiro-bonded to each other to form an aromatic hydrocarbon ring. Examples of the substituted fluorenyl group include 9,9'-spirobifluorene, spiro[cyclopentane-1,9'-fluorene], spiro[benzo[c]fluorene-7,9-fluorene], and the like, but are not limited thereto.

In the present specification, an aryloxy group is a group in which an aryl group is linked to an oxygen atom, and examples of an aryl group of the aryloxy group are the same as those of the above-described aryl group. Specifically, examples of the aryloxy group include a phenoxy group, a p-tolyloxy group, an m-tolyloxy group, a 3,5-dimethylphenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group, and the like, and examples of the arylthioxy group include a phenylthioxy group, a 2-methylphenylthioxy group, a 4-tert-butylphenylthioxy group, and the like, but the examples are not limited thereto.

In the present specification, a heterocyclic group includes one or more atoms other than carbon, that is, one or more heteroatoms, and specifically, the heteroatom may include one or more atoms selected from the group consisting of O, N, S, and the like. The number of carbon atoms thereof is not particularly limited, but is preferably 2 to 50; 2 to 30; 2 to 25; 2 to 20; 2 to 18; or 2 to 13, and the heterocyclic group may be monocyclic or polycyclic. Examples of the heterocyclic group include a thiophene group, a furanyl group, a pyrrole group, an imidazole group, a thiazole group, an oxazole group, an oxadiazole group, a pyridine group, a bipyridine group, a pyrimidine group, a triazine group, a triazole group, an acridine group, a pyridazine group, a pyrazine group, a quinoline group, a quinazoline group, a quinoxaline group, a phthalazine group, a pyridopyrimidine group, a pyridopyrazine group, a pyrazinopyrazine group, an isoquinoline group, an indole group, a carbazole group, a benzoxazole group, a benzimidazole group, a benzothiazole group, a benzocarbazole group, a benzothiophene group, a dibenzothiophene group, a benzofuran group, a phenanthrolinyl group, a thiazole group, an isoxazole group, an oxadiazole group, a thiadiazole group, a benzothiazole group, a phenothiazine group, a dibenzofuran group, a dihydrophenothiazine group, a dihydrobenzoisoquinoline group, a chromene group, a chromenone group, and the like, but are not limited thereto.

In the present specification, a heterocyclic group may be monocyclic or polycyclic, may be an aromatic ring, an aliphatic ring, or a fused ring of the aromatic ring and the aliphatic ring, and may be selected from the examples of the heterocyclic group.

In the present specification, a heteroaryl group means a monovalent aromatic hetero ring. Here, the aromatic hetero ring is a monovalent group of an aromatic ring or a derivative of the aromatic ring, and means a group including one or more of N, O, and S as a heteroatom in the ring. The derivative of the aromatic ring includes a structure in which an aromatic ring or an aliphatic ring is fused with an aromatic ring. Further, in the present specification, the heteroaryl group intends to include a monovalent group in which an aromatic ring including two or more heteroatoms or derivatives of an aromatic ring including a heteroatom are linked to each other.

The number of carbon atoms of the heteroaryl group is preferably 2 to 50; 2 to 30; 2 to 20; 2 to 18; or 2 to 13.

In the present specification, a hydrocarbon ring may be an aromatic ring, an aliphatic ring, or a fused ring of the aromatic ring and the aliphatic ring and may be selected from the examples of the cycloalkyl group or the aryl group except that the hydrocarbon ring is not a monovalent group, and examples of the fused ring of the aromatic ring and the aliphatic ring include 1,2,3,4-tetrahydronaphthalene group, a 2,3-dihydro-1H-indene group, and the like, but are not limited thereto.

In the present specification, an arylene group means a group having two bonding positions in an aryl group, that is, a divalent group. The above-described description on the aryl group may be applied to the arylene group, except for a divalent arylene group.

In the present specification, a heteroarylene group means a group having two bonding positions in a heteroaryl group, that is, a divalent group. The above-described description on the heteroaryl group may be applied to the heteroarylene group, except for a divalent heteroarylene group.

In the present specification, the "adjacent" group may mean a substituent substituted with an atom directly linked to an atom in which the corresponding substituent is substituted, a substituent disposed to be sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the "adjacent groups are bonded to each other to form a substituted or unsubstituted ring" among the substituents means that a substituent is bonded to an adjacent group to form a substituted or unsubstituted hydrocarbon ring; or a substituted or unsubstituted hetero ring.

In an exemplary embodiment of the present specification, X1 and X2 are the same as or different from each other, and are each independently N(A1); C(A2)(A3); O; or S.

In an exemplary embodiment of the present specification, X1 and X2 are the same as or different from each other, and are each independently C(A2)(A3).

In an exemplary embodiment of the present specification, X1 and X2 are the same as or different from each other, and are each independently N(A1).

In an exemplary embodiment of the present specification, X1 and X2 are the same as or different from each other, and are each independently O; or S.

In an exemplary embodiment of the present specification, X1 and X2 are the same as each other.

In an exemplary embodiment of the present specification, A2 and A3 are bonded to each other to form a substituted or unsubstituted ring.

In an exemplary embodiment of the present specification, A1 to A3 are the same as or different from each other, and are each independently one substituent selected from the group consisting of hydrogen; deuterium; a halogen group; a nitrile group; a substituted or unsubstituted alkyl group; a substituted or unsubstituted alkoxy group; a substituted or unsubstituted aryloxy group; a substituted or unsubstituted alkenyl group; a substituted or unsubstituted aryl group; and a substituted or unsubstituted heterocyclic group, or a substituent to which two or more groups selected from the group are linked, or adjacent substituents are bonded to each other to form a substituted or unsubstituted ring.

In an exemplary embodiment of the present specification, A1 to A3 are the same as or different from each other, and are each independently one substituent selected from the group consisting of hydrogen; deuterium; a halogen group; a nitrile group; a substituted or unsubstituted alkyl group having 1 to 20 carbon atoms; a substituted or unsubstituted alkoxy group having 1 to 20 carbon atoms; a substituted or unsubstituted aryloxy group having 6 to 30 carbon atoms; a substituted or unsubstituted alkenyl group having 2 to 20 carbon atoms; a substituted or unsubstituted aryl group having 6 to 30 carbon atoms; and a substituted or unsubstituted heterocyclic group having 2 to 30 carbon atoms, or a substituent to which two or more groups selected from the group are linked, or adjacent substituents are bonded to each other to form a substituted or unsubstituted ring having 3 to 30 carbon atoms.

In an exemplary embodiment of the present specification, A1 to A3 are the same as or different from each other, and are each independently one substituent selected from the group consisting of hydrogen; deuterium; a halogen group; a nitrile group; a substituted or unsubstituted alkyl group having 1 to 10 carbon atoms; a substituted or unsubstituted alkoxy group having 1 to 10 carbon atoms; a substituted or unsubstituted aryloxy group having 6 to 25 carbon atoms; a substituted or unsubstituted alkenyl group having 2 to 10 carbon atoms; a substituted or unsubstituted aryl group having 6 to 25 carbon atoms; and a substituted or unsubstituted heterocyclic group having 2 to 25 carbon atoms, or a substituent to which two or more groups selected from the group are linked, or adjacent substituents are bonded to each other to form a substituted or unsubstituted aromatic hydrocarbon ring having 3 to 25 carbon atoms.

In an exemplary embodiment of the present specification, A1 to A3 are the same as or different from each other, and are each independently one substituent selected from the group consisting of hydrogen; deuterium; a halogen group; a nitrile group; an alkyl group having 1 to 10 carbon atoms; an alkoxy group having 1 to 10 carbon atoms; an aryloxy group having 6 to 25 carbon atoms; an alkenyl group having 2 to 10 carbon atoms; an aryl group having 6 to 25 carbon atoms; and a heterocyclic group having 2 to 25 carbon atoms, or a substituent to which two or more groups selected from the group are linked, or adjacent substituents are bonded to each other to form a substituted or unsubstituted aromatic hydrocarbon ring having 3 to 25 carbon atoms.

In an exemplary embodiment of the present specification, A1 to A3 are the same as or different from each other, and are each independently one substituent selected from the group consisting of hydrogen; deuterium; a halogen group; a nitrile group; an alkyl group having 1 to 10 carbon atoms; an alkoxy group having 1 to 10 carbon atoms; an aryloxy group having 6 to 25 carbon atoms; an alkenyl group having 2 to 10 carbon atoms; an aryl group having 6 to 25 carbon atoms; and a heterocyclic group having 2 to 25 carbon atoms, or a substituent to which two or more groups selected from the group are linked, or A2 and A3 are bonded to each other to form a fluorene ring which is unsubstituted or substituted with an alkyl group having 1 to 10 carbon atoms.

In an exemplary embodiment of the present specification, A1 to A3 are the same as or different from each other, and are each independently one substituent selected from the group consisting of hydrogen; deuterium; a halogen group; a nitrile group; a methyl group; an ethyl group; a propyl group; a butyl group; a tert-butyl group; a methoxy group; an ethoxy group; a propoxy group; an isopropoxy group; a butoxy group; a tert-butoxy group; a phenoxy group; an ethylene group; a propylene group; a phenyl group; a biphenyl group; a terphenyl group; a naphthyl group; a fluorenyl group; a carbazole group; a dibenzofuran group; a dibenzothiophene group; a pyridine group; a pyrimidine group; and a triazine group, or a substituent to which two or more groups selected from the group are linked, or adjacent substituents may be bonded to each other to form a cyclopentane ring, a cyclohexane ring, a benzene ring, or a fluorene ring.

In an exemplary embodiment of the present specification, A1 to A3 are the same as or different from each other, and are each independently hydrogen; deuterium; an alkyl group having 1 to 6 carbon atoms; an aryl group having 6 to 20 carbon atoms, which is unsubstituted or substituted with an alkoxy group having 1 to 6 carbon atoms; or an aryl group having 6 to 20 carbon atoms, which is substituted with an aryloxy group having 6 to 20 carbon atoms, which is substituted with an alkenyl group having 2 to 6 carbon atoms, or A2 and A3 are bonded to each other to form an aromatic hydrocarbon ring having 3 to 25 carbon atoms, which is unsubstituted or substituted with an alkyl group having 1 to 6 carbon atoms.

In an exemplary embodiment of the present specification, A1 to A3 are the same as or different from each other, and are each independently hydrogen; deuterium; a methyl group; a phenyl group which is unsubstituted or substituted with a methoxy group; or

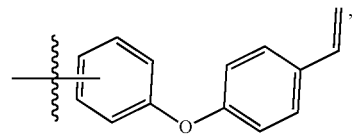

or A2 and A3 are bonded to each other to form a fluorene ring which is unsubstituted or substituted with a tert-butyl group.

In an exemplary embodiment of the present specification, A1 to A3 are the same as or different from each other, and are each independently hydrogen; deuterium; a methyl group; or a phenyl group, or A2 and A3 are bonded to each other to form a fluorene ring.

In an exemplary embodiment of the present specification, A1 is a phenyl group.

In an exemplary embodiment of the present specification, A2 and A3 are the same as or different from each other, and are each independently hydrogen; deuterium; a methyl group; a phenyl group which is unsubstituted or substituted with a methoxy group; or

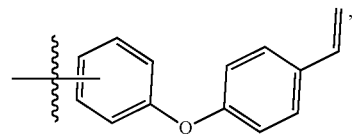

or A2 and A3 are bonded to each other to form a fluorene ring which is unsubstituted or substituted with a tert-butyl group.

In an exemplary embodiment of the present specification, A2 and A3 are the same as or different from each other, and are each independently a methyl group; or a phenyl group, or A2 and A3 are bonded to each other to form a fluorene ring.

In an exemplary embodiment of the present specification, A2 and A3 are the same as each other.

In an exemplary embodiment of the present specification, R1 and R2 are the same as or different from each other, and are each independently hydrogen; deuterium; a halogen group; a nitrile group; a substituted or unsubstituted alkyl group; a substituted or unsubstituted aryl group; or a substituted or unsubstituted heterocyclic group, or adjacent groups are bonded to each other to form a substituted or unsubstituted ring.

In an exemplary embodiment of the present specification, R1 and R2 are the same as or different from each other, and are each independently hydrogen; deuterium; a halogen group; a nitrile group; a substituted or unsubstituted alkyl group having 1 to 10 carbon atoms; a substituted or unsubstituted aryl group having 6 to 20 carbon atoms; or a substituted or unsubstituted heterocyclic group having 2 to 20 carbon atoms, or adjacent substituents may be bonded to each other to form a substituted or unsubstituted monocyclic to tricyclic ring.

In an exemplary embodiment of the present specification, R1 and R2 are the same as or different from each other, and are each independently hydrogen; or deuterium.

In an exemplary embodiment of the present specification, R1 and R2 are hydrogen.

In an exemplary embodiment of the present specification, r1 and r2 are the same as or different from each other, and are each independently an integer from 0 to 7, and when r1 is 2 or higher, a plurality of R1's are the same as or different from each other, and when r2 is 2 or higher, a plurality of R2's are the same as or different from each other.

In an exemplary embodiment of the present specification, r1 is 0.

In an exemplary embodiment of the present specification, r2 is 0.

In an exemplary embodiment of the present specification, r1 is 7.

In an exemplary embodiment of the present specification, r2 is 7.

In an exemplary embodiment of the present specification, L1 and L2 are the same as or different from each other, and are each independently a direct bond; —O—; a substituted or unsubstituted arylene group; or a substituted or unsubstituted heteroarylene group.

In an exemplary embodiment of the present specification, L1 and L2 are the same as or different from each other, and are each independently a direct bond; —O—; a substituted or unsubstituted arylene group having 6 to 30 carbon atoms; or a substituted or unsubstituted heteroarylene group having 2 to 30 carbon atoms.

In an exemplary embodiment of the present specification, L1 and L2 are the same as or different from each other, and are each independently a direct bond; —O—; a substituted or unsubstituted arylene group having 6 to 25 carbon atoms; or a substituted or unsubstituted heteroarylene group having 2 to 20 carbon atoms.

In an exemplary embodiment of the present specification, L1 and L2 are the same as or different from each other, and are each independently a direct bond; —O—; an arylene group having 6 to 25 carbon atoms, which is unsubstituted or substituted with an alkyl group having 1 to 10 carbon atoms or a heterocyclic group having 2 to 20 carbon atoms; or a heteroarylene group having 2 to 20 carbon atoms, which is unsubstituted or substituted with an alkyl group having 1 to 10 carbon atoms or an aryl group having 6 to 25 carbon atoms.

In an exemplary embodiment of the present specification, L1 and L2 are the same as or different from each other, and are each independently a direct bond; —O—; a substituted or unsubstituted phenylene group; a substituted or unsubstituted biphenyl group; a substituted or unsubstituted terphenylene group; a substituted or unsubstituted naphthylene group; a substituted or unsubstituted fluorenylene group; a substituted or unsubstituted spirobifluorenylene group; a substituted or unsubstituted divalent carbazole group; a substituted or unsubstituted divalent dibenzofuran group; a substituted or unsubstituted divalent dibenzothiophene group; a substituted or unsubstituted divalent quinoline group; a substituted or unsubstituted divalent pyridine group; a substituted or unsubstituted divalent pyrimidine group; or a substituted or unsubstituted divalent triazine group. In another exemplary embodiment, the 'substituted or unsubstituted' refers to being substituted with an alkyl group having 1 to 5 carbon atoms; an aryl group having 6 to 20 carbon atoms; or a heterocyclic group having 2 to 20 carbon atoms, or having no substituent.

In an exemplary embodiment of the present specification, L1 and L2 are the same as or different from each other, and are each independently a direct bond; —O—; a phenylene group; a biphenyl group; a terphenylene group; a naphthylene group; a fluorenylene group which is unsubstituted or substituted with a methyl group or a phenyl group; a spirobifluorenylene group; a divalent carbazole group which is unsubstituted or substituted with an ethyl group, a tert-butyl group, or a phenyl group; a divalent dibenzofuran group; a divalent dibenzothiophene group; a divalent quinoline group; a divalent pyridine group; a divalent pyrimidine group; or a divalent triazine group.

In an exemplary embodiment of the present specification, L1 and L2 are the same as or different from each other, and are each independently a direct bond; —O—; a phenylene group; a biphenylene group; a fluorenylene group which is unsubstituted or substituted with a methyl group or a phenyl group; a spirobifluorenylene group; a divalent carbazole group which is unsubstituted or substituted with an ethyl group, a tert-butyl group, or a phenyl group; a divalent dibenzofuran group; or a divalent quinoline group.

In an exemplary embodiment of the present specification, L1 and L2 are the same as or different from each other, and are each independently a direct bond; a phenylene group; a biphenylene group; a fluorenylene group which is unsubstituted or substituted with a methyl group or a phenyl group; a spirobifluorenylene group; a divalent carbazole group; a divalent dibenzofuran group; or a divalent quinoline group.

In an exemplary embodiment of the present specification, L1 and L2 are the same as or different from each other, and are each independently a direct bond; or a phenylene group.

In an exemplary embodiment of the present specification, L1 and L2 are each a direct bond.

In an exemplary embodiment of the present specification, L1 and L2 are the same as each other.

In an exemplary embodiment of the present specification, Ar1 and Ar2 are the same as or different from each other, and are each independently hydrogen; deuterium; a halogen group; a nitrile group; —C(=O)ORa; a substituted or unsubstituted alkyl group; a substituted or unsubstituted haloalkyl group; a substituted or unsubstituted alkoxy group; a substituted or unsubstituted aryloxy group; a substituted or unsubstituted alkenyl group; a substituted or unsubstituted aryl group; or a substituted or unsubstituted heterocyclic group, or adjacent substituents are bonded to each other to form a substituted or unsubstituted ring.

In an exemplary embodiment of the present specification, Ar1 and Ar2 are the same as or different from each other, and are each independently hydrogen; deuterium; a halogen group; a nitrile group; —C(=O)ORa; a substituted or unsubstituted alkyl group having 1 to 20 carbon atoms; a substituted or unsubstituted haloalkyl group having 1 to 20 carbon atoms; a substituted or unsubstituted alkoxy group having 1 to 20 carbon atoms; a substituted or unsubstituted aryloxy group having 6 to 30 carbon atoms; a substituted or unsubstituted alkenyl group having 2 to 20 carbon atoms; a substituted or unsubstituted aryl group having 6 to 30 carbon atoms; or a substituted or unsubstituted heterocyclic group having 2 to 30 carbon atoms, or adjacent substituents are bonded to each other to form a substituted or unsubstituted monocyclic to tetracyclic ring. In another exemplary embodiment, the 'substituted or unsubstituted' refers to being substituted with deuterium; a halogen group; a nitrile group; an alkyl group having 1 to 10 carbon atoms; a haloalkyl group having 1 to 10 carbon atoms; an alkoxy group having 1 to 10 carbon atoms; an aryl group having 6 to 25 carbon atoms; or a heterocyclic group having 2 to 25 carbon atoms, or having no substituent.

In an exemplary embodiment of the present specification, Ar1 and Ar2 are the same as or different from each other, and are each independently hydrogen; deuterium; a halogen group; a nitrile group; an alkyl group; an alkoxy group; an aryl group which is unsubstituted or substituted with a halogen group, a nitrile group, a haloalkyl group, an alkyl group, C(=O)ORa, an alkoxy group, an aryl group, or a heterocyclic group; or a heterocyclic group which is unsubstituted or substituted with an alkyl group, an aryl group, or an alkylaryl group, or adjacent substituents are bonded to each other to form a substituted or unsubstituted monocyclic to tricyclic ring.

In an exemplary embodiment of the present specification, Ar1 and Ar2 are the same as or different from each other, and are each independently hydrogen; deuterium; a halogen group; a nitrile group; an alkyl group having 1 to 10 carbon atoms; an alkoxy group having 1 to 10 carbon atoms; an aryl group having 6 to 30 carbon atoms, which is unsubstituted or substituted with a halogen group, a nitrile group, a haloalkyl group having 1 to 10 carbon atoms, an alkyl group having 1 to 10 carbon atoms, C(=O)ORa, an alkoxy group having 1 to 10 carbon atoms, an aryl group having 6 to 30 carbon atoms, or a heterocyclic group having 2 to 30 carbon atoms; or a heterocyclic group having 2 to 30 carbon atoms, which is unsubstituted or substituted with an alkyl group having 1 to 10 carbon atoms, an aryl group having 6 to 30 carbon atoms, or an alkylaryl group having 6 to 50 carbon atoms.

In an exemplary embodiment of the present specification, Ar1 and Ar2 are the same as or different from each other, and are each independently one substituent selected from the group consisting of hydrogen; deuterium; a halogen group; a nitrile group; an alkyl group having 1 to 6 carbon atoms; an alkoxy group having 1 to 6 carbon atoms; a haloalkyl group having 1 to 6 carbon atoms; C(=O)ORa; an aryl group having 6 to 30 carbon atoms, and a heterocyclic group having 2 to 30 carbon atoms, or a substituent to which two or more groups selected from the group are linked.

In an exemplary embodiment of the present specification, Ar1 and Ar2 are the same as or different from each other, and are each independently one substituent selected from the group consisting of hydrogen; deuterium; a halogen group; a nitrile group; a methyl group; an ethyl group; a propyl group; a butyl group; an isopropyl group; a tert-butyl group; a methoxy group; an ethoxy group; a propoxy group; an isopropoxy group; a butoxy group; an isobutoxy group; a tert-butoxy group; a trifluoromethyl group; C(=O)ORa; a phenyl group; a biphenyl group; a terphenyl group; a naphthyl group; a phenanthrenyl group; an anthracenyl group; a pyrene group; a phenalene group; an indenyl group; a chrysenyl group; a triphenylenyl group; a fluorenyl group; a spirobifluorenyl group; a carbazole group; a dibenzofuran group; a dibenzothiophene group; an oxazole group; a thiazole group; a benzoxazole group; a benzothiazole group; a chromenone group; an indole group; a pyridine group; a pyrimidine group; a triazine group; a phenothiazine group; a benzopyran group; a quinazoline group; and an isoquinazoline group or a substituent to which two or more groups selected from the group are linked.

In an exemplary embodiment of the present specification, Ar1 and Ar2 are the same as each other.

In an exemplary embodiment of the present specification, Ra is hydrogen; deuterium; or a substituted or unsubstituted alkyl group.

In an exemplary embodiment of the present specification, Ra is hydrogen; deuterium; or an alkyl group.

In an exemplary embodiment of the present specification, Ra is hydrogen; deuterium; or an alkyl group having 1 to 10 carbon atoms.

In an exemplary embodiment of the present specification, Ra is hydrogen; deuterium; a methyl group; or an ethyl group.

In an exemplary embodiment of the present specification, Ar1 and Ar2 are the same as or different from each other, and are each independently hydrogen; deuterium; a halogen group; or a nitrile group, or are any one selected from the following structures.

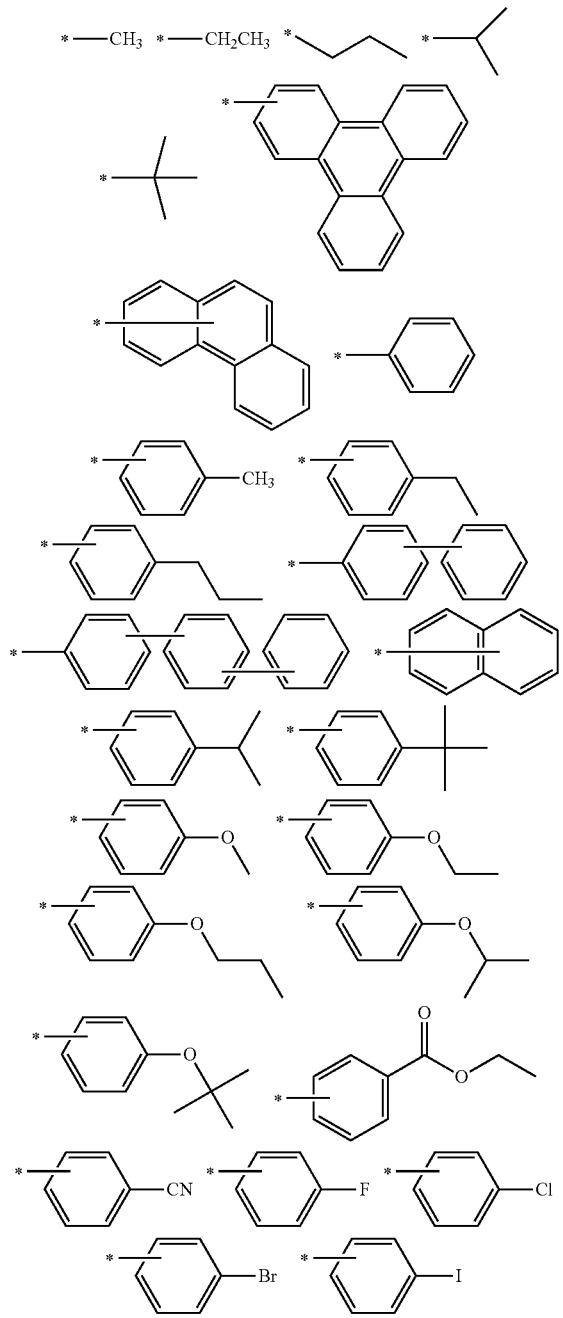

-continued
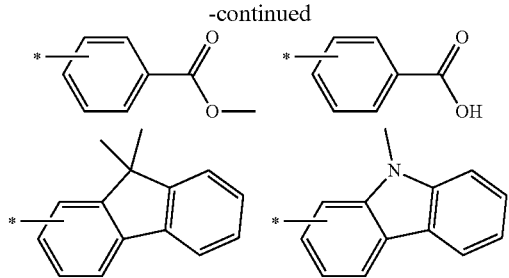
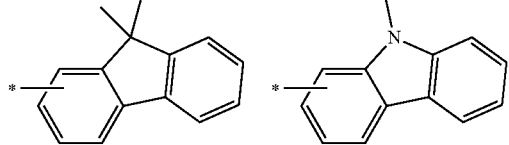
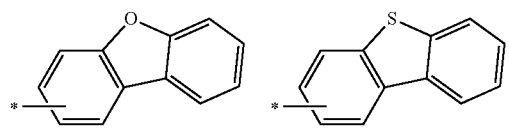
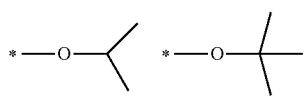
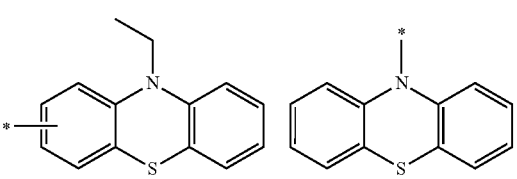
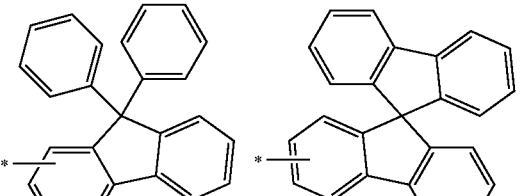
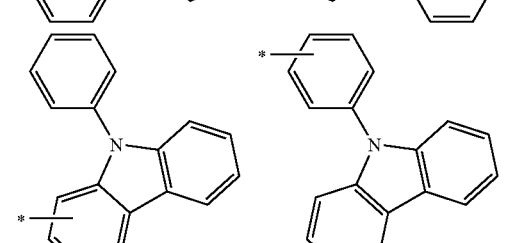
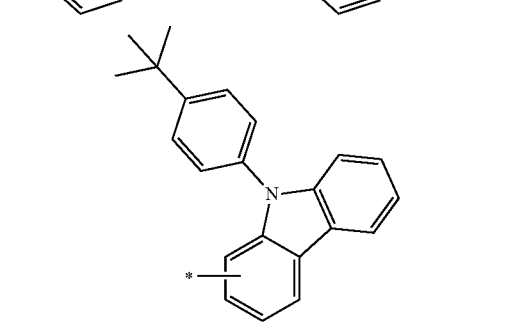
-continued
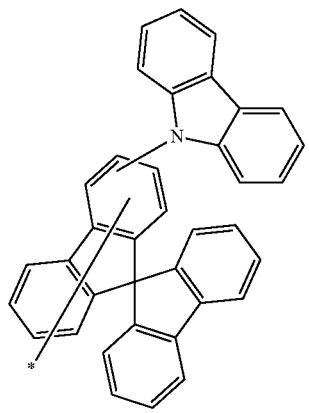
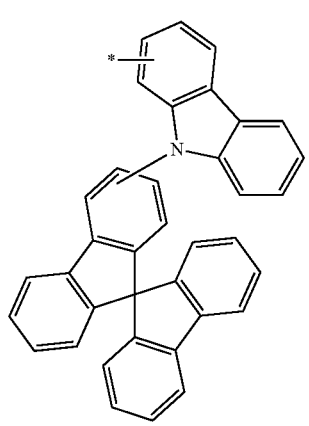
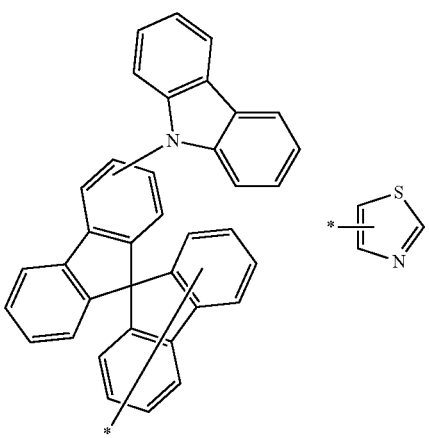
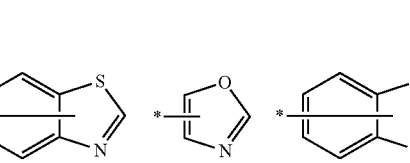
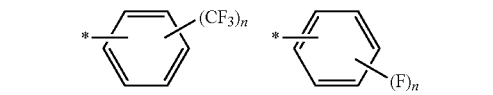

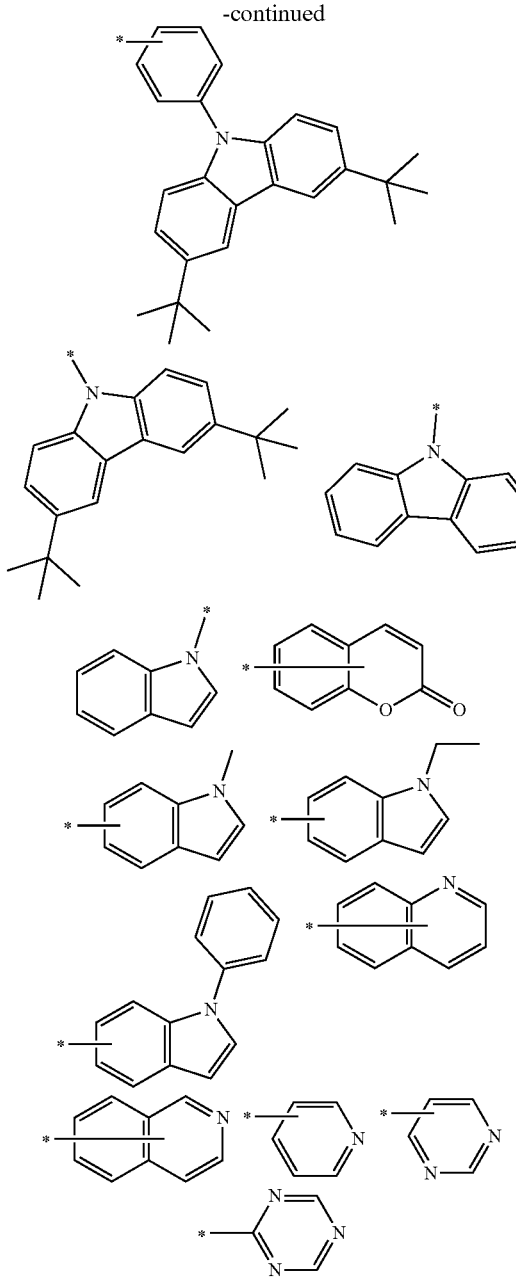

In the structures, * is a position linked to L1 or L2, and n is an integer from 1 to 5.

In an exemplary embodiment of the present specification, n1 and n2 are the same as or different from each other, and are each independently an integer from 0 to 4, when n1 is 2 or higher, a plurality of L1-Ar1's is the same as or different from each other, and when n2 is 2 or higher, a plurality of L2-Ar2's are the same as or different from each other.

In an exemplary embodiment of the present specification, n1 is 1.

In an exemplary embodiment of the present specification, n2 is 1.

In an exemplary embodiment of the present specification, -L1-Ar1 and -L2-Ar2 are the same as each other.

In an exemplary embodiment of the present specification, R1 and R2 are the same as each other.

In an exemplary embodiment of the present specification, Formula 1 is a symmetric structure. That is, the left and right substituents are the same as each other based on a center line passing through a sulfur element (S) of dibenzo[f,h]thieno[3,4-b]quinoxaline (symmetric). In the following structural formula, the center line passing through the sulfur element (S) refers to a line connecting Q1 and Q2, and the left and right substituents are the same as each other based on the center line.

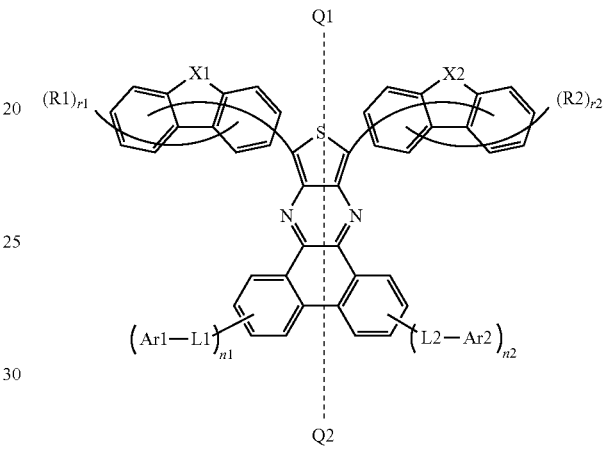

In an exemplary embodiment of the present specification, Formula 1 is represented by any one of the following Formulae 2-1 to 2-4.

[Formula 2-1]
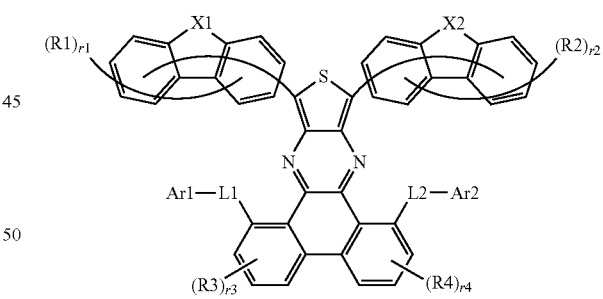

[Formula 2-2]
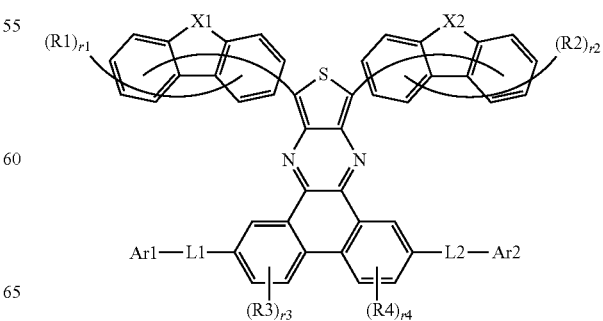

[Formula 2-3]

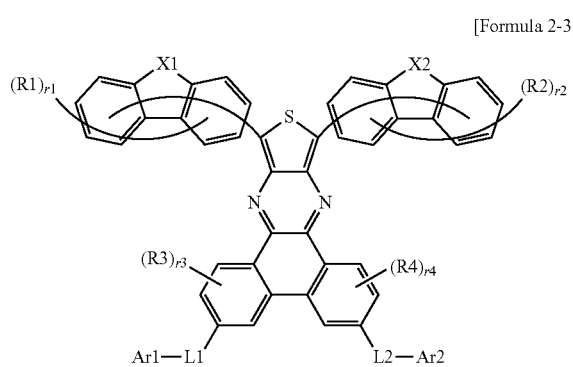

[Formula 3-1]

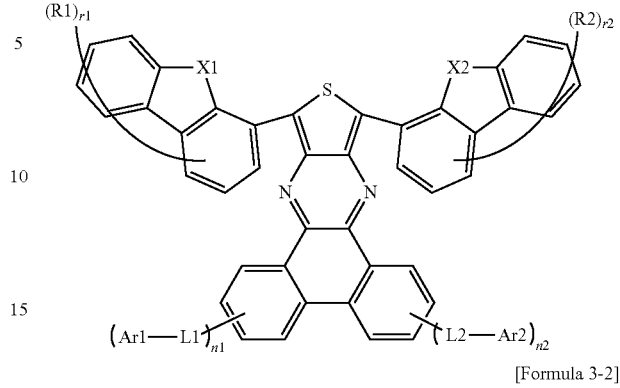

[Formula 2-4]

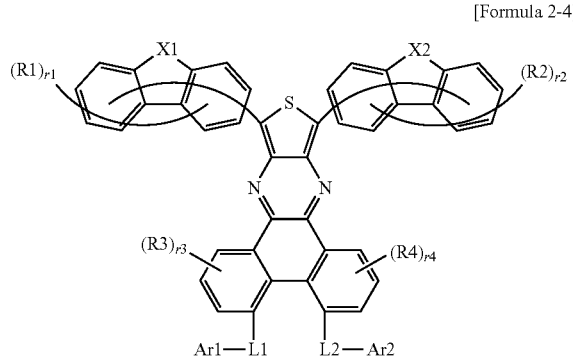

[Formula 3-2]

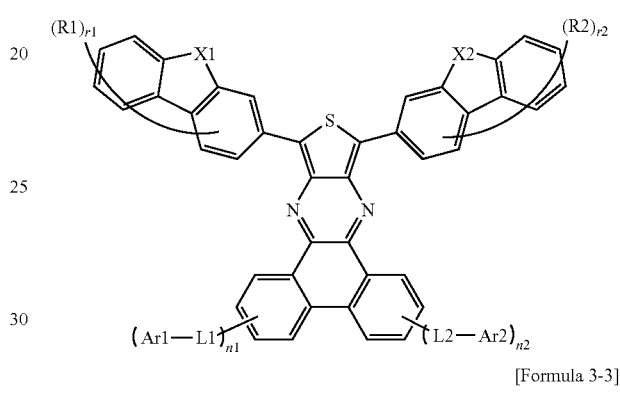

[Formula 3-3]

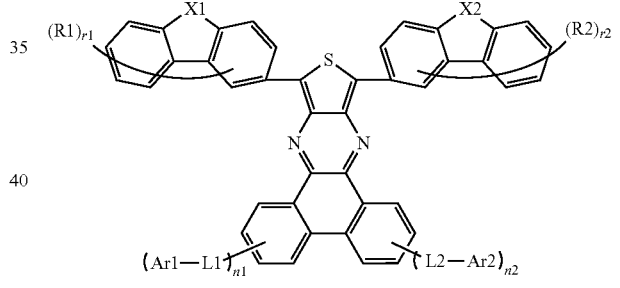

In Formulae 2-1 to 2-4, definitions of X1, X2, L1, L2, Ar1, Ar2, R1, R2, r1, and r2 are the same as those defined in Formula 1, R3 and R4 are the same as or different from each other, and are each independently hydrogen; deuterium; a halogen group; a nitrile group; a substituted or unsubstituted alkyl group; a substituted or unsubstituted aryl group; or a substituted or unsubstituted heterocyclic group, or adjacent groups are bonded to each other to form a substituted or unsubstituted ring, r3 and r4 are the same as or different from each other, and are each independently an integer from 0 to 3, when r3 is 2 or higher, a plurality of R3's are the same as or different from each other, and when r4 is 2 or higher, a plurality of R4's are the same as or different from each other.

In an exemplary embodiment of the present specification, R3 and R4 are the same as or different from each other, and are each independently hydrogen; or deuterium.

In an exemplary embodiment of the present specification, R3 and R4 are each hydrogen.

In an exemplary embodiment of the present specification, r3 is 0.

In an exemplary embodiment of the present specification, r4 is 0.

In an exemplary embodiment of the present specification, r3 is 3.

In an exemplary embodiment of the present specification, r4 is 3.

In an exemplary embodiment of the present specification, Formula 1 is represented by any one of the following Formulae 3-1 to 3-4.

[Formula 3-4]

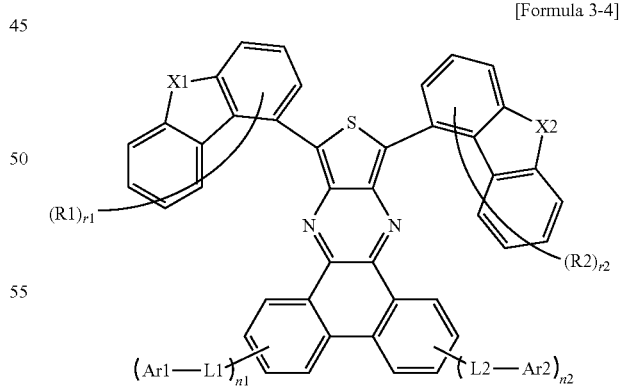

In Formulae 3-1 to 3-4,

X1, X2, L1, L2, Ar1, Ar2, R1, R2, r1, r2, n1, and n2 are the same as those defined in Formula 1.

In an exemplary embodiment of the present specification, the compound represented by Formula 1 is represented by any one of the following compounds.

21 22
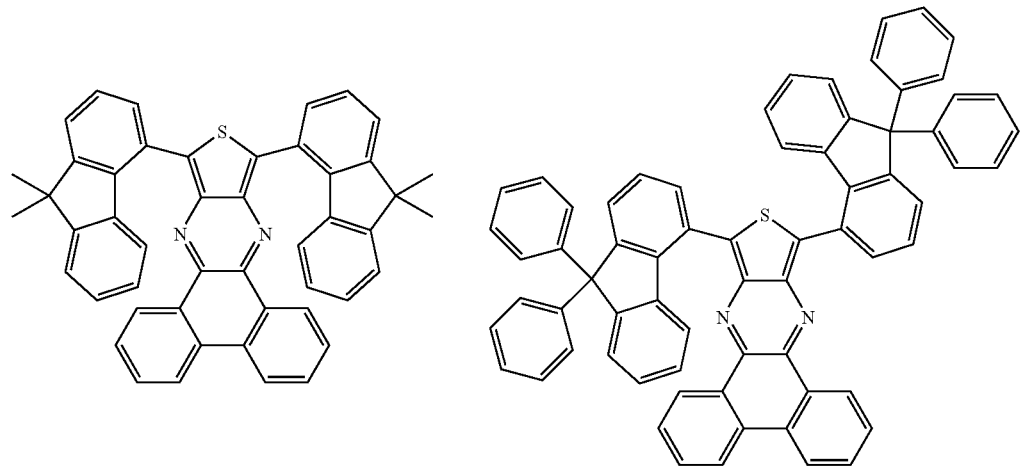
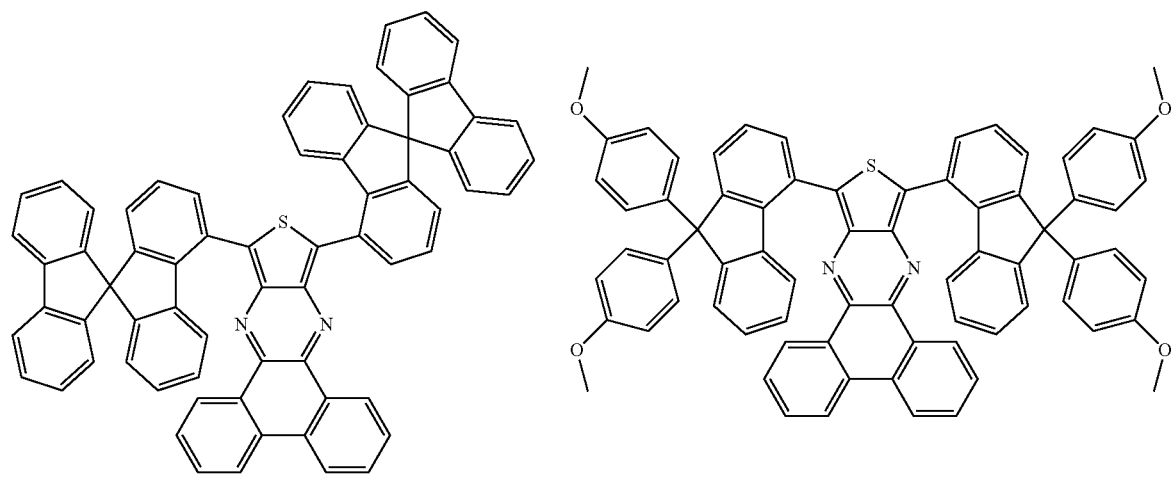
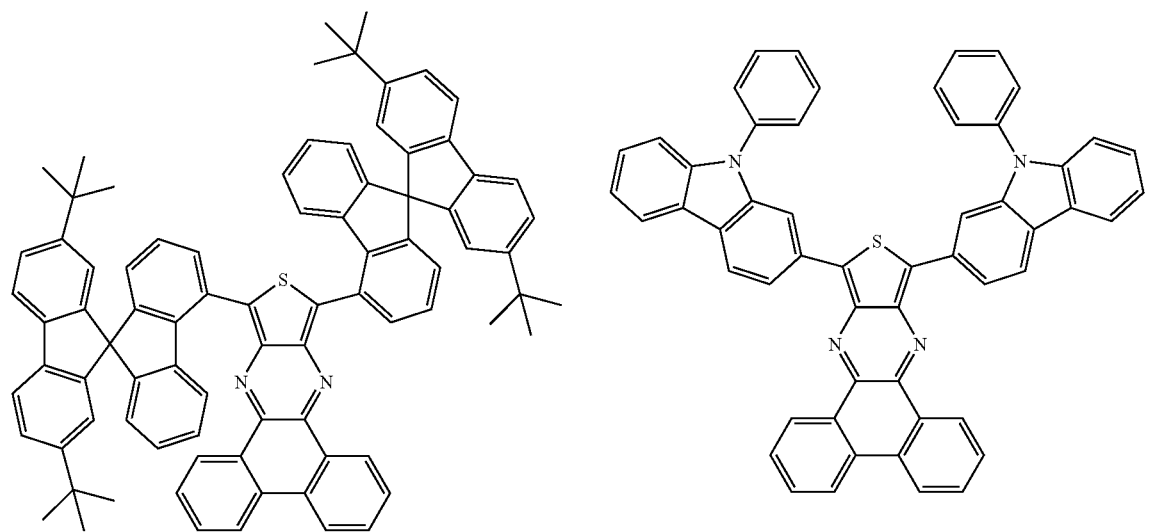

-continued
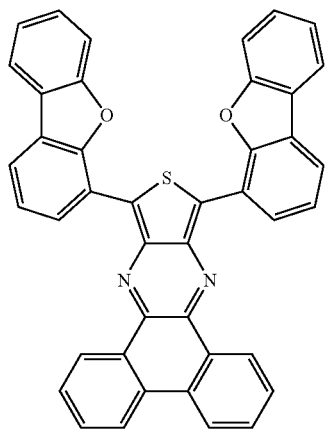
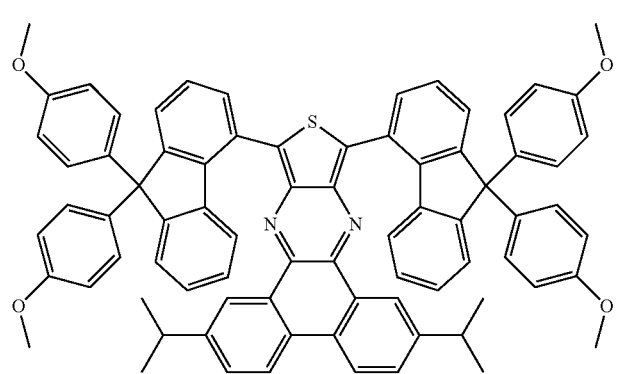
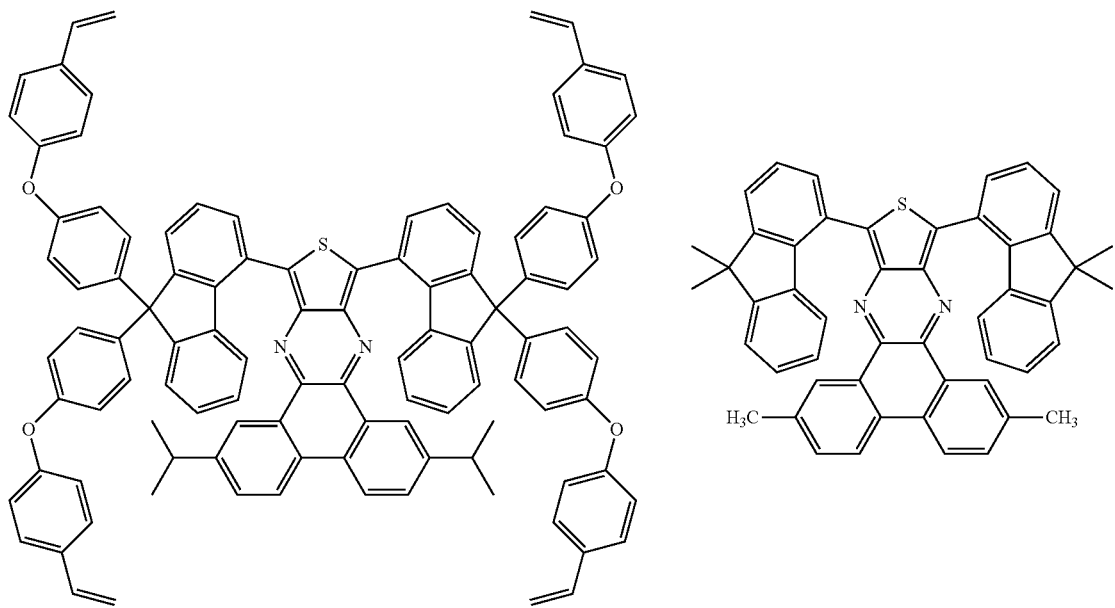
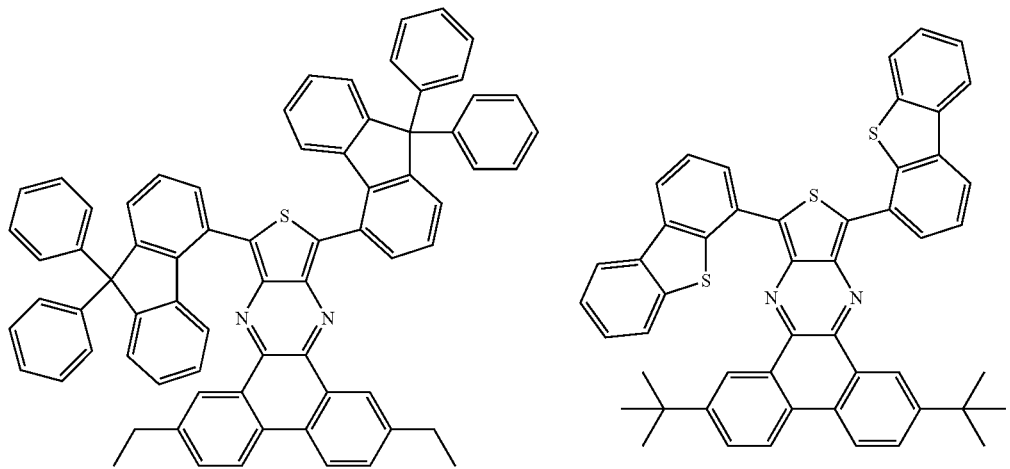

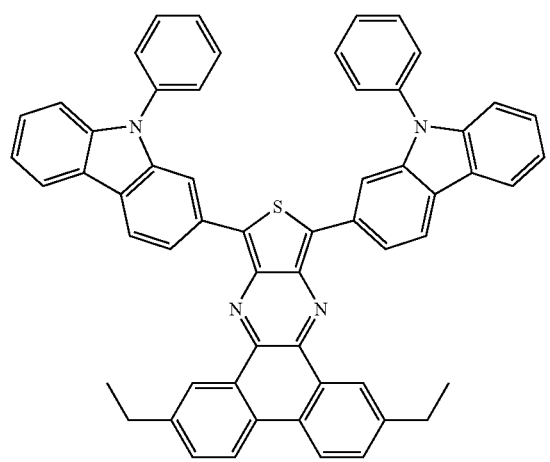
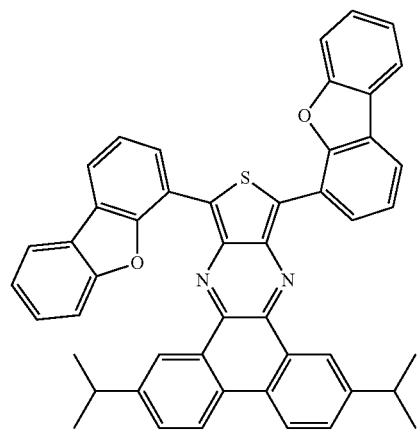
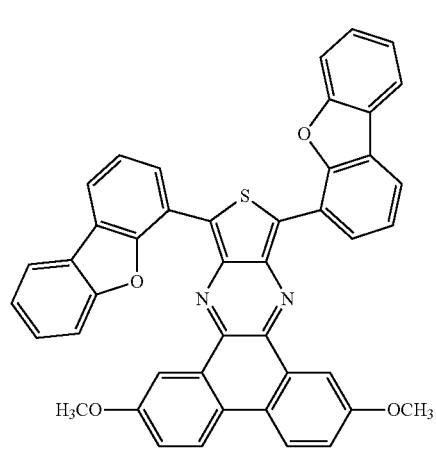
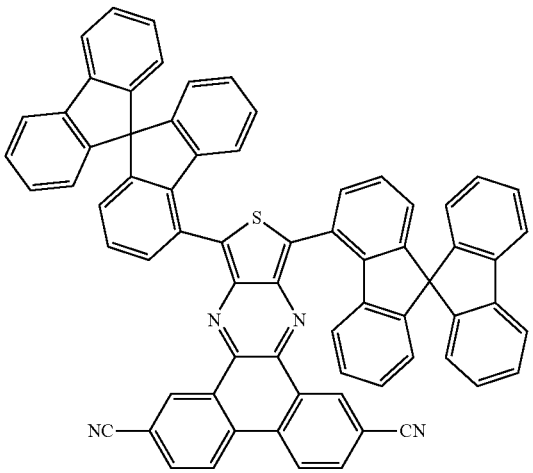
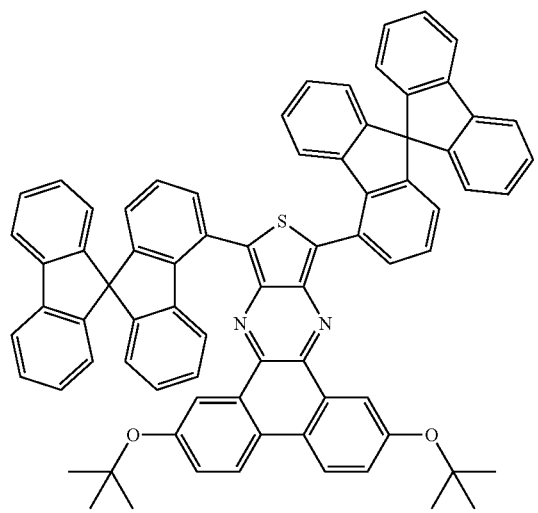
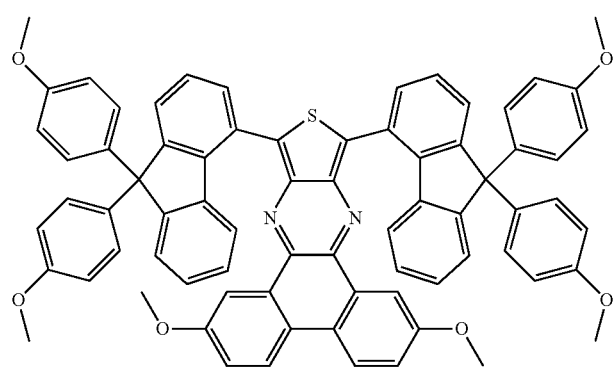

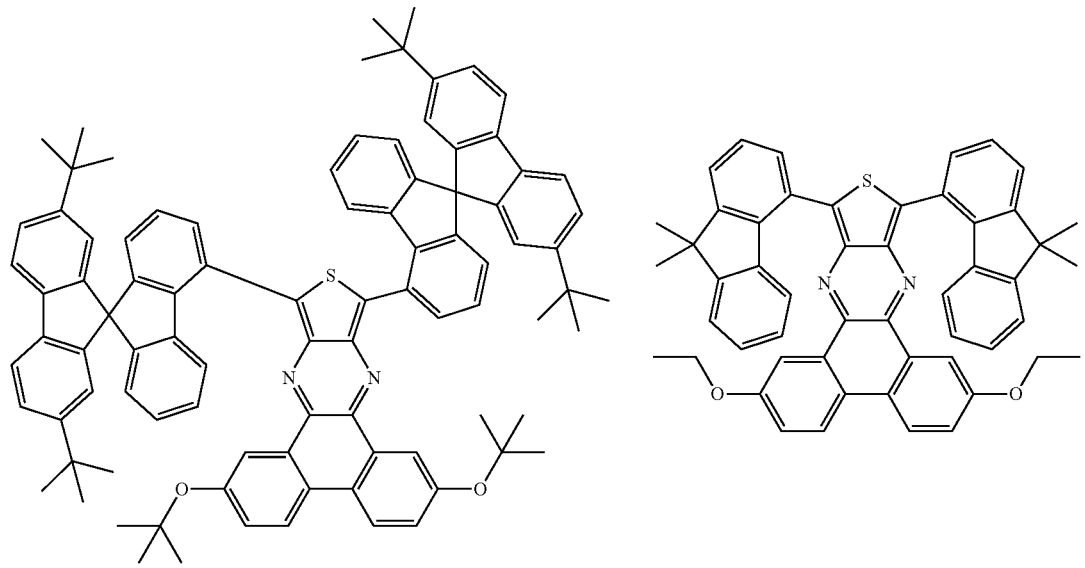
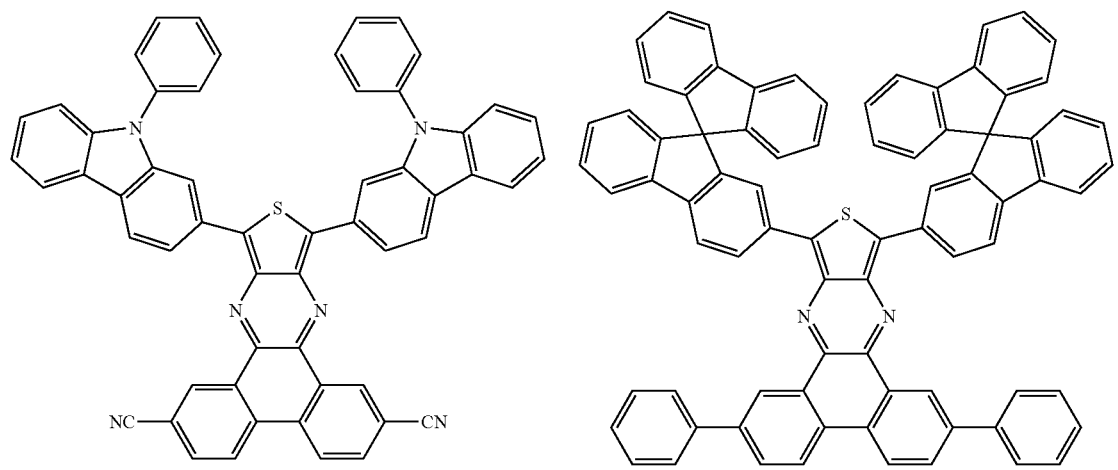
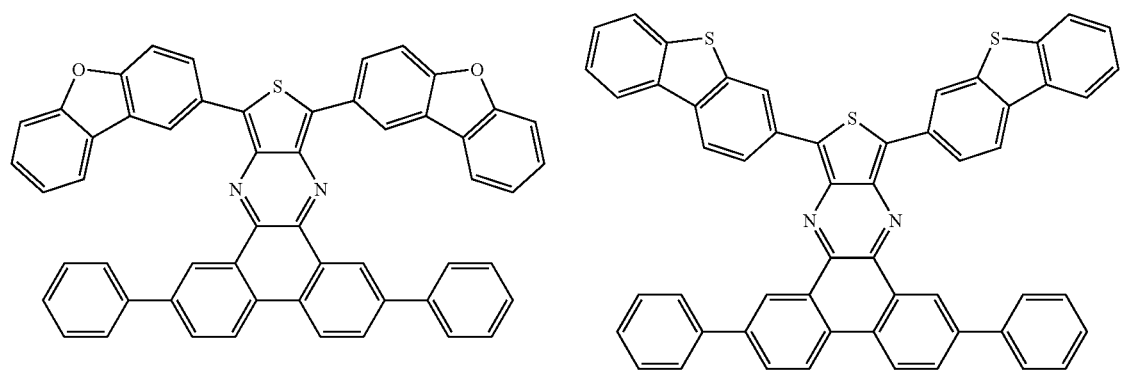

-continued
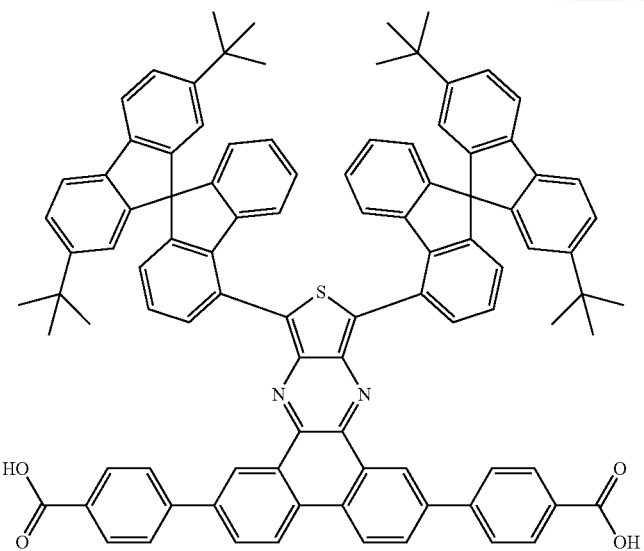
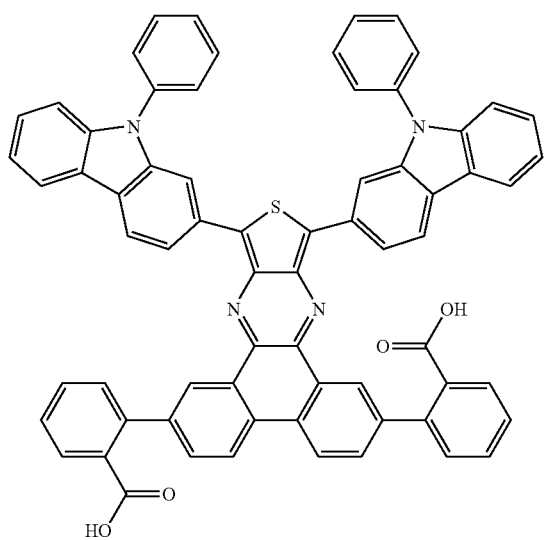
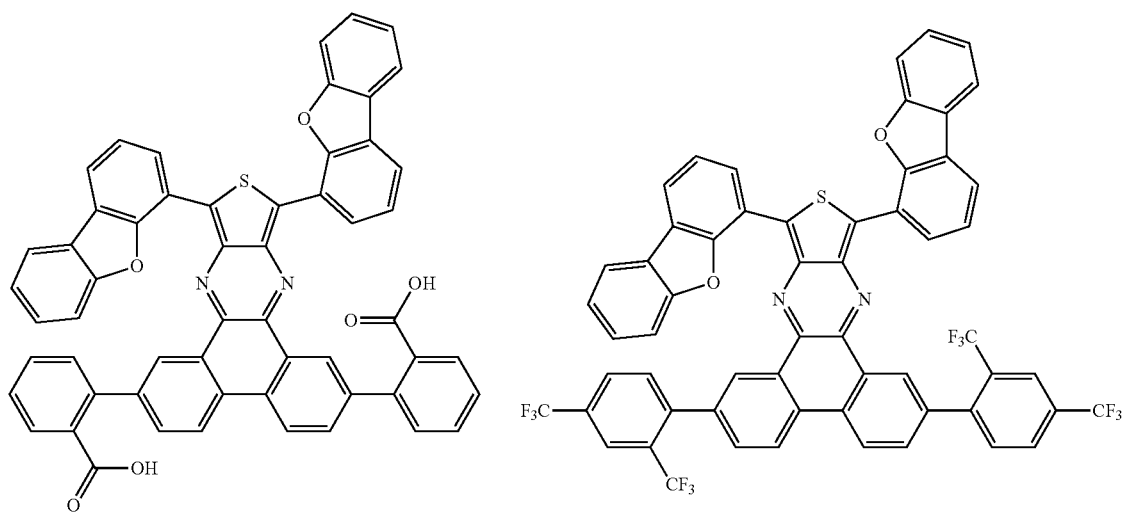

-continued
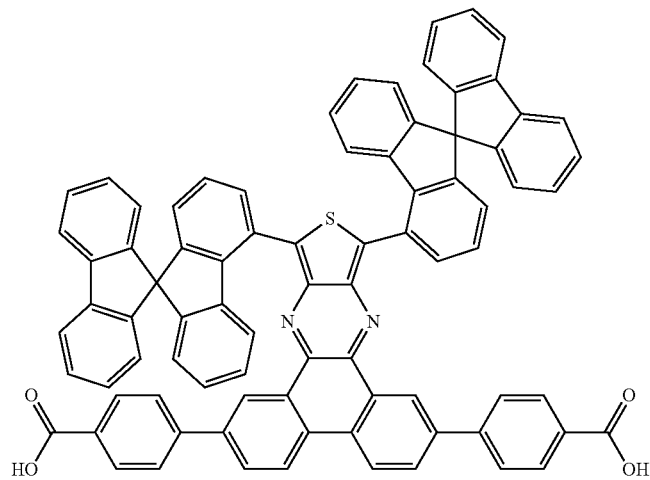
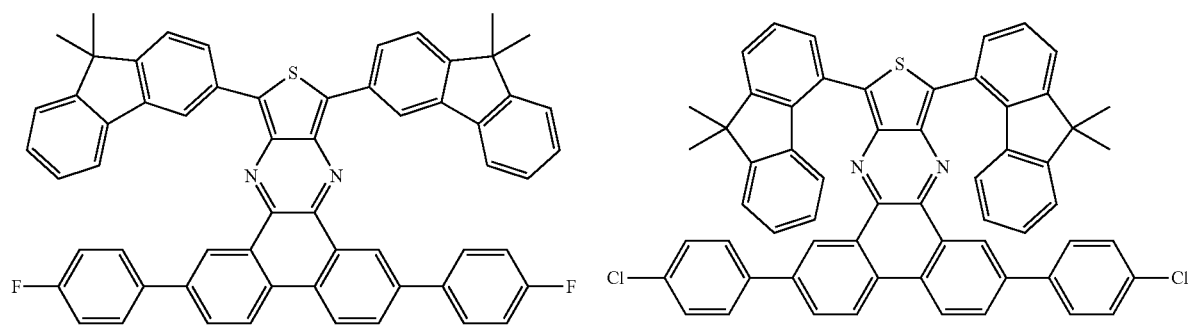
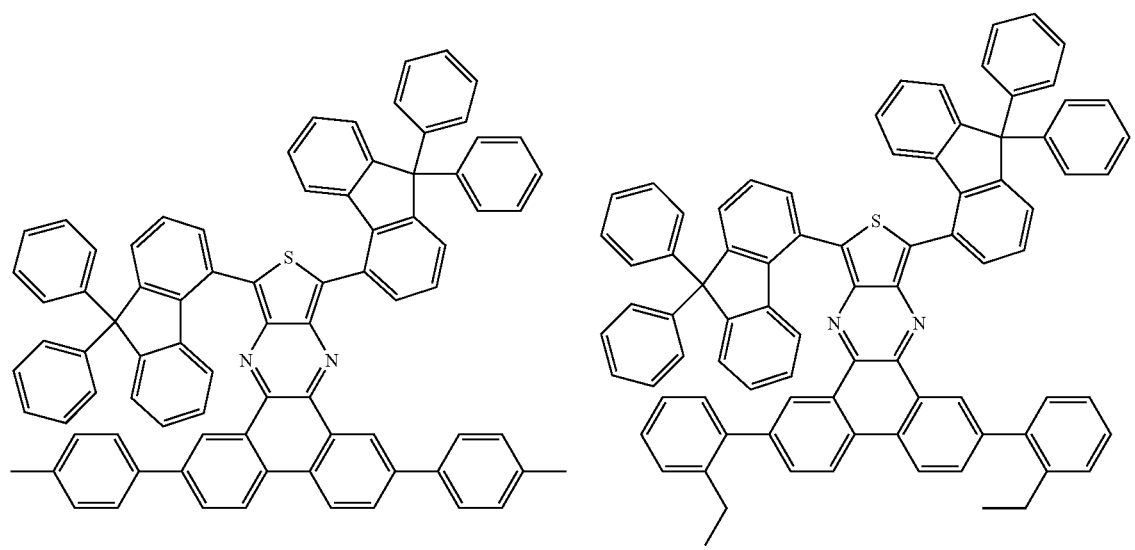

-continued
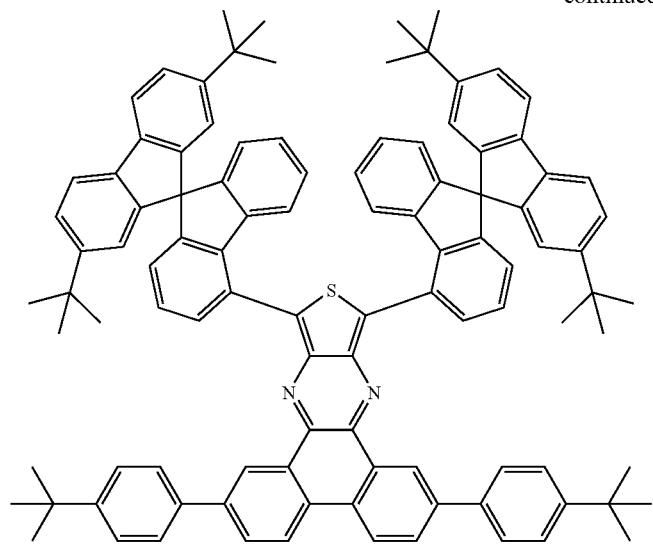
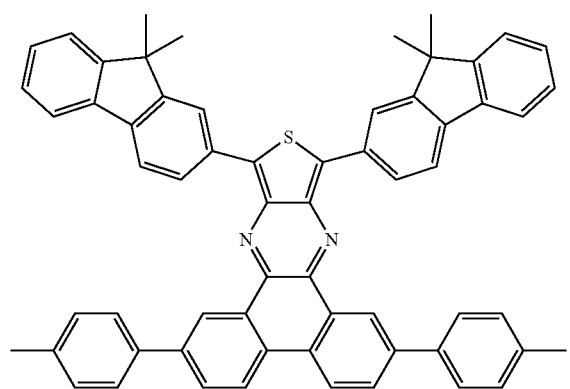
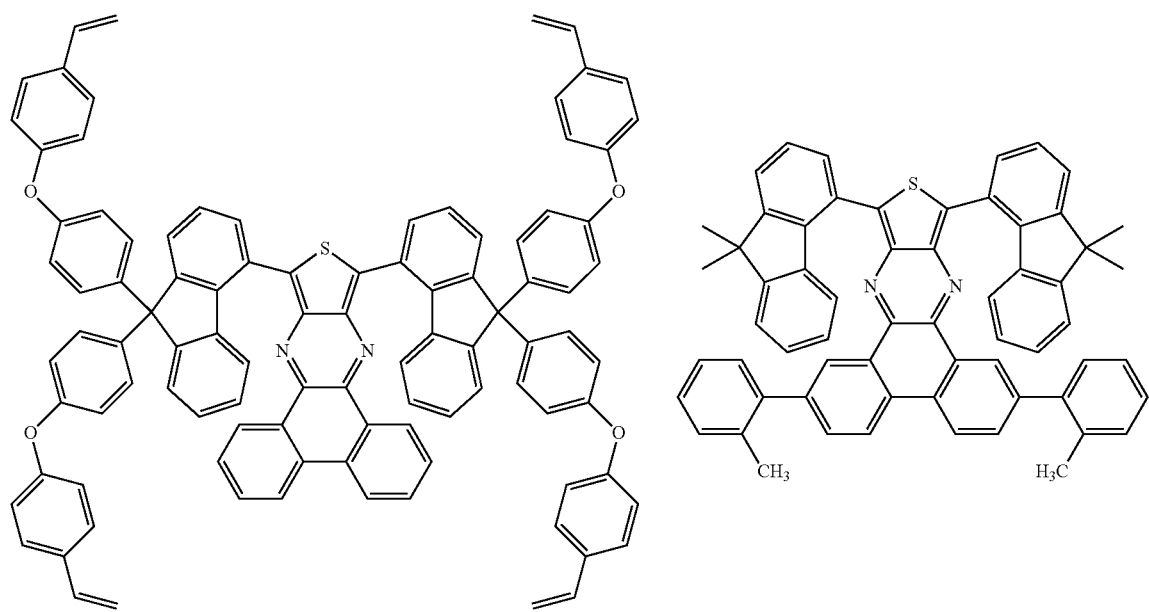

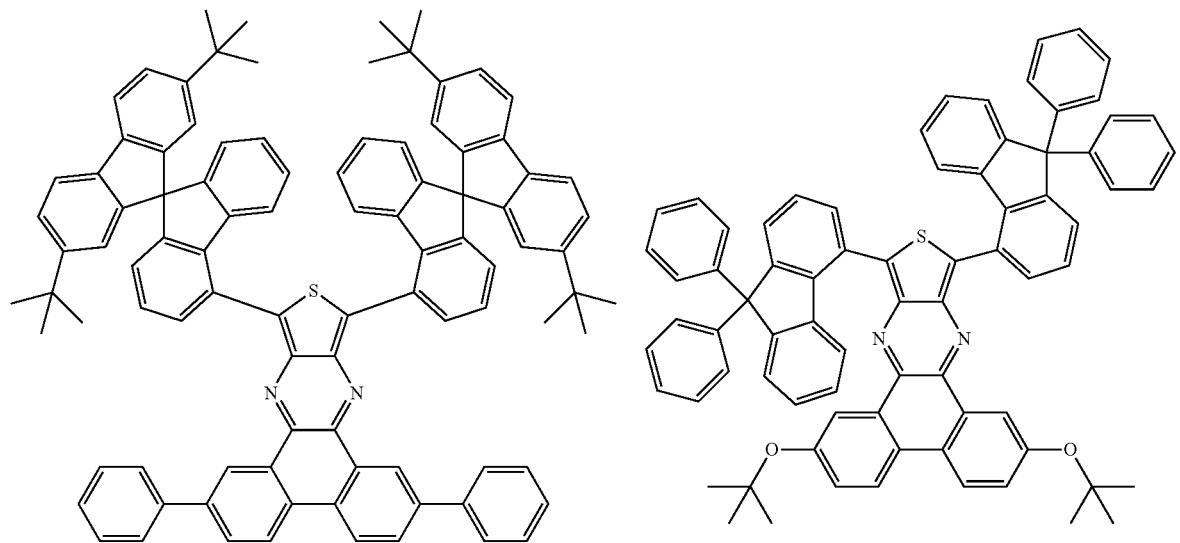
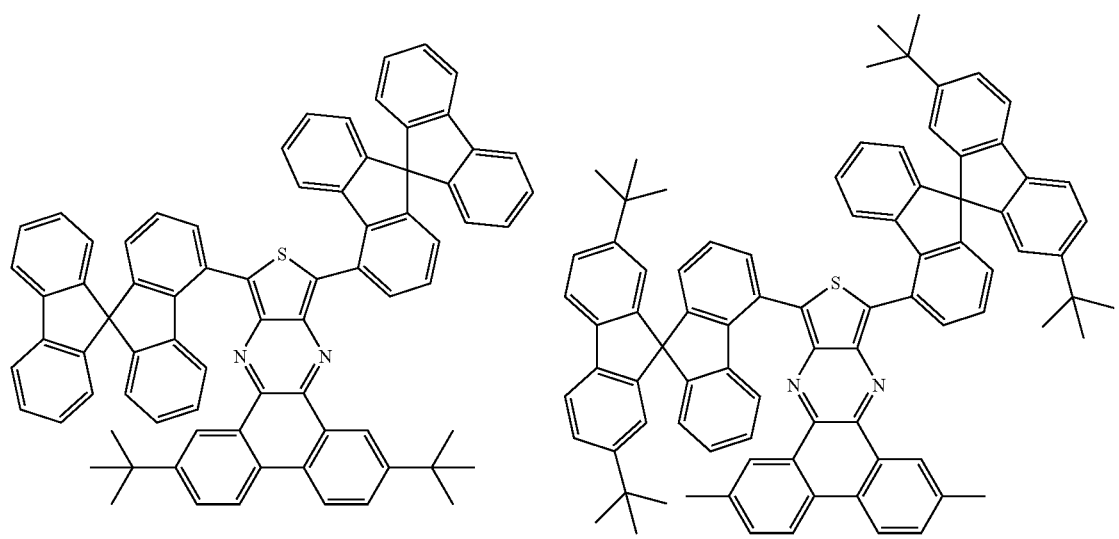
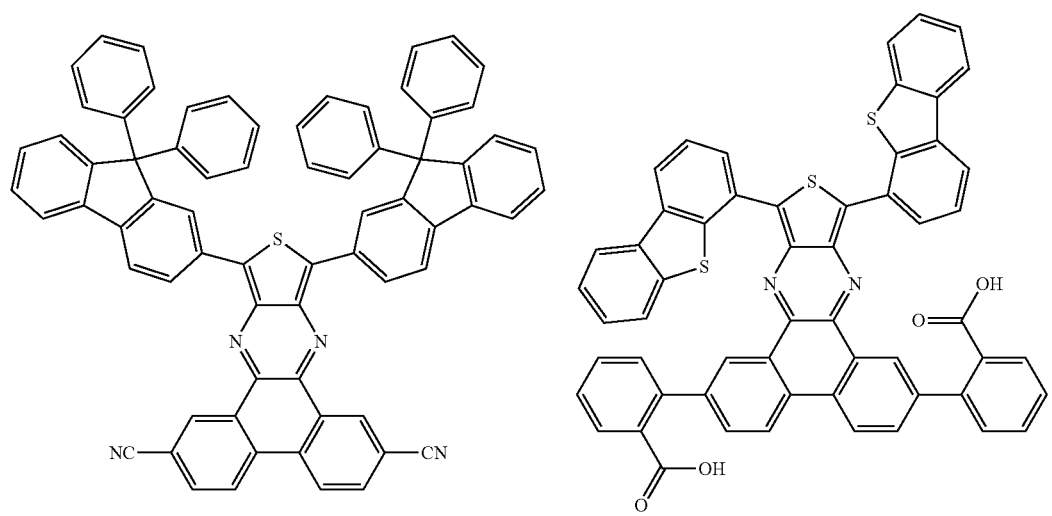

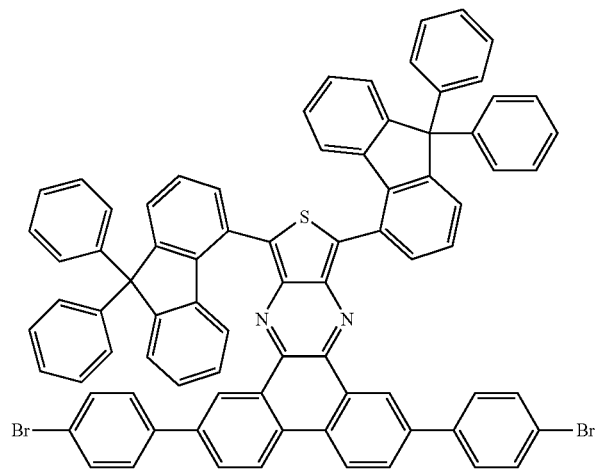
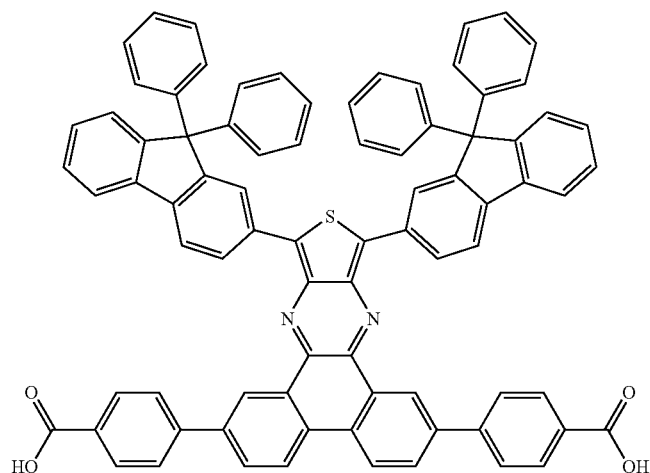
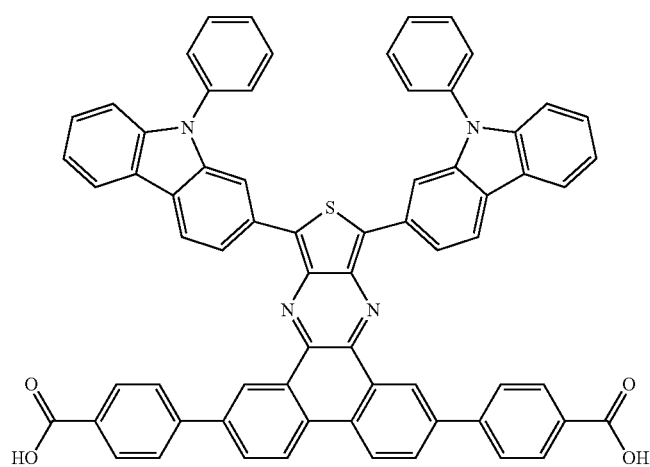

-continued
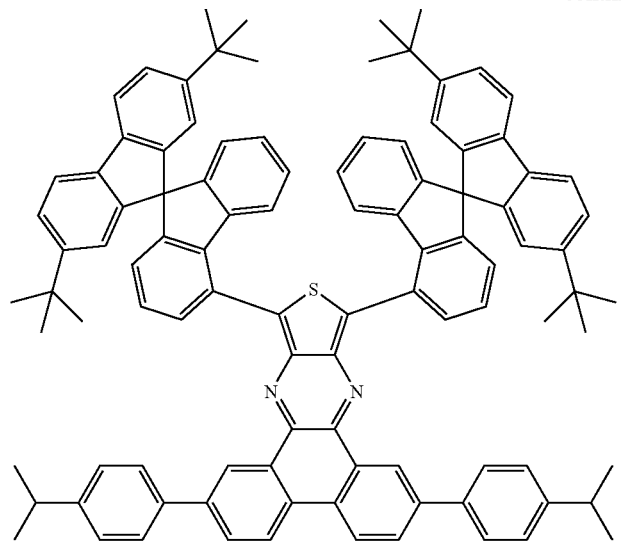
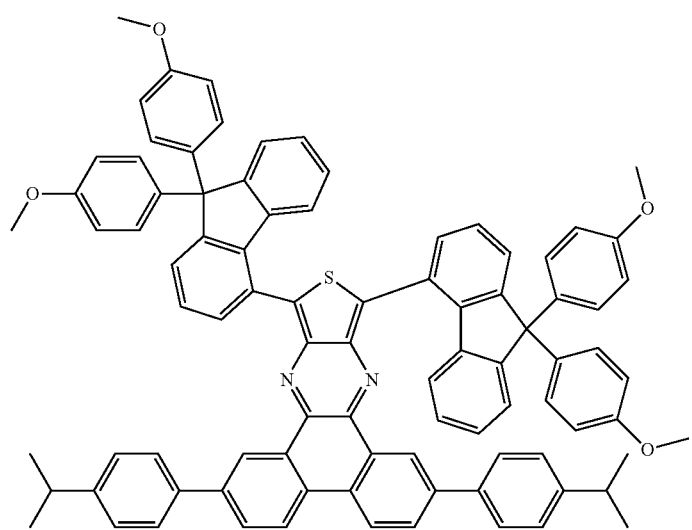

-continued
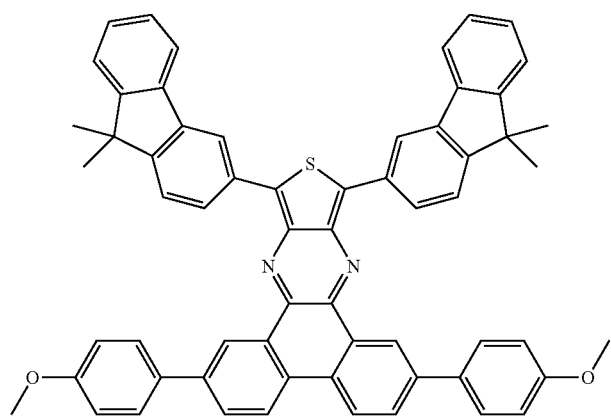
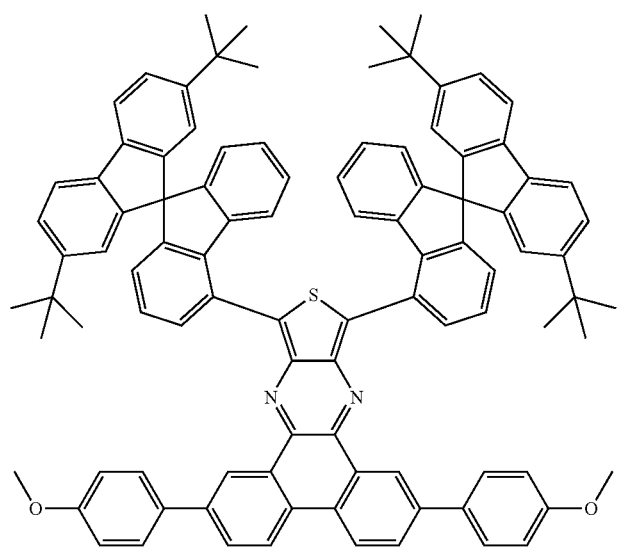
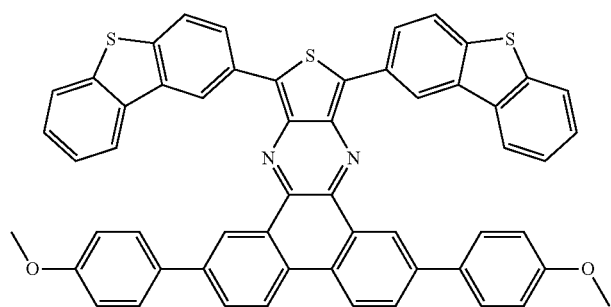

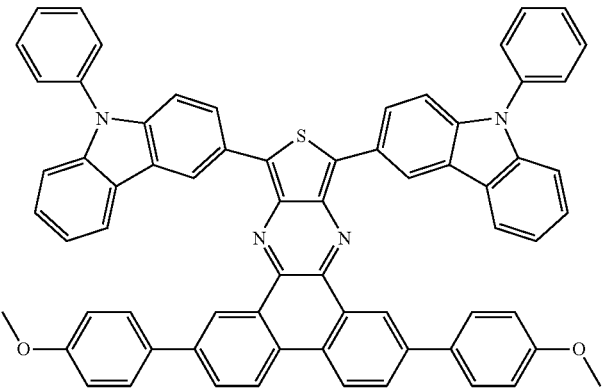
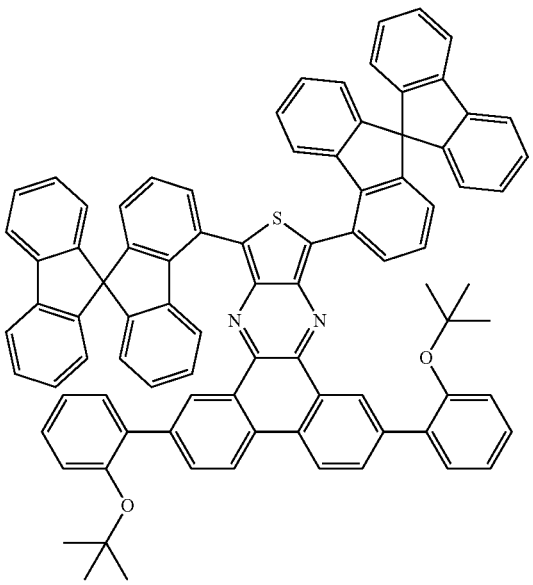
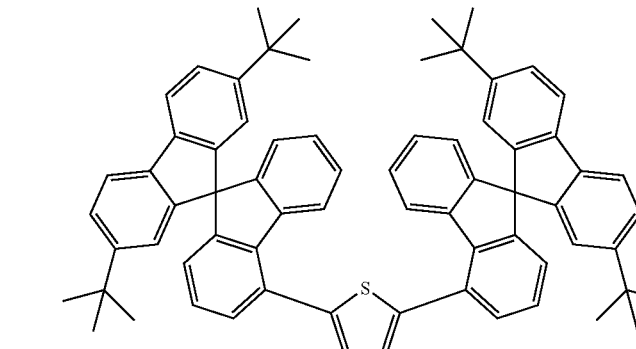
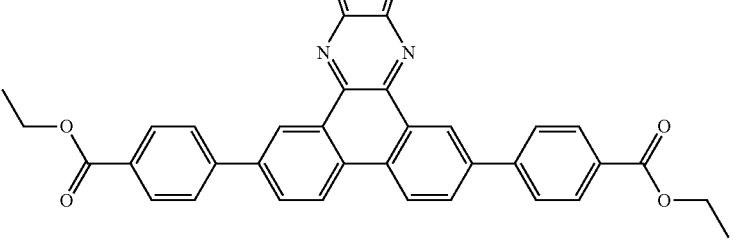
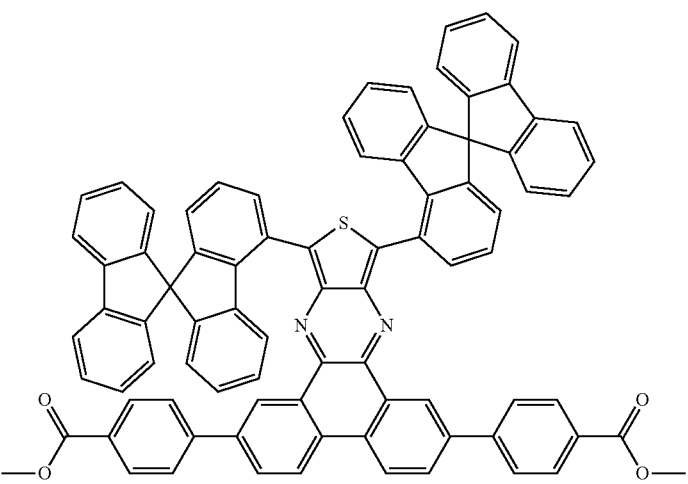

-continued
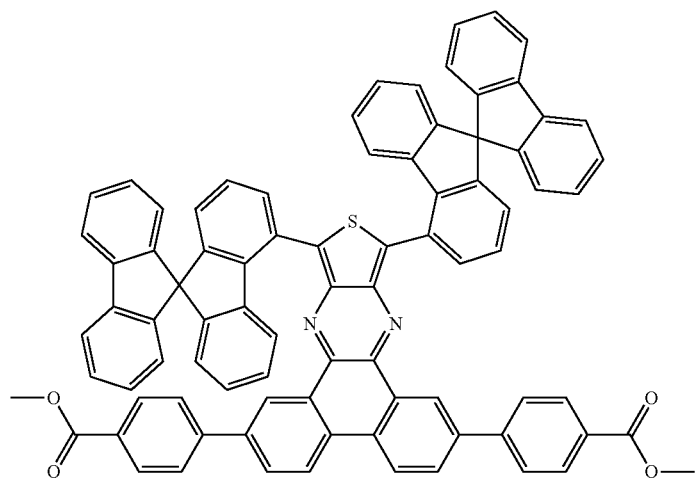
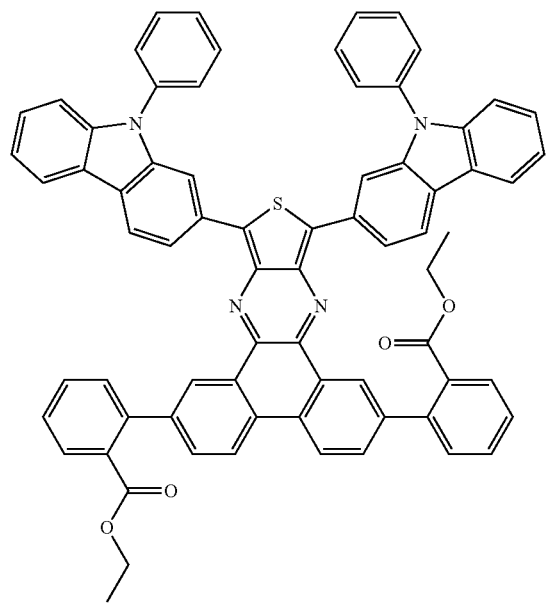
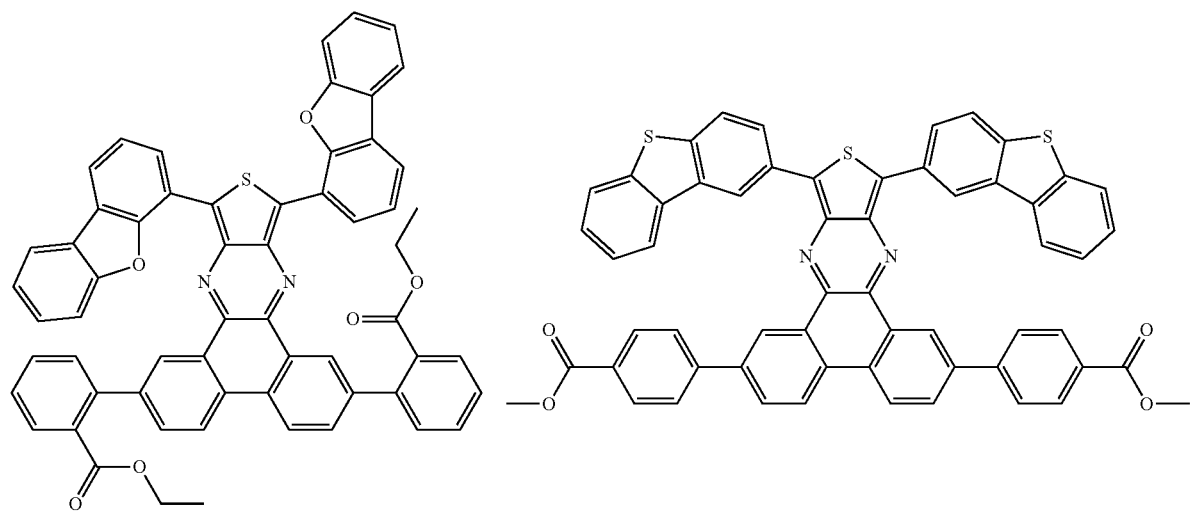

-continued
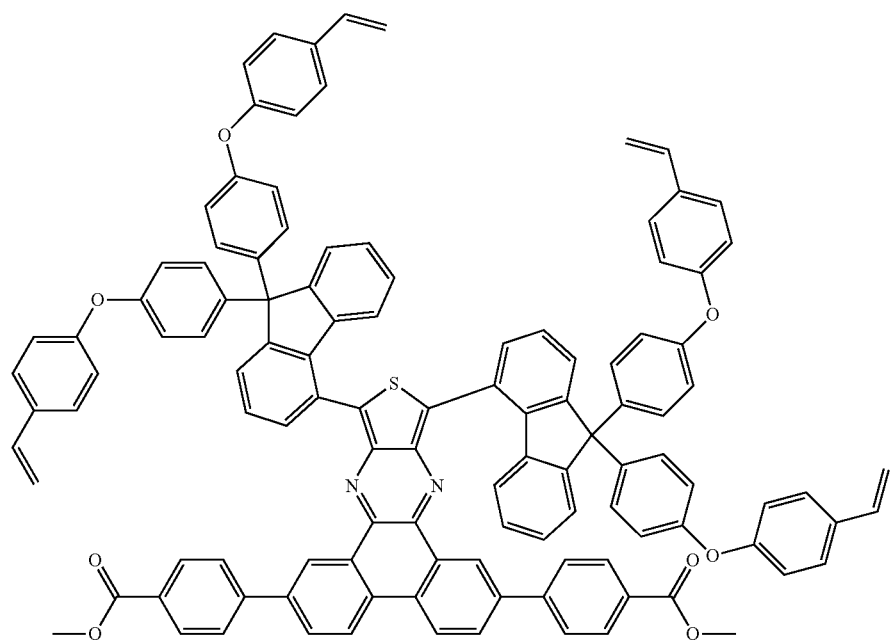
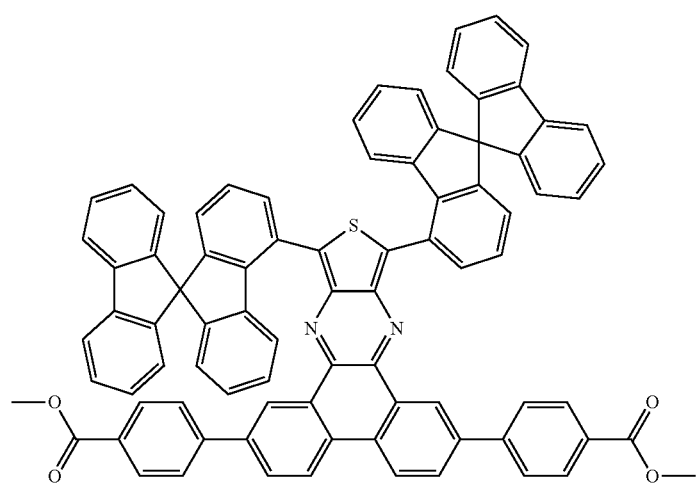
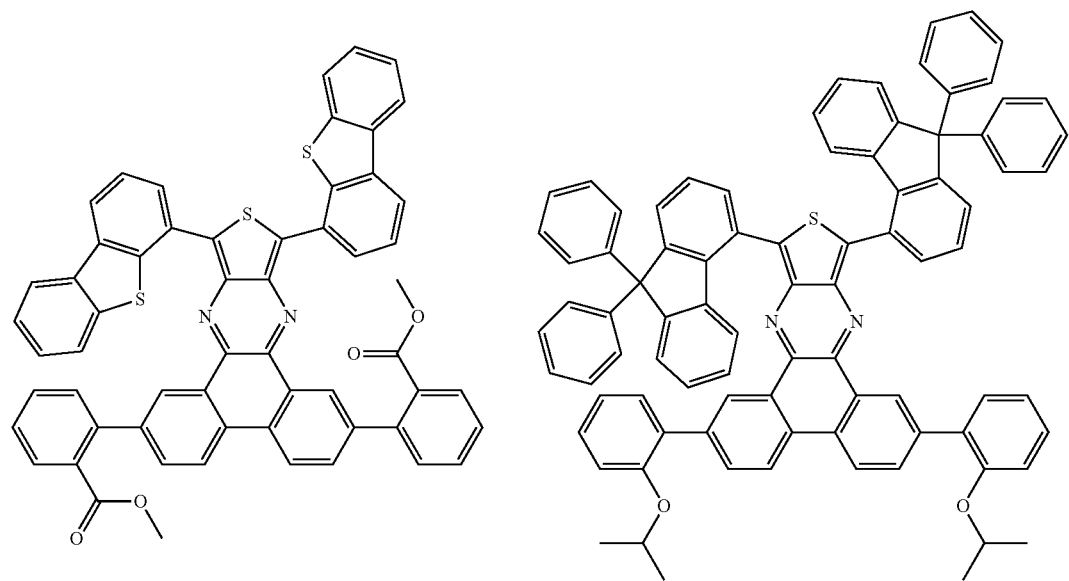

-continued
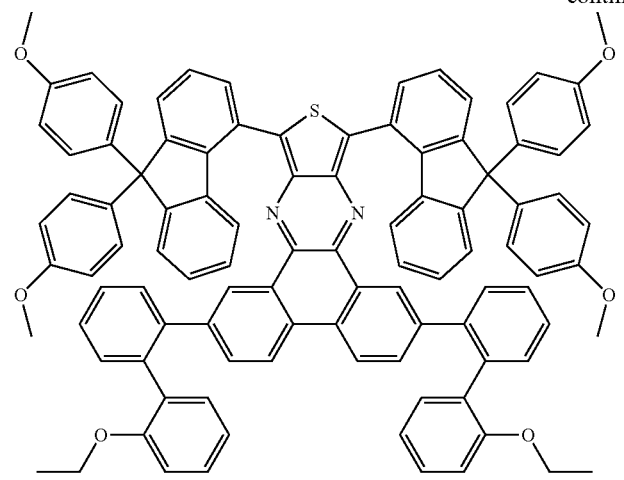
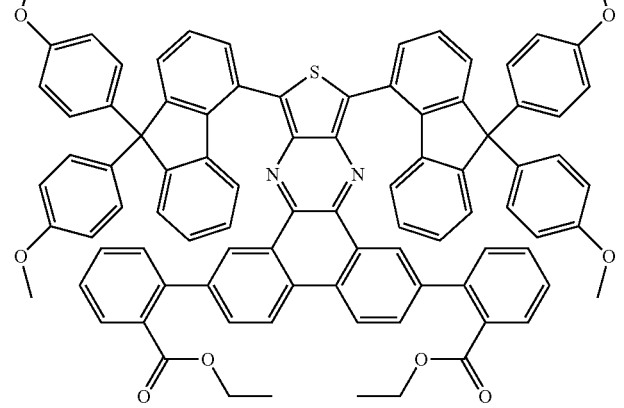
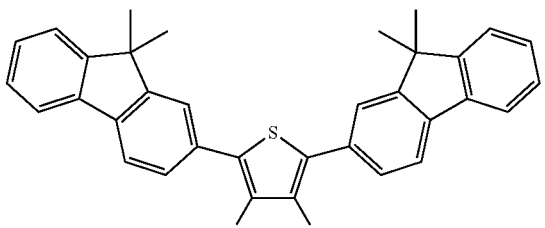
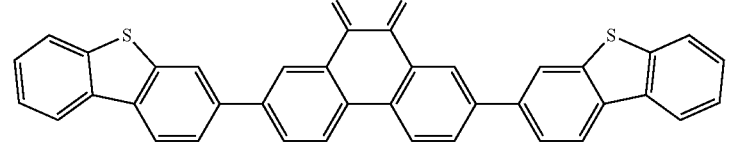
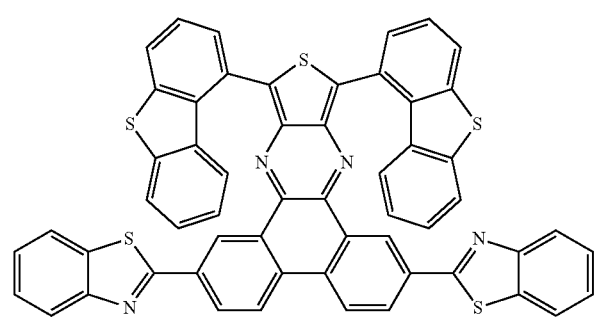
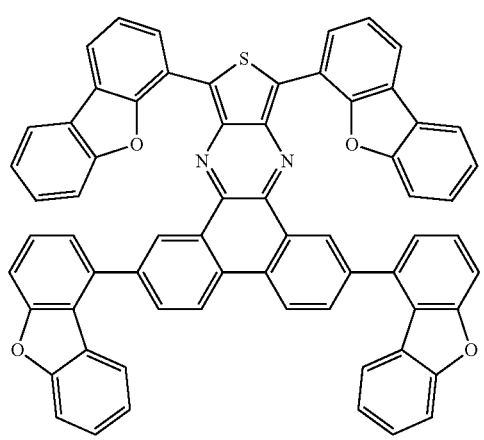

-continued
51
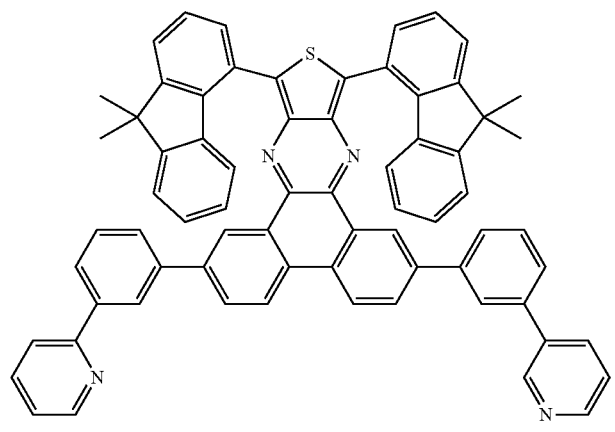
52
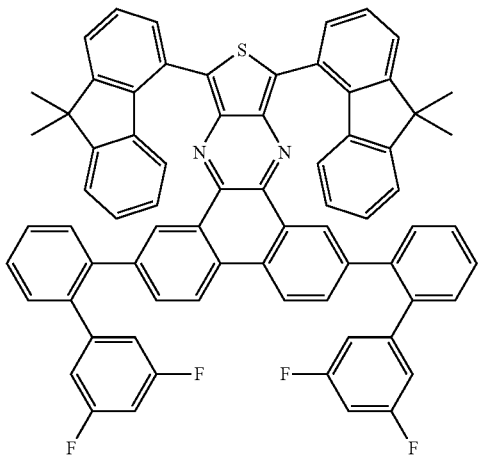
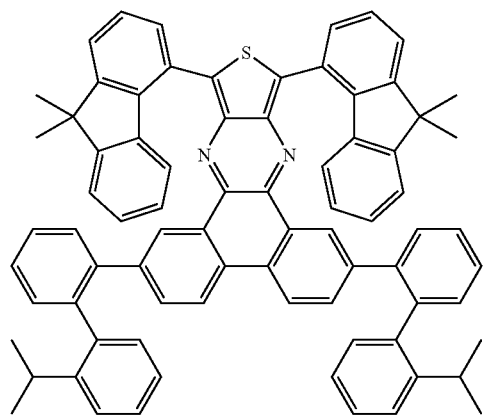
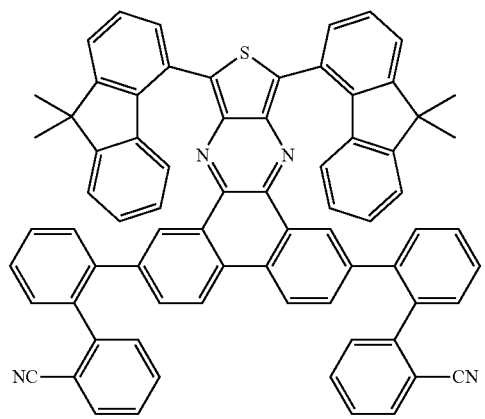
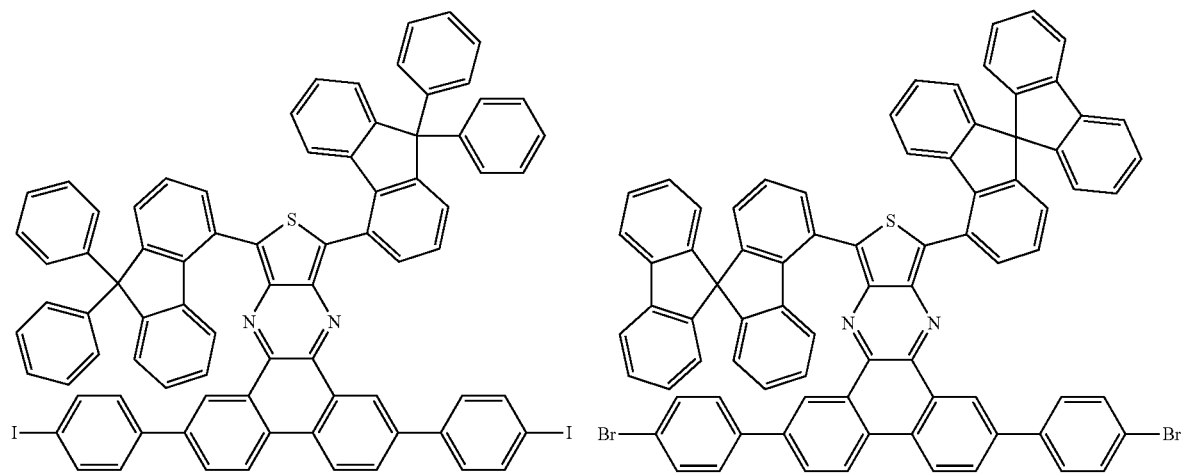

-continued
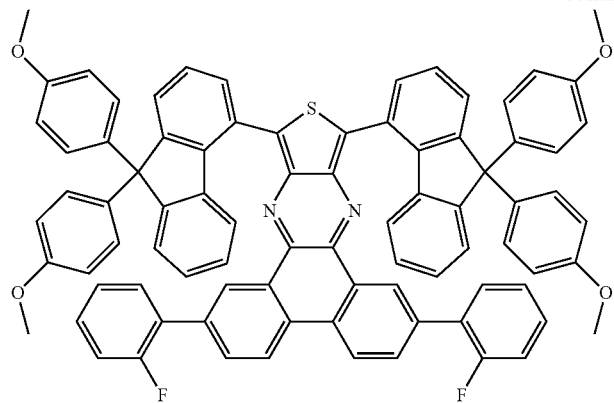
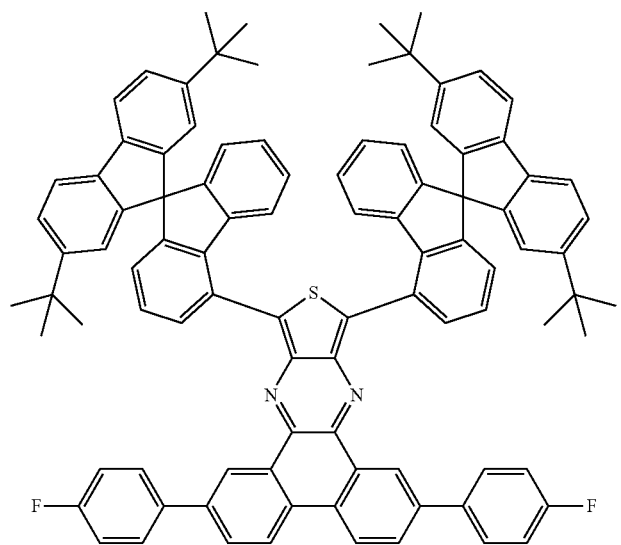
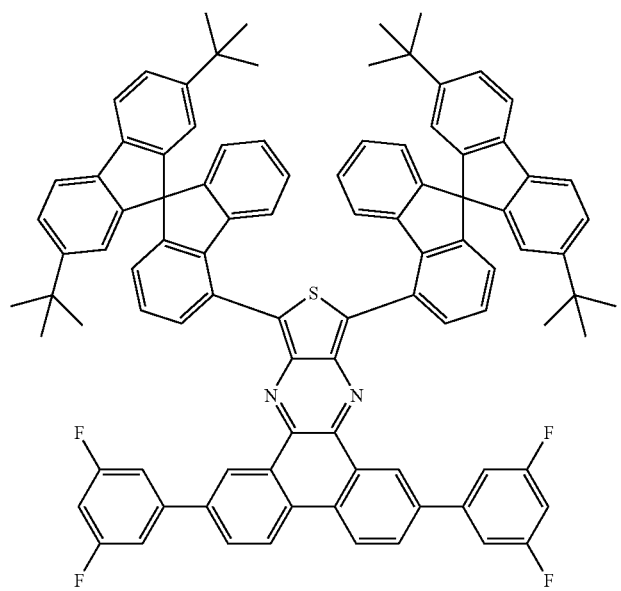

-continued
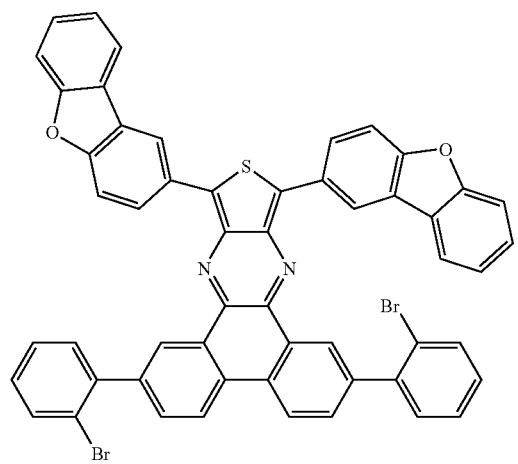
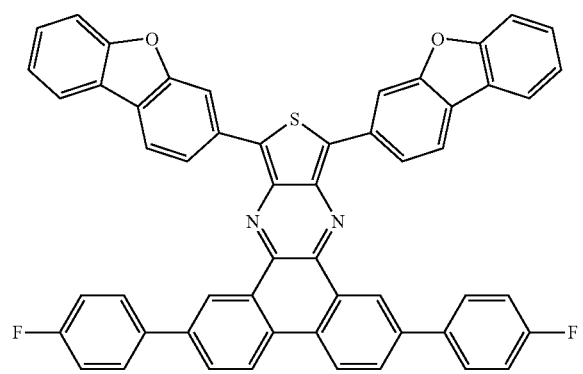
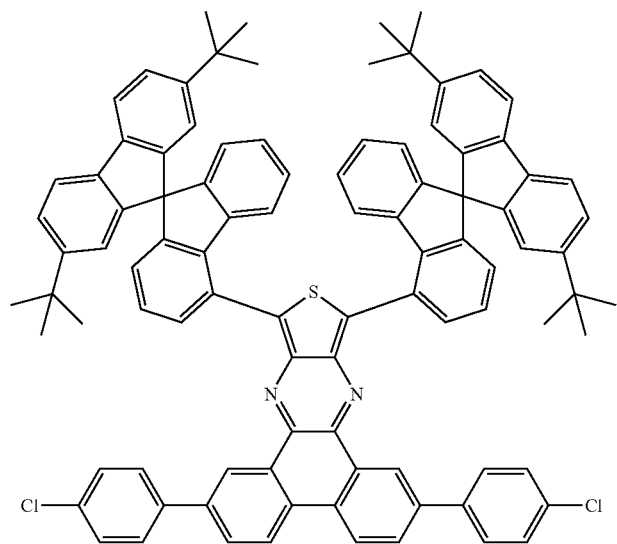
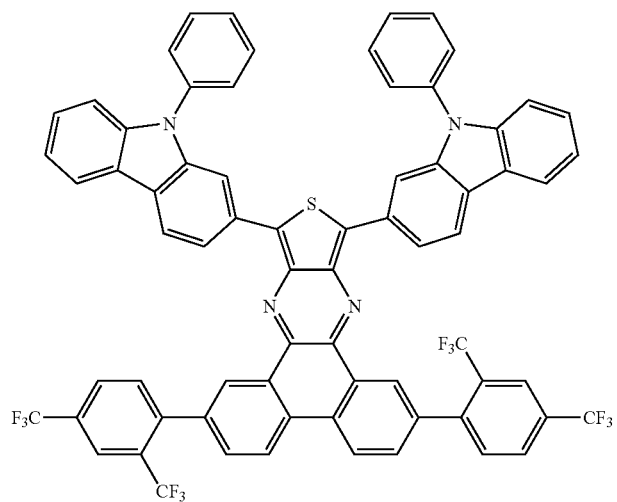

-continued
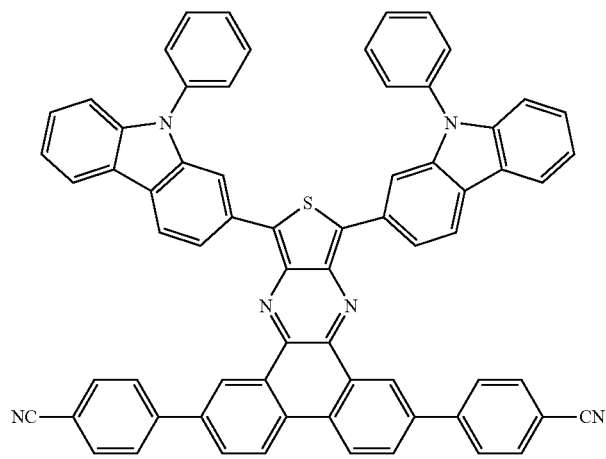
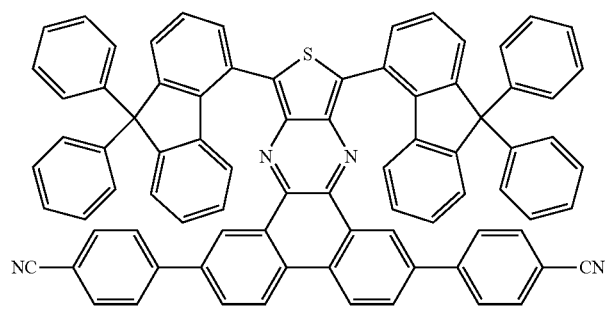
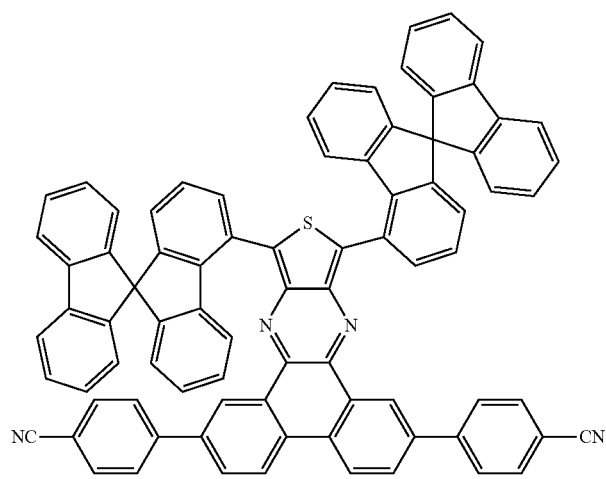

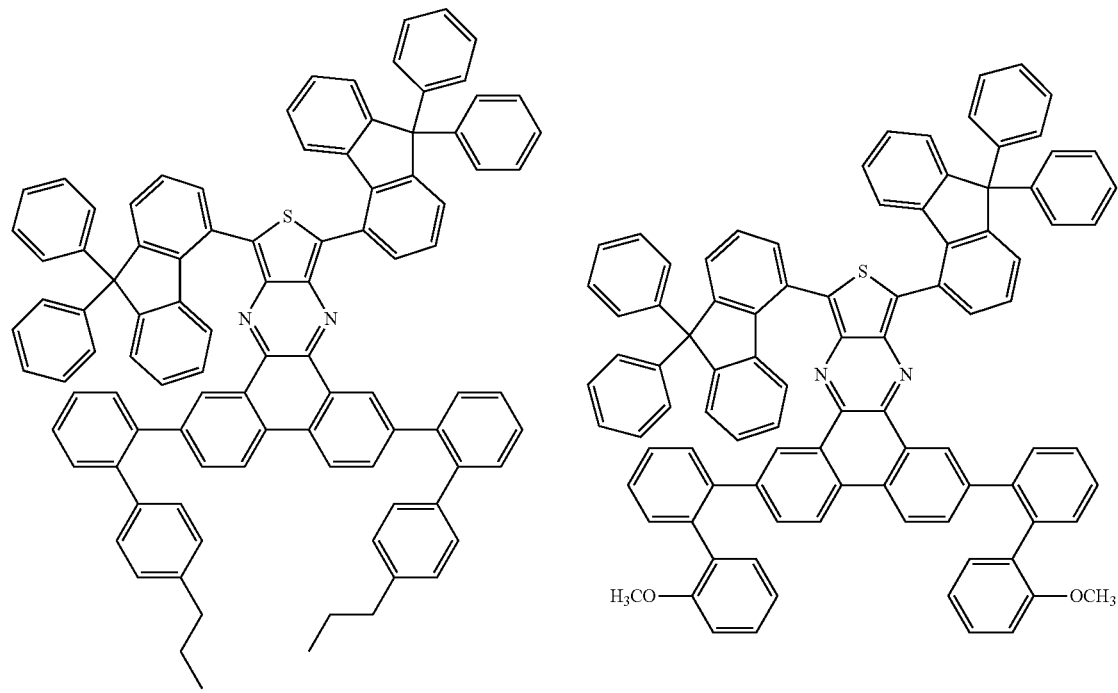
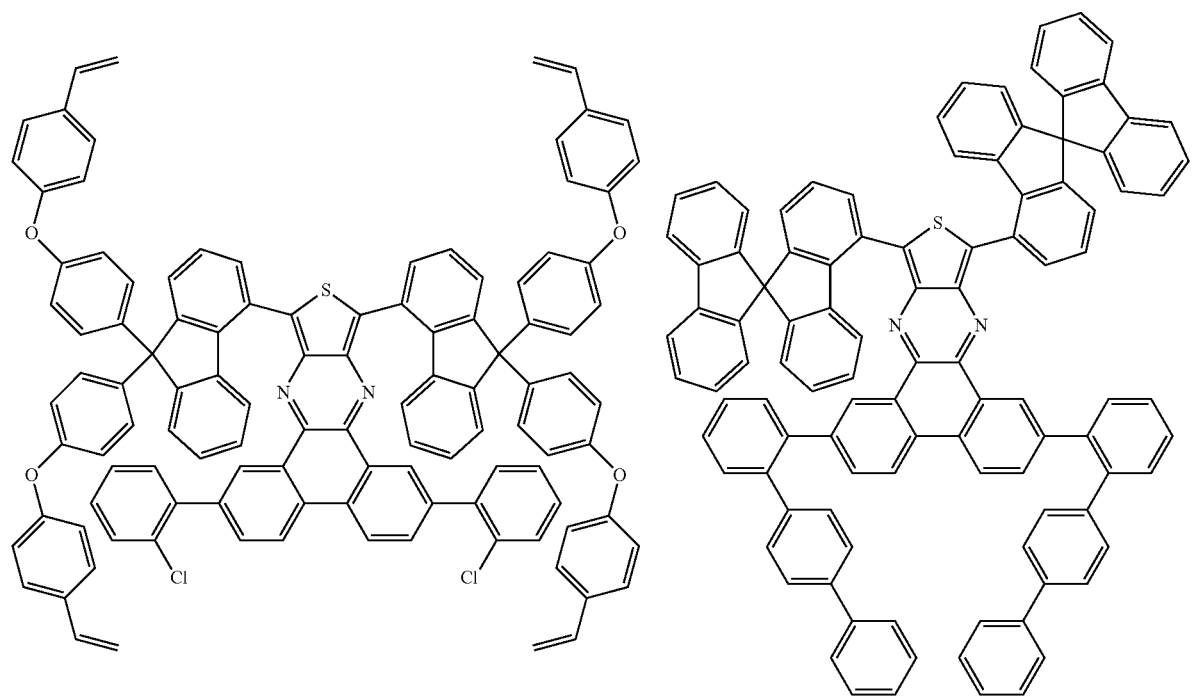

-continued
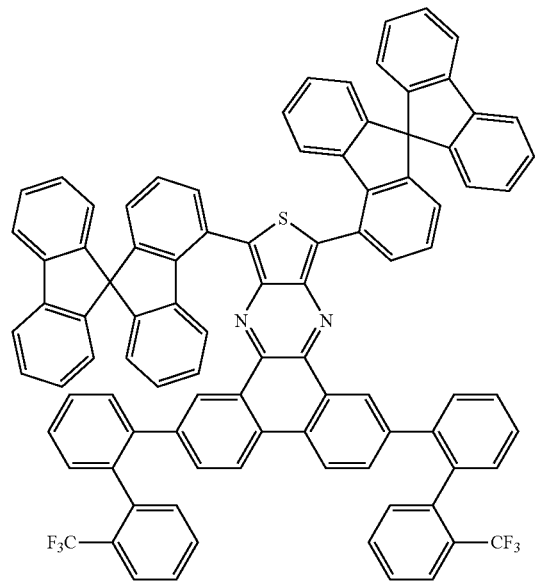
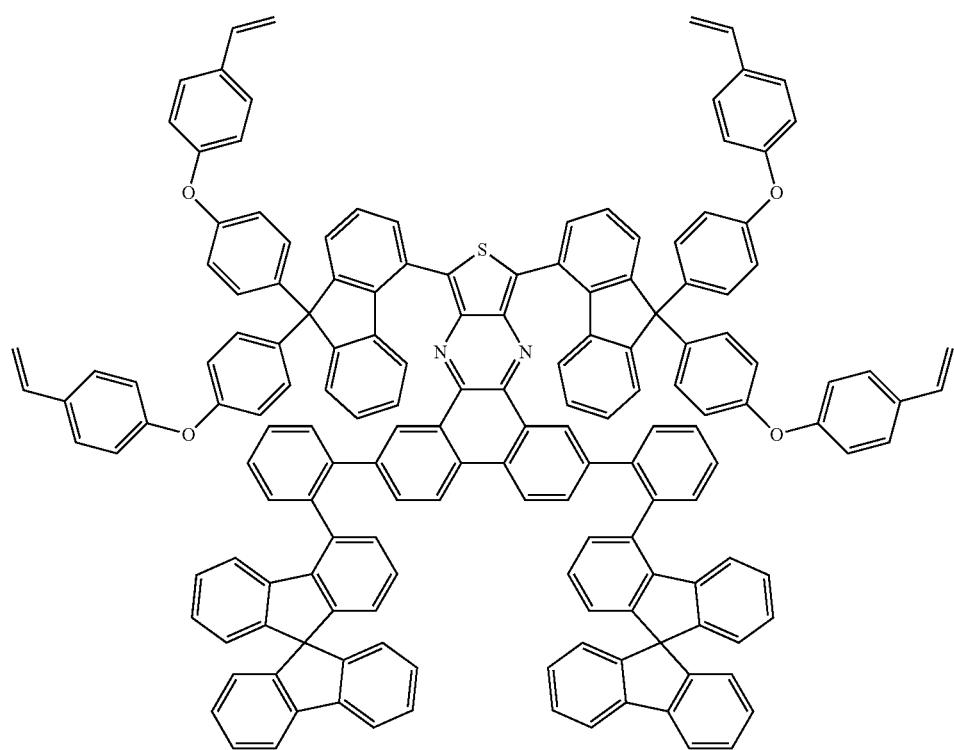

-continued
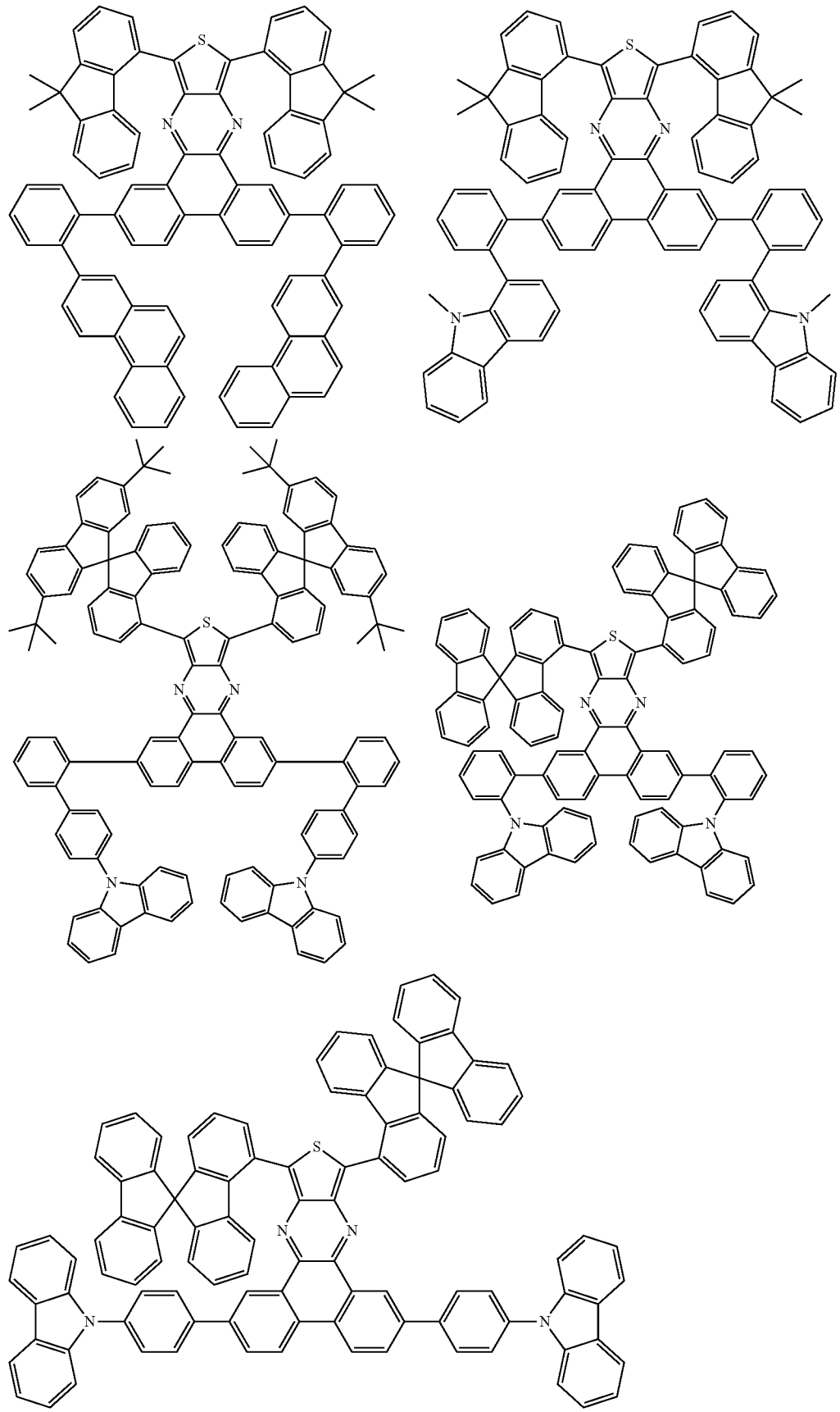

-continued
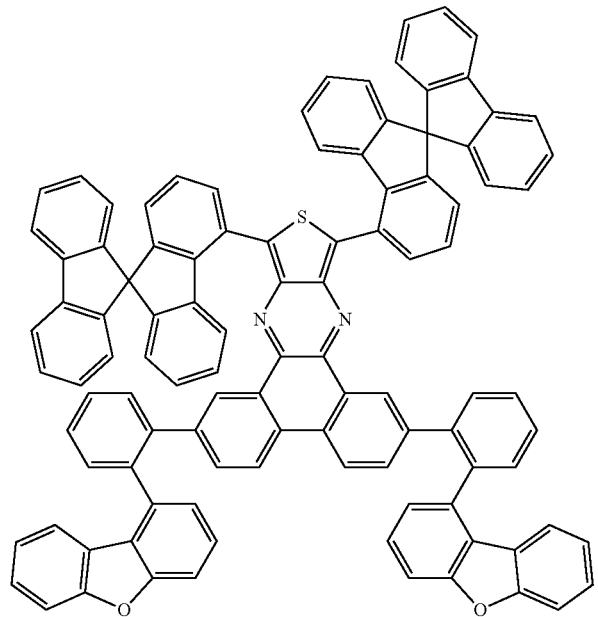
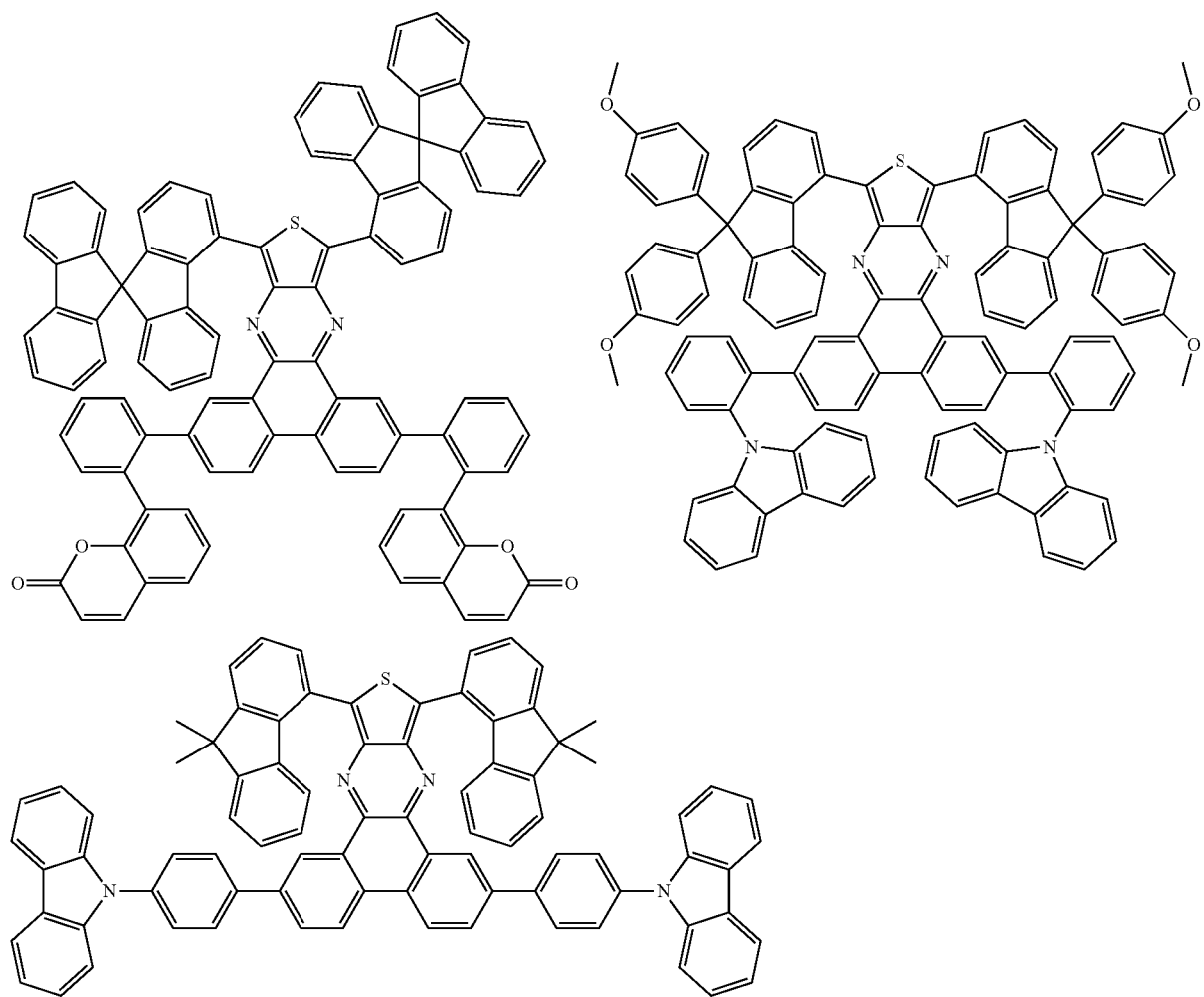

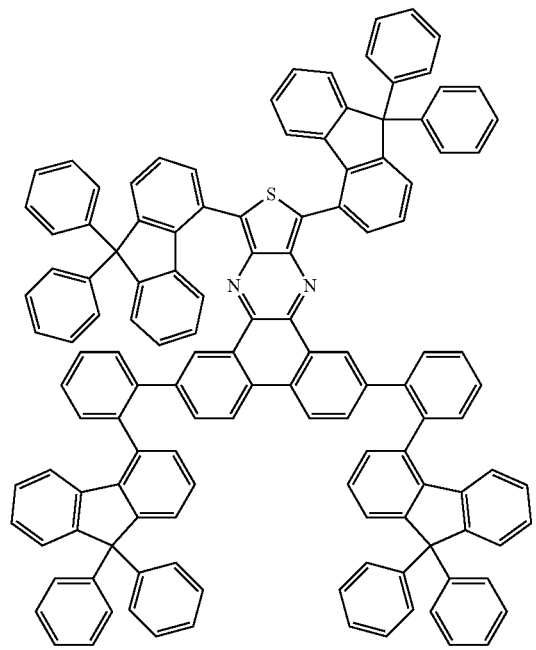
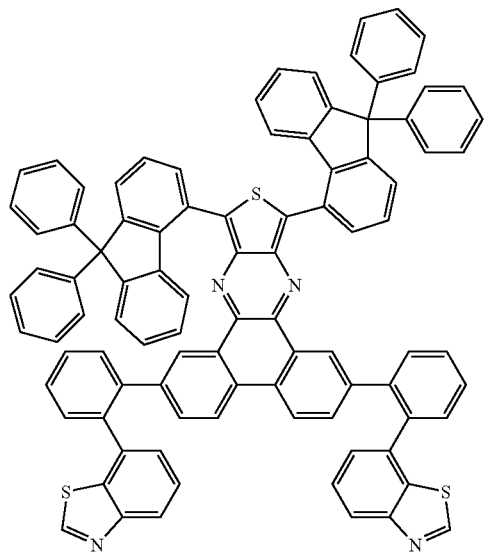
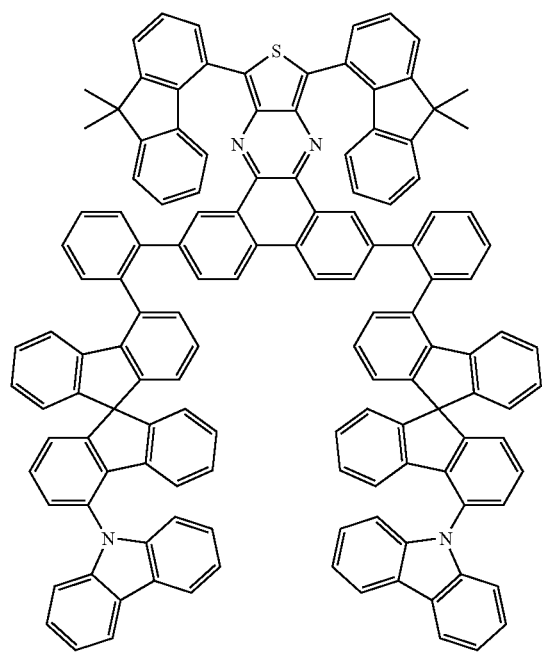

-continued
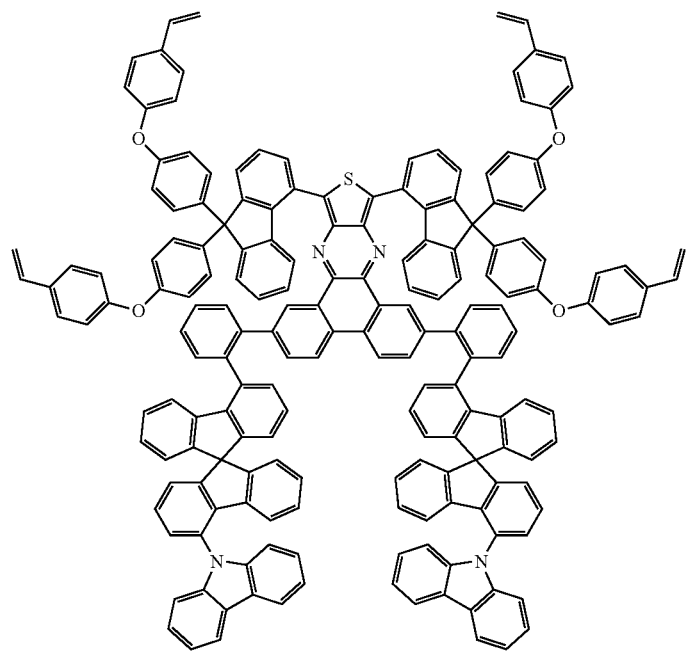 [SMILES: C=Cc1ccc(Oc2ccc(C3(c4ccc(Oc5ccc(C=C)cc5)cc4)c4ccccc4-c4c(-c5sc(-c6cccc7c6-c6ccccc6C7(c6ccc(Oc7ccc(C=C)cc7)cc6)c6ccc(Oc7ccc(C=C)cc7)cc6)c6nc7c8cc(-c9ccccc9-c9cccc%10c9-c9ccccc9C%109c%10ccccc%10-c%10c(-n%11c%12ccccc%12c%12ccccc%12%11)cccc%109)ccc8c8ccc(-c9ccccc9-c9cccc%10c9-c9ccccc9C%109c%10ccccc%10-c%10c(-n%11c%12ccccc%12c%12ccccc%12%11)cccc%109)cc8c7nc56)cccc43)cc2)cc1]
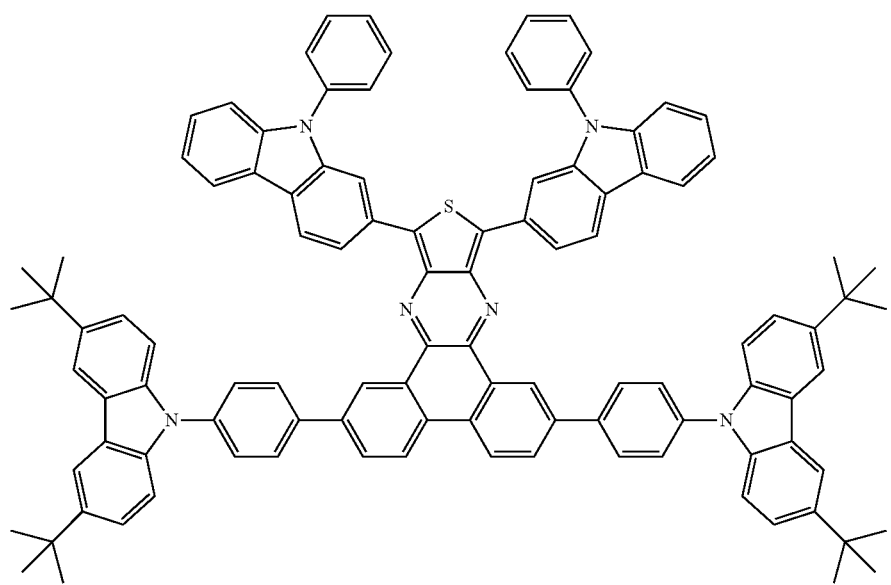

71
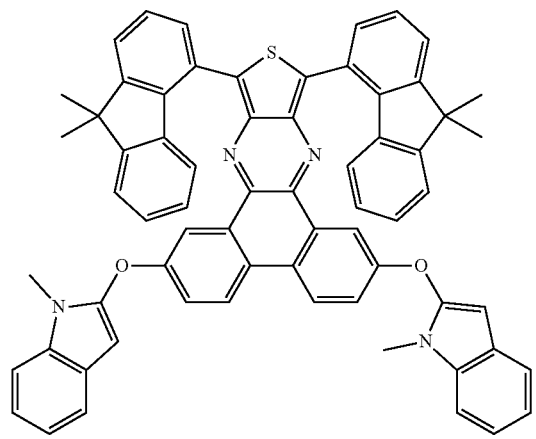
72
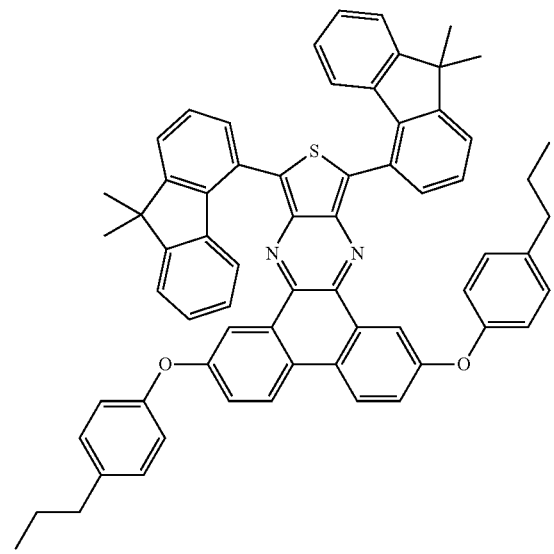
-continued
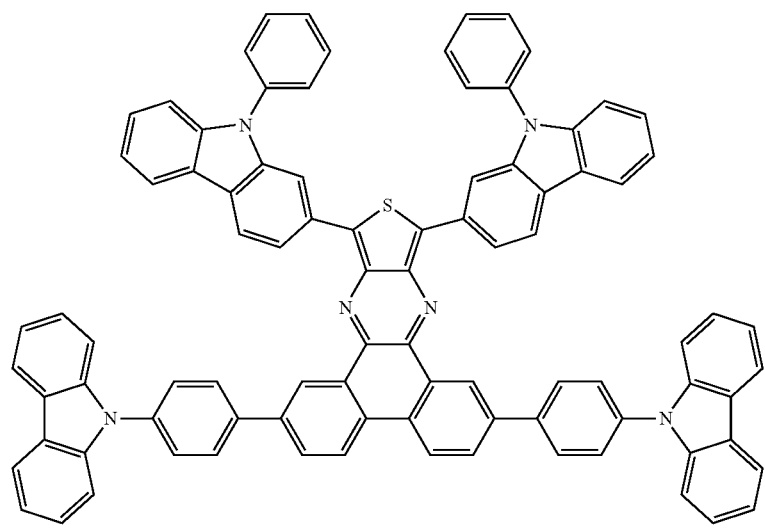
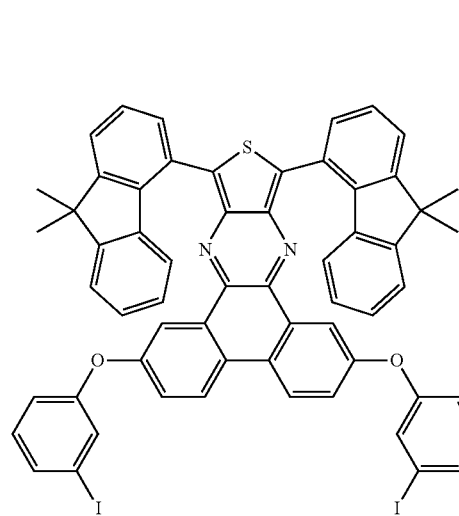
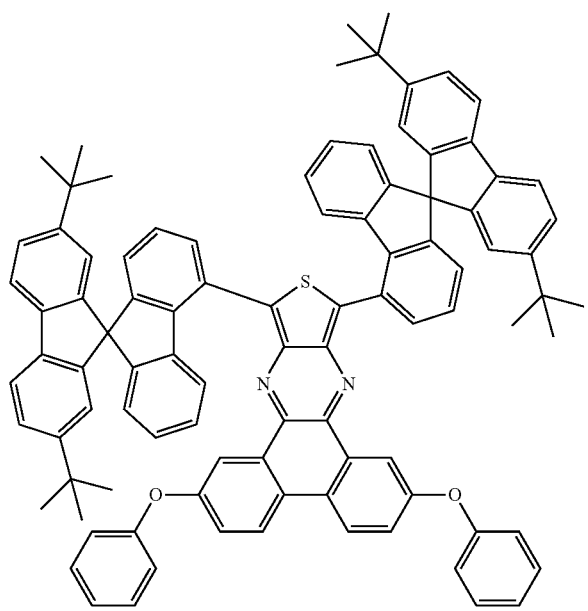

-continued
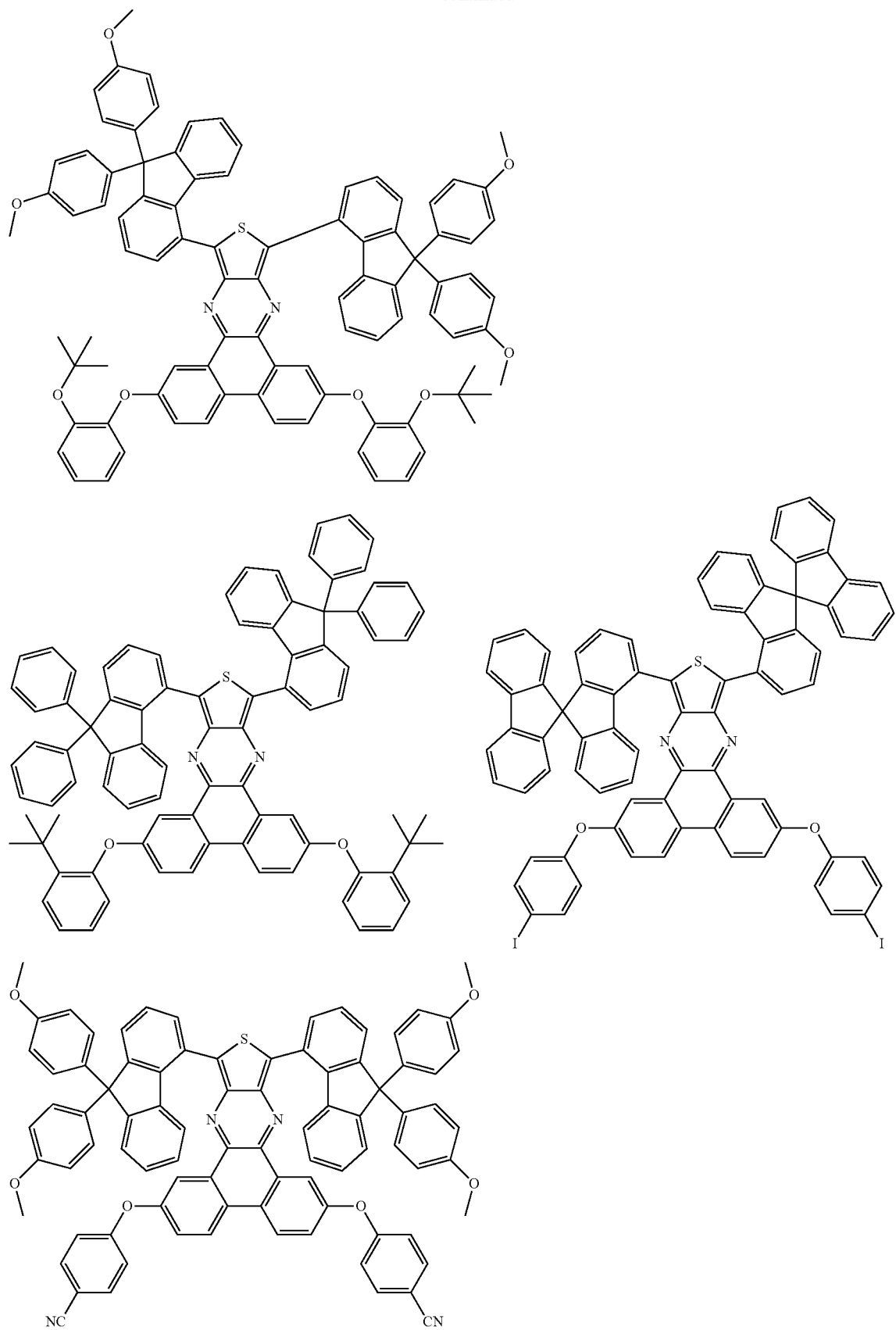

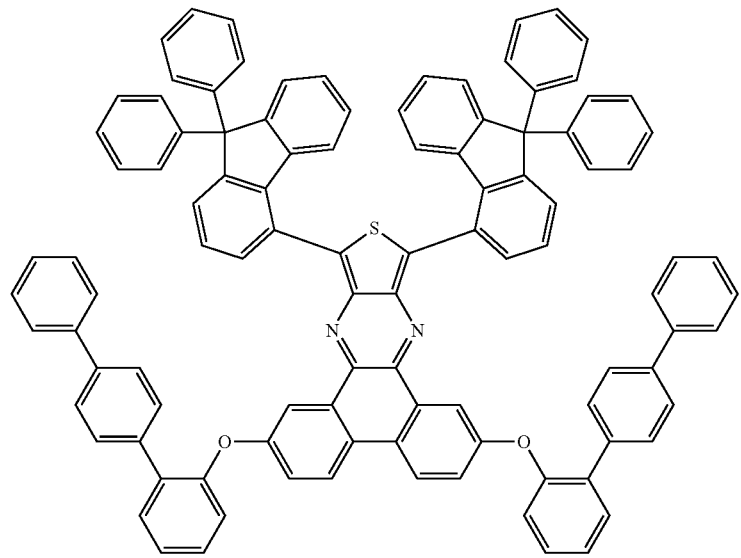
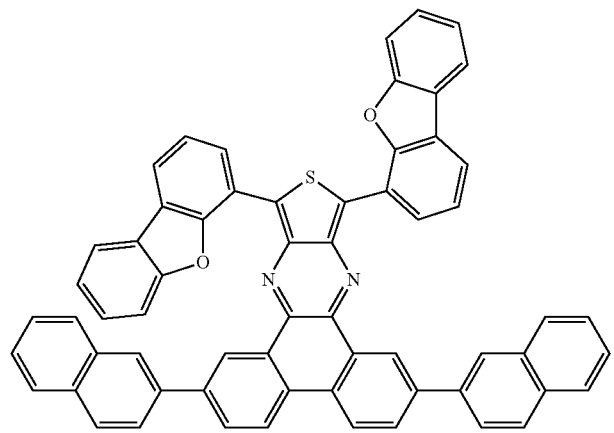
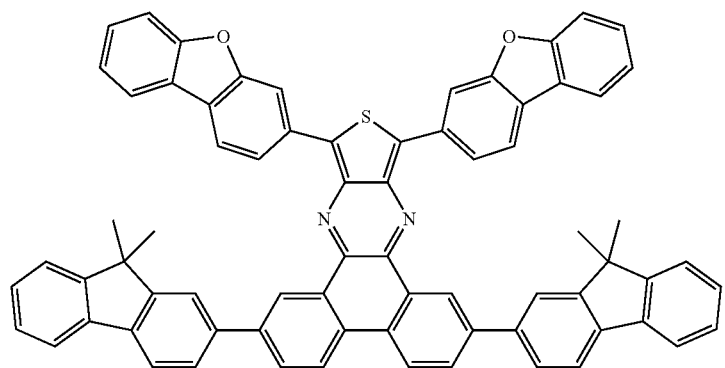

-continued
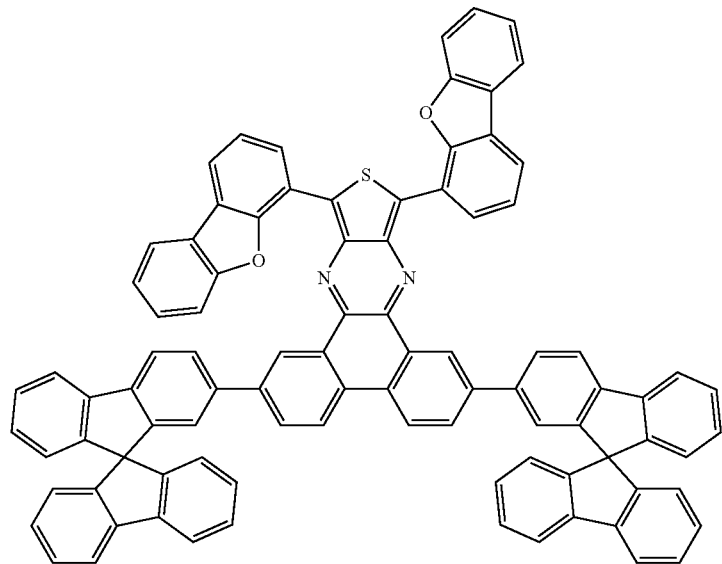
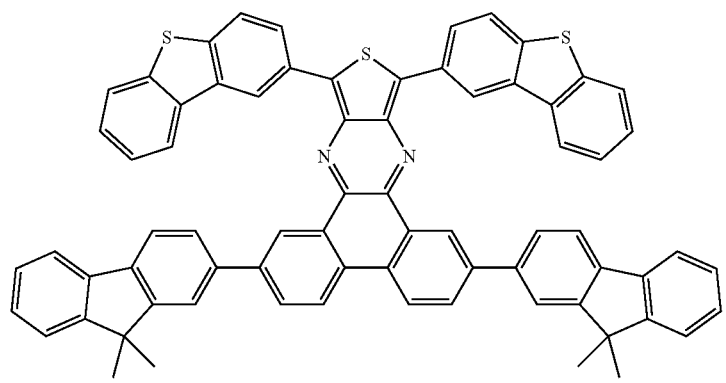
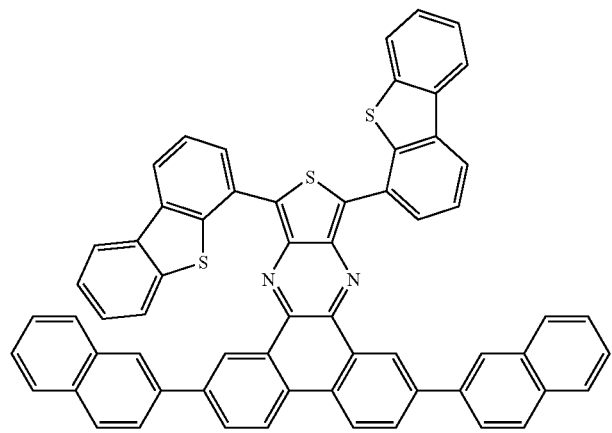

-continued
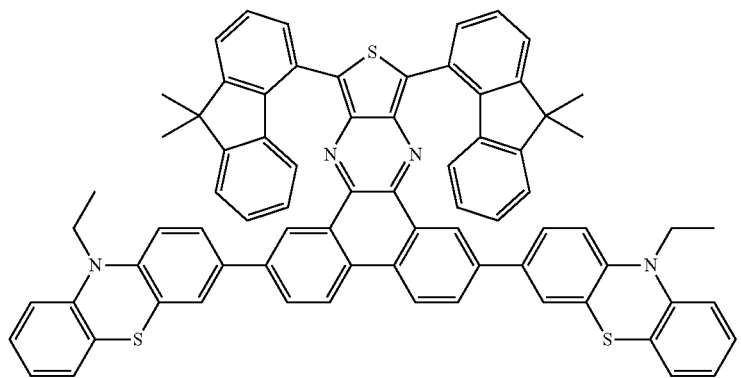
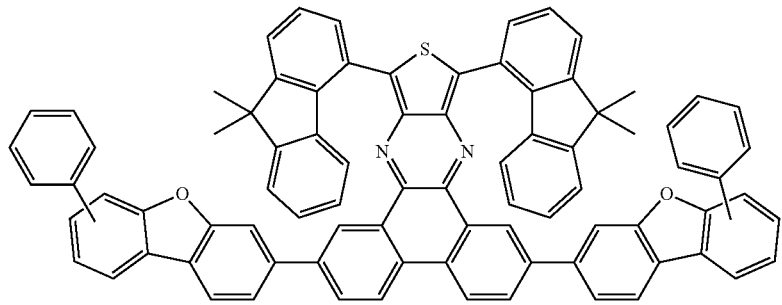
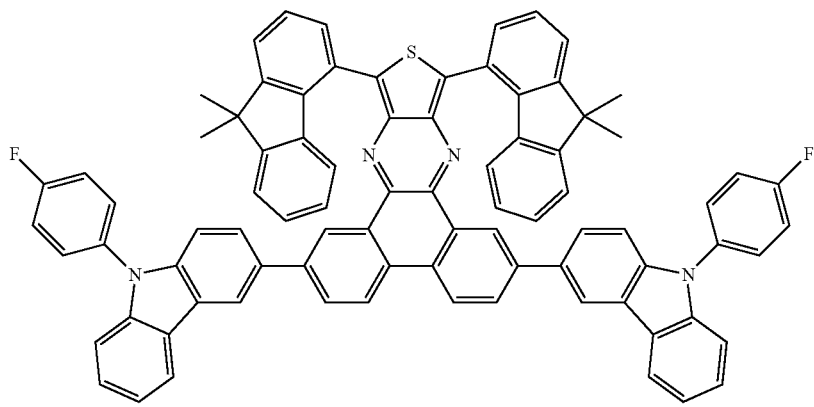
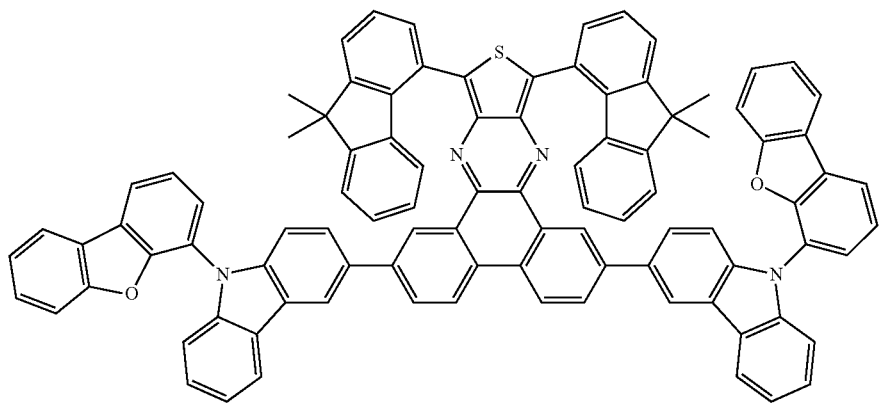

-continued
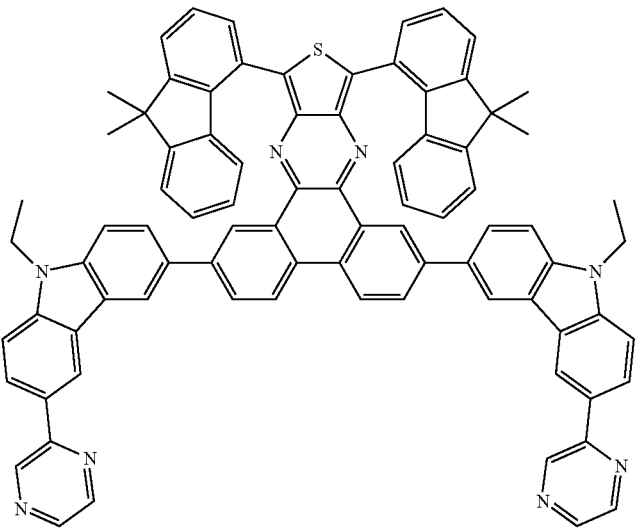
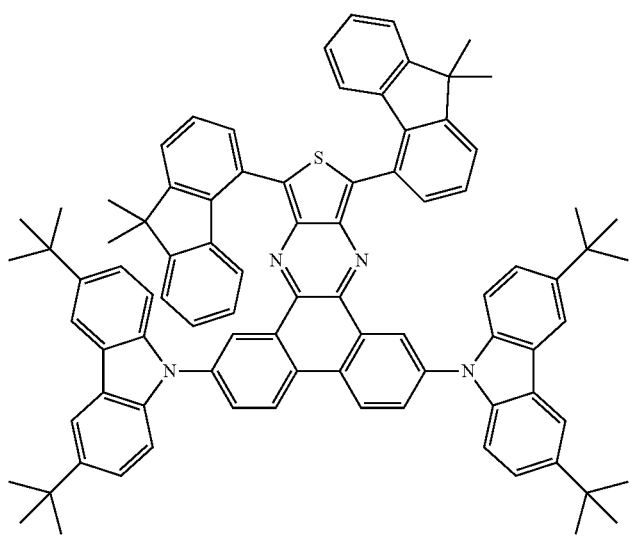
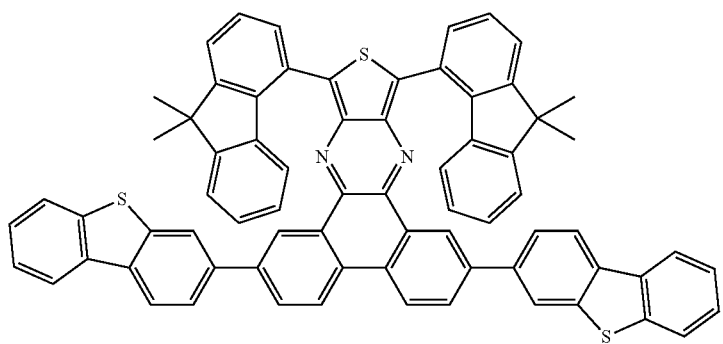

-continued
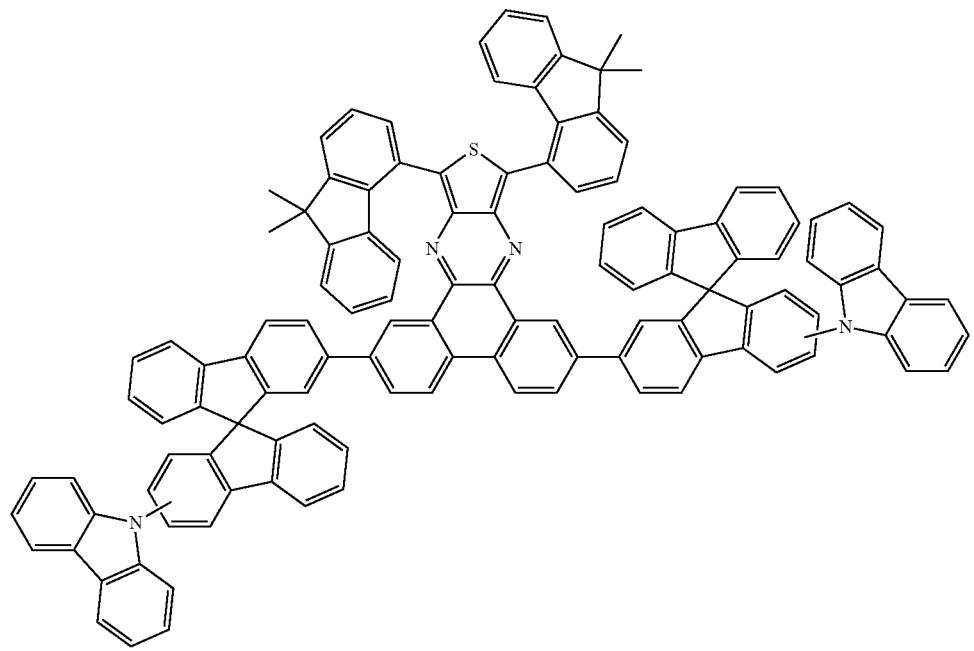
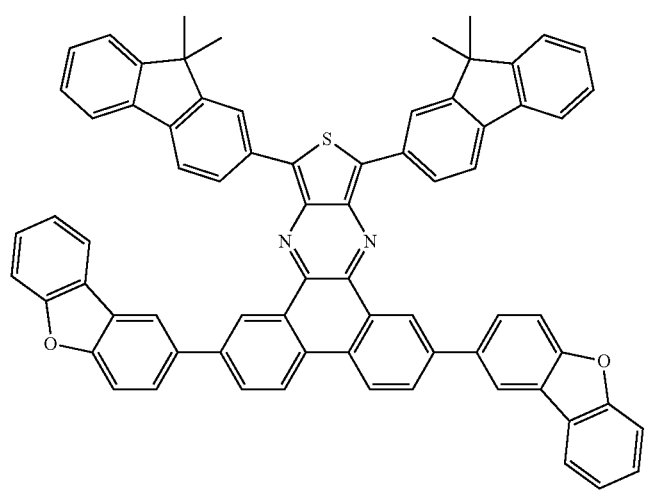

-continued
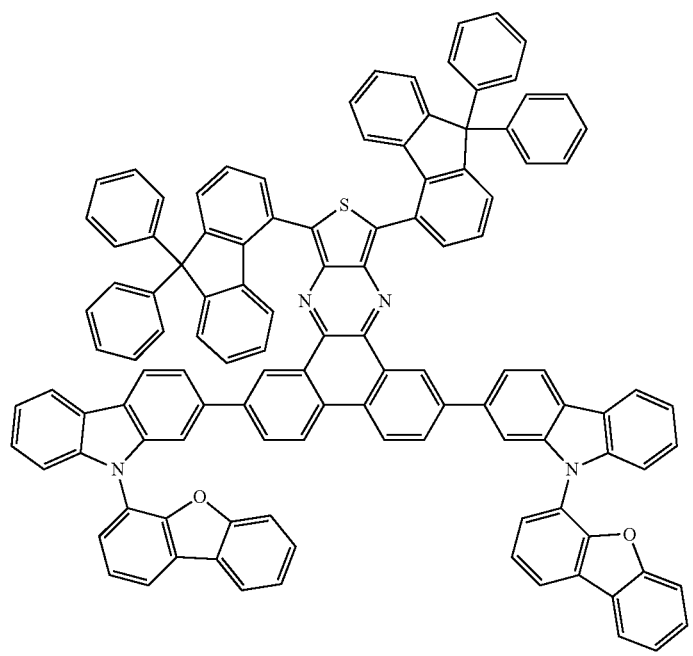
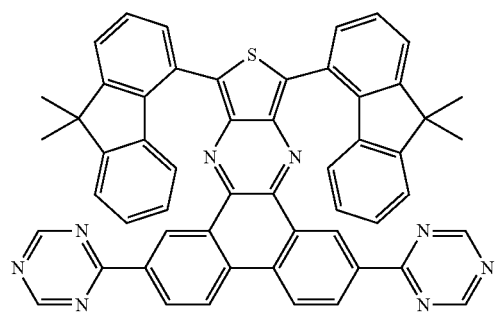
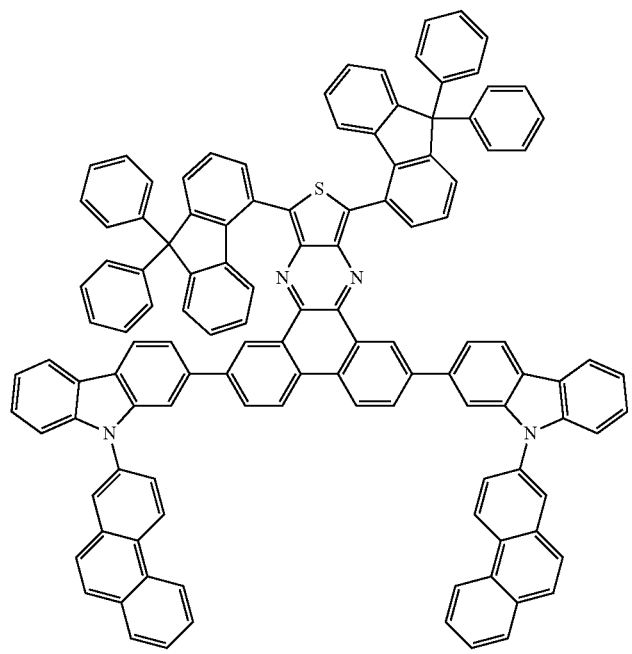

-continued
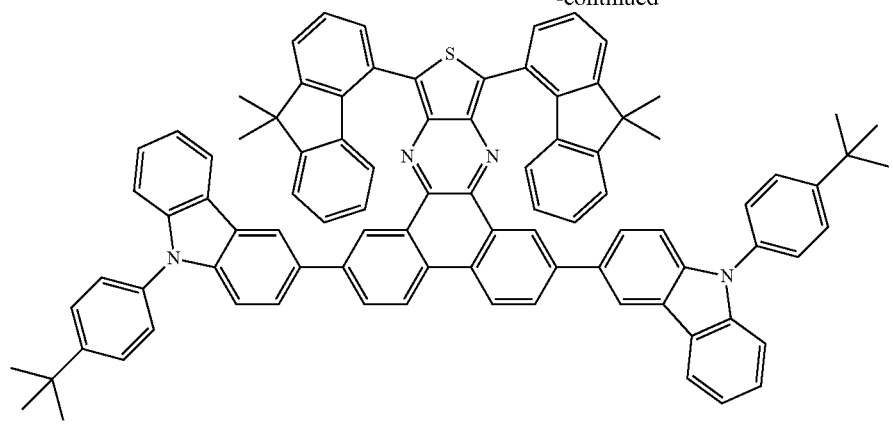
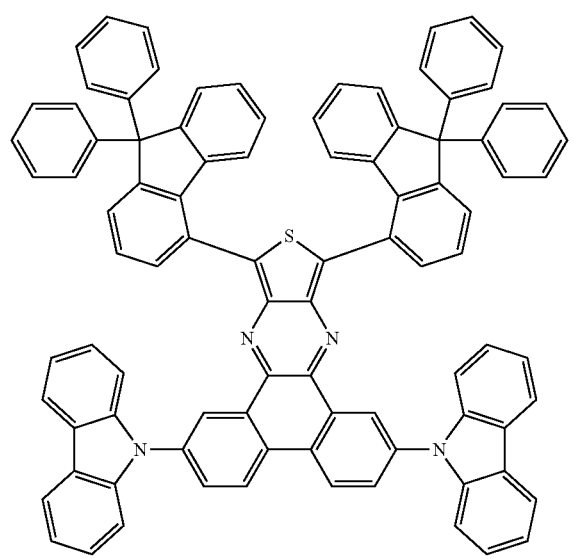
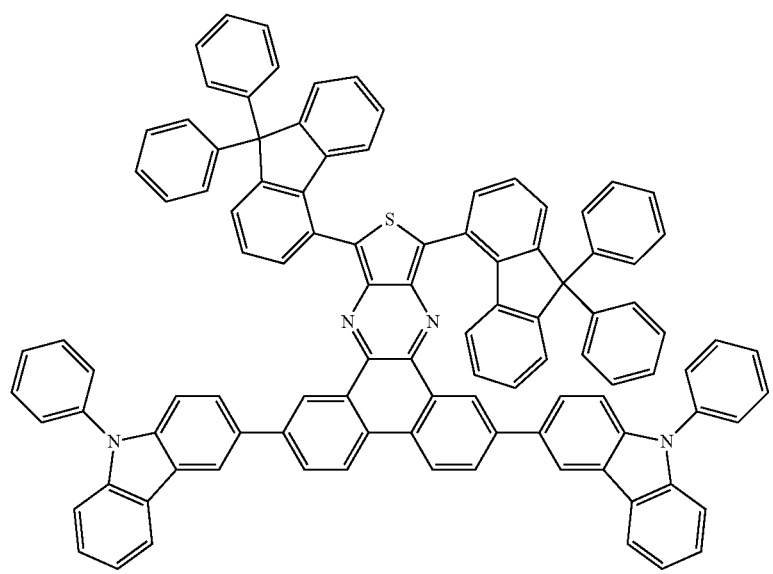

-continued
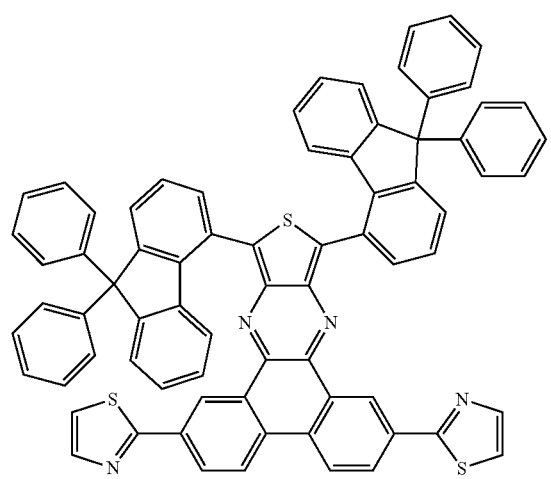
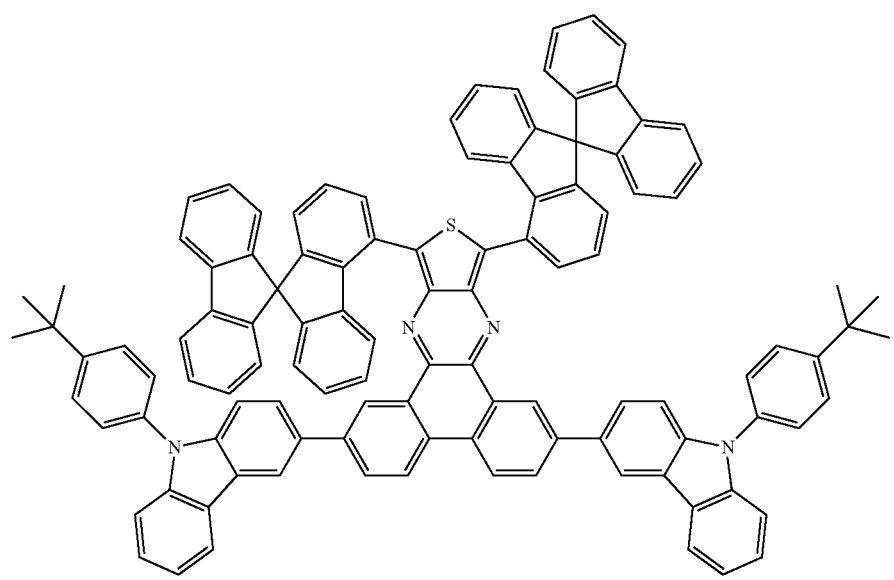
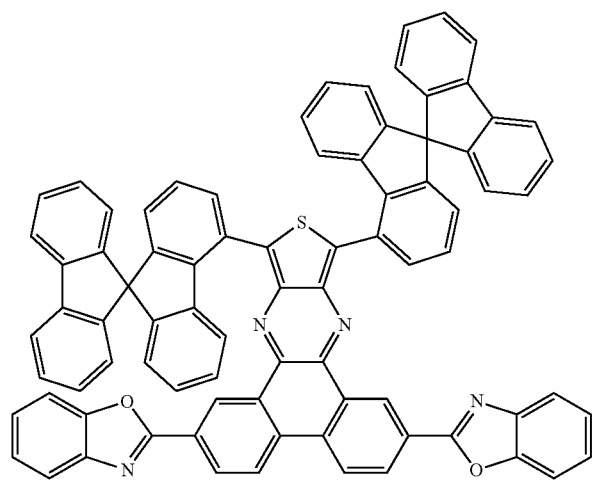

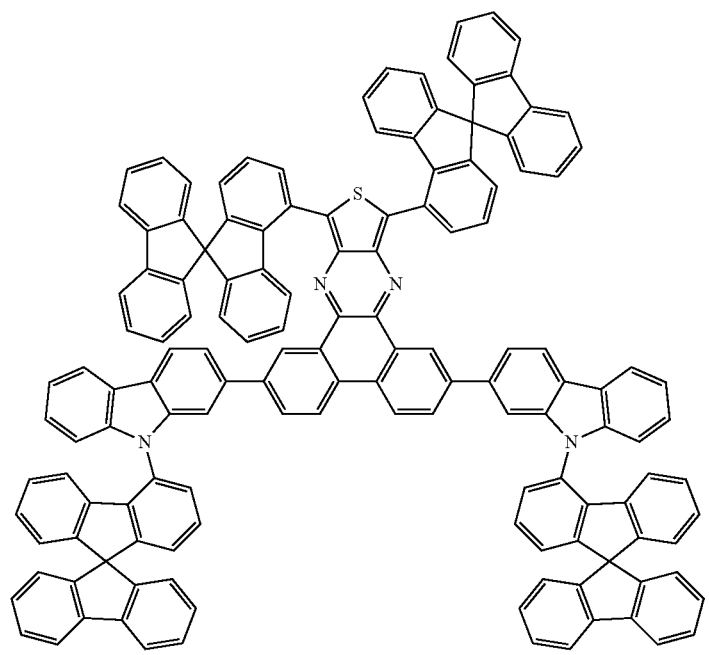
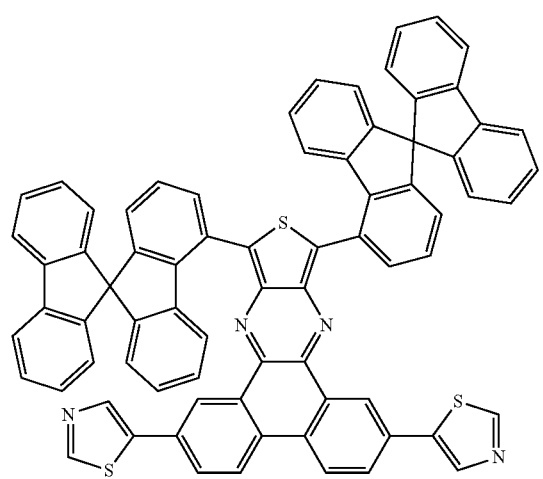

-continued
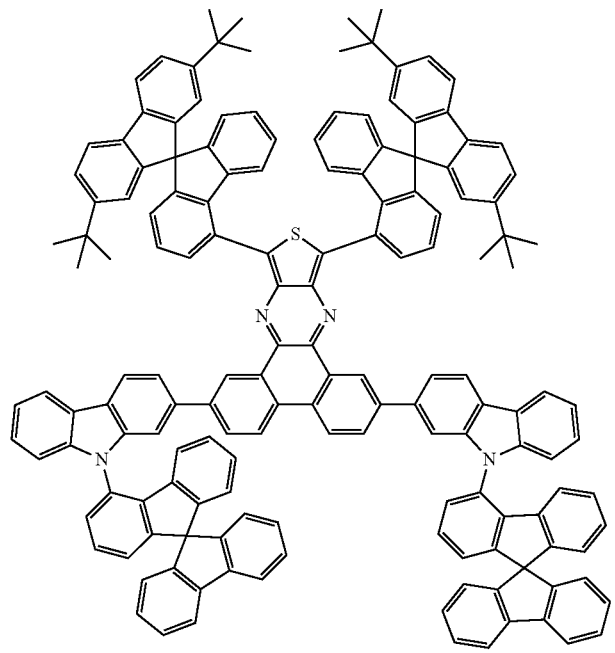
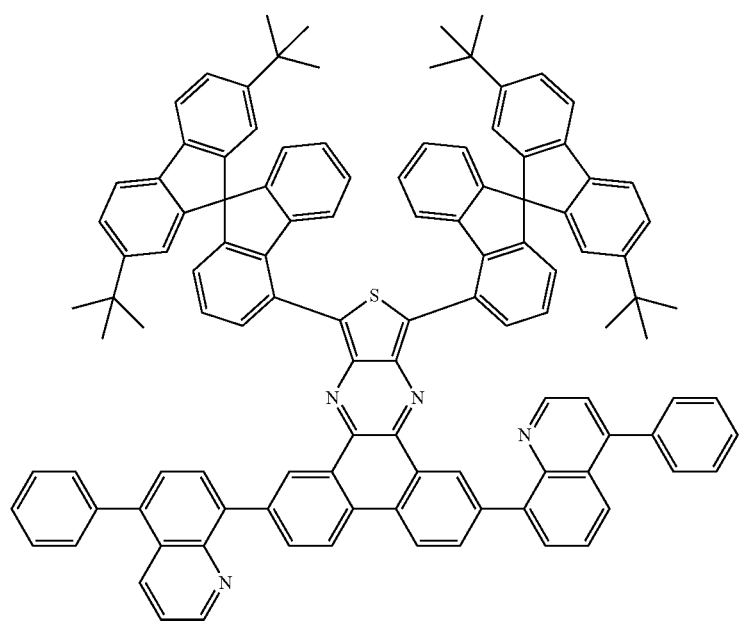

-continued
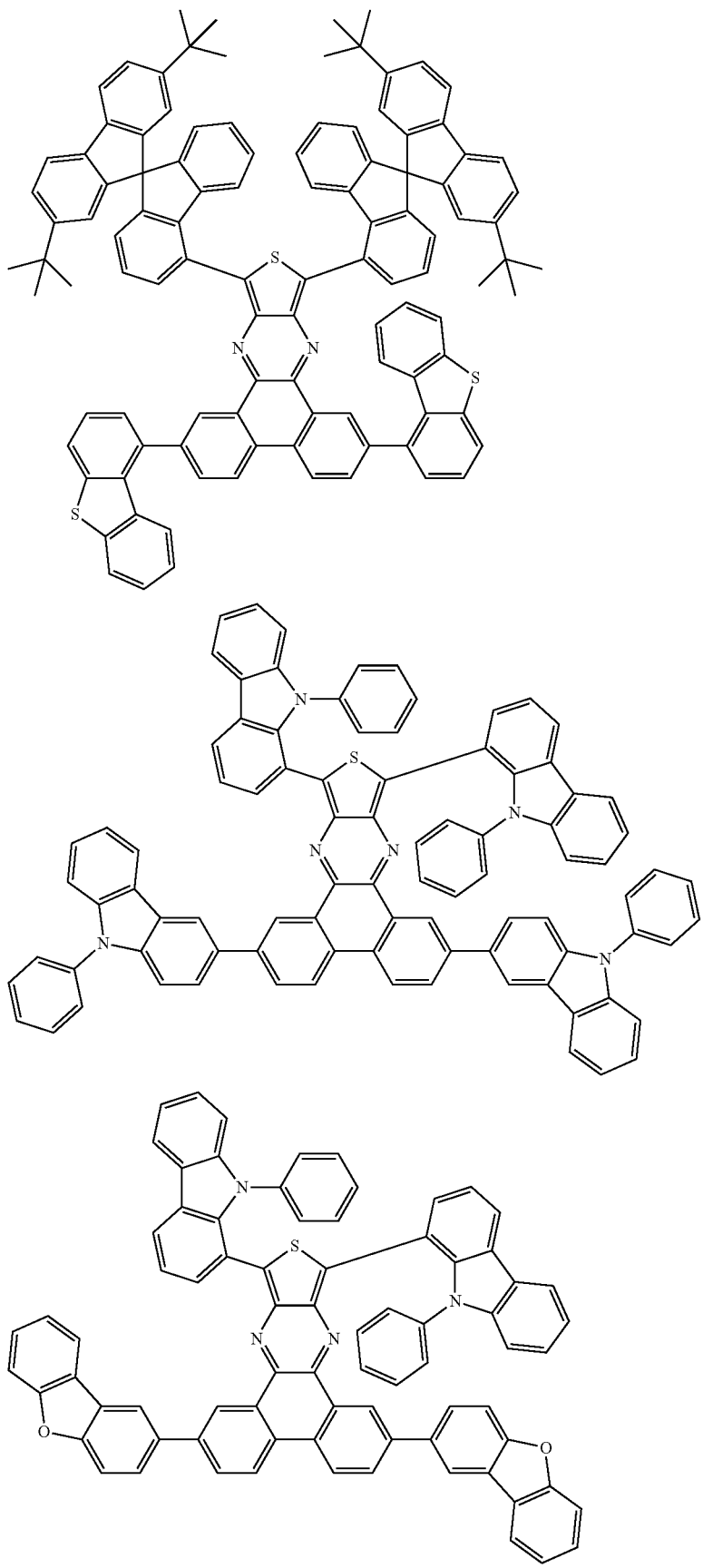

-continued
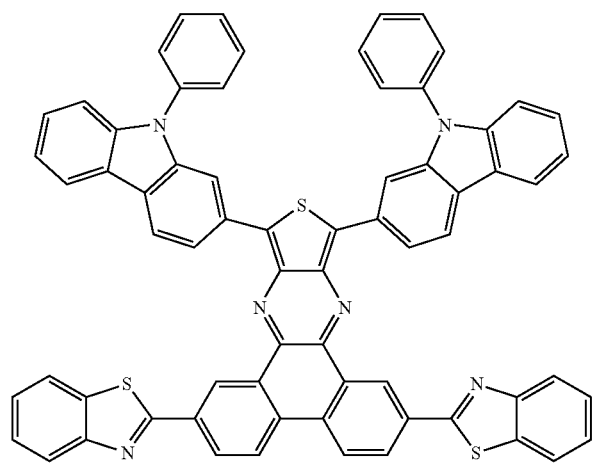
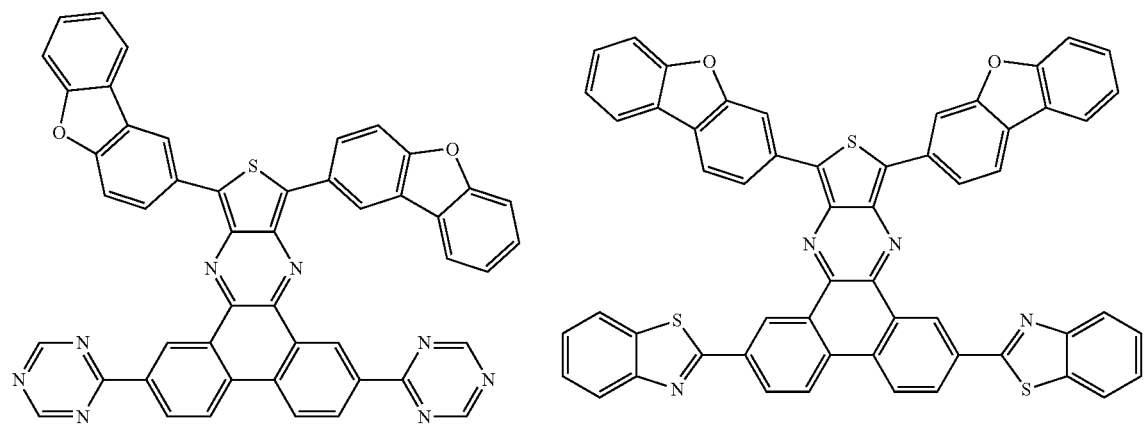
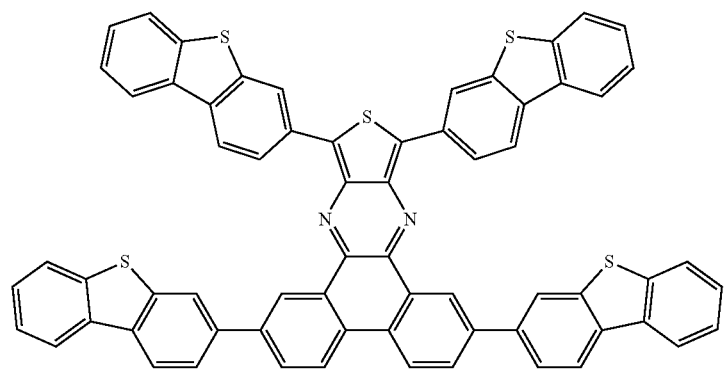

-continued
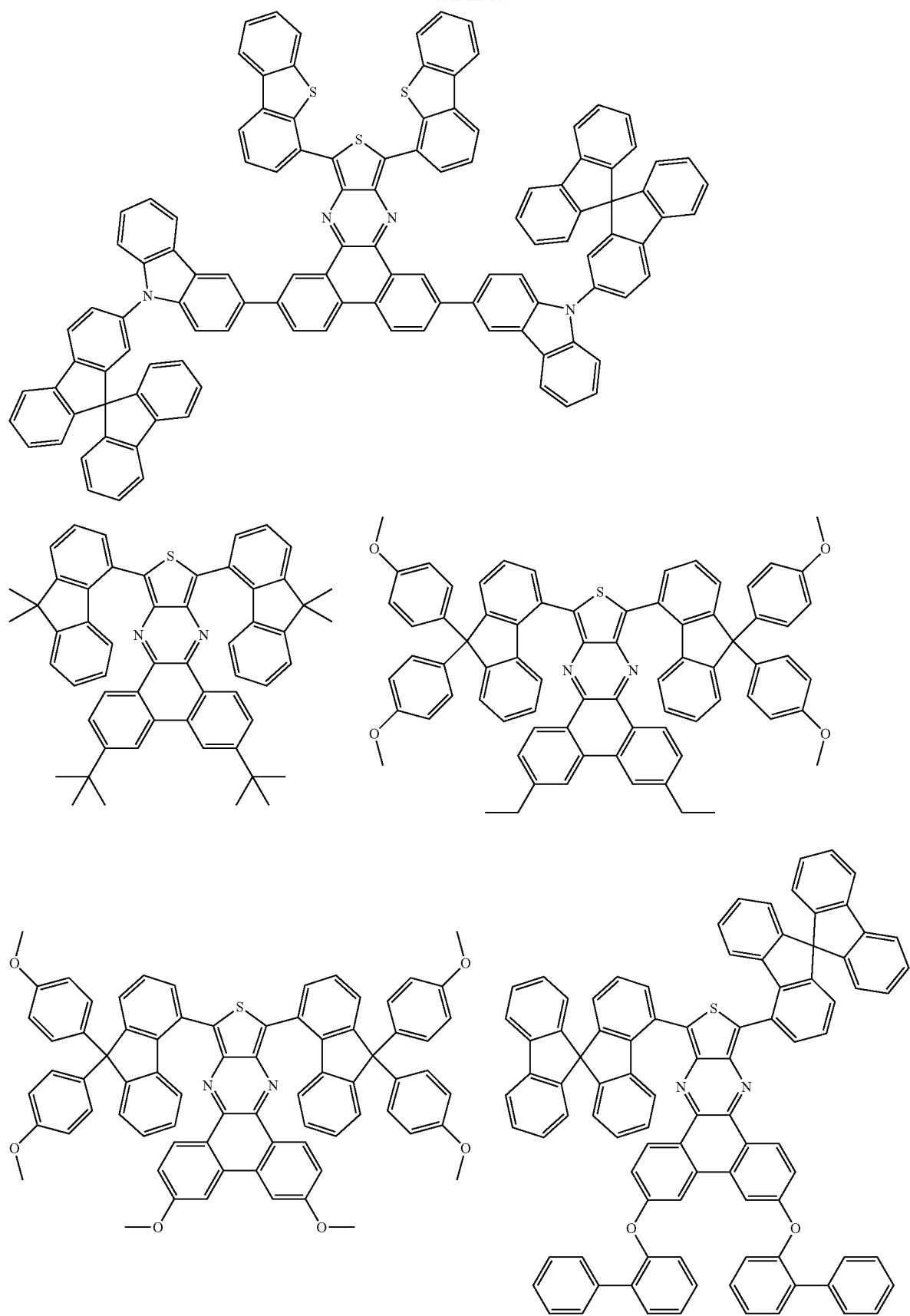

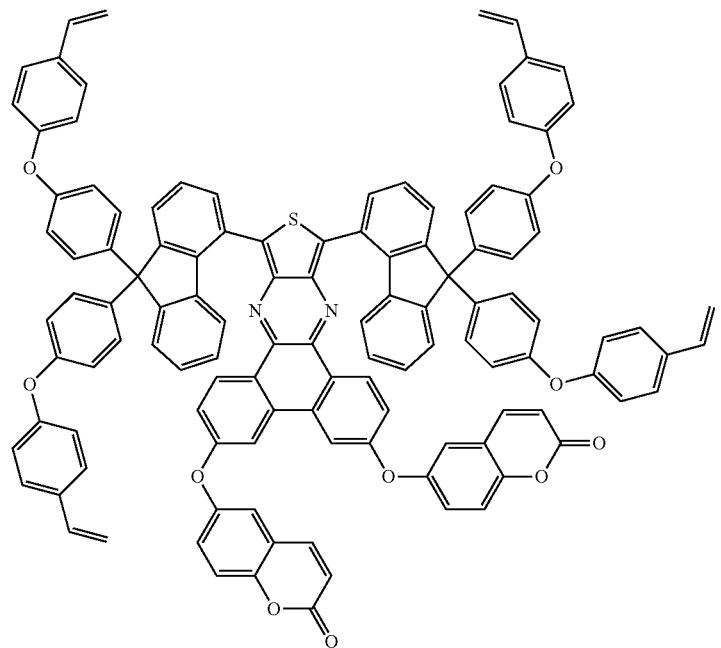
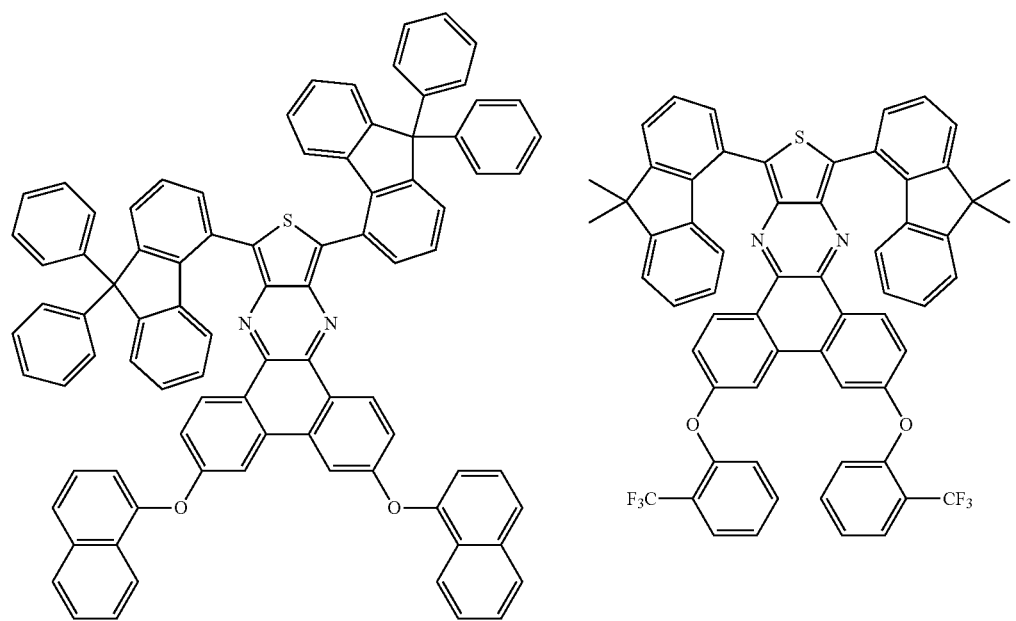

-continued
| 103 | 104 |
|---|---|
| 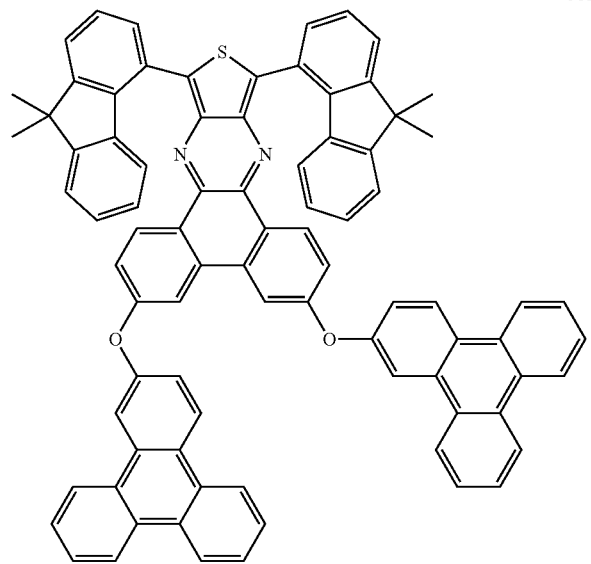 | 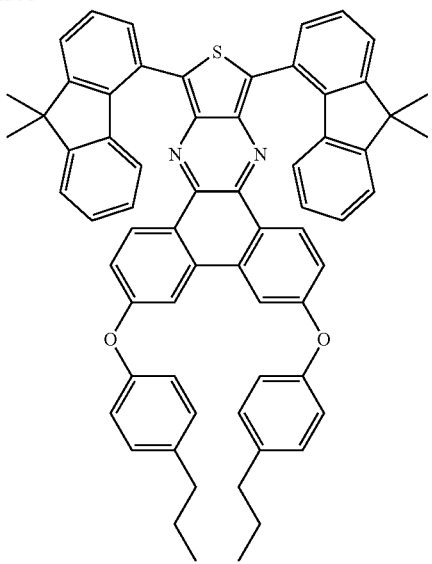 |
| 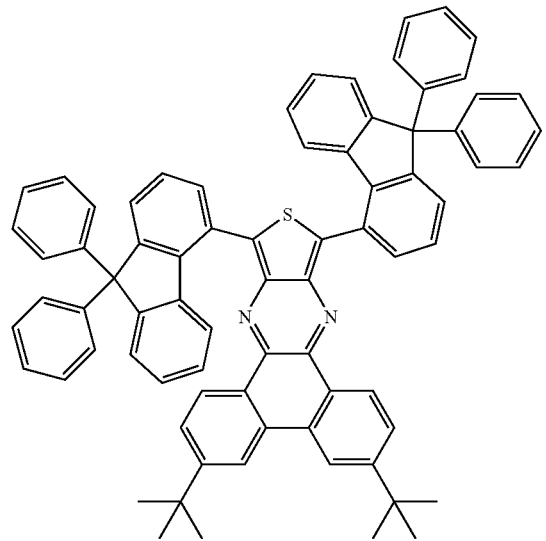 | 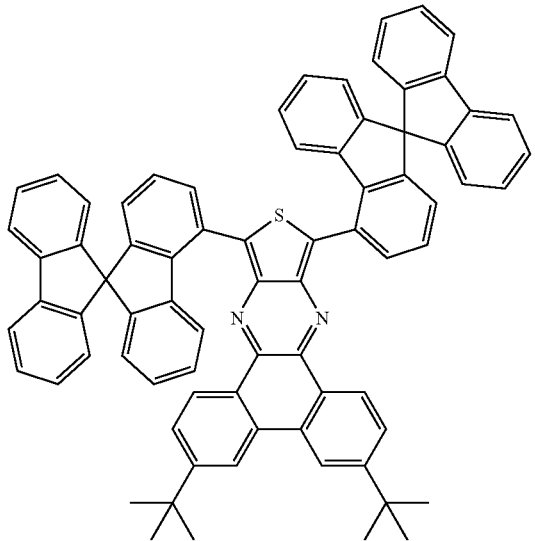 |
| 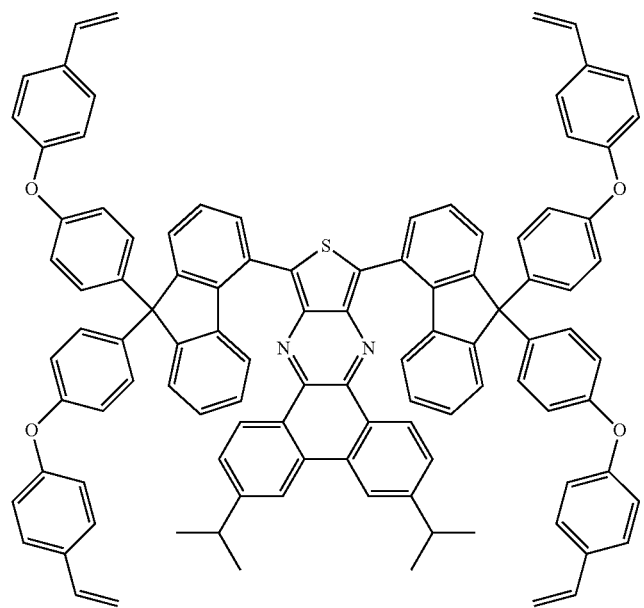 | 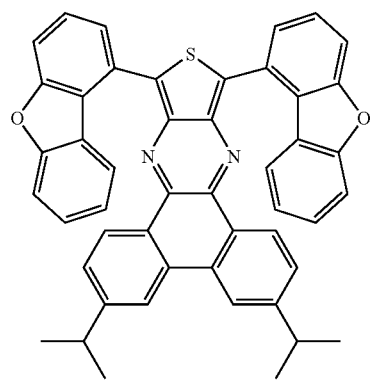 |

-continued
105
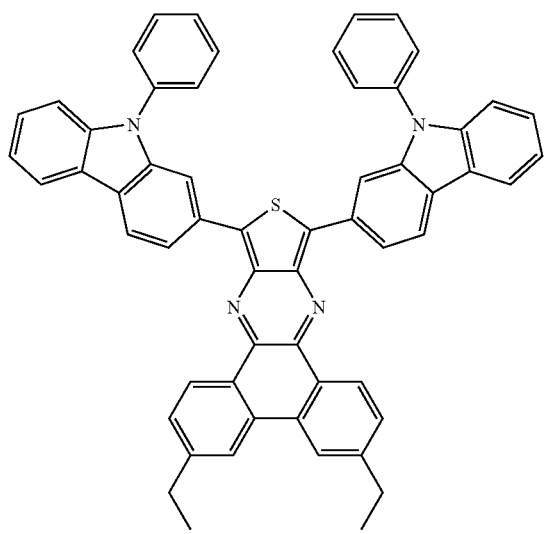
106
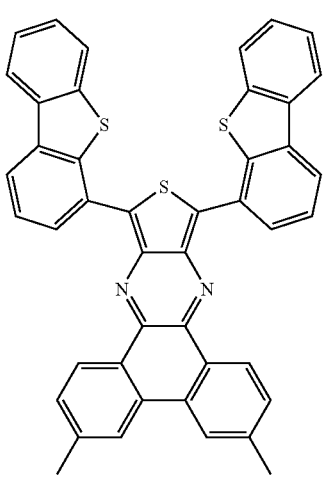
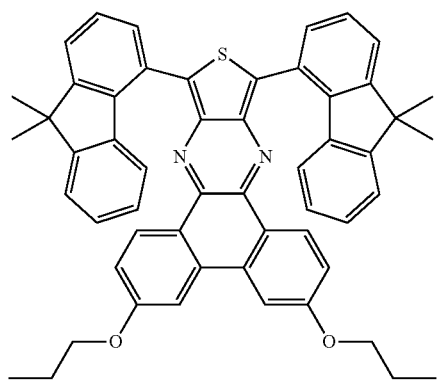
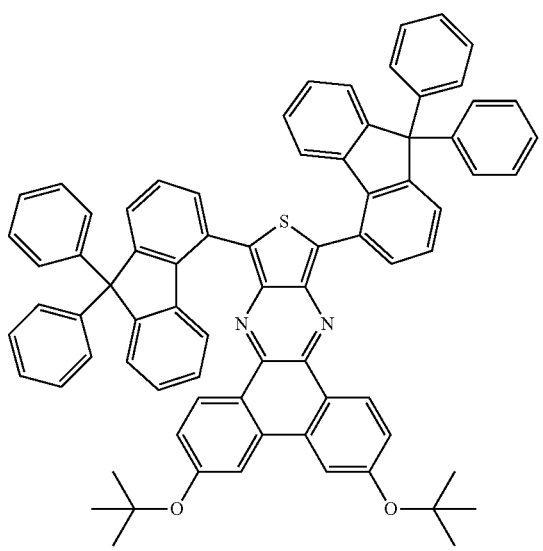
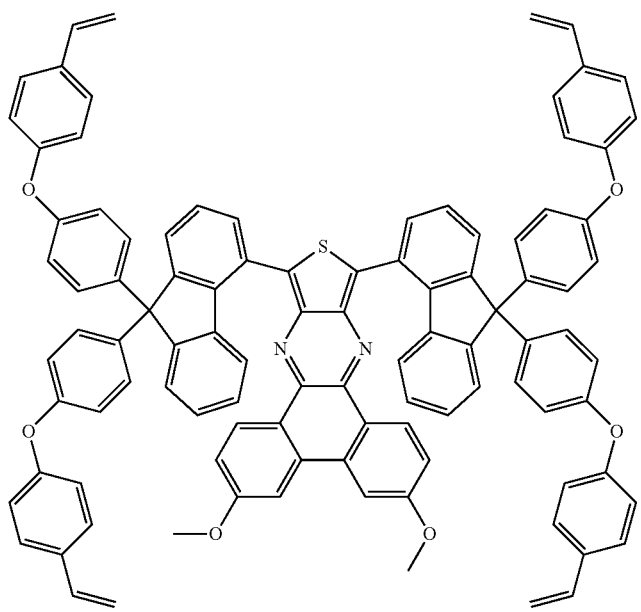
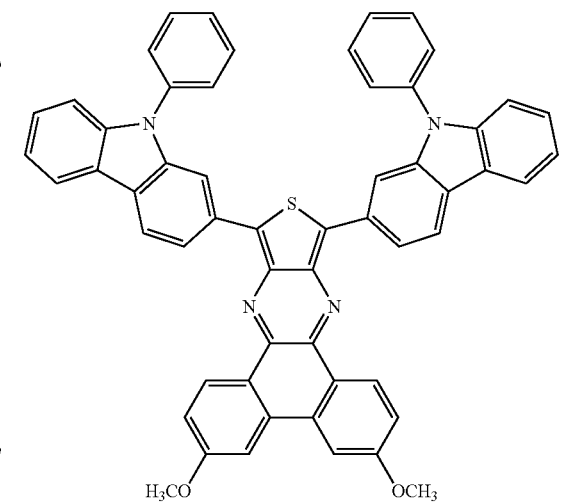

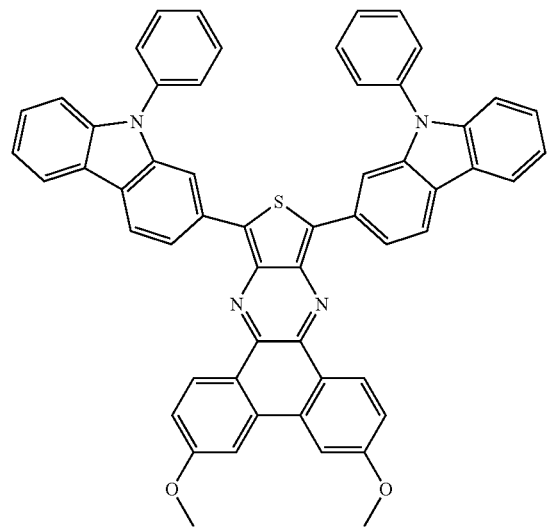
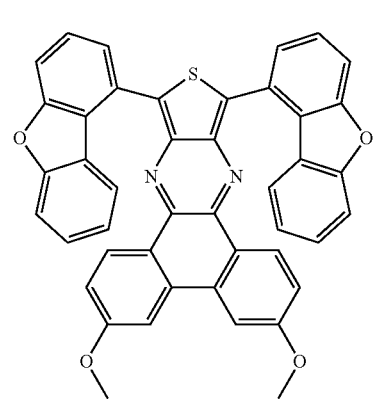
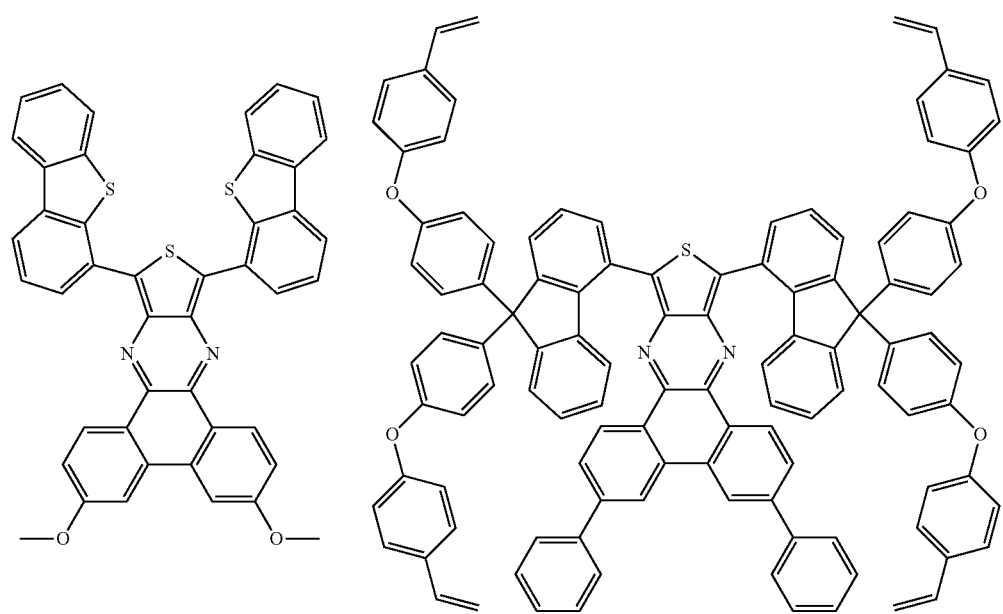

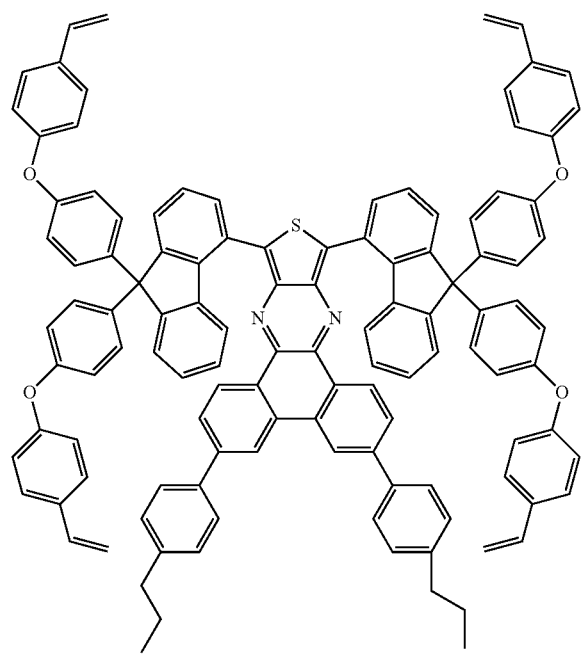
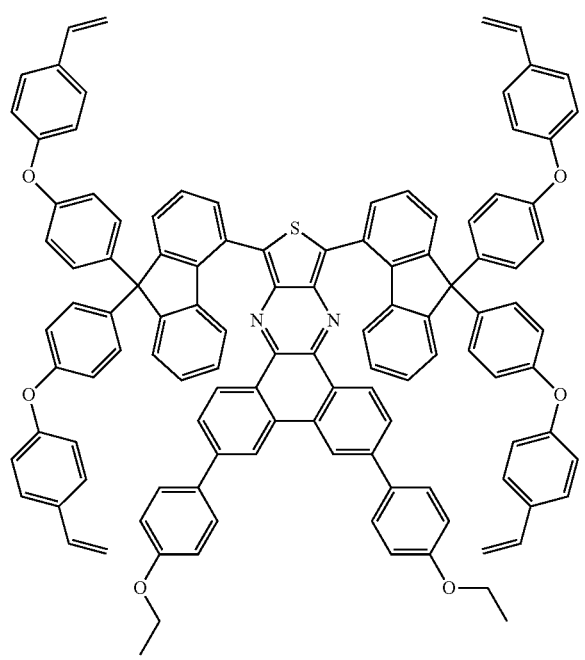

111
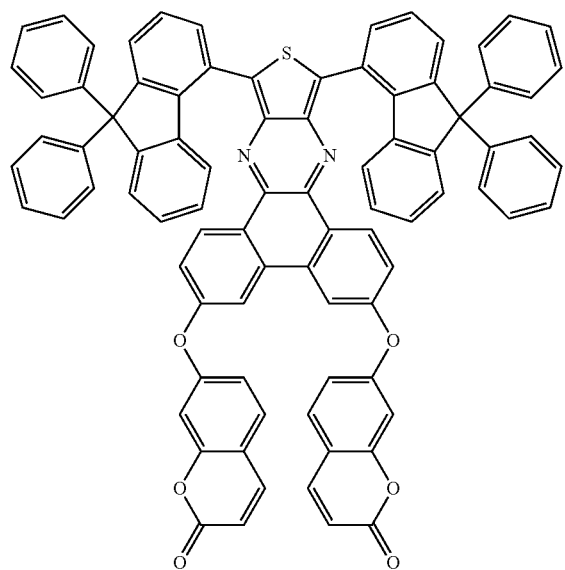
112
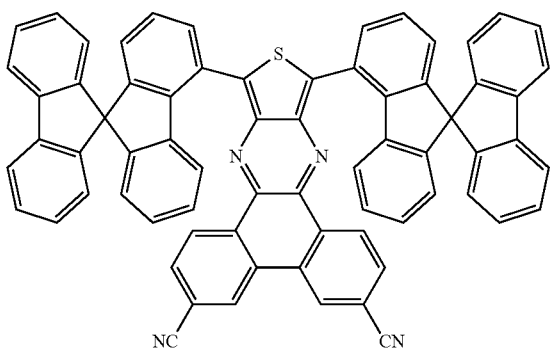
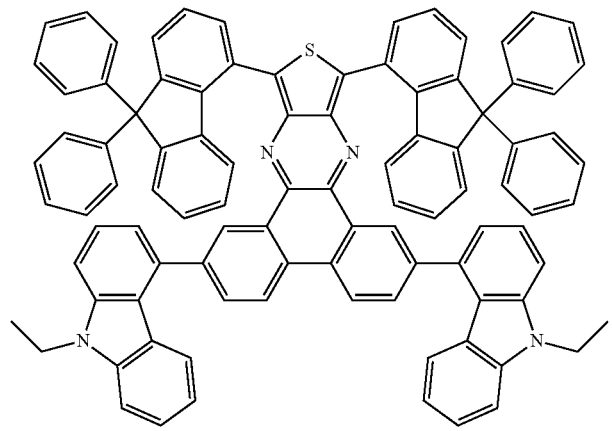
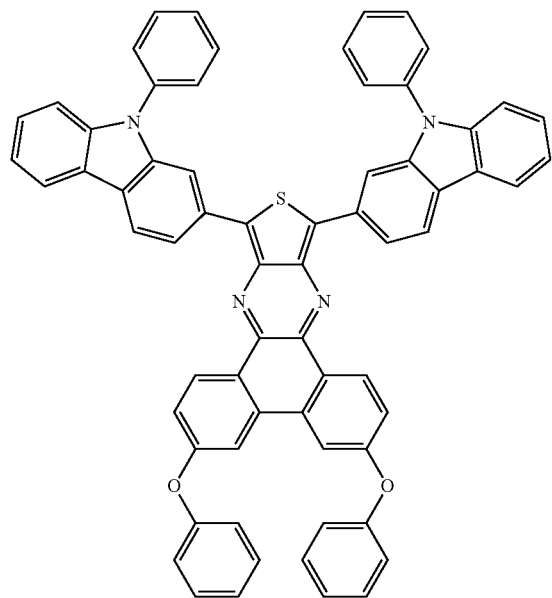
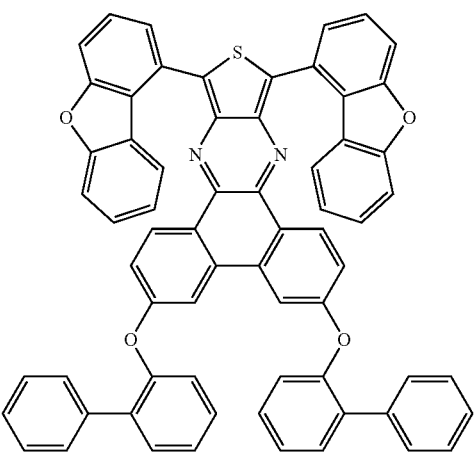

113
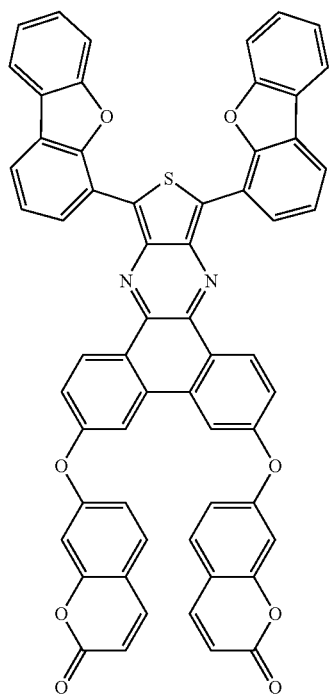
114
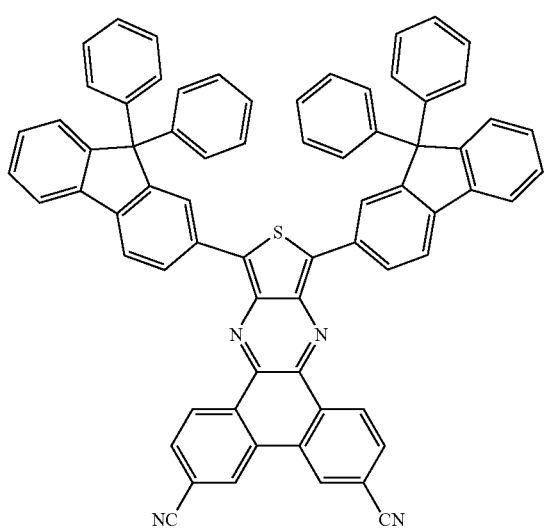
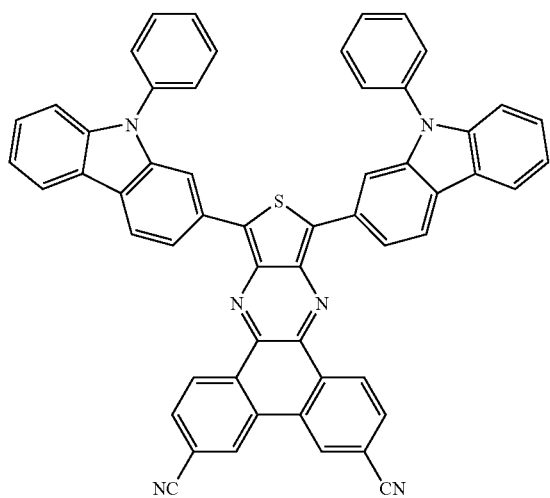
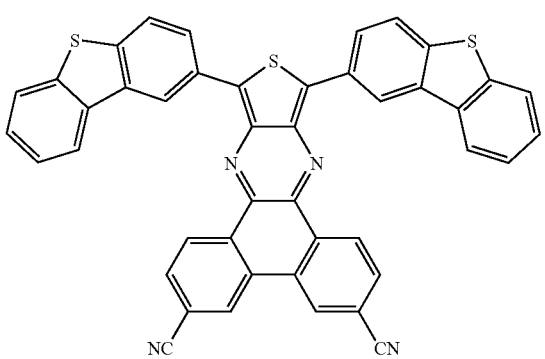
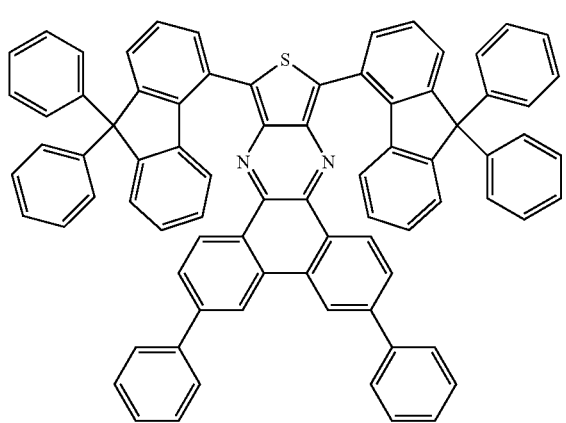
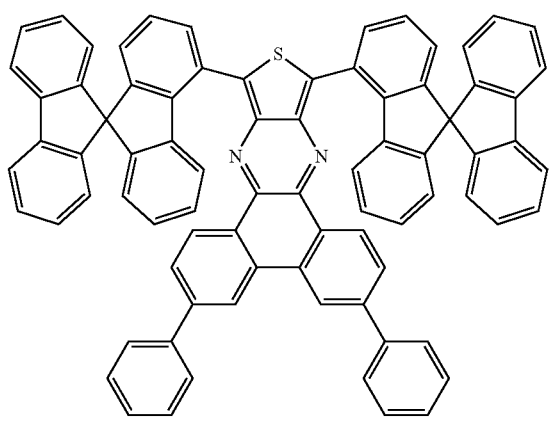

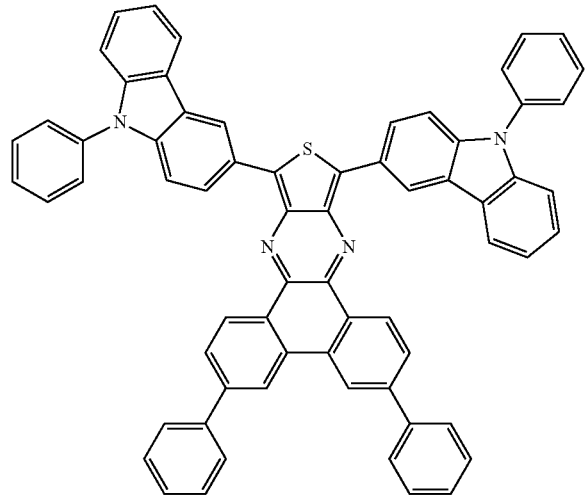
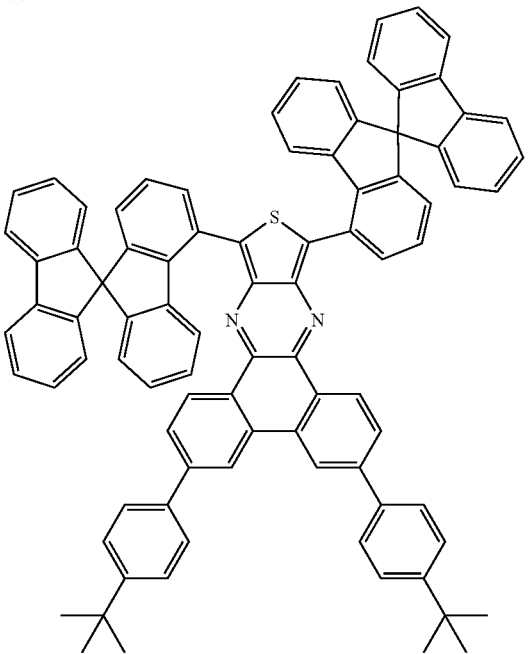
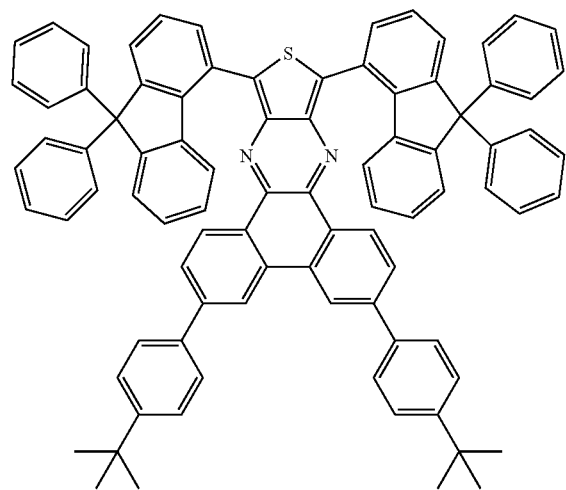
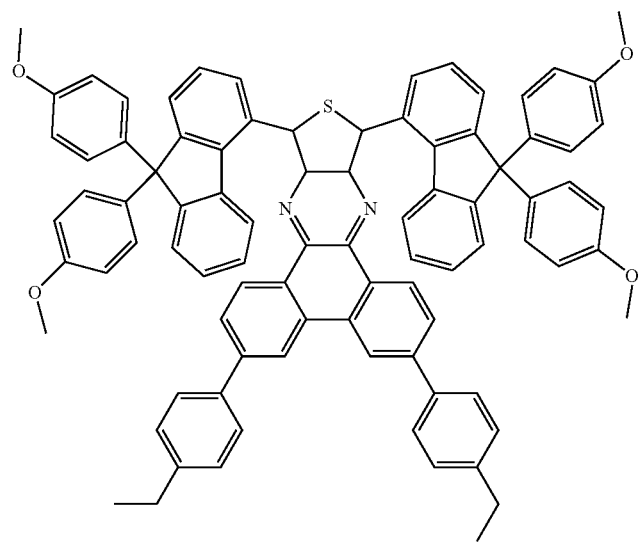
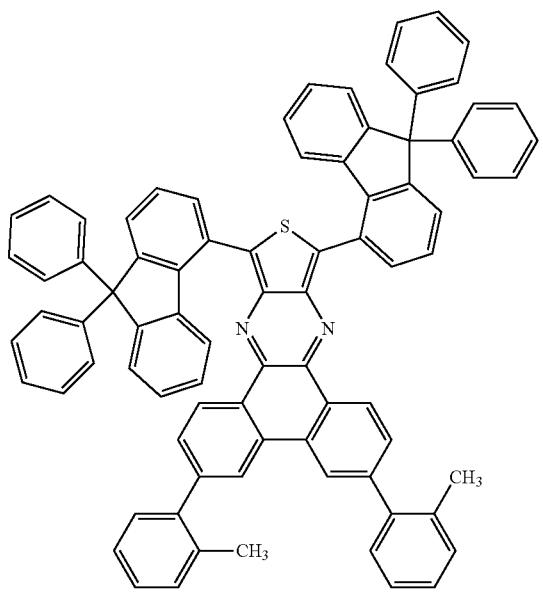

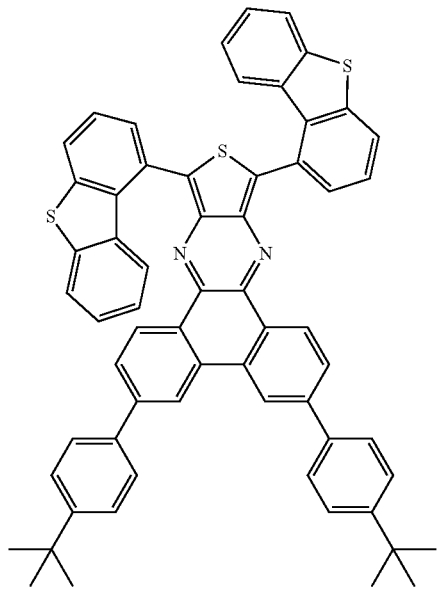
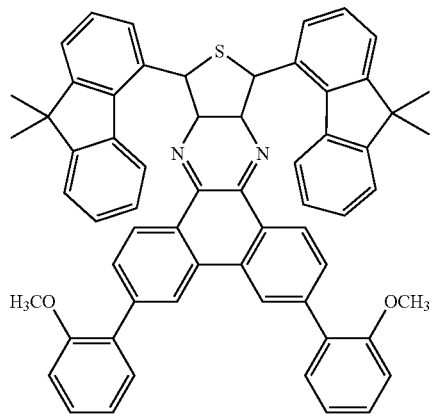
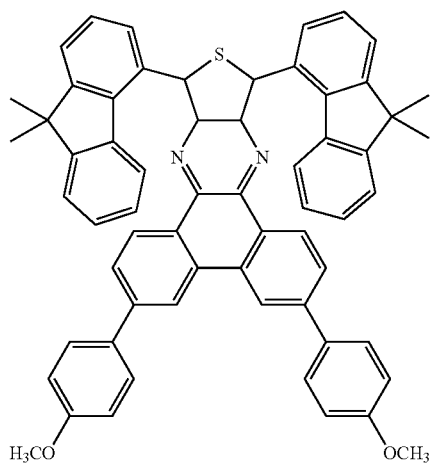
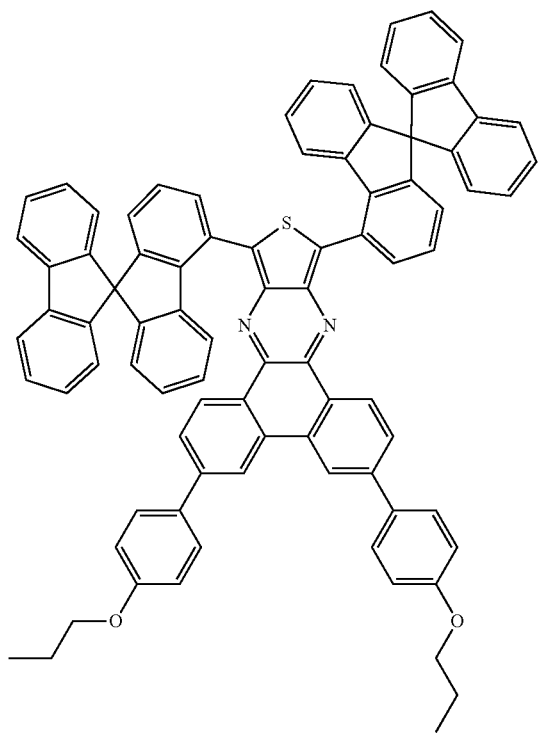

-continued
119
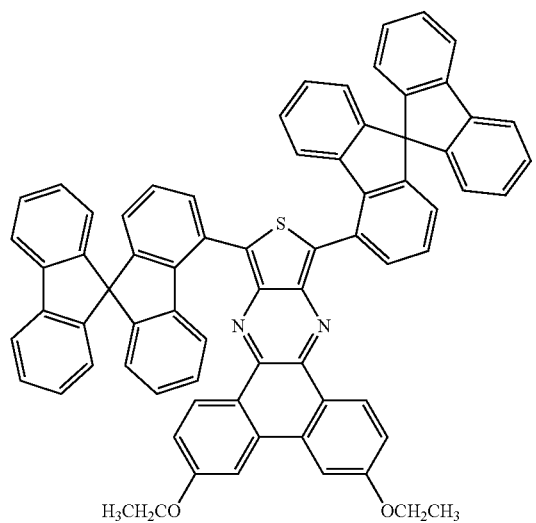
120
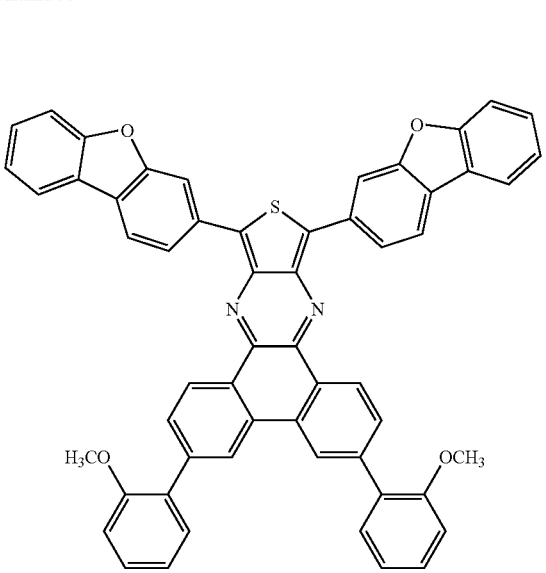
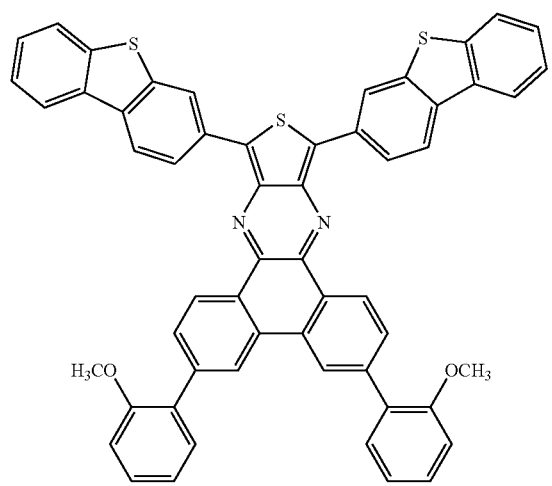
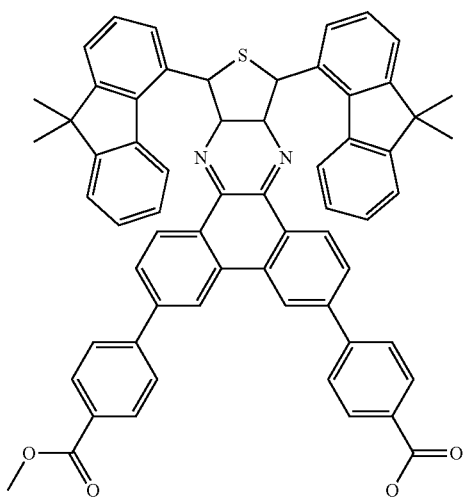
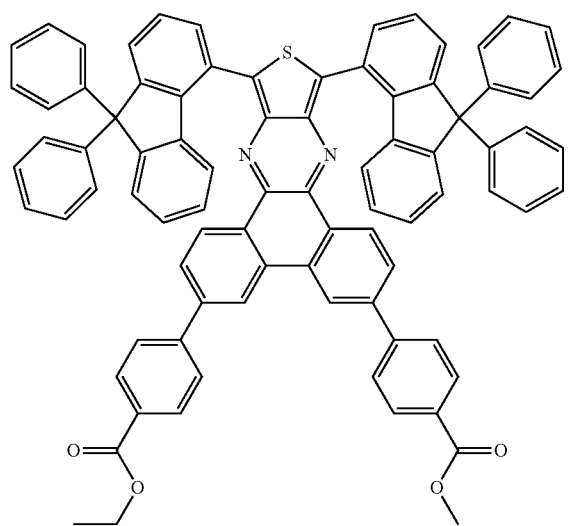
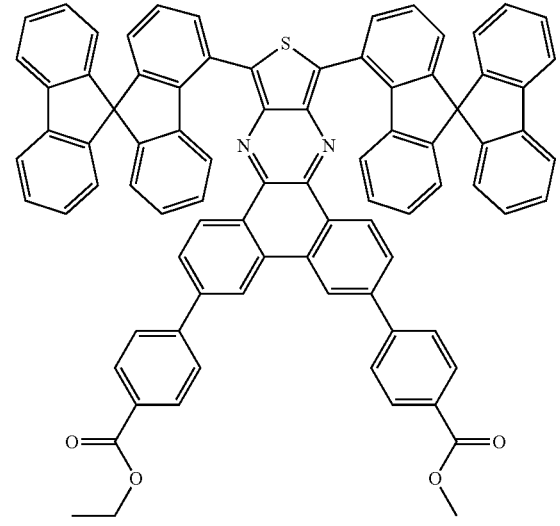

-continued
121
122
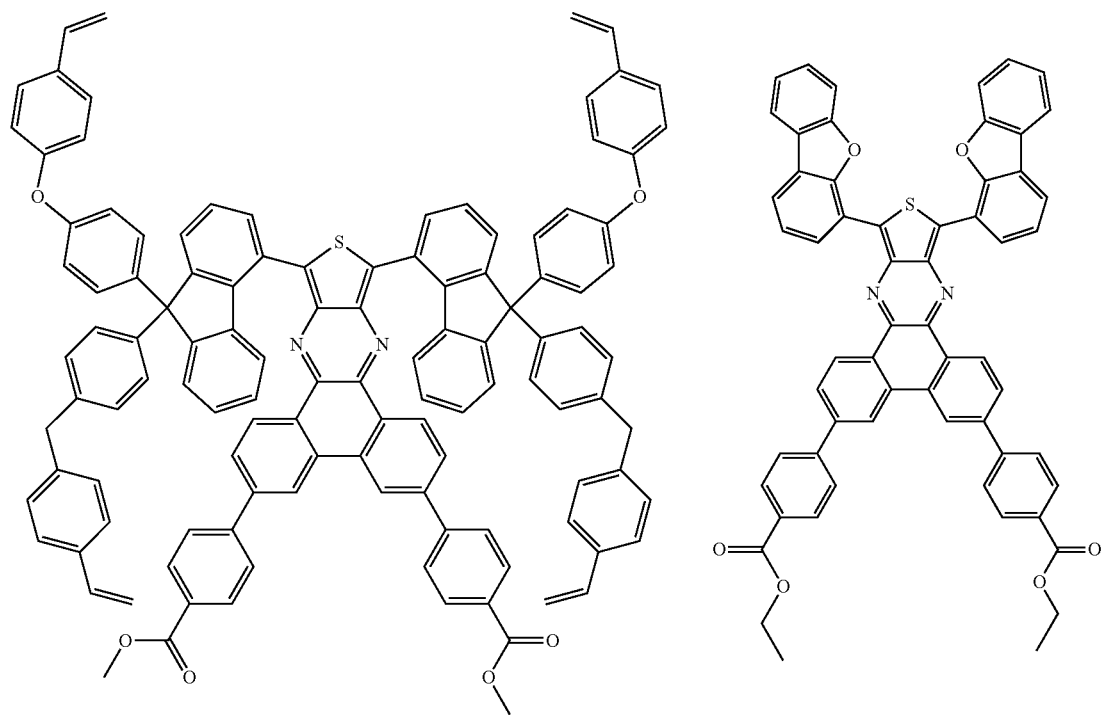
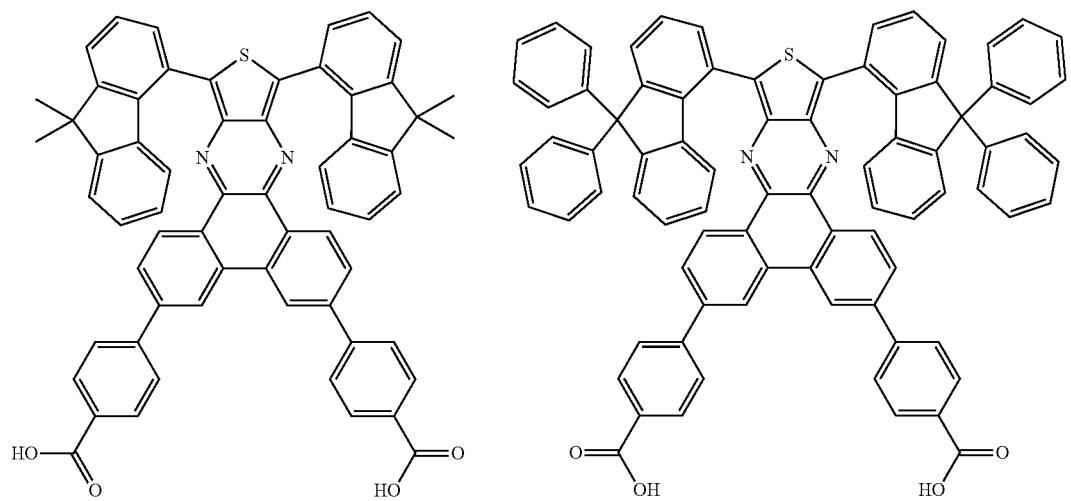
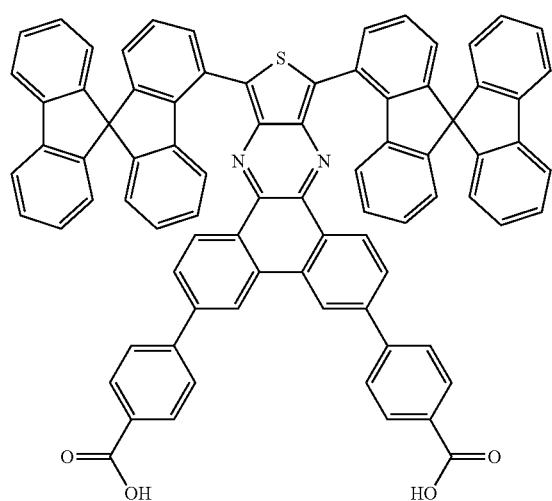

123 124
-continued
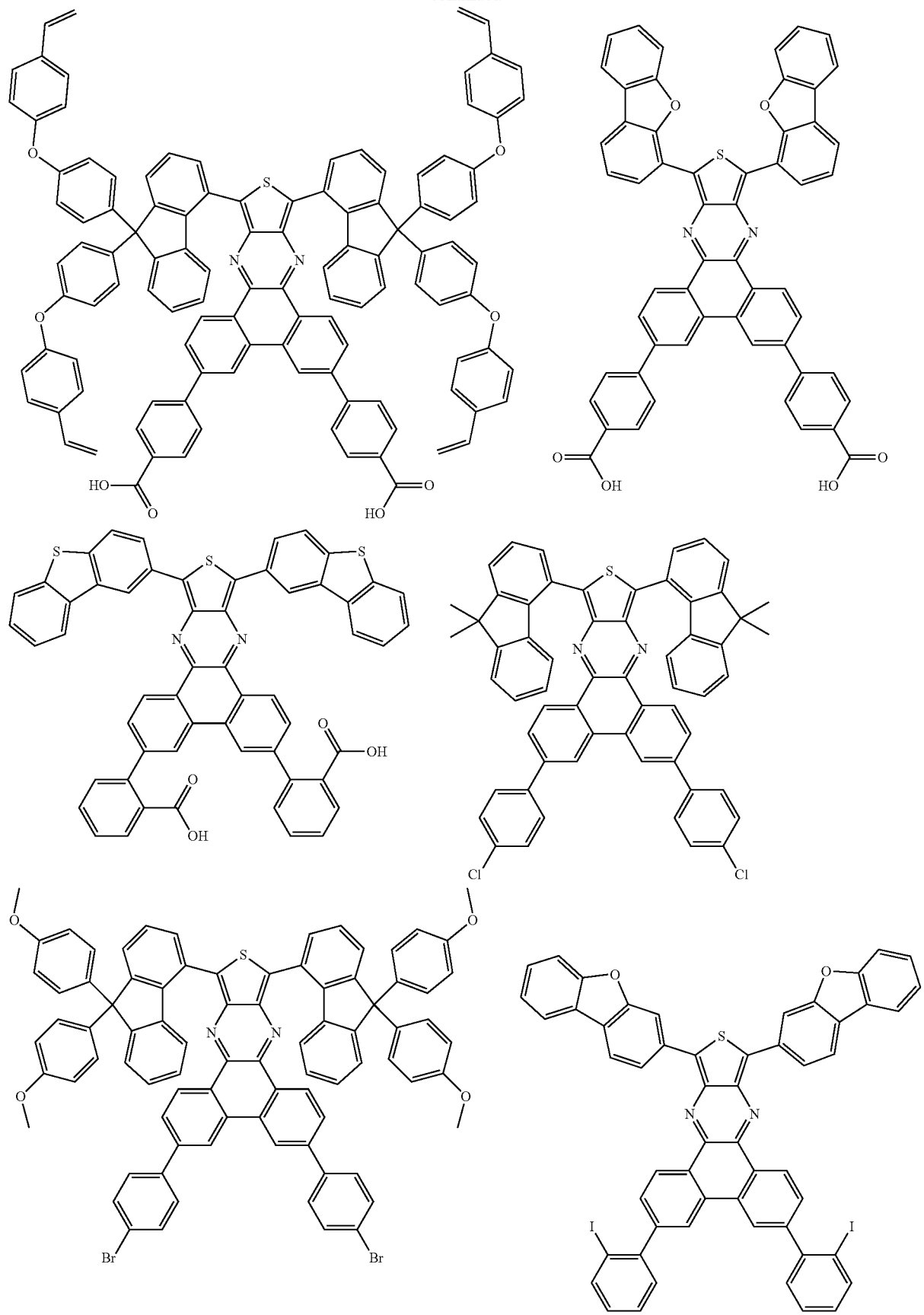

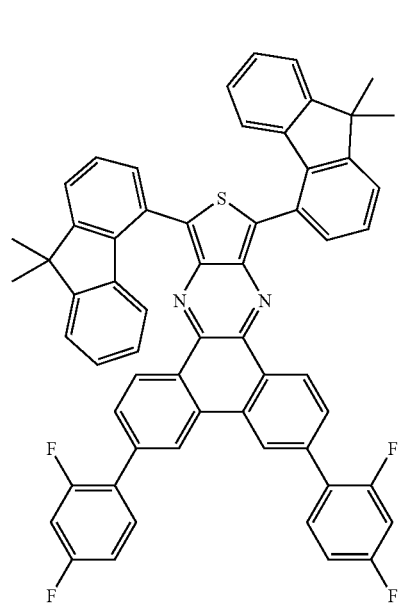
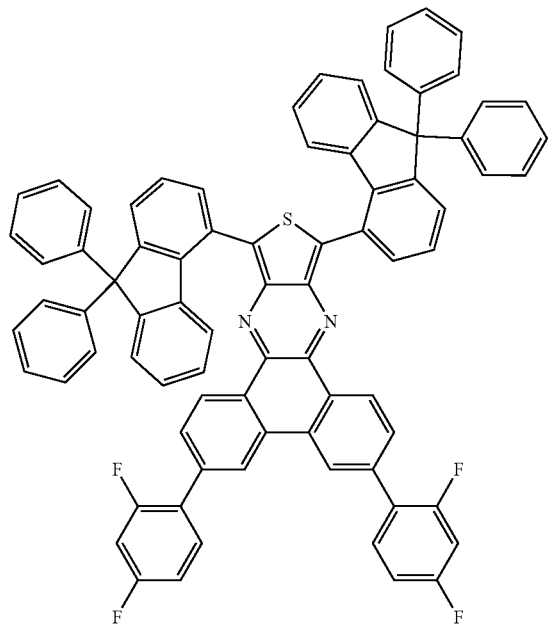
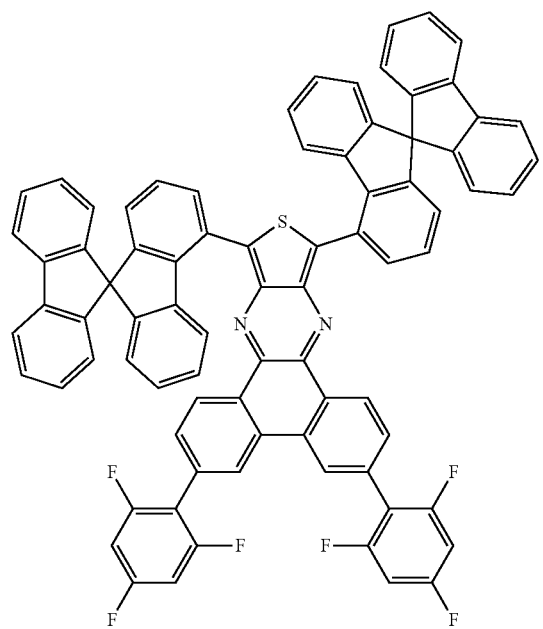
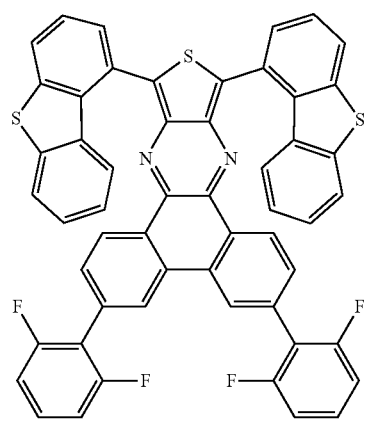

127
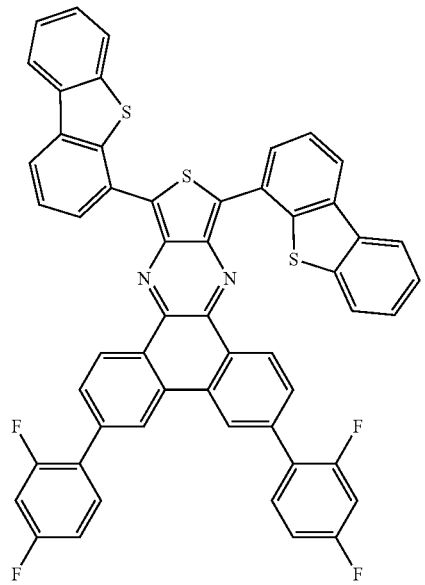
128
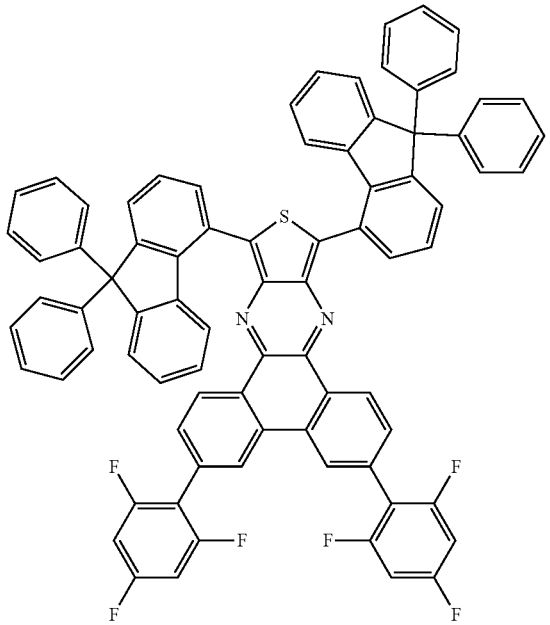
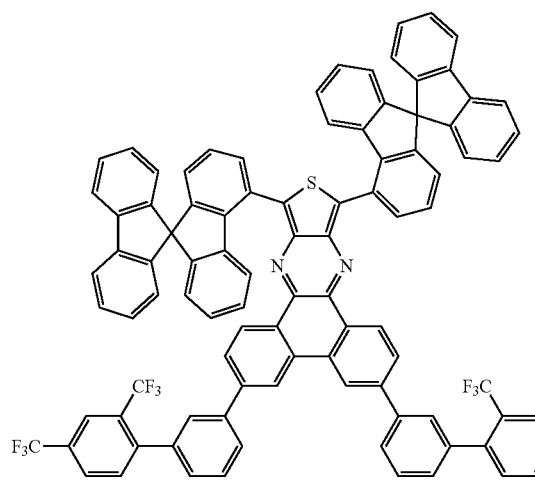
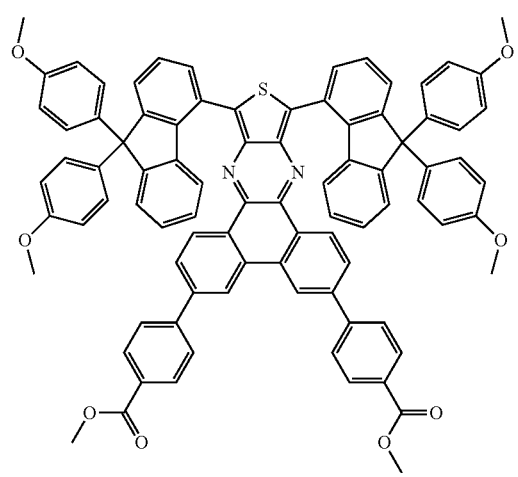
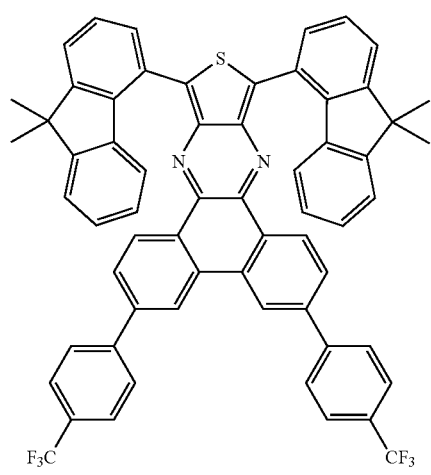
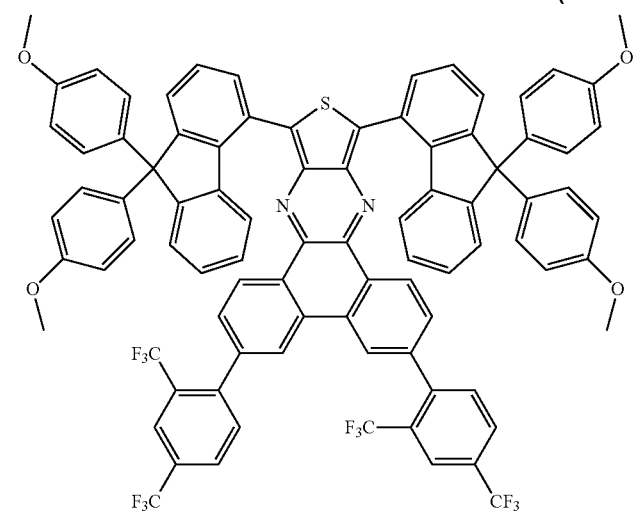

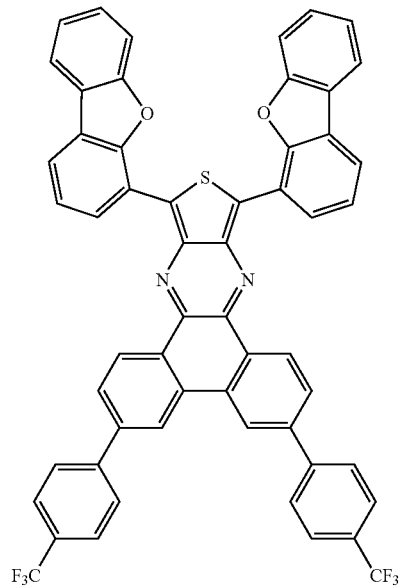
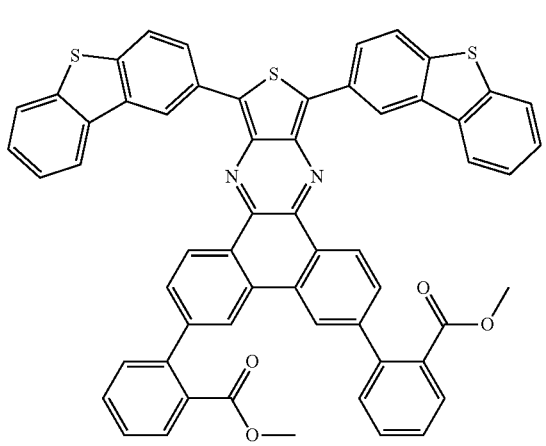
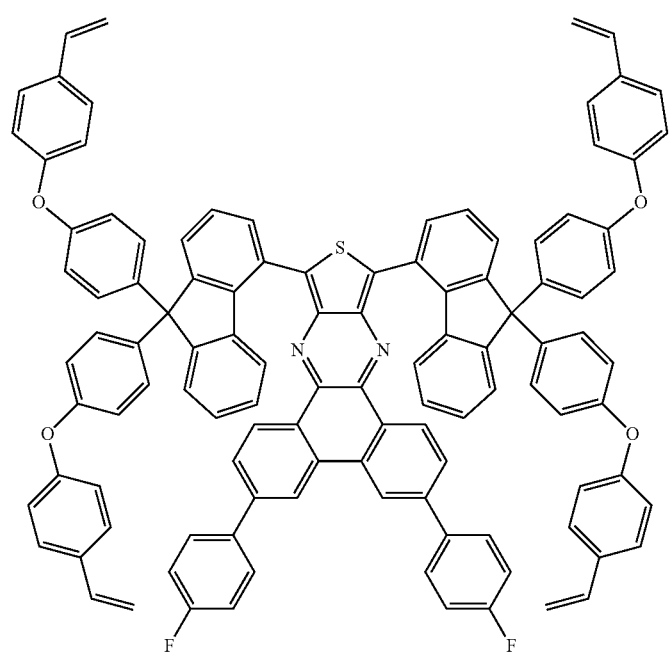

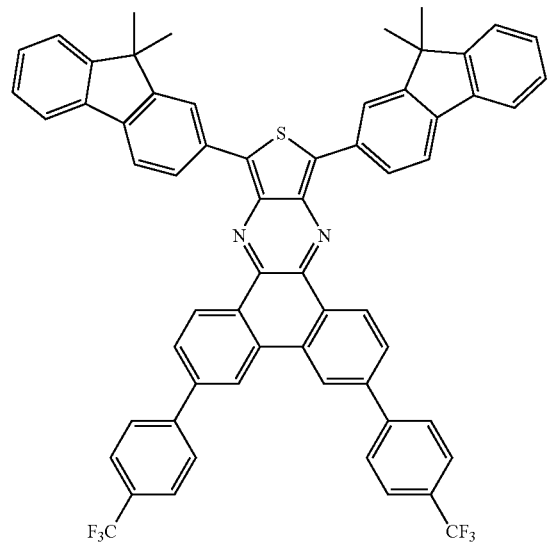
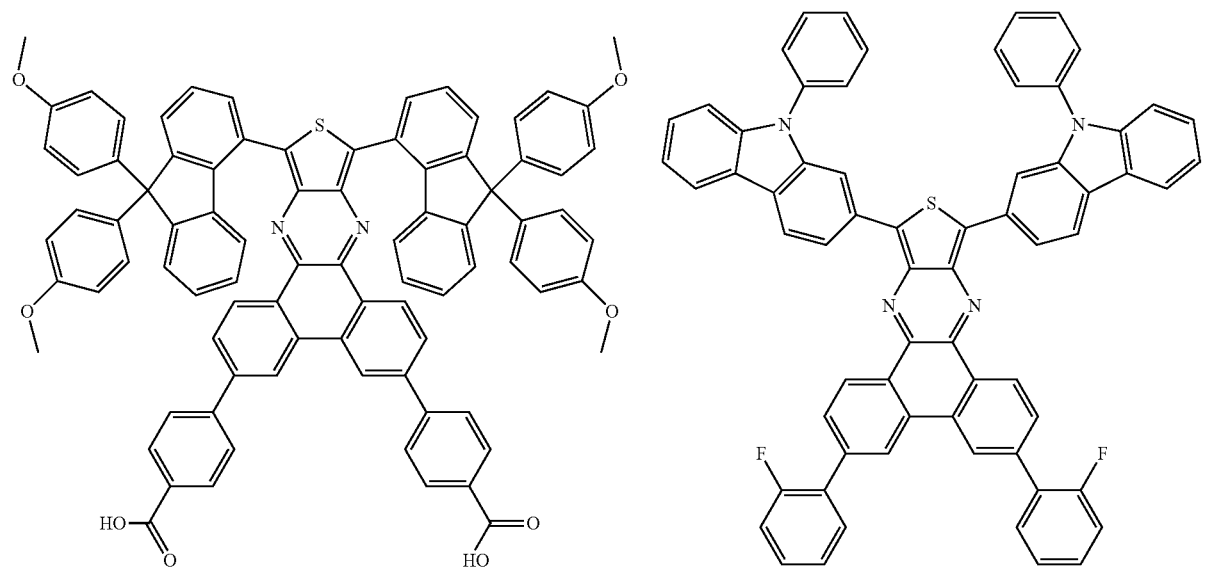

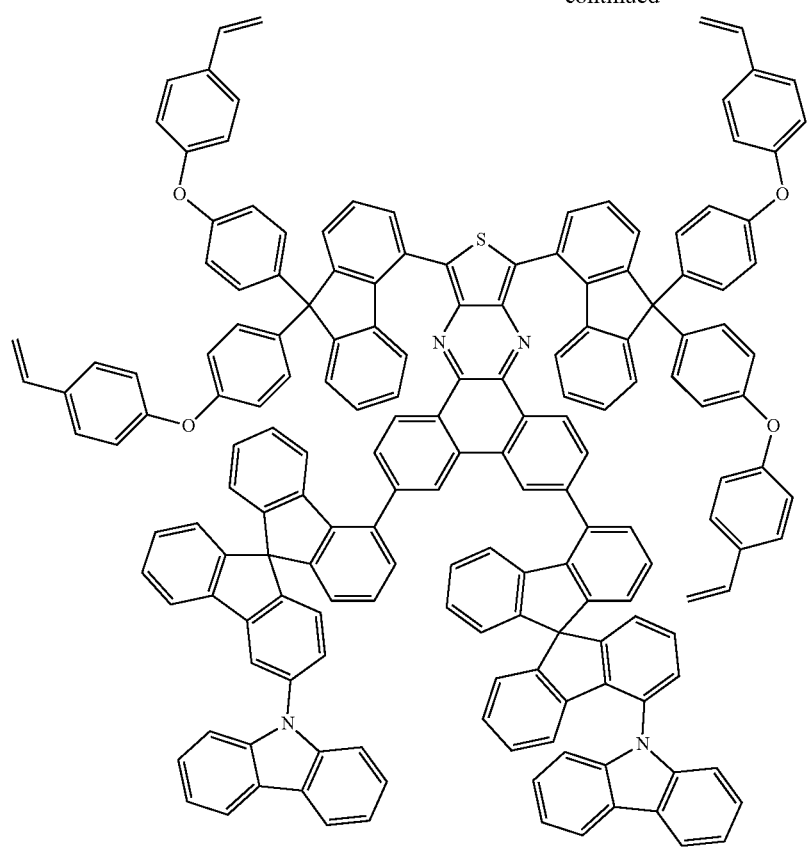
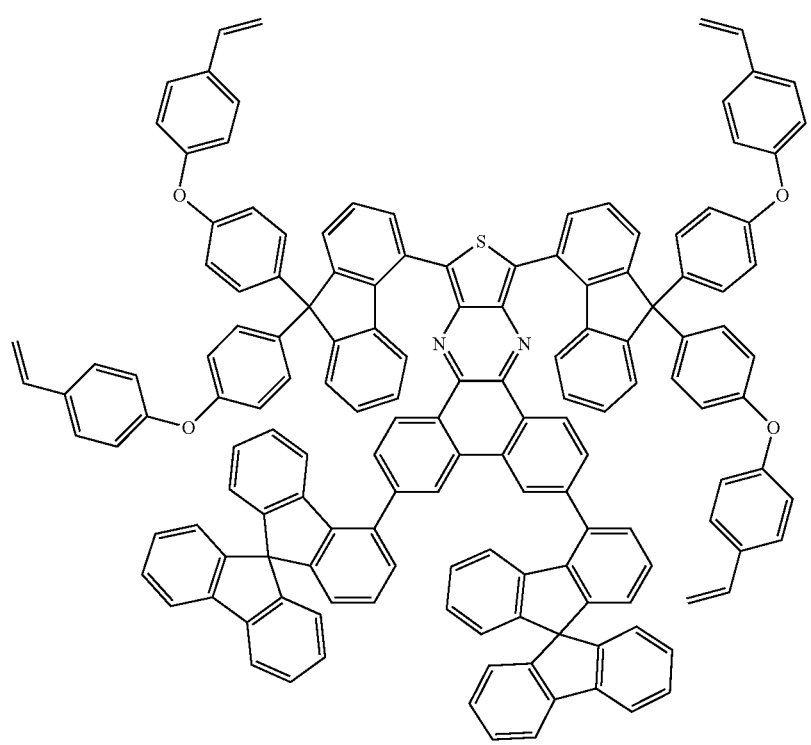

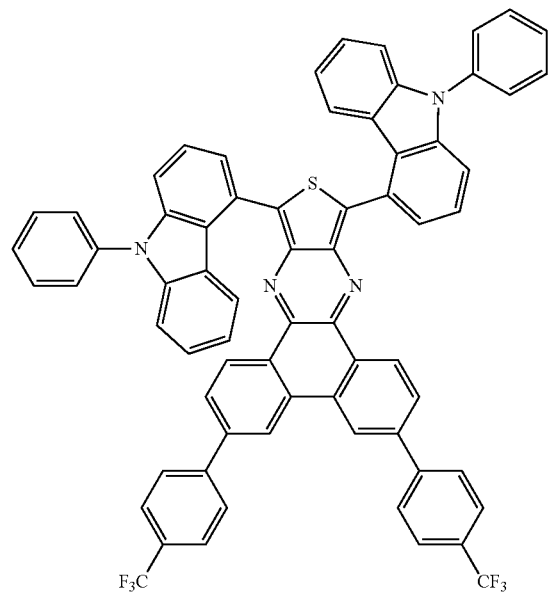
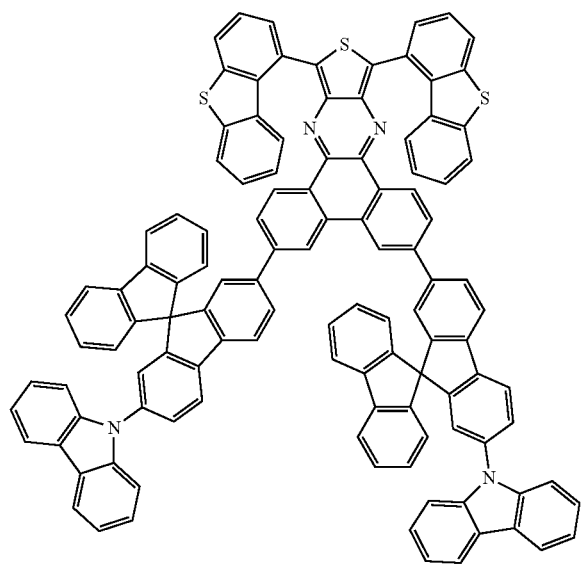
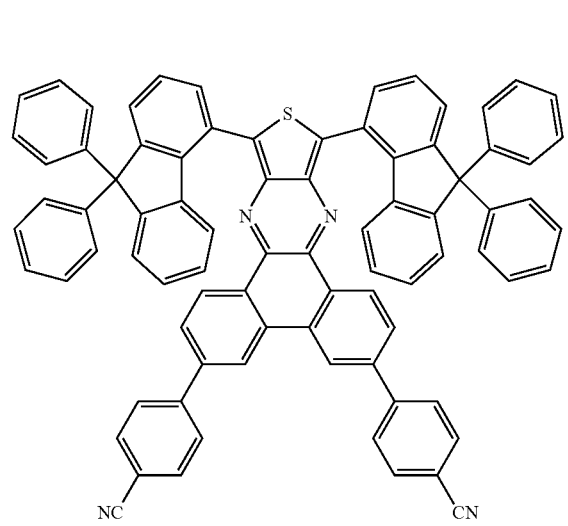
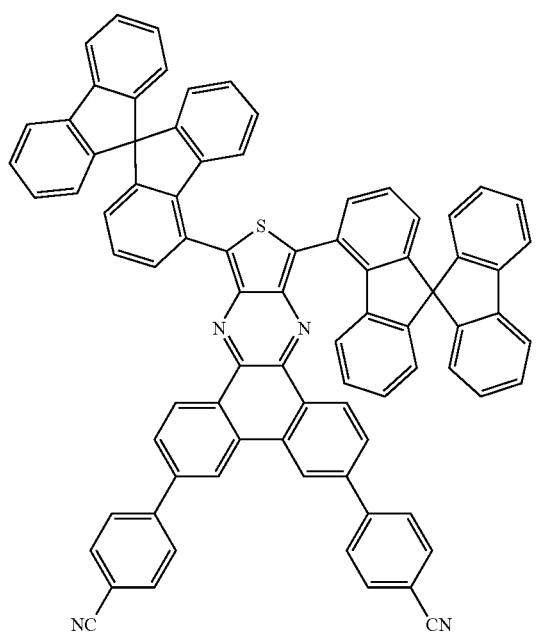

137 138
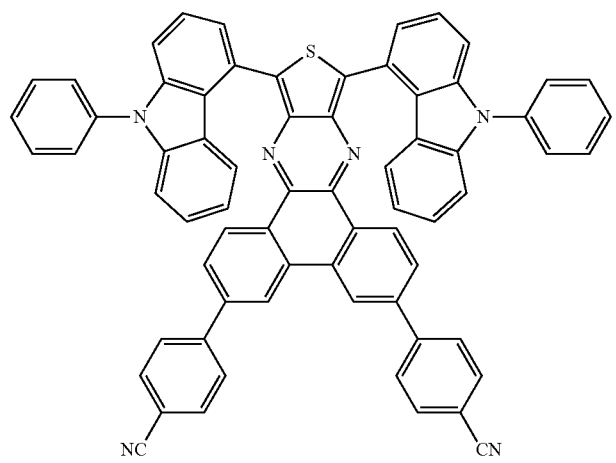
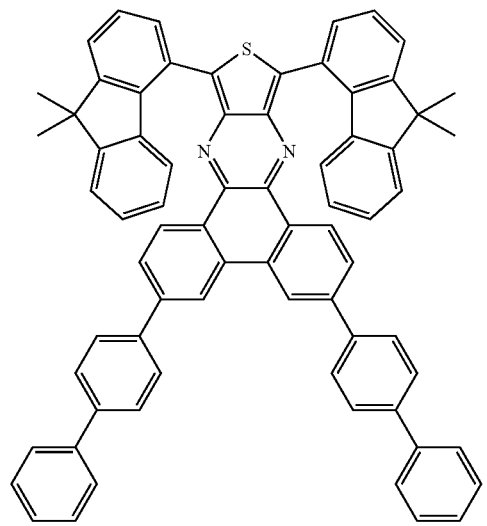
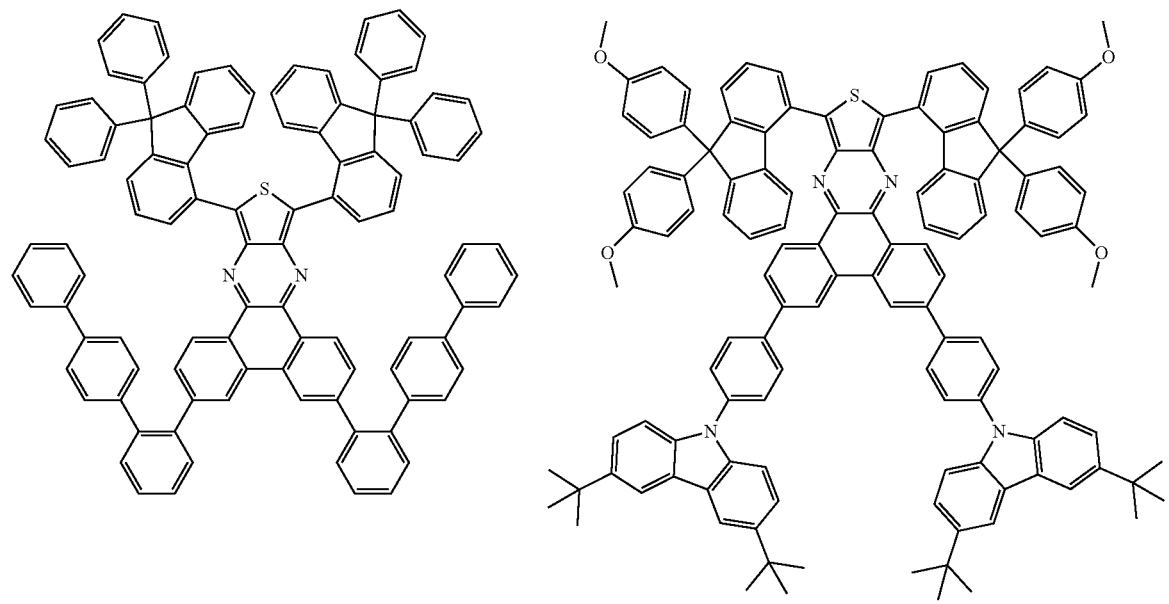

-continued
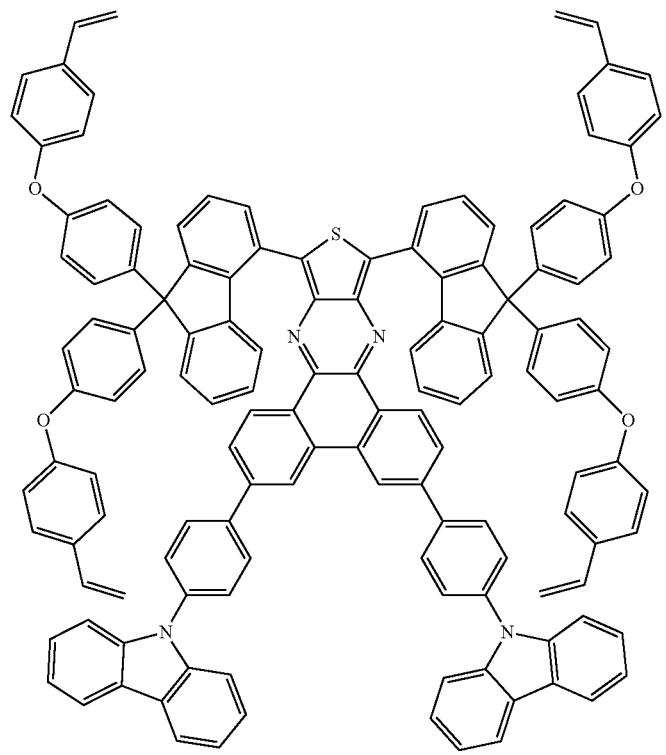
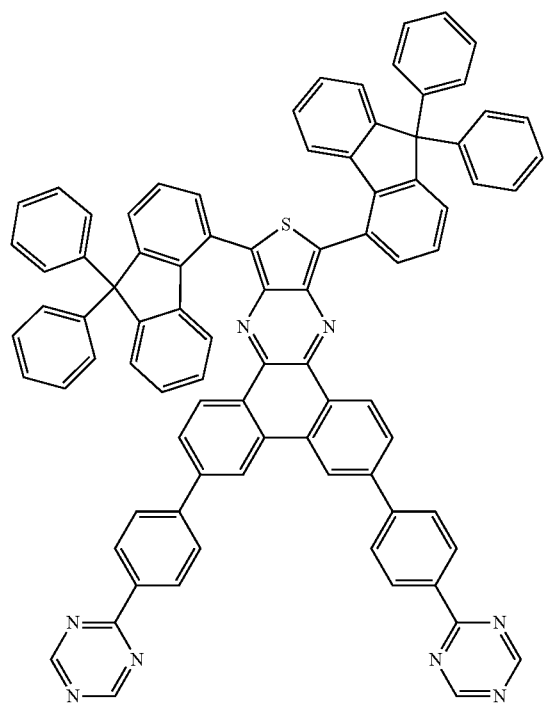

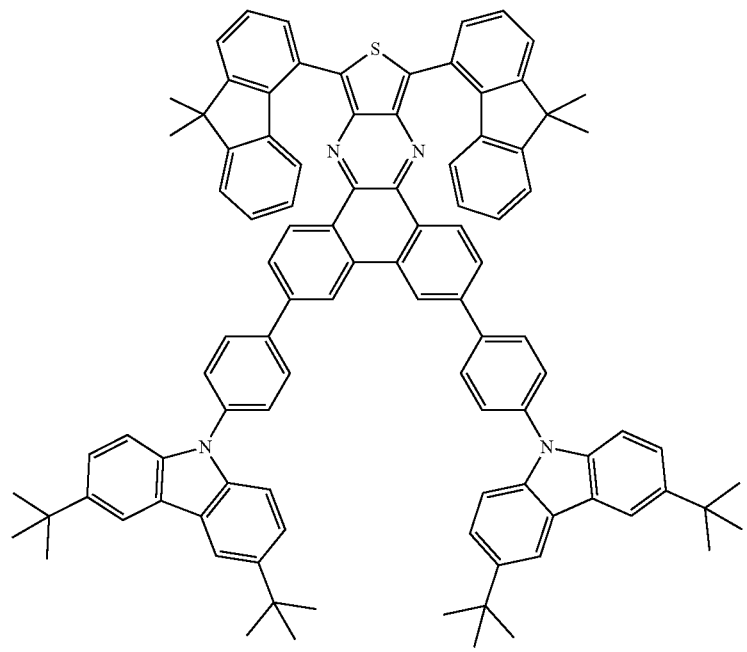
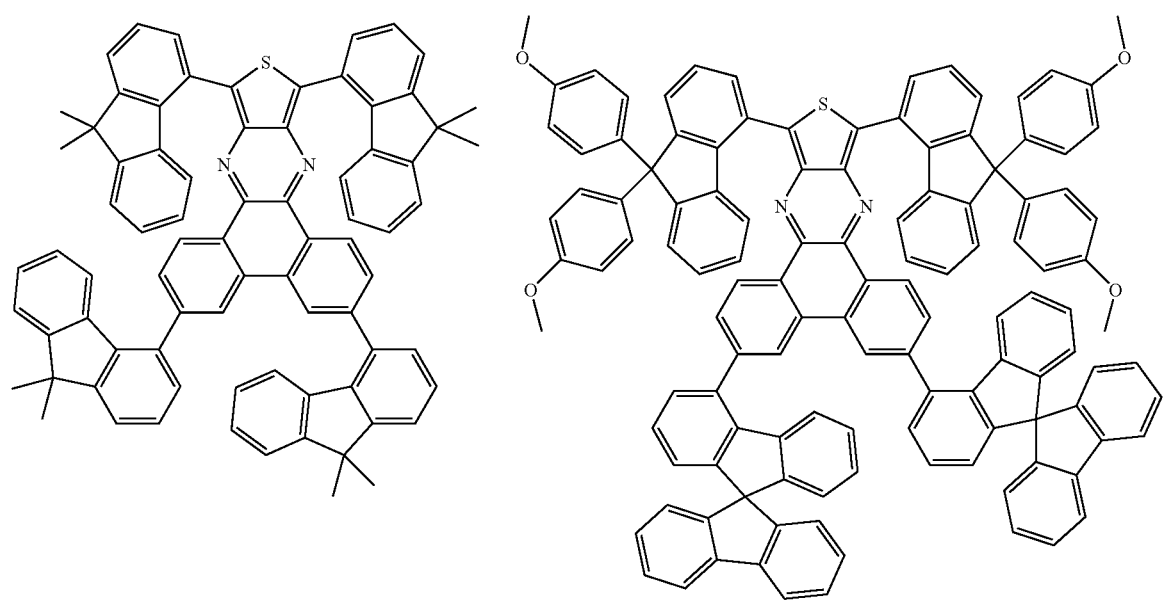

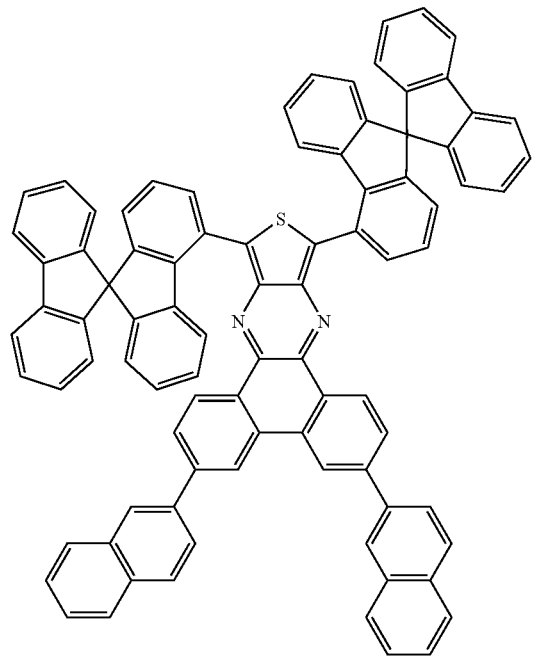
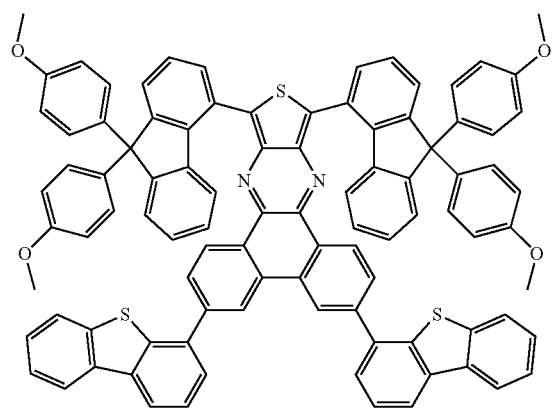
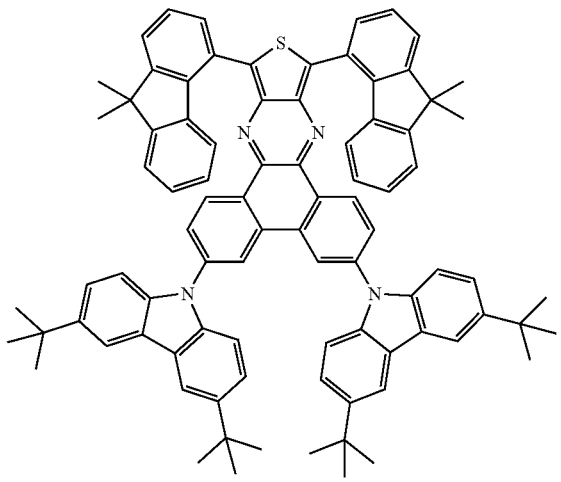

145 146
-continued
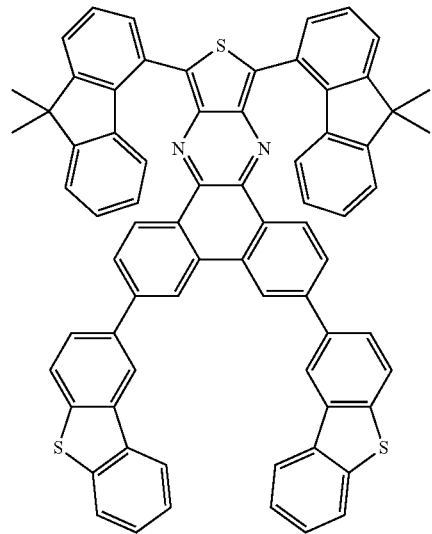
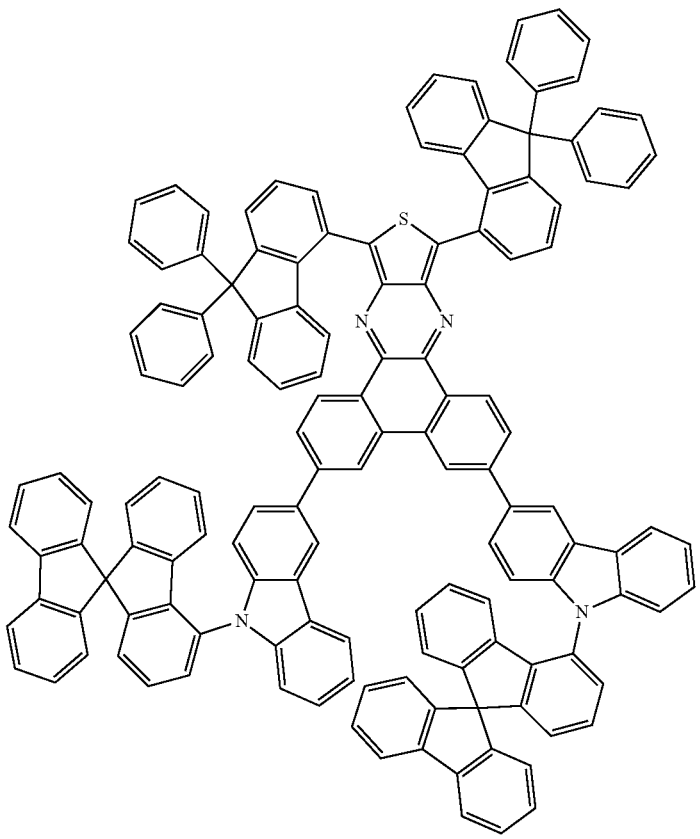
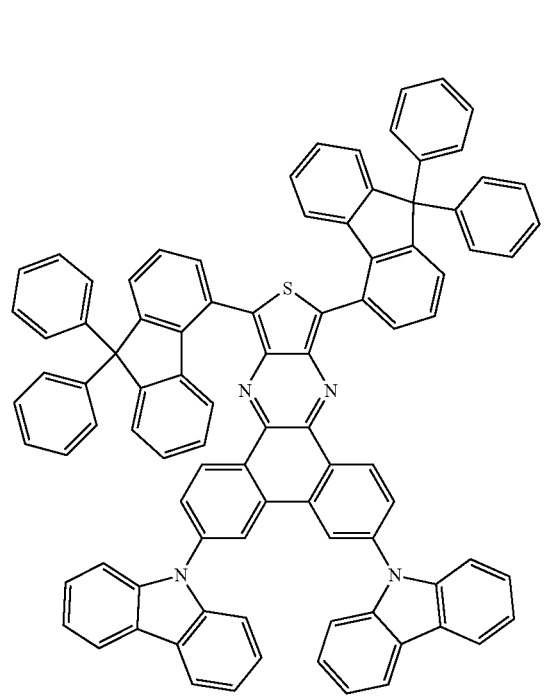
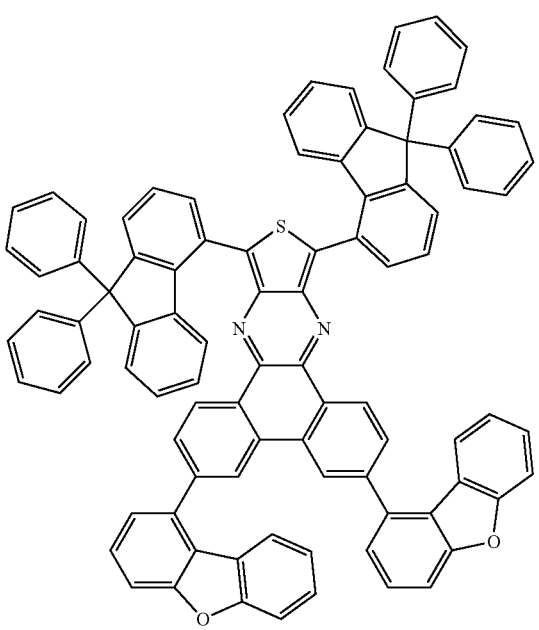

-continued
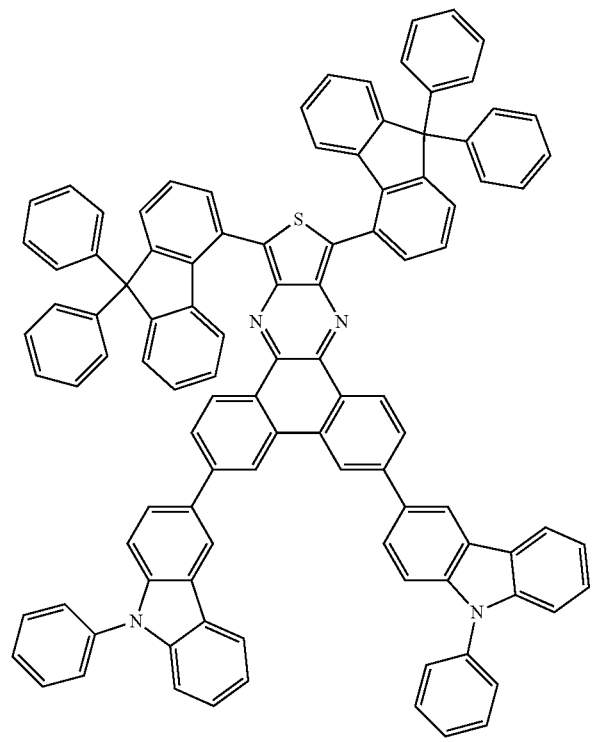
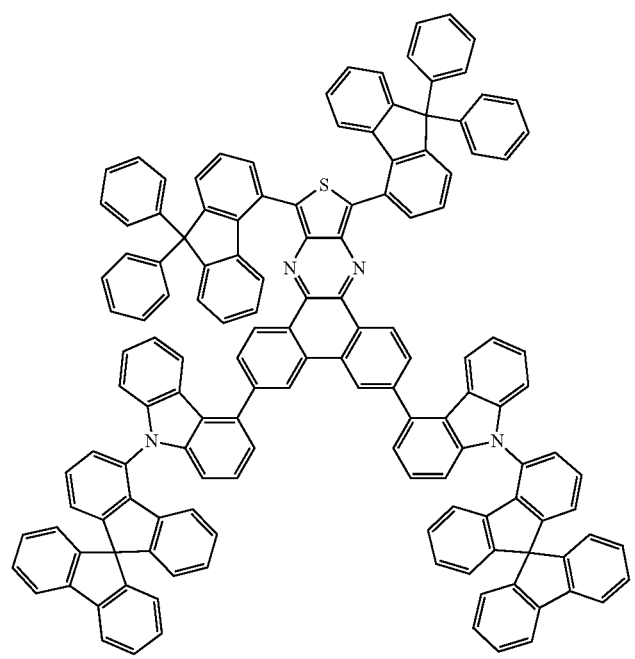
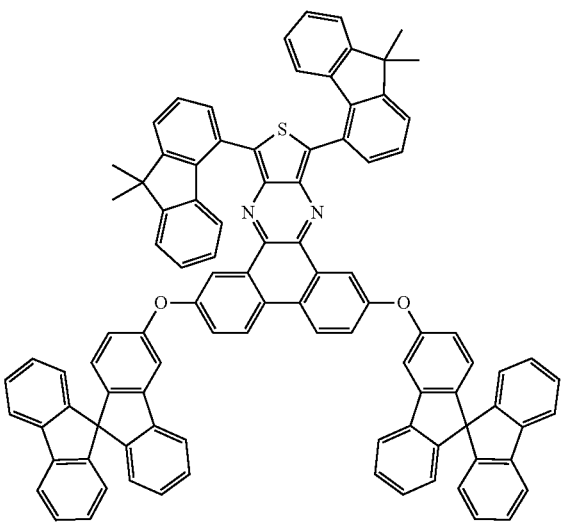

149
150
-continued
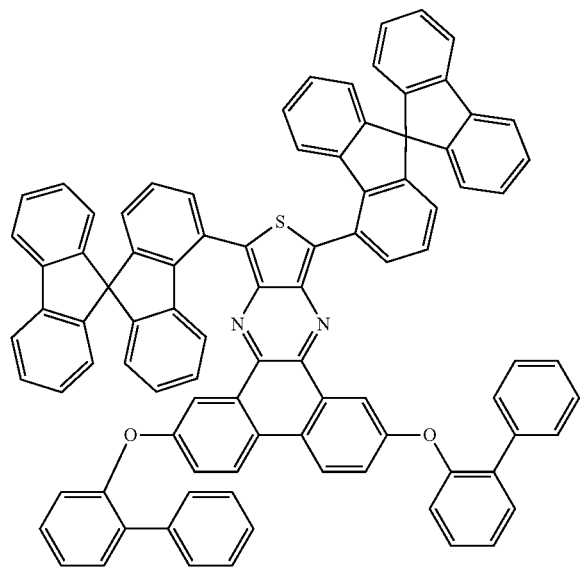
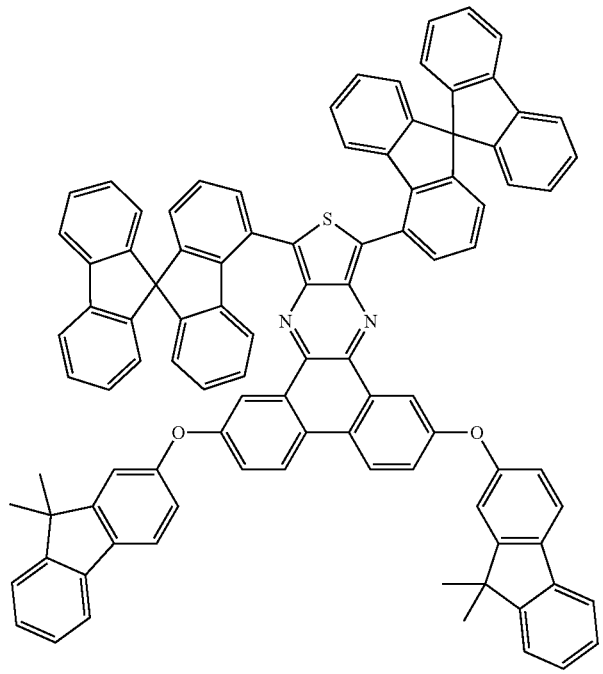
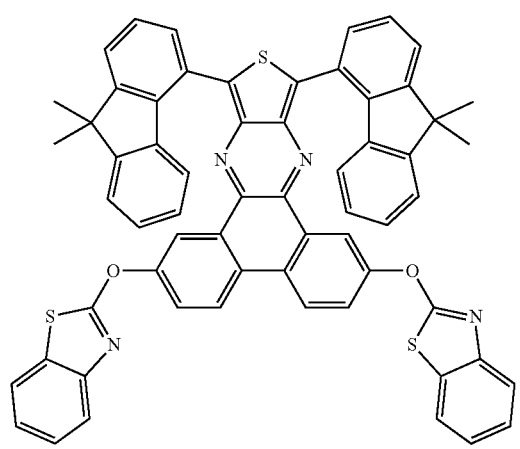
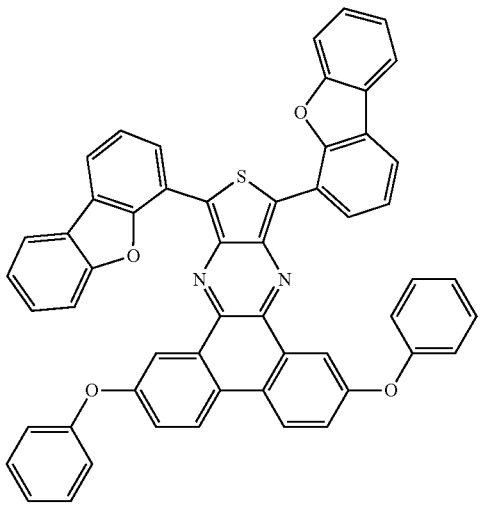
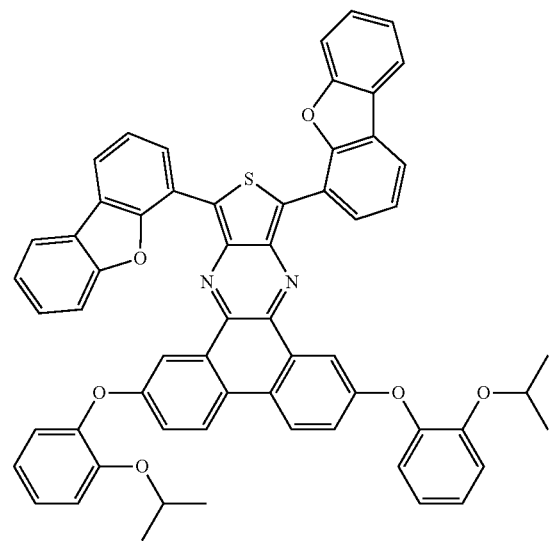
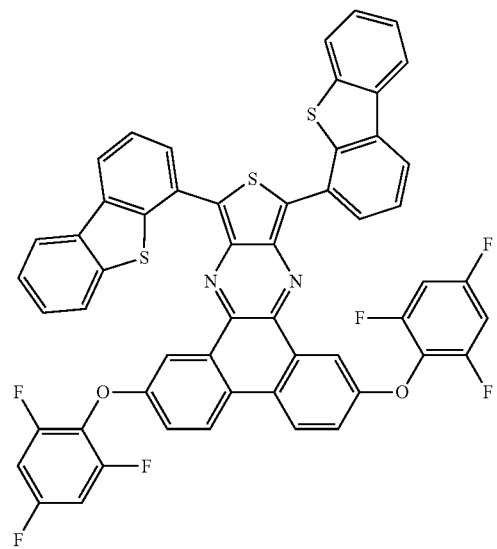

-continued
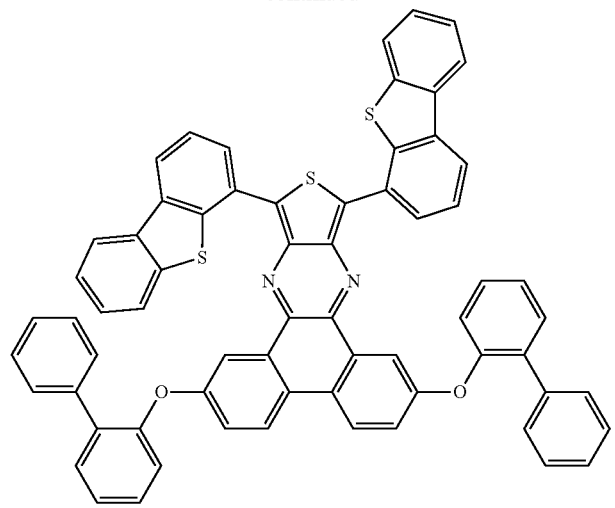
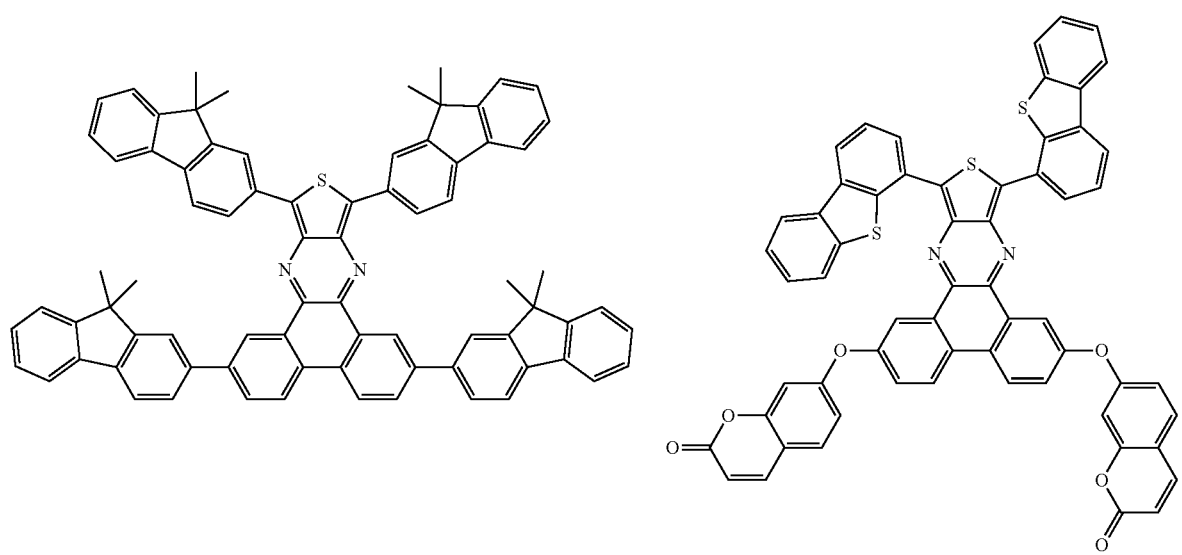
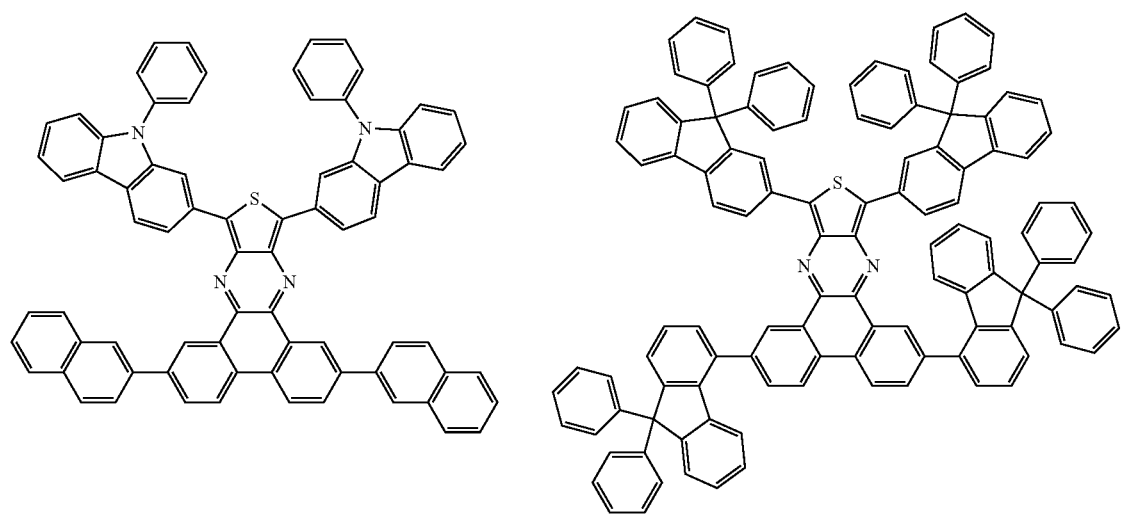

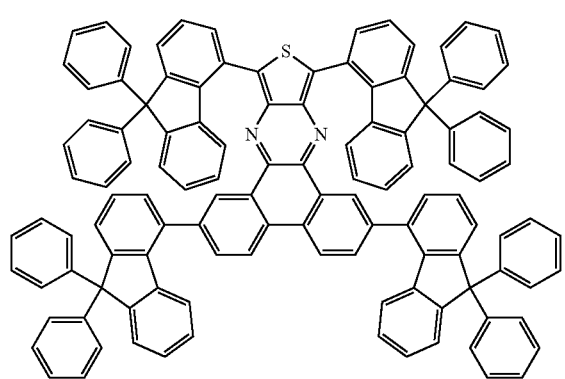
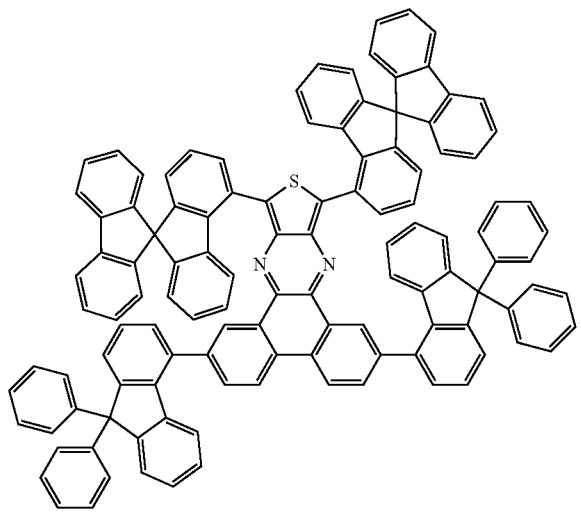
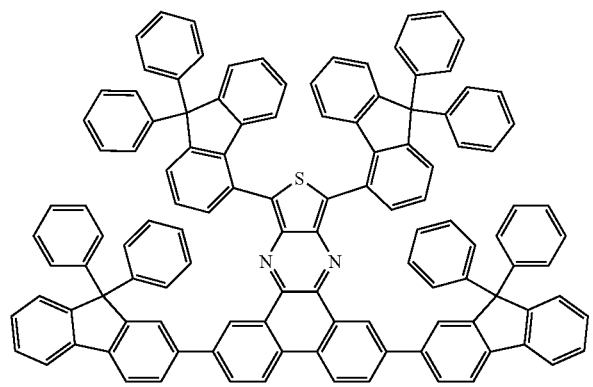
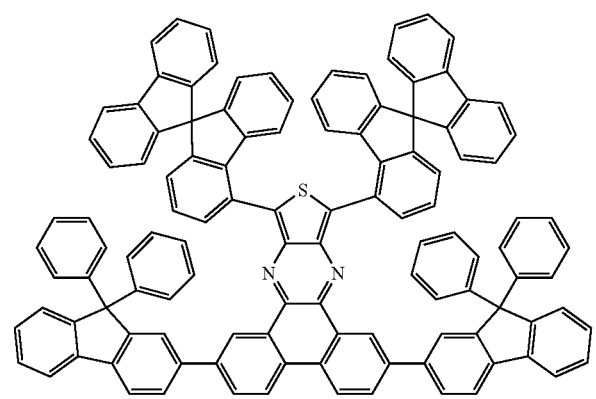
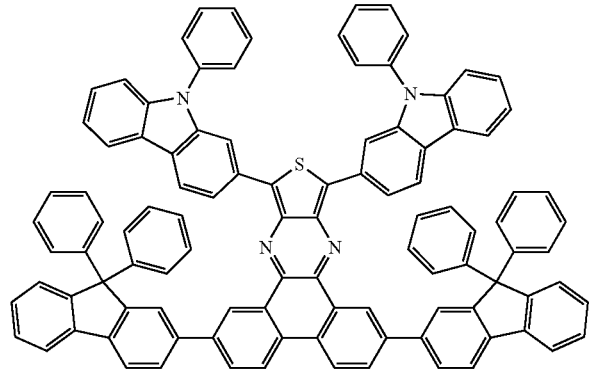
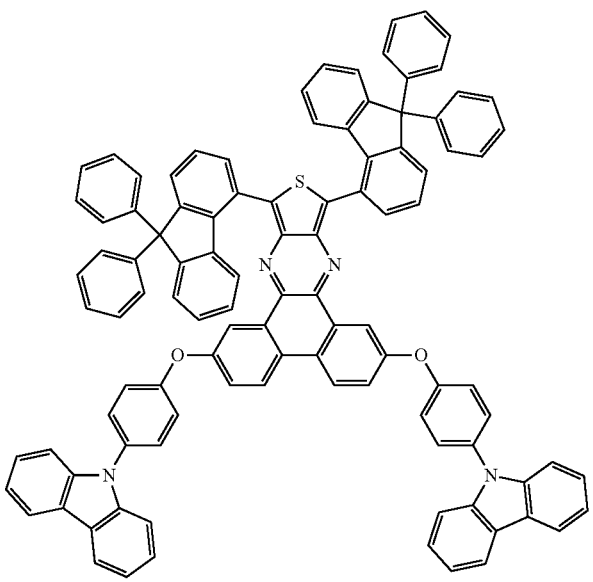

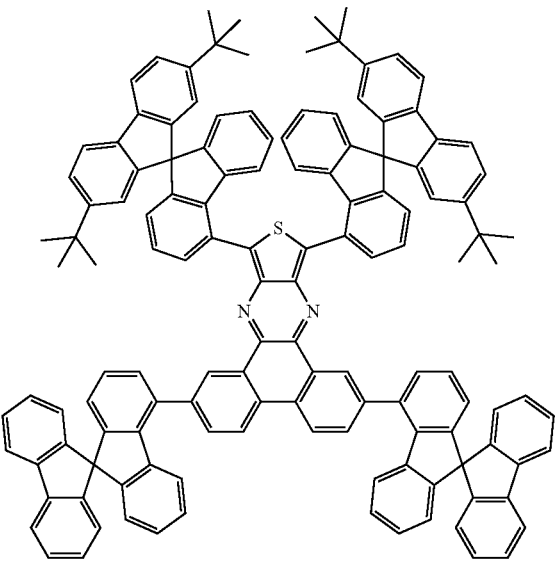
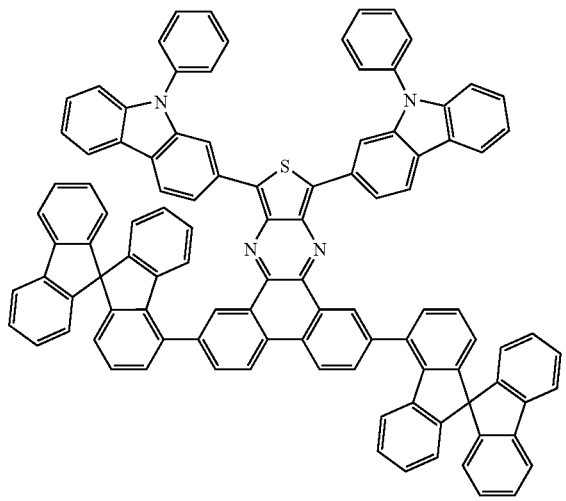
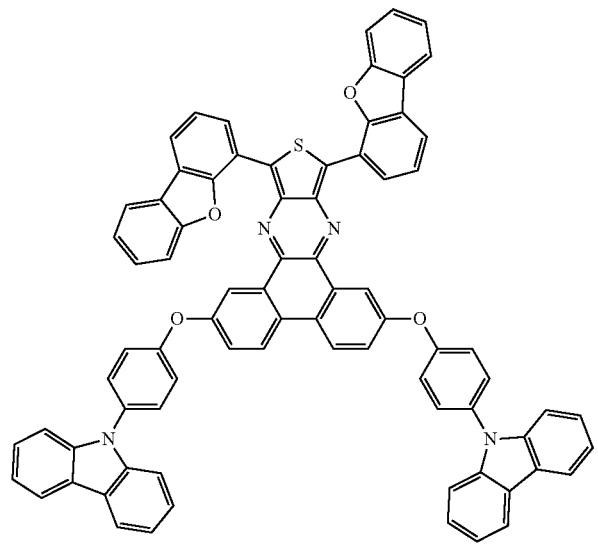
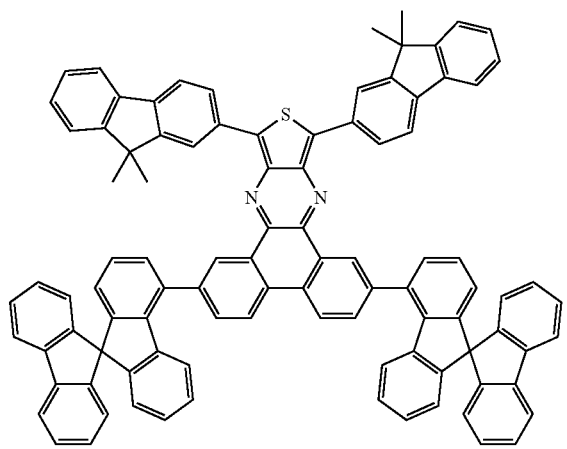

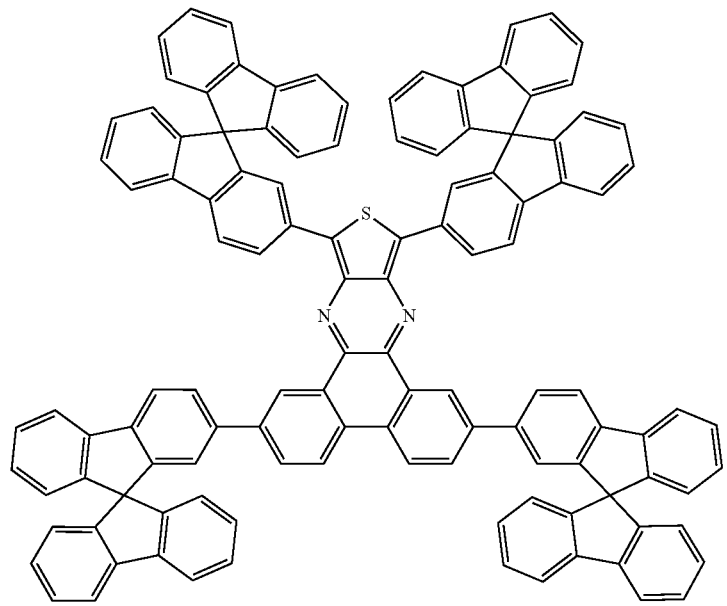
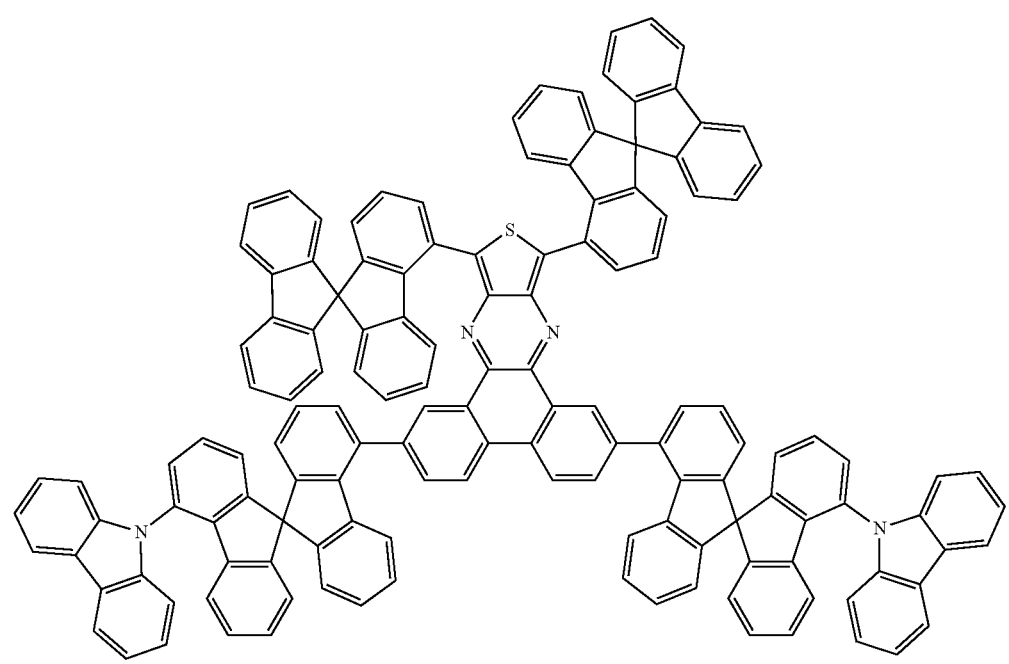 [SMILES: c1ccc2c(c1)-c1ccccc1C21c2ccccc2-c2c(-c3sc(-c4cccc5c4-c4ccccc4C54c5ccccc5-c5ccccc54)c4nc5c6cc(-c7cccc8c7-c7ccccc7C87c8ccccc8-c8c(-n9c%10ccccc%10c%10ccccc%109)cccc87)ccc6c6ccc(-c7cccc8c7-c7ccccc7C87c8ccccc8-c8c(-n9c%10ccccc%10c%10ccccc%109)cccc87)cc6c5nc34)cccc21]

-continued
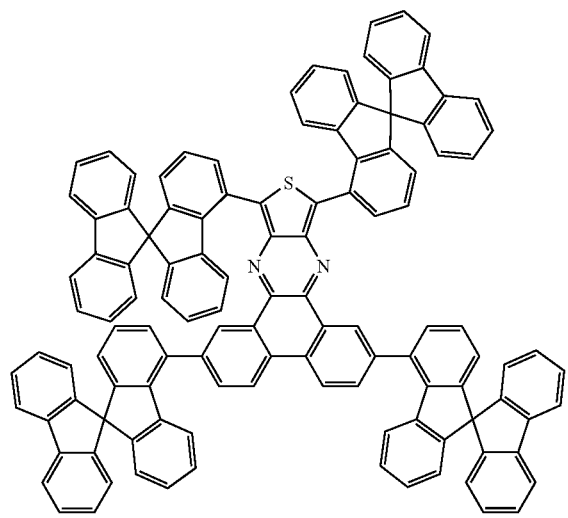
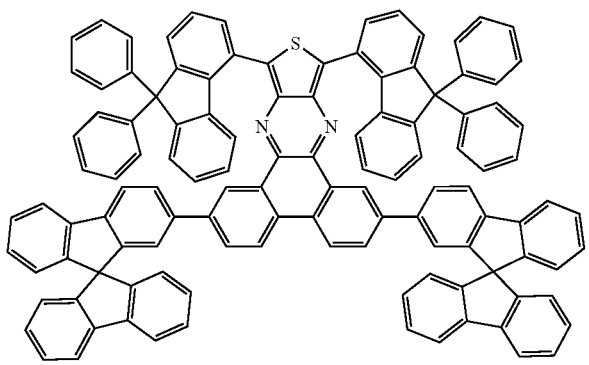
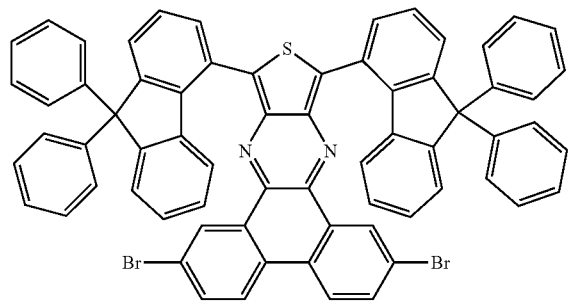
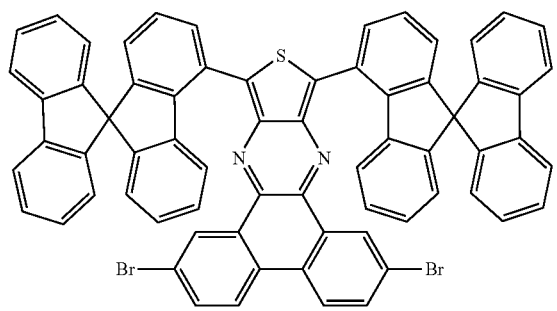
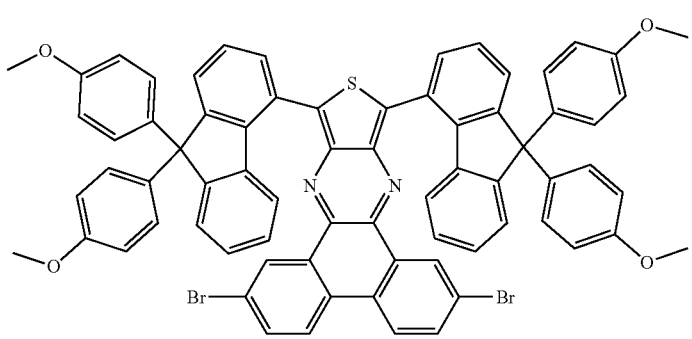
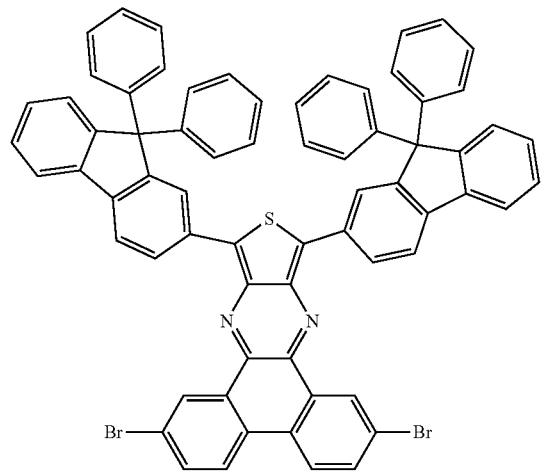
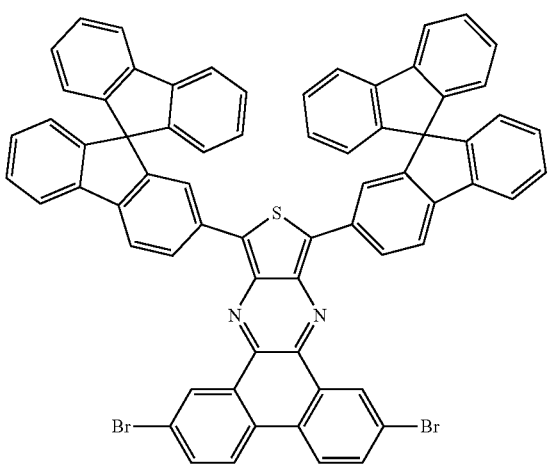

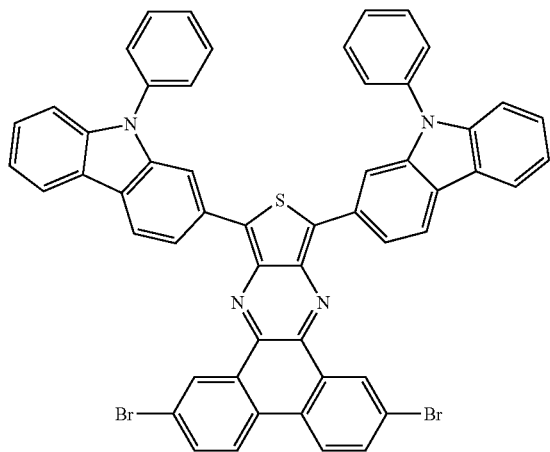
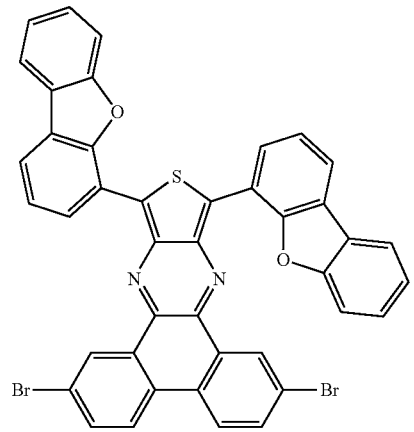
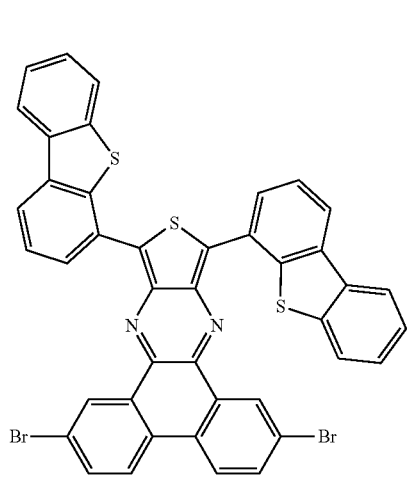
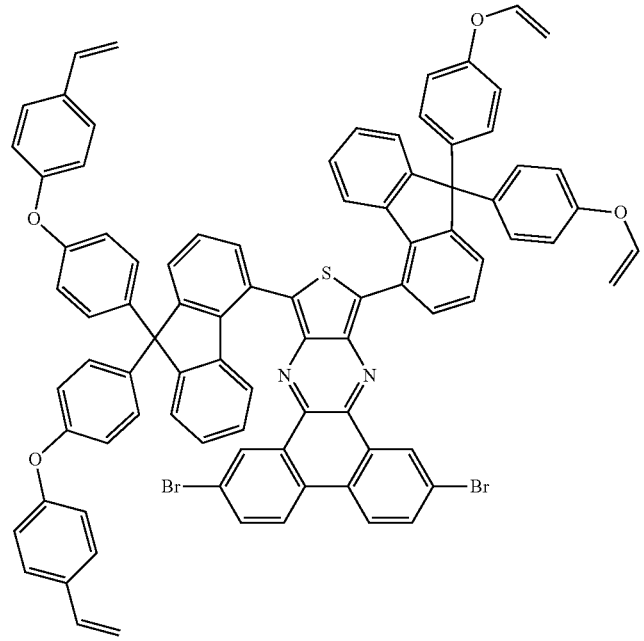
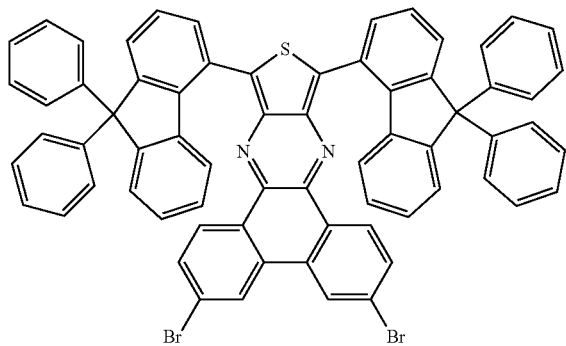
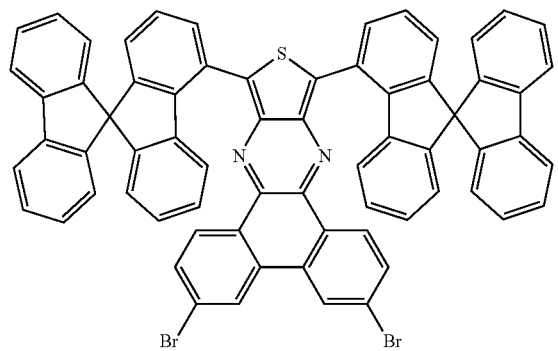

163 164
-continued
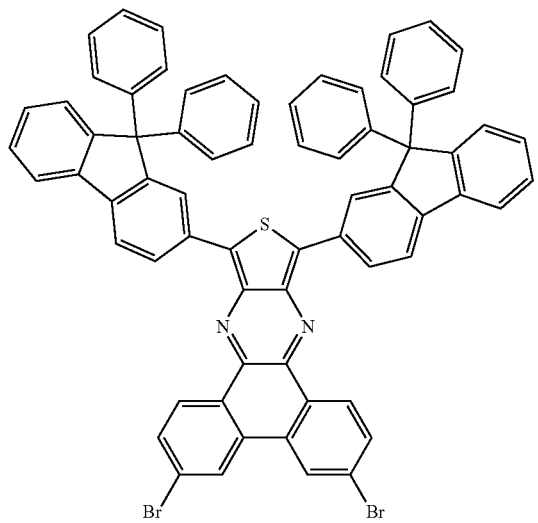
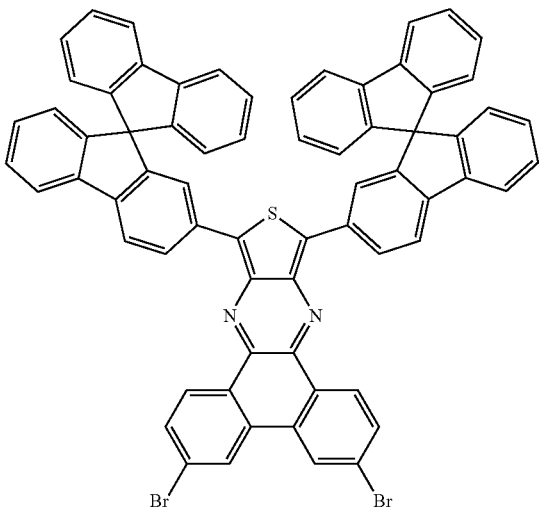
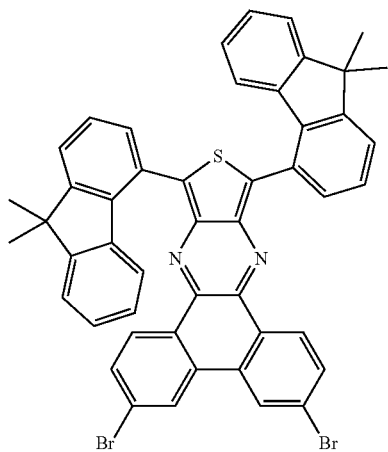
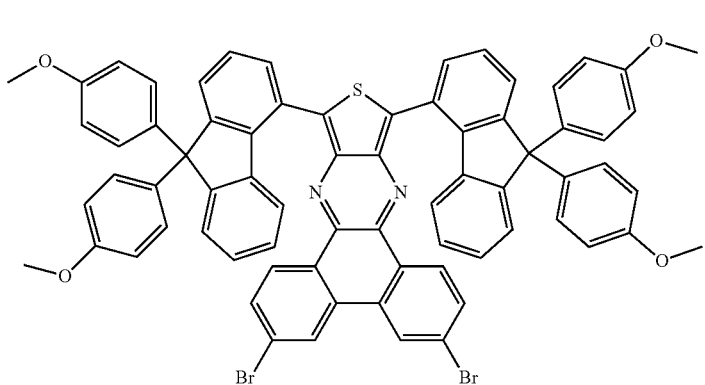
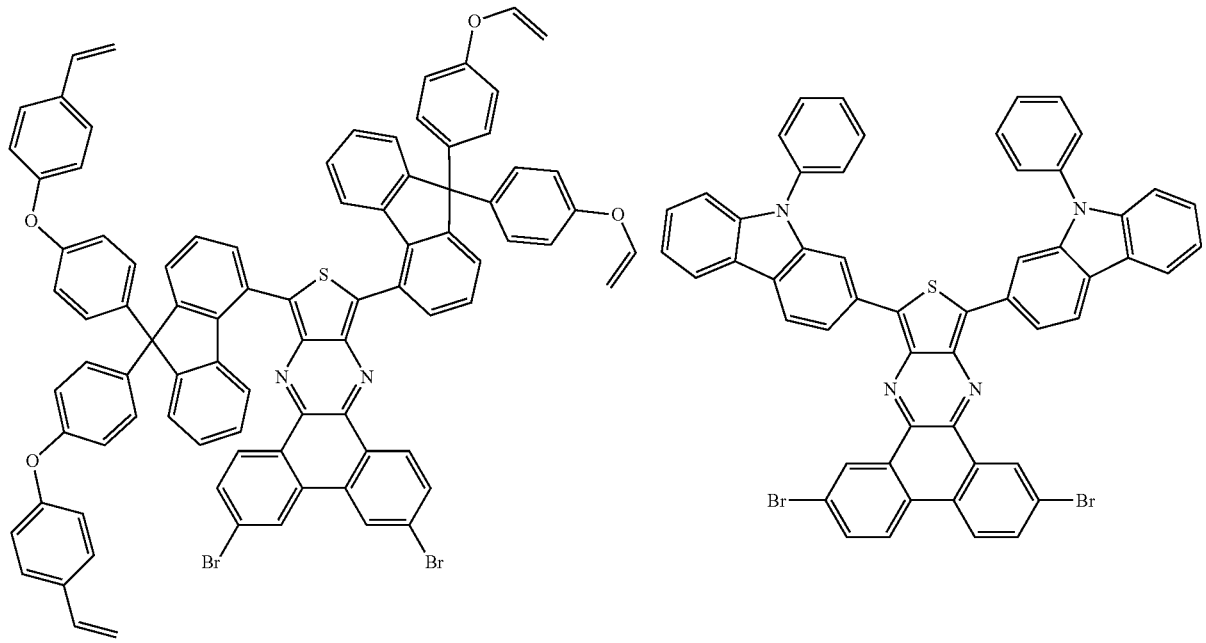

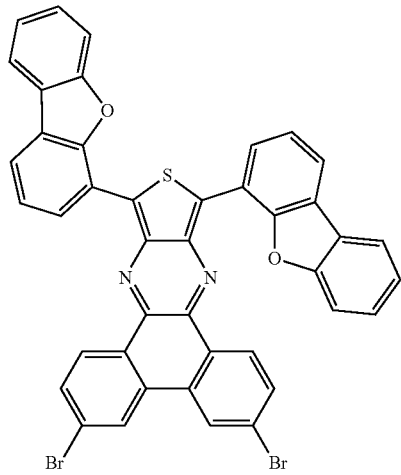
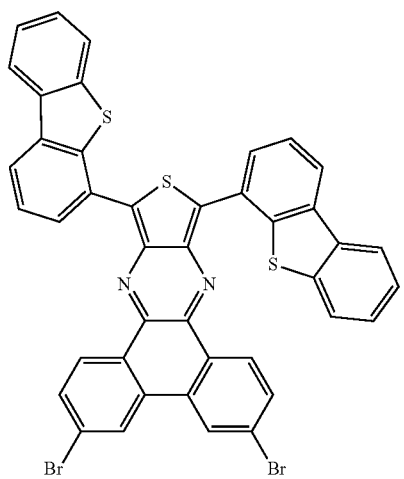
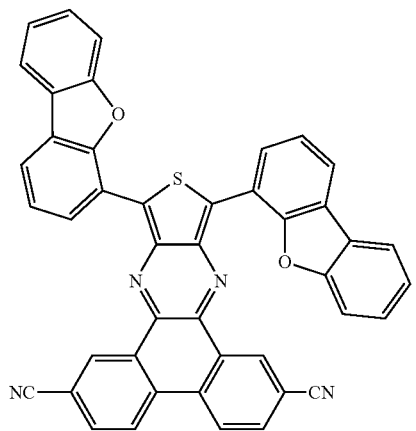
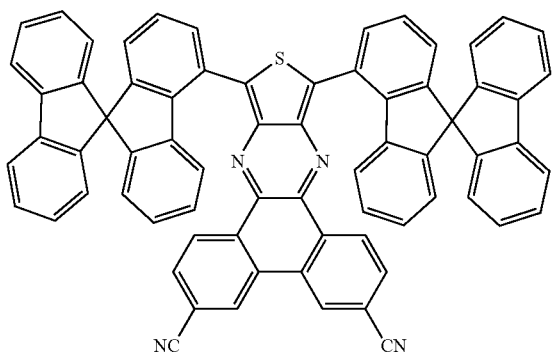
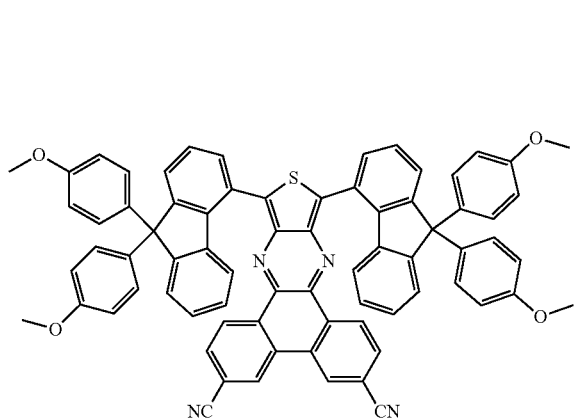
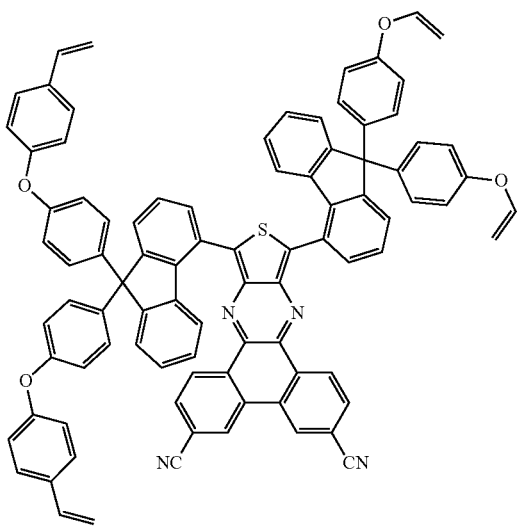

-continued
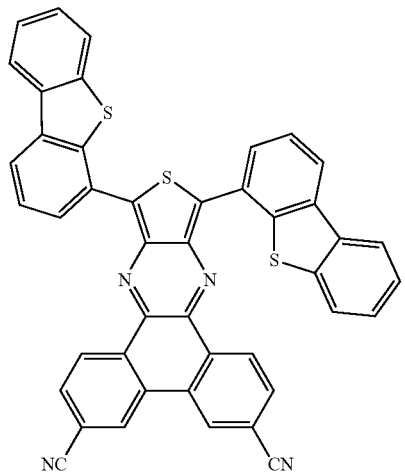 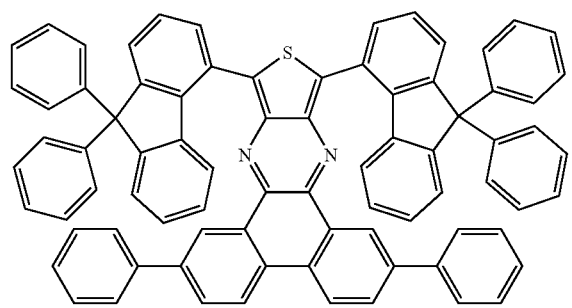
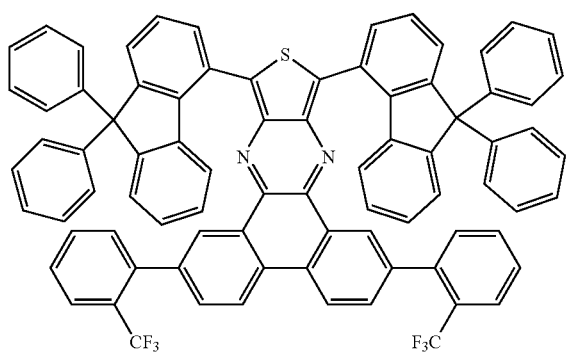 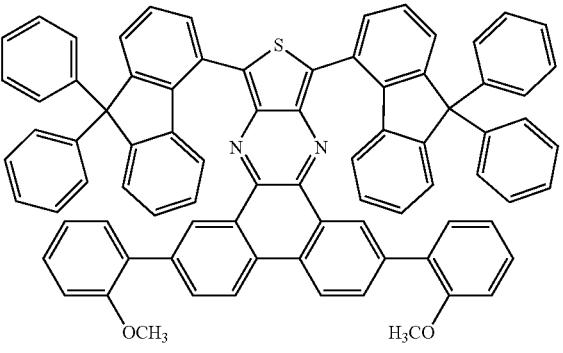
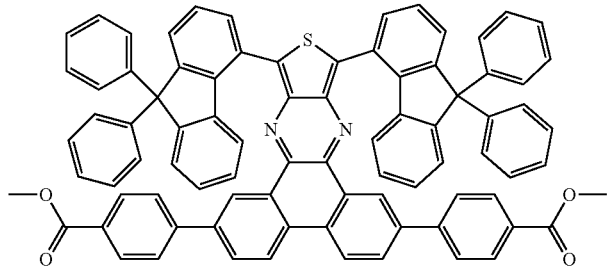 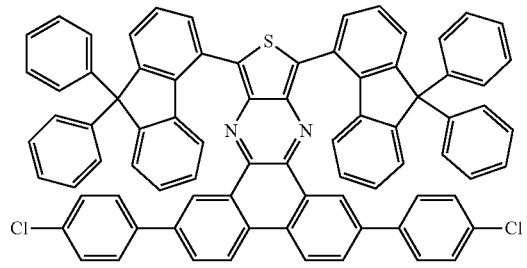
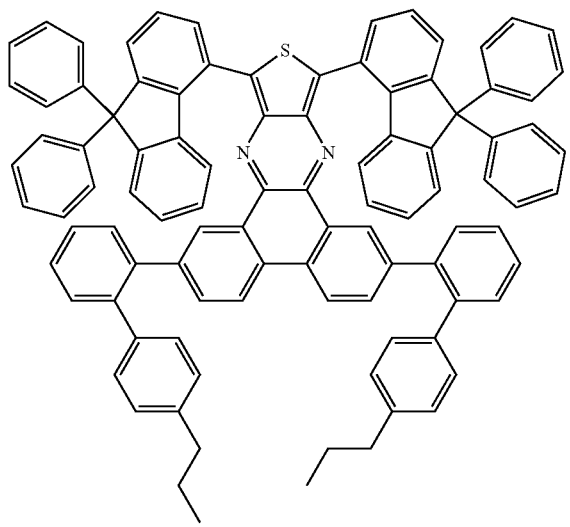

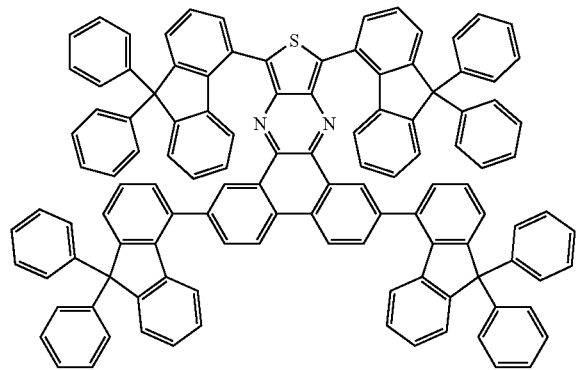
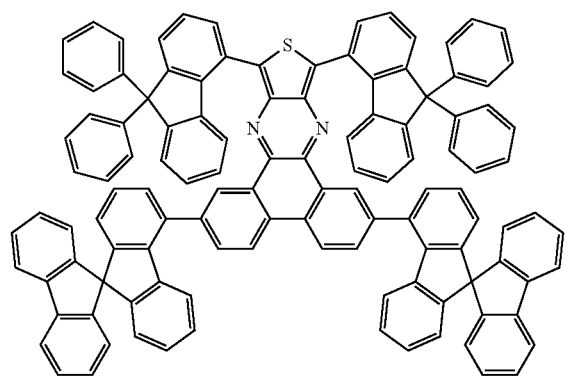
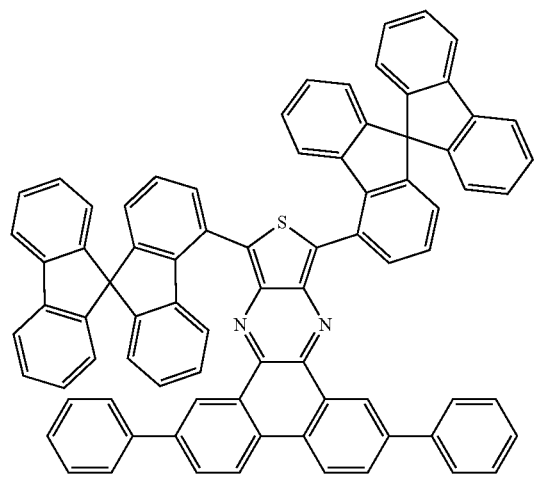
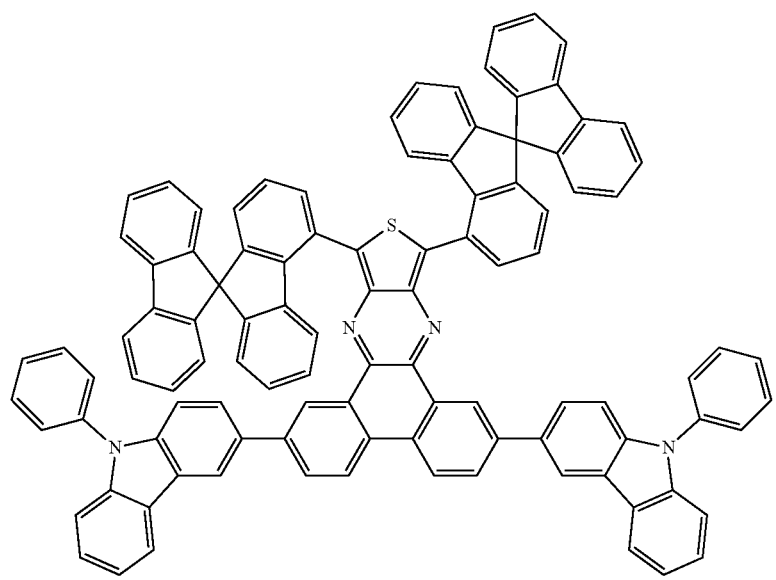

171
172
-continued
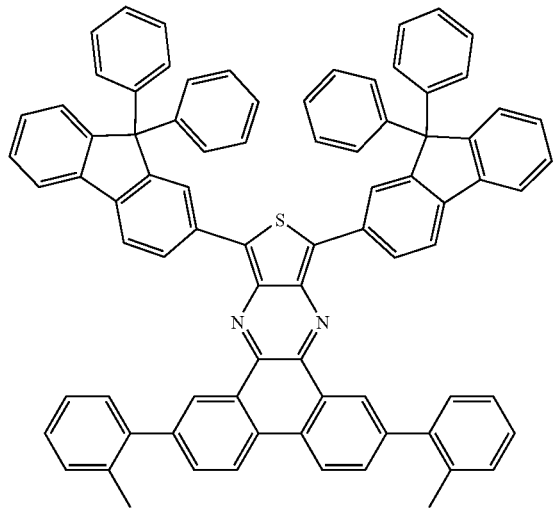
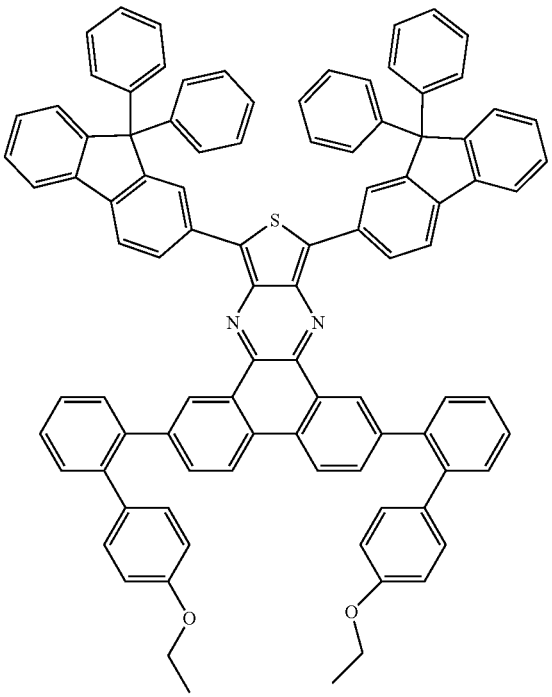
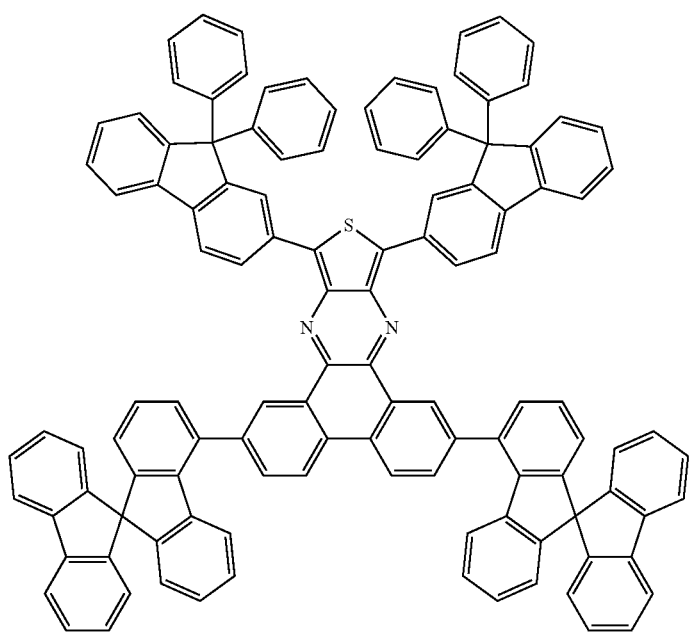

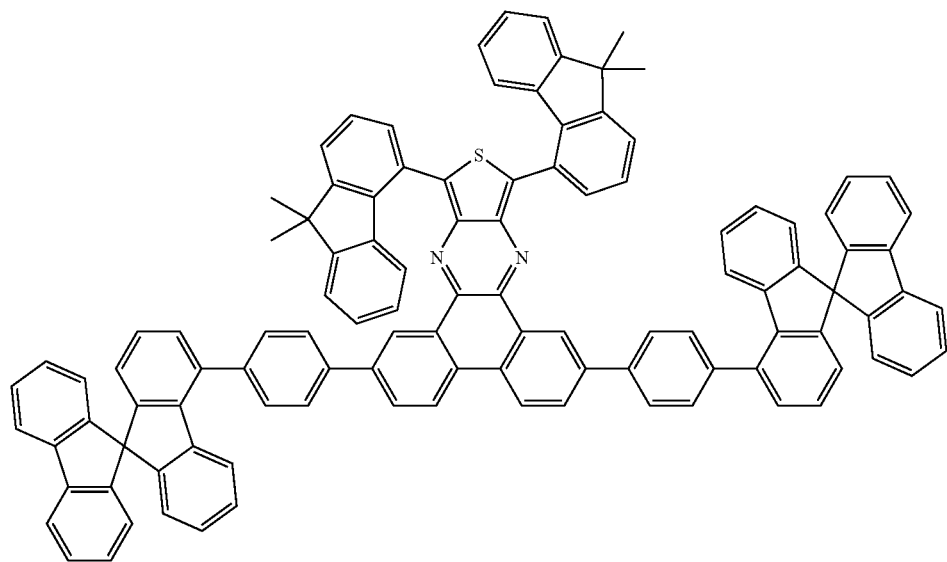
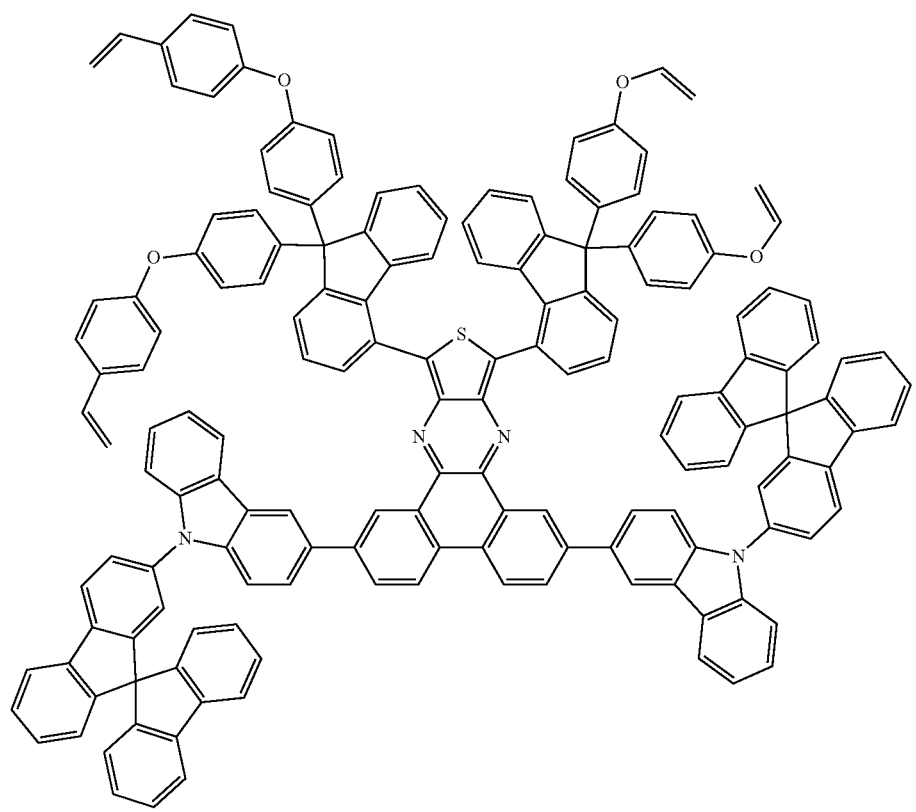

-continued
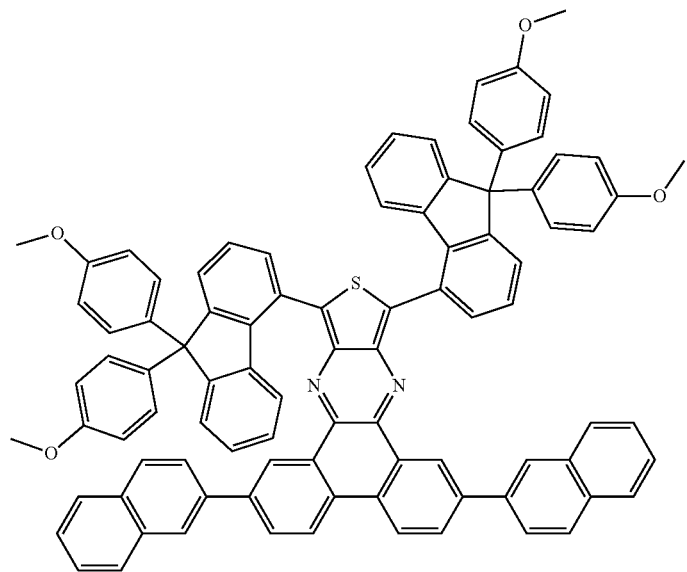
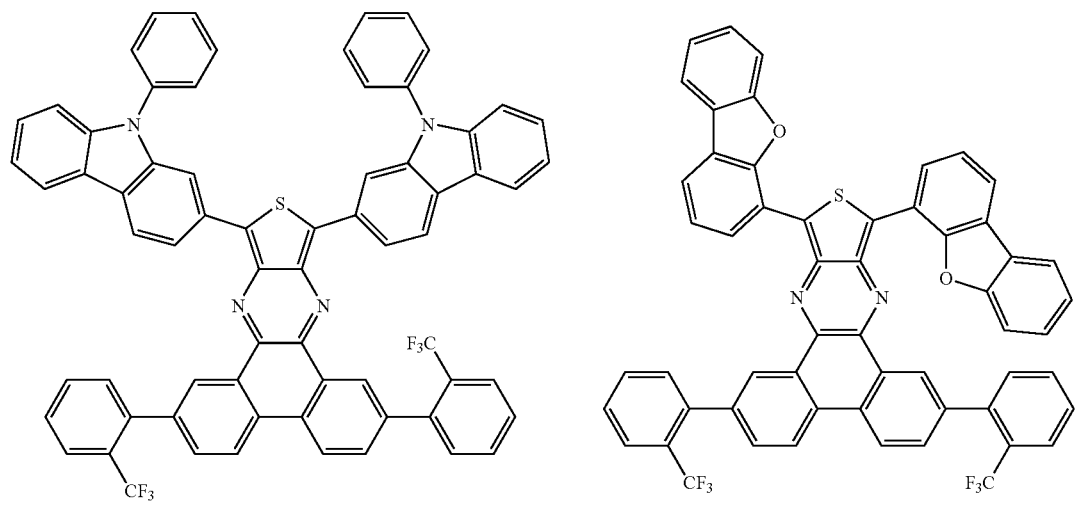
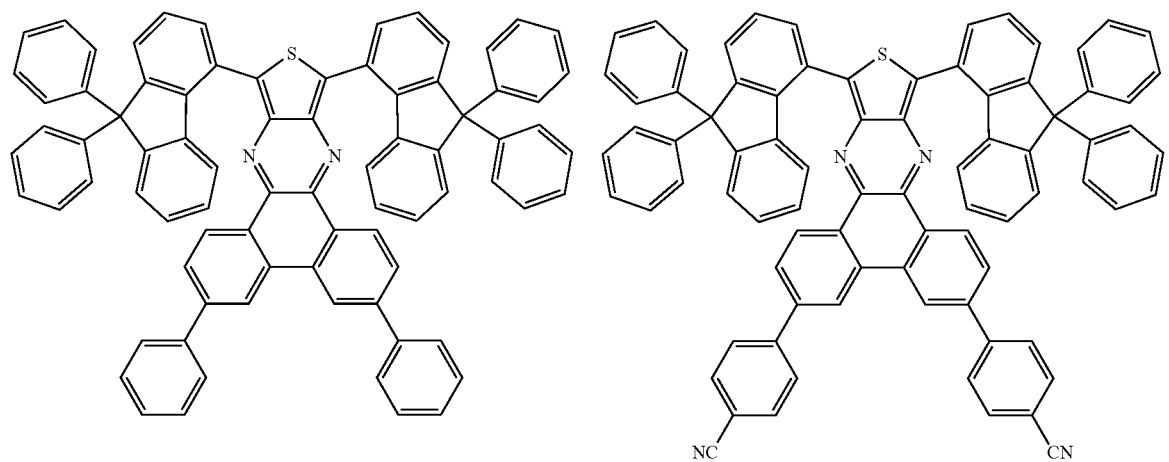

-continued
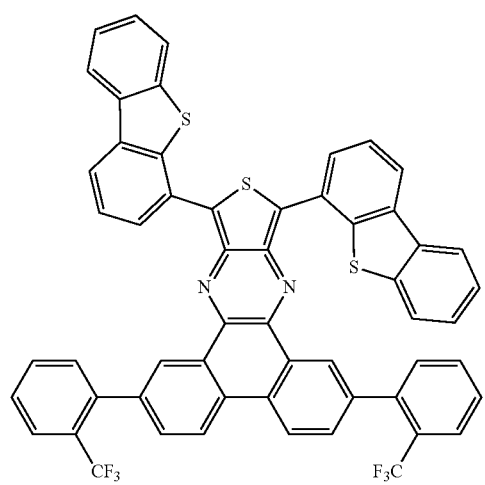
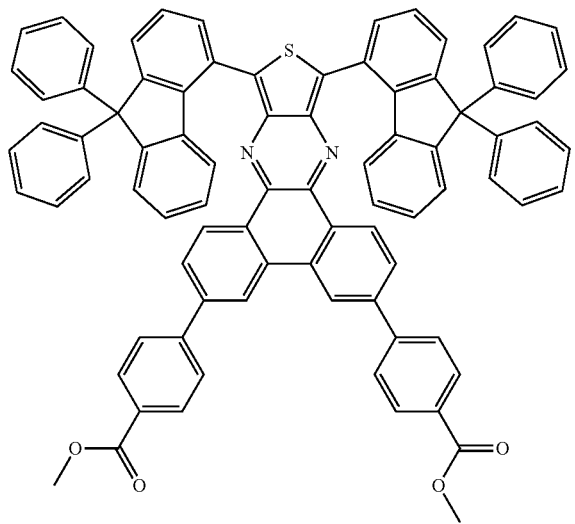
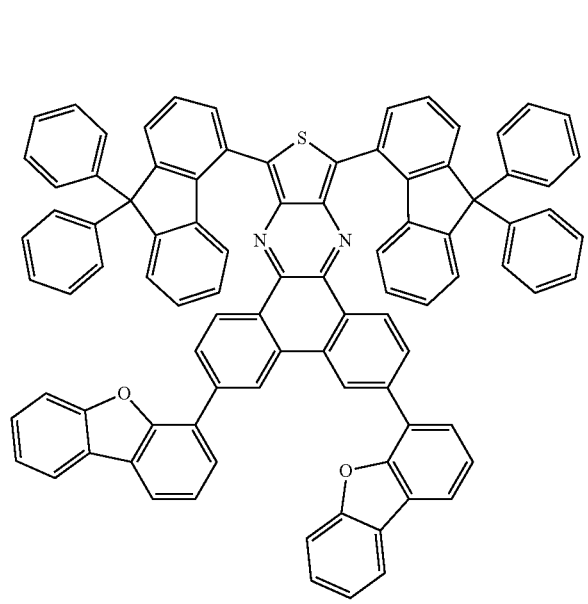
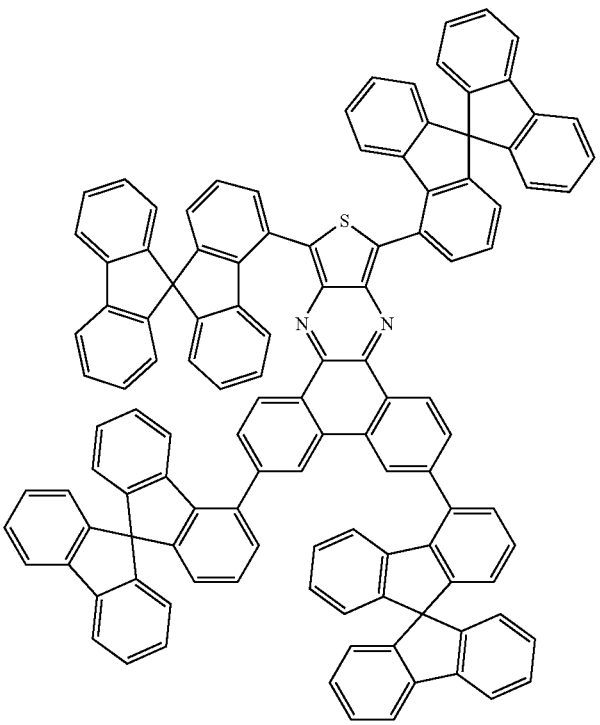

-continued
179
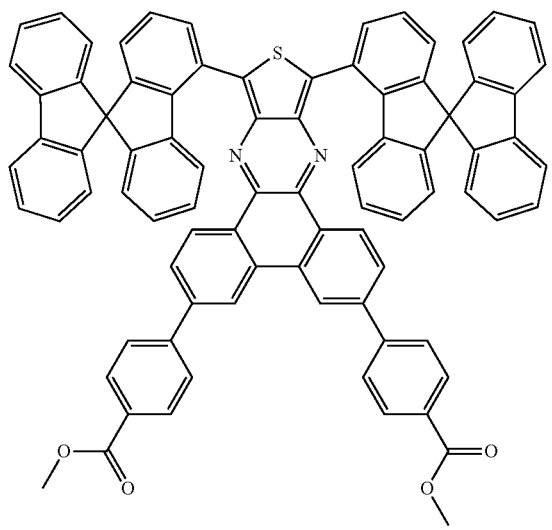
180
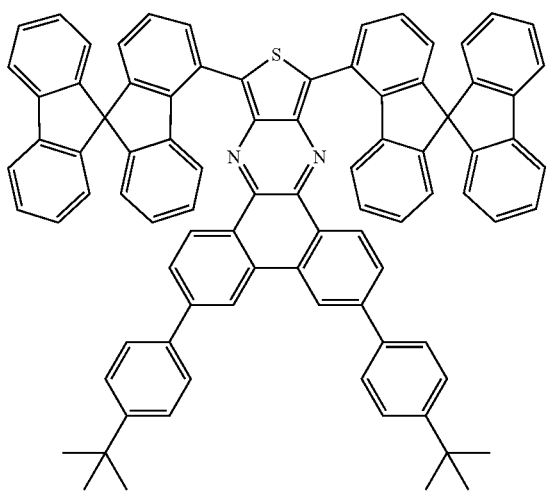
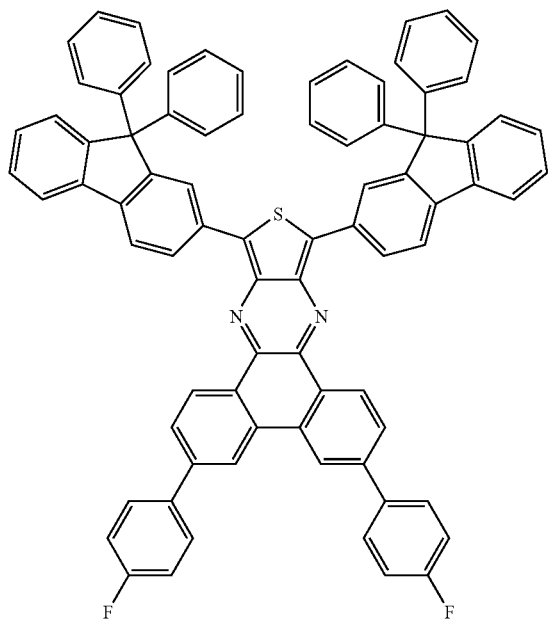
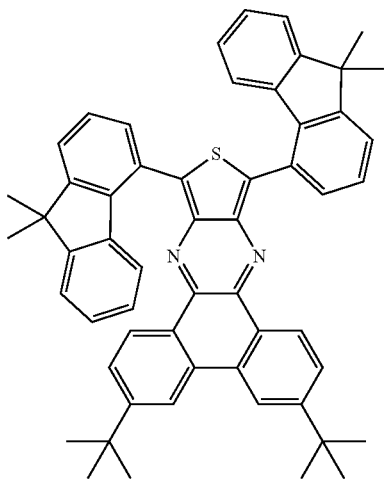
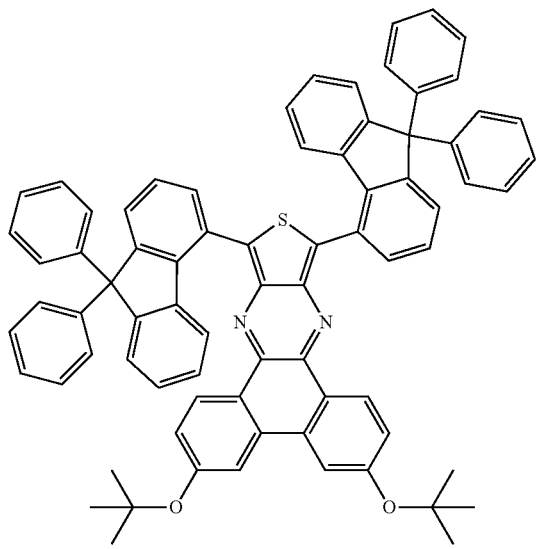
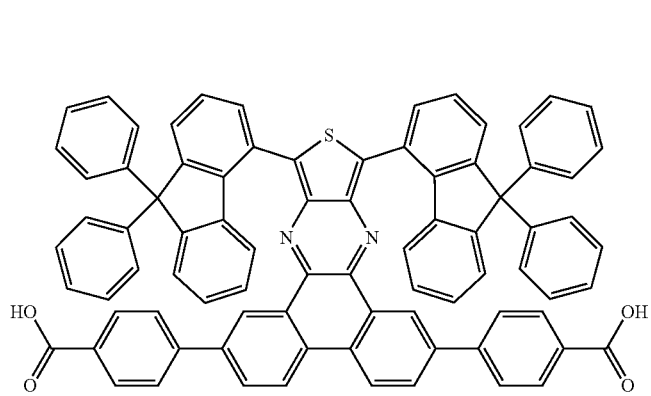

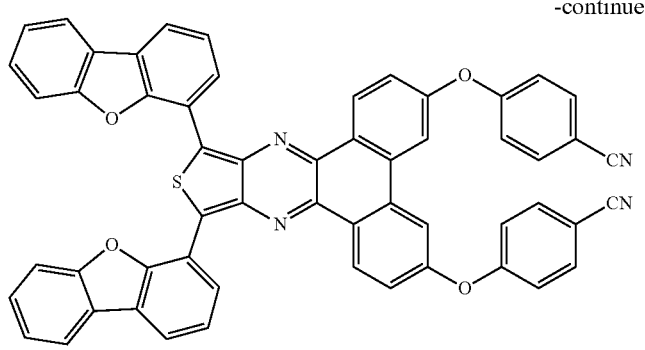

The compound according to an exemplary embodiment of the present specification may be prepared by a preparation method described below. Representative examples will be described in the Preparation Examples described below, but if necessary, a substituent may be added or excluded, and the position of the substituent may be changed. Further, a starting material, a reactant, reaction conditions, and the like may be changed based on the technology known in the art.

For example, a core structure of the compound represented by Formula 1 may be prepared as in the following General Formula 1. The substituents may be bonded by a method known in the art, and the type or position of the substituent or the number of substituents may be changed according to the technology known in the art. The substituent may be bonded as in the following General Formula 1, but the bonding method is not limited thereto.

[General Formula 1]

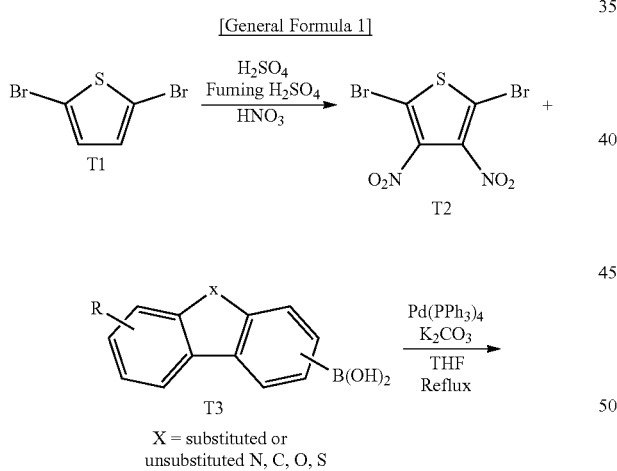

In General Formula 1, X corresponds to X1 and X2 of Formula 1, and R corresponds to R1 and R2. In the general formulae, L1, L2, Ar1, and Ar2 are not represented, but a reactant in which L1, L2, Ar1, and Ar2 are substituted may be used or L1, L2, Ar1, and Ar2 may be substituted with a product produced by General Formula 1 by a method known in the art.

An exemplary embodiment of the present specification provides a color conversion film including: a resin matrix; and the compound represented by Formula 1, which is dispersed in the resin matrix.

The content of the compound represented by Formula 1 in the color conversion film may be within a range of 0.001 to 20 wt %.

The color conversion film may include one or two or more of the compounds represented by Formula 1. For example, the color conversion film may include one compound, which emits green light, among the compounds represented by Formula 1. As another example, the color conversion film may include one compound, which emits red light, among the compounds represented by Formula 1. As still another example, the color conversion film may include one compound, which emits green light, and two or more compounds, which emit red light, among the compounds represented by Formula 1.

The color conversion film may further include an additional fluorescent material in addition to the compound represented by Formula 1. When a light source which emits blue light is used, it is preferred that the color conversion film includes both a fluorescent material which emits green light and a fluorescent material which emits red light. Further, when light sources which emit blue light and green light are used, the color conversion film may include only a fluorescent material which emits red light. However, the color conversion film is not limited thereto, and even when a light source which emits blue light is used, the color conversion film may include only a compound, which emits red light, in the case where a separate film including a fluorescent material which emits green light is stacked. Conversely, even when a light source which emits blue light is used, the color conversion film may include only a compound, which emits green light, in the case where a separate film including a fluorescent material which emits red light is stacked.

The color conversion film may further include: a resin matrix; and an additional layer including a compound which is dispersed in the resin matrix and emits light having a wavelength different from that of the compound represented by Formula 1. The compound which emits light having a wavelength different from that of the compound represented by Formula 1 may also be the compound represented by Formula 1, and may also be another publicly-known fluorescent material.

The resin matrix (binder resin) is not particularly limited as long as the resin matrix may exhibit physical properties, such as strength and developability, of a film manufactured using a resin solution. It is preferred that a material for the resin matrix is a thermoplastic polymer or a thermosetting polymer. Specifically, as the material for the resin matrix, it is possible to use a poly(meth)acrylic material such as polymethylmethacrylate (PMMA), a polycarbonate (PC)-based material, a polystyrene (PS)-based material, a polyarylene (PAR)-based material, a polyurethane (TPU)-based material, a styrene-acrylonitrile (SAN)-based material, a polyvinylidenefluoride (PVDF)-based material, a modified-polyvinylidenefluoride (modified-PVDF)-based material, and the like.

According to an exemplary embodiment of the present specification, the resin matrix is an acrylic copolymerized resin. In an exemplary embodiment, the resin matrix is a copolymer of (meth)acrylate, (meth)acrylic acid, imide, and styrene.

According to an exemplary embodiment of the present specification, the color conversion film according to the above-described exemplary embodiment additionally includes light diffusion particles. By dispersing light diffusion particles in the color conversion film instead of a light diffusion film used in the related art in order to improve brightness, an attachment process may be omitted, and higher brightness may be exhibited, as compared to the case where a separate light diffusion film is used.

As the light diffusion particle, a resin matrix and a particle having a high refractive index may be used, and it is possible to use, for example, $TiO_2$, silica, borosilicate, alumina, sapphire, air or another gas, air- or gas-filled hollow beads or particles (for example, air/gas-filled glass or polymer); polymer particles including polystyrene, polycarbonate, polymethylmethacrylate, acryl, methyl methacrylate, styrene, a melamine resin, a formaldehyde resin, or a melamine and formaldehyde resin, or any suitable combination thereof.

The particle diameter of the light diffusion particles may be within a range of 0.1 μm to 5 μm, for example, within a range of 0.3 μm to 1 μm. The content of the light diffusion particles may be determined, if necessary, and may be, for example, within a range of about 1 part by weight to about 30 parts by weight based on 100 parts by weight of the resin matrix.

The color conversion film according to the above-described exemplary embodiment may have a thickness of 0.1 μm to 200 μm. In particular, the color conversion film may exhibit high brightness even with a small thickness of 0.1 μm to 20 μm. This is because the content of the fluorescent material molecules included in a unit volume is higher than that of a quantum dot.

A base material may be provided on one surface of the color conversion film according to the above-described exemplary embodiment. The base material may function as a support at the time of preparing the color conversion film. The type of base material is not particularly limited, and the material or thickness thereof is not limited as long as the base material is transparent and may function as the support. Here, transparency means that the transmittance in visible light is 70% or more. For example, as the base material, a PET film or glass may be used. According to an exemplary embodiment of the present specification, the base material is glass.

The above-described color conversion film may be prepared by coating a base material with a resin solution, in which the above-described compound represented by Formula 1 is dissolved, and drying the resin solution, or extruding the above-described compound represented by Formula 1 together with the resin to produce a film.

Since the above-described compound represented by Formula 1 is dissolved in the resin solution, the compound represented by Formula 1 is uniformly distributed in the solution. This is different from a process of preparing a quantum dot film, which requires a separate dispersing process.

The preparation method of the resin solution in which the compound represented by Formula 1 is dissolved is not particularly limited as long as the above-described compound represented by Formula 1 and a resin are dissolved in a solution.

According to an example, the resin solution in which the compound represented by Formula 1 is dissolved may be prepared by a method of dissolving the compound represented by Formula 1 in a solvent to prepare a first solution, dissolving a resin in a solvent to prepare a second solution, and mixing the first solution with the second solution. When the first solution and the second solution are mixed, it is preferred to homogeneously mix the solutions. However, the method is not limited thereto, and it is possible to use a method of simultaneously adding the compound represented by Formula 1 and a resin to a solvent to dissolve the compound and the resin, a method of dissolving the compound represented by Formula 1 in a solvent, and subsequently adding a resin thereto to dissolve the resin, a method of dissolving a resin in a solvent, and subsequently adding the compound represented by Formula 1 thereto to dissolve the compound, and the like.

As the resin included in the solution, it is possible to use the above-described resin matrix material, a monomer which is curable by the resin matrix resin, a polyfunctional monomer or a mixture thereof. Examples of the monomer which is curable by the resin matrix resin include a (meth)acrylic monomer, and the monomer may be formed of a resin matrix material by UV curing. When a curable monomer is used as described above, an initiator required for curing may be further added, if necessary.

The polyfunctional monomer is a monomer which serves to form a photoresist image by light, and specifically, may be one or a mixture of two or more selected from the group consisting of propylene glycol methacrylate, dipentaerythritol hexaacrylate, dipentaerythritol acrylate, neopentyl glycol diacrylate, 6-hexanediol diacrylate, 1,6-hexanediol acrylate, tetraethylene glycol methacrylate, bisphenoxy ethyl alcohol diacrylate, trishydroxyethyl isocyanurate trimethacrylate, trimethyl propane trimethacrylate, diphenylpentaerythritol hexaacrylate, pentaerythritol trimethacrylate, pentaerythritol tetramethacrylate, and dipentaerythritol hexamethacrylate.

The photoinitiator is not particularly limited as long as the photoinitiator is an initiator which generates radicals by light to initiate cross-linking, but may be one or more selected from the group consisting of, for example, an acetophenone-based compound, a biimidazole-based compound, a triazine-based compound, and an oxime-based compound.

The solvent is not particularly limited, and is not particularly limited as long as the solvent does not adversely affect the coating process and may be removed by a subsequent drying. As a non-limiting example of the solvent, it is possible to use toluene, xylene, acetone, chloroform, various alcohol-based solvents, methyl ethyl ketone (MEK), methyl isobutyl ketone (MIBK), ethyl acetate (EA), butyl acetate, dimethylformamide (DMF), dimethylacetamide (DMAc), dimethylsulfoxide (DMSO), N-methyl-pyrrolidone (NMP), and the like, and one or a mixture of two or more may be used. When the first solution and the second solution are used, the solvents included in the respective solutions may also be the same as or different from each other. Even when different types of solvents are used as the first solution and the second solution, it is preferred that these solvents have compatibility so as to be mixed with each other.

According to an exemplary embodiment of the present specification, based on a total weight of 100 parts by weight of a solid content in the resin solution, the content of the resin matrix is 1 part by weight to 60 parts by weight, the content of the photoinitiator is 0.1 part by weight to 15 parts by weight, and the content of the polyfunctional monomer is 0.1 part by weight to 70 parts by weight.

According to an exemplary embodiment of the present specification, the content of the compound represented by Formula 1 is more than 0 part by weight and 30 parts by weight; 0.00001 part by weight to 15 parts by weight; 0.00001 part by weight to 10 parts by weight; 0.0001 part by weight to 5 parts by weight; or 0.00001 part by weight to 3 parts by weight, based on a total weight of 100 parts by weight of a solid content in the resin solution.

The total weight of the solid content means the sum of total weights of components in the resin solution except for the solvent. The basis of parts by weight based on the solid content and a solid content of each component may be measured by a general analysis means used in the art, such as liquid chromatography or gas chromatography.

According to an exemplary embodiment of the present specification, the content of the solvent is 100 parts by weight to 500 parts by weight based on a total weight of 100 parts by weight of the solid content in the resin solution.

According to an exemplary embodiment of the present specification, the resin solution additionally includes one or two or more additives selected from the group consisting of a photocrosslinking sensitizer, a curing accelerator, a bonding aid, a surfactant, a thermal polymerization preventing agent, a UV absorber, a dispersant, and a leveling agent.

According to an exemplary embodiment of the present specification, the content of the additive is 0.1 part by weight to 20 parts by weight based on the total weight of the solid content in the resin solution.

As the bonding aid used in the present specification, it is possible to select and use one or more among methacryloyl silane coupling agents such as methacryloyloxypropyltrimethoxysilane, methacryloyloxypropyl dimethoxysilane, methacryloyloxypropyltriethoxysilane, and methacryloyloxypropyl dimethoxysilane, and as an alkyl trimethoxy silane, it is possible to select and use one or more among octyltrimethoxy silane, dodecyltrimethoxy silane, octadecyltrimethoxy silane, and the like.

The surfactant is a silicone-based surfactant or a fluorine-based surfactant, and specifically, as the silicone-based surfactant, it is possible to use BYK-077, BYK-085, BYK-300, BYK-301, BYK-302, BYK-306, BYK-307, BYK-310, BYK-320, BYK-322, BYK-323, BYK-325, BYK-330, BYK-331, BYK-333, BYK-335, BYK-341v344, BYK-345v346, BYK-348, BYK-354, BYK-355, BYK-356, BYK-358, BYK-361, BYK-370, BYK-371, BYK-375, BYK-380, BYK-390 and the like, which are manufactured by BYK-Chemie Co., Ltd., and as the fluorine-based surfactant, it is possible to use F-114, F-177, F-410, F-411, F-450, F-493, F-494, F-443, F-444, F-445, F-446, F-470, F-471, F-472SF, F-474, F-475, F-477, F-478, F-479, F-480SF, F-482, F-483, F-484, F-486, F-487, F-172D, MCF-350SF, TF-1025SF, TF-1117SF, TF-1026SF, TF-1128, TF-1127, TF-1129, TF-1126, TF-1130, TF-1116SF, TF-1131, TF1132, TF1027SF, TF-1441, TF-1442 and the like, which are manufactured by DaiNippon Ink & Chemicals, Inc. (DIC), but the surfactants are not limited thereto.

For the process of coating a base material with the resin solution, in which the compound represented by Formula 1 is dissolved, a roll-to-roll process may be used. For example, the roll-to-roll process may be performed by a process of unwinding a base material from a roll on which the base material is wound, coating one surface of the base material with a resin solution, in which the compound represented by Formula 1 is dissolved, drying the resin solution, and then winding the base material again on the roll. When the roll-to-roll process is used, it is preferred that the viscosity of the resin solution is determined within a range in which the process may be implemented, and the viscosity may be determined within a range of, for example, 200 to 2,000 cps.

As the coating method, various publicly-known methods may be used, and for example, a die coater may also be used, and various bar-coating methods such as a comma coater and a reverse comma coater may also be used.

After the coating, a drying process is performed. The drying process may be performed under conditions required for removing the solvent. For example, it is possible to obtain a color conversion film including a fluorescent material including the compound represented by Formula 1, which has a desired thickness and concentration, on a base material by carrying out the drying in an oven located close to a coater under a condition to sufficiently evaporate a solvent, in a direction in which the base material progresses during the coating process.

When the monomer which is curable by the resin matrix resin is used as a resin included in the solution, curing, for example, UV curing may be performed before the drying or simultaneously with the drying.

When the compound represented by Formula 1 is extruded with a resin to produce a film, an extrusion method known in the art may be used, and for example, a color conversion film may be prepared by extruding the compound represented by Formula 1 with a resin such as a polycarbonate (PC)-based resin, a poly(meth)acrylic resin, and a styrene-acrylonitrile (SAN)-based resin.

According to an exemplary embodiment of the present specification, a protective film or a barrier film may be provided on at least one surface of the color conversion film. As the protective film and the barrier film, films known in the art may be used.

An exemplary embodiment of the present specification provides a backlight unit including a color conversion film including the compound represented by Formula 1. The backlight unit may have a backlight unit configuration known in the art, except that the backlight unit includes the color conversion film. FIG. 1 illustrates a schematic view of a backlight unit structure according to an example. According to FIG. 1, a color conversion film including the compound represented by Formula 1 is provided on a surface opposite to a surface of a light guide plate facing a reflective plate. FIG. 1 exemplifies a configuration including a light source and a reflective plate surrounding the light source, but the configuration is not limited to such a structure, and may be modified depending on the structure of the backlight unit known in the art. Further, as a light source, a direct type as well as a side chain type may be used, and a reflective plate or a reflective layer may be omitted or replaced with other configurations, if necessary, and an additional film, for example, a light diffusion film, a light collecting film, a brightness enhancement film, and the like may be further provided, if necessary. Preferably, on the color conversion film, a prism sheet, a multilayer reflective polarizer film, a light collecting film or a brightness enhancement film is additionally provided.

In the configuration of the backlight unit illustrated in FIG. 1, a scattering pattern may be provided on an upper or lower surface of the light guide plate, if necessary. Light incident into the light guide plate has a non-uniform light distribution caused by repeated optical processes such as reflection, total reflection, refraction, and transmission, and the scattering pattern may be used for inducing the non-uniform light distribution to uniform luminance.

An exemplary embodiment of the present specification provides a display device including the backlight unit. The display device is not particularly limited as long as the display device is a display device including a backlight unit. For example, the display device includes a display module and a backlight unit. FIG. 2 illustrates a structure of a display device. However, the structure is not limited thereto, and an additional film, for example, a light diffusion film, a light collecting film, a brightness enhancement film, and the like may be further provided between the display module and the backlight unit, if necessary.

Hereinafter, the present specification will be described in detail with reference to Examples for specifically describing the present specification. However, the Examples according to the present specification may be modified in various forms, and it is not interpreted that the scope of the present application is limited to the Examples described in detail below. The Examples of the present application are provided to more completely explain the present specification to a person with ordinary skill in the art.

PREPARATION EXAMPLES

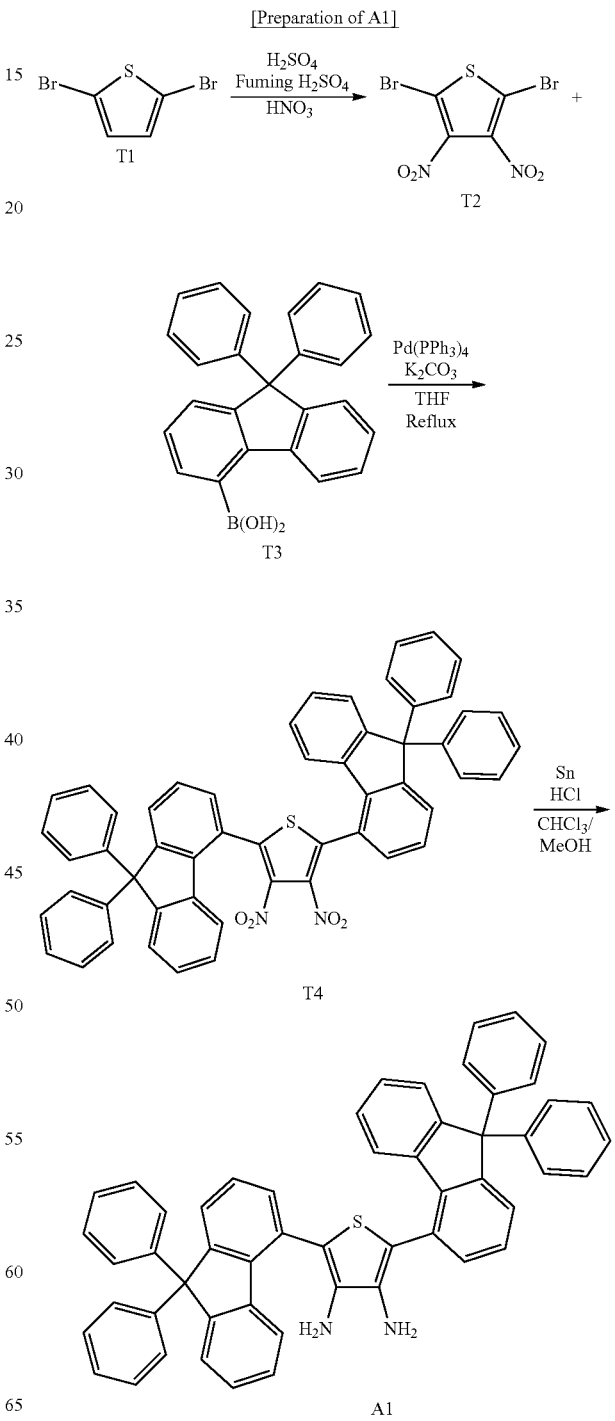

[Preparation of A1]

1) Synthesis of T2

After 10 equivalents of sulfuric acid and 10 equivalents of fuming sulfuric acid were mixed in a 1 LK reaction vessel, the resulting solution was slowly stirred at 0° C. After the temperature was stabilized for 30 minutes, 1 equivalent of Compound T1 was slowly added dropwise thereto, and then 5 equivalents of nitric acid was slowly put thereinto. After the nitric acid was completely added dropwise thereto, the reaction was performed at room temperature for 3 hours. After the reaction was completed, the acid was diluted by putting ice water thereinto, and then the reactant was filtered. After the filtered reactant was dissolved in tetrahydrofuran (THF) and neutralized using a $NaHCO_3$ solution, an extraction was performed, moisture was removed from the extracted organic layer using magnesium sulfate, and then the solvent was concentrated through distillation under reduced pressure. The concentrated product was recrystallized using THF and ethanol to secure Compound T2. (Yield 72%) HR LC/MS/MS m/z calcd for $C_4Br_2N_2O_4S$ (M+): 331.7925; found: 331.7924

2) Synthesis of T4

1 equivalent of the prepared Compound T2 and 2.5 equivalents of Compound T3 were dissolved in a THF solvent in a 1 L reaction vessel, and the resulting solution was stirred under nitrogen. 6 equivalents of potassium carbonate were dissolved in water, and the resulting solution was added to the solution of T2 and T3 which was being stirred. After the addition was completed, the solution was stirred under nitrogen by increasing the temperature to 80° C. After the heating, the temperature was stabilized for 30 minutes, and then the reaction was performed by adding 0.05 equivalent of a catalyst Pd(PPh3)4 thereto. After 3 hours, when the reaction was completed, the reactant was purified by lowering the temperature to room temperature. An extraction was performed by additionally introducing water and tetrahydrofuran (THF) into the completed reactant, and moisture was removed from the extracted organic layer using anhydrous magnesium sulfate, and then the solvent was concentrated through distillation under reduced pressure. The concentrated product was recrystallized using tetrahydrofuran (THF) and ethanol to secure Compound T4.

3) Synthesis of A1

After 1 equivalent of the prepared Compound T4 was dissolved in a 1 L reaction vessel using a chloroform/methanol solvent (4/1), 20 equivalents of tin were added thereto, and the resulting solution was stirred together. Thereafter, the reaction was performed by slowly adding 80 equivalents of hydrochloric acid thereto. After the reaction was completed, filtration was performed using celite, and then the product was neutralized using an aqueous NaOH solution, and then the reactant was purified. An extraction was performed by introducing water and tetrahydrofuran (THF) into the reactant, and moisture was removed from the extracted organic layer using anhydrous magnesium sulfate, and then the solvent was concentrated through distillation under reduced pressure. The concentrated product was recrystallized using tetrahydrofuran (THF) and ethanol to secure Compound A1.

In addition to A1, A2 to A10 may be prepared by changing T3 during the synthesis process of T4.

Preparation Example 1

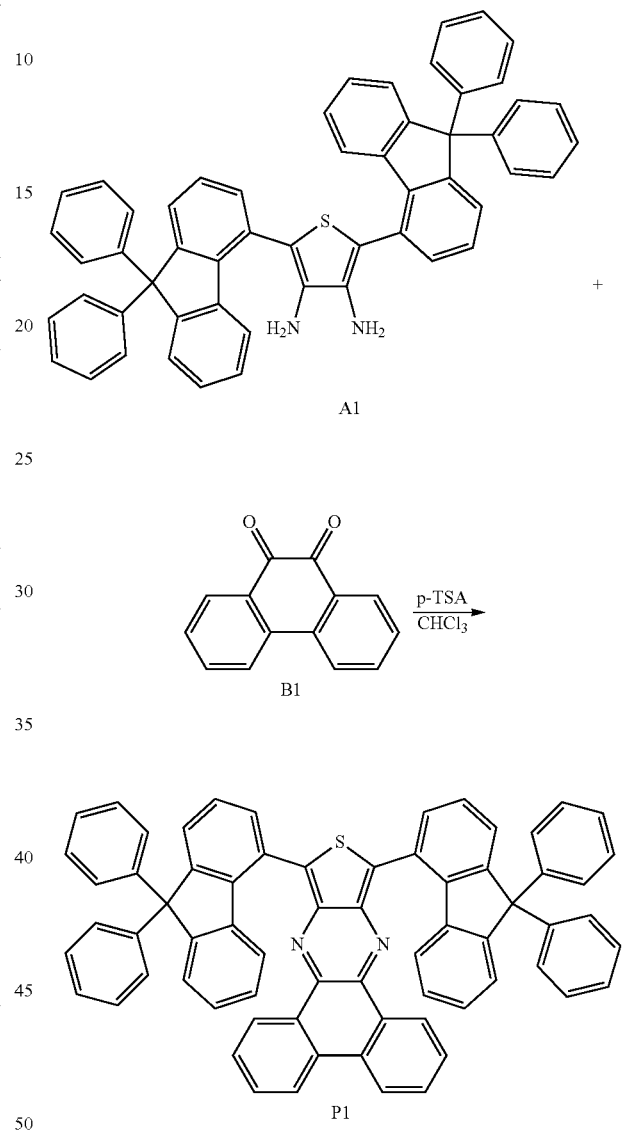

Compound A1 (3 g, 1 equivalent) secured above was dissolved in a chloroform solvent together with 0.81 g (1.05 equivalent) of Compound B1 and a catalytic amount of para toluene sulfonic acid. The reaction was performed at room temperature under nitrogen, and 3 hours after the reaction, the purification was performed by completing the reaction. An extraction was performed by additionally introducing water and chloroform into the completed reactant, and moisture was removed from the extracted organic layer using anhydrous magnesium sulfate, and then the solvent was concentrated through distillation under reduced pressure. The concentrated product was recrystallized using chloroform and ethanol to secure Compound P1. (3.17 g, yield 86%) HR LC/MS/MS m/z calcd for $C_{68}H_{42}N_2S$ (M+): 918.3069; found: 918.3068

Preparation Example 2

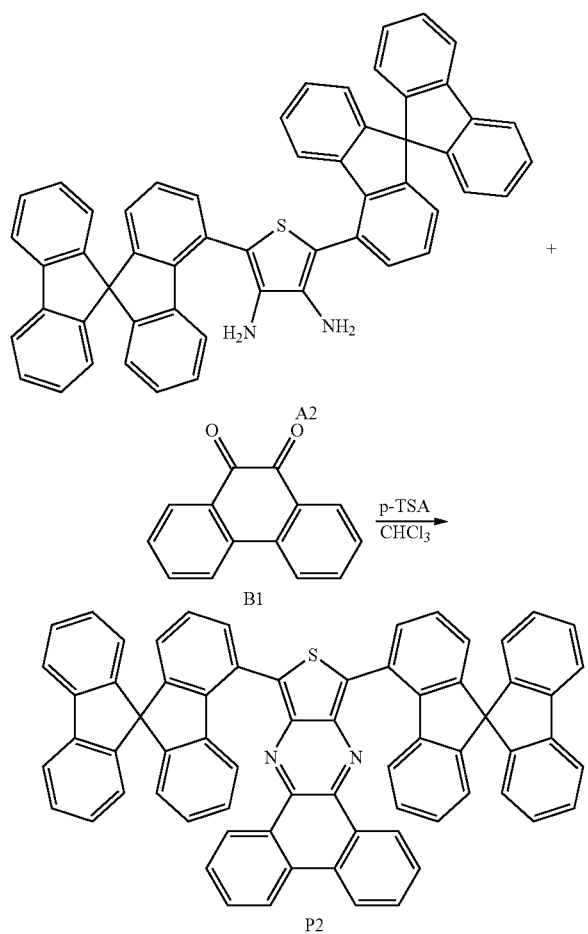

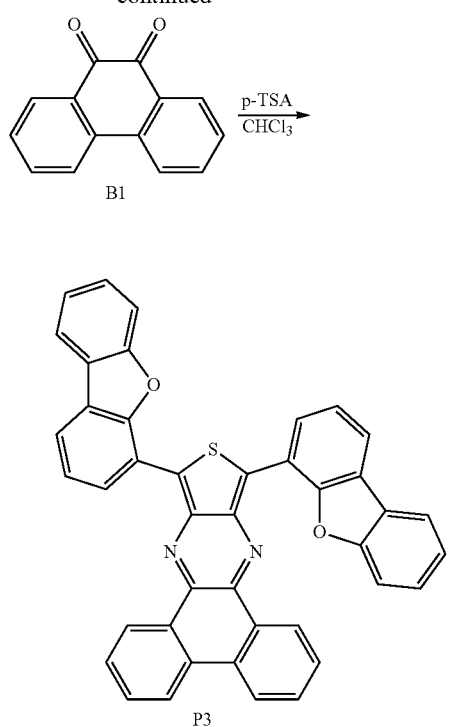

Compound P2 was secured by performing the synthesis along with Compound B1 (0.82 g, 1.05 equivalents) and para toluene sulfonic acid in the same manner as in Preparation Example 1, except that Compound A2 (3 g, 1 equivalent) was used instead of Compound A1. (2.88 g, yield 78%) HR LC/MS/MS m/z calcd for $C_{68}H_{38}N_2S$ (M+):914.2756; found: 914.2757

Preparation Example 3

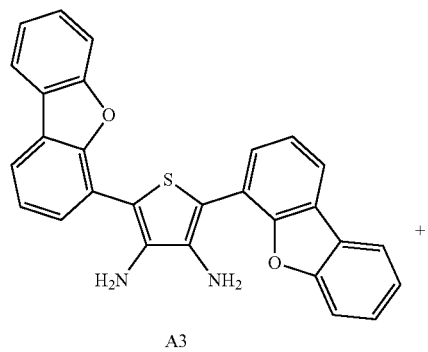

Compound P3 was secured by performing the synthesis along with Compound B1 (1.29 g, 1.05 equivalents) and para toluene sulfonic acid in the same manner as in Preparation Example 1, except that Compound A3 (3 g, 1 equivalent) was used instead of Compound A1. (3.20 g, yield 77%) HR LC/MS/MS m/z calcd for $C_{42}H_{22}N_2O_2S$ (M+): 618.1402; found: 618.1400

Preparation Example 4

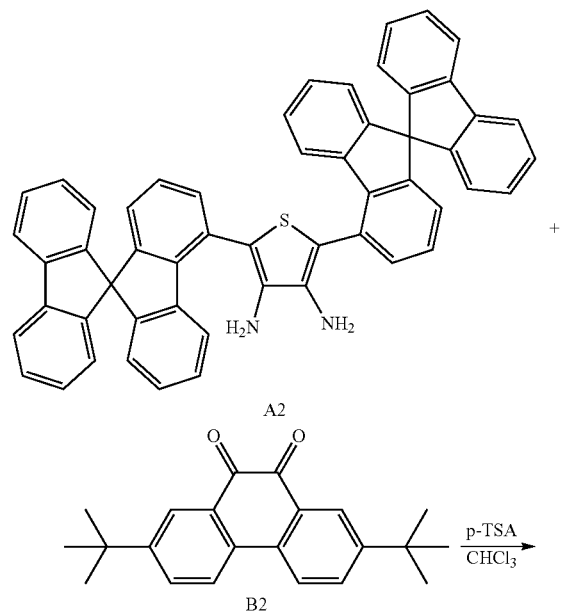

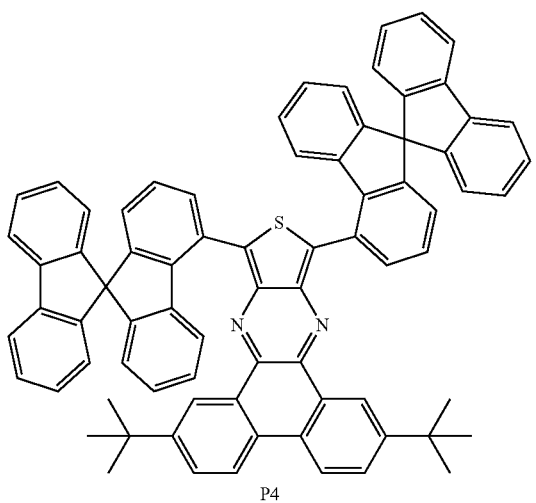

P4

Compound P4 was secured by performing the synthesis in the same manner as in Preparation Example 1, except that Compound A2 (3 g, 1 equivalent) was used instead of Compound A1 and Compound B2 (2.21 g, 1.05 equivalents) was used instead of Compound B1. (2.99 g, yield 72%) HR LC/MS/MS m/z calcd for $C_{76}H_{54}N_2O_2S$ (M+):1026.4088; found: 1026.4087

Preparation Example 5

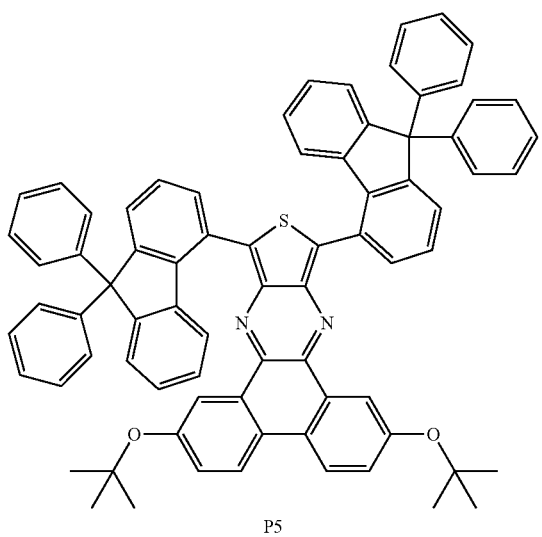

P5

Compound P5 was secured by performing the synthesis in the same manner as in Preparation Example 1, except that Compound A1 (3 g, 1 equivalent) and Compound B3 (1.38 g, 1.05 equivalents) were used instead of Compound B1. (3.58 g, yield 84%) HR LC/MS/MS m/z calcd for $C_{76}H_{58}N_2O_2S$ (M+):1062.4219; found: 1062.4219

Preparation Example 6

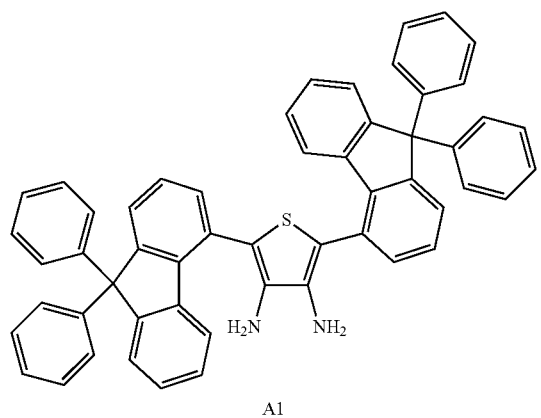

A1

+

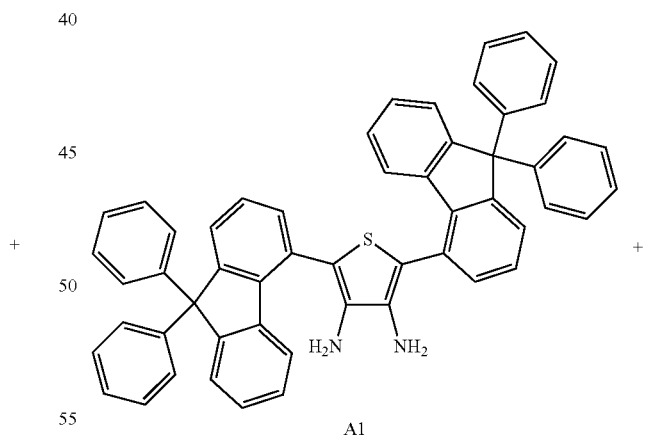

A1

+

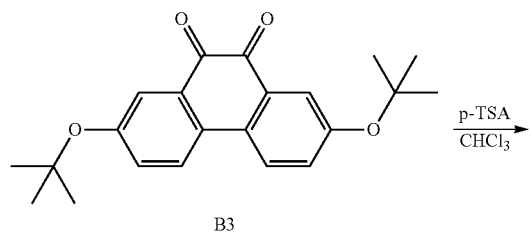

B3

$\xrightarrow{\text{p-TSA}}{\text{CHCl}_3}$

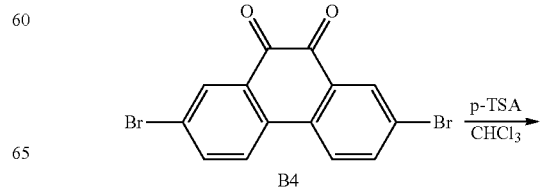

B4

$\xrightarrow{\text{p-TSA}}{\text{CHCl}_3}$

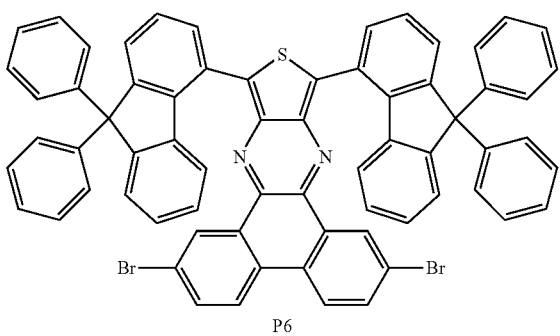

P6

Compound P6 was secured by performing the synthesis in the same manner as in Preparation Example 1, except that Compound A1 (3 g, 1 equivalent) and Compound B4 (1.43 g, 1.05 equivalents) were used instead of Compound B1. (2.34 g, yield 54%) HR LC/MS/MS m/z calcd for $C_{76}H_{40}Br_2N_2S$ (M+):1076.1258; found: 1076.1258

Preparation Example 7

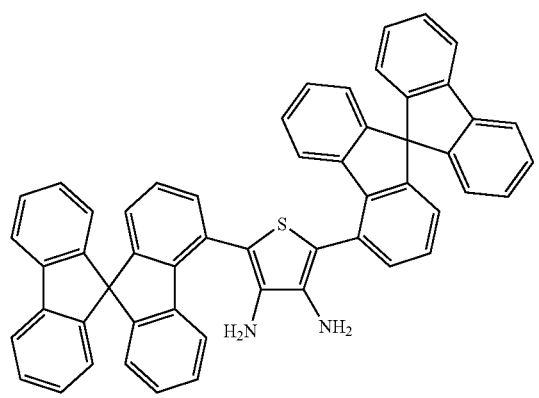

A2

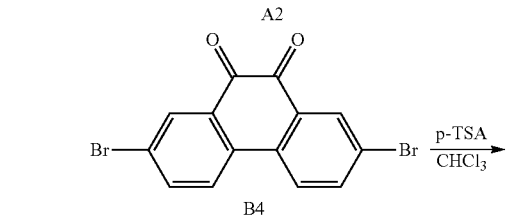

B4

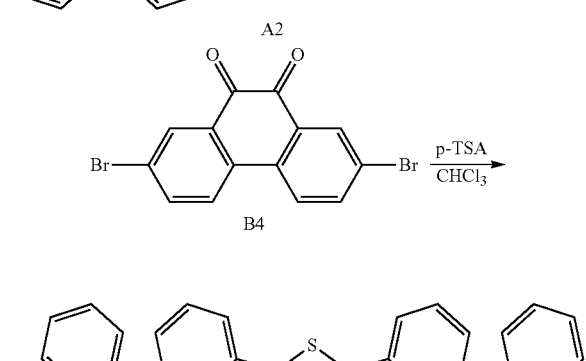

P7

Compound P7 was secured by performing the synthesis in the same manner as in Preparation Example 1, except that Compound A2 (5 g, 1 equivalent) was used instead of Compound A1 and Compound B4 (2.39 g, 1.05 equivalents) was used instead of Compound B1. (5.13 g, yield 71%) HR LC/MS/MS m/z calcd for $C_{68}H_{36}Br_2N_2S$ (M+):1072.0945; found: 1072.0944

Preparation Example 8

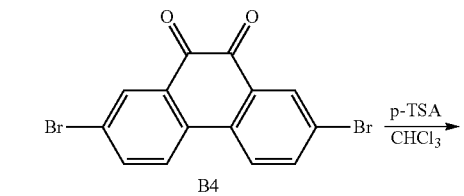

A4

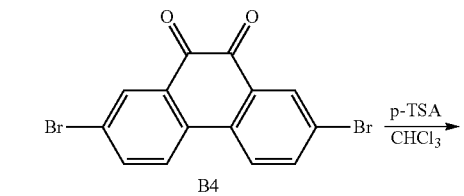

B4

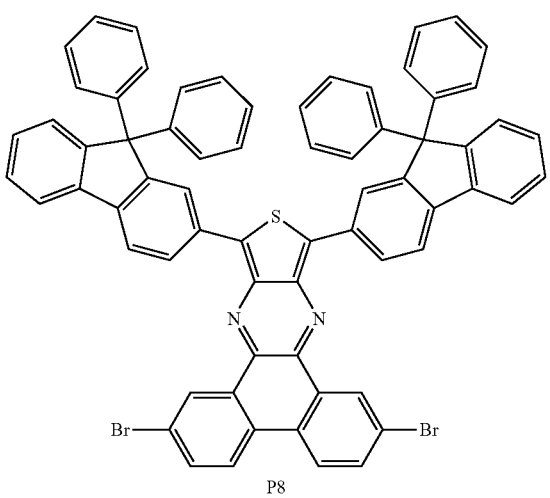

P8

Compound P8 was secured by performing the synthesis in the same manner as in Preparation Example 1, except that Compound A4 (5 g, 1 equivalent) was used instead of Compound A1 and Compound B4 (2.38 g, 1.05 equivalents) was used instead of Compound B1. (4.47 g, yield 67%) HR LC/MS/MS m/z calcd for $C_{68}H_{40}Br_2N_2S$ (M+):1076.1258; found: 1076.1257

Preparation Example 9

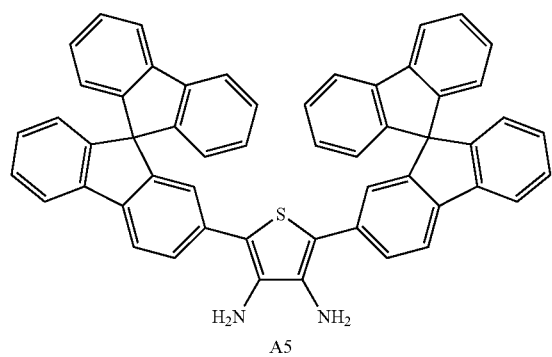

A5

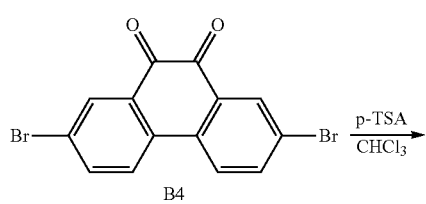

B4

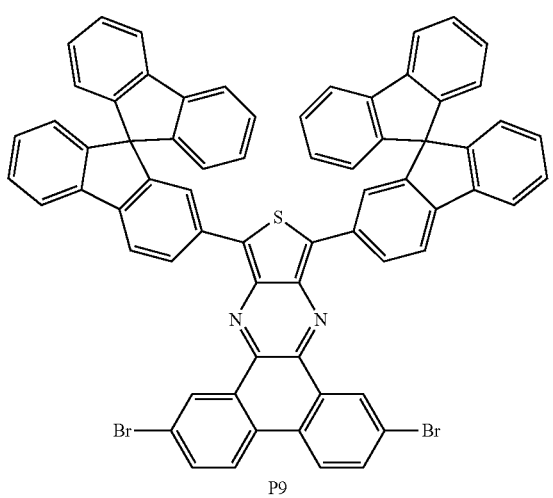

P9

Compound P9 was secured by performing the synthesis in the same manner as in Preparation Example 1, except that Compound A5 (5 g, 1 equivalent) was used instead of Compound A1 and Compound B4 (2.39 g, 1.05 equivalents) was used instead of Compound B1. (4.91 g, yield 68%) HR LC/MS/MS m/z calcd for $C_{68}H_{36}Br_2N_2S$ (M+):1072.0945; found: 1072.0944

Preparation Example 10

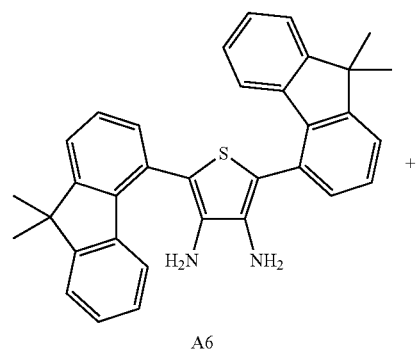

A6

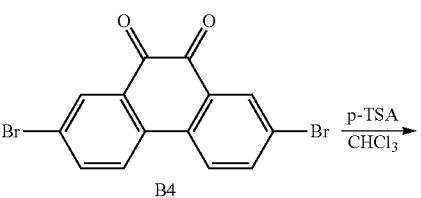

B4

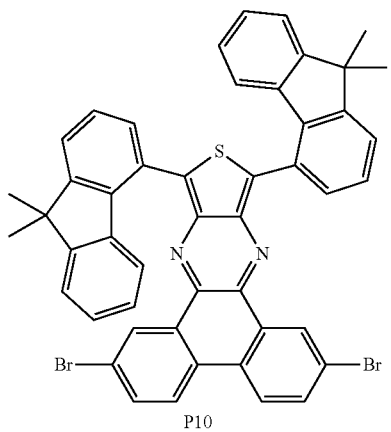

P10

Compound P10 was secured by performing the synthesis in the same manner as in Preparation Example 1, except that Compound A6 (5 g, 1 equivalent) was used instead of Compound A1 and Compound B4 (3.44 g, 1.05 equivalents) was used instead of Compound B1. (4.74 g, yield 57%) HR LC/MS/MS m/z calcd for $C_{48}H_{32}Br_2N_2S$ (M+):828.0632; found: 828.0633

Preparation Example 11

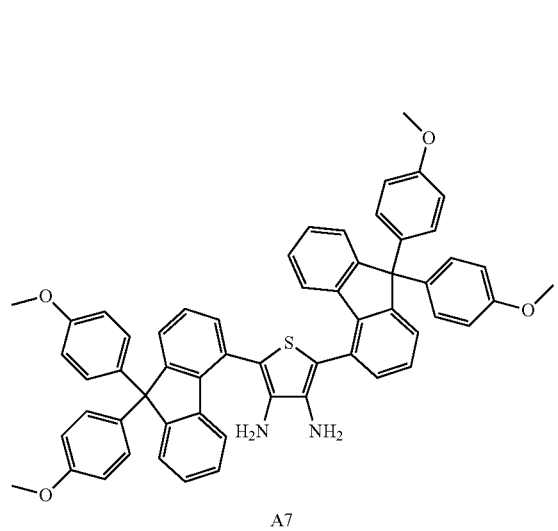

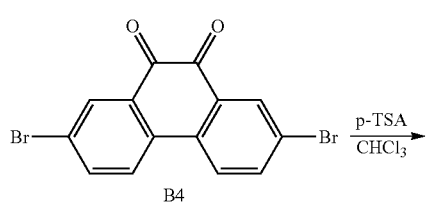

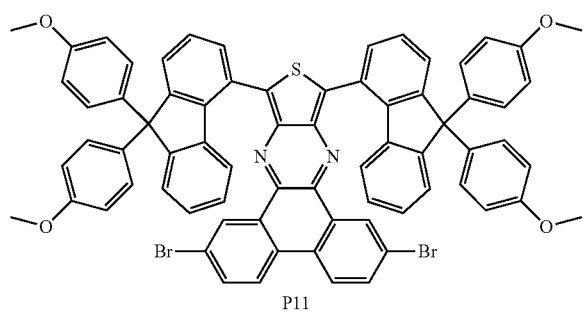

Compound P11 was secured by performing the synthesis in the same manner as in Preparation Example 1, except that Compound A7 (3 g, 1 equivalent) was used instead of Compound A1 and Compound B4 (1.24 g, 1.05 equivalents) was used instead of Compound B1. (3.11 g, yield 75%) HR LC/MS/MS m/z calcd for $C_{72}H_{48}Br_2N_2O_4S$ (M+): 1196.1681; found: 1196.1682

Preparation Example 12

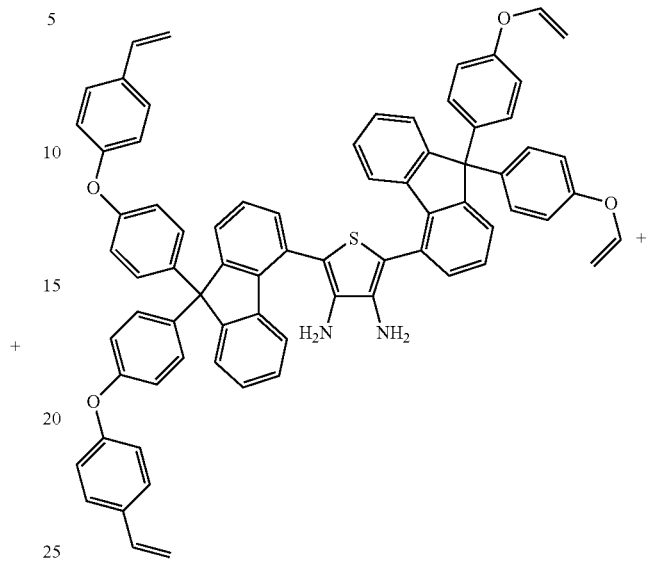

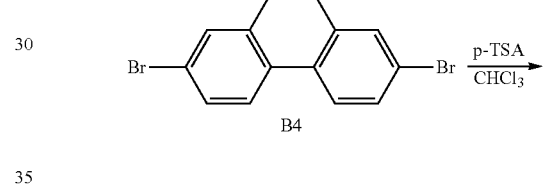

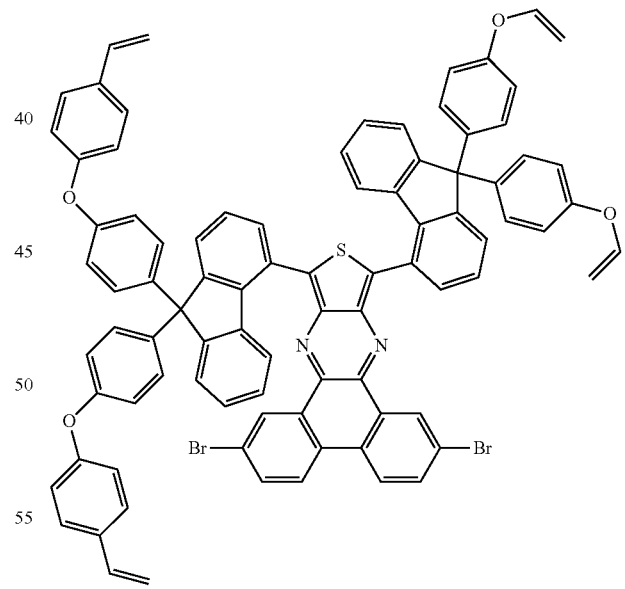

Compound P12 was secured by performing the synthesis in the same manner as in Preparation Example 1, except that Compound A8 (3 g, 1 equivalent) was used instead of Compound A1 and Compound B4 (1.02 g, 1.05 equivalents) was used instead of Compound B1. (2.59 g, yield 66%) HR LC/MS/MS m/z calcd for $C_{86}H_{68}Br_2N_2O_4S$ (M+): 1396.2307; found: 1396.2306

Preparation Example 13

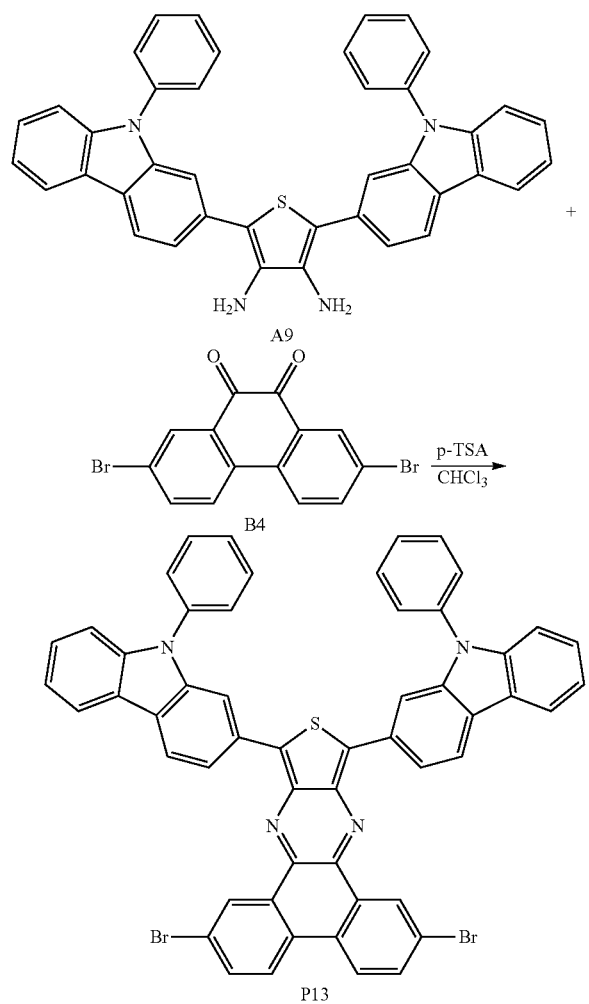

Compound P13 was secured by performing the synthesis in the same manner as in Preparation Example 1, except that Compound A9 (3 g, 1 equivalent) was used instead of Compound A1 and Compound B4 (1.76 g, 1.05 equivalents) was used instead of Compound B1. (3.18 g, yield 75%) HR LC/MS/MS m/z calcd for $C_{54}H_{30}Br_2N_2S$ (M+):926.0537; found: 926.0537

Preparation Example 14

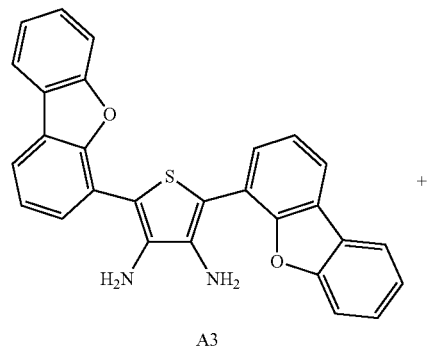

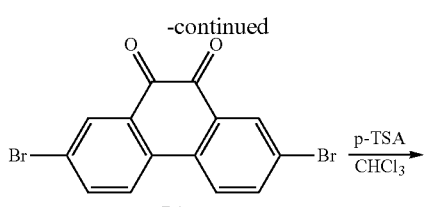

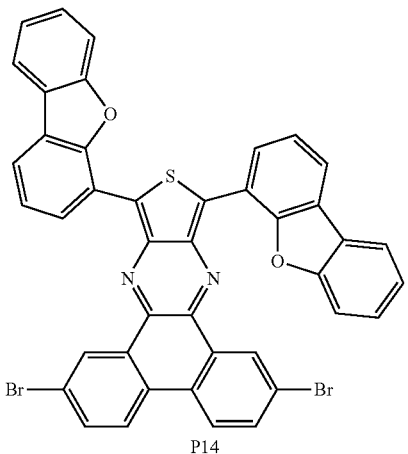

Compound P14 was secured by performing the synthesis in the same manner as in Preparation Example 1, except that Compound A3 (3 g, 1 equivalent) was used instead of Compound A1 and Compound B4 (2.28 g, 1.05 equivalents) was used instead of Compound B1. (2.35 g, yield 62%) HR LC/MS/MS m/z calcd for $C_{42}H_{20}Br_2N_2O_2S$ (M+): 775.9592; found: 775.9593

Preparation Example 15

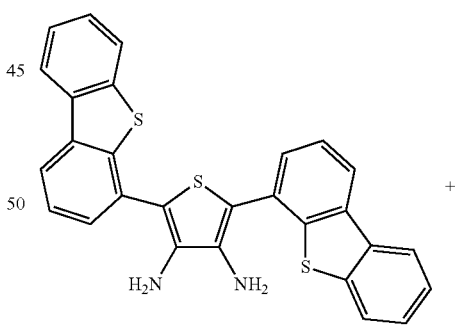

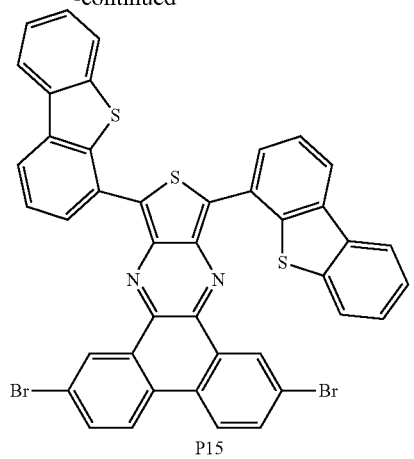

P15

Compound P15 was secured by performing the synthesis in the same manner as in Preparation Example 1, except that Compound A10 (3 g, 1 equivalent) was used instead of Compound A1 and Compound B4 (2.14 g, 1.05 equivalents) was used instead of Compound B1. (2.84 g, yield 63%) HR LC/MS/MS m/z calcd for $C_{42}H_{20}Br_2N_2S$ (M+):807.9135; found: 807.9135

Preparation Example 16

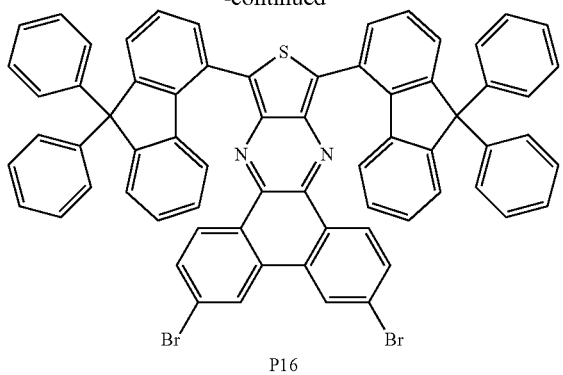

P16

Compound P16 was secured by performing the synthesis in the same manner as in Preparation Example 1, except that Compound A1 (5 g, 1 equivalent) and Compound B5 (2.38 g, 1.05 equivalents) were used instead of Compound B1. (4.47 g, yield 62%) HR LC/MS/MS m/z calcd for $C_{68}H_{40}Br_2N_2S$ (M+):1076.1258; found: 1076.1257

Preparation Example 17

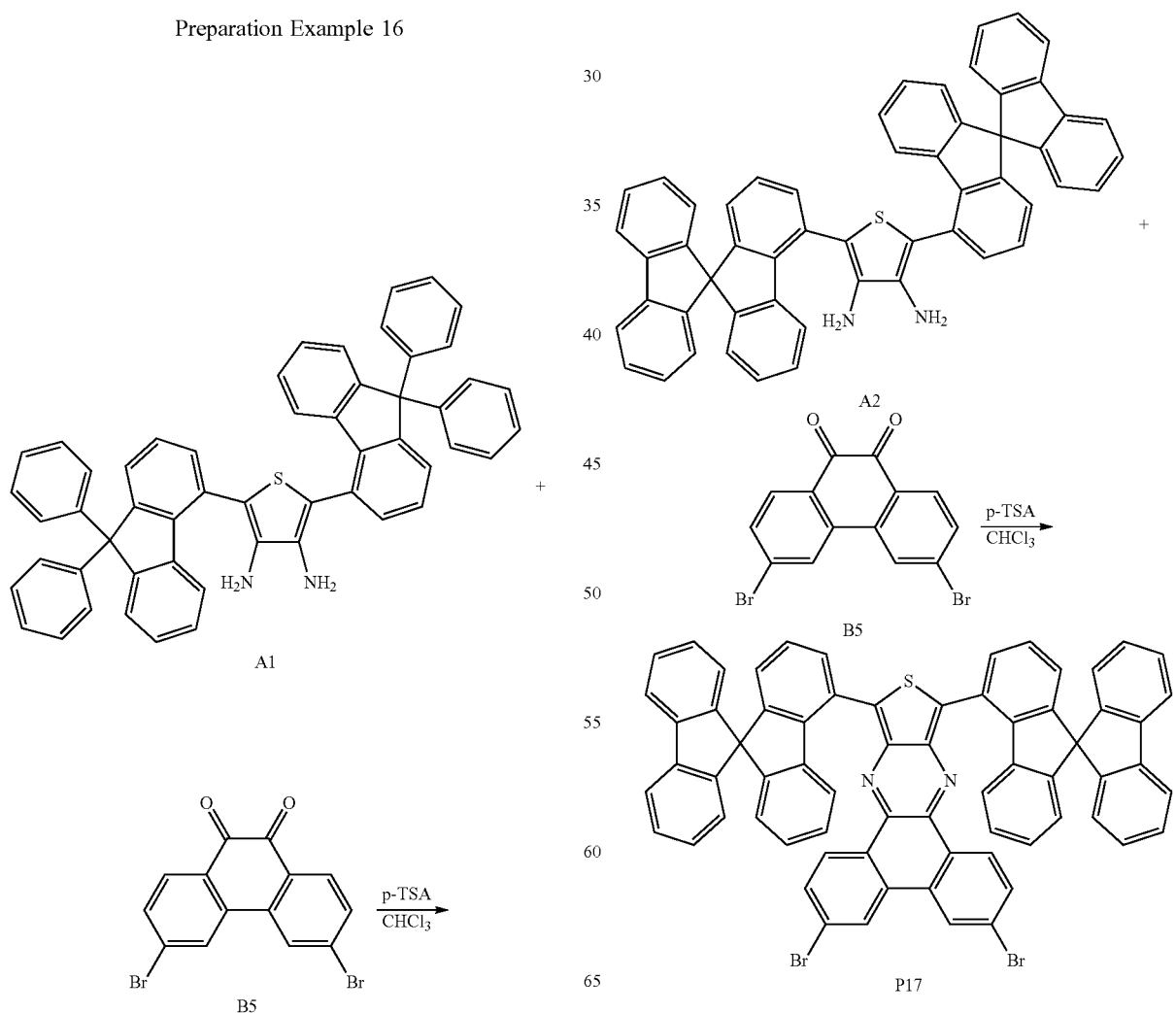

Compound P17 was secured by performing the synthesis in the same manner as in Preparation Example 1, except that Compound A2 (5 g, 1 equivalent) was used instead of Compound A1 and Compound B5 (2.39 g, 1.05 equivalents) was used instead of Compound B1. (5.13 g, yield 71%) HR LC/MS/MS m/z calcd for $C_{68}H_{36}Br_2N_2S$ (M+):1072.0945; found: 1072.0944 was used instead of Compound B1. (3.87 g, yield 58%) HR LC/MS/MS m/z calcd for $C_{68}H_{40}Br_2N_2S$ (M+):1076.0945; found: 1076.0944

Preparation Example 18

Preparation Example 19

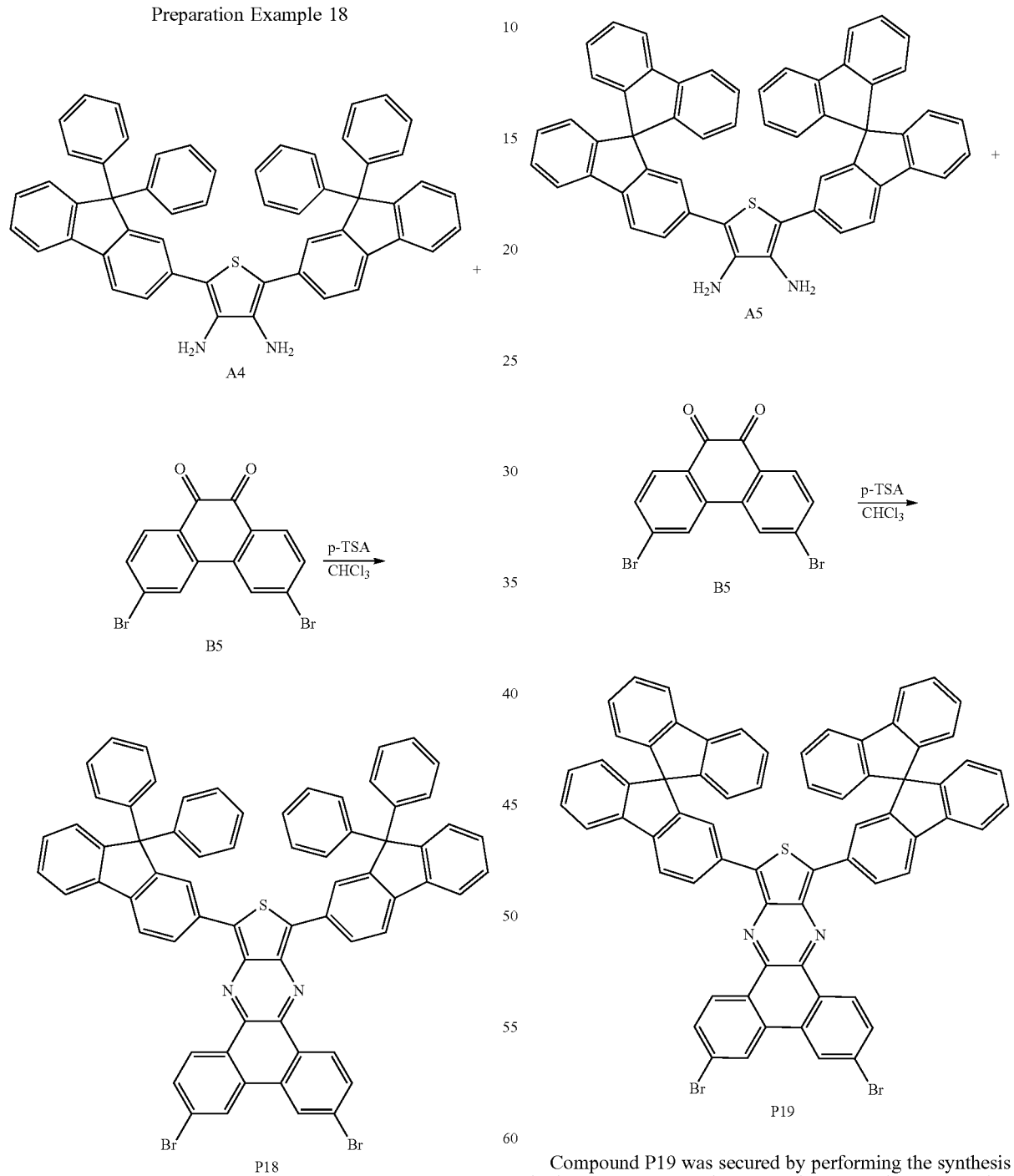

Compound P18 was secured by performing the synthesis in the same manner as in Preparation Example 1, except that Compound A4 (5 g, 1 equivalent) was used instead of Compound A1 and Compound B5 (2.38 g, 1.05 equivalents)

Compound P19 was secured by performing the synthesis in the same manner as in Preparation Example 1, except that Compound A5 (5 g, 1 equivalent) was used instead of Compound A1 and Compound B5 (2.39 g, 1.05 equivalents) was used instead of Compound B1. (5.56 g, yield 77%) HR LC/MS/MS m/z calcd for $C_{68}H_{36}Br_2N_2S$ (M+):1072.0945; found: 1072.0945

Preparation Example 20

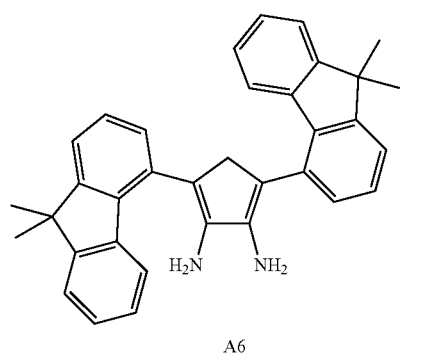

A6

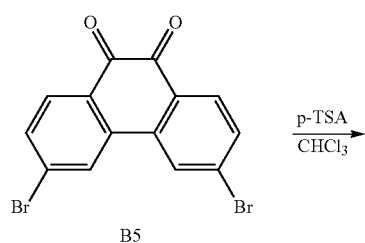

B5

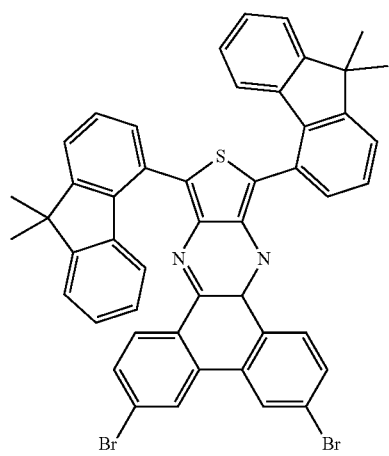

P20

Compound P20 was secured by performing the synthesis in the same manner as in Preparation Example 1, except that Compound A6 (5 g, 1 equivalent) was used instead of Compound A1 and Compound B5 (3.44 g, 1.05 equivalents) was used instead of Compound B1. (5.98 g, yield 72%) HR LC/MS/MS m/z calcd for $C_{48}H_{32}Br_2N_2S$ (M+):828.0632; found: 828.0633

Preparation Example 21

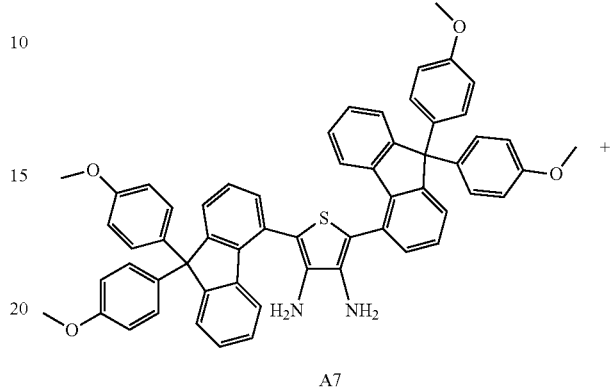

A7

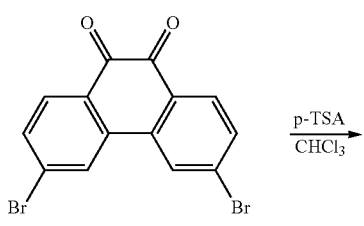

B5

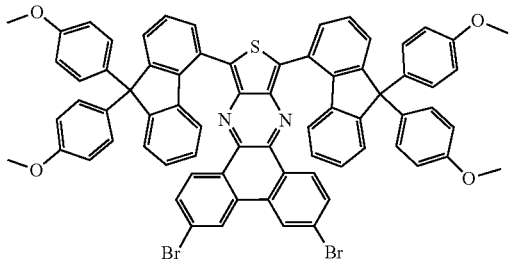

P21

Compound P21 was secured by performing the synthesis in the same manner as in Preparation Example 1, except that Compound A7 (3 g, 1 equivalent) was used instead of Compound A1 and Compound B5 (1.24 g, 1.05 equivalents) was used instead of Compound B1. (2.03 g, yield 49%) HR LC/MS/MS m/z calcd for $C_{72}H_{48}Br_2N_2O_4S$ (M+): 1196.1681; found: 1196.1682

Preparation Example 22

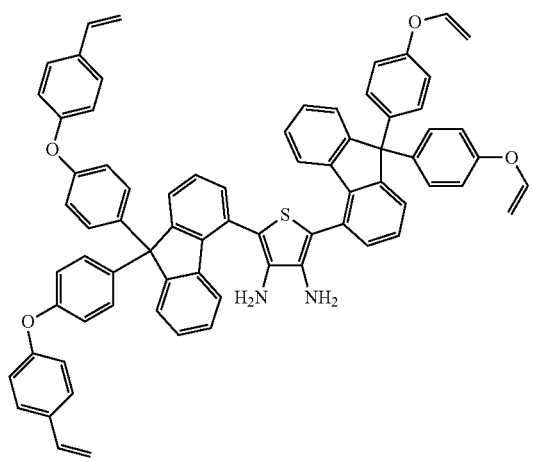

A8

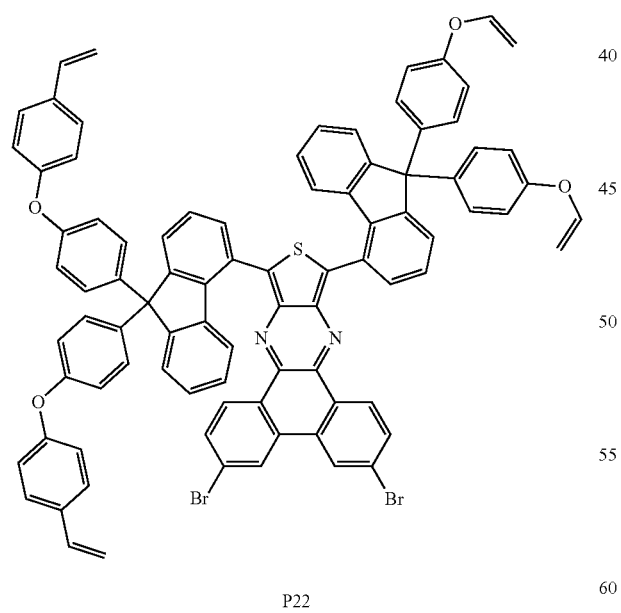

P22

Compound P22 was secured by performing the synthesis in the same manner as in Preparation Example 1, except that Compound A8 (3 g, 1 equivalent) was used instead of Compound A1 and Compound B5 (1.02 g, 1.05 equivalents) was used instead of Compound B1. (2.28 g, yield 58%) HR LC/MS/MS m/z calcd for $C_{86}H_{56}Br_2N_2O_4S$ (M+): 1396.2307; found: 1396.2306

Preparation Example 23

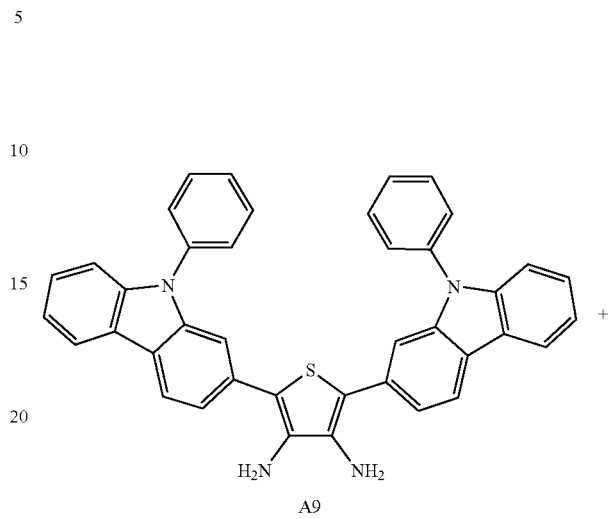

A9

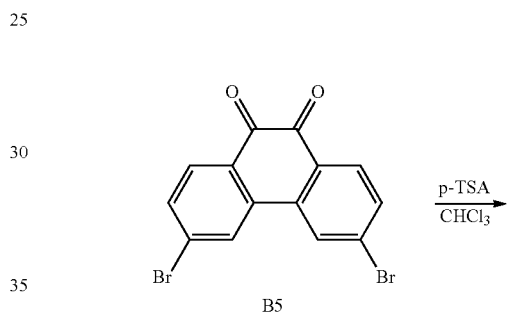

B5

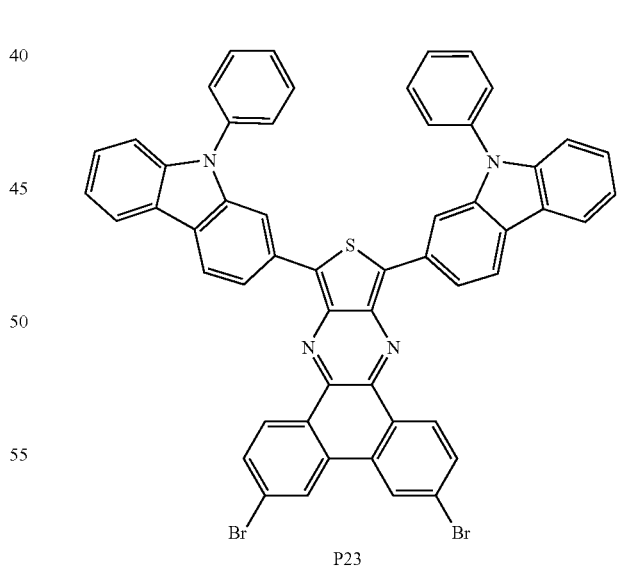

P23

Compound P23 was secured by performing the synthesis in the same manner as in Preparation Example 1, except that Compound A9 (3 g, 1 equivalent) was used instead of Compound A1 and Compound B5 (1.76 g, 1.05 equivalents) was used instead of Compound B1. (2.67 g, yield 63%) HR LC/MS/MS m/z calcd for $C_{54}H_{30}Br_2N_2S$ (M+):1396.2307; found: 1396.2307

Preparation Example 24

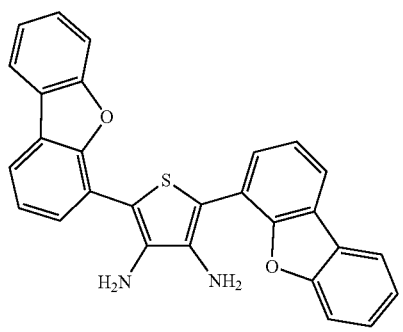

A3

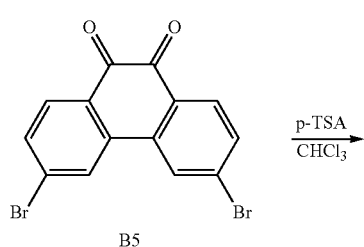

B5

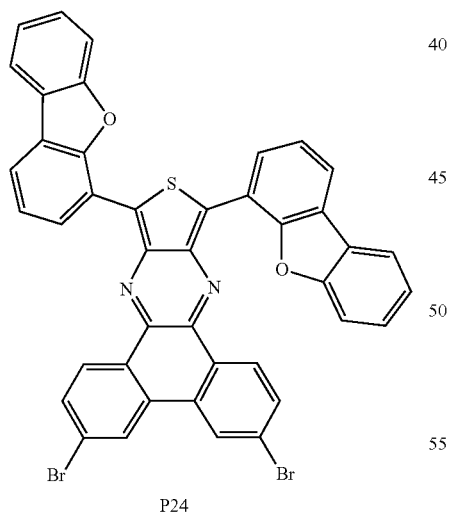

P24

Compound P24 was secured by performing the synthesis in the same manner as in Preparation Example 1, except that Compound A3 (3 g, 1 equivalent) was used instead of Compound A1 and Compound B5 (2.28 g, 1.05 equivalents) was used instead of Compound B1. (3.77 g, yield 82%) HR LC/MS/MS m/z calcd for $C_{42}H_{20}Br_2N_2O_2S$ (M+): 775.9592; found: 775.9593

Preparation Example 25

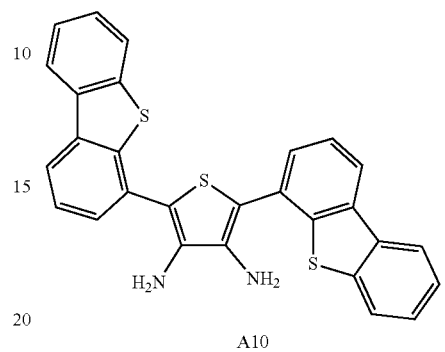

A10

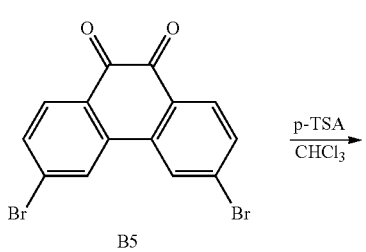

B5

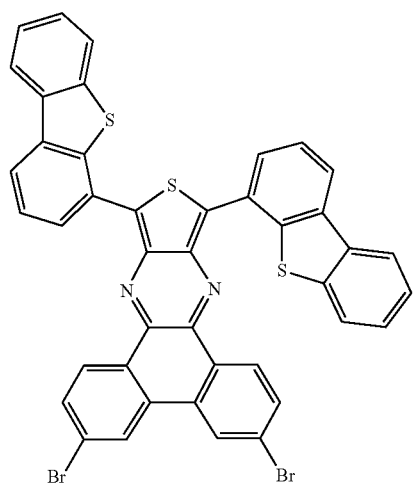

P25

Compound P25 was secured by performing the synthesis in the same manner as in Preparation Example 1, except that Compound A10 (3 g, 1 equivalent) was used instead of Compound A1 and Compound B5 (2.14 g, 1.05 equivalents) was used instead of Compound B1. (2.97 g, yield 66%) HR LC/MS/MS m/z calcd for $C_{42}H_{20}Br_2N_2S_3$ (M+):807.9135; found: 807.9134.

Preparation Example 26

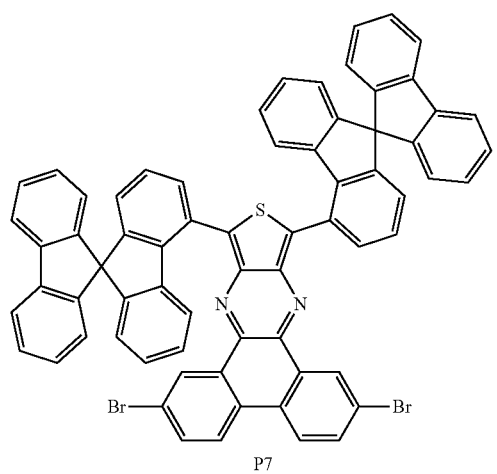

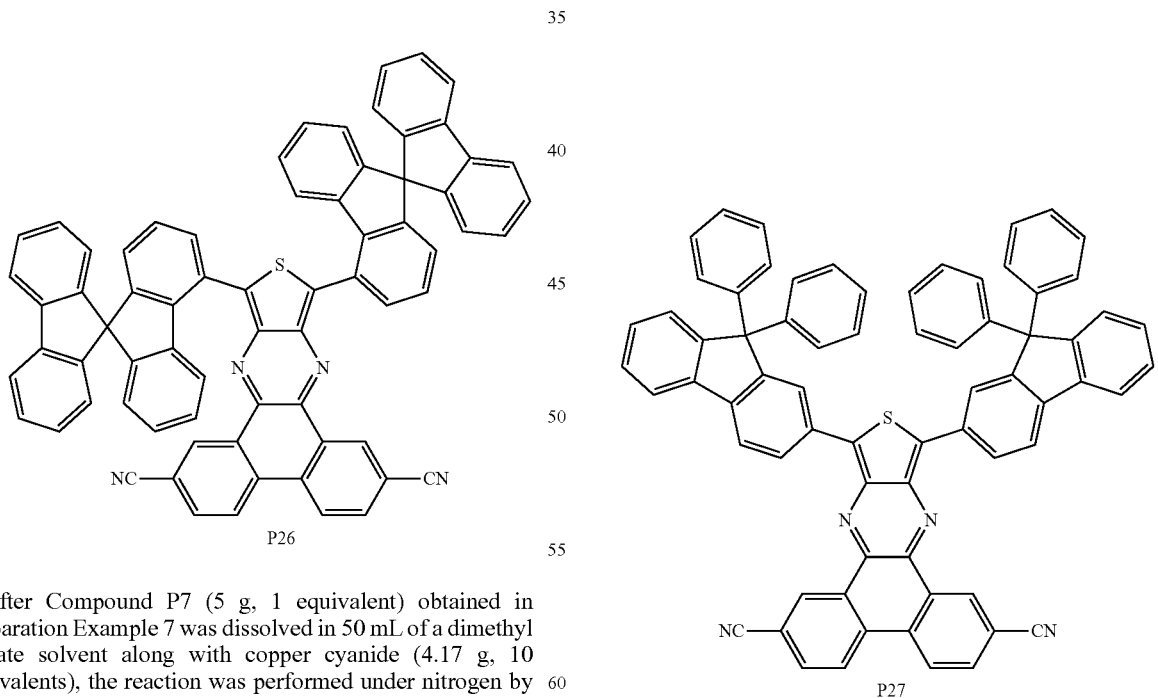

After Compound P7 (5 g, 1 equivalent) obtained in Preparation Example 7 was dissolved in 50 mL of a dimethyl acetate solvent along with copper cyanide (4.17 g, 10 equivalents), the reaction was performed under nitrogen by increasing the temperature to 160° C. After the reaction was performed for 3 days, the reaction was completed by lowering the temperature to room temperature and adding water thereto. In this case, the produced solid compound was secured through filtration under reduced pressure, and in this case, the solid compound was secured while being washed using an aqueous ammonium solution. Compound P26 was secured by putting the solid compound, secured through filtration under reduced pressure, into a dichlorobenzene solvent and performing recrystallization. (1.44 g, yield 32%) HR LC/MS/MS m/z calcd for $C_{70}H_{36}N_4S$ (M+):964.2661; found: 964.2662

Preparation Example 27

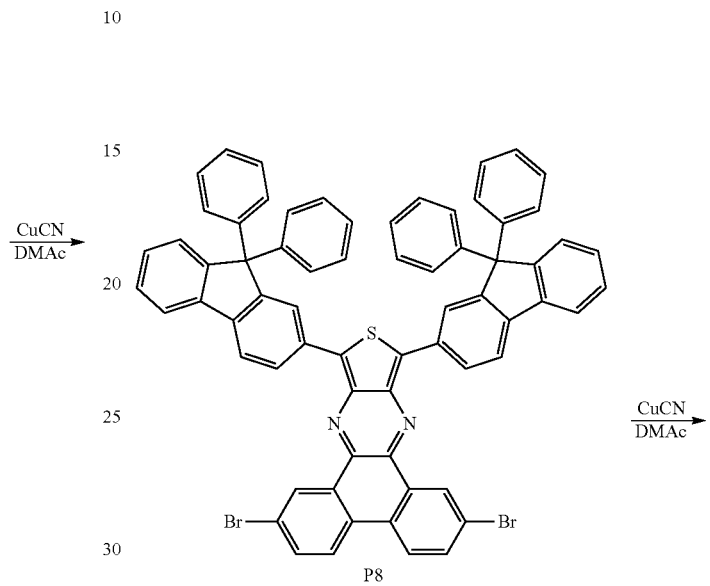

Compound P27 was secured by performing the synthesis in the same manner as in Preparation Example 26, except that Compound P8 (5 g, 1 equivalent) was used instead of Compound P7. (1.75 g, yield 39%) HR LC/MS/MS m/z calcd for $C_{70}H_{40}N_6S$ (M+):968.2974; found: 968.2973

Preparation Example 28

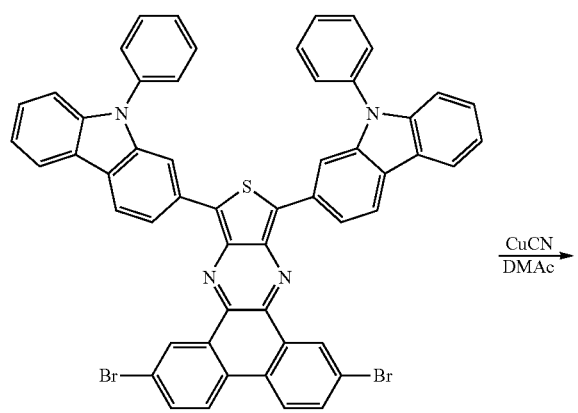

P13

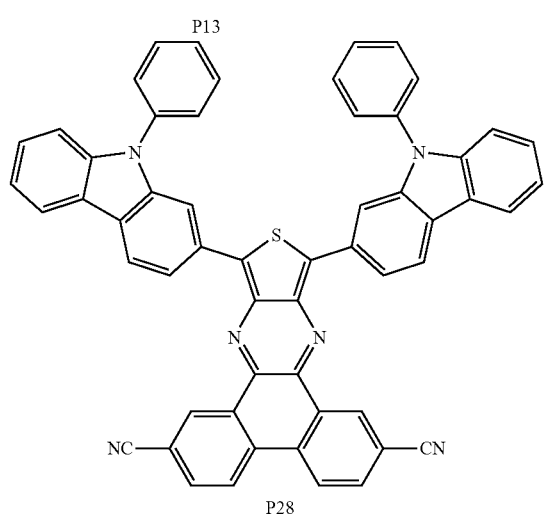

P28

Compound P28 was secured by performing the synthesis in the same manner as in Preparation Example 26, except that Compound P13 (5 g, 1 equivalent) was used instead of Compound P7. (1.09 g, yield 41%) HR LC/MS/MS m/z calcd for $C_{56}H_{30}N_6S$ (M+):818.2253; found: 818.2254

Preparation Example 29

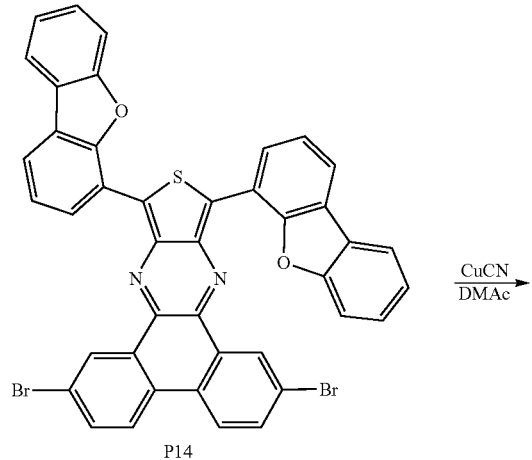

P14

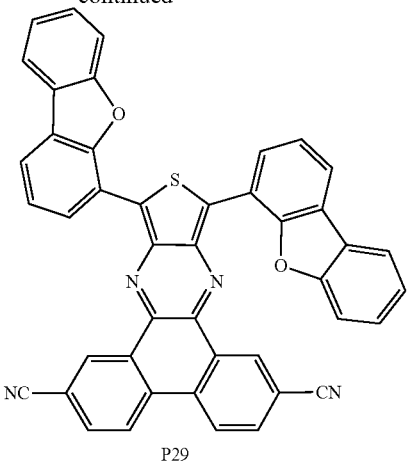

P29

Compound P29 was secured by performing the synthesis in the same manner as in Preparation Example 26, except that Compound P14 (5 g, 1 equivalent) was used instead of Compound P7. (1.46 g, yield 34%) HR LC/MS/MS m/z calcd for $C_{44}H_{20}N_2O_2S$ (M+):668.1307; found: 668.1308

Preparation Example 30

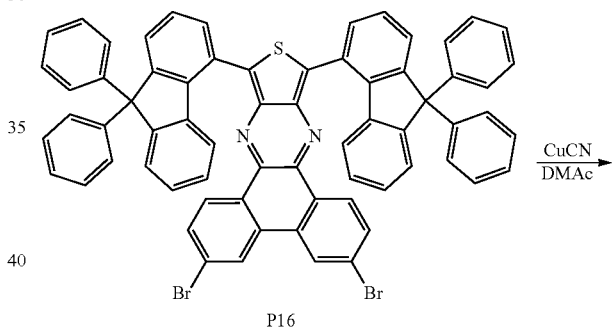

P16

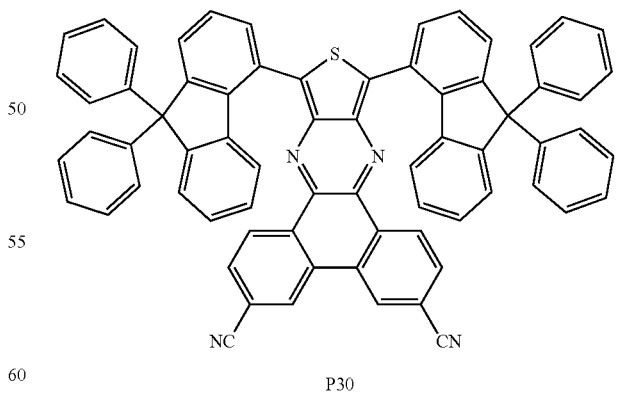

P30

Compound P30 was secured by performing the synthesis in the same manner as in Preparation Example 26, except that Compound P16 (2 g, 1 equivalent) was used instead of Compound P7. (1.17 g, yield 32%) HR LC/MS/MS m/z calcd for $C_{70}H_{36}N_4S$ (M+):968.2974; found: 968.2975

Preparation Example 31

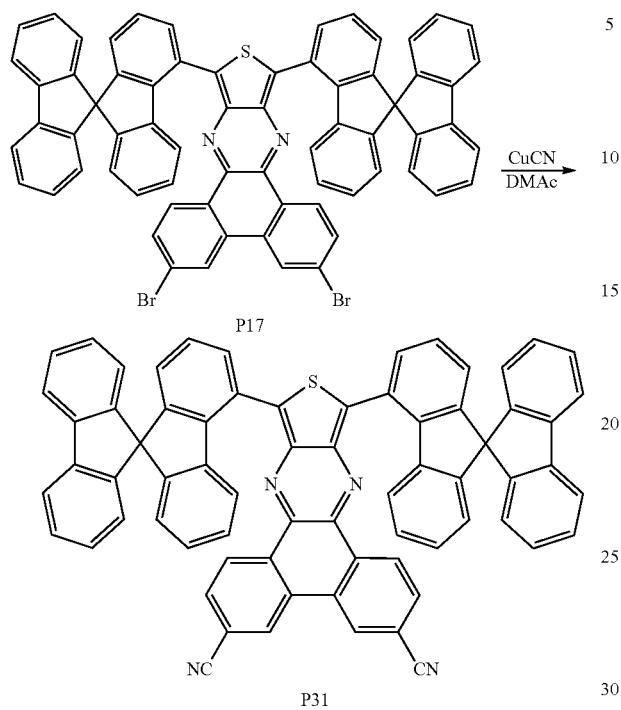

Compound P31 was secured by performing the synthesis in the same manner as in Preparation Example 26, except that Compound P17 (2 g, 1 equivalent) was used instead of Compound P7. (0.92 g, yield 28%) HR LC/MS/MS m/z calcd for $C_{68}H_{36}N_4S$ (M+):964.2661; found: 964.2662

Preparation Example 32

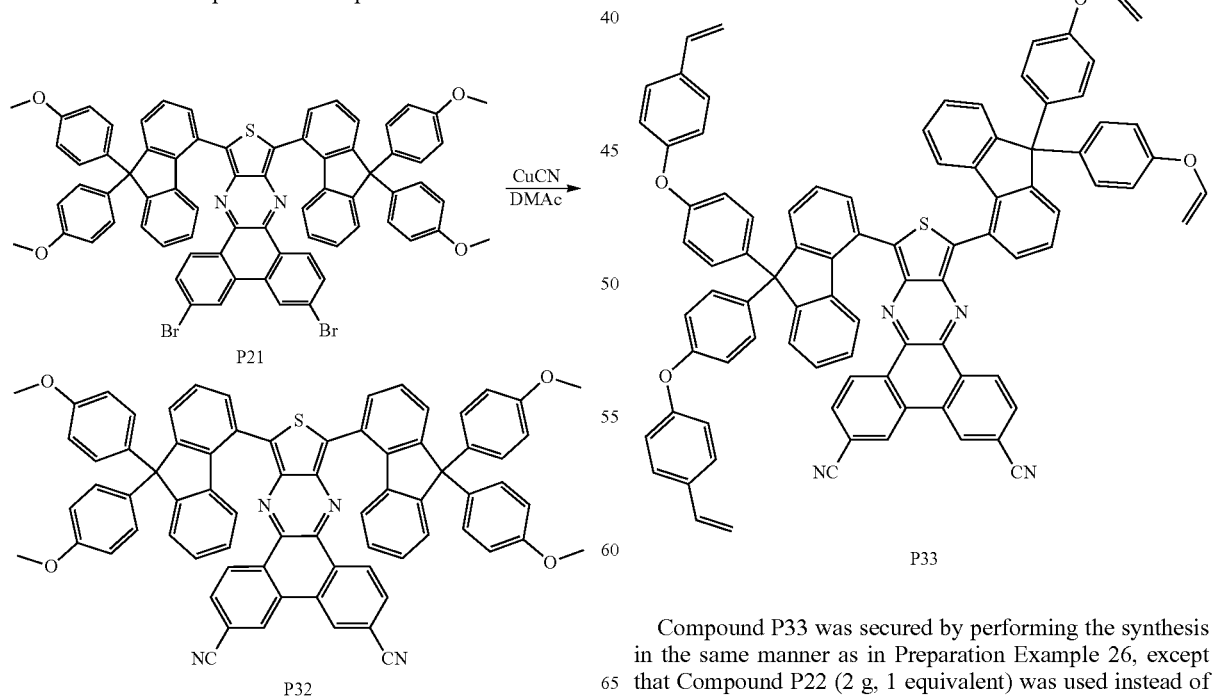

Compound P32 was secured by performing the synthesis in the same manner as in Preparation Example 26, except that Compound P21 (2 g, 1 equivalent) was used instead of Compound P7. (1.15 g, yield 27%) HR LC/MS/MS m/z calcd for $C_{90}H_{56}N_4O_2S$ (M+):1088.3396; found: 1088.3396

Preparation Example 33

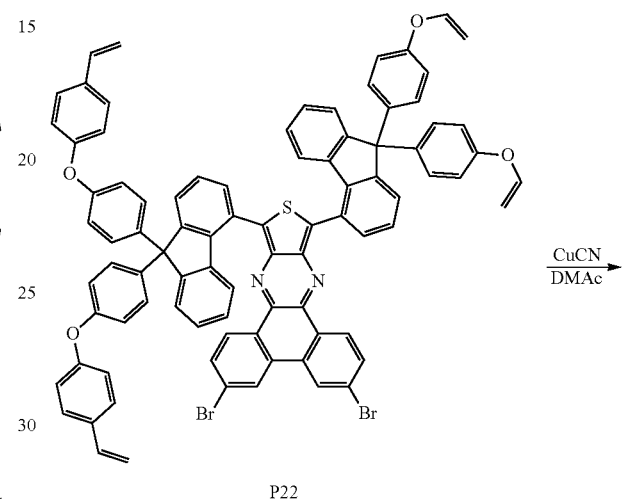

Compound P33 was secured by performing the synthesis in the same manner as in Preparation Example 26, except that Compound P22 (2 g, 1 equivalent) was used instead of Compound P7. (1.02 g, yield 27%) HR LC/MS/MS m/z calcd for $C_{90}H_{56}N_4O_4S$ (M+):1288.4022; found: 1288.4022

Preparation Example 34

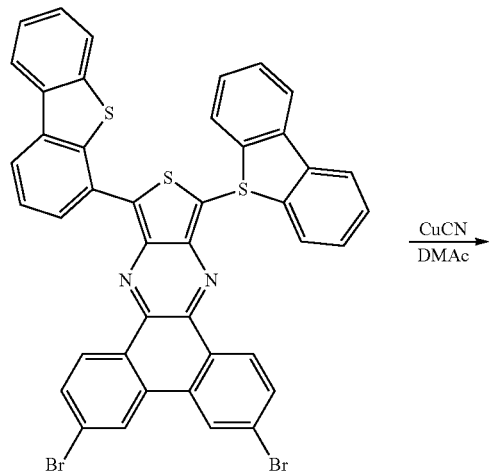

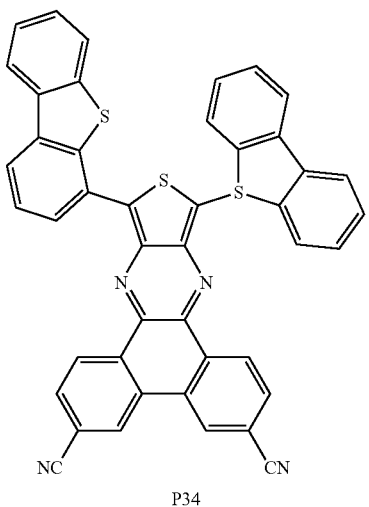

Compound P34 was secured by performing the synthesis in the same manner as in Preparation Example 26, except that Compound P25 (2 g, 1 equivalent) was used instead of Compound P7. (0.78 g, yield 33%) HR LC/MS/MS m/z calcd for $C_{44}H_{20}N_4S_3$(M+):700.0850; found: 700.0851

Preparation Example 35

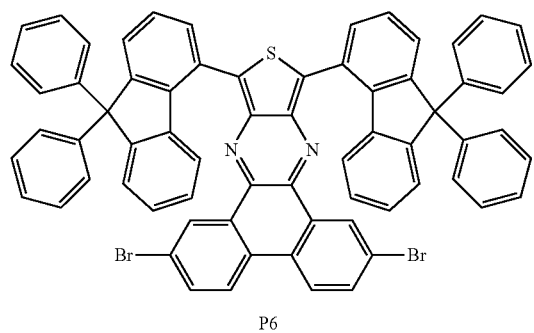

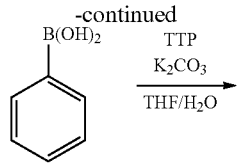

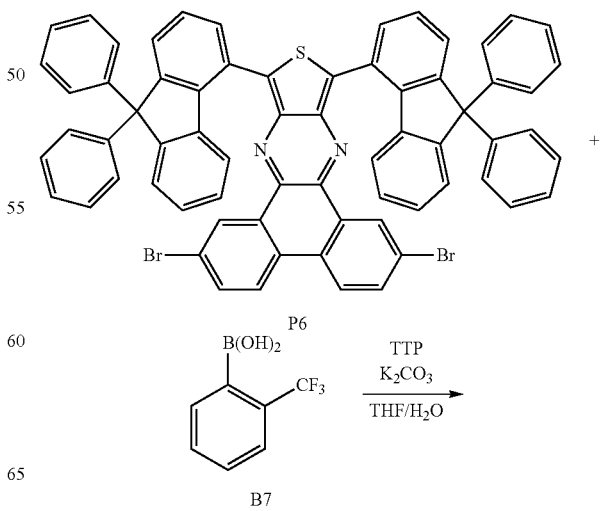

After Compound P6 (3 g, 1 equivalent) obtained in Preparation Example 6 was mixed with Compound B6 (0.85 g, 2.5 equivalents) and the resulting mixture was diluted in 40 mL of a THF solvent, 5 equivalents of potassium carbonate were dissolved in 10 mL of water and the resulting solution was introduced into the foregoing solution. After the temperature was stabilized by heating the solution to 80° C. under nitrogen, the reaction was performed by adding 5 mol % of a catalyst Pd(PPh3)4 thereto. After the reaction was completed, the temperature was lowered, water and the THF solvent were additionally added thereto, and an extraction was performed. After moisture was removed from the extracted organic solvent over anhydrous magnesium sulfate, the solvent was concentrated through distillation under reduced pressure. The concentrated solution was recrystallized using THF and ethanol solvents, and Compound P35 was secured by performing filtration under reduced pressure on the solid secured through the recrystallization. (2.33 g, yield 78%) HR LC/MS/MS m/z calcd for $C_{48}H_{50}N_2S$ (M+): 1070.3695; found: 1070.3695

Preparation Example 36

-continued

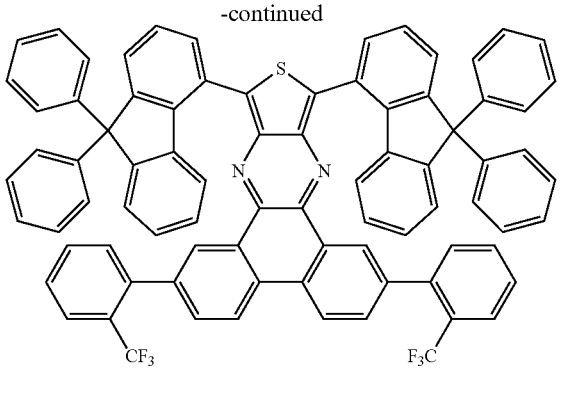

P36

Compound P36 was secured by performing the synthesis in the same manner as in Preparation Example 35, except that Compound B7 (1.32 g, 2.5 equivalents) was used instead of Compound B6. (2.42 g, yield 72%) HR LC/MS/MS m/z calcd for $C_{82}H_{48}F_6N_2S$ (M+):1206.3442; found: 1206.3441

Preparation Example 37

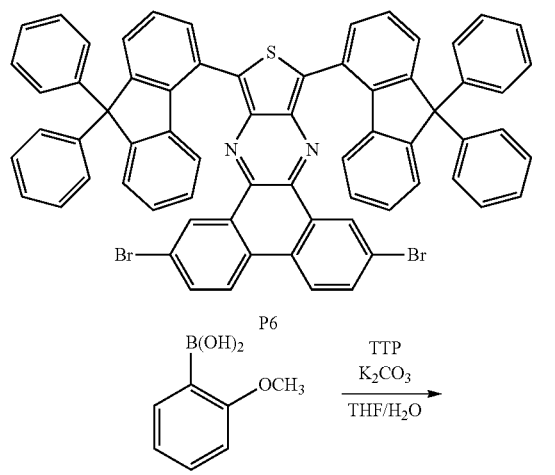

P37

Compound P37 was secured by performing the synthesis in the same manner as in Preparation Example 35, except that Compound B8 (1.06 g, 2.5 equivalents) was used instead of Compound B6. (2.27 g, yield 69%) HR LC/MS/MS m/z calcd for $C_{82}H_{54}N_2O_2S$ (M+):1130.3906; found: 1130.3905

Preparation Example 38

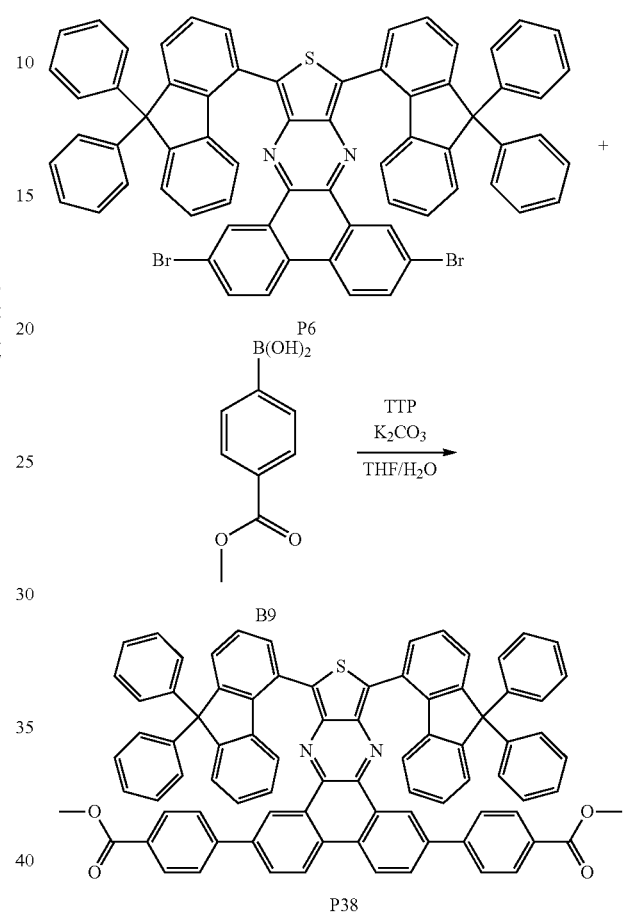

P38

Compound P38 was secured by performing the synthesis in the same manner as in Preparation Example 35, except that Compound B9 (1.25 g, 2.5 equivalents) was used instead of Compound B6. (2.71 g, yield 82%) HR LC/MS/MS m/z calcd for $C_{84}H_{54}N_2O_4S$ (M+):1186.3804; found: 1186.3805

Preparation Example 39

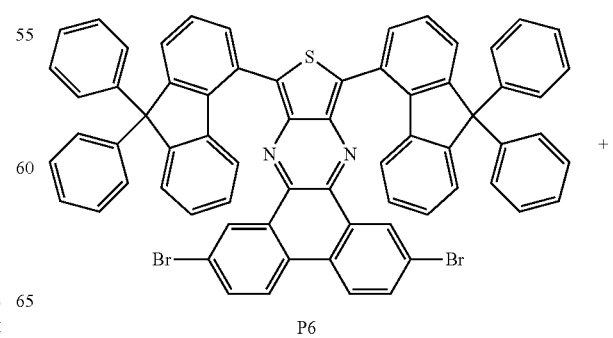

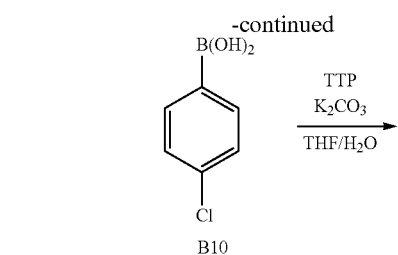

B10

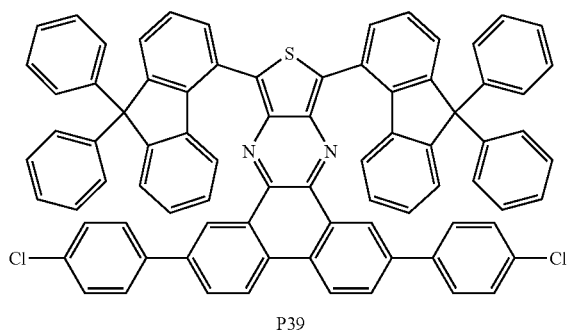

P39

Compound P39 was secured by performing the synthesis in the same manner as in Preparation Example 35, except that Compound B10 (1.09 g, 2.5 equivalents) was used instead of Compound B6. (2.71 g, yield 82%) HR LC/MS/MS m/z calcd for $C_{80}H_{48}Cl_2N_2S$ (M+):1138.2915; found: 1138.2914

Preparation Example 40

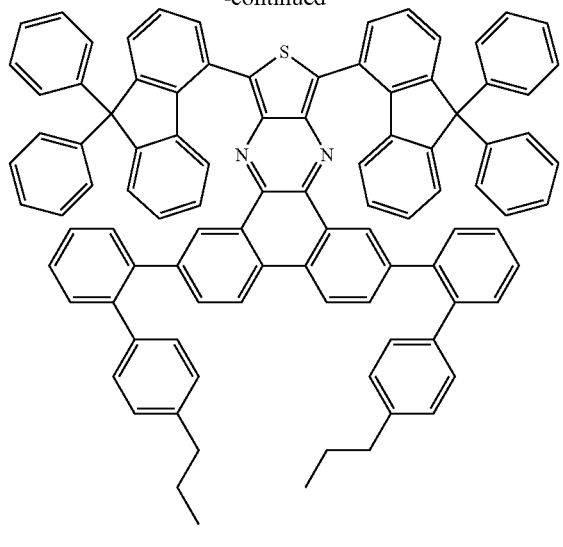

P40

Compound P40 was secured by performing the synthesis in the same manner as in Preparation Example 35, except that Compound B11 (1.67 g, 2.5 equivalents) was used instead of Compound B6. (2.80 g, yield 77%) HR LC/MS/MS m/z calcd for $C_{98}H_{70}N_2S$ (M+):1307.5293; found: 1307.5294

Preparation Example 41

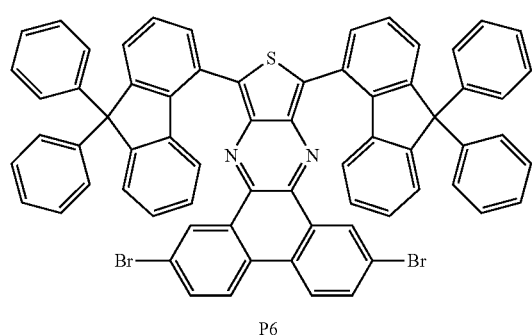

P6

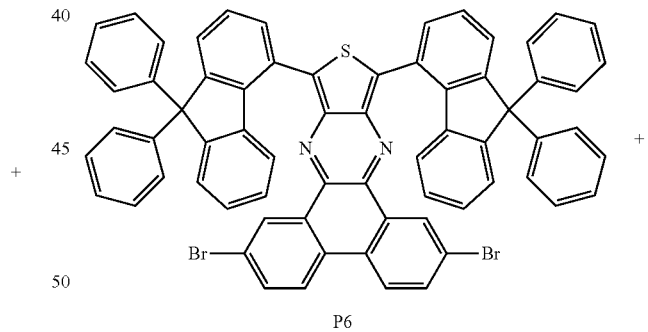

P6

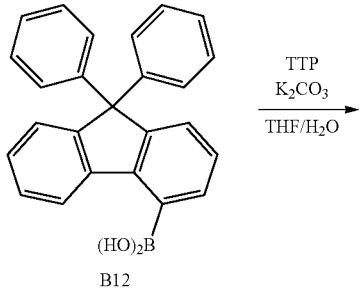

B11

B12

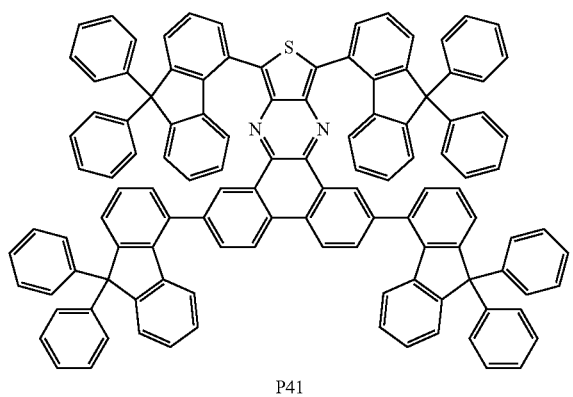

P41

Compound P41 was secured by performing the synthesis in the same manner as in Preparation Example 35, except that Compound B12 (2.52 g, 2.5 equivalents) was used instead of Compound B6. (2.90 g, yield 67%) HR LC/MS/MS m/z calcd for $C_{118}H_{74}N_2S$ (M+):1551.5606; found: 1551.5605

Preparation Example 42

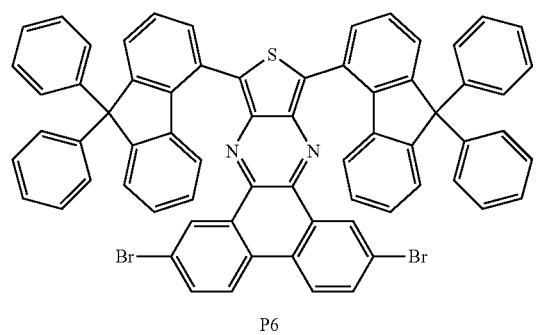

P6

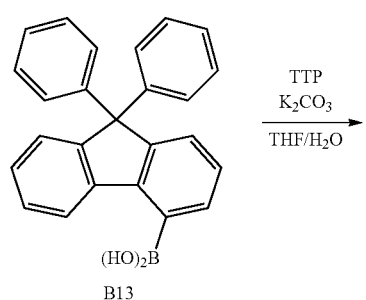

B13

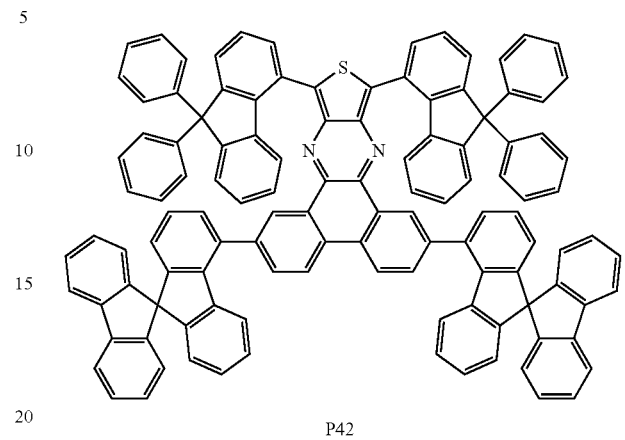

P42

Compound P42 was secured by performing the synthesis in the same manner as in Preparation Example 35, except that Compound B13 (2.51 g, 2.5 equivalents) was used instead of Compound B6. (3.10 g, yield 72%) HR LC/MS/MS m/z calcd for $C_{118}H_{70}N_2S$ (M+):1547.5293; found: 1547.5294

Preparation Example 43

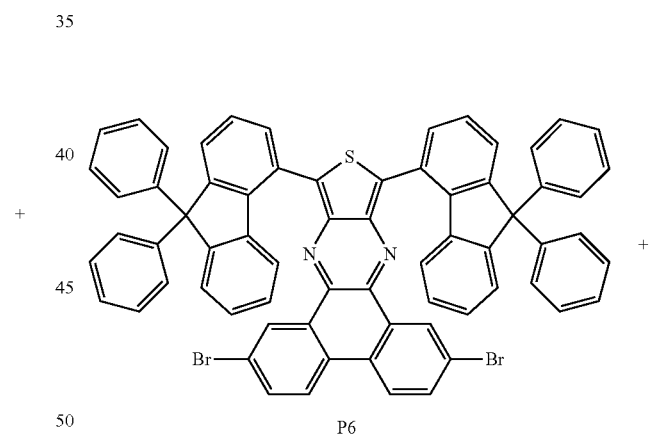

P6

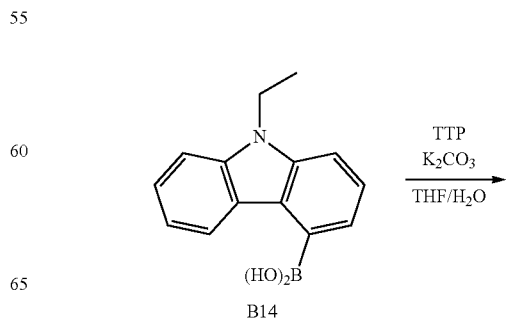

B14

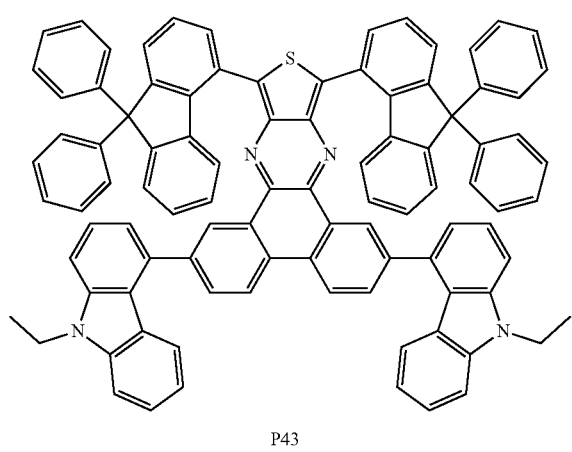

P43

Compound P43 was secured by performing the synthesis in the same manner as in

Preparation Example 35, except that Compound B14 (1.67 g, 2.5 equivalents) was used instead of Compound B6. (2.98 g, yield 82%) HR LC/MS/MS m/z calcd for $C_{96}H_{64}N_2S$ (M+):1305.4885; found: 1305.4885

Preparation Example 44

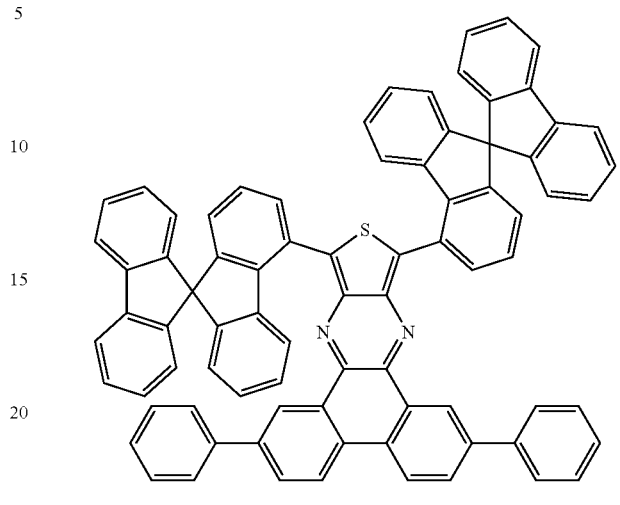

P44

Compound P44 was secured by performing the synthesis in the same manner as in Preparation Example 35, except that Compound P7 (4 g, 1 equivalent) was used instead of Compound P6 and Compound B6 (1.67 g, 2.5 equivalents) was used. (3.10 g, yield 78%) HR LC/MS/MS m/z calcd for $C_{80}H_{46}N_2S$ (M+):1066.3382; found: 1066.3382

Preparation Example 45

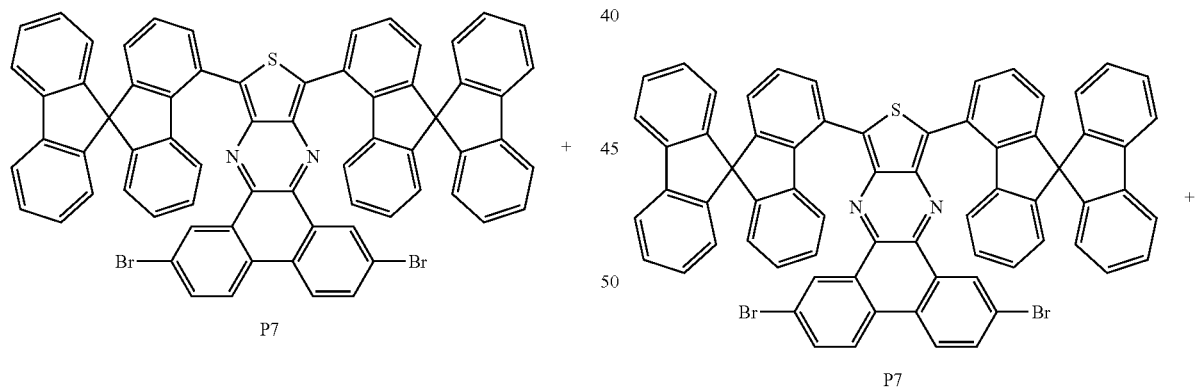

P7  +   P7  +

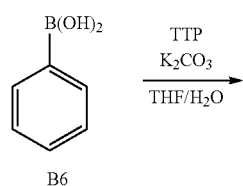

B6

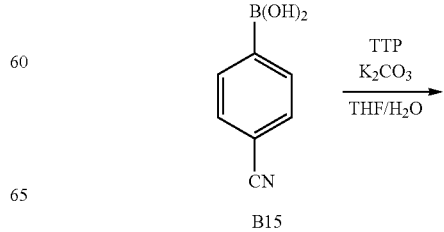

B15

-continued

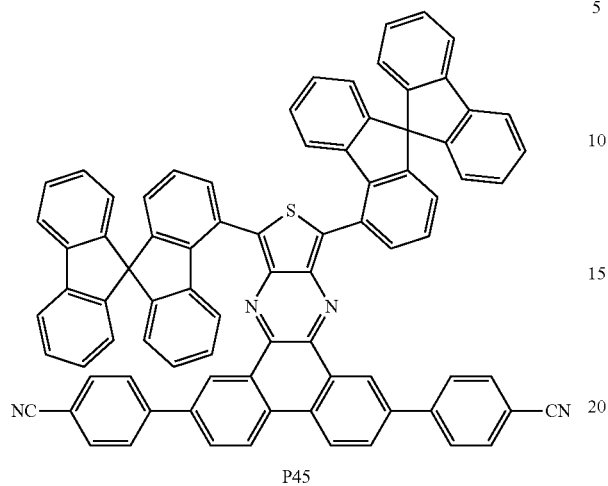

P45

Compound P45 was secured by performing the synthesis in the same manner as in Preparation Example 35, except that Compound P7 (5 g, 1 equivalent) was used instead of Compound P6 and Compound B15 (1.14 g, 2.5 equivalents) was used instead of Compound B6. (3.54 g, yield 68%) HR LC/MS/MS m/z calcd for $C_{82}H_{44}N_4S$ (M+):1116.3287; found: 1116.3287

Preparation Example 46

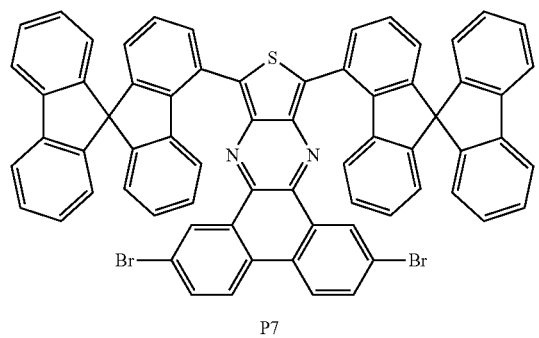

P7

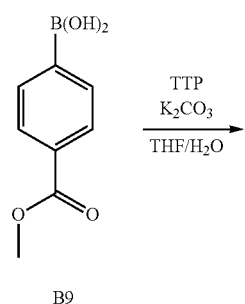

B9

-continued

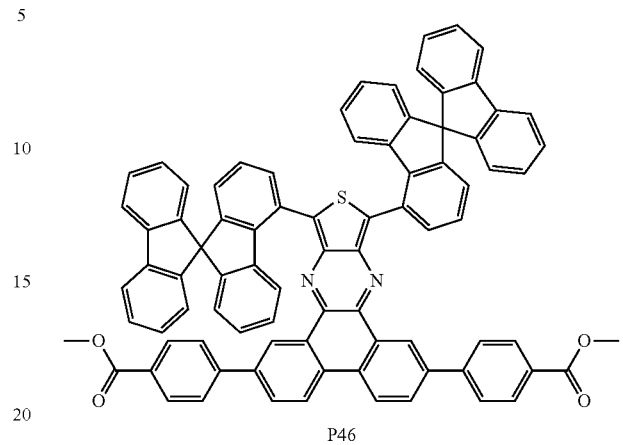

P46

Compound P46 was secured by performing the synthesis in the same manner as in Preparation Example 35, except that Compound P7 (5 g, 1 equivalent) was used instead of Compound P6 and Compound B9 (2.10 g, 2.5 equivalents) was used instead of Compound B6. (4.47 g, yield 81%) HR LC/MS/MS m/z calcd for $C_{84}H_{50}N_2O_4S$ (M+):1182.3492; found: 1182.3493

Preparation Example 47

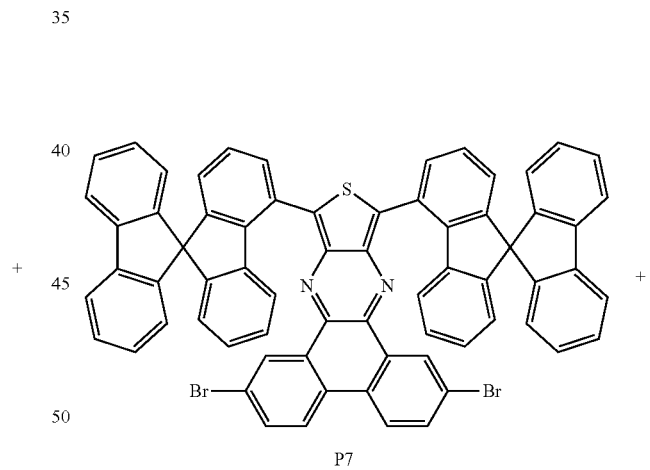

P7

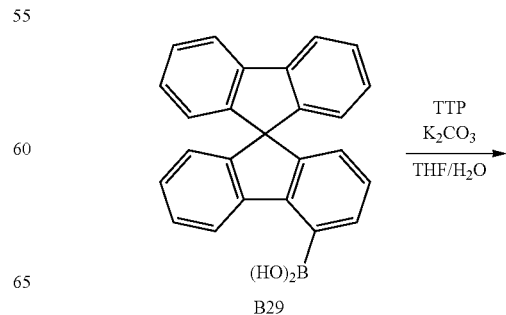

B29

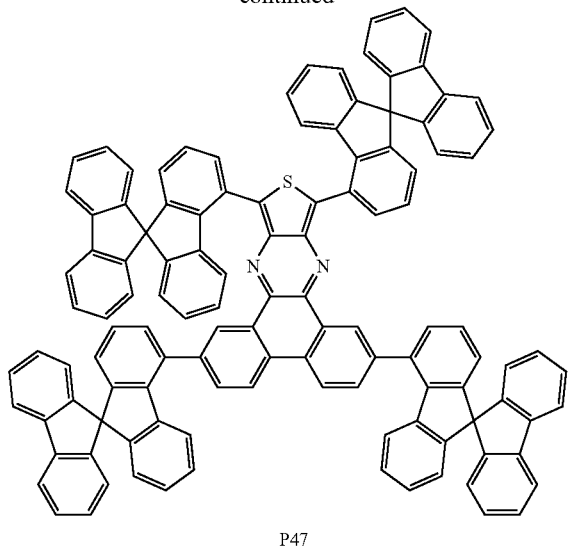

P47

Compound P47 was secured by performing the synthesis in the same manner as in Preparation Example 35, except that Compound P7 (5 g, 1 equivalent) was used instead of Compound P6 and Compound B29 (4.20 g, 2.5 equivalents) was used instead of Compound B6. (5.32 g, yield 74%) HR LC/MS/MS m/z calcd for $C_{118}H_{66}N_2S$ (M+):1543.4980; found: 1543.4980

Preparation Example 48

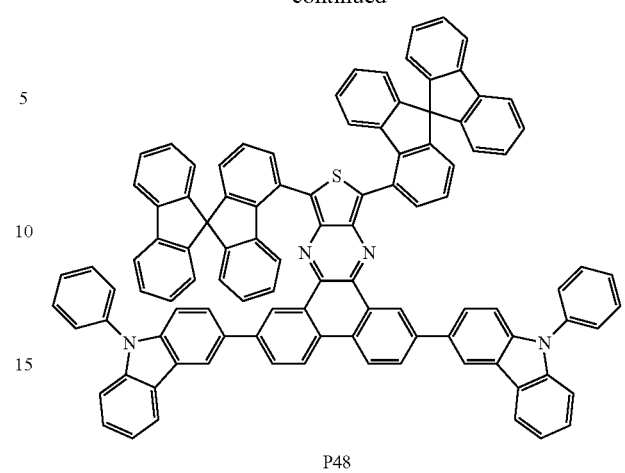

P48

Compound P48 was secured by performing the synthesis in the same manner as in Preparation Example 35, except that Compound P7 (5 g, 1 equivalent) was used instead of Compound P6 and Compound B30 (3.35 g, 2.5 equivalents) was used instead of Compound B6. (4.30 g, yield 66%) HR LC/MS/MS m/z calcd for $C_{104}H_{60}N_4S$ (M+):1397.4572; found: 1397.4572

Preparation Example 49

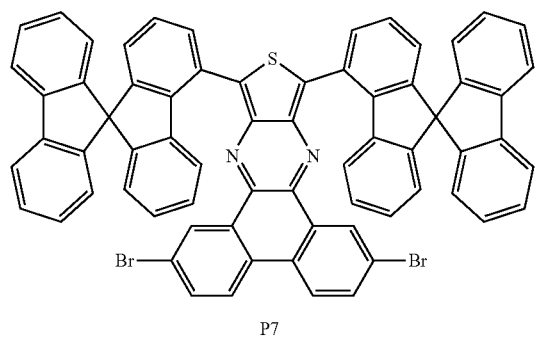

P7

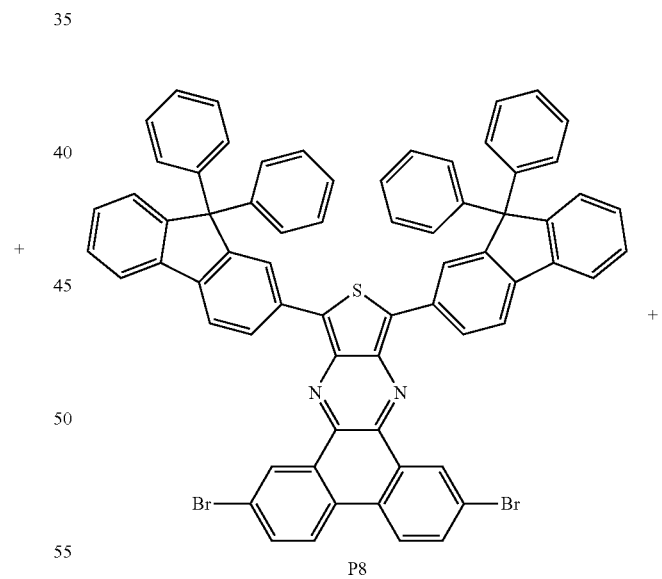

P8

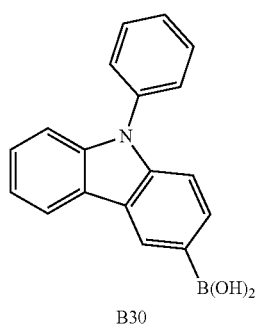

B30

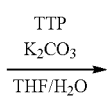 TTP K₂CO₃ / THF/H₂O →

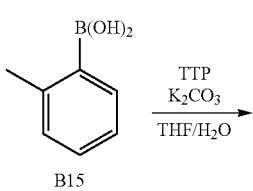

B15

 TTP K₂CO₃ / THF/H₂O →

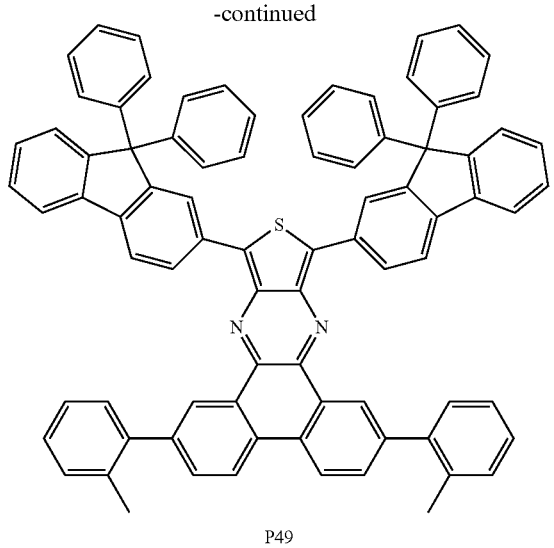

P49

Compound P49 was secured by performing the synthesis in the same manner as in Preparation Example 35, except that Compound P8 (5 g, 1 equivalent) was used instead of Compound P6 and Compound B15 (1.27 g, 2.5 equivalents) was used instead of Compound B6. (3.07 g, yield 75%) HR LC/MS/MS m/z calcd for $C_{82}H_{54}N_2S$ (M+):1098.4008; found: 1098.4007

Preparation Example 50

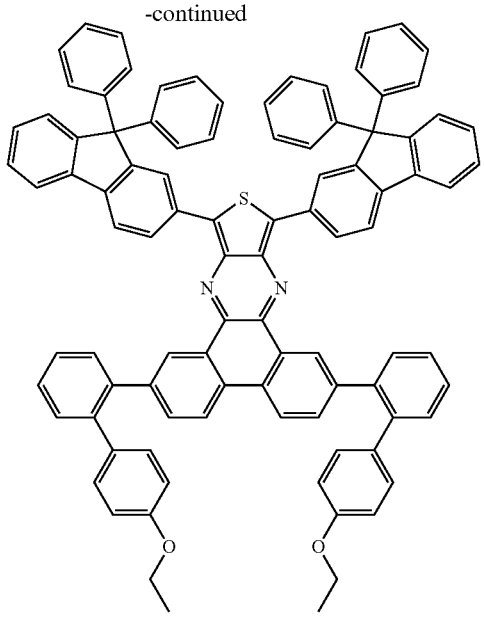

P50

Compound P50 was secured by performing the synthesis in the same manner as in Preparation Example 35, except that Compound P8 (5 g, 1 equivalent) was used instead of Compound P6 and Compound B16 (1.69 g, 2.5 equivalents) was used instead of Compound B6. (2.49 g, yield 75%) HR LC/MS/MS m/z calcd for $C_{96}H_{66}N_2O_2S$ (M+):1311.4879; found: 1311.4878

Preparation Example 51

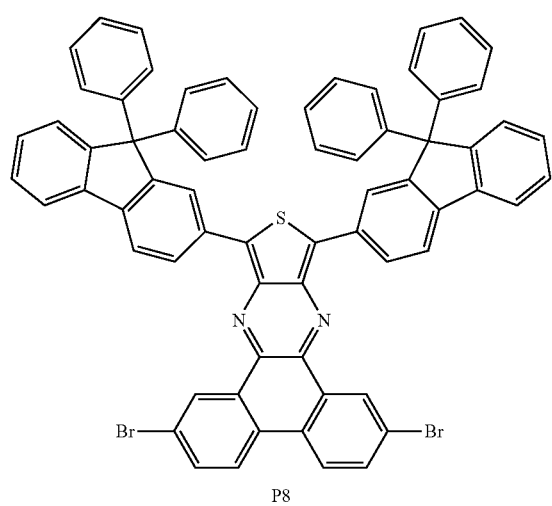

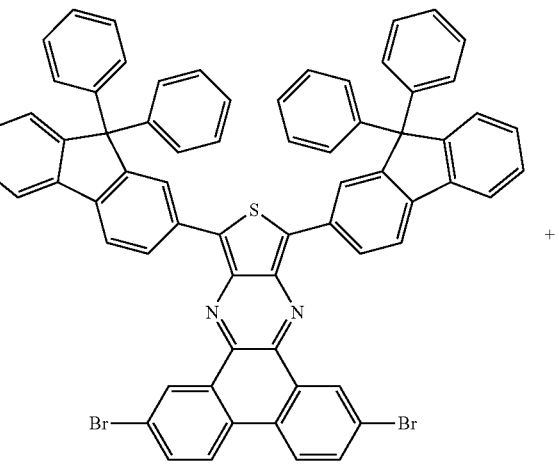

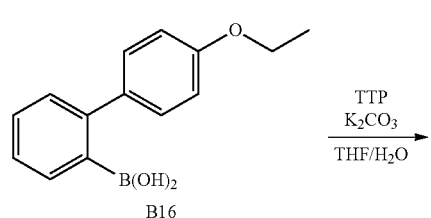

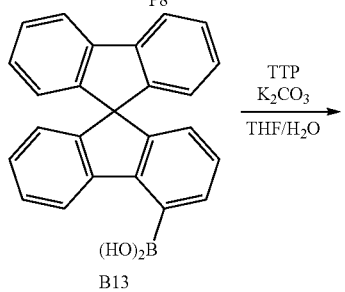

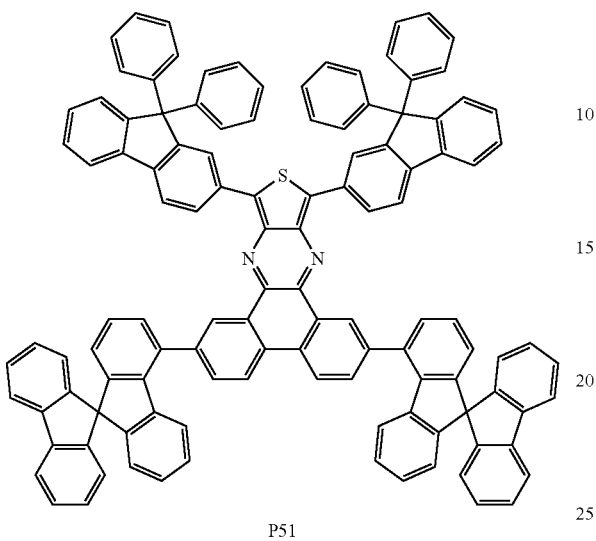
P51
Compound P51 was secured by performing the synthesis in the same manner as in Preparation Example 35, except that Compound P8 (5 g, 1 equivalent) was used instead of Compound P6 and Compound B13 (2.52 g, 2.5 equivalents) was used instead of Compound B6. (3.07 g, yield 71%) HR LC/MS/MS m/z calcd for $C_{118}H_{70}N_2S$ (M+):1547.5293; found: 1547.5293
Preparation Example 52
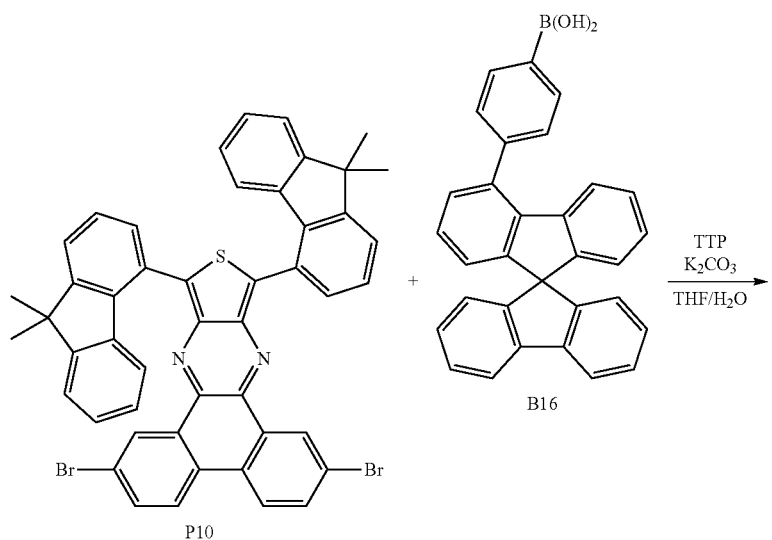

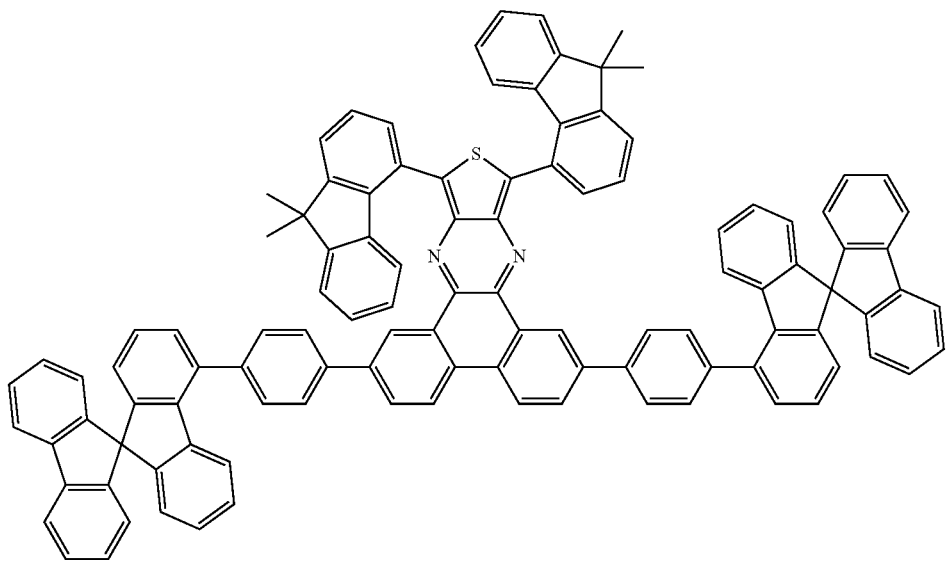

P52

Compound P52 was secured by performing the synthesis in the same manner as in Preparation Example 35, except that Compound P10 (3 g, 1 equivalent) was used instead of Compound P6 and Compound B16 (3.95 g, 2.5 equivalents) was used instead of Compound B6. (3.26 g, yield 62%) HR LC/MS/MS m/z calcd for $C_{118}H_{17}N_2S$ (M+):1451.5293; found: 1451.5294

Preparation Example 53

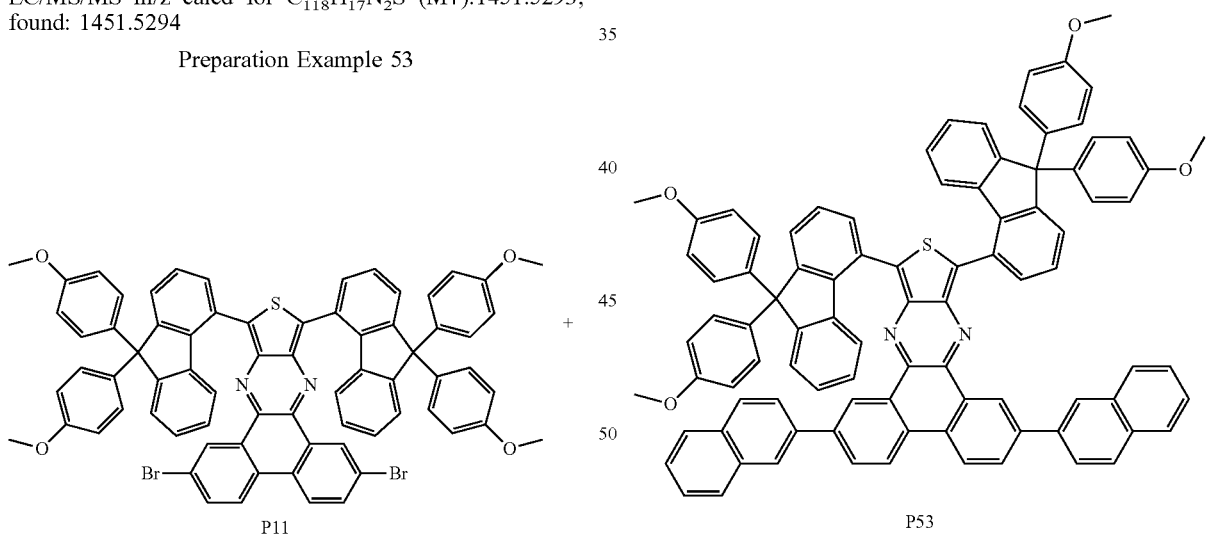

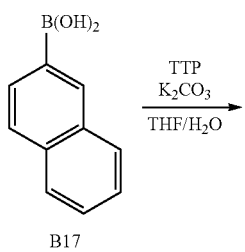

Compound P53 was secured by performing the synthesis in the same manner as in Preparation Example 35, except that Compound P11 (3 g, 1 equivalent) was used instead of Compound P6 and Compound B17 (1.08 g, 2.5 equivalents) was used instead of Compound B6. (1.85 g, yield 57%) HR LC/MS/MS m/z calcd for $C_{92}H_{62}N_2O_4S$ (M+):1290.4430; found: 1290.4431

Preparation Example 54

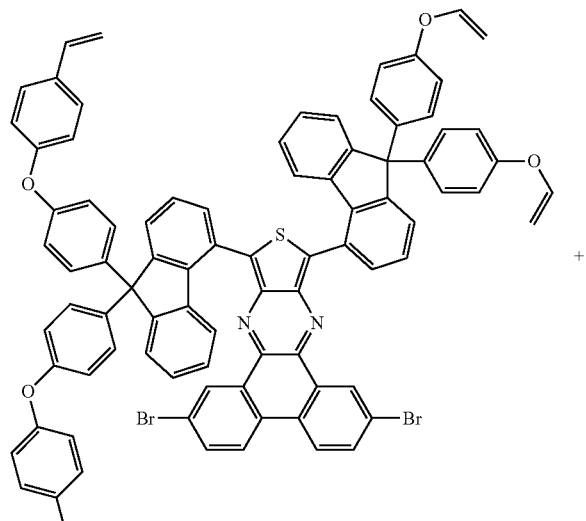

P12

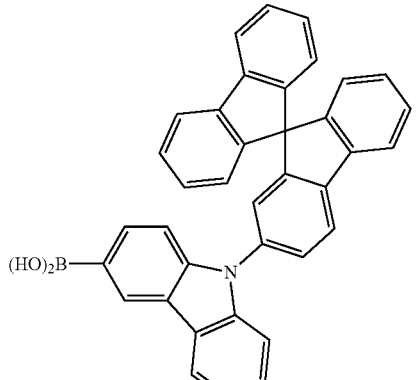

B18

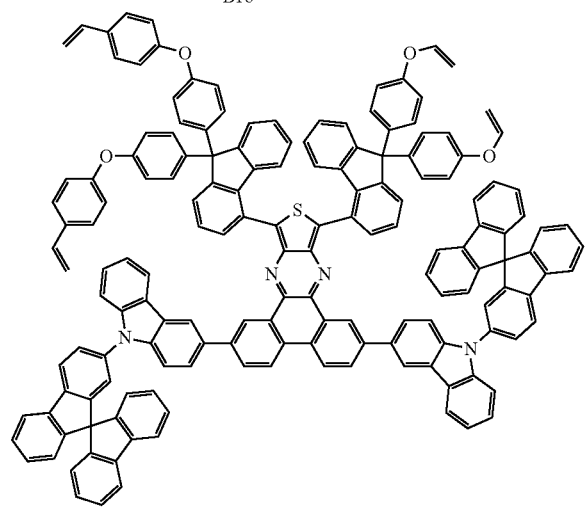

P54

Compound P54 was secured by performing the synthesis in the same manner as in Preparation Example 35, except that Compound P12 (3 g, 1 equivalent) was used instead of Compound P6 and Compound B18 (2.82 g, 2.5 equivalents) was used instead of Compound B6. (2.93 g, yield 62%) HR LC/MS/MS m/z calcd for $C_{68}H_{38}F_6N_4S$ (M+):2197.7499; found: 2197.7499

Preparation Example 55

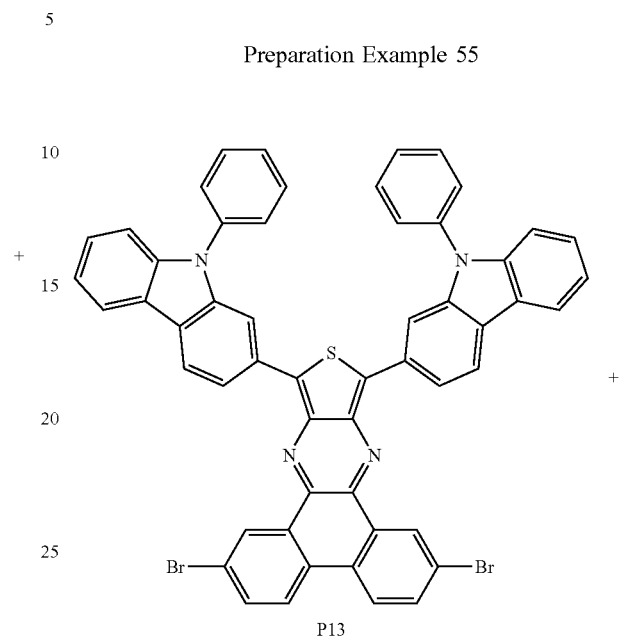

P13

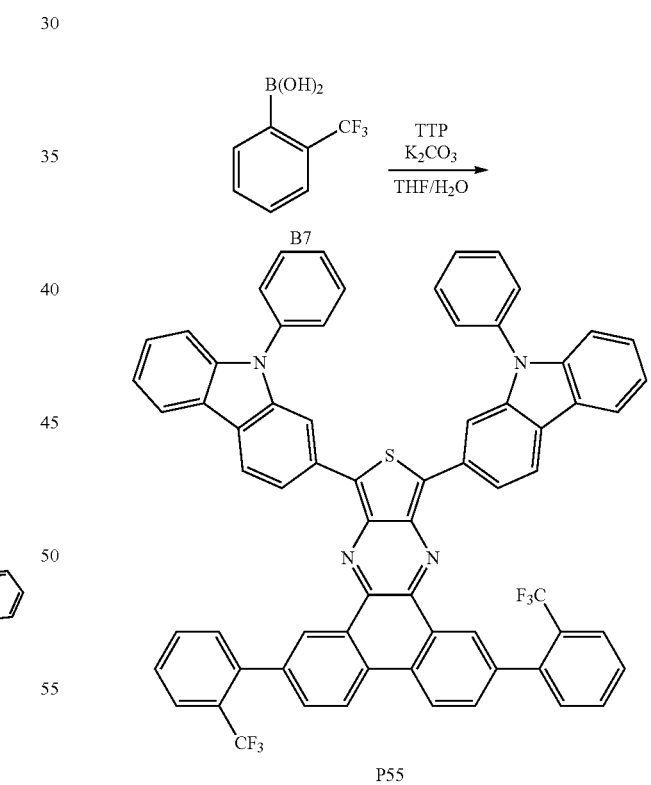

P55

Compound P55 was secured by performing the synthesis in the same manner as in Preparation Example 35, except that Compound P13 (3 g, 1 equivalent) was used instead of Compound P6 and Compound B7 (1.54 g, 2.5 equivalents) was used instead of Compound B6. (1.98 g, yield 58%) HR LC/MS/MS m/z calcd for $C_{68}H_{38}F_6N_4S$ (M+):1056.2721; found: 1056.2721

Preparation Example 56

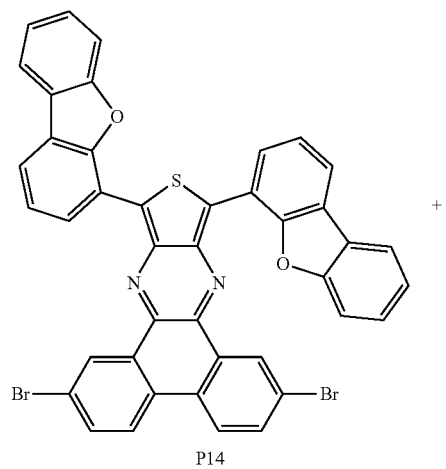

P14

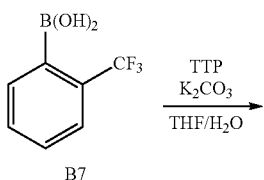

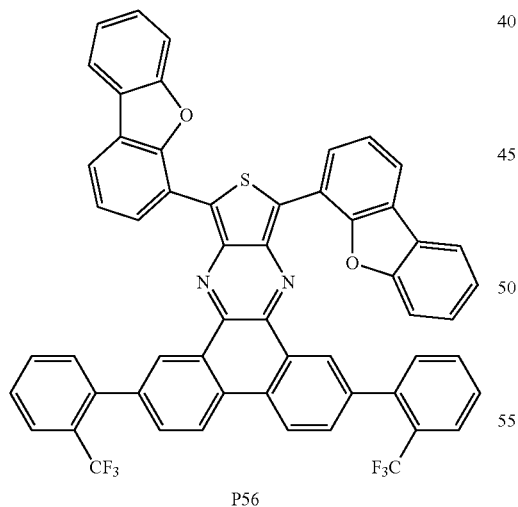

P56

Compound P56 was secured by performing the synthesis in the same manner as in Preparation Example 35, except that Compound P14 (3 g, 1 equivalent) was used instead of Compound P6 and Compound B7 (1.83 g, 2.5 equivalents) was used instead of Compound B6. (2.21 g, yield 63%) HR LC/MS/MS m/z calcd for $C_{58}H_{26}F6N_2O_2S$ (M+):906.1776; found: 906.1777

Preparation Example 57

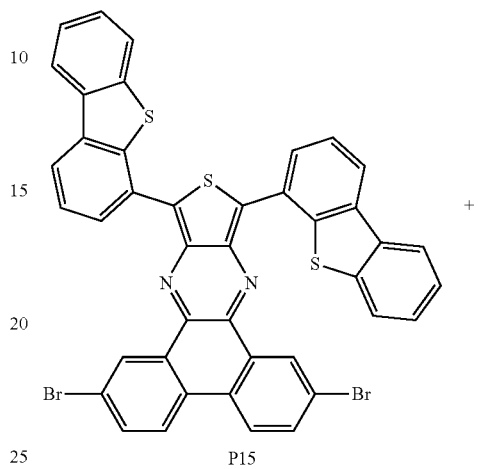

P15

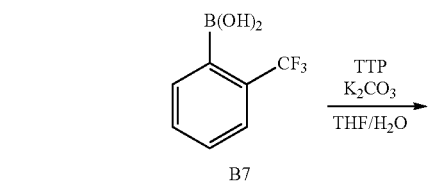

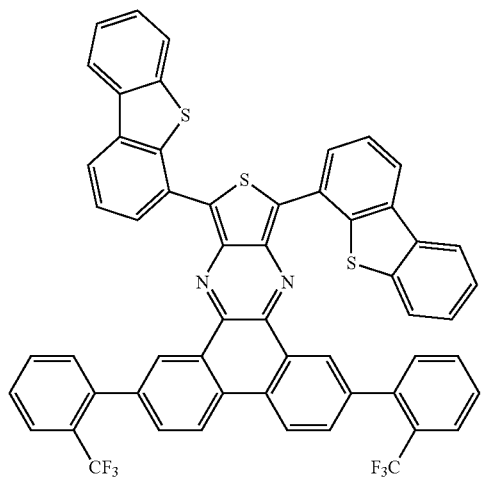

P57

Compound P57 was secured by performing the synthesis in the same manner as in Preparation Example 35, except that Compound P15 (3 g, 1 equivalent) was used instead of Compound P6 and Compound B7 (1.76 g, 2.5 equivalents) was used instead of Compound B6. (1.92 g, yield 55%) HR LC/MS/MS m/z calcd for $C_{56}H_{28}F6N_2S_3$ (M+):938.1319; found: 938.1319

Preparation Example 58

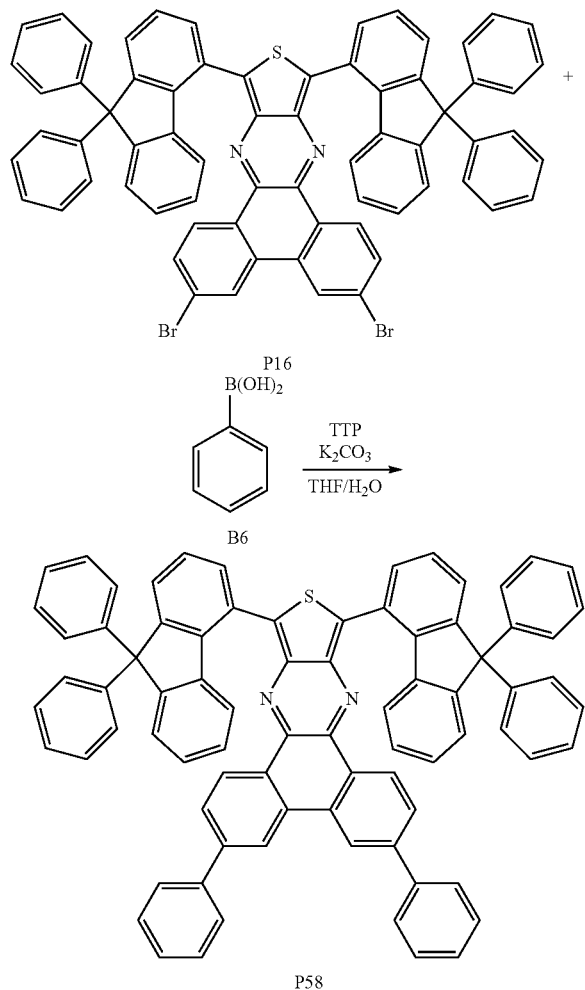

P16

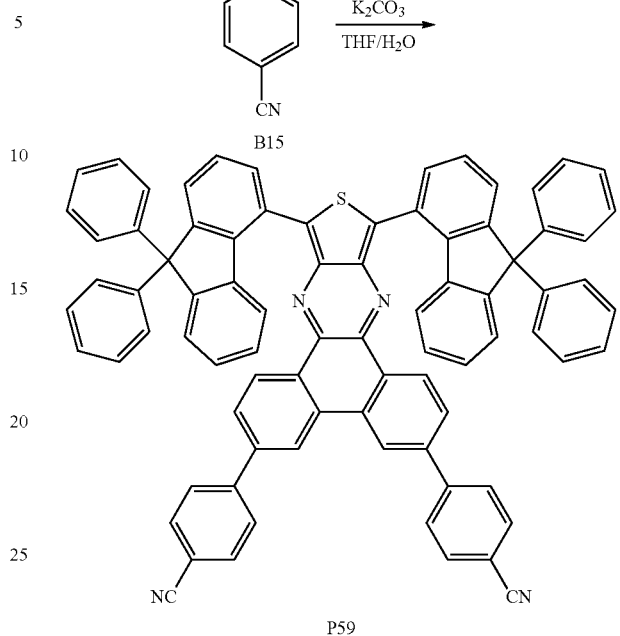

Compound P58 was secured by performing the synthesis in the same manner as in Preparation Example 35, except that Compound P16 (4 g, 1 equivalent) was used instead of Compound P6 and Compound B6 (1.13 g, 2.5 equivalents) was used. (2.67 g, yield 67%) HR LC/MS/MS m/z calcd for $C_{118}H_{70}N_2S$ (M+):1070.3695; found: 1070.3696

Preparation Example 59

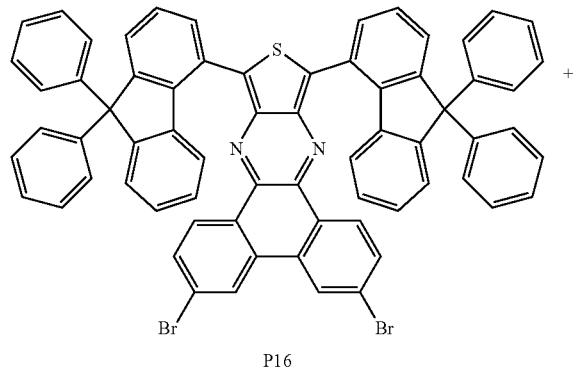

P16

Compound P59 was secured by performing the synthesis in the same manner as in Preparation Example 35, except that Compound P16 (4 g, 1 equivalent) was used instead of Compound P6 and Compound B15 (1.36 g, 2.5 equivalents) was used instead of Compound B6. (2.96 g, yield 71%) HR LC/MS/MS m/z calcd for $C_{82}H_{48}N_4S$ (M+):1120.3600; found: 1120.3601

Preparation Example 60

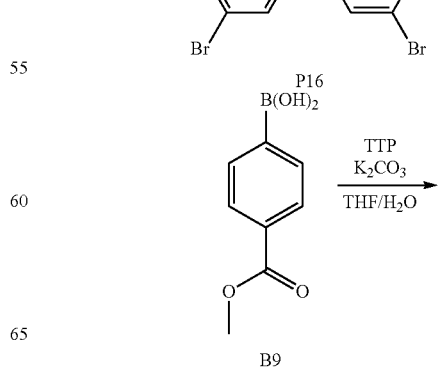

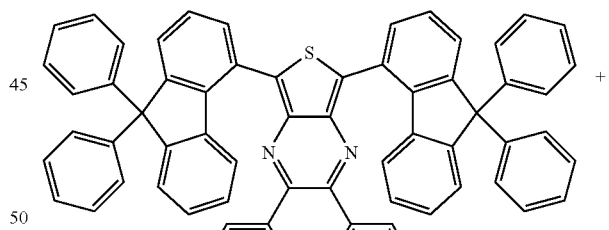

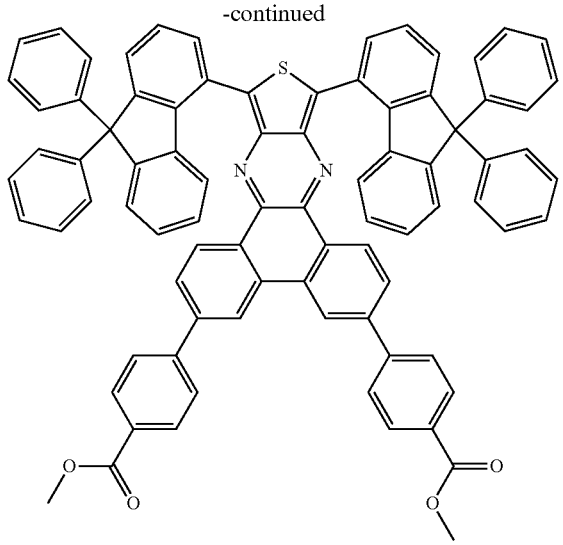

P60

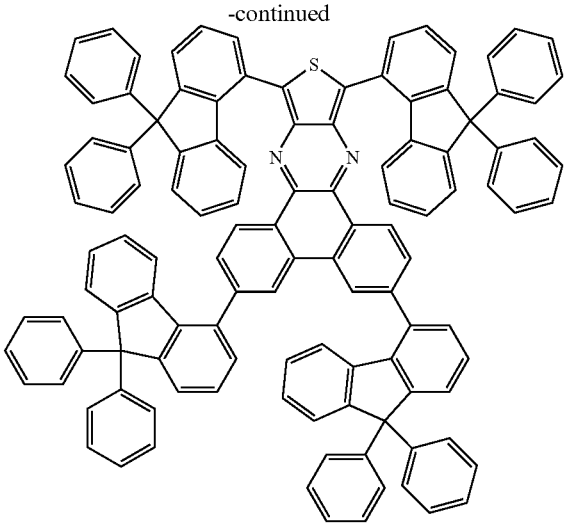

P61

Compound P60 was secured by performing the synthesis in the same manner as in Preparation Example 35, except that Compound P16 (4 g, 1 equivalent) was used instead of Compound P6 and Compound B9 (1.67 g, 2.5 equivalents) was used instead of Compound B6. (3.53 g, yield 80%) HR LC/MS/MS m/z calcd for $C_{118}H_{70}N_2S$ (M+):1186.3840; found: 1186.3840

Preparation Example 61

Compound P61 was secured by performing the synthesis in the same manner as in Preparation Example 35, except that Compound P16 (4 g, 1 equivalent) was used instead of Compound P6 and Compound B12 (3.36 g, 2.5 equivalents) was used instead of Compound B6. (4.27 g, yield 74%) HR LC/MS/MS m/z calcd for $C_{118}H_{74}N_2S$ (M+):1551.5606; found: 1551.5105

Preparation Example 62

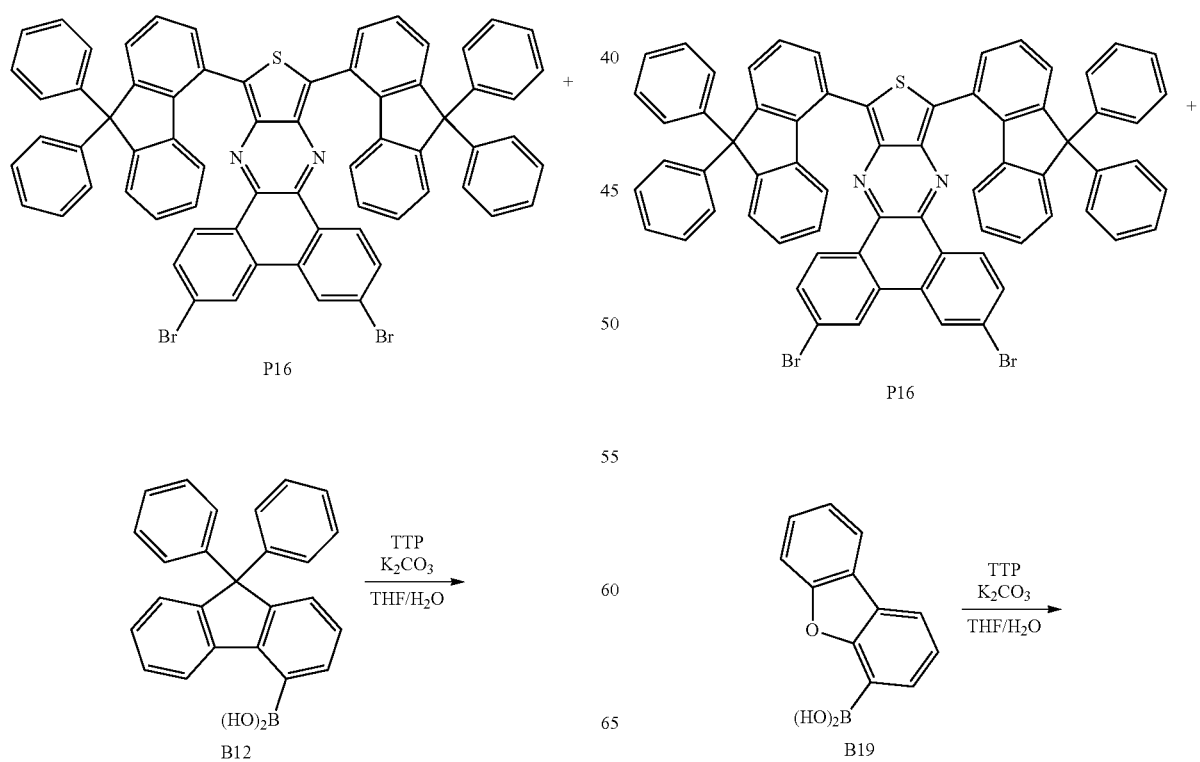

-continued

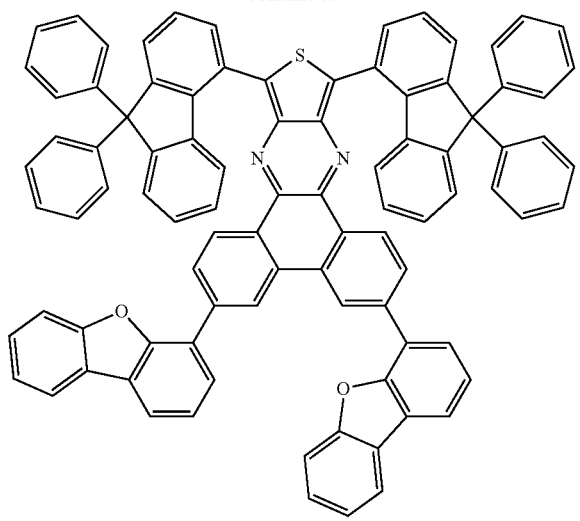

P62

Compound P62 was secured by performing the synthesis in the same manner as in Preparation Example 35, except that Compound P16 (4 g, 1 equivalent) was used instead of Compound P6 and Compound B19 (1.97 g, 2.5 equivalents) was used instead of Compound B6. (3.07 g, yield 66%) HR LC/MS/MS m/z calcd for $C_{92}H_{54}N_2O_2S$ (M+):1250.3906; found: 1250.3906

Preparation Example 63

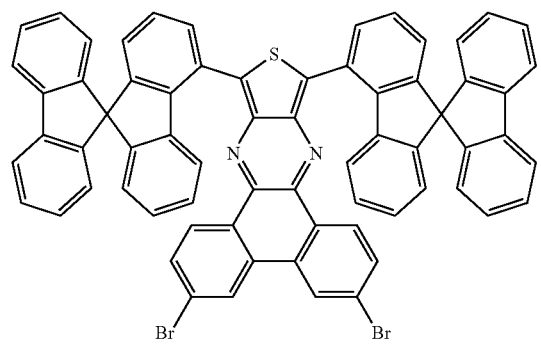

P17

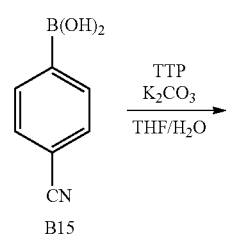

B15

-continued

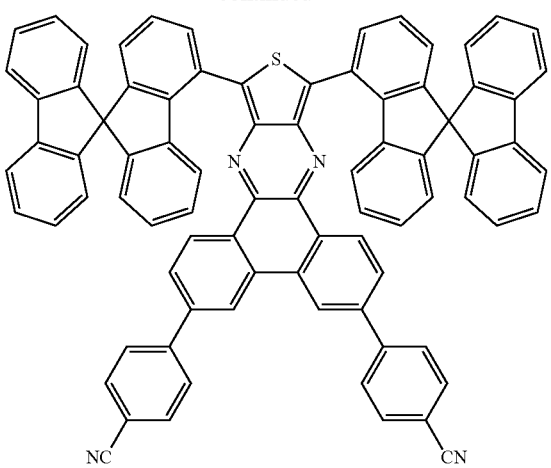

P63

Compound P63 was secured by performing the synthesis in the same manner as in Preparation Example 35, except that Compound P17 (5 g, 1 equivalent) was used instead of Compound P6 and Compound B15 (1.71 g, 2.5 equivalents) was used instead of Compound B6. (3.91 g, yield 75%) HR LC/MS/MS m/z calcd for $C_{82}H_{44}N_4S$ (M+):1116.3287; found: 1116.3288

Preparation Example 64

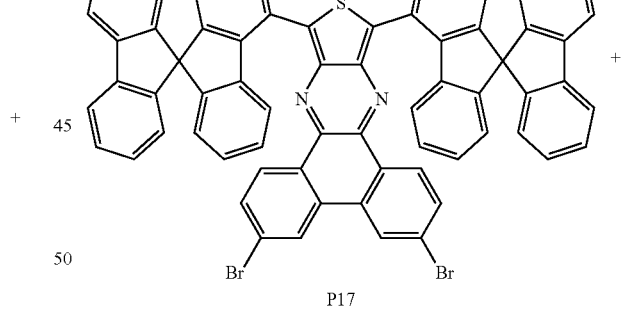

P17

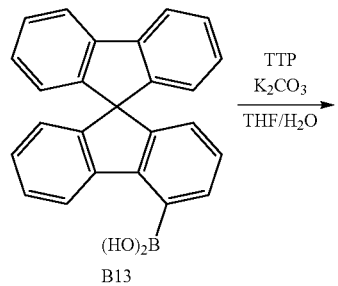

B13

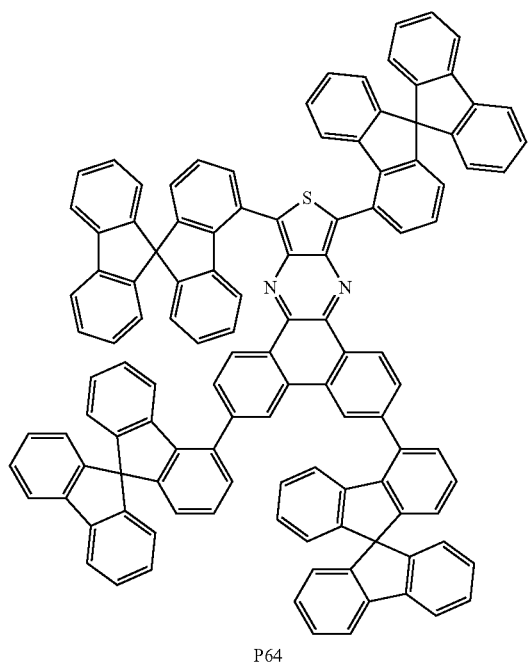

P64

Compound P64 was secured by performing the synthesis in the same manner as in Preparation Example 35, except that Compound P17 (5 g, 1 equivalent) was used instead of Compound P6 and Compound B13 (4.20 g, 2.5 equivalents) was used instead of Compound B6. (3.07 g, yield 66%) HR LC/MS/MS m/z calcd for $C_{118}H_{66}N_2S$ (M+):1543.4980; found: 1543.4981

Preparation Example 65

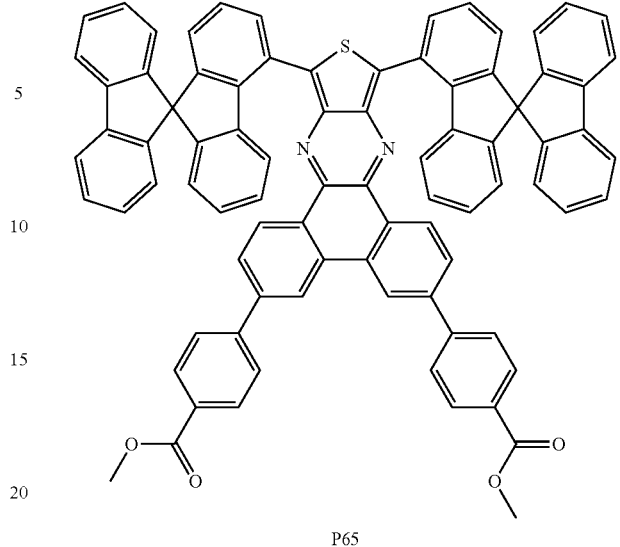

P65

Compound P65 was secured by performing the synthesis in the same manner as in Preparation Example 35, except that Compound P17 (5 g, 1 equivalent) was used instead of Compound P6 and Compound B9 (2.10 g, 2.5 equivalents) was used instead of Compound B6. (4.25 g, yield 77%) HR LC/MS/MS m/z calcd for $C_{84}H_{50}N_2O_4S$ (M+):1182.3492; found: 1182.3491

Preparation Example 66

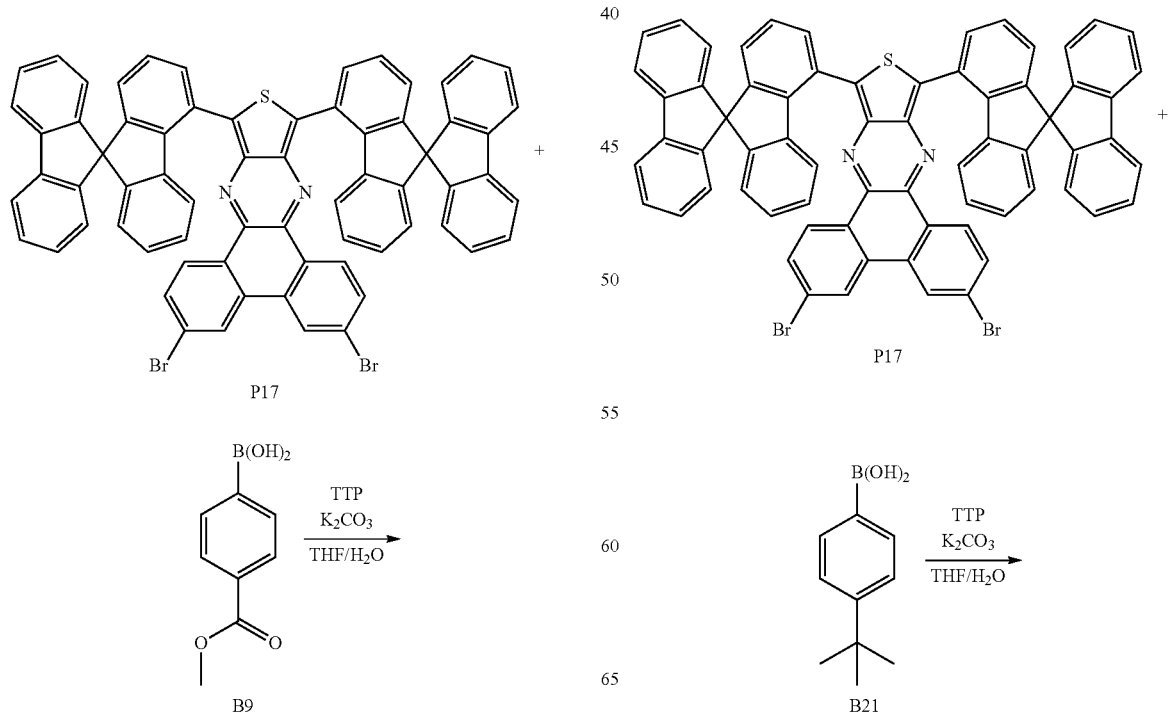

-continued

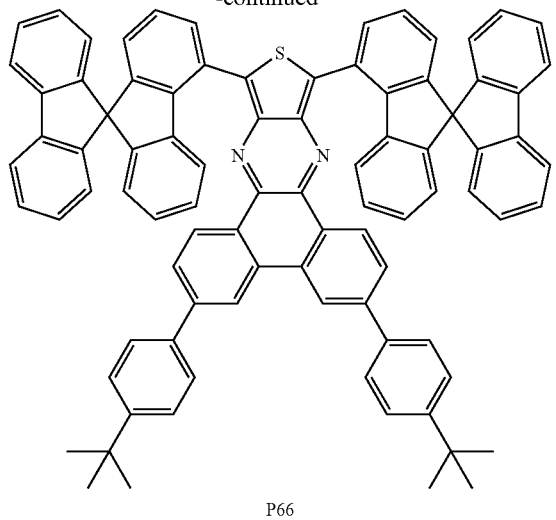

P66

Compound P66 was secured by performing the synthesis in the same manner as in Preparation Example 35, except that Compound P17 (5 g, 1 equivalent) was used instead of Compound P6 and Compound B21 (2.07 g, 2.5 equivalents) was used instead of Compound B6. (4.51 g, yield 82%) HR LC/MS/MS m/z calcd for $C_{88}H_{62}N_2S$ (M+):1178.4634; found: 1178.4635

Preparation Example 67

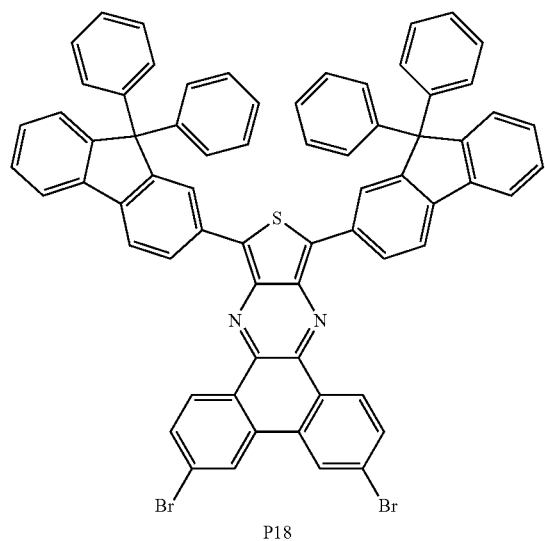

P18

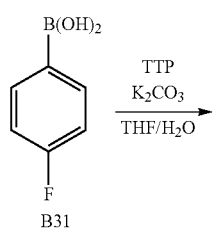

B31

-continued

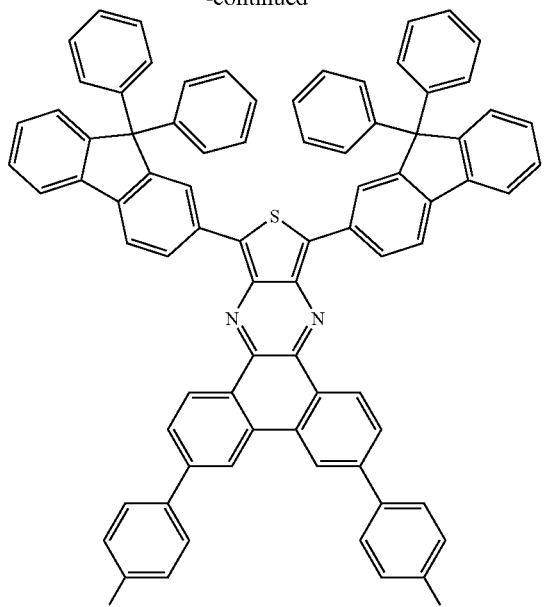

P67

Compound P67 was secured by performing the synthesis in the same manner as in Preparation Example 35, except that Compound P18 (5 g, 1 equivalent) was used instead of Compound P6 and Compound B31 (1.62 g, 2.5 equivalents) was used instead of Compound B6. (3.44 g, yield 67%) HR LC/MS/MS m/z calcd for $C_{80}H_{48}F_2N_2S$ (M+):1106.3506; found: 1106.3506

Preparation Example 68

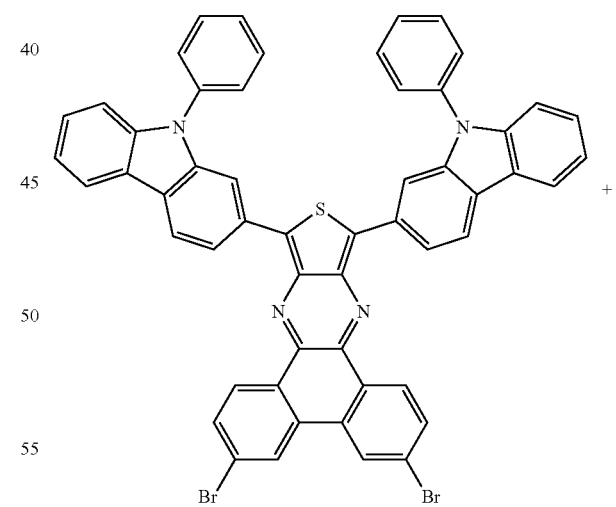

P23

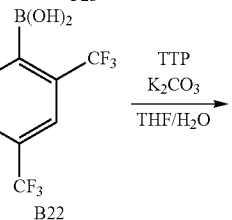

B22

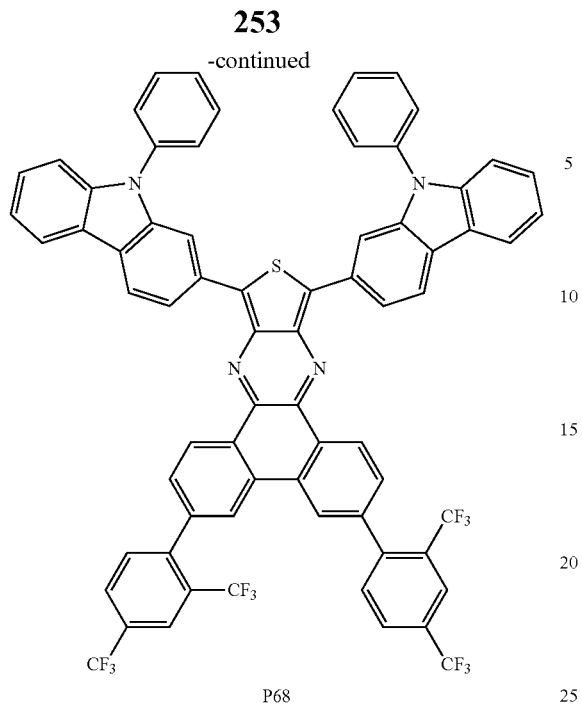

P68

Compound P68 was secured by performing the synthesis in the same manner as in Preparation Example 35, except that Compound P23 (5 g, 1 equivalent) was used instead of Compound P6 and Compound B22 (3.48 g, 2.5 equivalents) was used instead of Compound B6. (3.73 g, yield 58%) HR LC/MS/MS m/z calcd for $C_{70}H_{36}F12N_4S$ (M+):1192.2469; found: 1192.2469

Preparation Example 69

P69

Compound P69 was secured by performing the synthesis in the same manner as in Preparation Example 1, except that Compound A6 (3 g, 1 equivalent) was used instead of Compound A1 and Compound B23 (1.81 g, 1.05 equivalents) was used instead of Compound B1. (4.10 g, yield 87%) HR LC/MS/MS m/z calcd for $C_{56}H_{50}N_2S$ (M+): 782.3965; found: 782.3965

Preparation Example 70

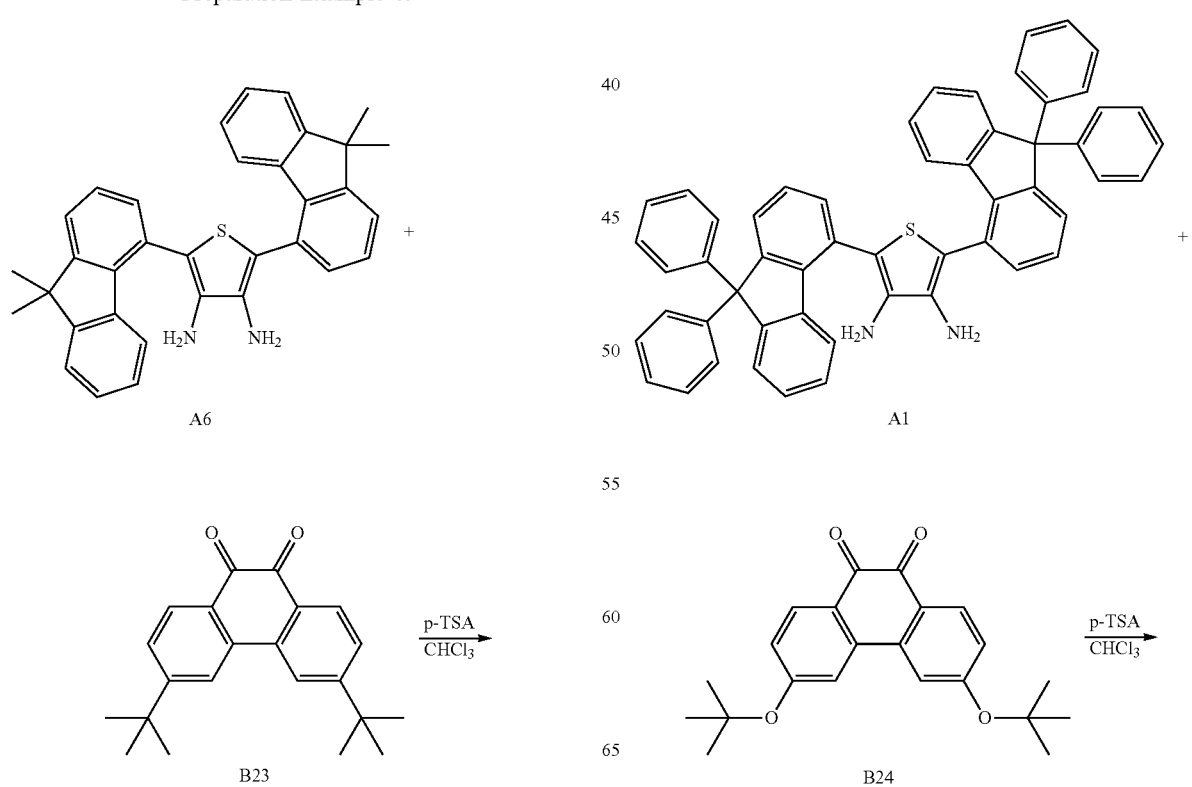

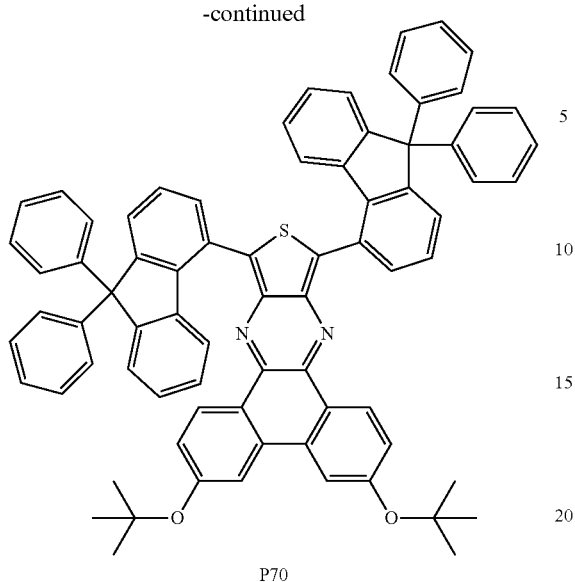

P70

Compound P70 was secured by performing the synthesis in the same manner as in Preparation Example 1, except that Compound A1 (3 g, 1 equivalent) and Compound B24 (1.38 g, 1.05 equivalents) were used instead of Compound B1. (2.88 g, yield 91%) HR LC/MS/MS m/z calcd for $C_{76}H_{58}N_2O_2S$ (M+):1062.4219; found: 1062.4219

Preparation Example 71

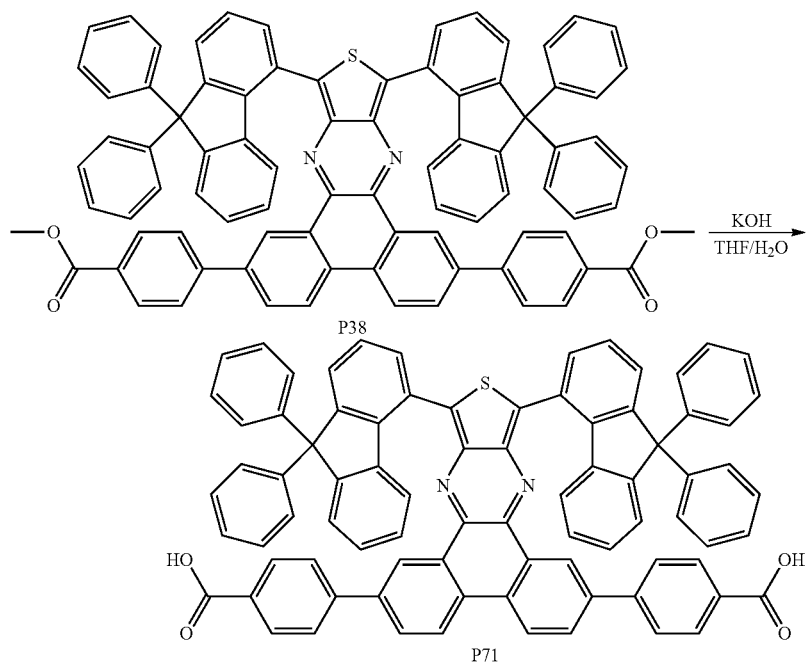

After Compound P38 (5 g, 1 equivalent) secured through Preparation Example 38 was dissolved in THF, 10 equivalents of KOH were dissolved in water and the resulting solution was added thereto. Thereafter, the reaction was performed by increasing the temperature to 80° C. After the reaction was performed for 3 days, the reaction temperature was lowered to room temperature, and then a solid was formed by adding hydrochloric acid thereto. The produced solid was secured through filtration under reduced pressure while being washed with water and ethanol. After the remaining monomer was removed by putting the formed solid into chloroform and stirring the resulting solution, Compound P71 was secured by performing the filtration under reduced pressure again. (2.88 g, yield 59%) HR LC/MS/MS m/z calcd for C82H50N2O4S (M+): 1158.3491; found: 1158.3491
Preparation Example 72
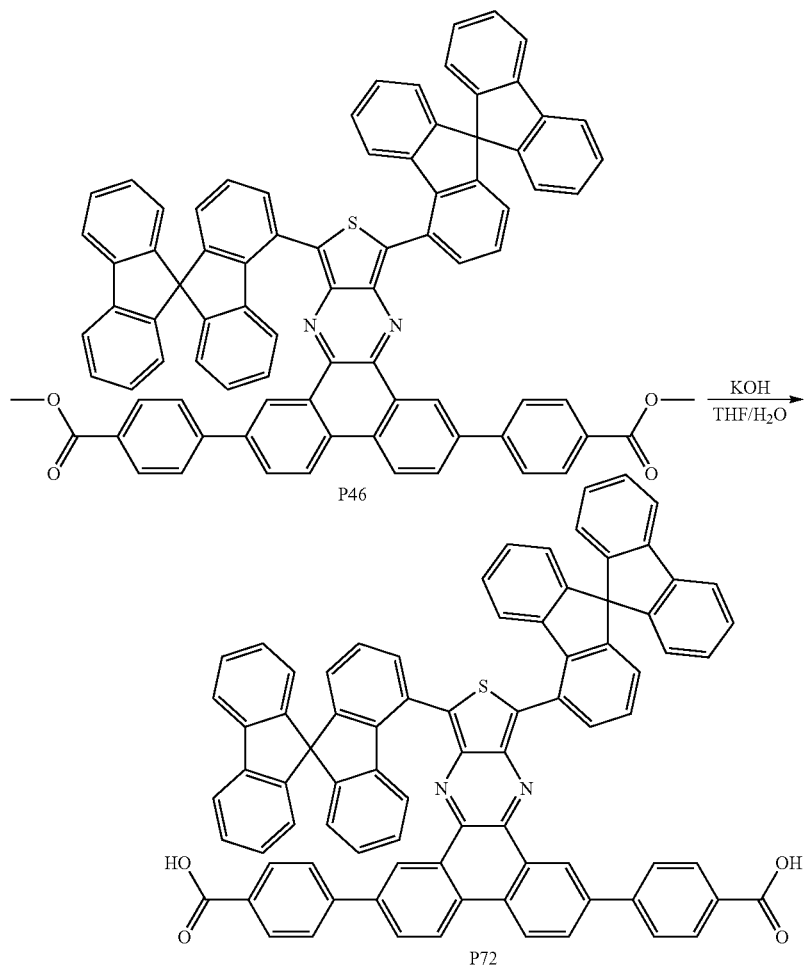
Compound P72 was secured by performing the synthesis in the same manner as in Preparation Example 71, except that Compound P46 (5 g, 1 equivalent) was used instead of Compound P38. (2.34 g, yield 48%) HR LC/MS/MS m/z calcd for $C_{85}H_{50}N_2O_4S$ (M+):1154.3178; found: 115.3177
Preparation Example 73
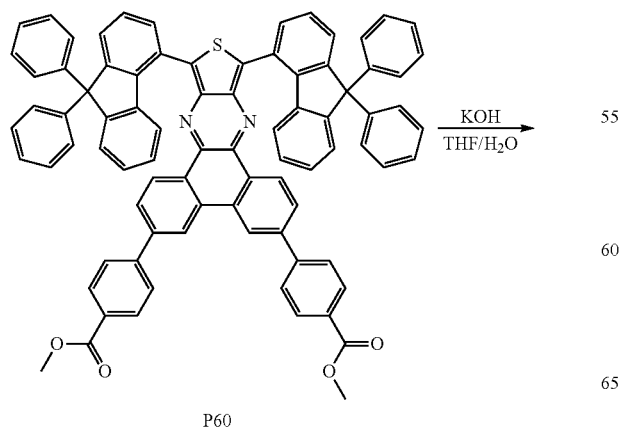

-continued

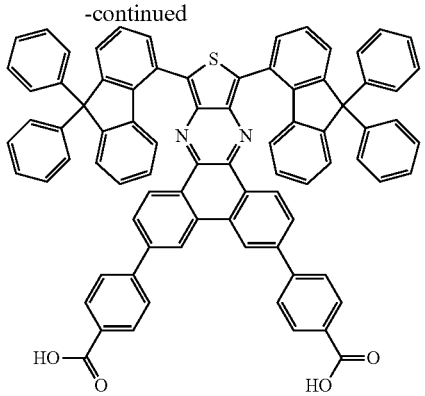

P73

Compound P73 was secured by performing the synthesis in the same manner as in Preparation Example 71, except that Compound P60 (5 g, 1 equivalent) was used instead of Compound P38. (3.47 g, yield 71%) HR LC/MS/MS m/z calcd for $C_{82}H_{50}N_2O_4S$ (M+):1158.3491; found: 1158.3490

Preparation Example 74

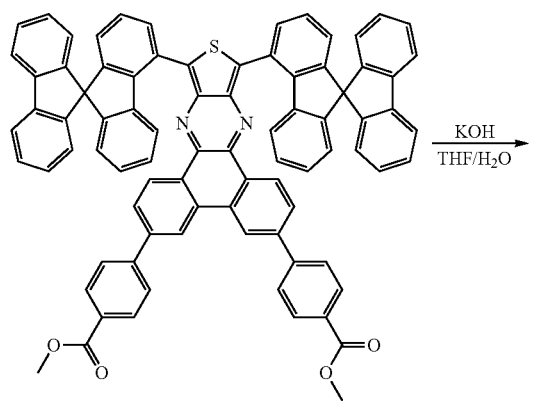

P65

P74

Compound P74 was secured by performing the synthesis in the same manner as in Preparation Example 71, except that Compound P65 (5 g, 1 equivalent) was used instead of Compound P38. (2.68 g, yield 55%) HR LC/MS/MS m/z calcd for $C_{85}H_{50}N_2O_4S$ (M+):1154.3178; found: 115.3179

Preparation Example 75

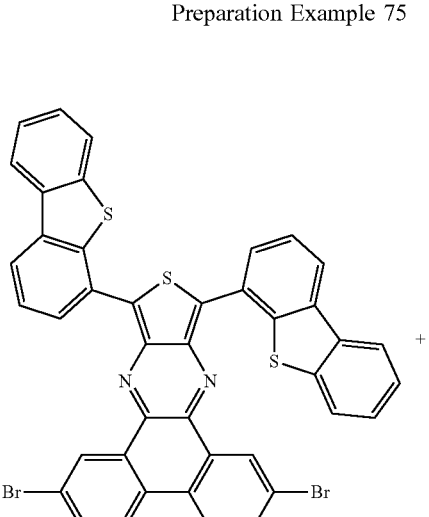

P15

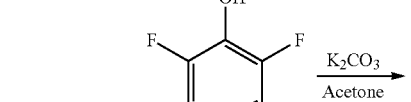

B25

P75

After Compound P15 (5 g, 1 equivalent) secured through Preparation Example 15 was dissolved in acetone along with Compound B25 (2.75 g, 3 equivalents), 3 equivalents of potassium carbonate were added thereto, and the resulting solution was stirred under nitrogen by increasing the temperature to 60° C. After the reaction was performed for 3 days, the temperature was lowered to room temperature, and then an extraction was performed by adding THF and water thereto. After moisture was removed from the extracted organic solvent through treatment with anhydrous magnesium sulfate, the solution was concentrated. The concentrated solution was recrystallized through THF and ethanol to secure Compound P75. (3.50 g, yield 60%) HR LC/MS/MS m/z calcd for $C_{54}H_{24}F6N_2O_2S_3$ (M+):942.0904; found: 942.0904.

Preparation Example 76

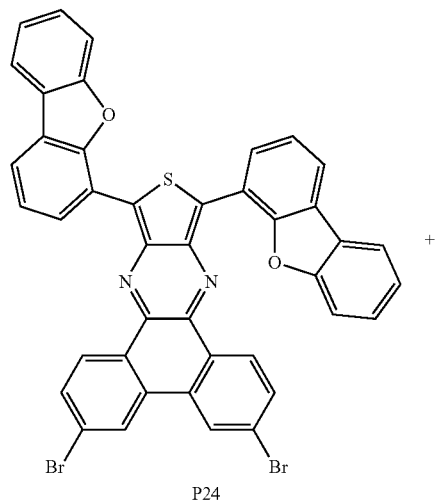

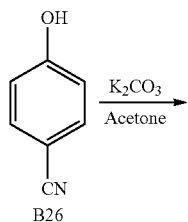

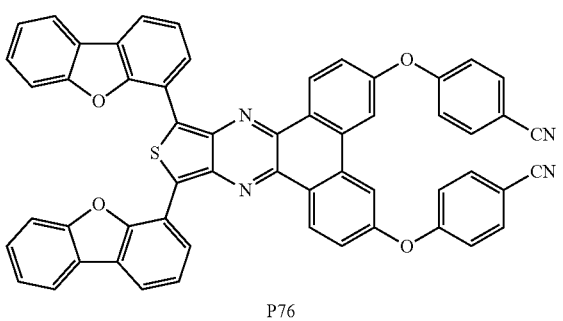

Compound P76 was secured by performing the synthesis in the same manner as in Preparation Example 75, except that Compound P24 (5 g, 1 equivalent) was used instead of Compound P15 and Compound B26 (2.30 g, 3 equivalents) was used instead of Compound B25. (2.86 g, yield 52%) HR LC/MS/MS m/z calcd for $C_{56}H_{28}N_4O_4S$ (M+):1154.3178; found: 115.3179

Comparative Preparation Example 1

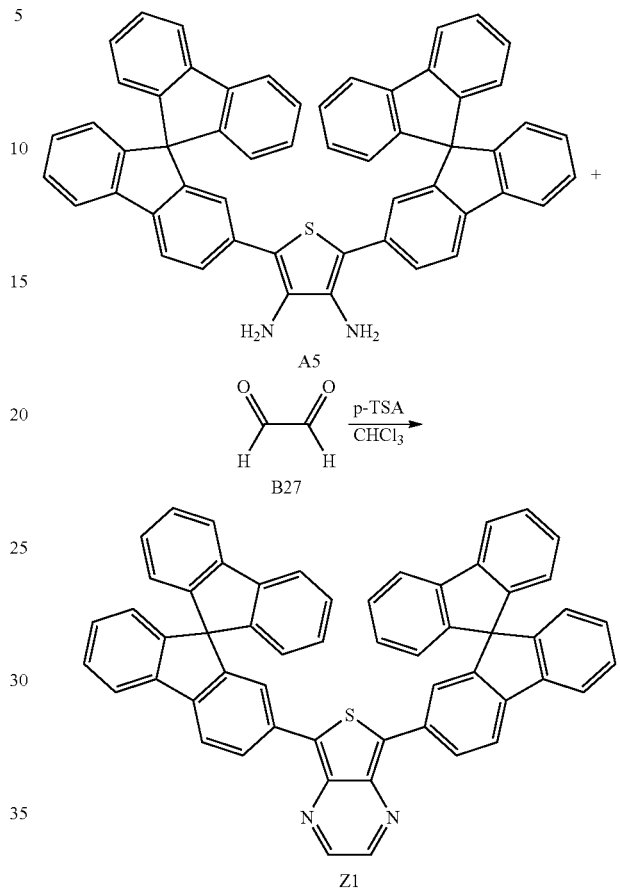

Comparative Compound Z1 was secured by performing the synthesis in the same manner as in Preparation Example 1, except that Compound A5 (2 g, 1 equivalent) was used instead of Compound A1 and Compound B27 (0.16 g, 1.05 equivalents) was used instead of Compound B1. (1.54 g, yield 75%) HR LC/MS/MS m/z calcd for $C_{56}H_{32}N_2S$ (M+): 764.2286; found: 764.2286

Comparative Preparation Example 2

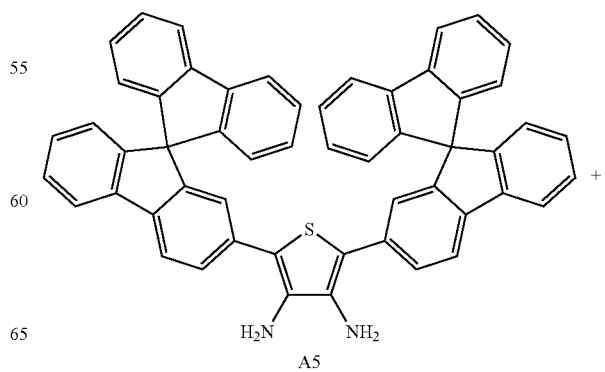

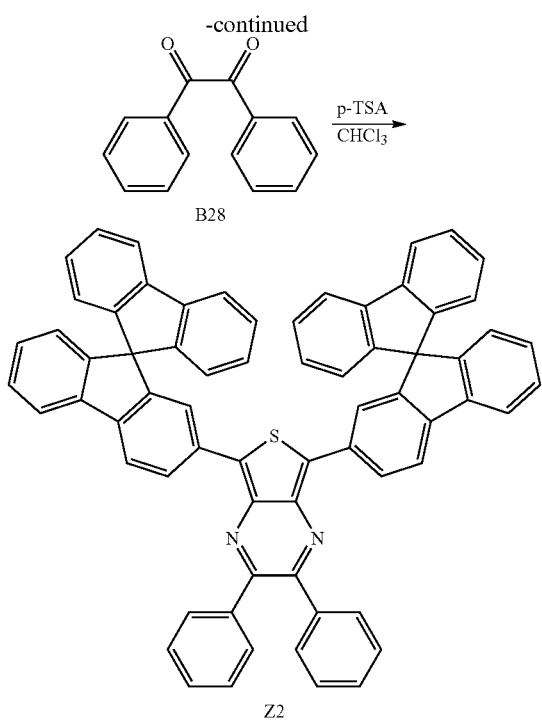

Comparative Compound Z2 was secured by performing the synthesis in the same manner as in Preparation Example 1, except that Compound A5 (2 g, 1 equivalent) was used instead of Compound A1 and Compound B28 (1.70 g, 1.05 equivalents) was used instead of Compound B1. (2.00 g, yield 81%) HR LC/MS/MS m/z calcd for $C_{68}H_{40}N_2S$ (M+): 916.2912; found: 916.2912

EXAMPLES

Example 1

1.5 parts by weight of Compound P1 (maximum absorption wavelength of 490 nm and maximum light emission wavelength of 631 nm in a toluene solution) prepared in Preparation Example 1 was dissolved in a solvent propylene glycol monomethyl ether acetate (PGMEA), such that 33.9 parts by weight of an acrylic binder (resin matrix), 59.3 parts by weight of a polyfunctional monomer (pentaerythritol triacrylate, Nippon Kayaku Co., Ltd.), 2.3 parts by weight of a bonding aid and a surfactant (KBM 503, Shinetsu), and 3.0 parts by weight of a photoinitiator (Tinuvin® 477, BASF) had a solid content of 21 wt %, thereby preparing a solution. The acrylic binder is a copolymer of benzyl methacrylate, methacrylic acid, n-phenylmaleimide, and styrene. After the mixed solution was sufficiently stirred, a glass substrate was coated with the solution as a thin film, and then the solution was dried to prepare a color conversion film. The brightness spectrum of the prepared color conversion film was measured by a spectroradiometer (SR series manufactured by Topcon, Inc.). Specifically, the prepared color conversion film was stacked on one surface of a light guide plate of a backlight unit including an LED blue backlight (maximum light emission wavelength of 450 nm) and the light guide plate, a prism sheet and a multilayer reflective polarizer film were stacked on the color conversion film, and then an initial value was set, such that the luminance of the blue LED light was 600 nit based on the film.

Example 2

A color conversion film was prepared in the same manner as in Example 1, except that in Example 1, Compound P2 (maximum absorption wavelength of 494 nm and maximum light emission wavelength of 633 nm in a toluene solution) was used instead of Compound P1.

Example 3

A color conversion film was prepared in the same manner as in Example 1, except that in Example 1, Compound P26 (maximum absorption wavelength of 484 nm and maximum light emission wavelength of 62 nm in a toluene solution) was used instead of Compound P1.

Example 4

A color conversion film was prepared in the same manner as in Example 1, except that in Example 1, Compound P27 (maximum absorption wavelength of 494 nm and maximum light emission wavelength of 628 nm in a toluene solution) was used instead of Compound P1.

Example 5

A color conversion film was prepared in the same manner as in Example 1, except that in Example 1, Compound P28 (maximum absorption wavelength of 510 nm and maximum light emission wavelength of 630 nm in a toluene solution) was used instead of Compound P1.

Example 6

A color conversion film was prepared in the same manner as in Example 1, except that in Example 1, Compound P29 (maximum absorption wavelength of 517 nm and maximum light emission wavelength of 638 nm in a toluene solution) was used instead of Compound P1.

Example 7

A color conversion film was prepared in the same manner as in Example 1, except that in Example 1, Compound P30 (maximum absorption wavelength of 484 nm and maximum light emission wavelength of 624 nm in a toluene solution) was used instead of Compound P1.

Example 8

A color conversion film was prepared in the same manner as in Example 1, except that in Example 1, Compound P31 (maximum absorption wavelength of 485 nm and maximum light emission wavelength of 625 nm in a toluene solution) was used instead of Compound P1.

Example 9

A color conversion film was prepared in the same manner as in Example 1, except that in Example 1, Compound P35 (maximum absorption wavelength of 500 nm and maximum light emission wavelength of 623 nm in a toluene solution) was used instead of Compound P1.

Example 10

A color conversion film was prepared in the same manner as in Example 1, except that in Example 1, Compound P36

(maximum absorption wavelength of 489 nm and maximum light emission wavelength of 618 nm in a toluene solution) was used instead of Compound P1.

Example 11

A color conversion film was prepared in the same manner as in Example 1, except that in Example 1, Compound P41 (maximum absorption wavelength of 500 nm and maximum light emission wavelength of 618 nm in a toluene solution) was used instead of Compound P1.

Example 12

A color conversion film was prepared in the same manner as in Example 1, except that in Example 1, Compound P42 (maximum absorption wavelength of 503 nm and maximum light emission wavelength of 619 nm in a toluene solution) was used instead of Compound P1.

Example 13

A color conversion film was prepared in the same manner as in Example 1, except that in Example 1, Compound P44 (maximum absorption wavelength of 506 nm and maximum light emission wavelength of 623 nm in a toluene solution) was used instead of Compound P1.

Example 14

A color conversion film was prepared in the same manner as in Example 1, except that in Example 1, Compound P45 (maximum absorption wavelength of 502 nm and maximum light emission wavelength of 615 nm in a toluene solution) was used instead of Compound P1.

Example 15

A color conversion film was prepared in the same manner as in Example 1, except that in Example 1, Compound P46 (maximum absorption wavelength of 507 nm and maximum light emission wavelength of 620 nm in a toluene solution) was used instead of Compound P1.

Example 16

A color conversion film was prepared in the same manner as in Example 1, except that in Example 1, Compound P47 (maximum absorption wavelength of 506 nm and maximum light emission wavelength of 621 nm in a toluene solution) was used instead of Compound P1.

Example 17

A color conversion film was prepared in the same manner as in Example 1, except that in Example 1, Compound P52 (maximum absorption wavelength of 484 nm and maximum light emission wavelength of 612 nm in a toluene solution) was used instead of Compound P1.

Example 18

A color conversion film was prepared in the same manner as in Example 1, except that in Example 1, Compound P58 (maximum absorption wavelength of 500 nm and maximum light emission wavelength of 623 nm in a toluene solution) was used instead of Compound P1.

Example 19

A color conversion film was prepared in the same manner as in Example 1, except that in Example 1, Compound P59 (maximum absorption wavelength of 496 nm and maximum light emission wavelength of 618 nm in a toluene solution) was used instead of Compound P1.

Example 20

A color conversion film was prepared in the same manner as in Example 1, except that in Example 1, Compound P66 (maximum absorption wavelength of 506 nm and maximum light emission wavelength of 628 nm in a toluene solution) was used instead of Compound P1.

Example 21

A color conversion film was prepared in the same manner as in Example 1, except that in Example 1, Compound P68 (maximum absorption wavelength of 506 nm and maximum light emission wavelength of 628 nm in a toluene solution) was used instead of Compound P1.

Example 22

A color conversion film was prepared in the same manner as in Example 1, except that in Example 1, Compound P69 (maximum absorption wavelength of 502 nm and maximum light emission wavelength of 617 nm in a toluene solution) was used instead of Compound P1.

Example 23

A color conversion film was prepared in the same manner as in Example 1, except that in Example 1, Compound P75 (maximum absorption wavelength of 515 nm and maximum light emission wavelength of 633 nm in a toluene solution) was used instead of Compound P1.

Comparative Example 1

A color conversion film was prepared in the same manner as in Example 1, except that in Example 1, Compound Z1 (maximum absorption wavelength of 509 nm and maximum light emission wavelength of 625 nm in a toluene solution) was used instead of Compound P1.

Comparative Example 2

A color conversion film was prepared in the same manner as in Example 1, except that in Example 1, Compound Z2 (maximum absorption wavelength of 532 nm and maximum light emission wavelength of 633 nm in a toluene solution) was used instead of Compound P1.

267 268
P1
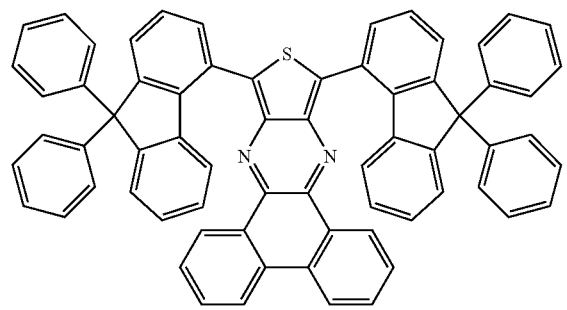
P2
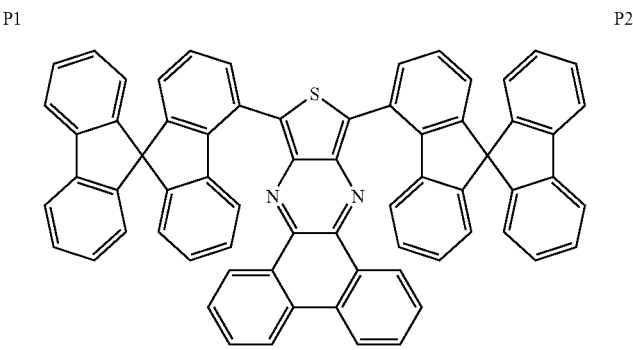
P26
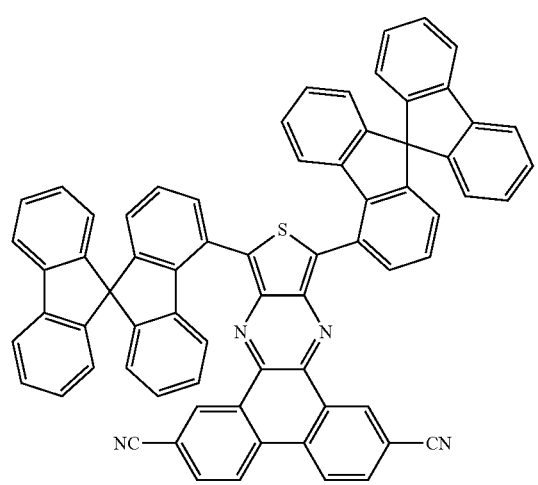
P27
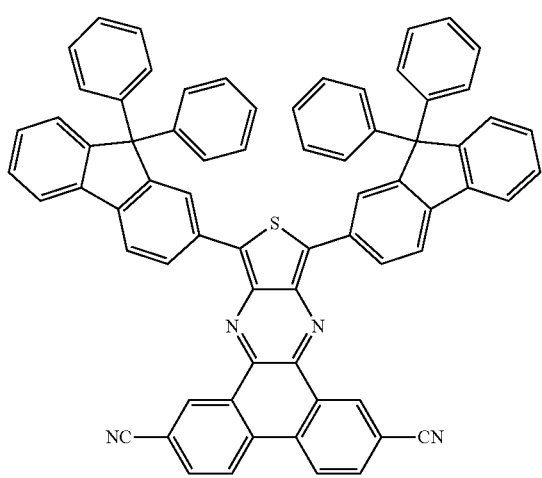
P28
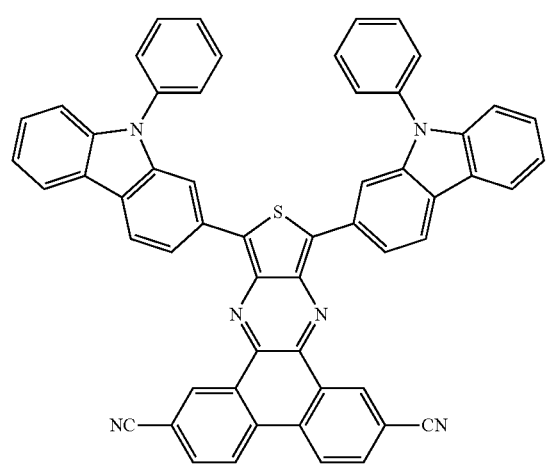
P29
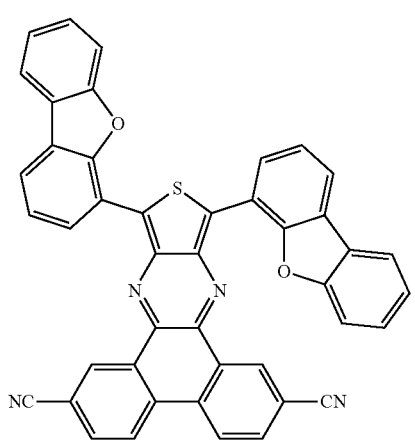
P30
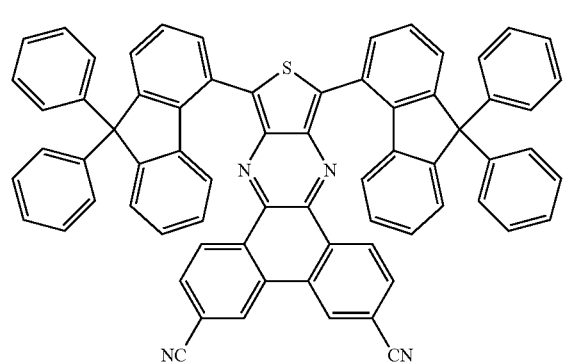
P31
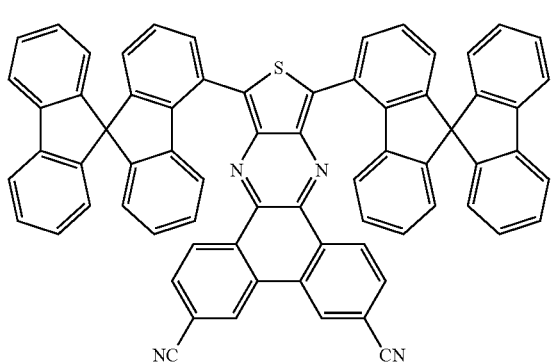

-continued
P35
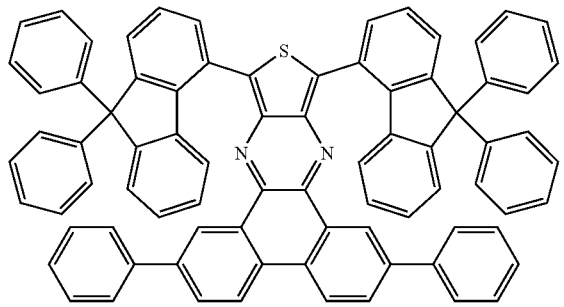
P36
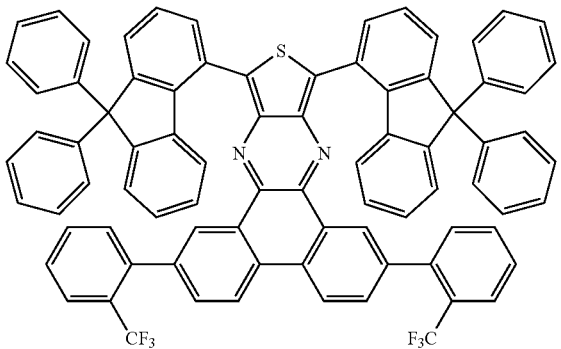
P41
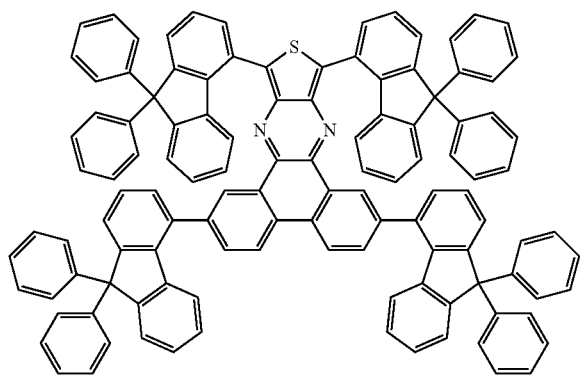
P42
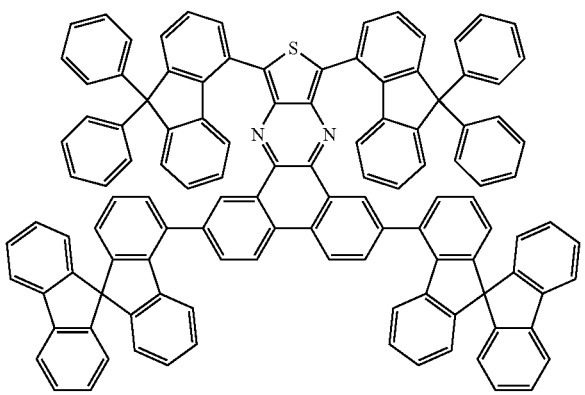
P44
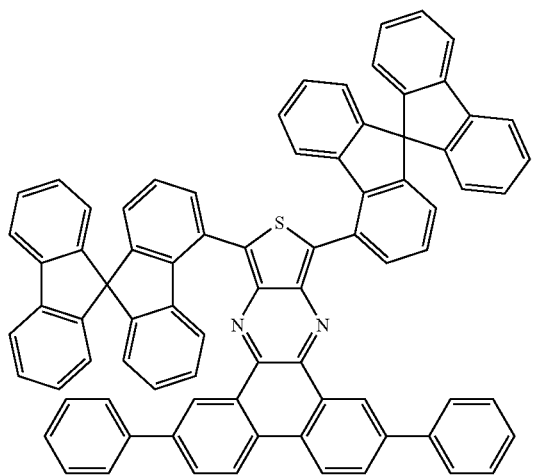
P45
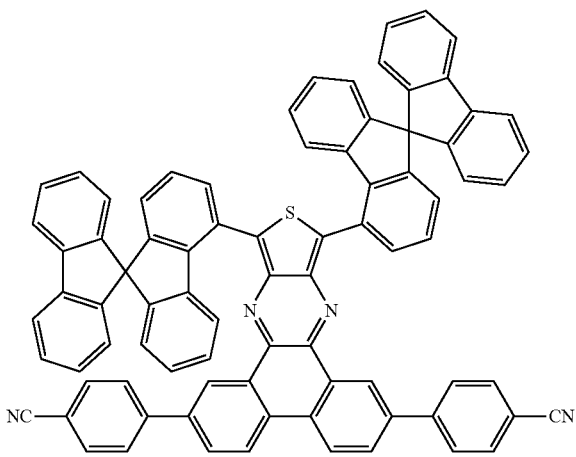

-continued
P46
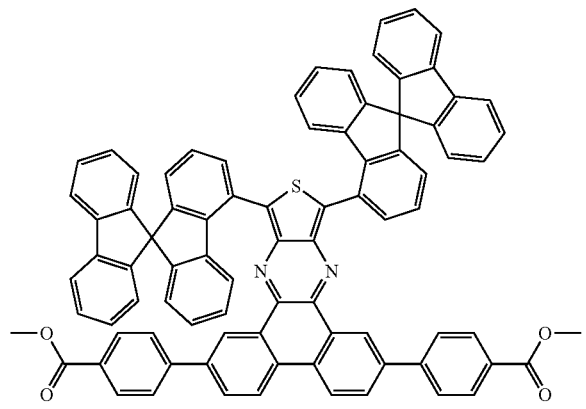
P47
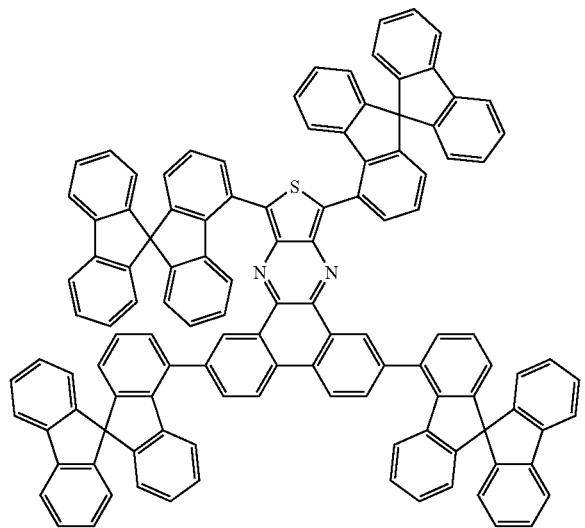
P52
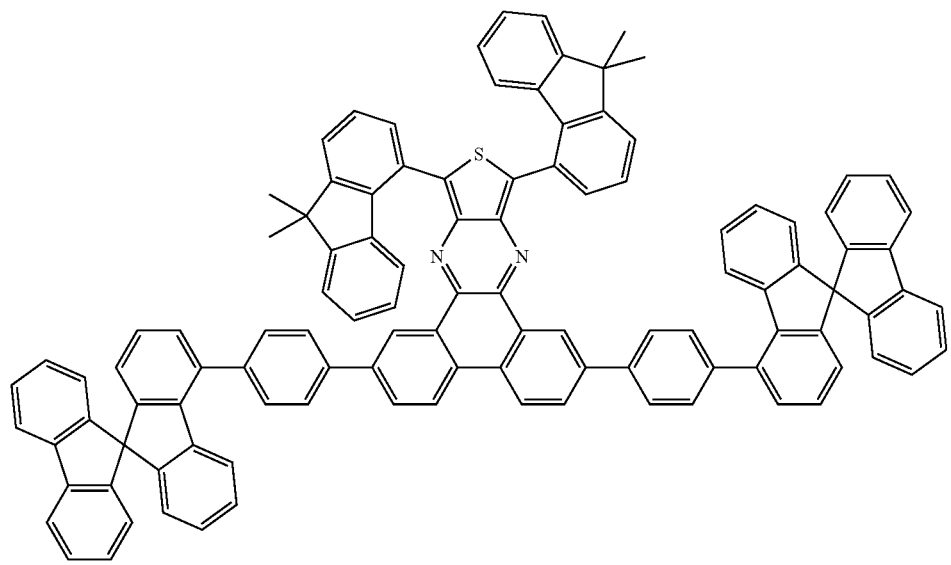
P58
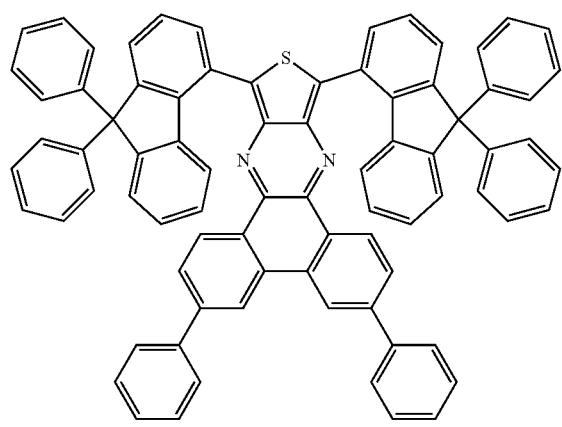
P59
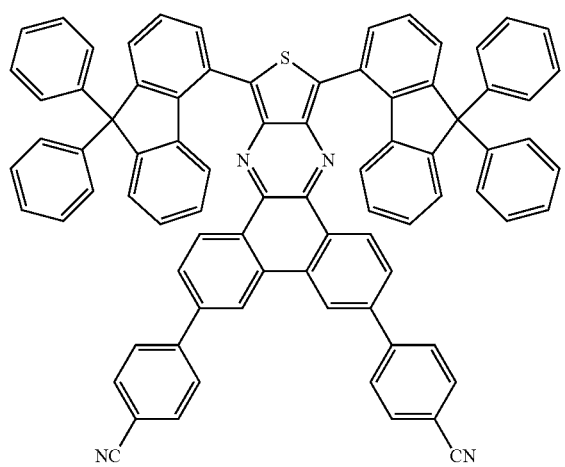

-continued
P66
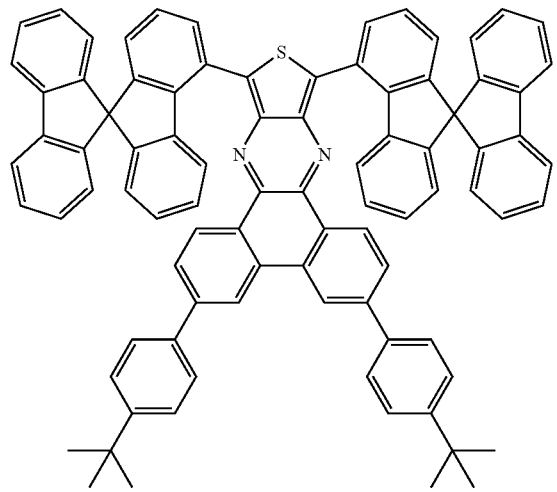
P68
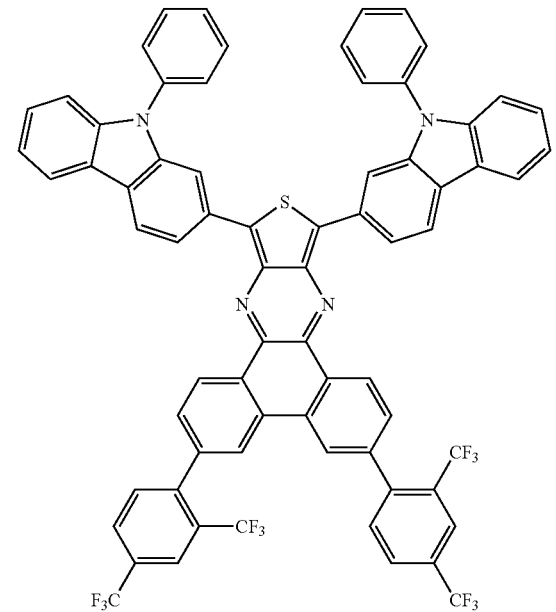
P69
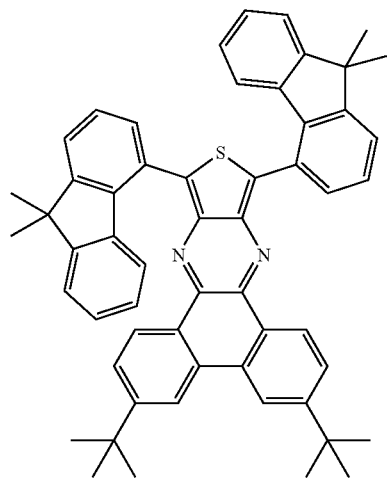
P75
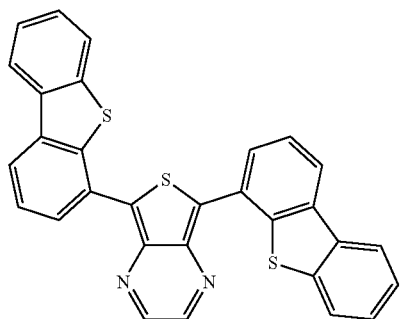
Z1
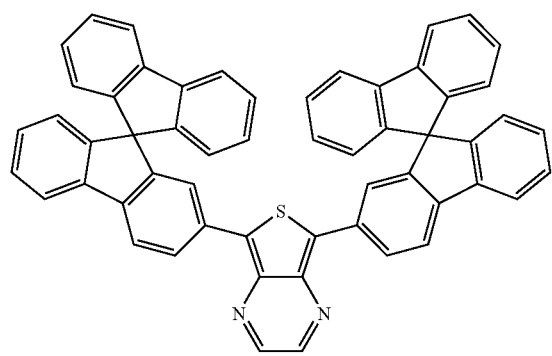
Z2
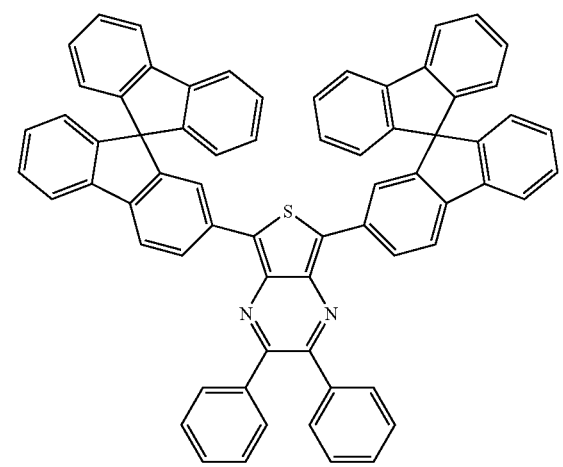

The thin film light emission wavelength and thin film quantum efficiency (PLQY (%)) when each of the compounds used in Examples 1 to 23 and Comparative Examples 1 and 2 is applied to the color conversion film are as the following Table 1.

The thin film light emission wavelength was measured using FS-2 equipment manufactured by SCINCO Co., Ltd., and the quantum efficiency was measured using Quantaurus-QY equipment manufactured by Hamamatsu Corp.

TABLE 1

| | | Thin film | |
|---|---|---|---|
| Classification | Compound | $\lambda_{PL, max}$ (nm) | PLQY (%) |
| Example 1 | P1 | 635 | 30.9 |
| Example 2 | P2 | 618 | 59.2 |
| Example 3 | P26 | 605 | 43 |
| Example 4 | P27 | 637 | 27.9 |
| Example 5 | P28 | 645 | 25.3 |
| Example 6 | P29 | 650 | 26.2 |
| Example 7 | P30 | 627 | 34.0 |
| Example 8 | P31 | 625 | 58.0 |
| Example 9 | P35 | 625 | 29.2 |
| Example 10 | P36 | 617 | 45.2 |
| Example 11 | P41 | 635 | 29.4 |
| Example 12 | P42 | 636 | 33.5 |
| Example 13 | P44 | 610 | 42.7 |
| Example 14 | P45 | 617 | 45.2 |
| Example 15 | P46 | 618 | 49.5 |
| Example 16 | P47 | 636 | 53.8 |
| Example 17 | P52 | 610 | 49.2 |
| Example 18 | P58 | 624 | 30.5 |
| Example 19 | P59 | 618 | 35.7 |
| Example 20 | P66 | 639 | 47.1 |
| Example 21 | P68 | 638 | 29.2 |
| Example 22 | P69 | 630 | 50.1 |
| Example 23 | P75 | 647 | 25.1 |
| Comparative Example 1 | Z1 | 640 | 20.9 |
| Comparative Example 2 | Z2 | 649 | 24 |

In Table 1, $\lambda_{PL,max}$ means a maximum light emission wavelength of a material appearing in a thin film state, and PLQY (%) means quantum efficiency of a material appearing in a thin film state.

As confirmed in Table 1, it could be confirmed that the color conversion films manufactured in Examples 1 to 23 had the better thin film quantum efficiency than that of the color conversion films manufactured through Comparative Examples 1 and 2. Example 2 has the quantum efficiency which is 2.83 times higher than Comparative Example 1. In particular, when in Formula 1 of the present application, X1 and X2 are C(A2)(A3), and A2 and A3 are bonded to each other to form a fluorene ring (Examples 2, 3, 8, 13 to 16, and 20), the quantum efficiency in a thin film state is excellent.

Therefore, it can be seen that a color conversion film including the compound represented by Formula 1 is excellent in quantum efficiency.

The invention claimed is:
1. A compound represented by Formula 1:

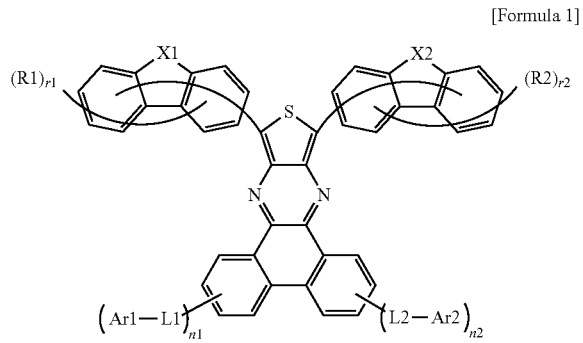

[Formula 1]

in the Formula 1,
X1 and X2 are the same as or different from each other, and are each independently N(A1), C(A2)(A3), O, or S,
L1 and L2 are the same as or different from each other, and are each independently a direct bond, —O—, a substituted or unsubstituted arylene group, or a substituted or unsubstituted heteroarylene group,
Ar1 and Ar2 are the same as or different from each other, and are each independently hydrogen, deuterium, a halogen group, a nitrile group, —C(=O)ORa, a substituted or unsubstituted alkyl group, a substituted or unsubstituted haloalkyl group, a substituted or unsubstituted alkoxy group, a substituted or unsubstituted aryloxy group, a substituted or unsubstituted alkenyl group, a substituted or unsubstituted aryl group, or a substituted or unsubstituted heterocyclic group, or bonding to at least one adjacent group to form a substituted or unsubstituted ring,
Ra is hydrogen, deuterium, or a substituted or unsubstituted alkyl group,
R1 and R2 are the same as or different from each other, and are each independently hydrogen, deuterium, a halogen group, a nitrile group, a substituted or unsubstituted alkyl group, a substituted or unsubstituted aryl group, or a substituted or unsubstituted heterocyclic group, or bonding to at least one adjacent group to form a substituted or unsubstituted ring,
A1 to A3 are the same as or different from each other, and are each independently hydrogen, deuterium, a methyl group, a phenyl group unsubstituted or substituted with a methoxy group, or

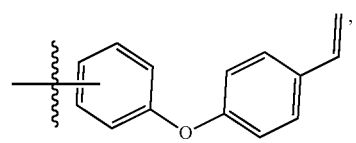

or
A2 and A3 are bonded to each other to form a fluorene ring unsubstituted or substituted with a tert-butyl group,
r1 and r2 are the same as or different from each other, and are each independently an integer from 0 to 7,
when r1 is 2 or higher, a plurality of R1's are the same as or different from each other,
when r2 is 2 or higher, a plurality of R2's are the same as or different from each other,
n1 and n2 are the same as or different from each other, and are each independently an integer from 0 to 4, when n1 is 2 or higher, a plurality of L1-Ar1's are the same as or different from each other, and when n2 is 2 or higher, a plurality of L2-Ar2's are the same as or different from each other.

2. The compound of claim 1, wherein the Formula 1 is represented by any one of the following Formulae 2-1 to 2-4:

[Formula 2-1]

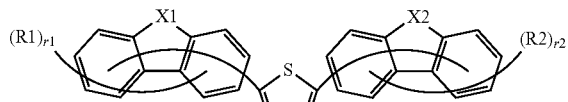

[Formula 2-2]

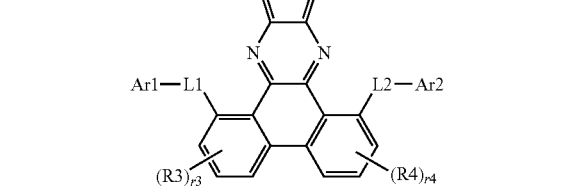

[Formula 2-3]

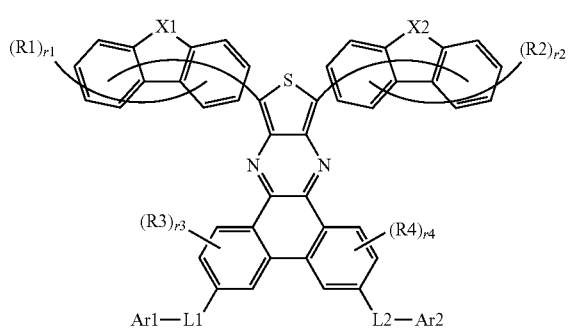

[Formula 2-4]

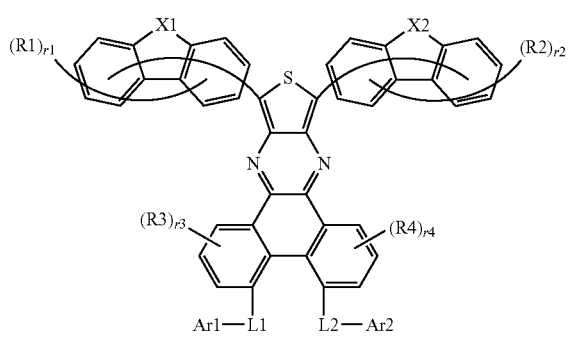

in the Formulae 2-1 to 2-4, definitions of X1, X2, L1, L2, Ar1, Ar2, R1, R2, r1, and r2 are the same as those defined in the Formula 1, R3 and R4 are the same as or different from each other, and are each independently hydrogen, deuterium, a halogen group, a nitrile group, a substituted or unsubstituted alkyl group, a substituted or unsubstituted aryl group, or a substituted or unsubstituted heterocyclic group, or bonding to at least one adjacent group to form a substituted or unsubstituted ring, r3 and r4 are the same as or different from each other, and are each independently an integer from 0 to 3, when r3 is 2 or higher, a plurality of R3's are the same as or different from each other, and when r4 is 2 or higher, a plurality of R4's are the same as or different from each other.

3. The compound of claim 1, wherein the Formula 1 is represented by any one of the following Formulae 3-1 to 3-4:

[Formula 3-1]

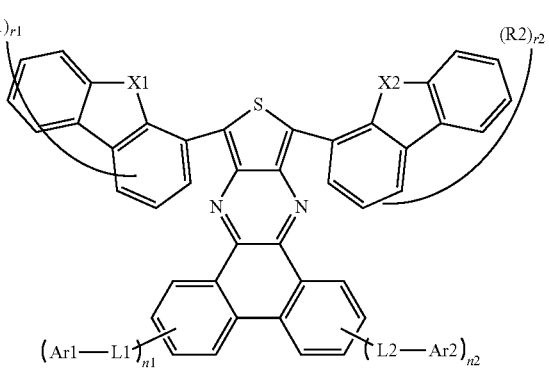

[Formula 3-2]

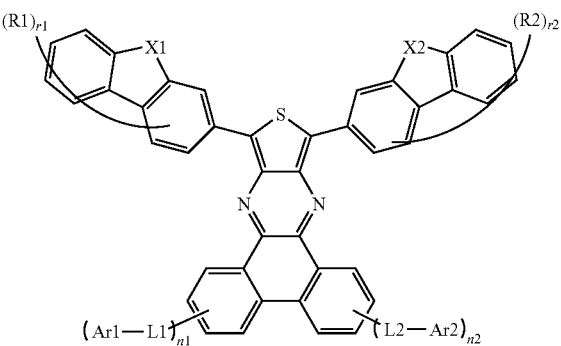

[Formula 3-3]

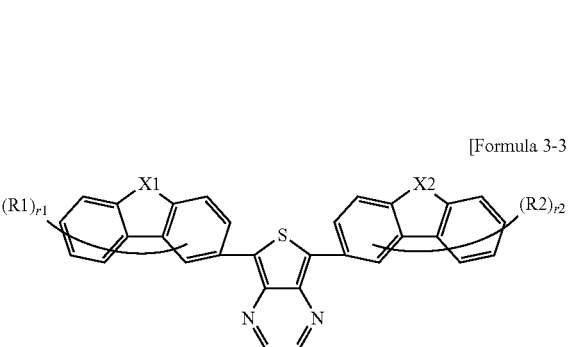

-continued

[Formula 3-4]

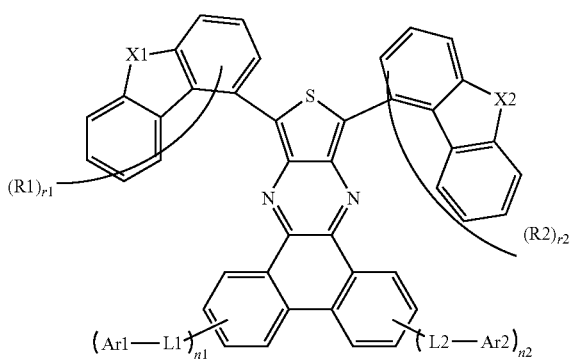

4. The compound of claim 1, wherein Ar1 and Ar2 are the same as or different from each other, and are each independently hydrogen, deuterium, a halogen group, a nitrile group, an alkyl group, an alkoxy group, an aryl group unsubstituted or substituted with a halogen group, a nitrile group, a haloalkyl group, an alkyl group, C(=O)ORa, an alkoxy group, an aryl group, or a heterocyclic group which is unsubstituted or substituted with an alkyl group, an aryl group, or an alkylaryl group, or bonding to at least one adjacent group to form an unsubstituted monocyclic to tricyclic ring, and Ra is hydrogen, deuterium, or an alkyl group.

5. The compound of claim 1, wherein L1 and L2 are the same as or different from each other, and are each independently a direct bond, —O—, a phenylene group, a biphenylene group, a fluorenylene group unsubstituted or substituted with a methyl group or a phenyl group, a spirobifluorenylene group, a divalent carbazole group, a divalent dibenzofuran group, or a divalent quinoline group.

6. The compound of claim 1, wherein R1 and R2 are each hydrogen.

7. A color conversion film comprising:
   a resin matrix; and
   the compound according to claim 1, the compound being dispersed in the resin matrix.

8. A backlight unit comprising the color conversion film according to claim 7.

9. A display device comprising the backlight unit according to claim 8.

10. The color conversion film of claim 7, comprising the compound in amount of 0.001 to 20 wt % based on the total weight of the color conversion film.

11. The color conversion film of claim 7, wherein the resin matrix is a thermoplastic polymer or a thermosetting polymer.

12. A compound represented by Formula 1:

[Formula 1]

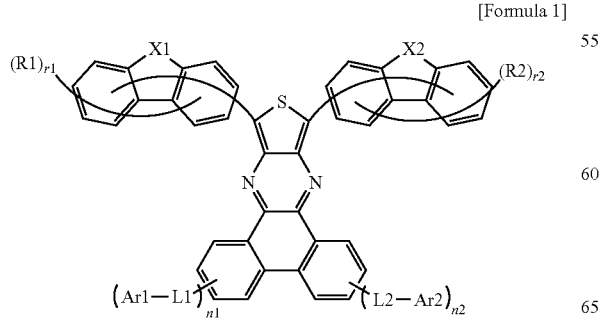

in the Formula 1,

X1 and X2 are the same as or different from each other, and are each independently N(A1), C(A2)(A3), O, or S, L1 and L2 are the same as or different from each other, and are each independently a direct bond, —O—, a substituted or unsubstituted arylene group, wherein Ar1 and Ar2 are the same as or different from each other, and are each independently hydrogen, deuterium, a halogen group, a nitrile group, or any one selected from the following structures:

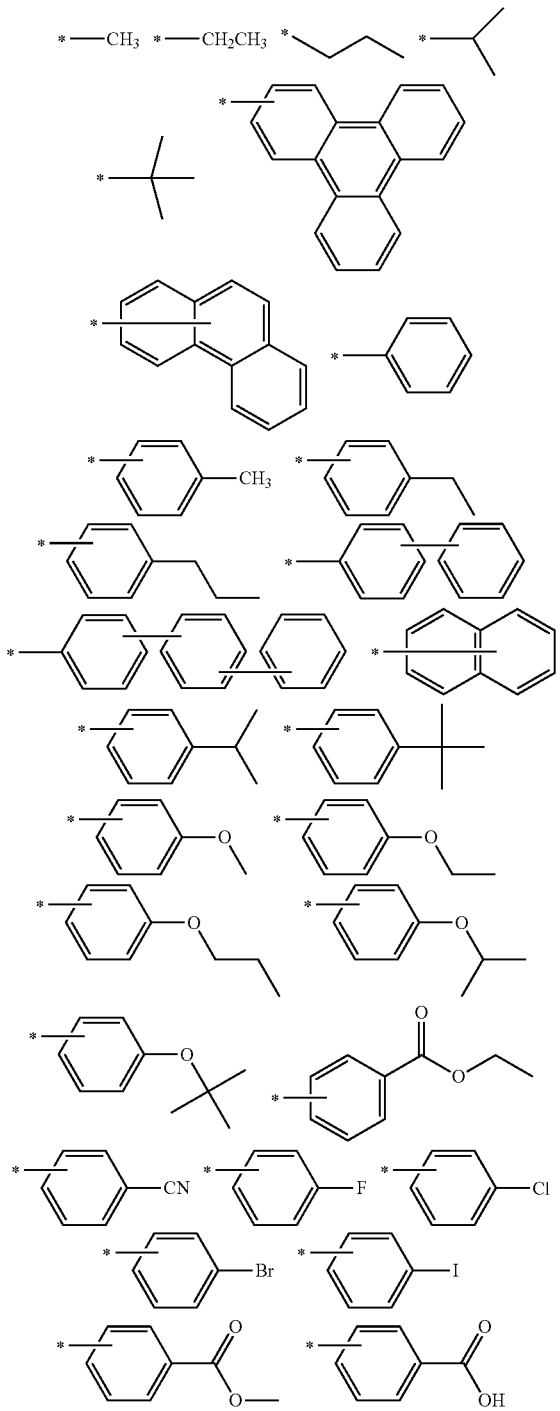

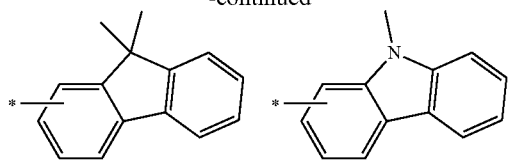
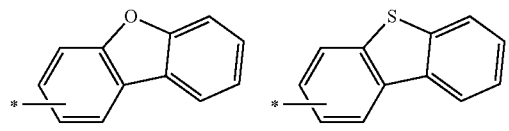
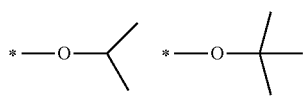
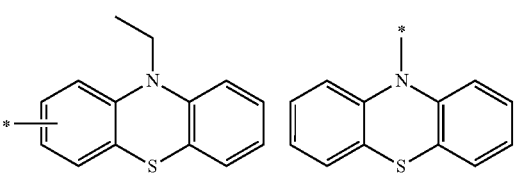
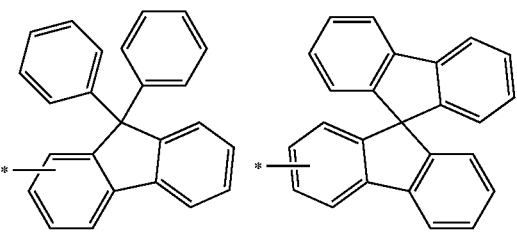
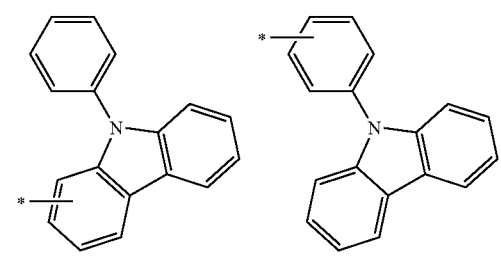
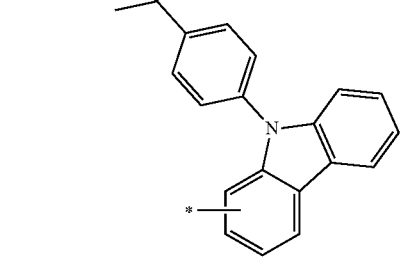
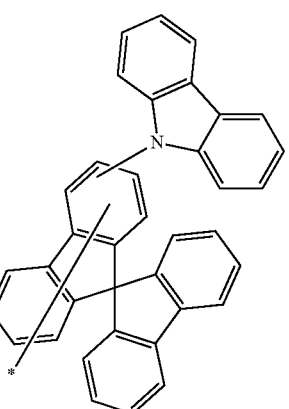
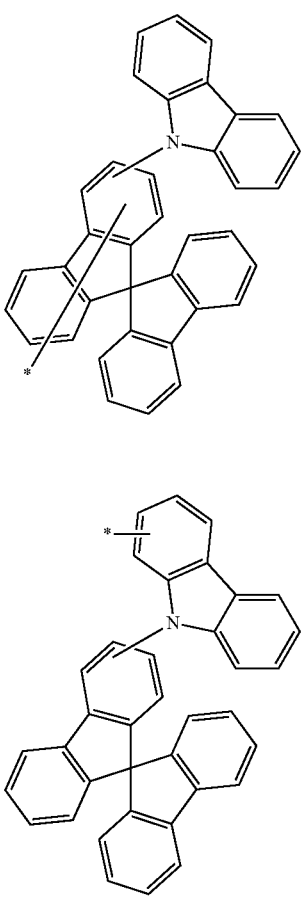
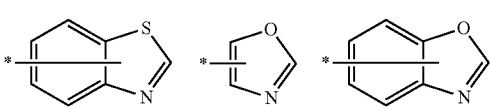

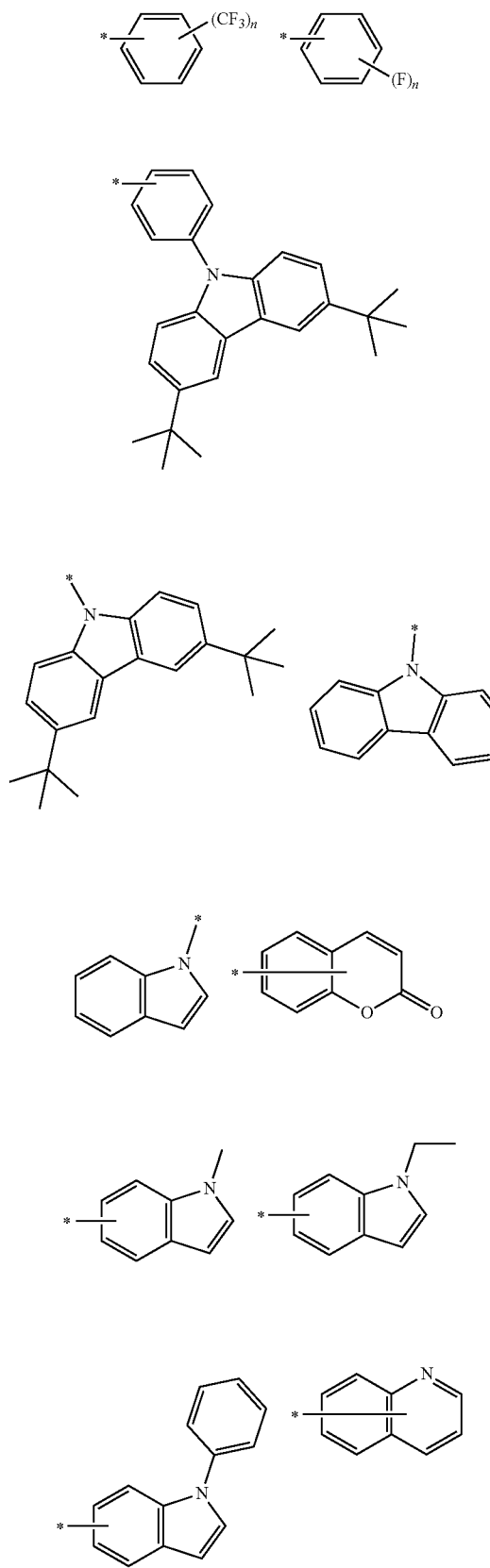

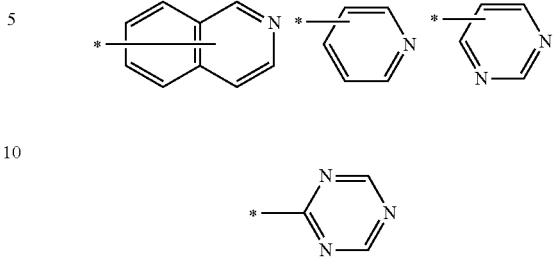

in the structures, * is a position linked to L1 or L2, and n is an integer from 1 to 5, R1 and R2 are the same as or different from each other, and are each independently hydrogen, deuterium, a halogen group, a nitrile group, a substituted or unsubstituted alkyl group, a substituted or unsubstituted aryl group, or a substituted or unsubstituted heterocyclic group, or bonding to at least one adjacent group to form a substituted or unsubstituted ring, A1 to A3 are the same as or different from each other, and are each independently a substituent selected from the group consisting of hydrogen, deuterium, a halogen group, a nitrile group, a substituted or unsubstituted alkyl group, a substituted or unsubstituted alkoxy group, a substituted or unsubstituted aryloxy group, a substituted or unsubstituted alkenyl group, a substituted or unsubstituted aryl group, and a substituted or unsubstituted heterocyclic group, or a substituent to which two or more groups selected from the group are linked, or bonding to at least one adjacent group to form a substituted or unsubstituted ring, r1 and r2 are the same as or different from each other, and are each independently an integer from 0 to 7, when r1 is 2 or higher, a plurality of R1's are the same as or different from each other, when r2 is 2 or higher, a plurality of R2's are the same as or different from each other, n1 and n2 are the same as or different from each other, and are each independently an integer from 0 to 4, when n1 is 2 or higher, a plurality of L1-Ar1's are the same as or different from each other, and when n2 is 2 or higher, a plurality of L2-Ar2's are the same as or different from each other.

13. A color conversion film comprising:
a resin matrix; and
the compound according to claim 12, the compound being dispersed in the resin matrix.

14. The color conversion film of claim 13, comprising the compound in amount of 0.001 to 20 wt % based on the total weight of the color conversion film.

15. The color conversion film of claim 13, wherein the resin matrix is a thermoplastic polymer or a thermosetting polymer.

16. A compound according to any one of the following compounds:

285 286
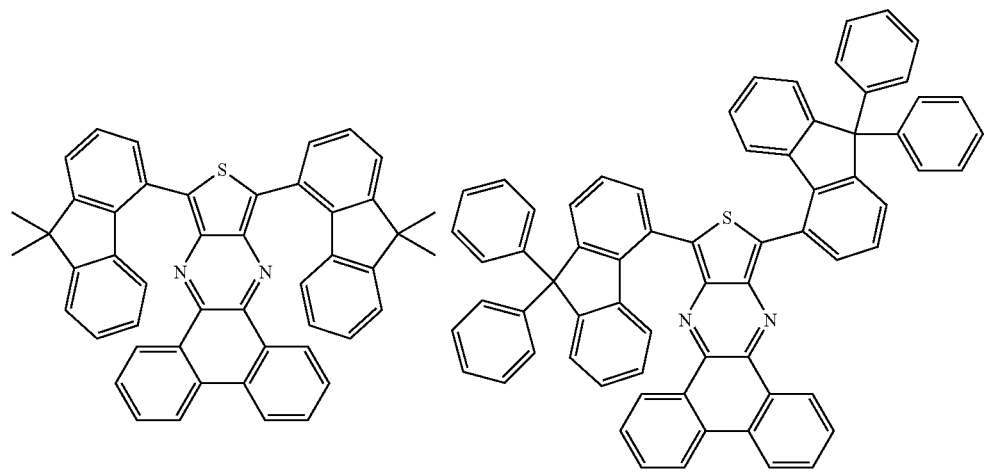
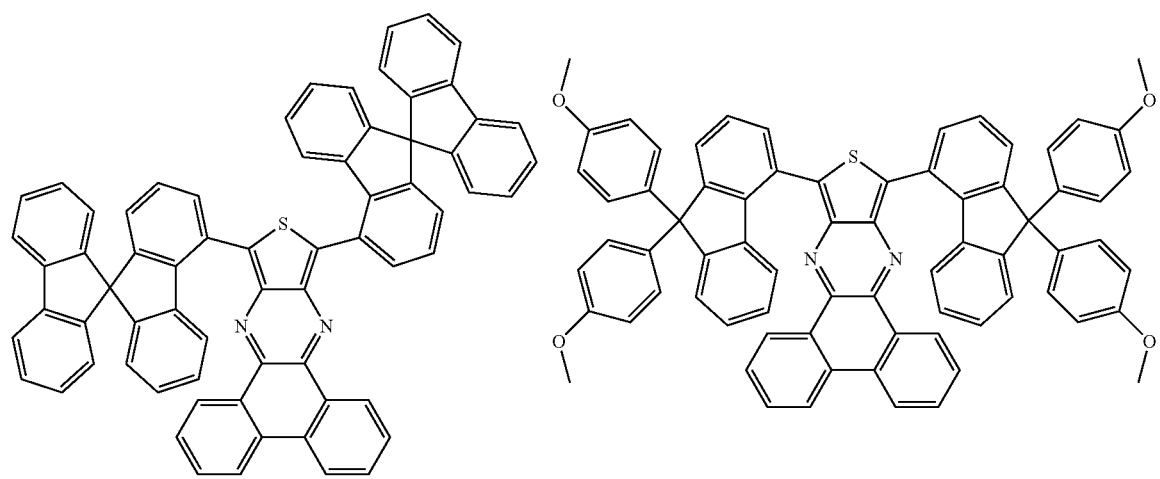
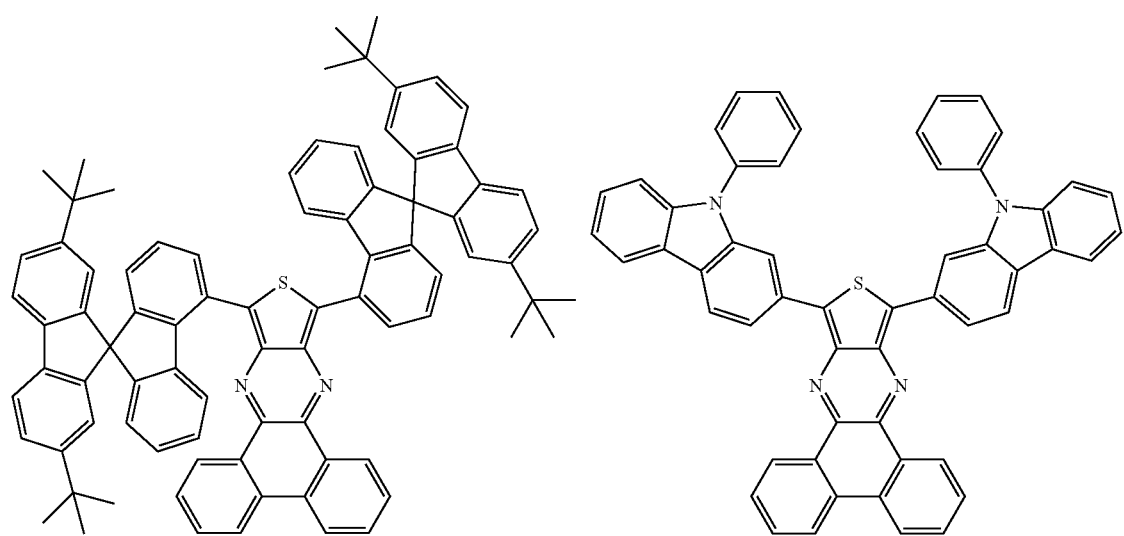

287 288
-continued
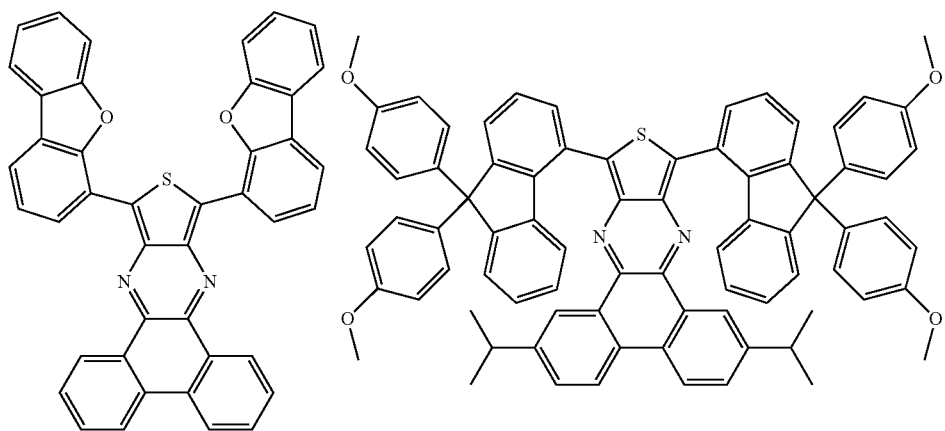
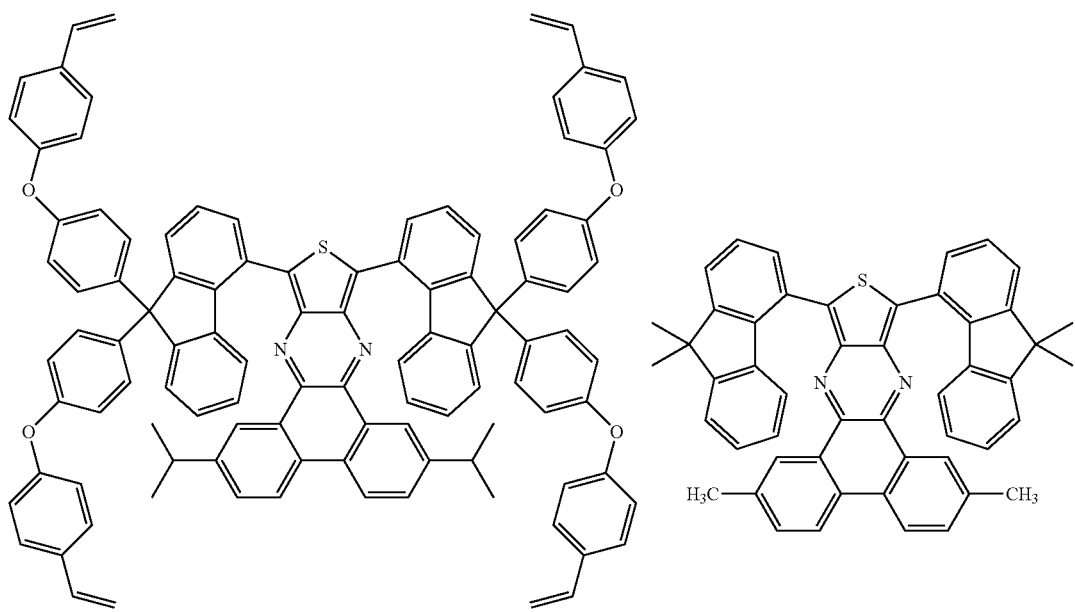
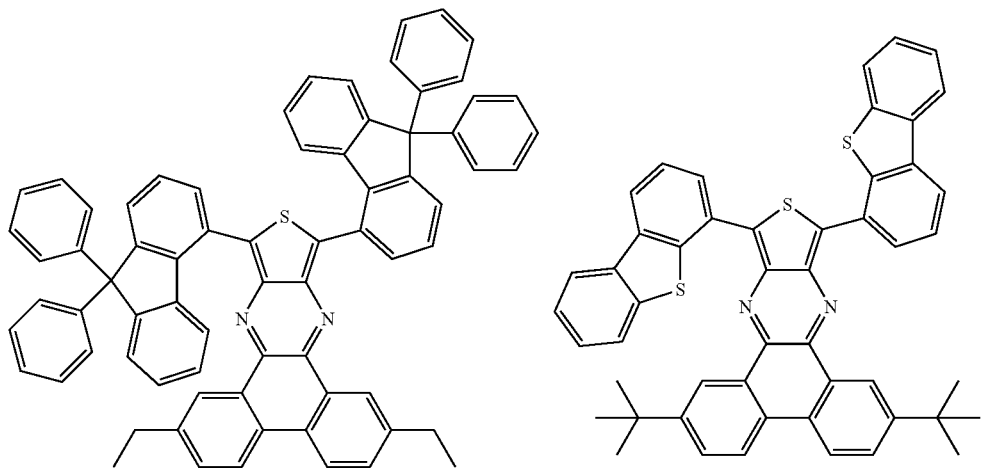

-continued
289
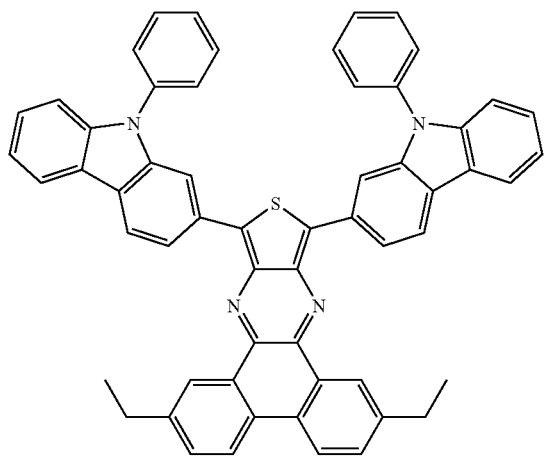
290
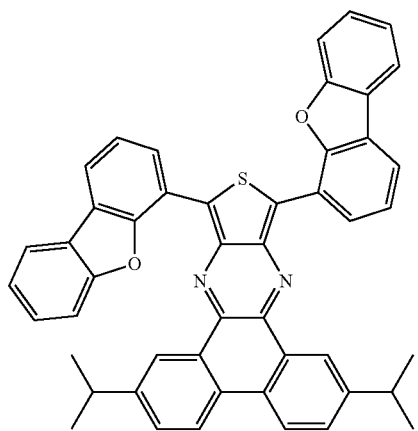
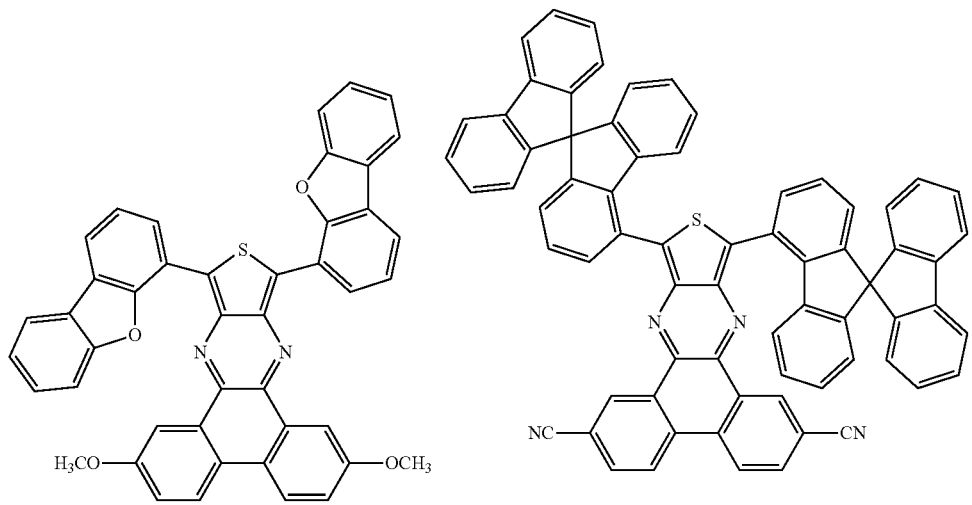
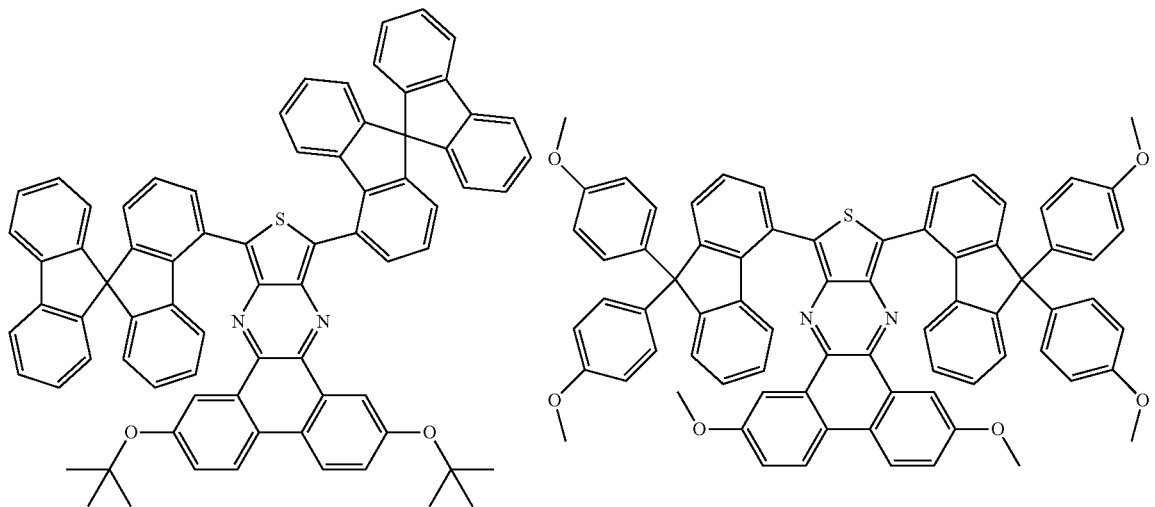

291 292
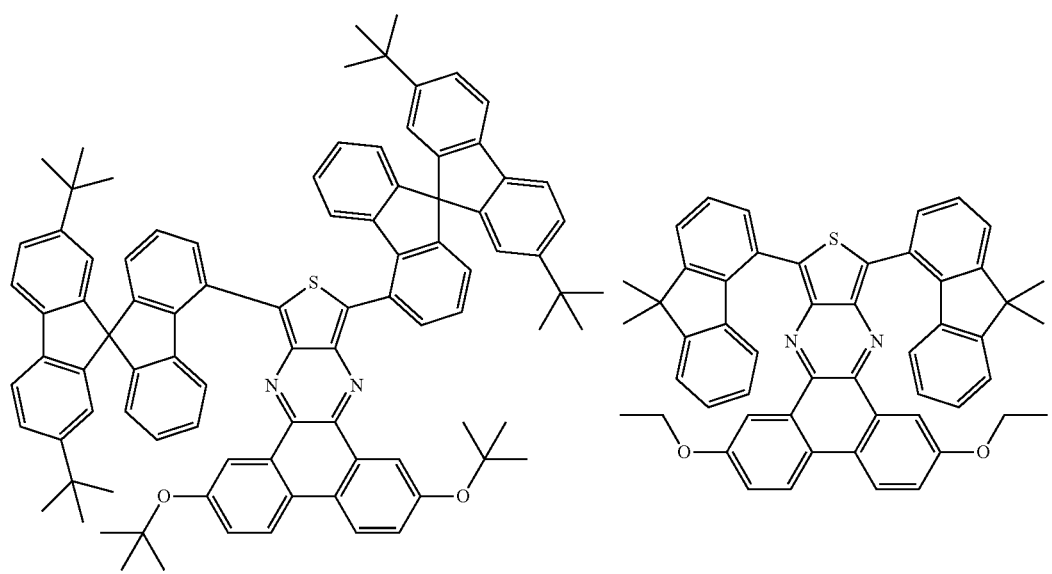
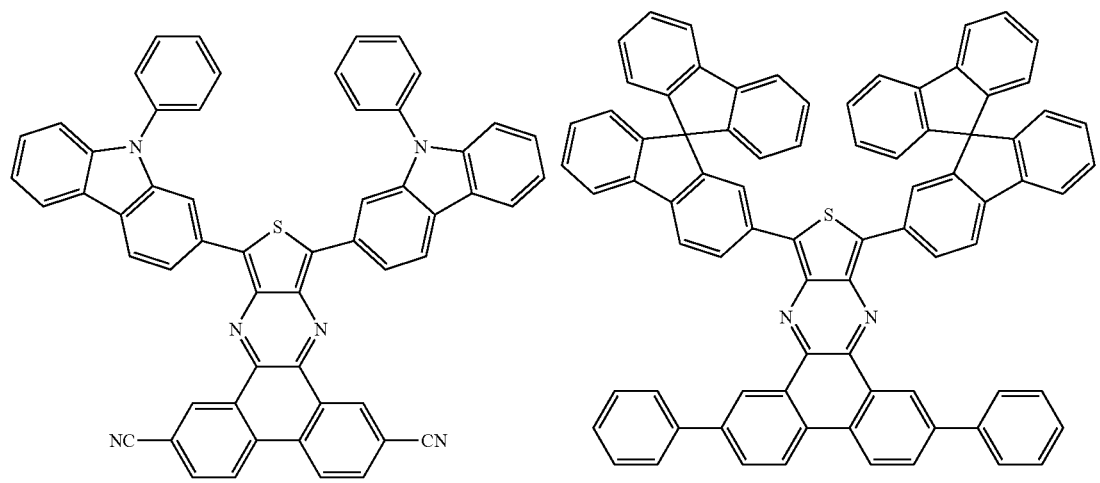
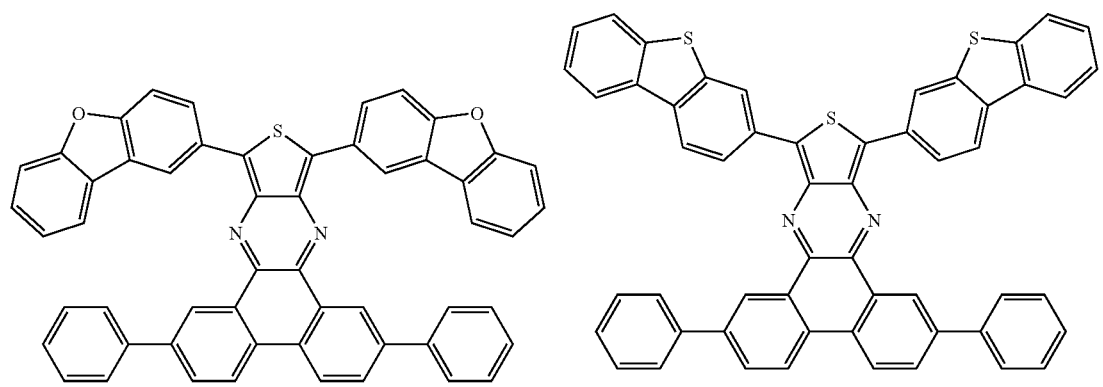

293 294
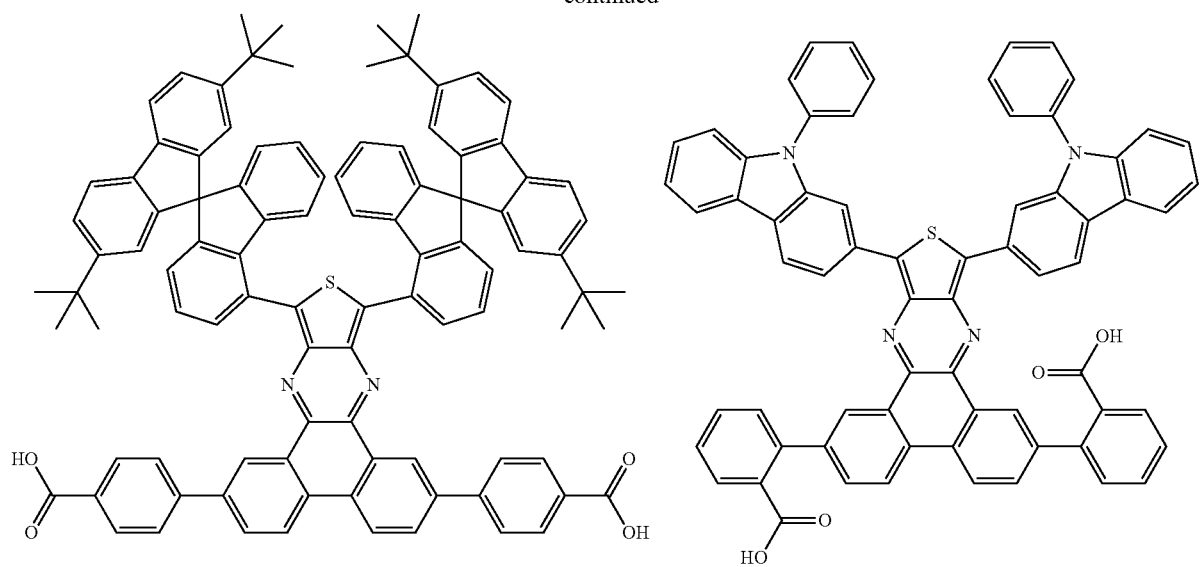
-continued
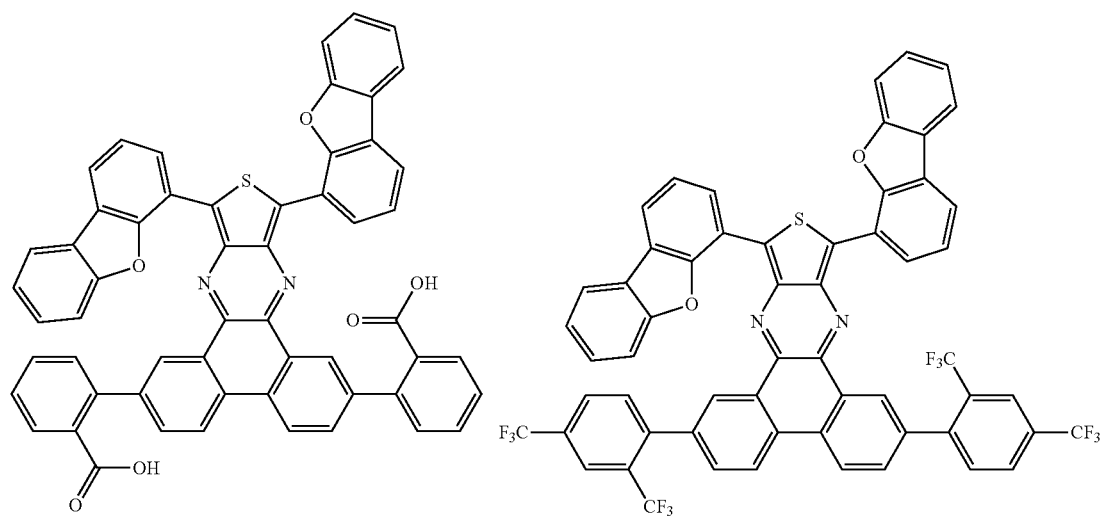
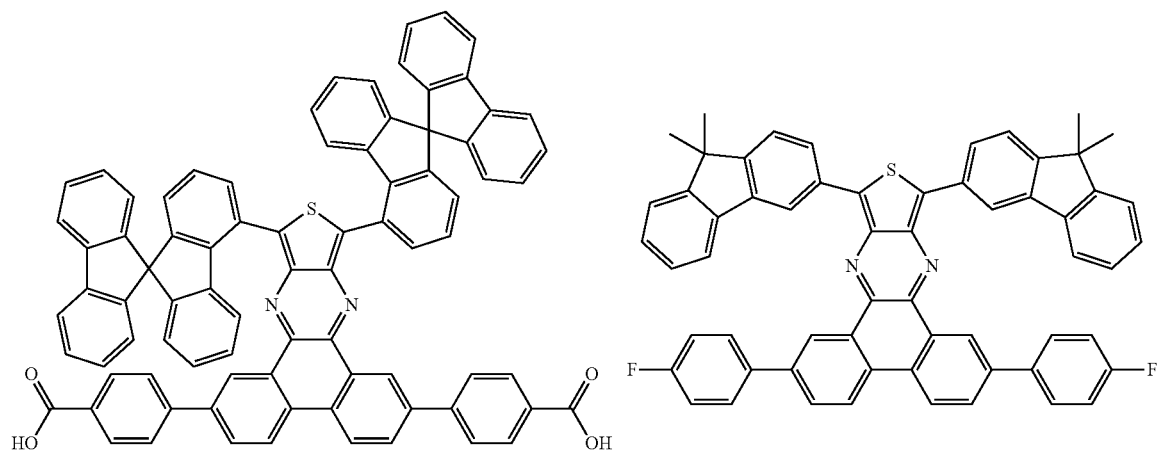

295
296
-continued
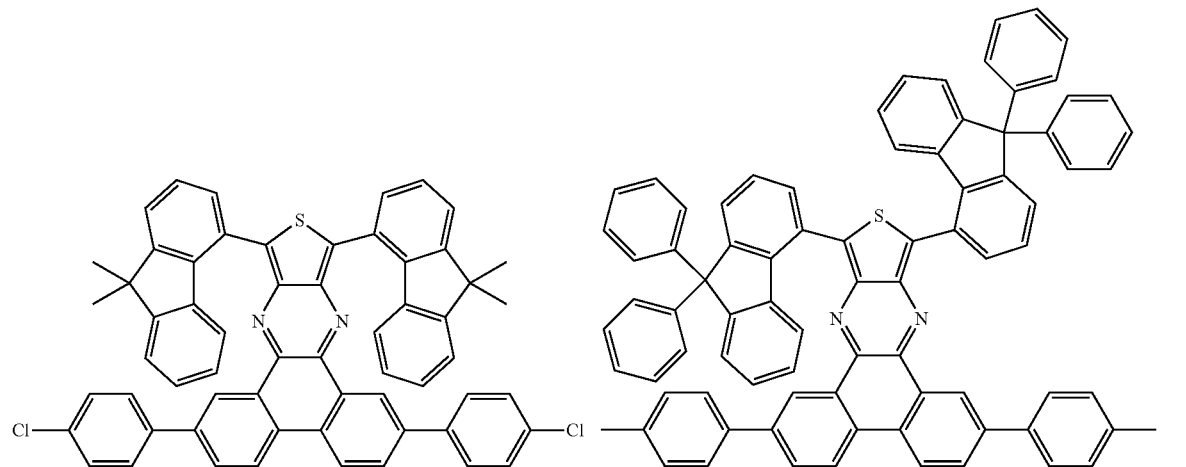
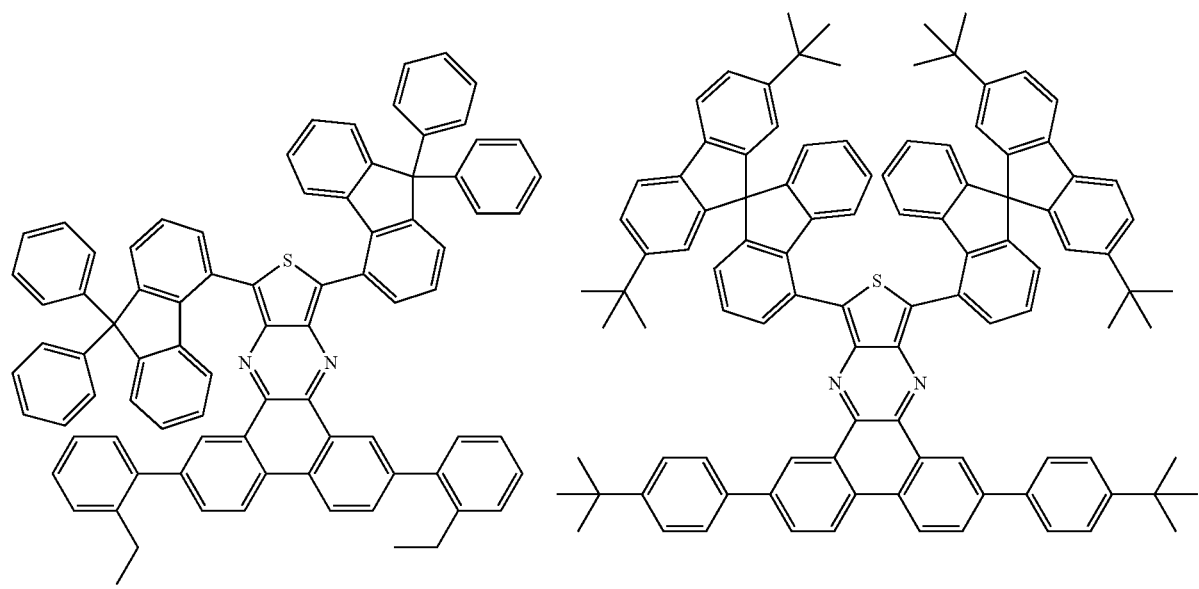
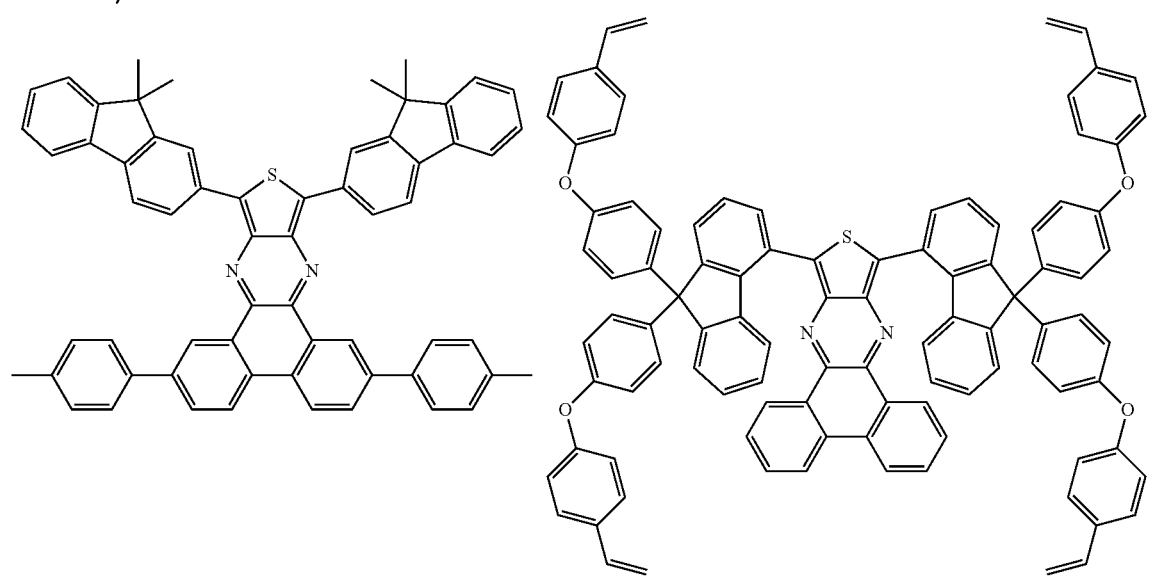

297   298
-continued
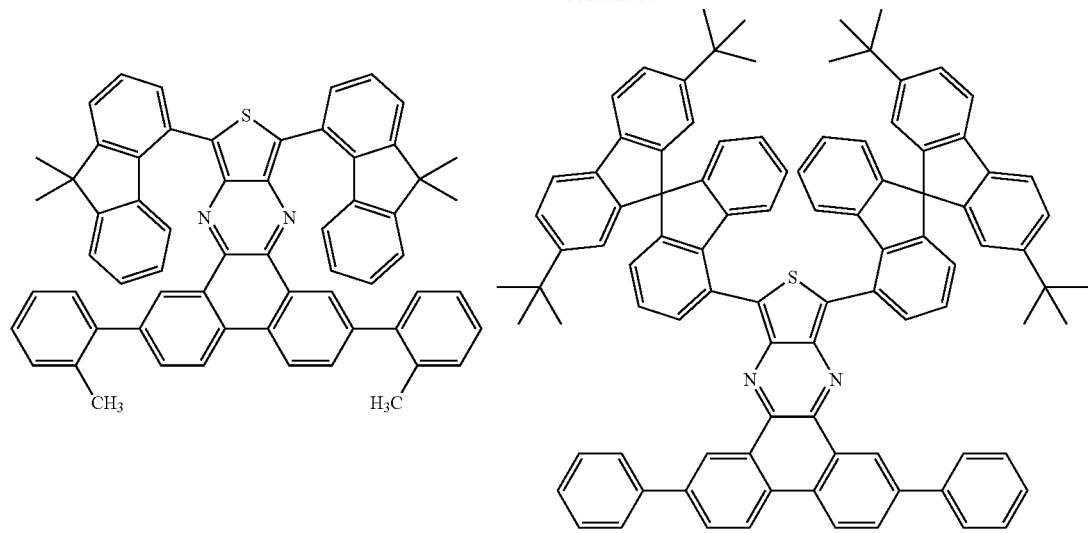
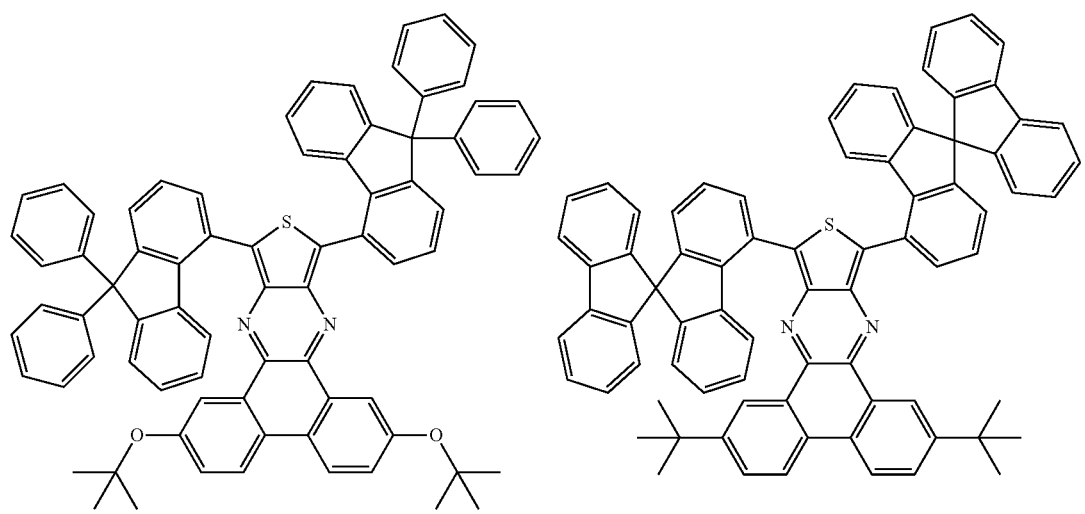
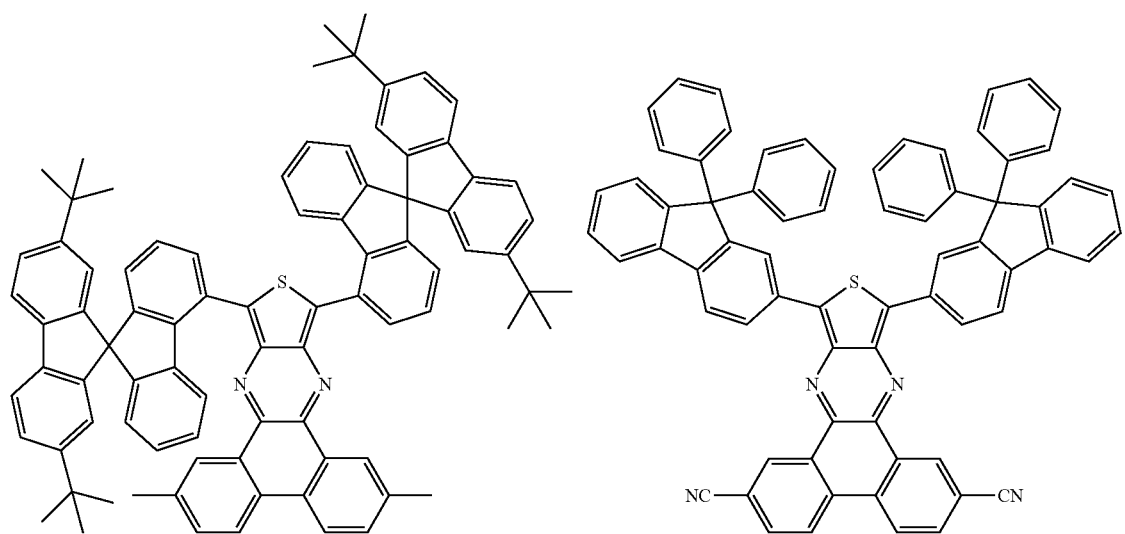

299 300
-continued
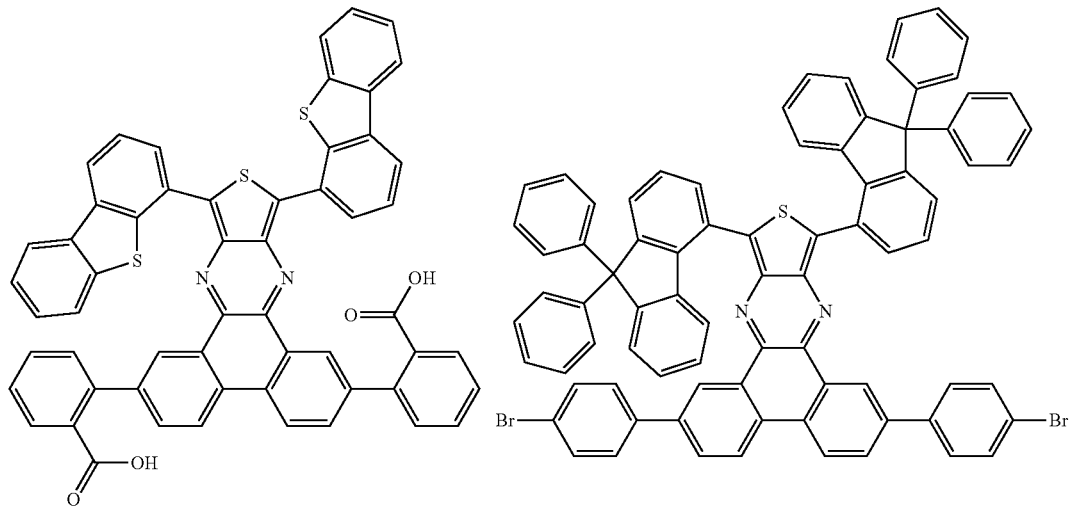
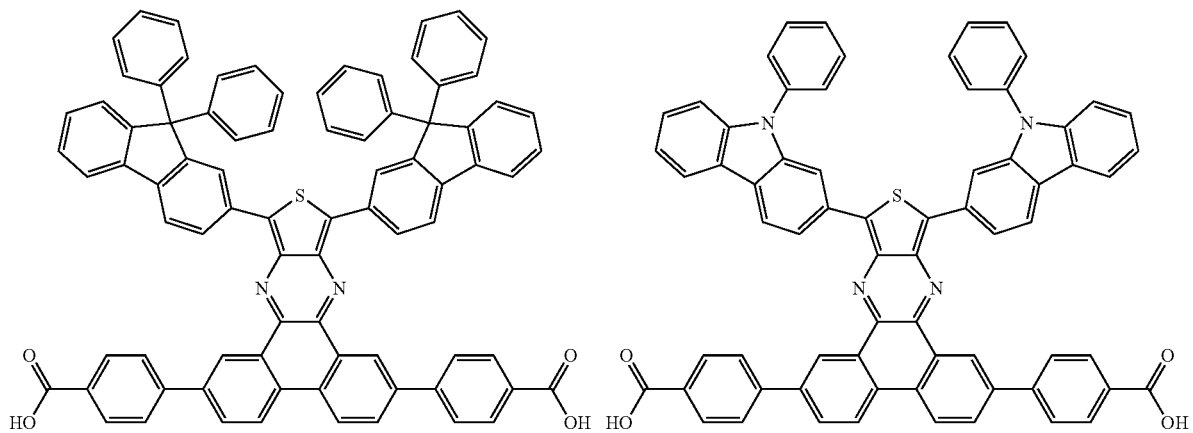
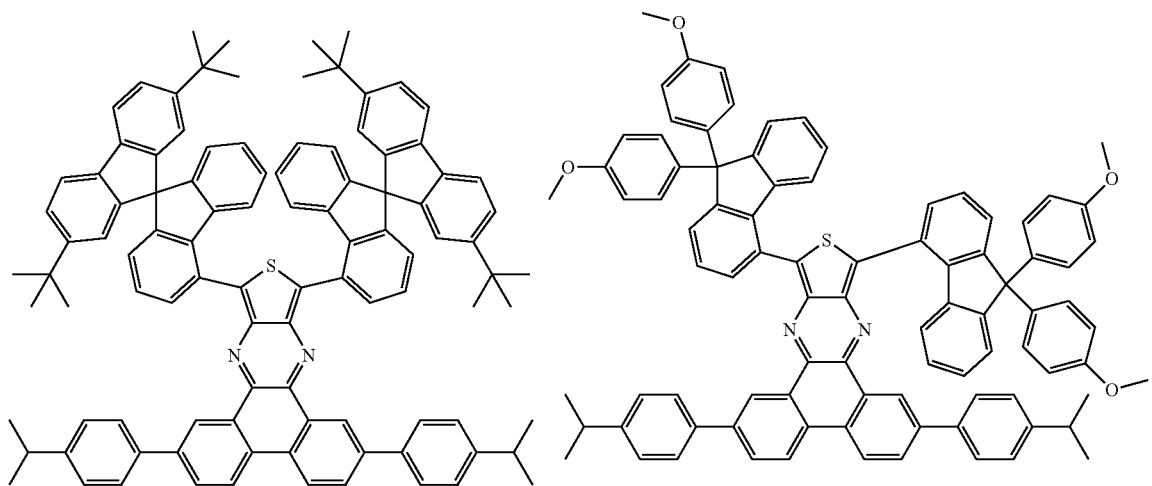

301 302
-continued
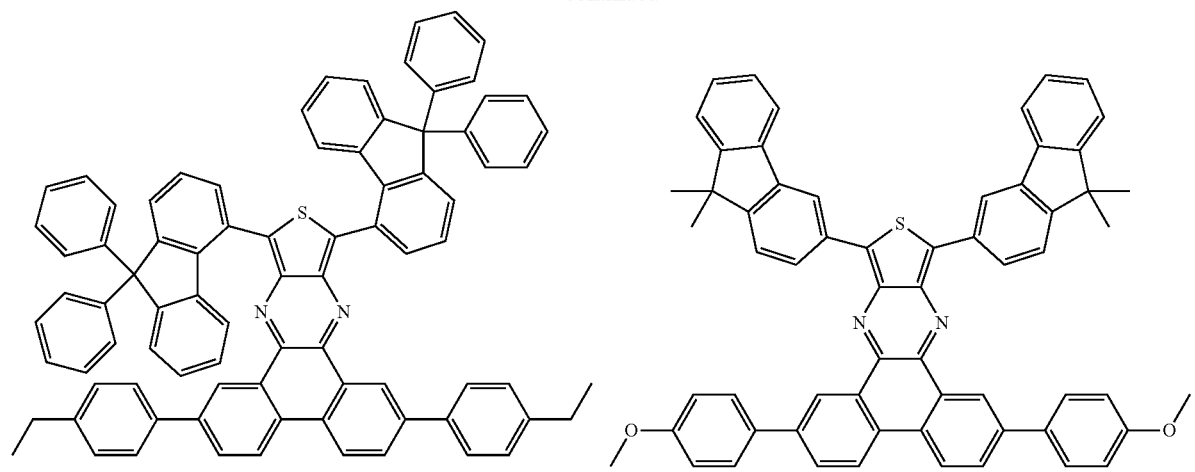
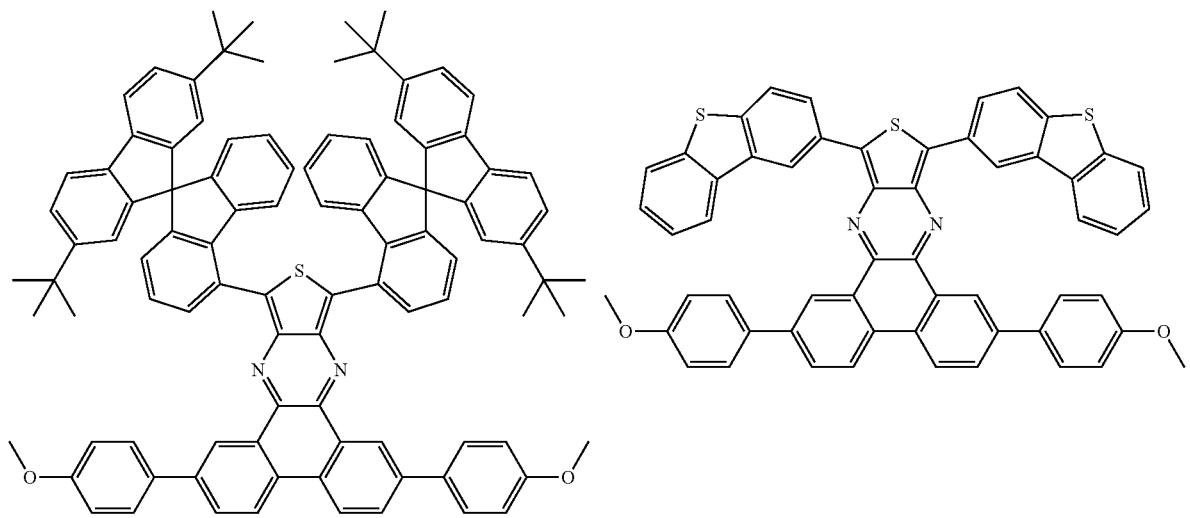
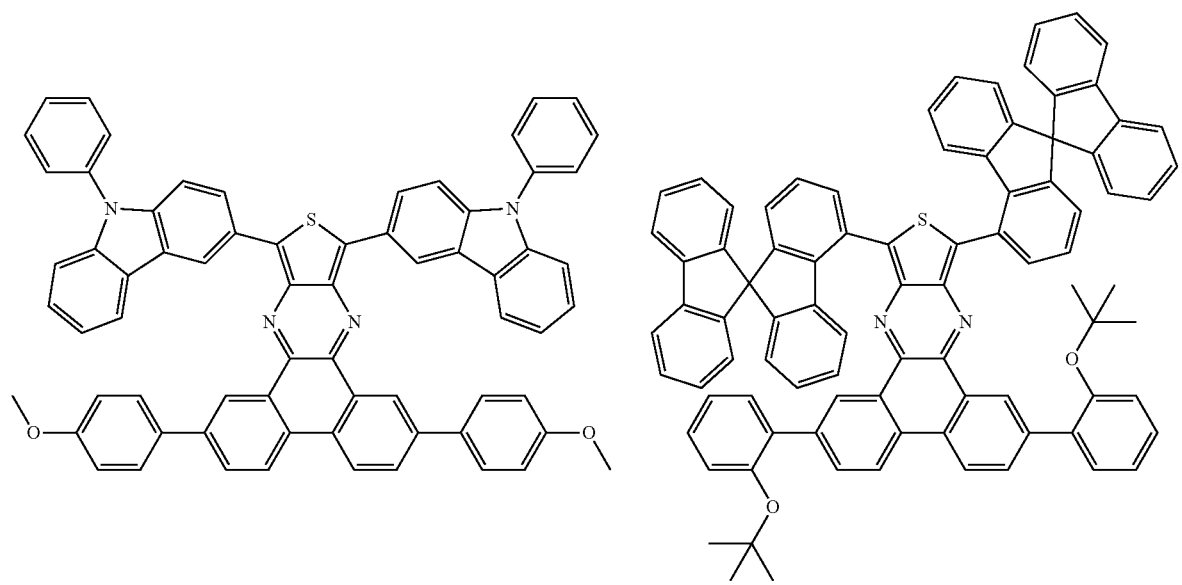

-continued
303
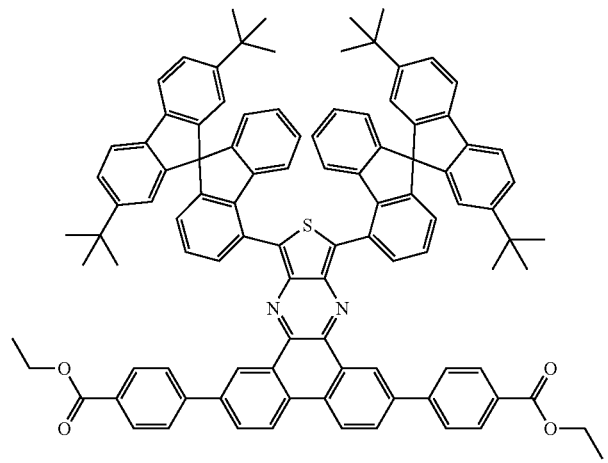
304
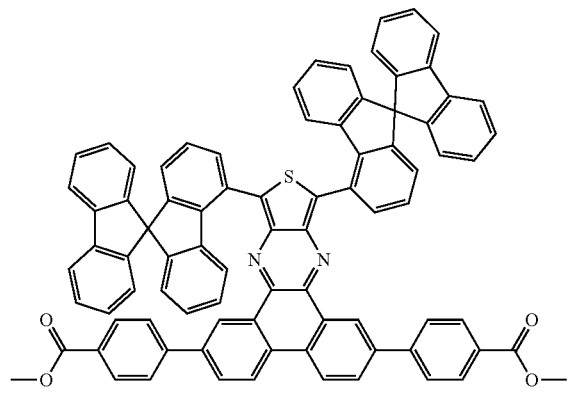
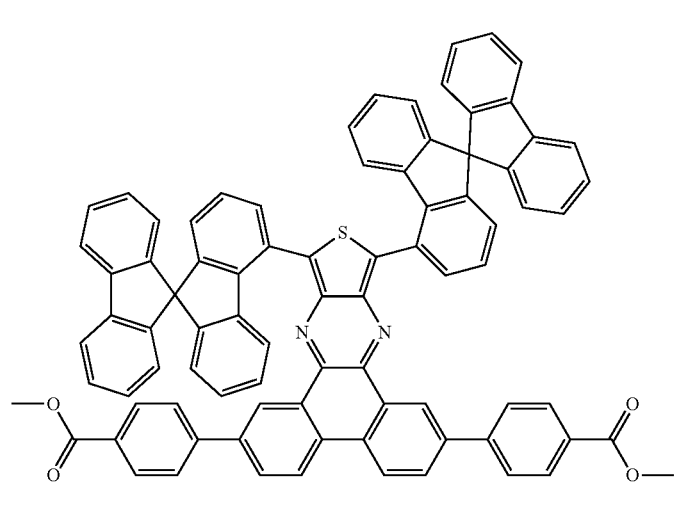
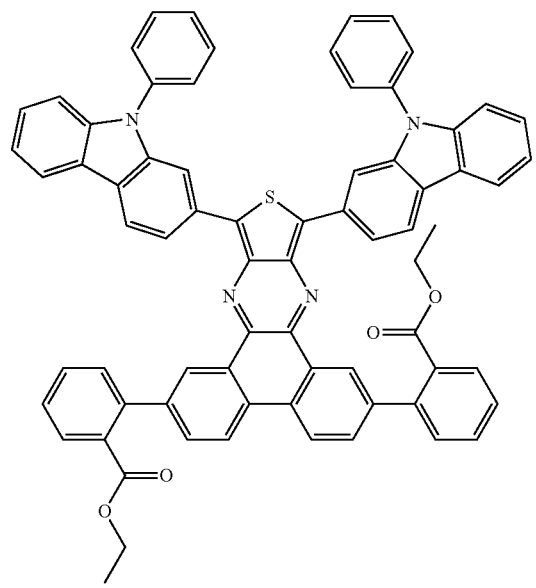
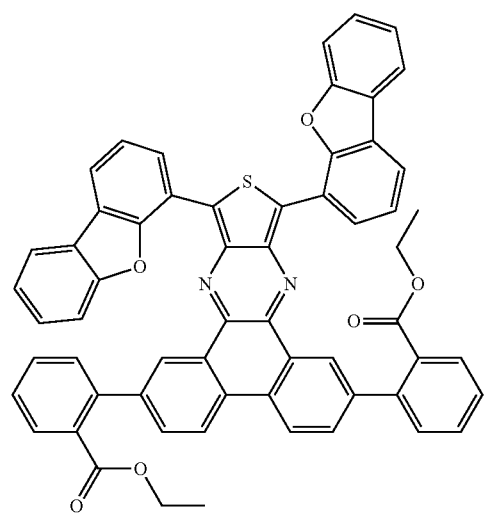
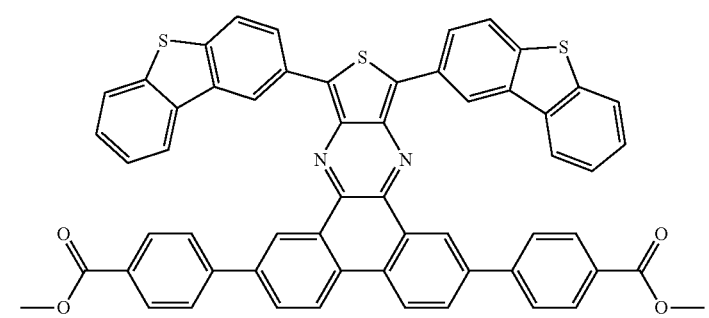

305 306
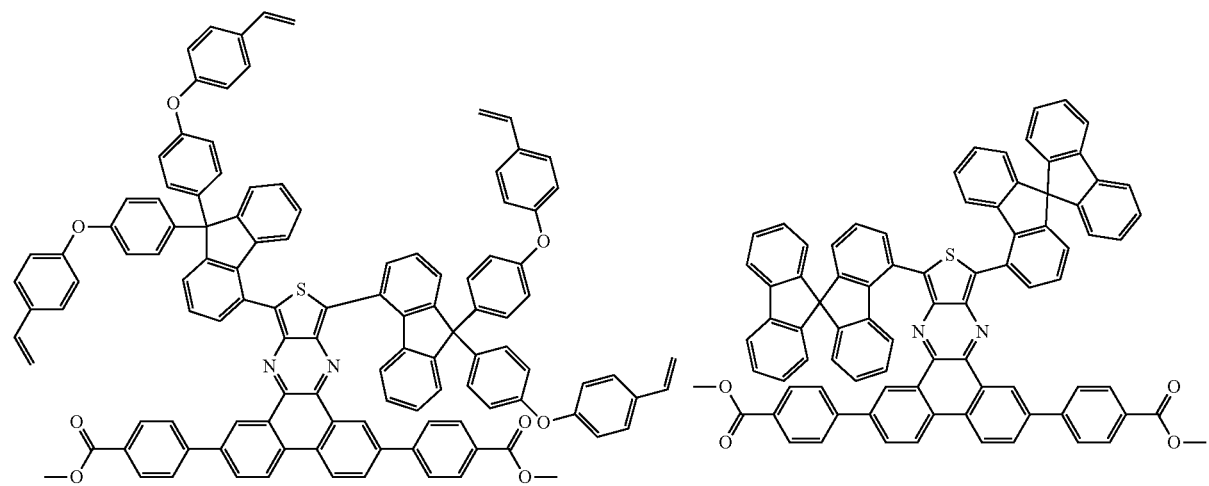
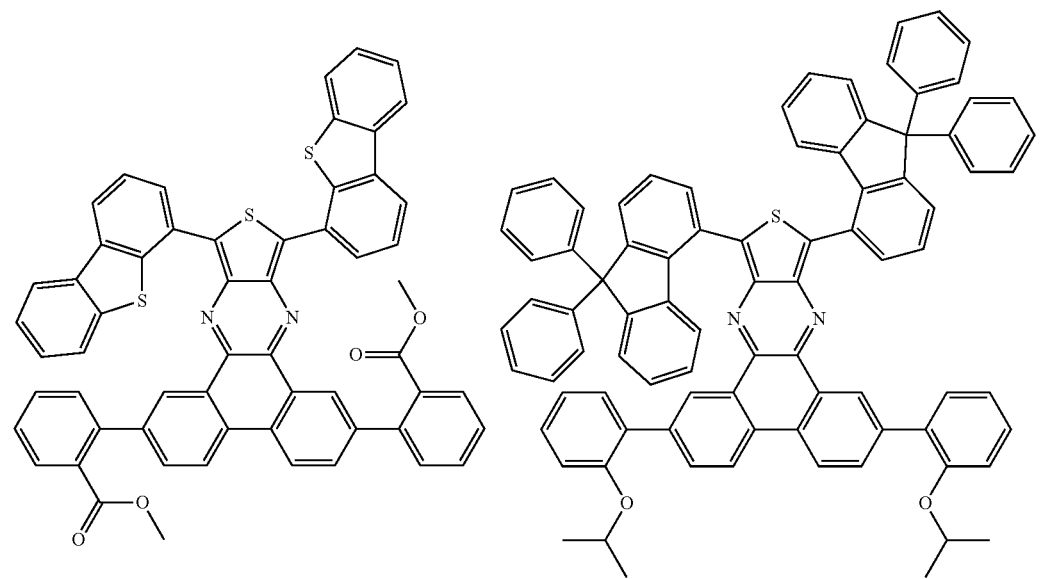
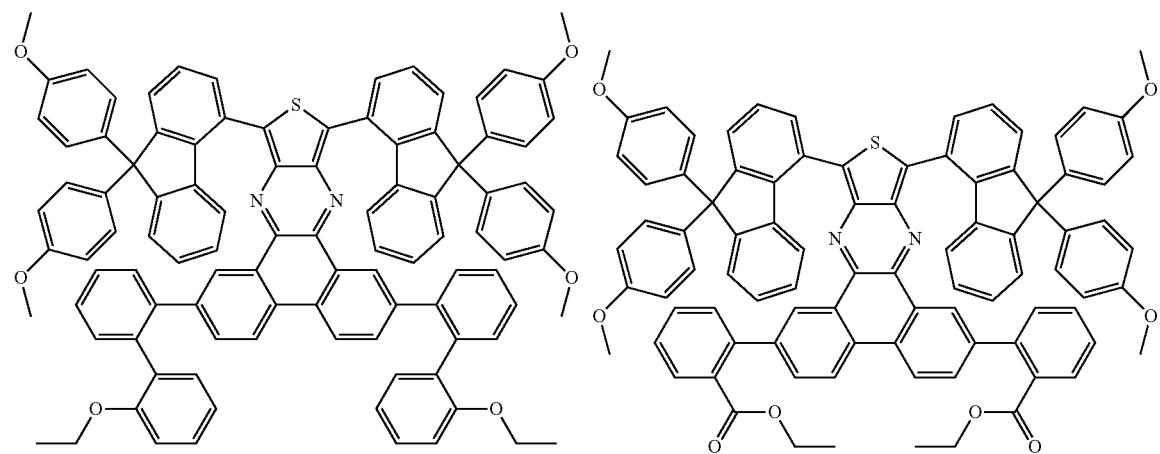

307 308
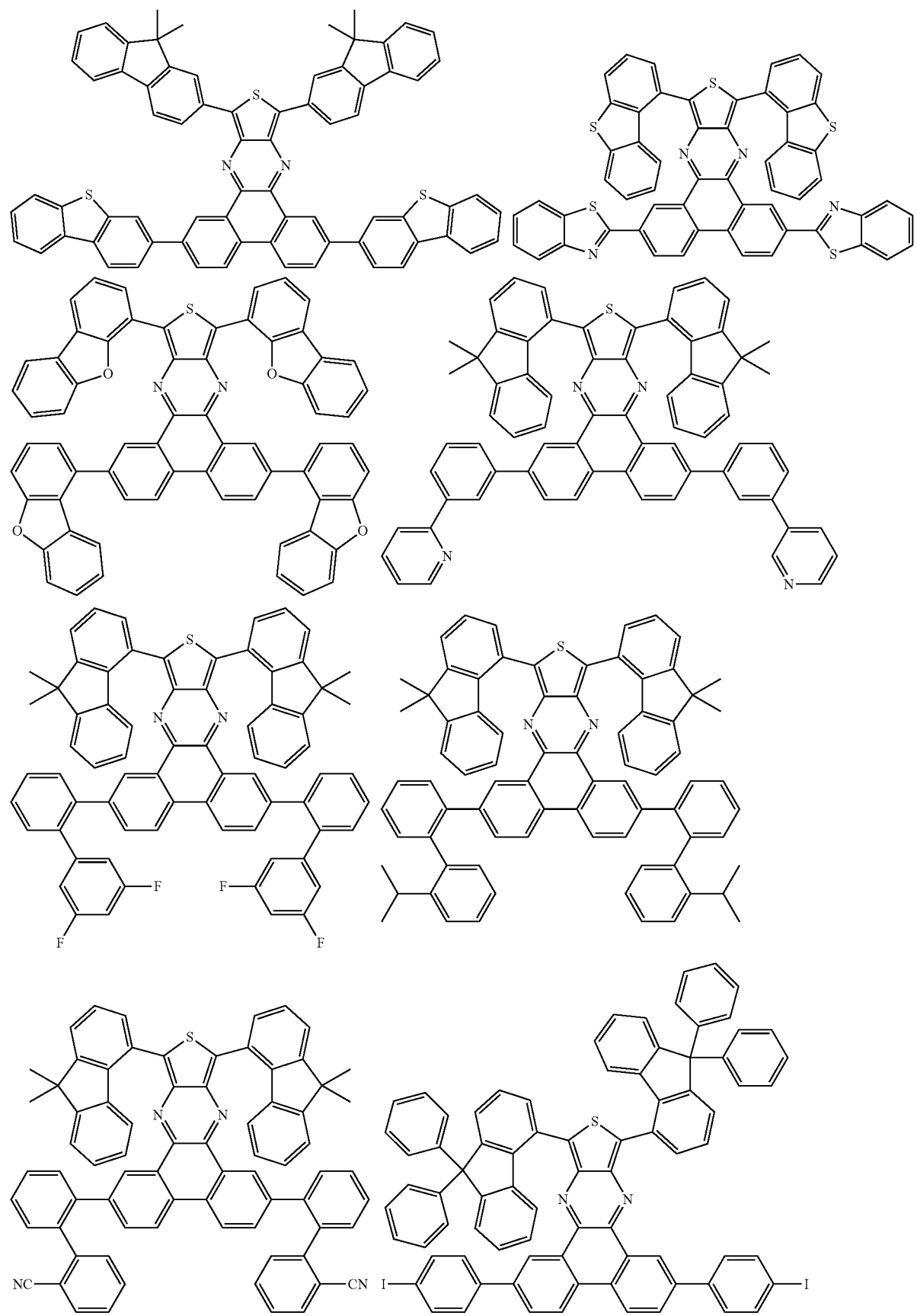
-continued 309 310
-continued
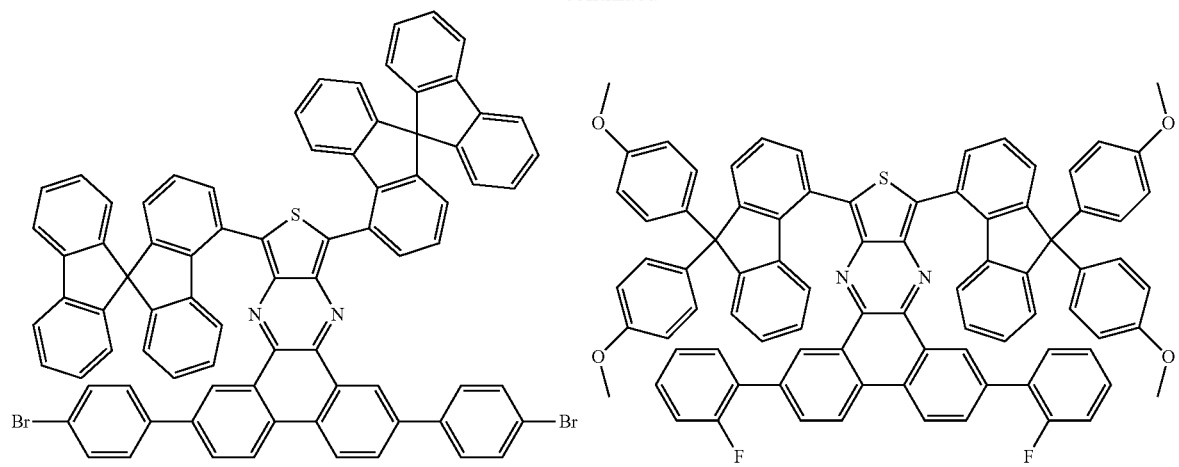
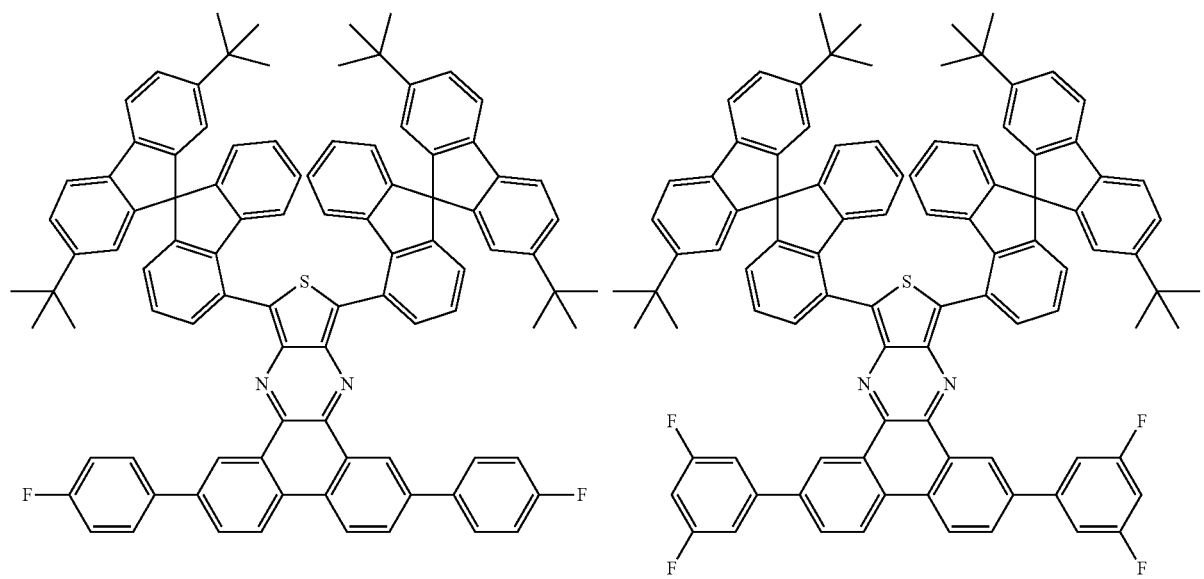
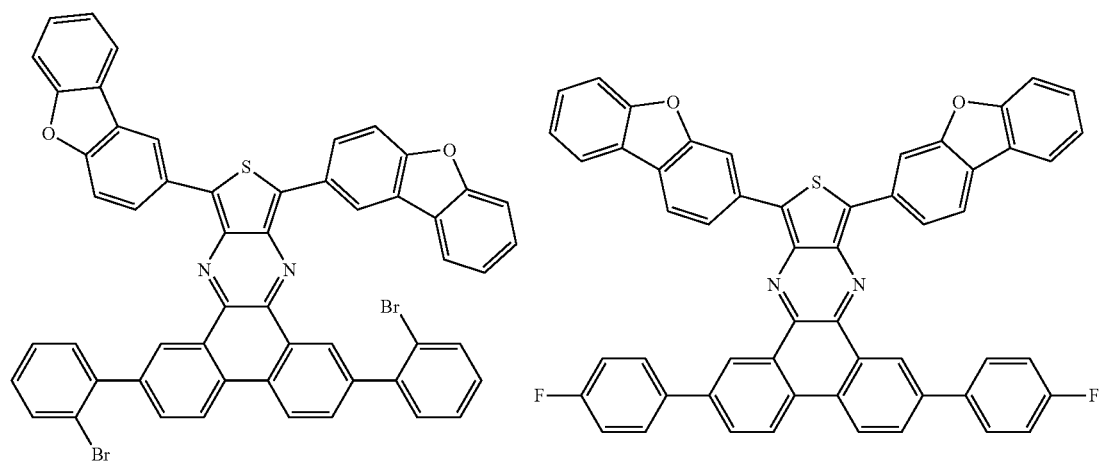

311
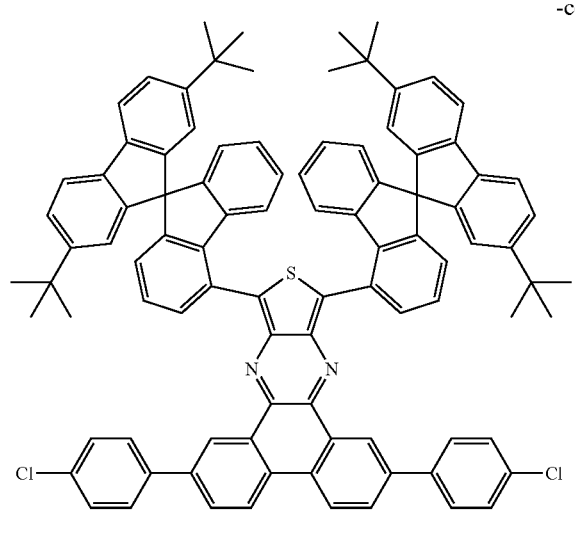
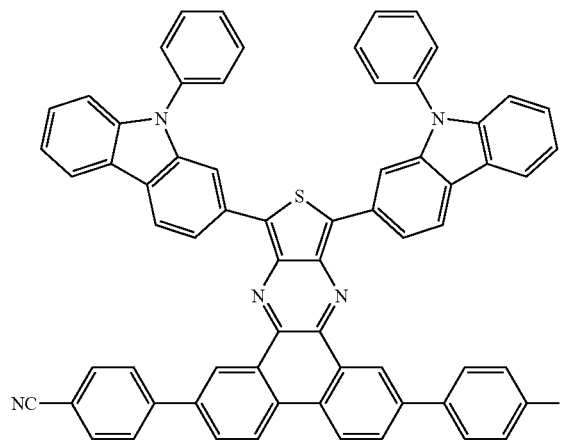
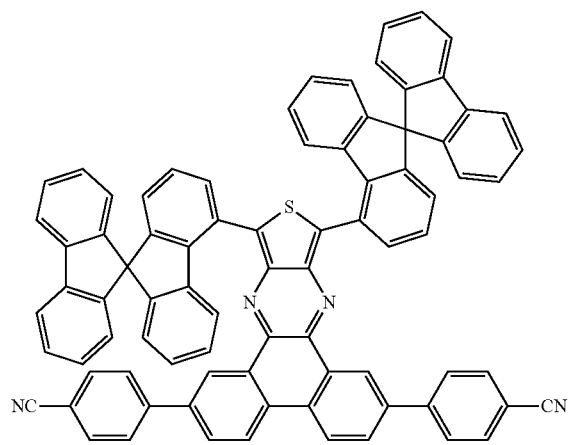
312
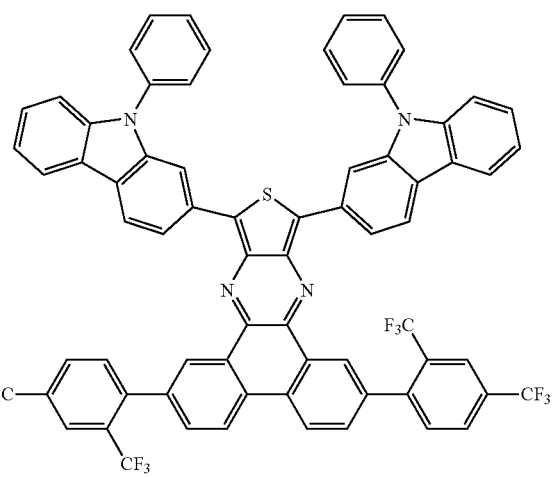
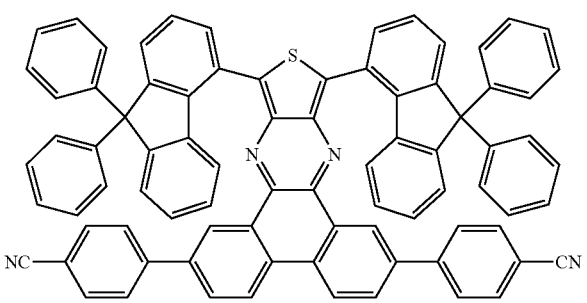
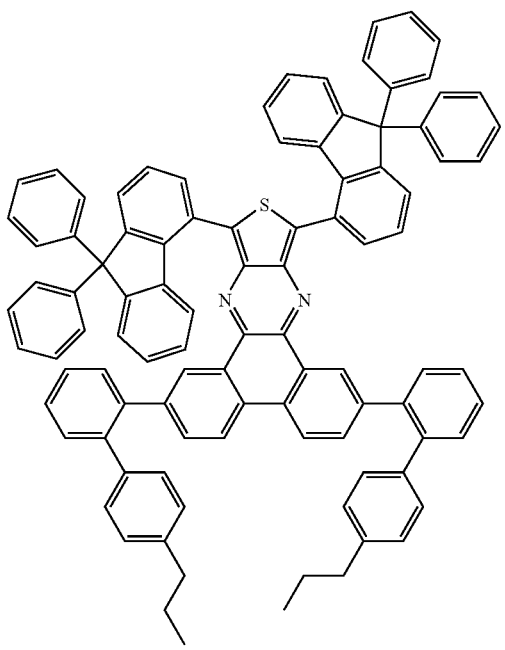

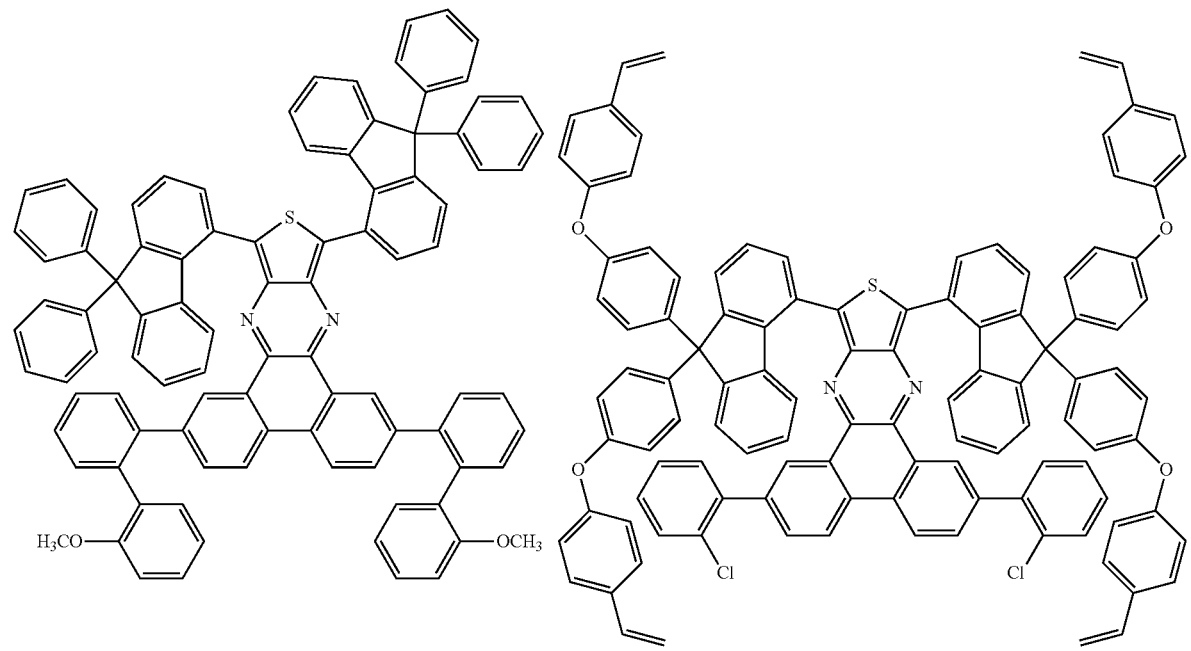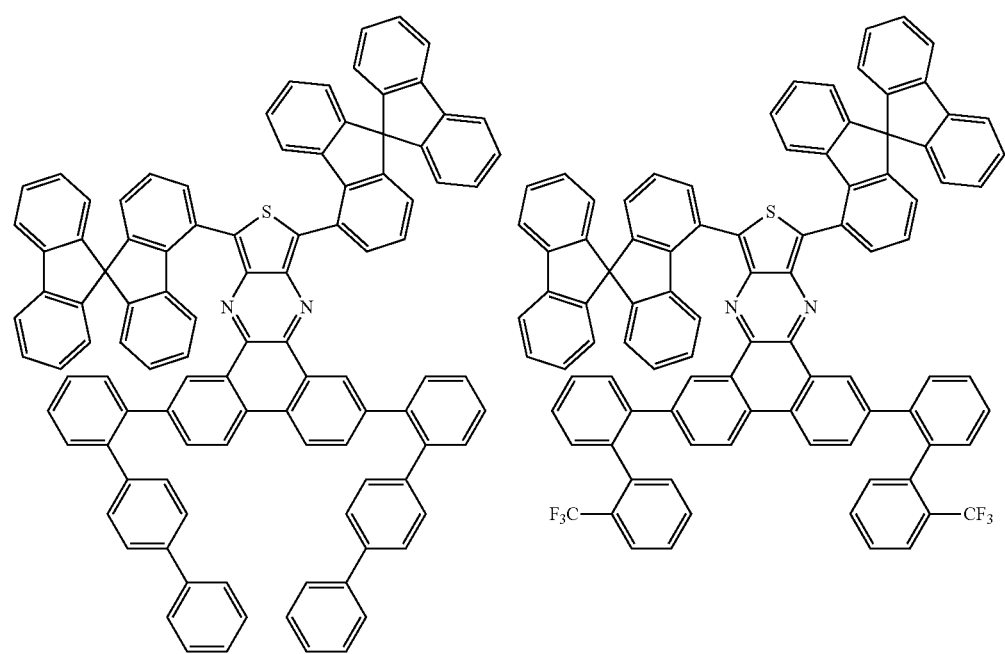

-continued
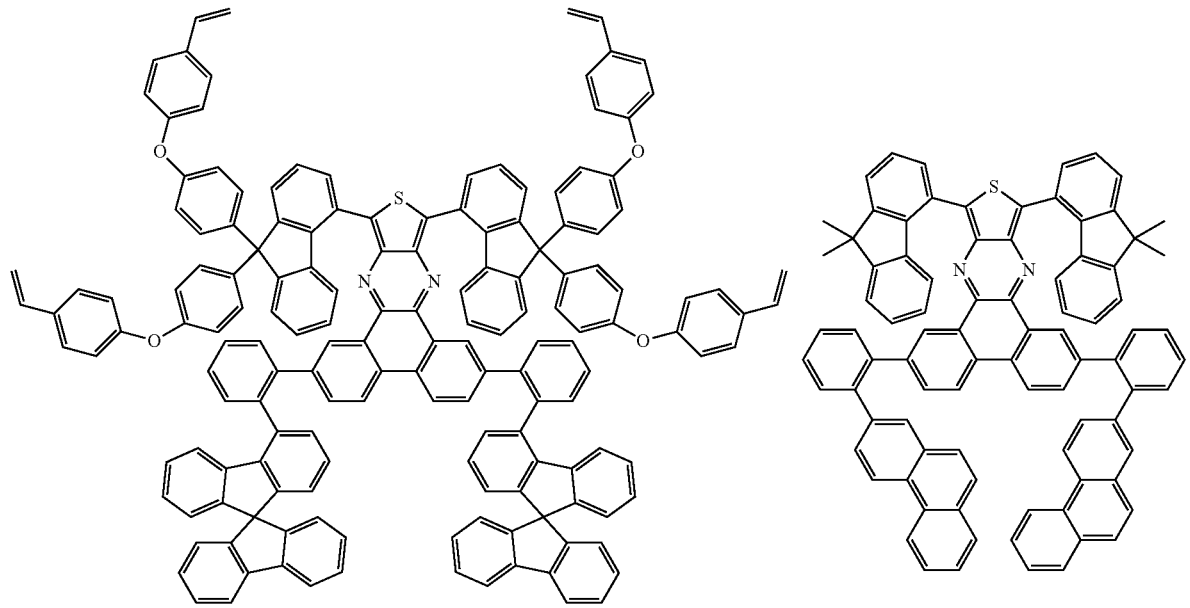
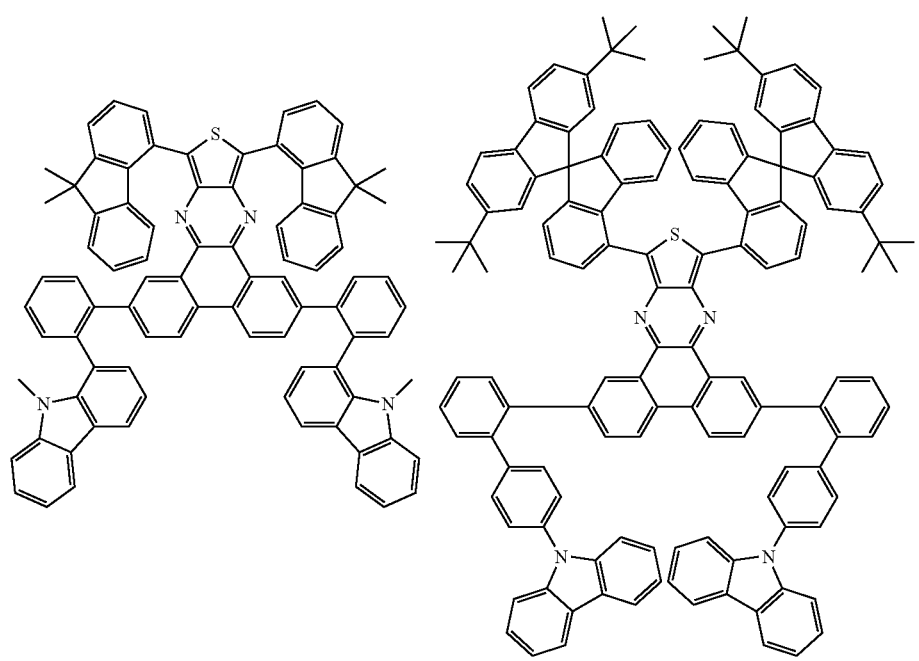

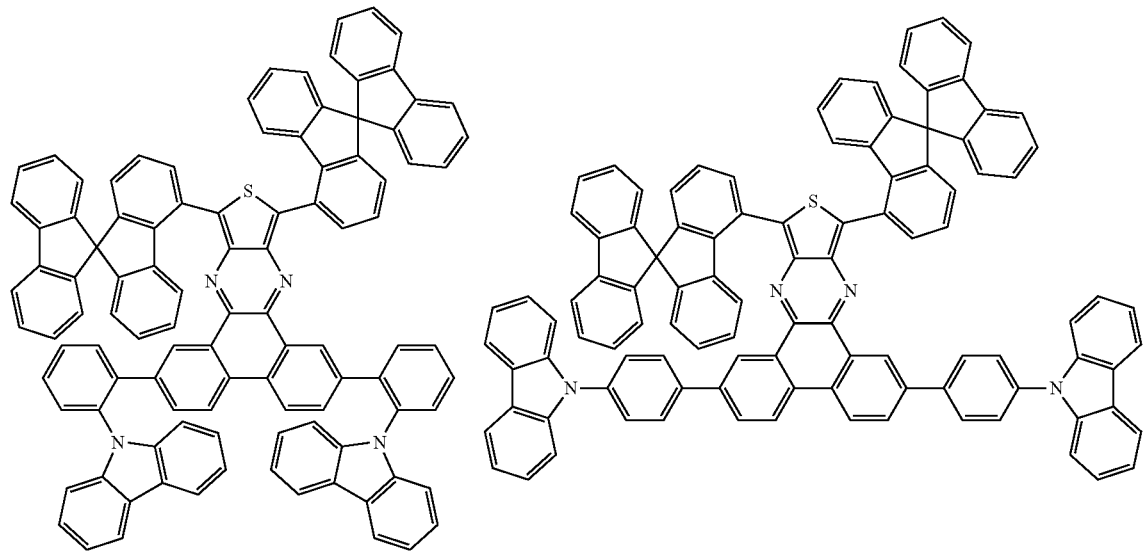
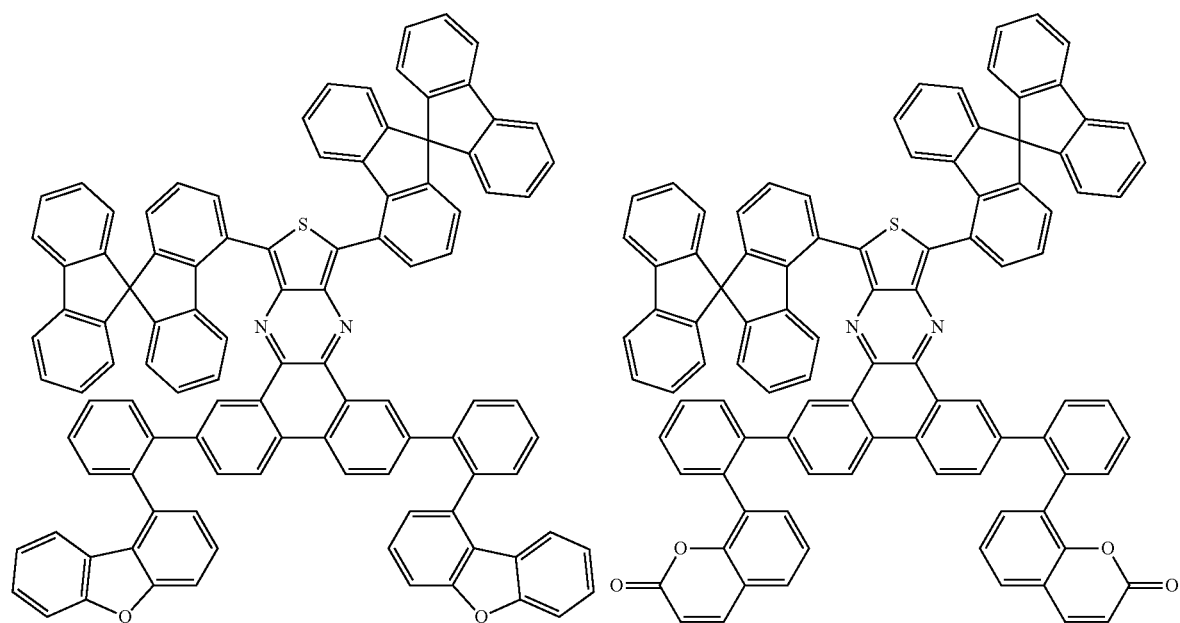

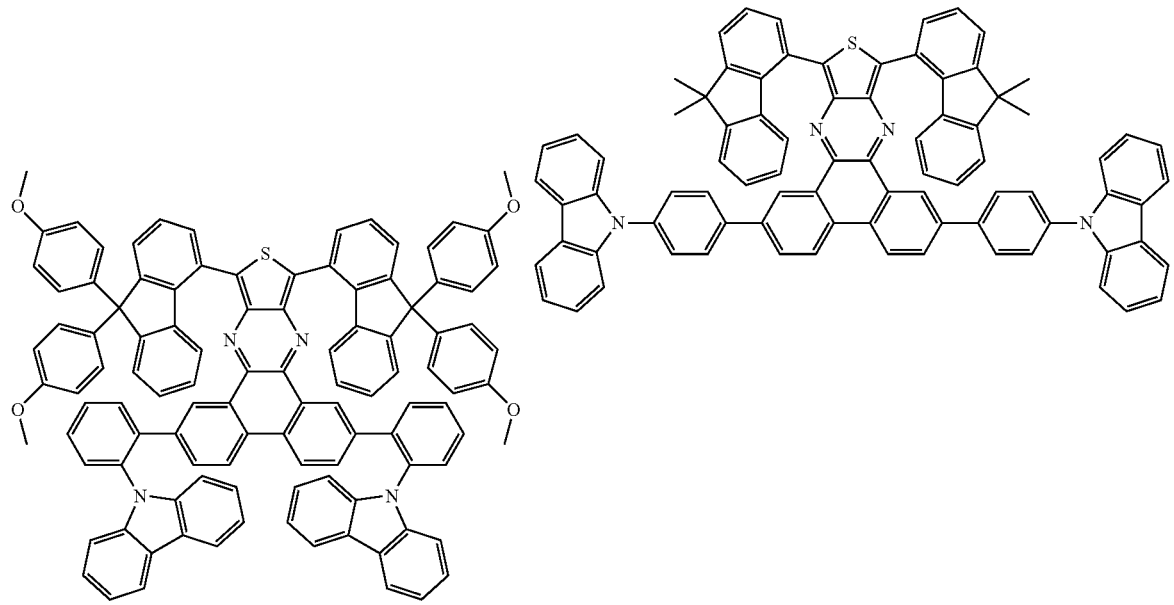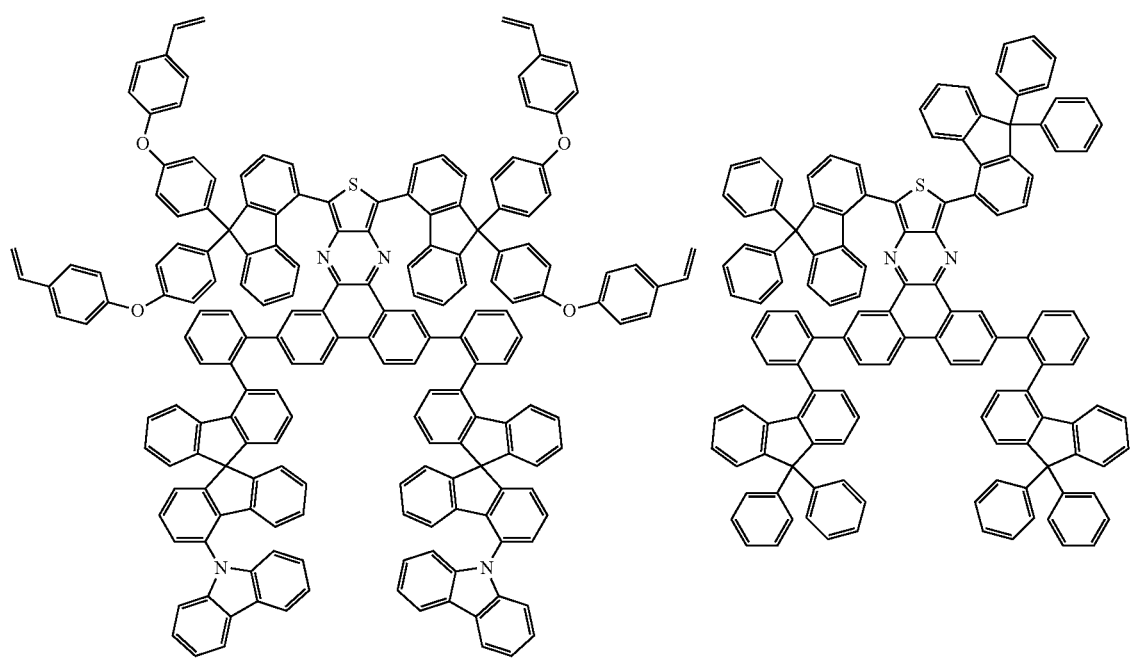

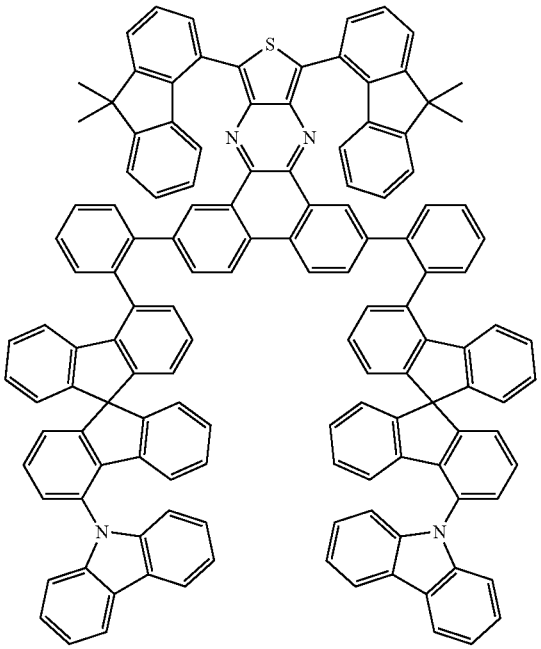
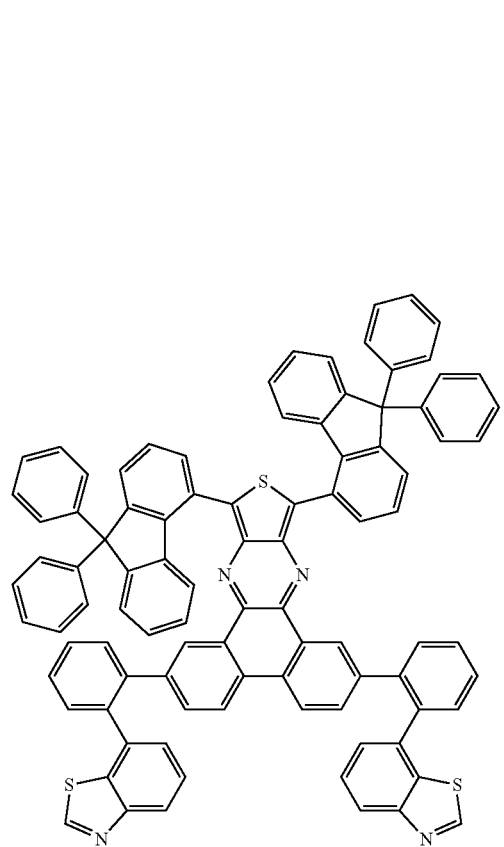
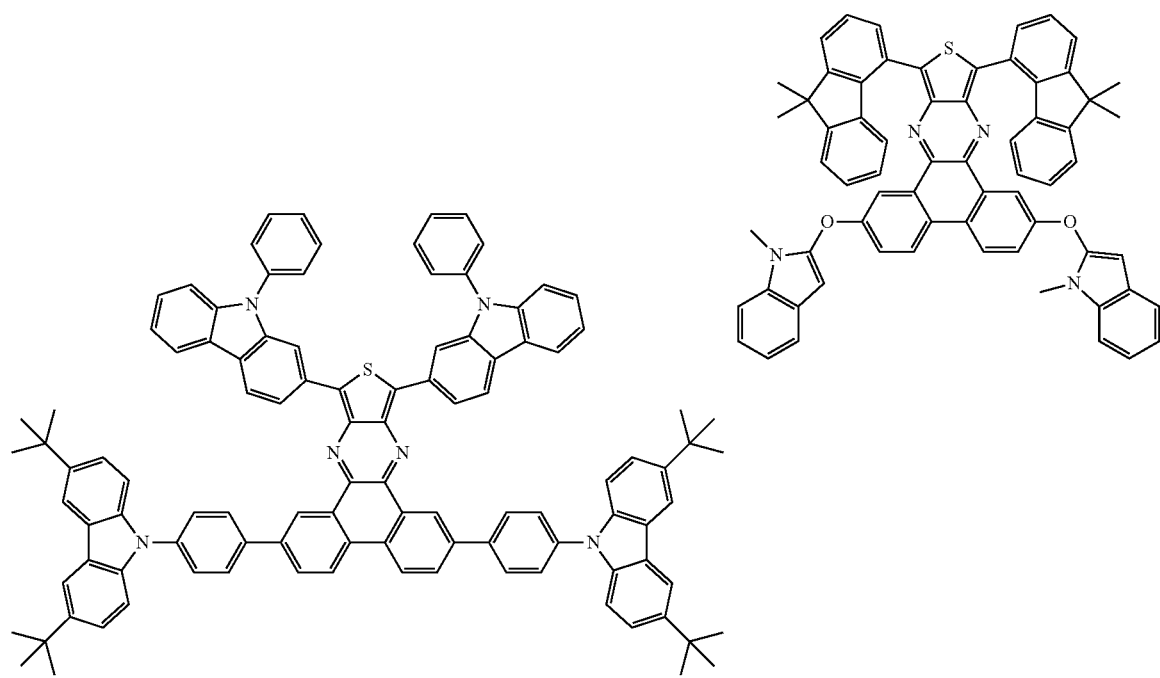

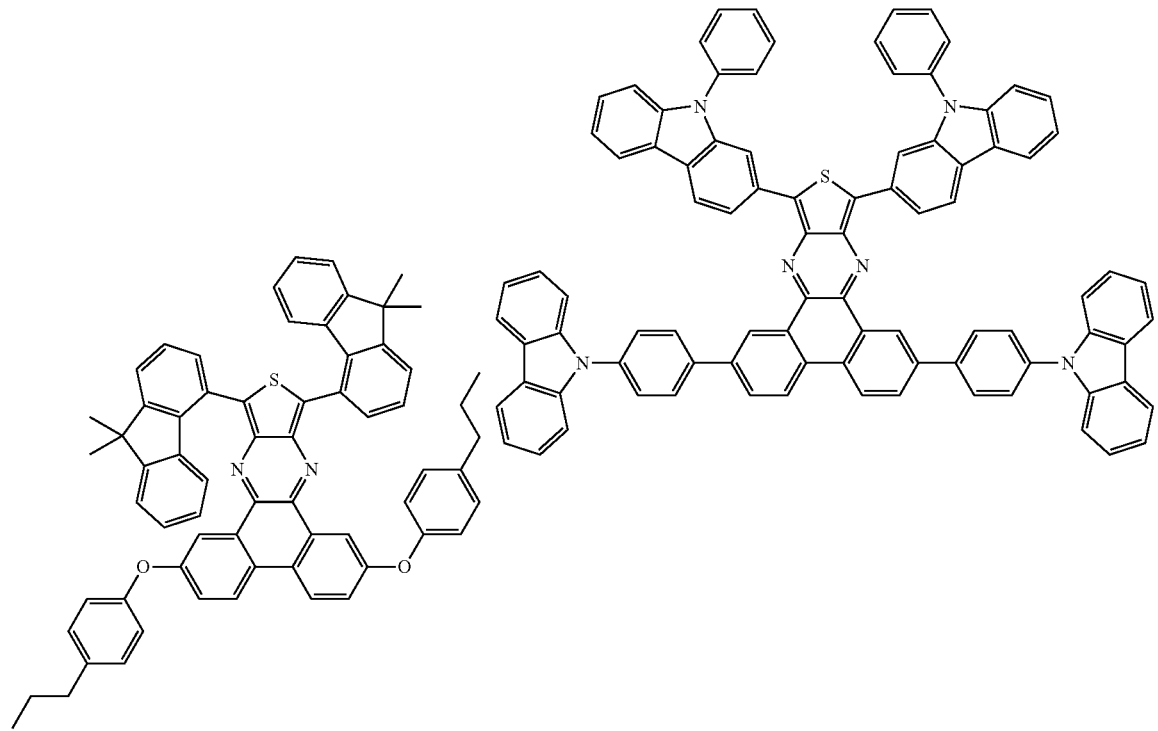
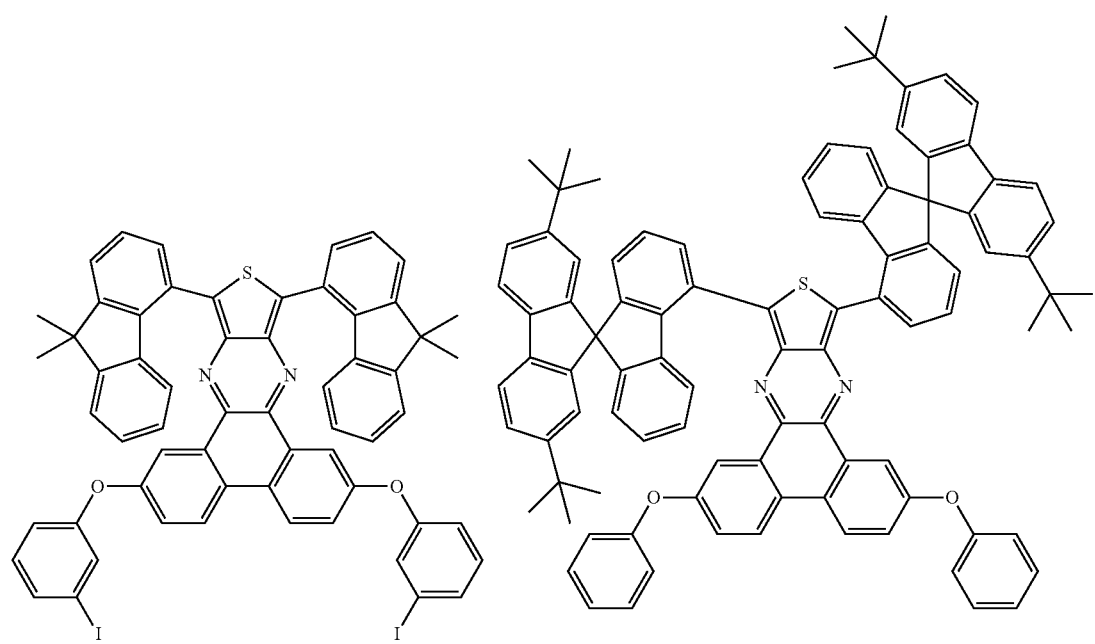

-continued
325 326
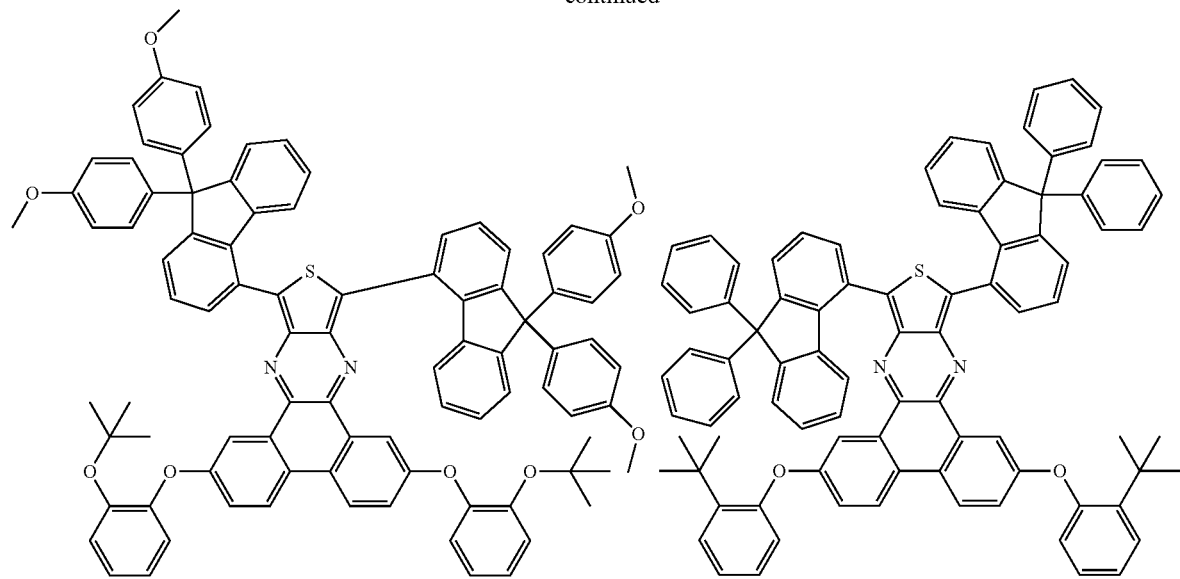
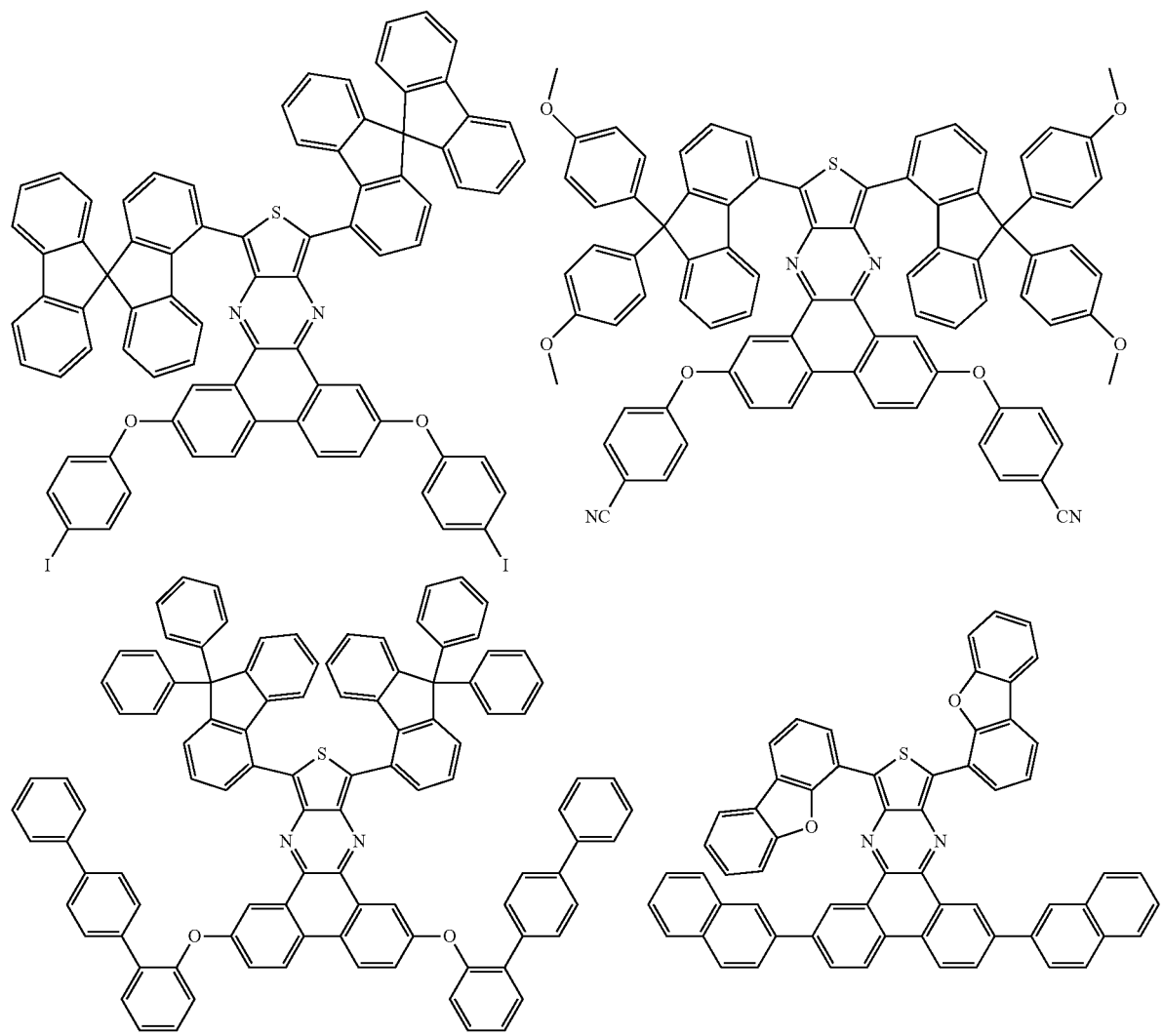

327
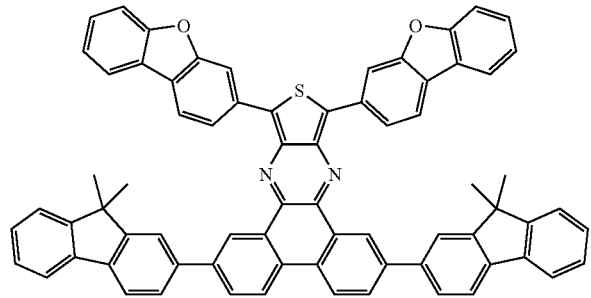
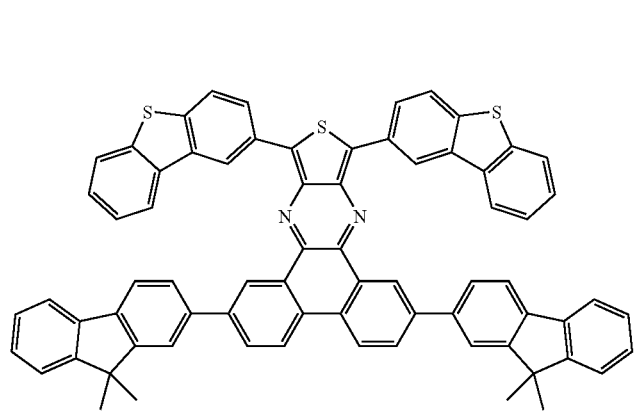
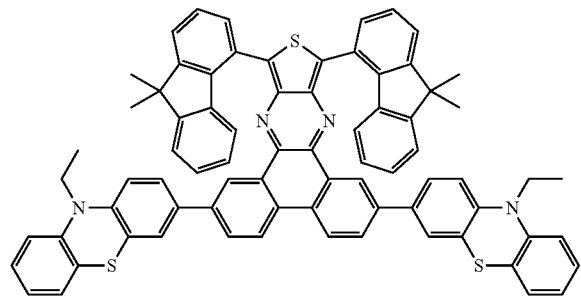
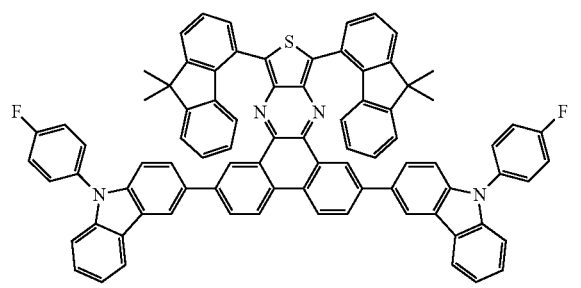
328
-continued
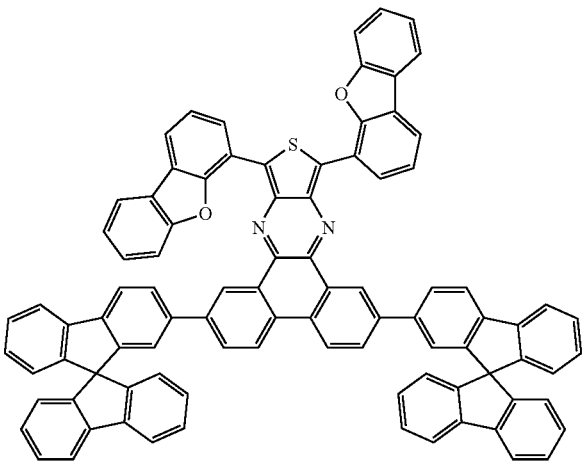
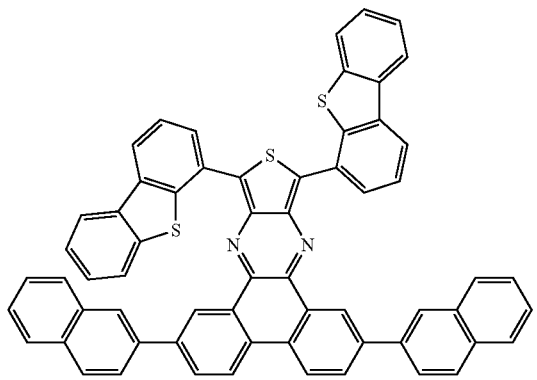
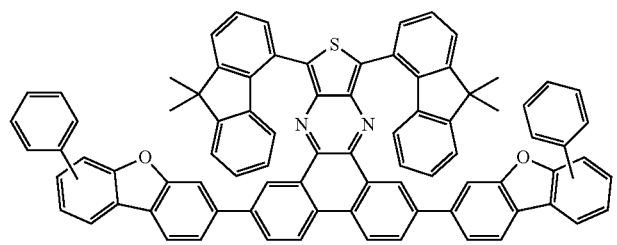
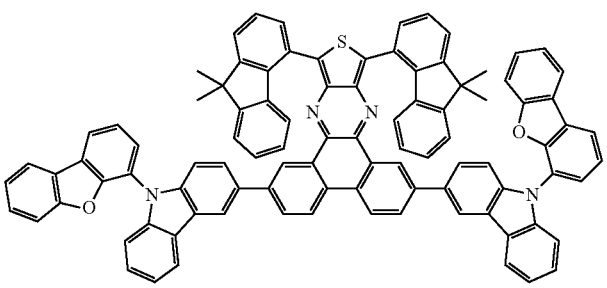

-continued
329
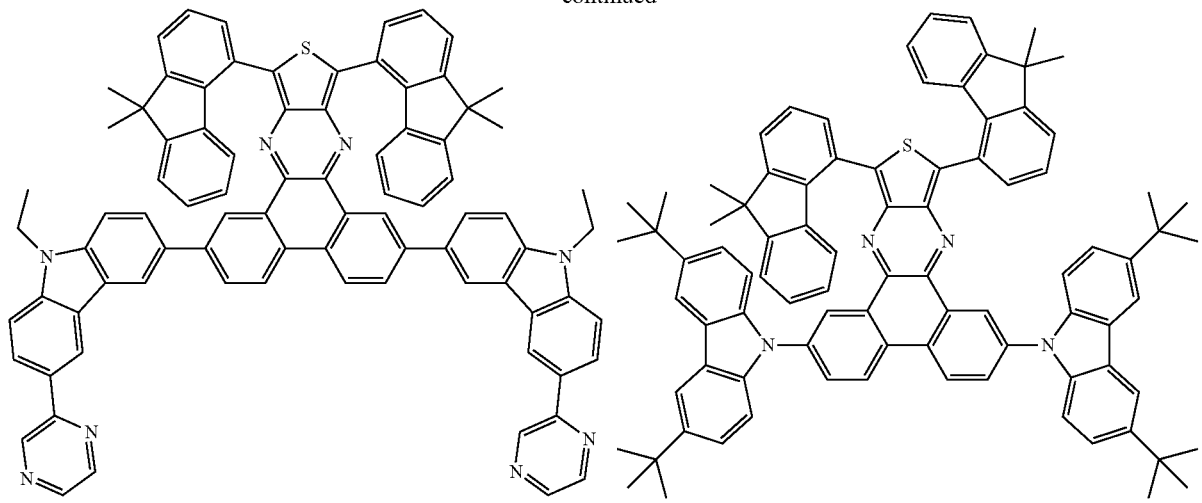
330
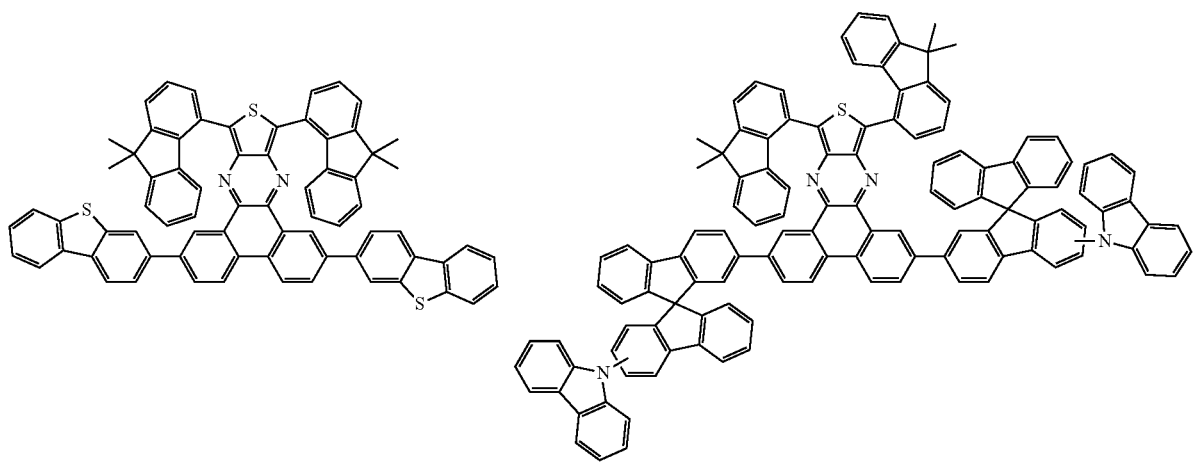
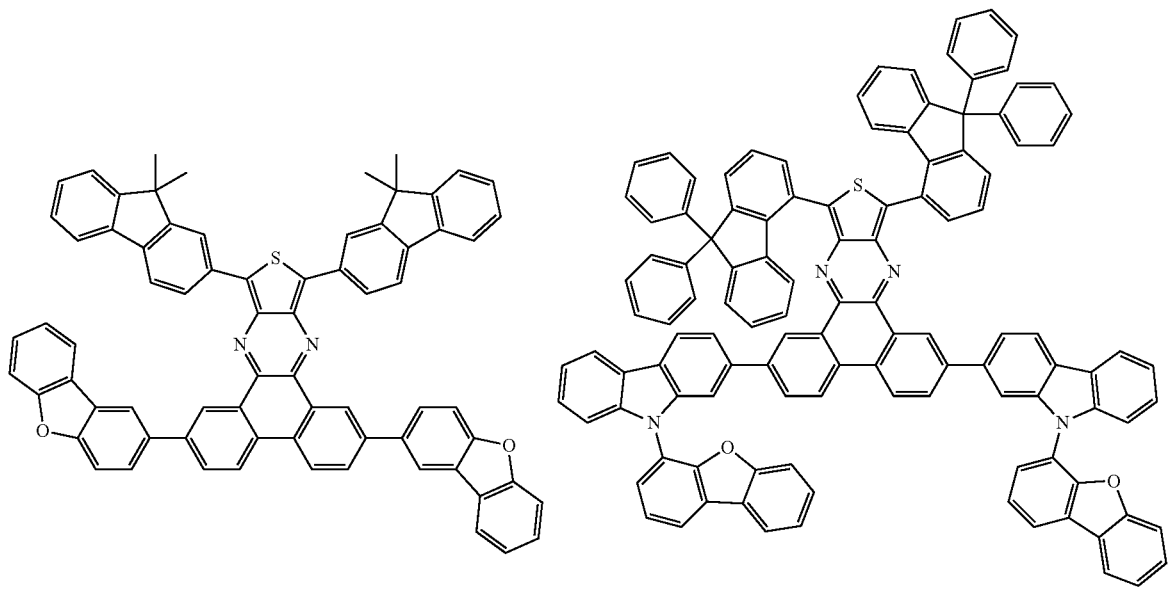

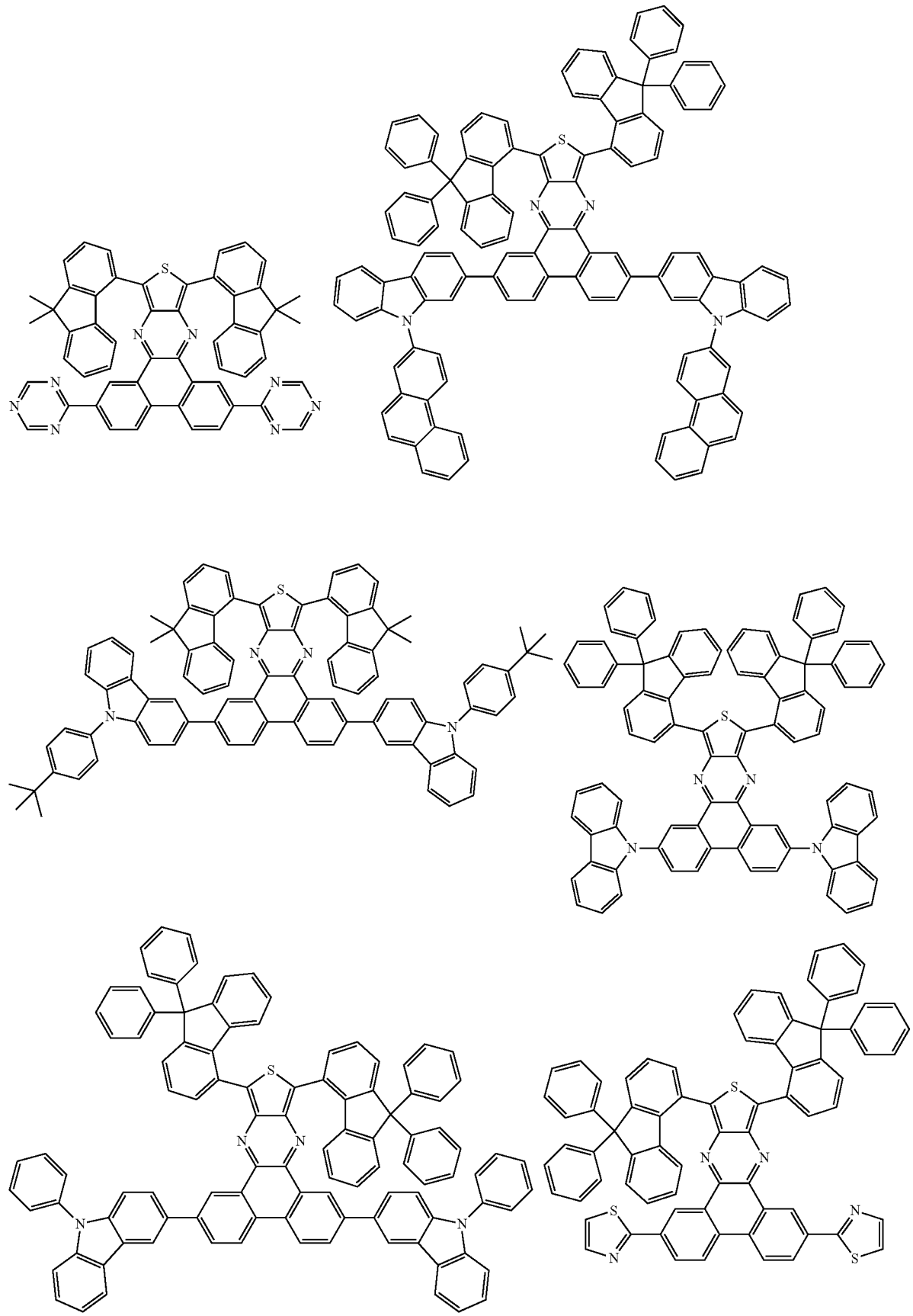

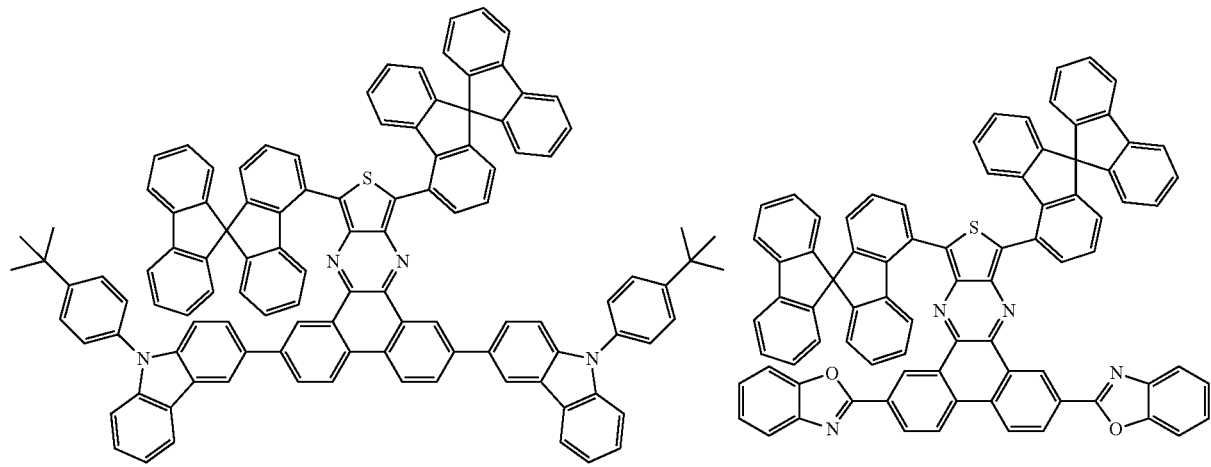
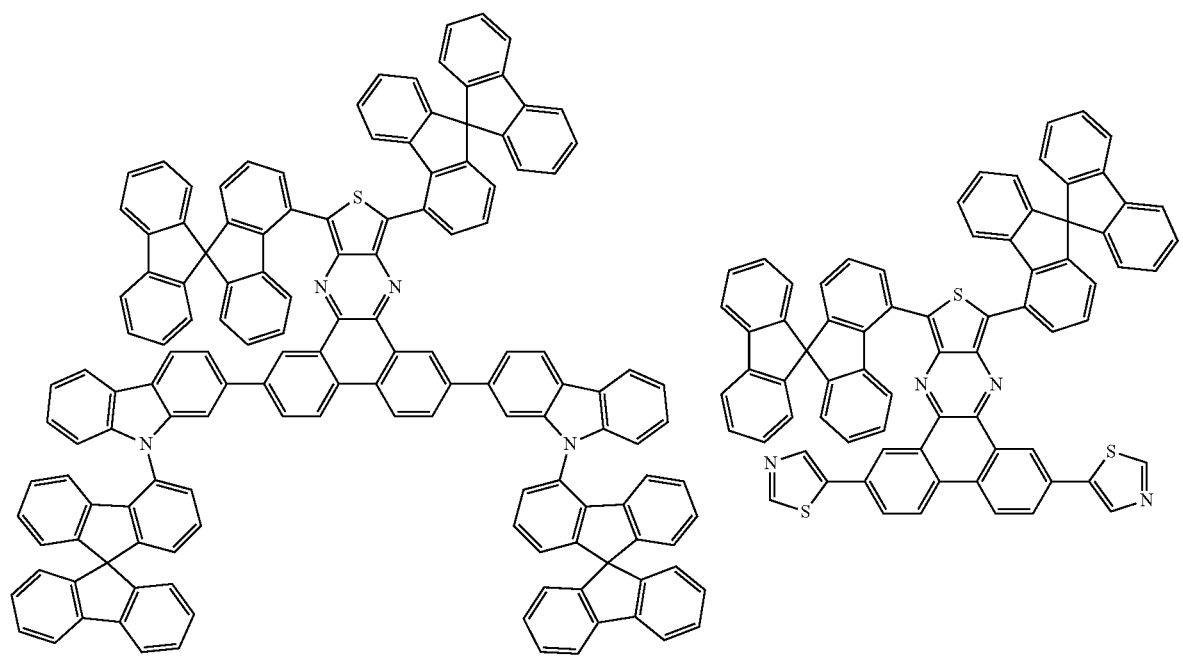

335 336
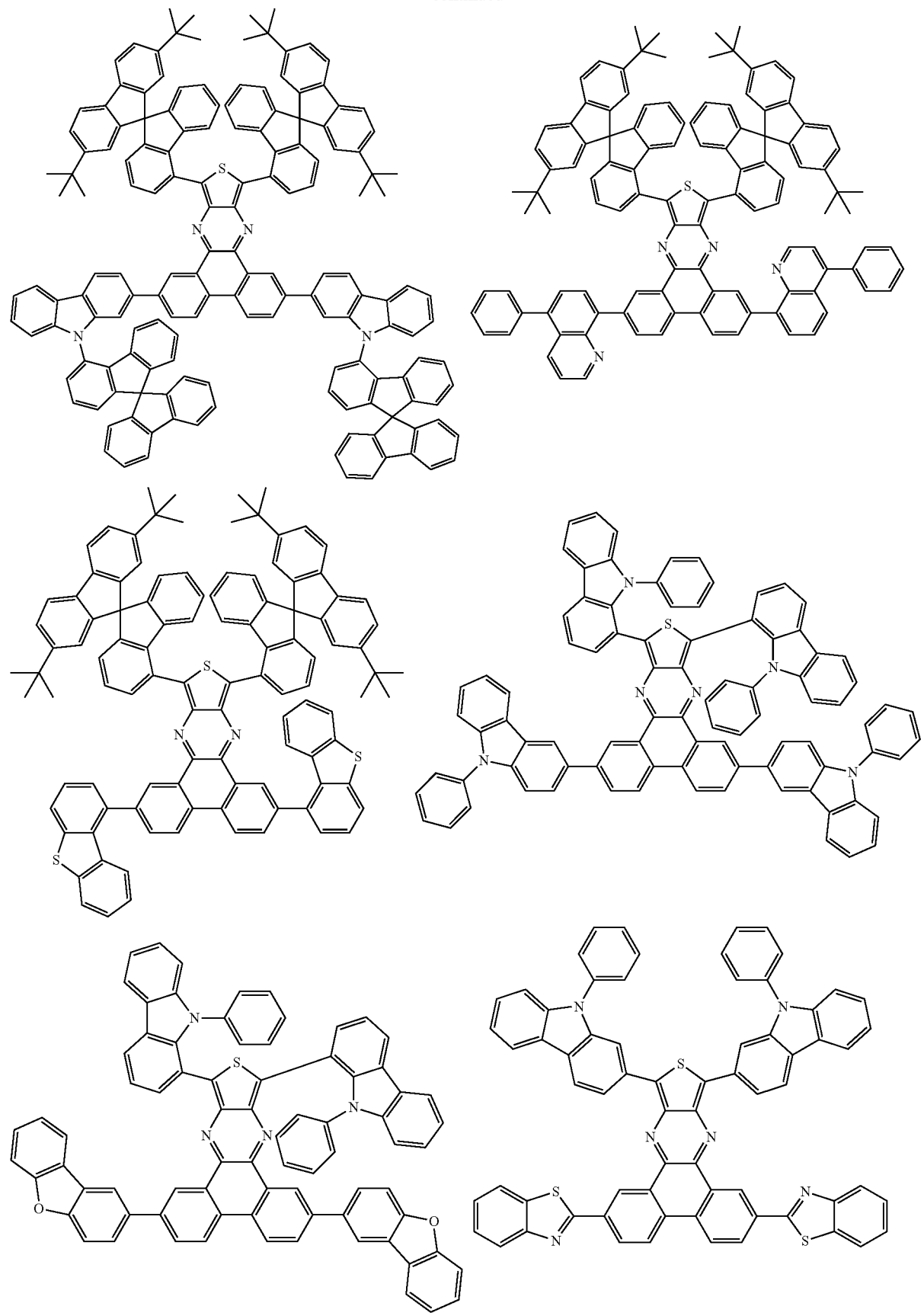
-continued

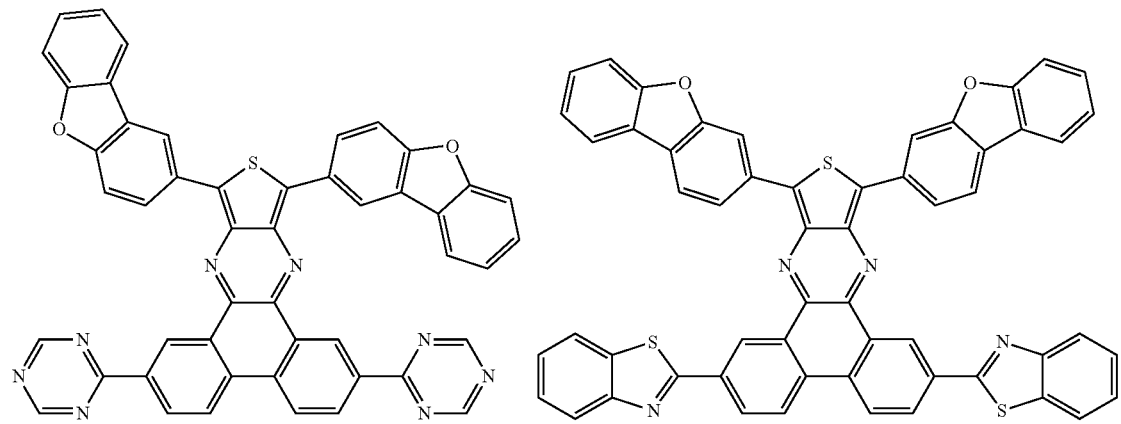
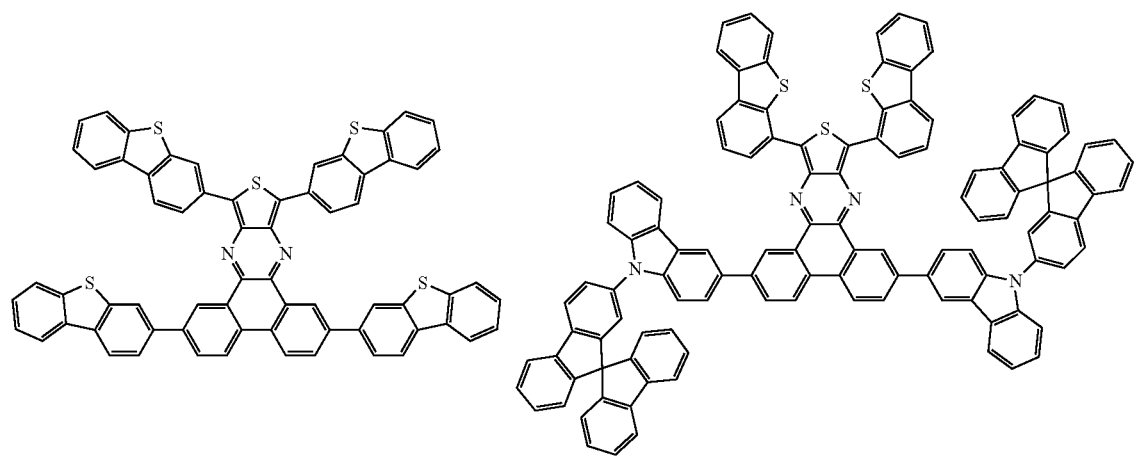
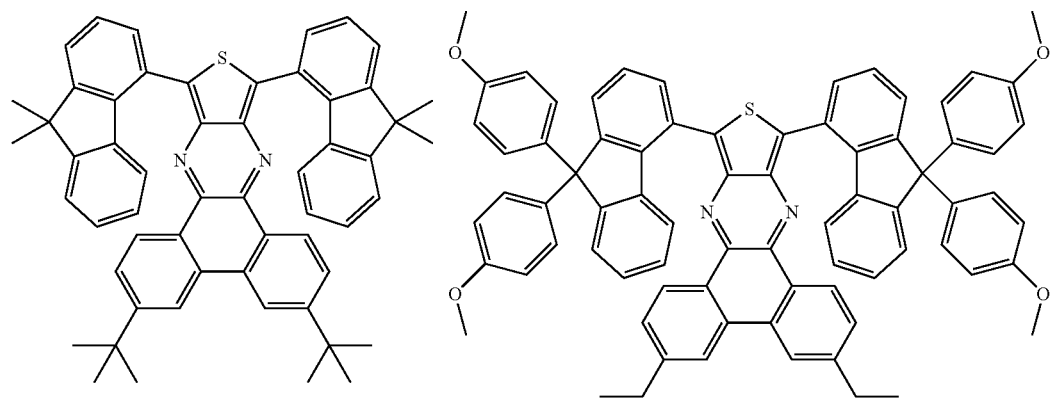

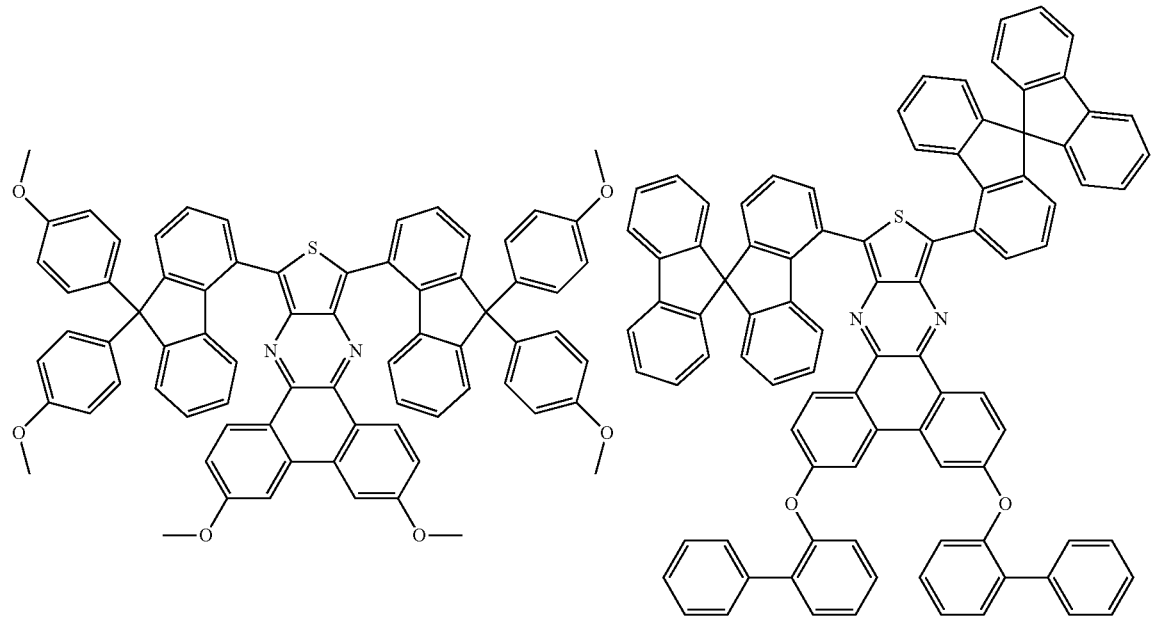
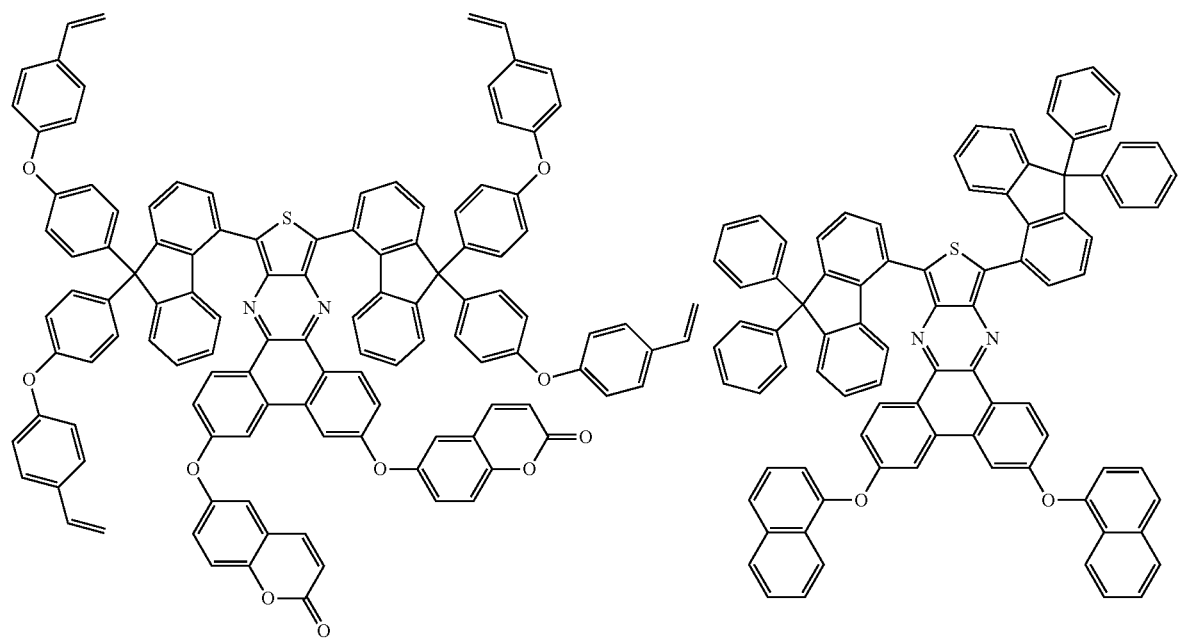

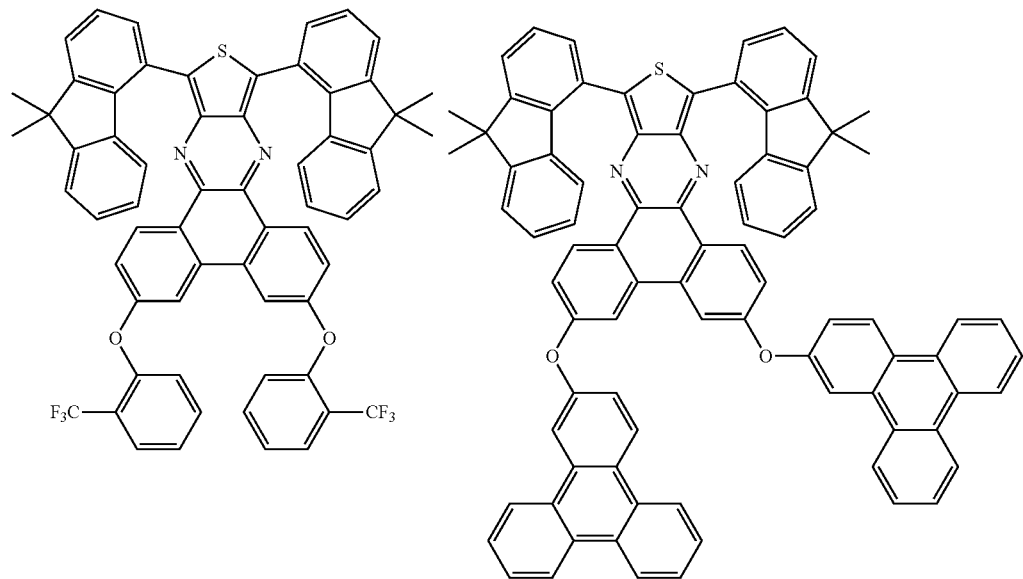
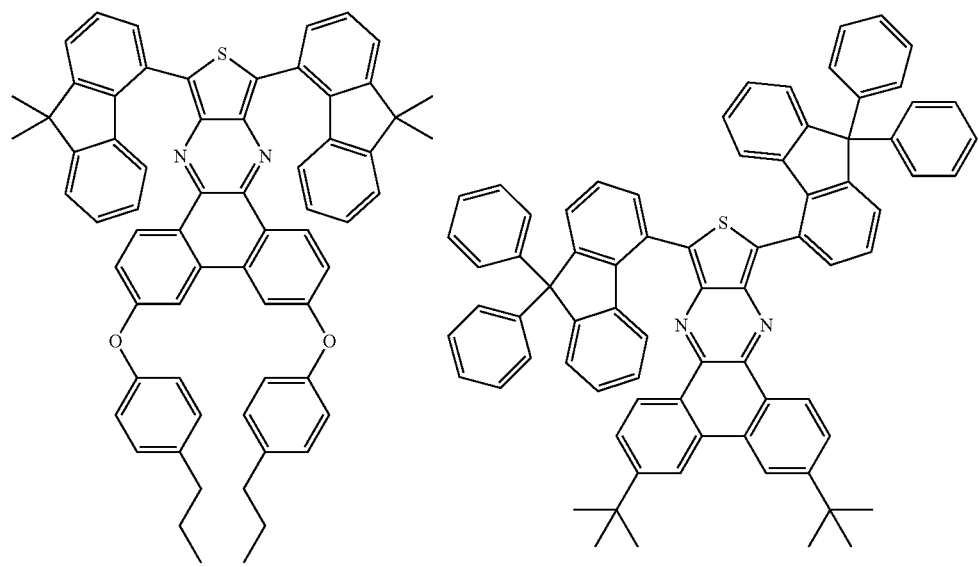

343
344
-continued
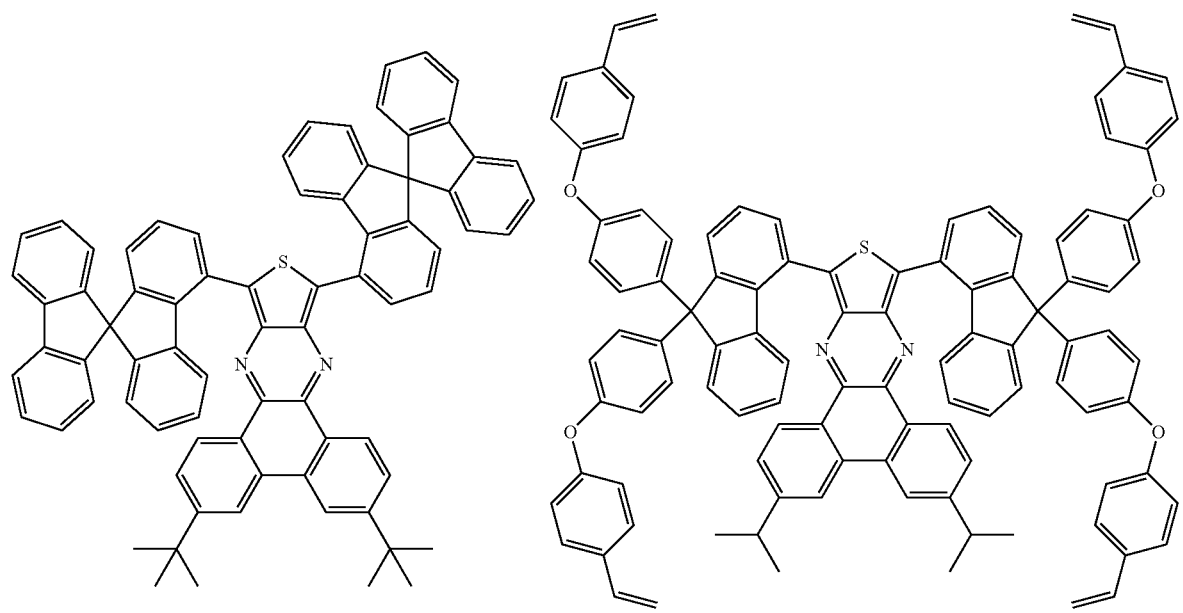
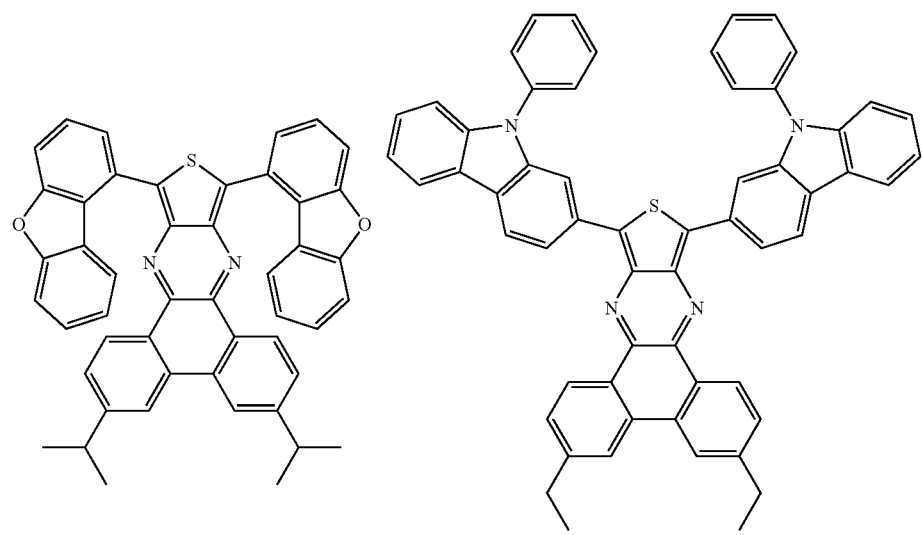
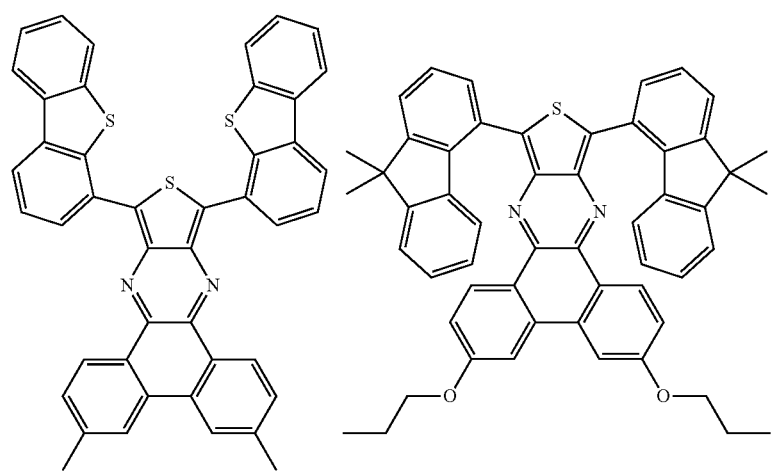

345 346
-continued
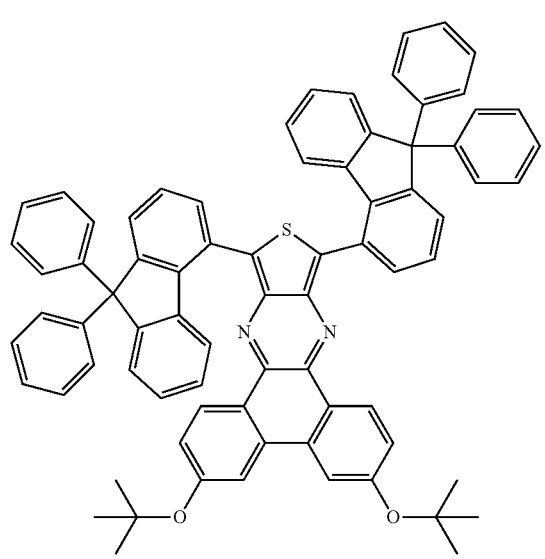
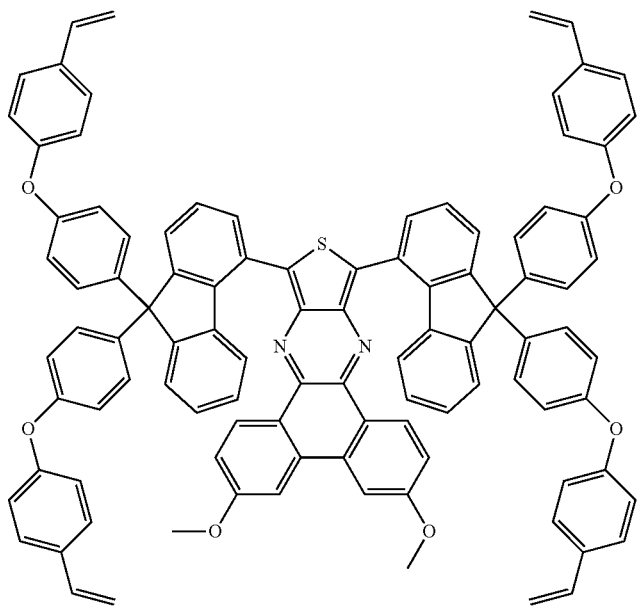
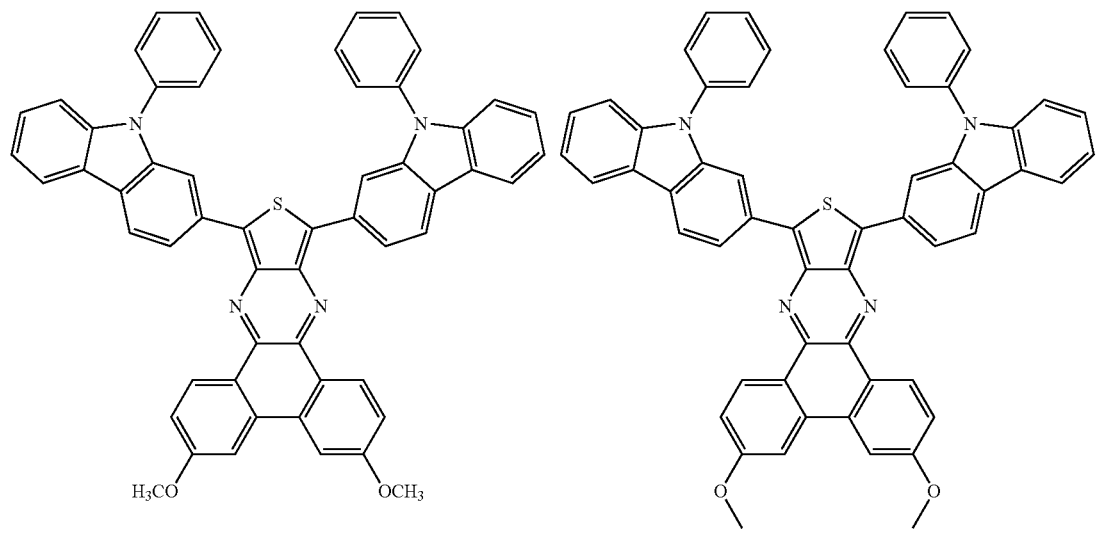
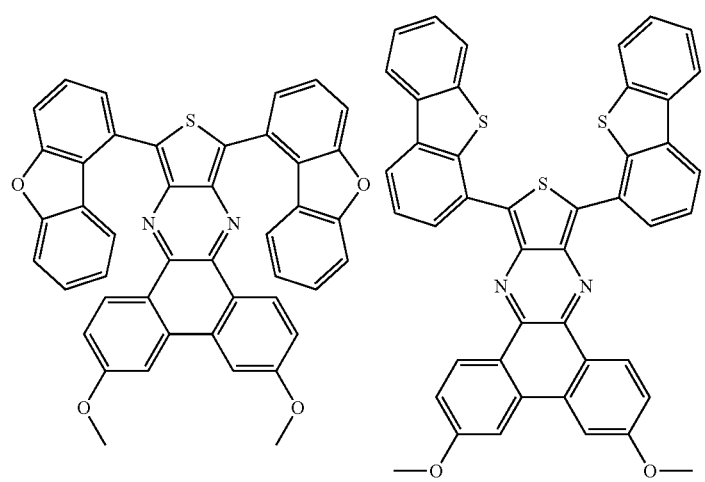

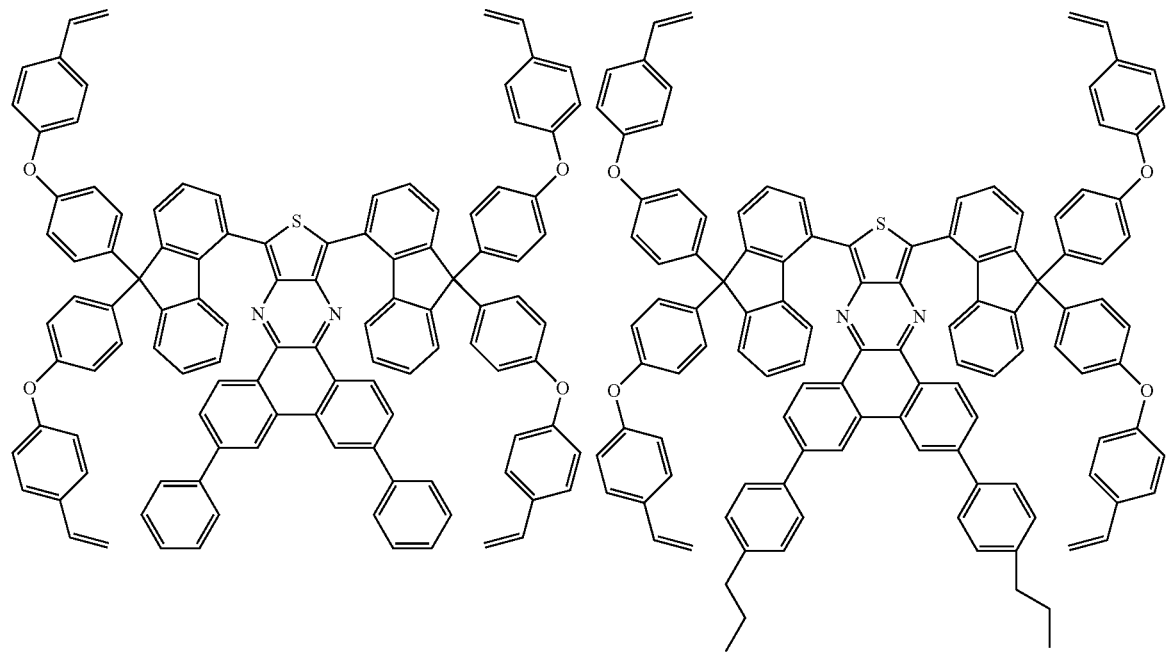
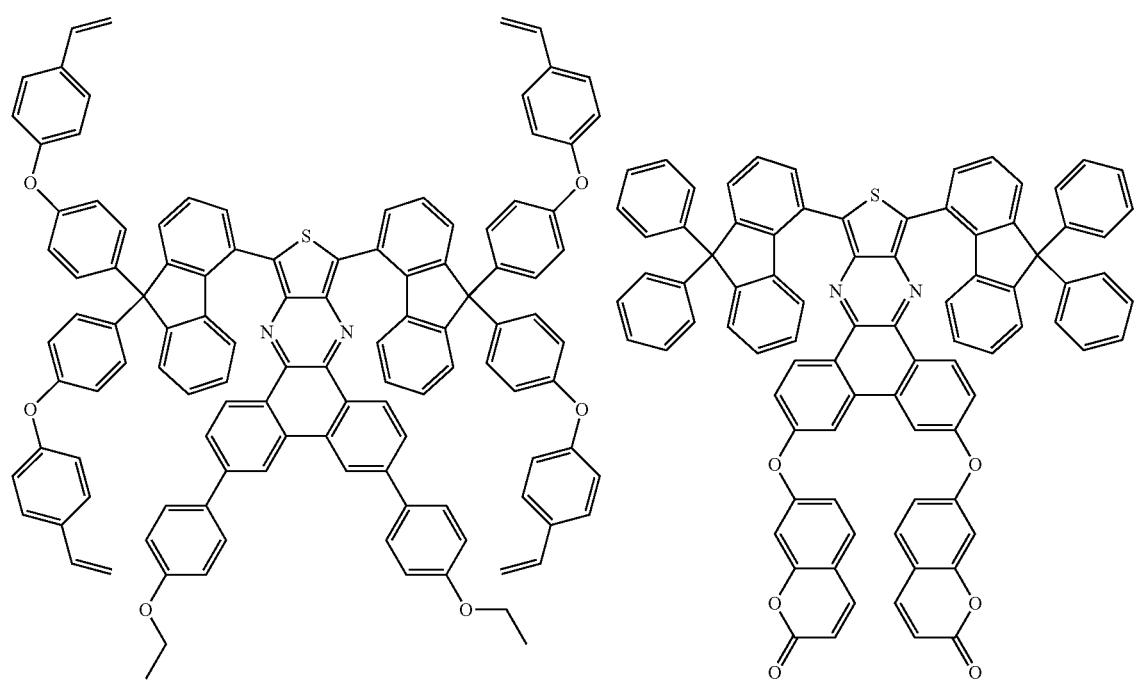

-continued
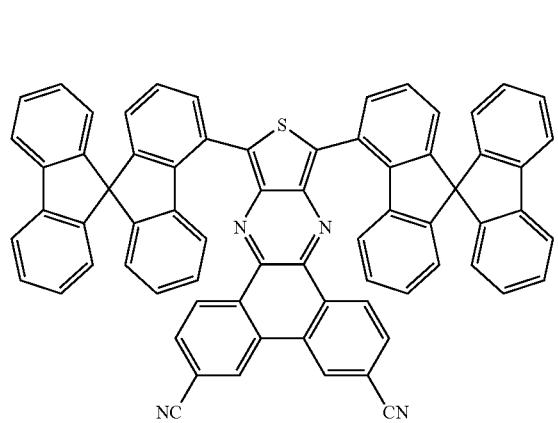
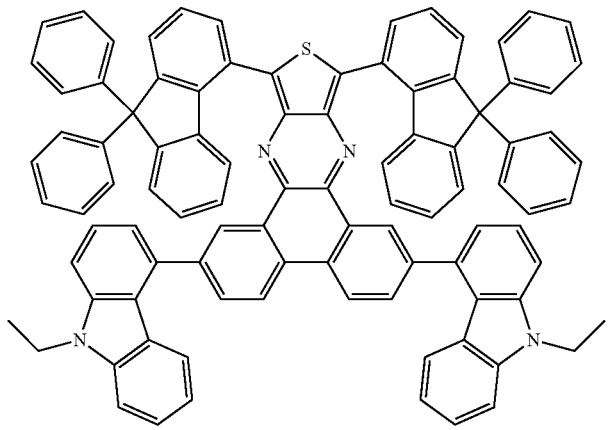
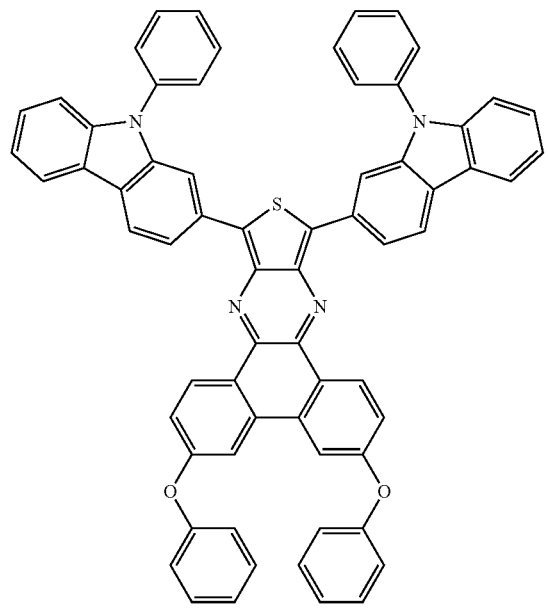
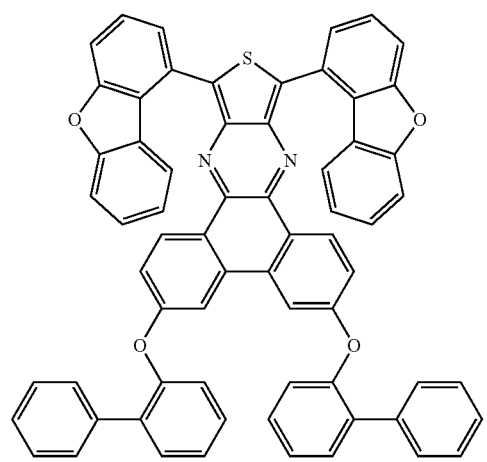

351
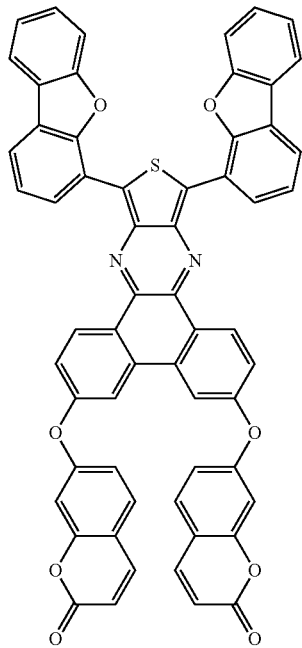
352
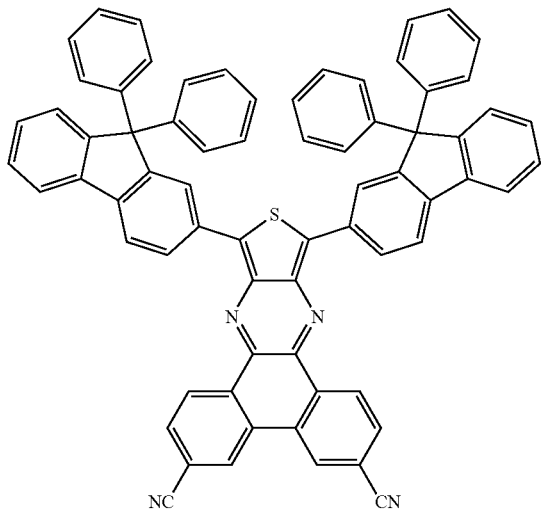
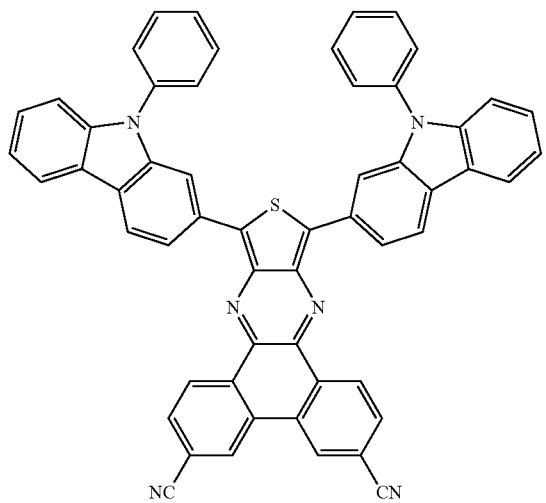
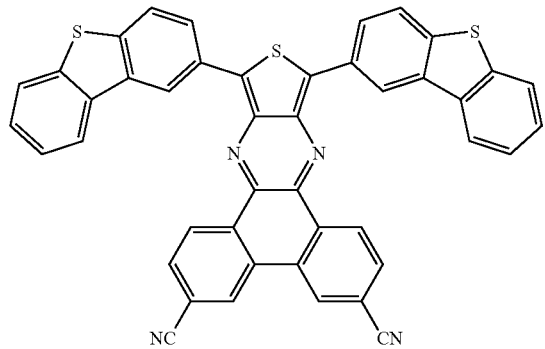
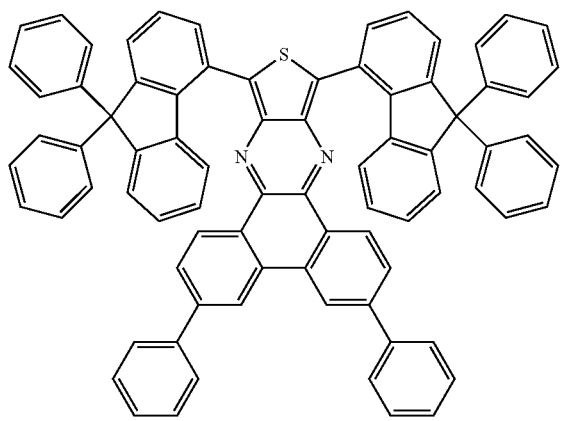
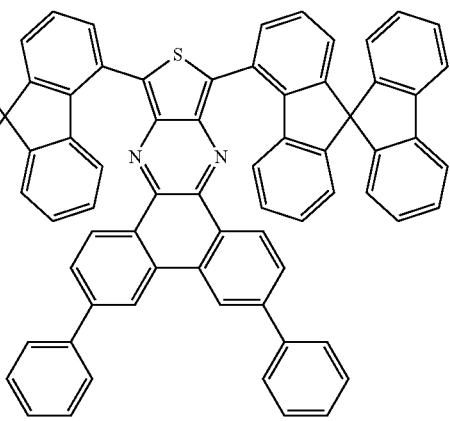

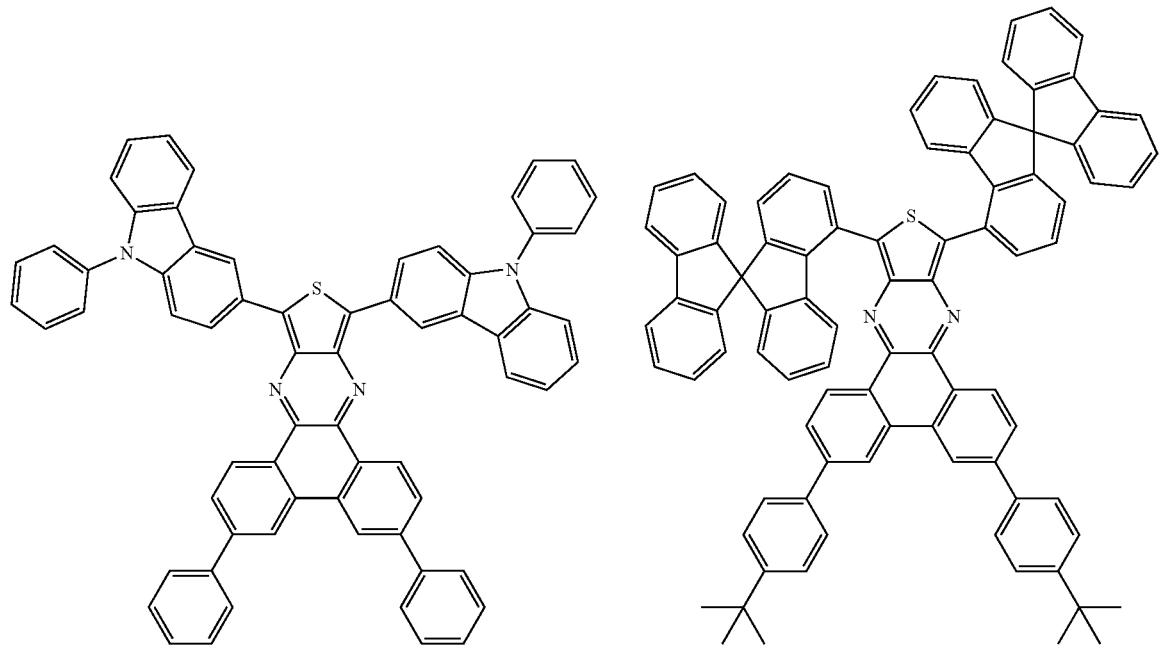
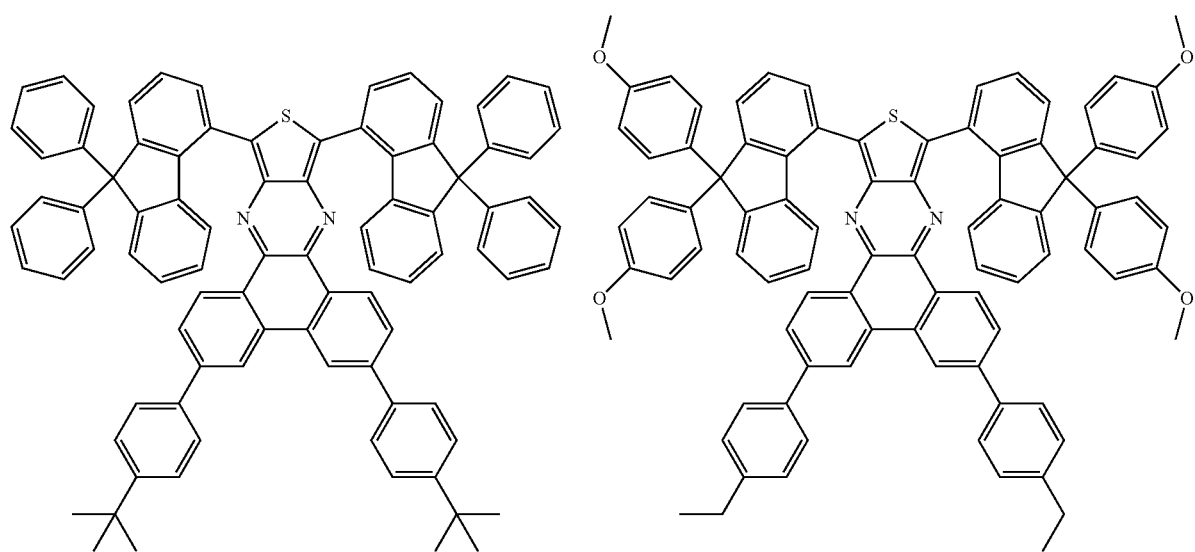

355
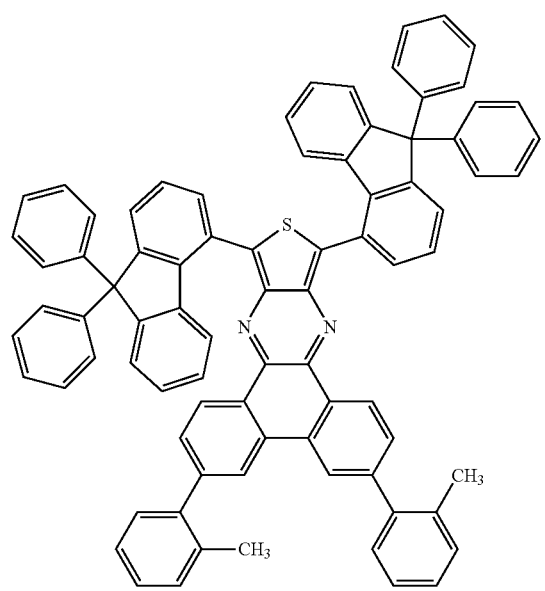
356
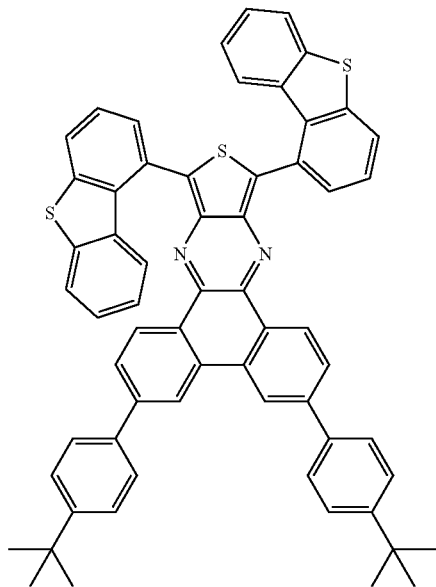
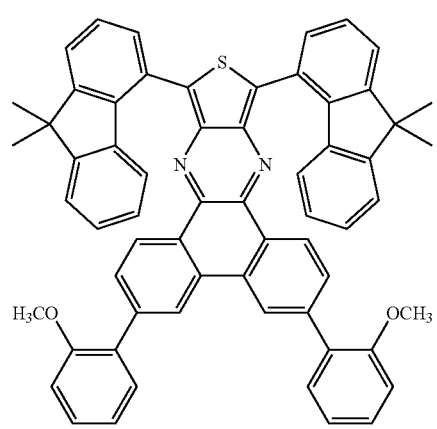
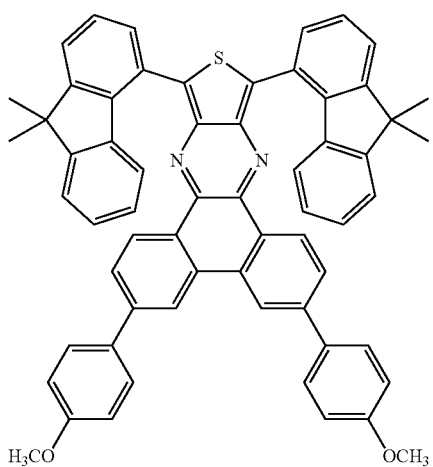
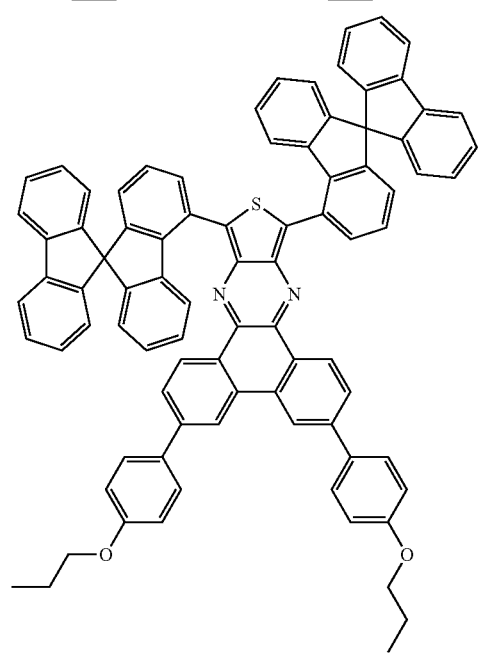

357
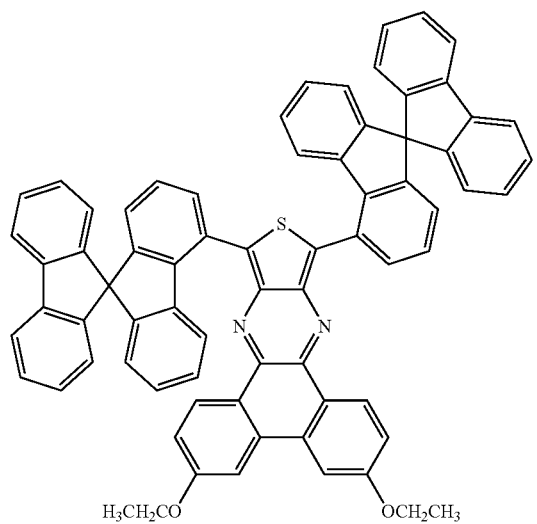
358
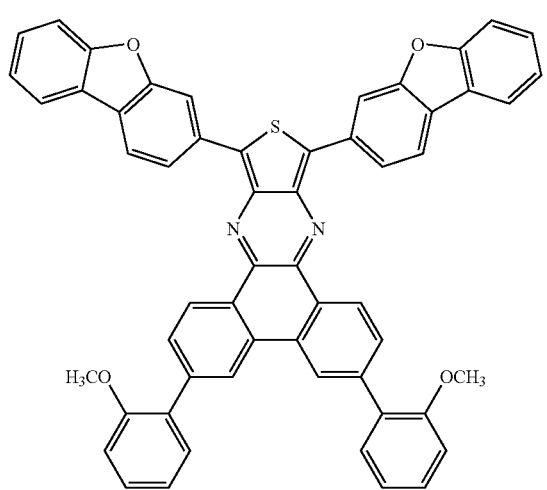
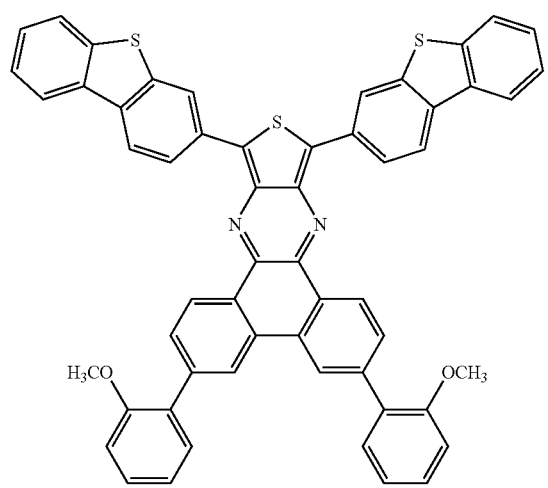
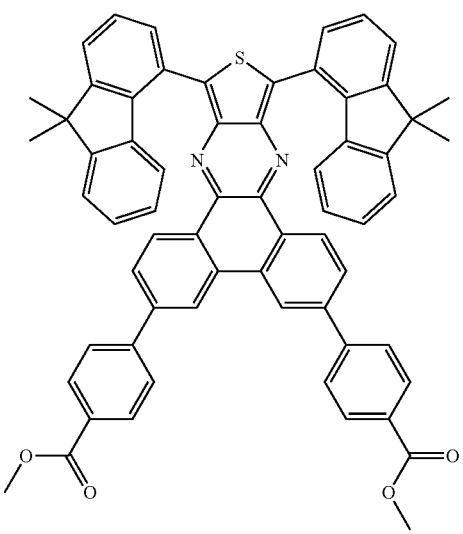
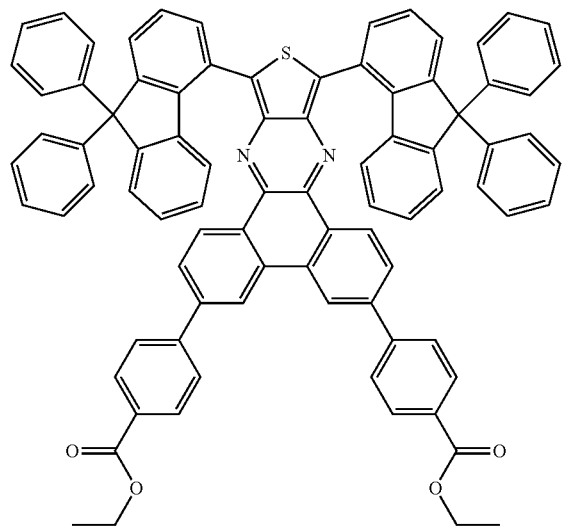
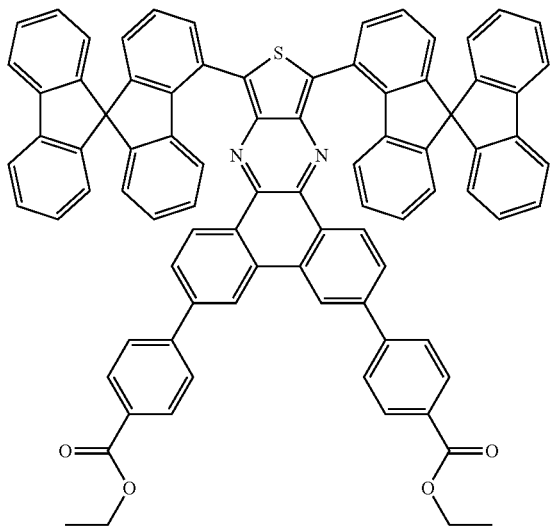

359 360
-continued
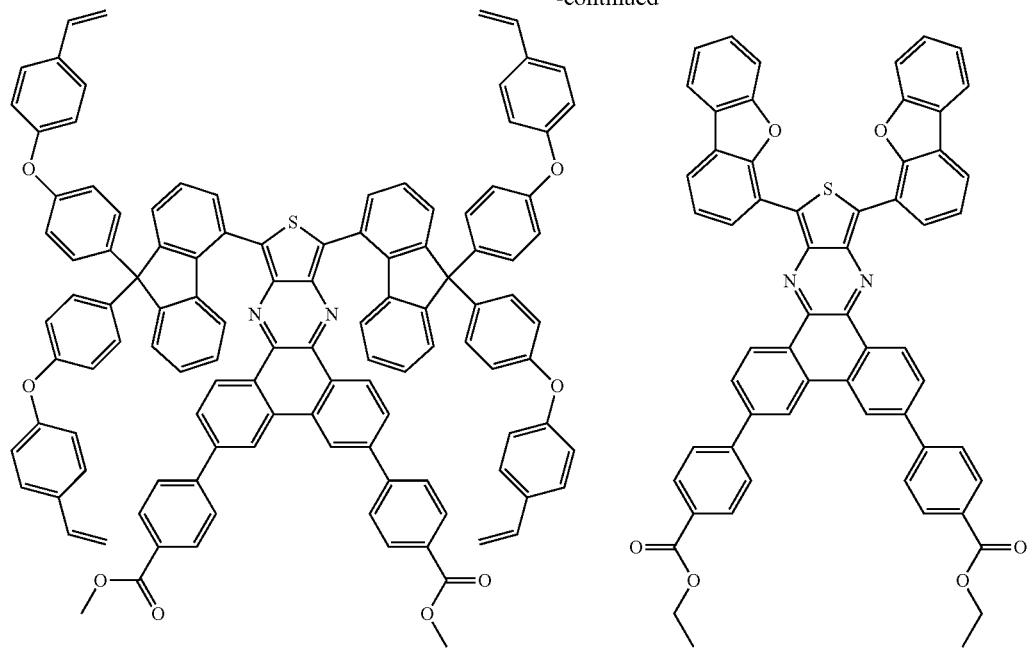
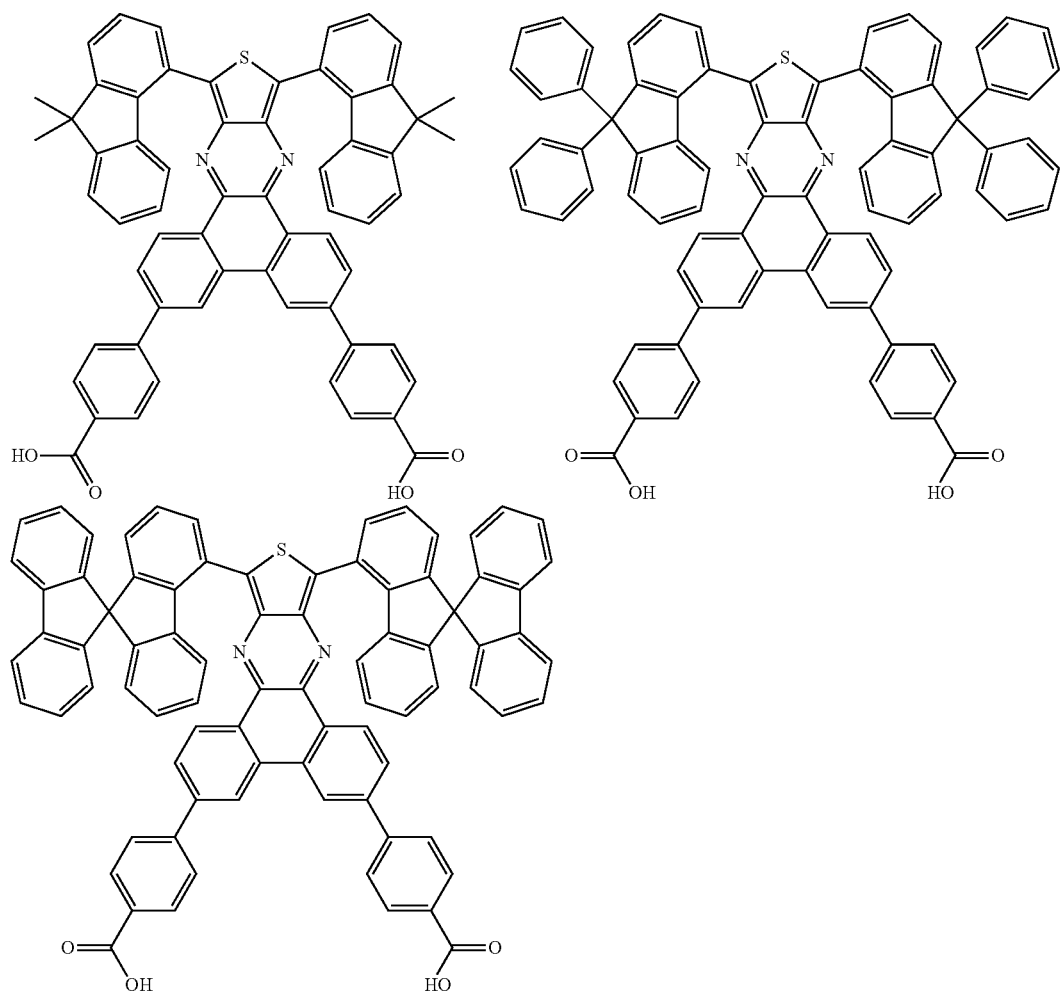

-continued
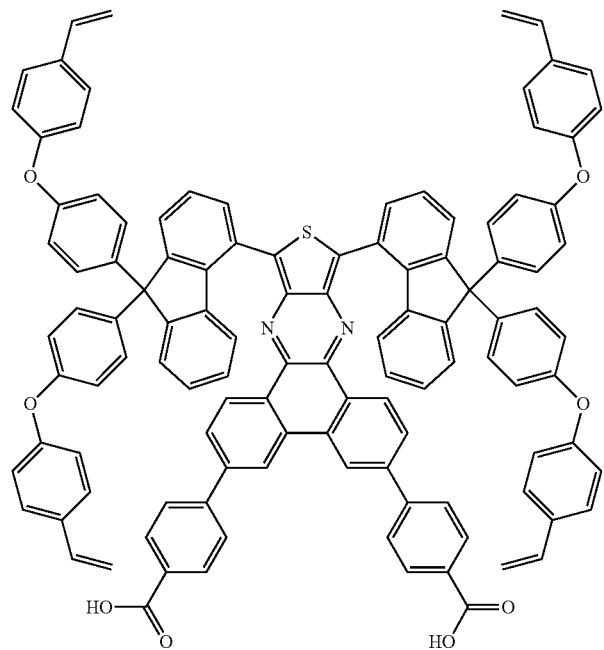
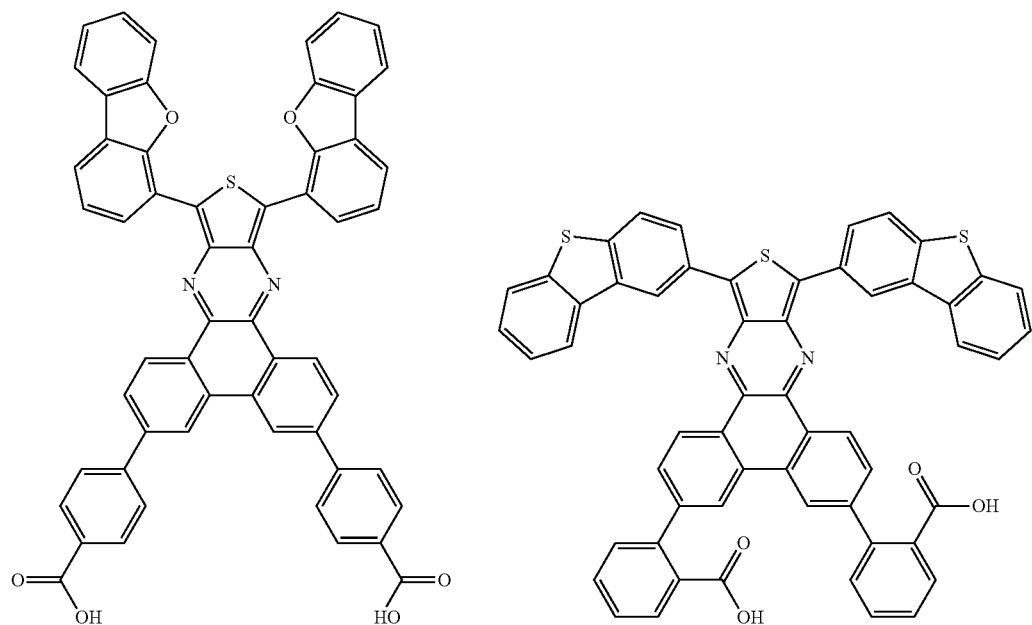

-continued
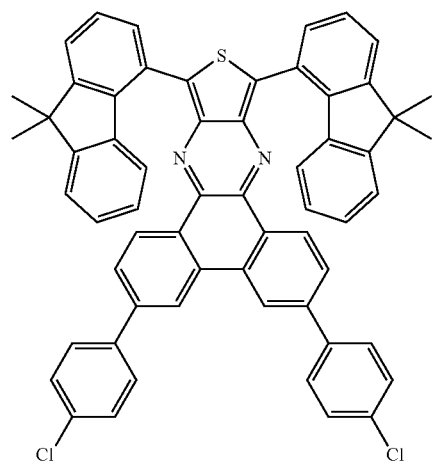
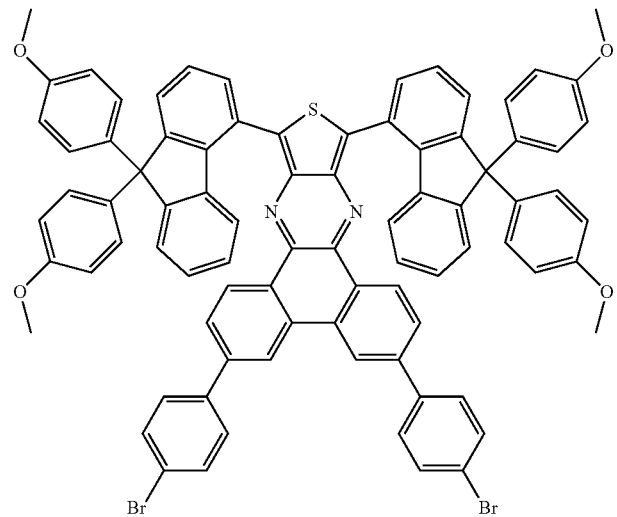
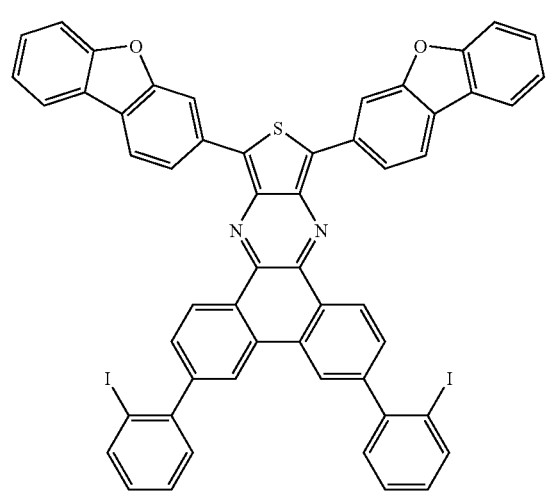
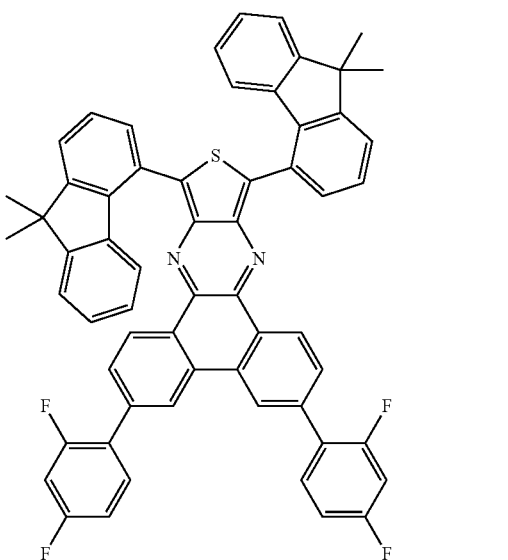
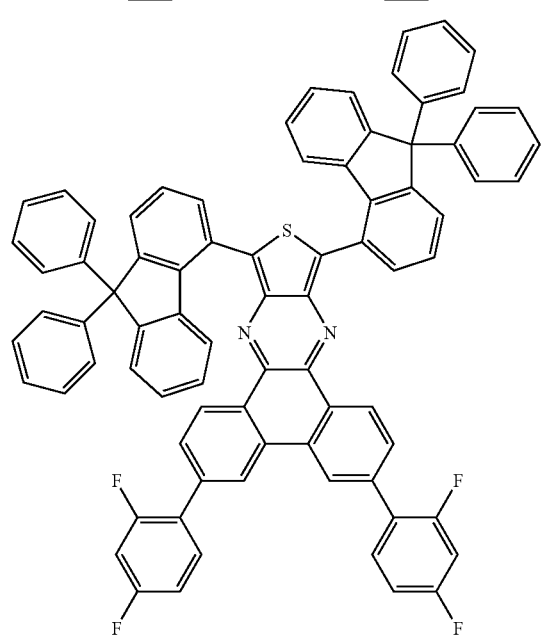
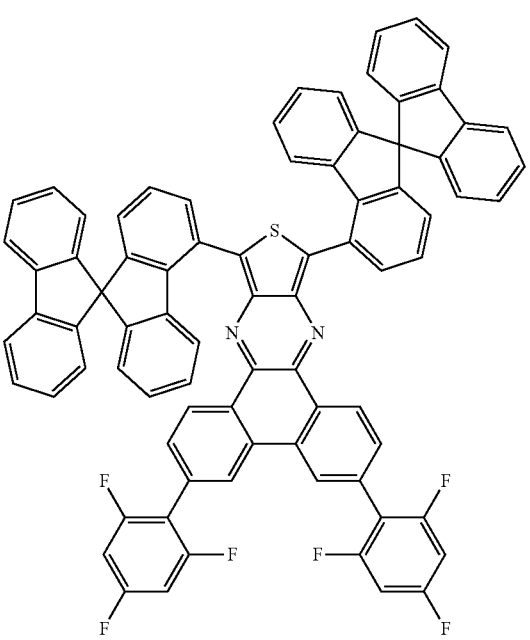

-continued
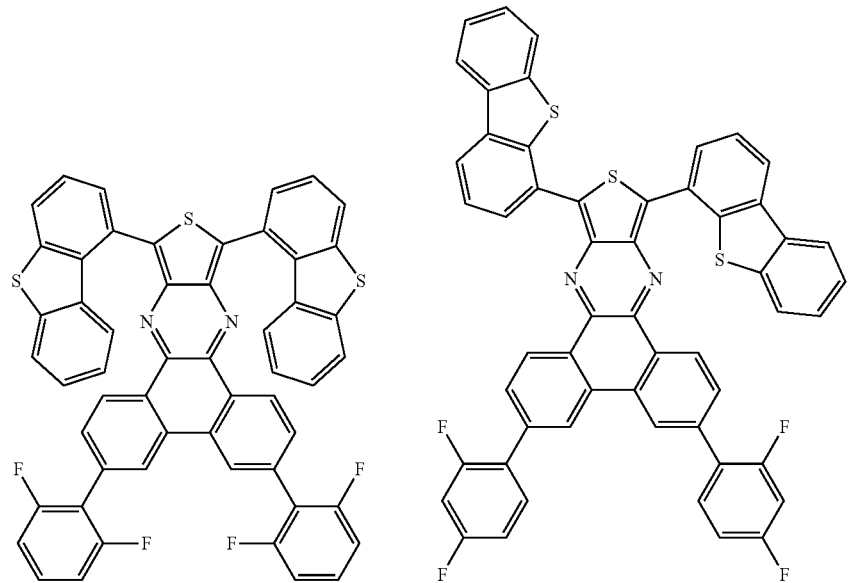
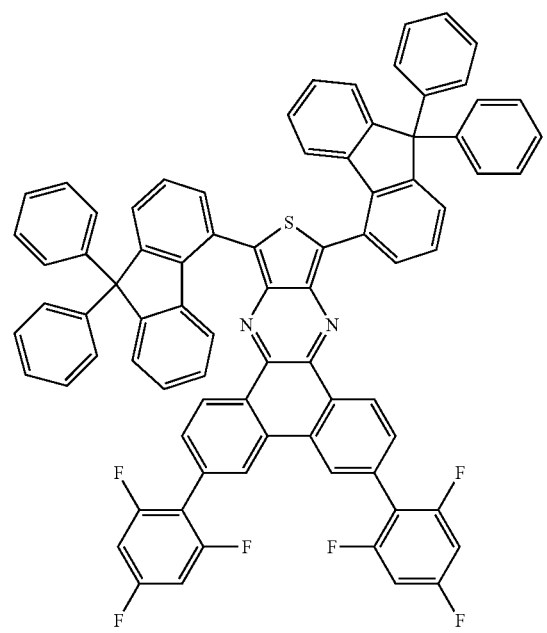

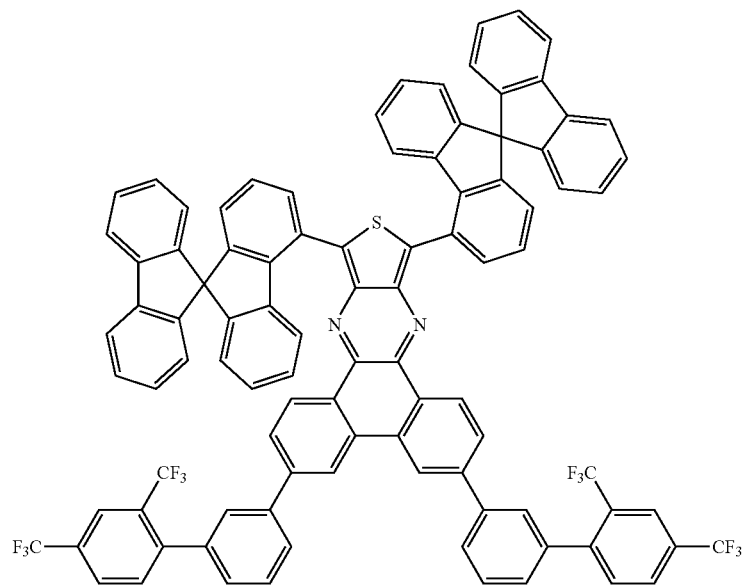
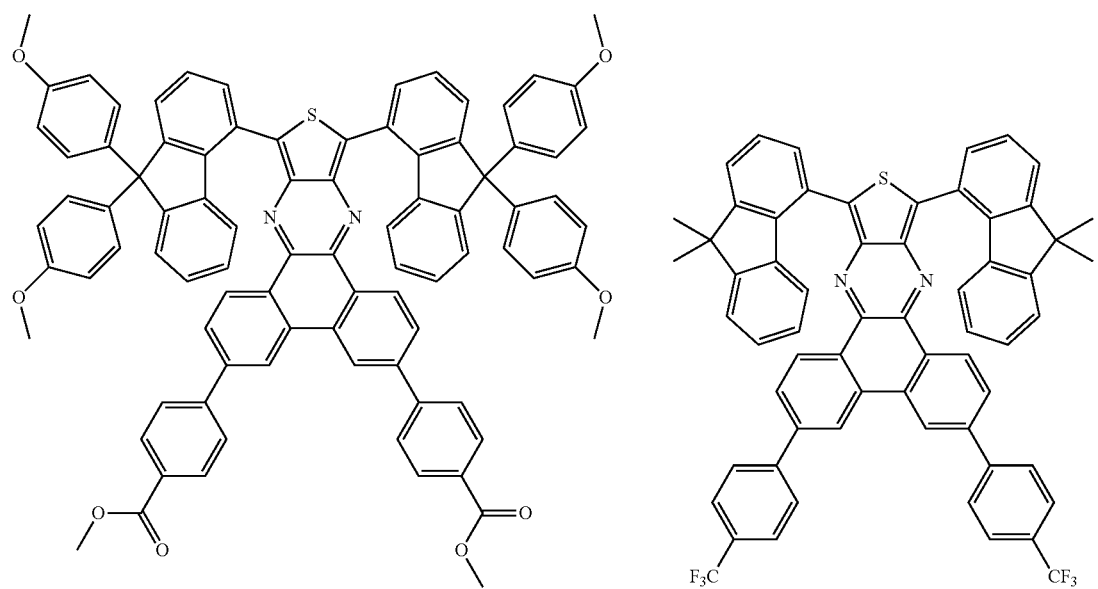

369
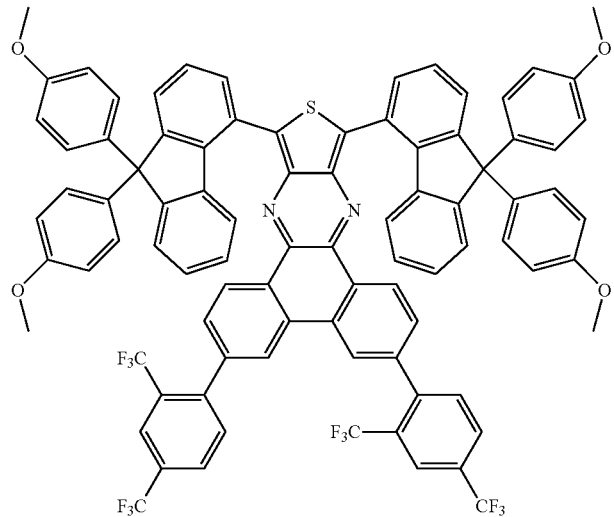
370
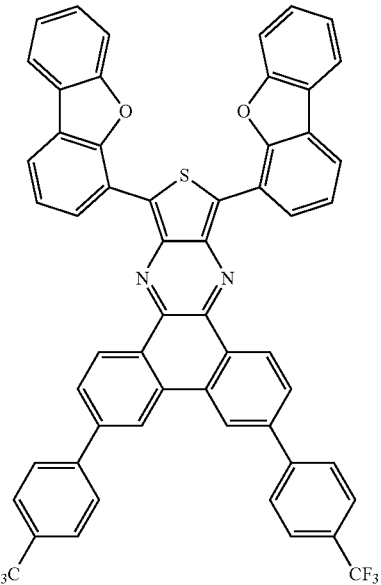
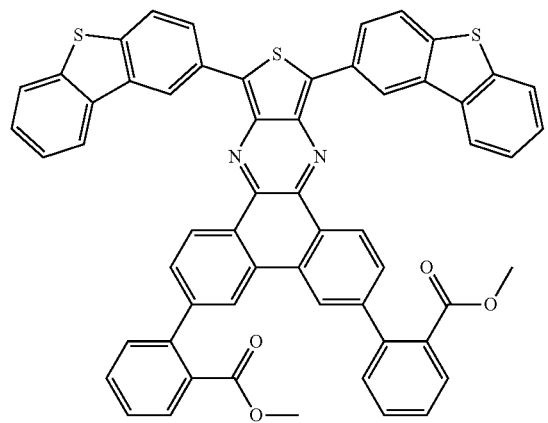
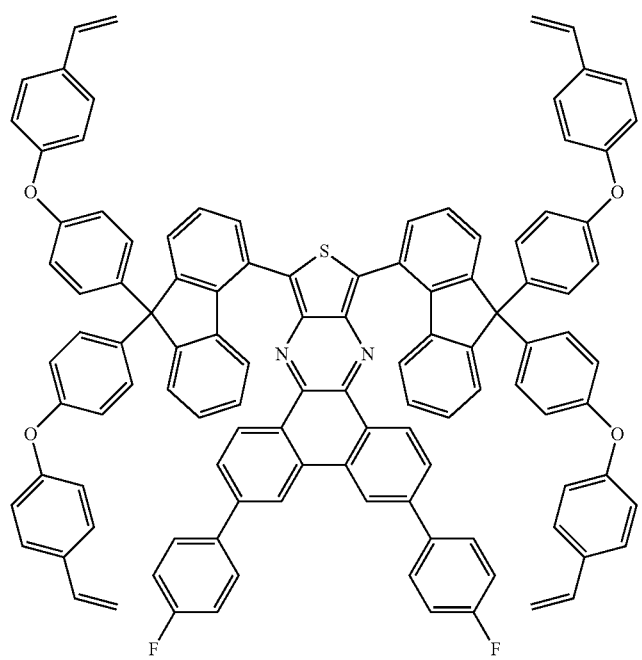
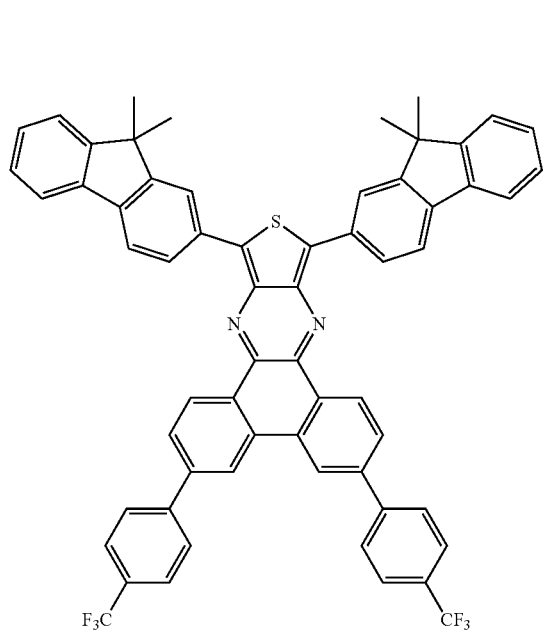

-continued
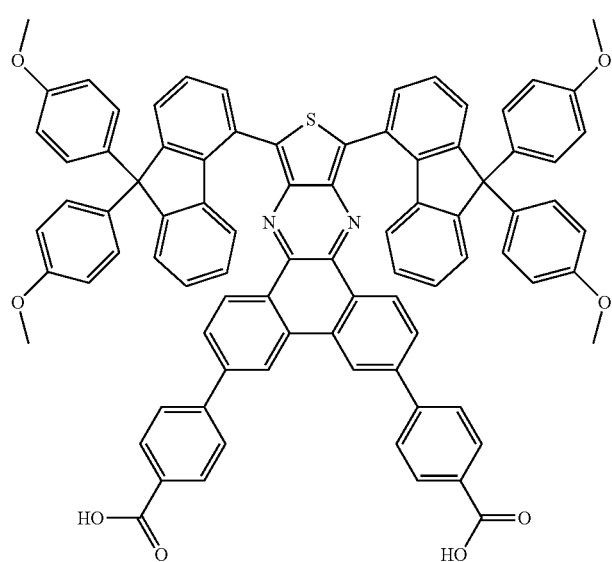
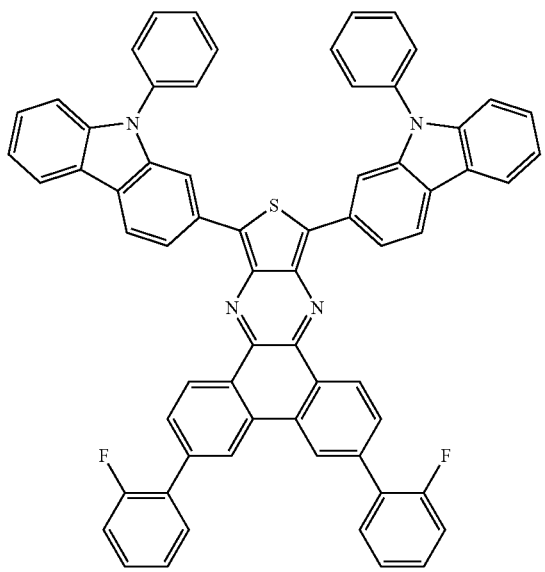
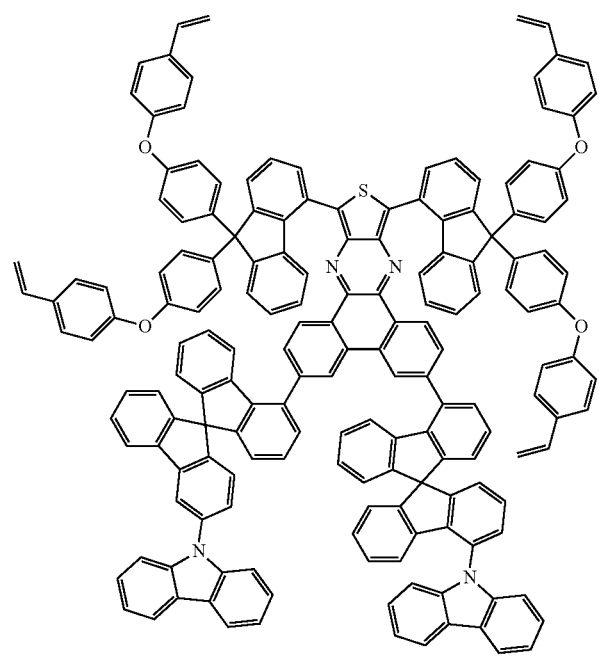

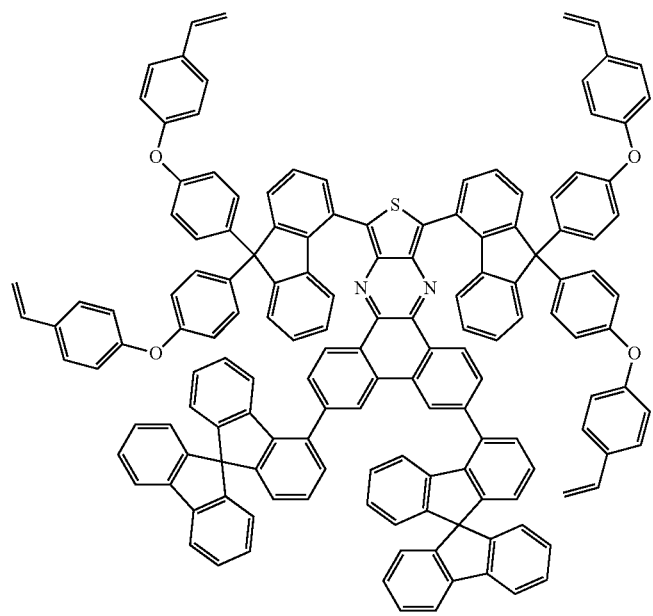
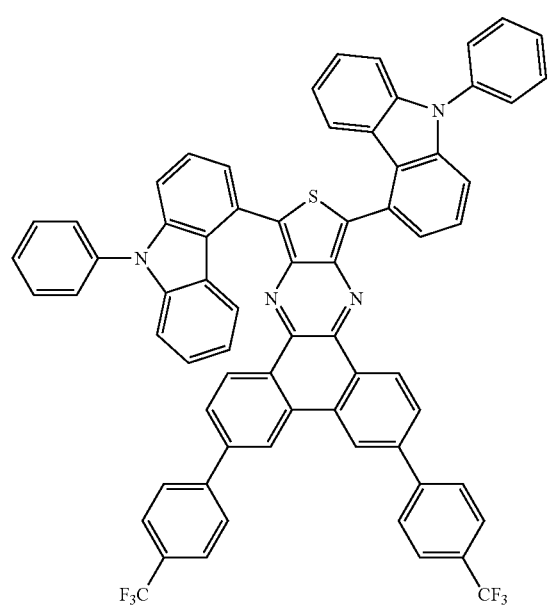

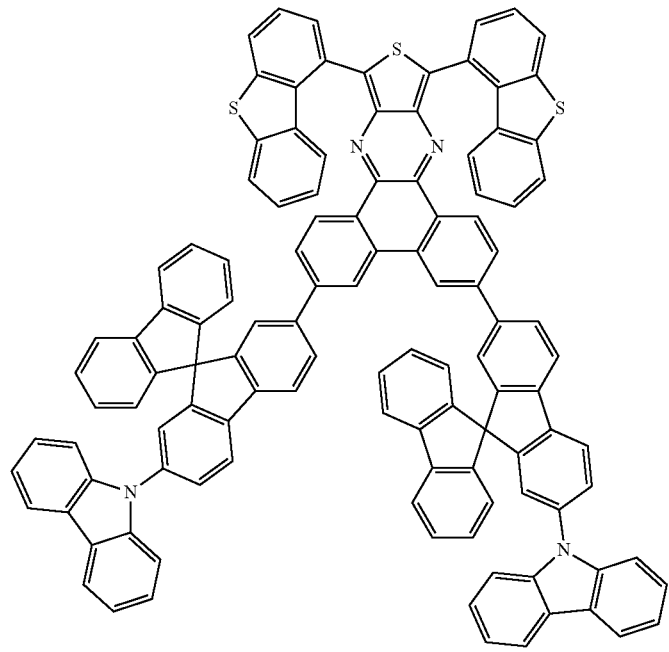
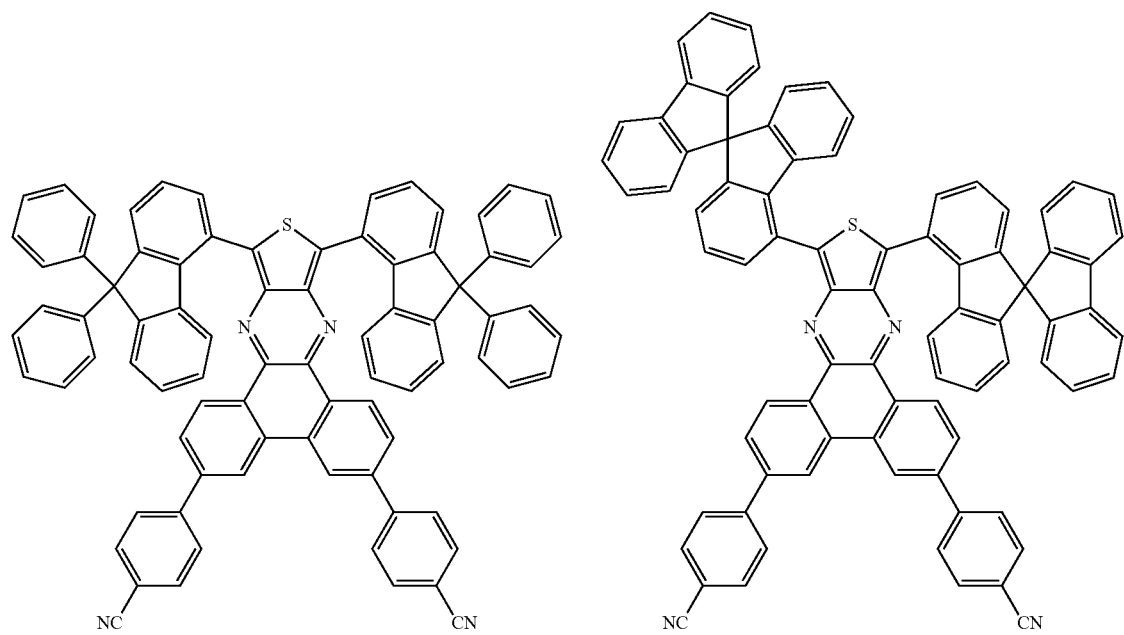

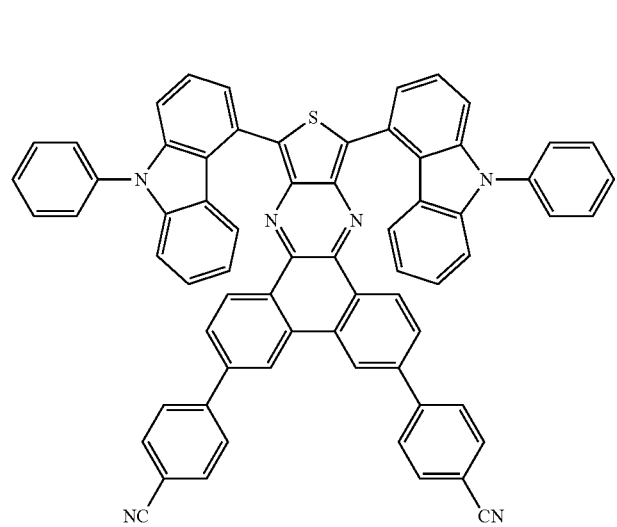
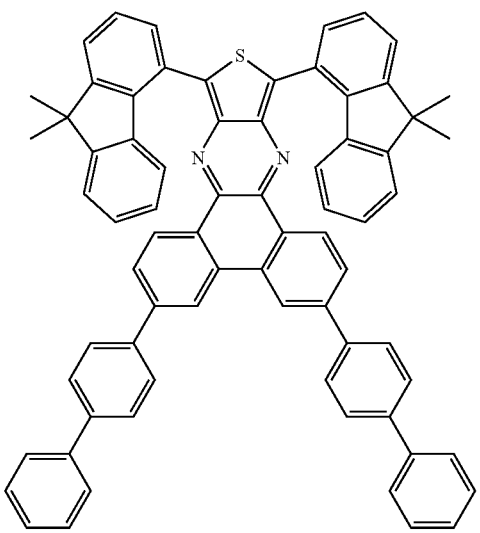
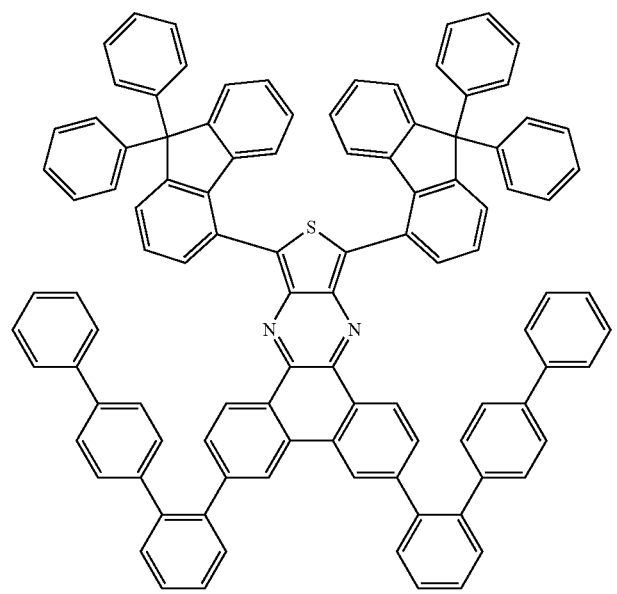

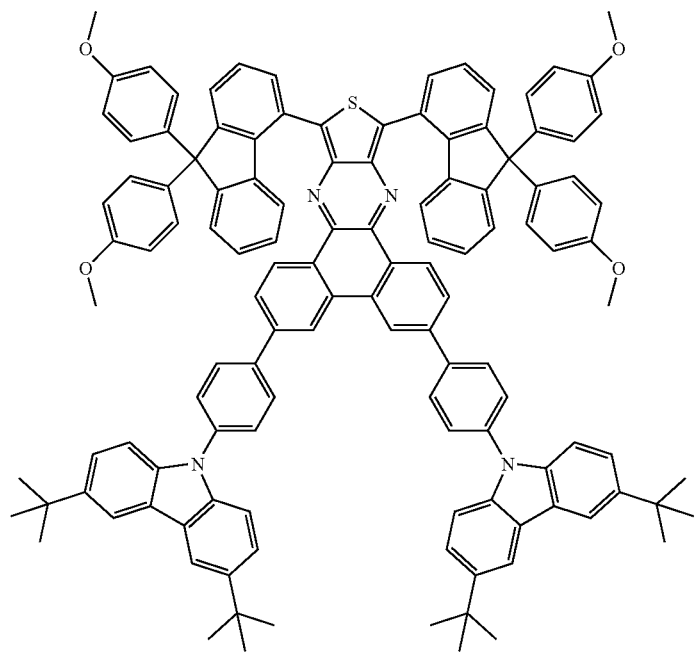
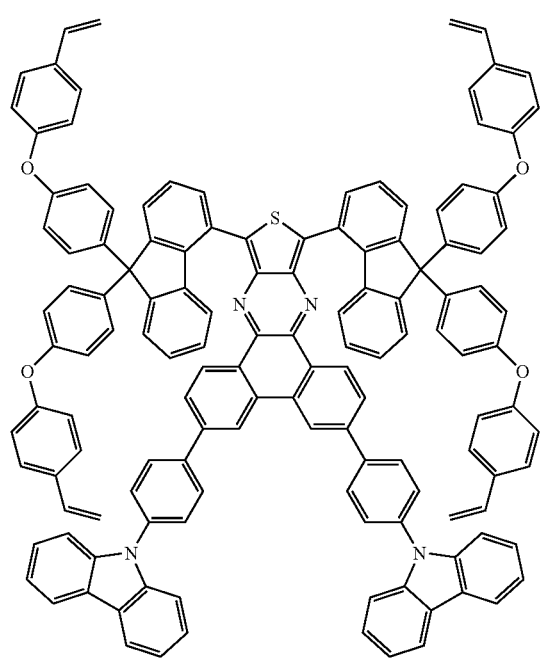

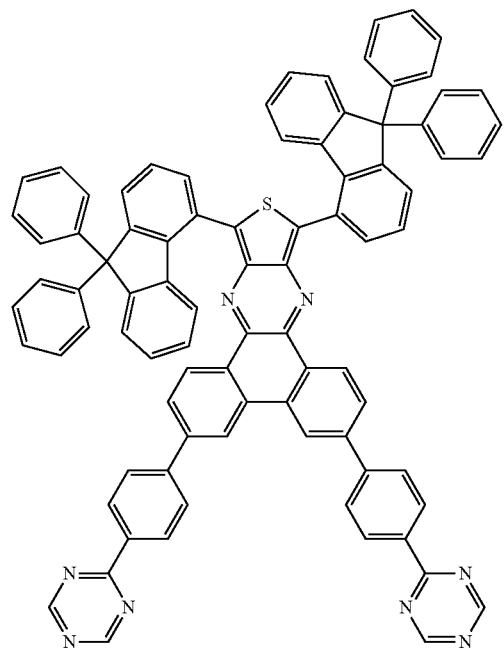
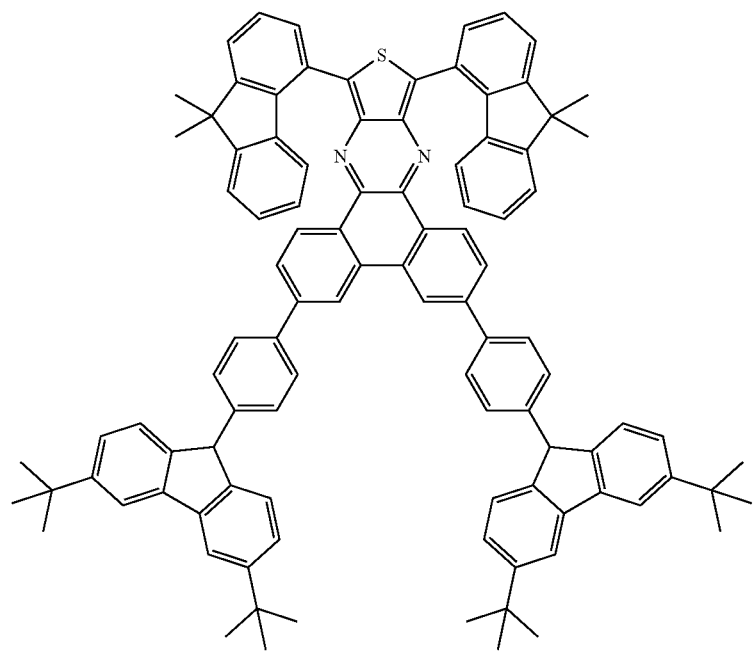

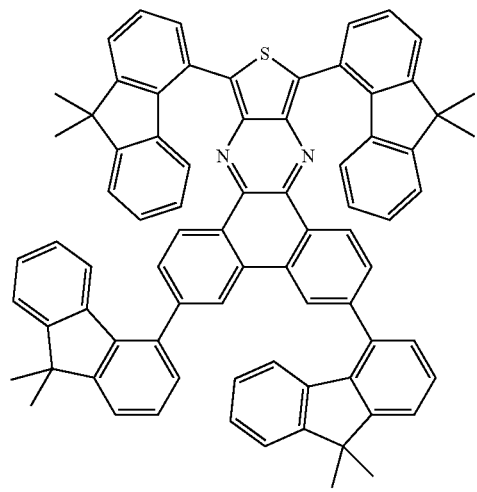
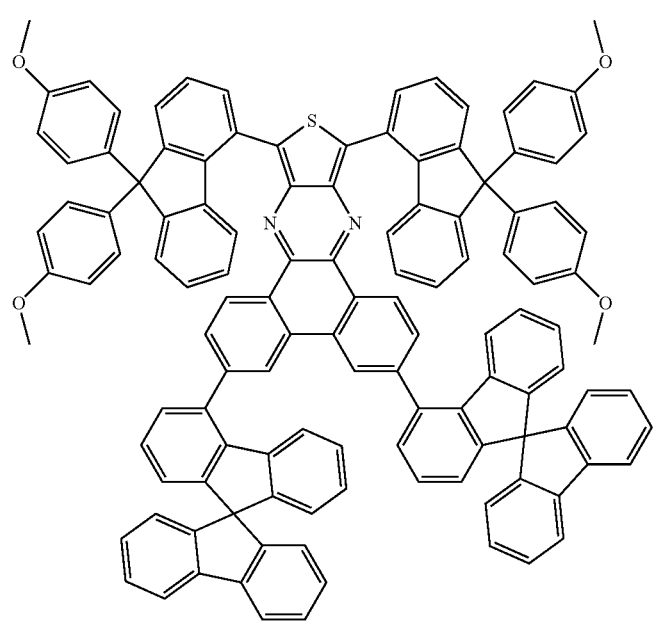

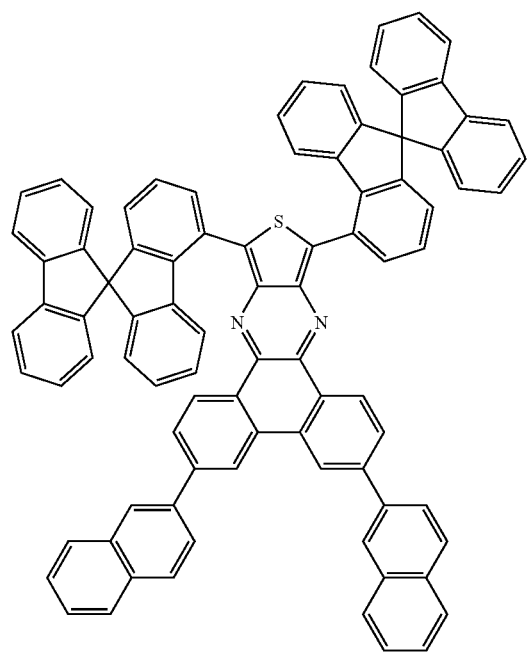
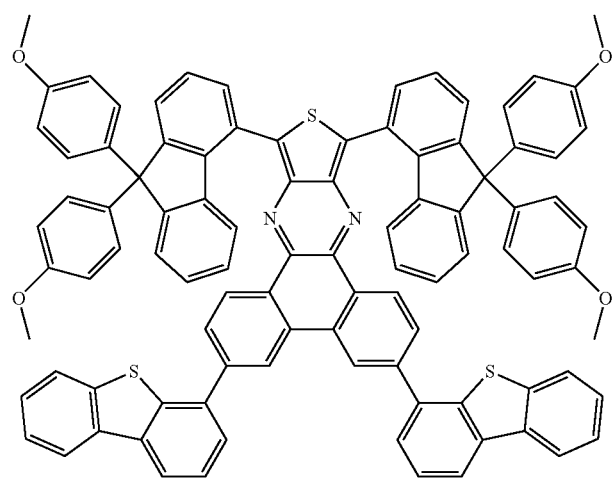
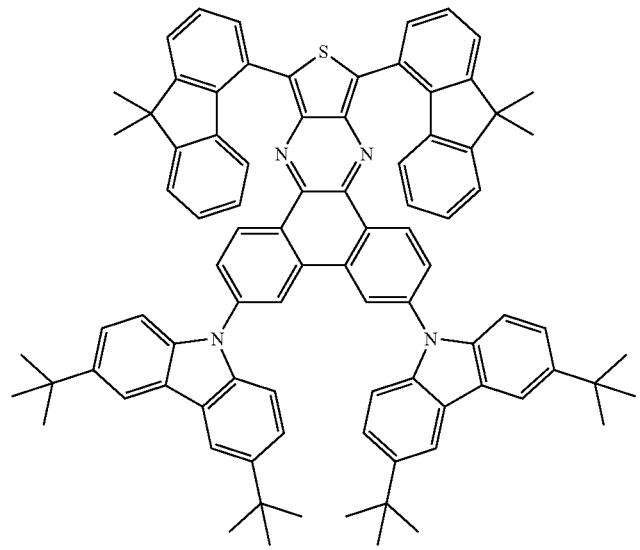
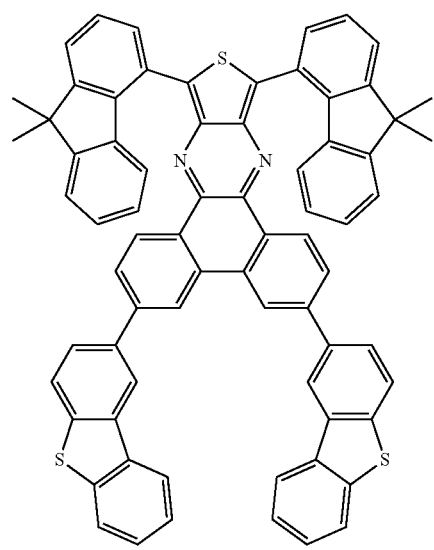

-continued
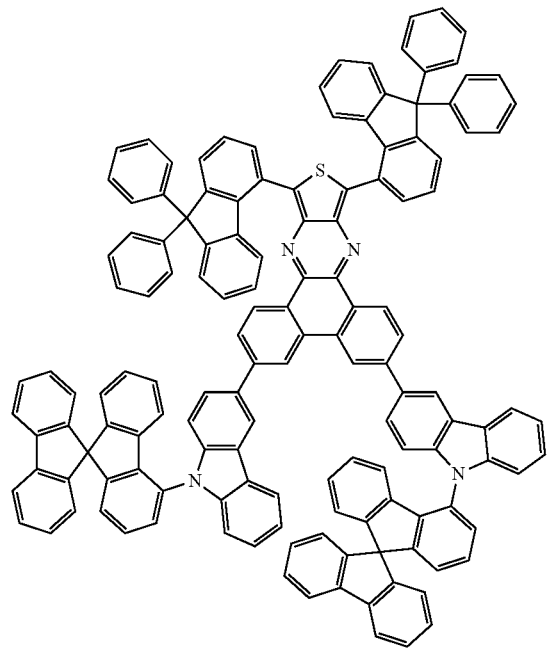
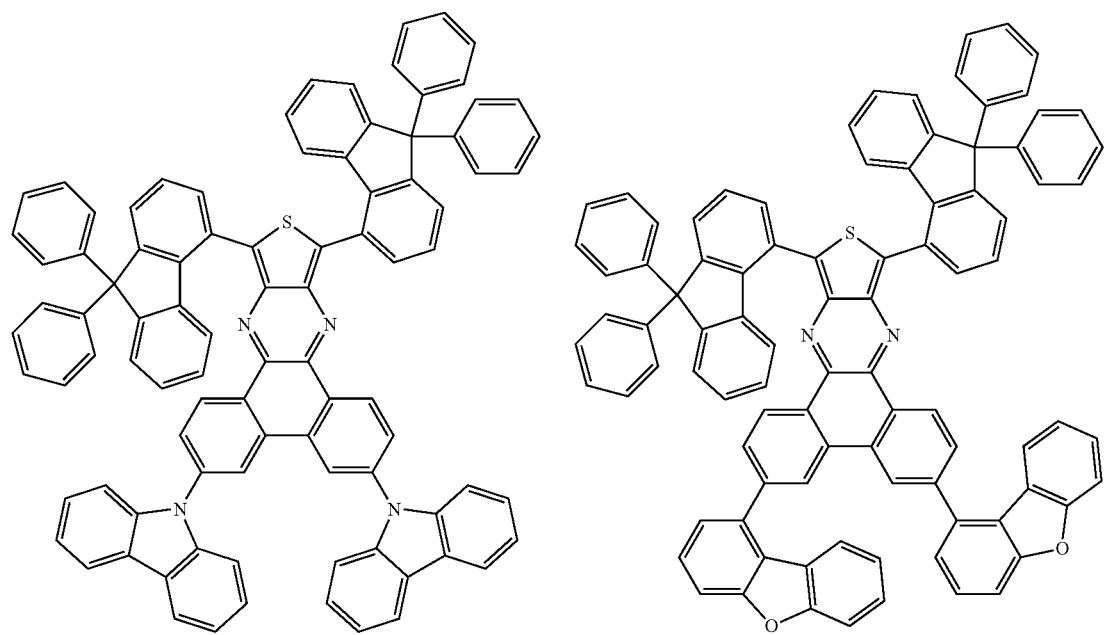

-continued
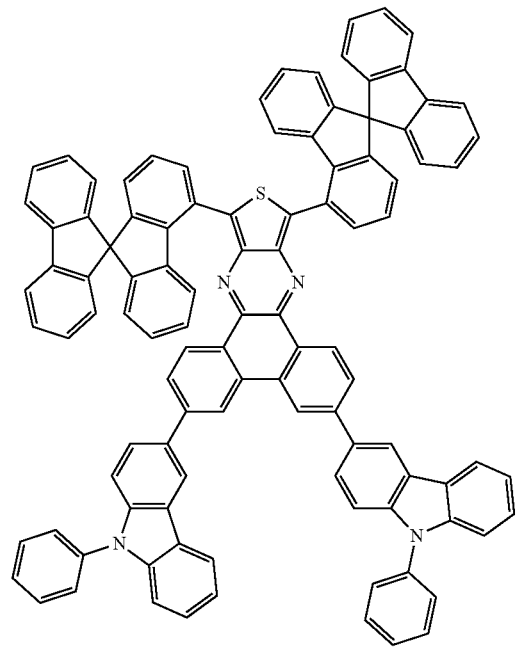
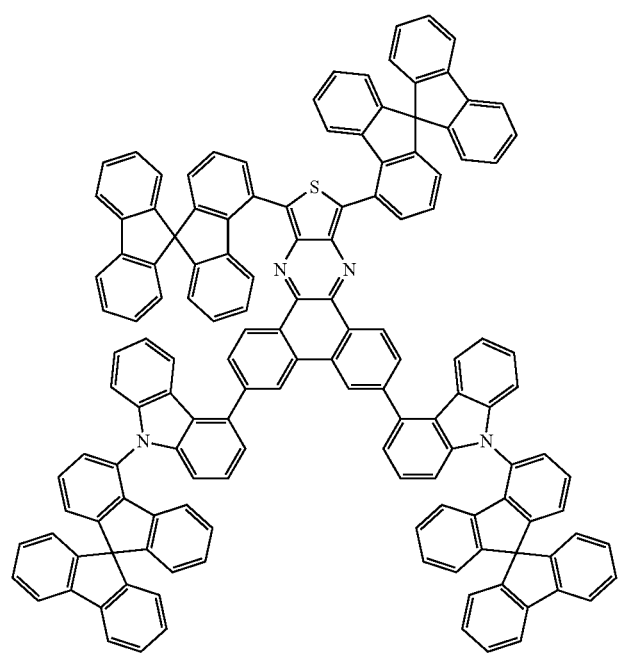

-continued
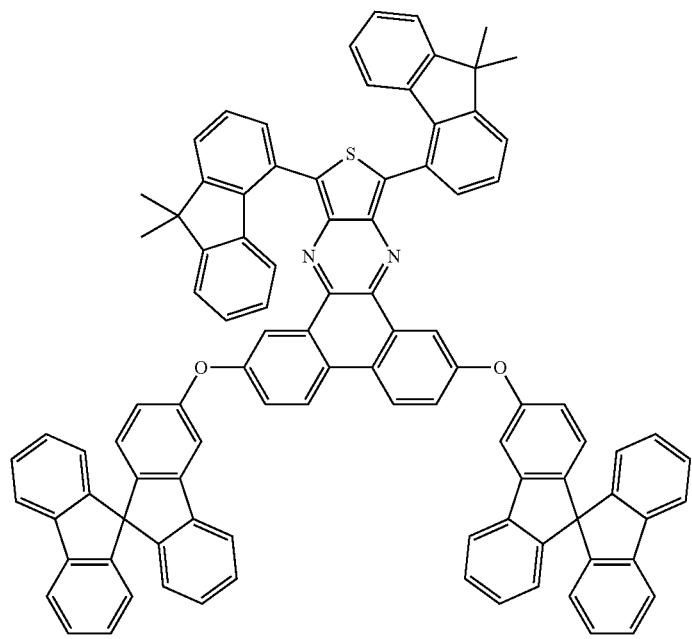
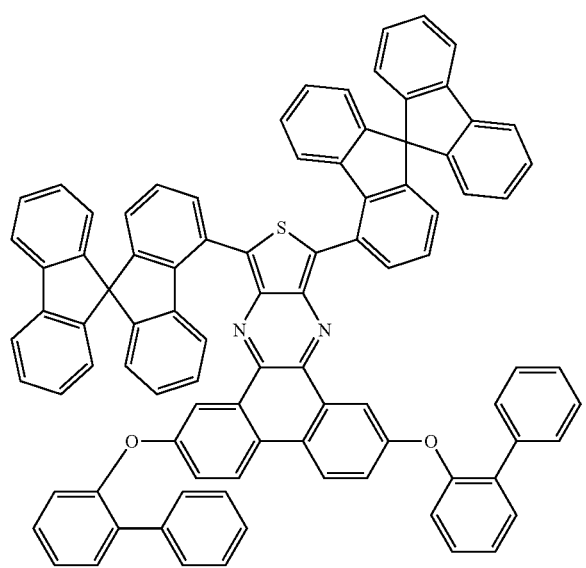

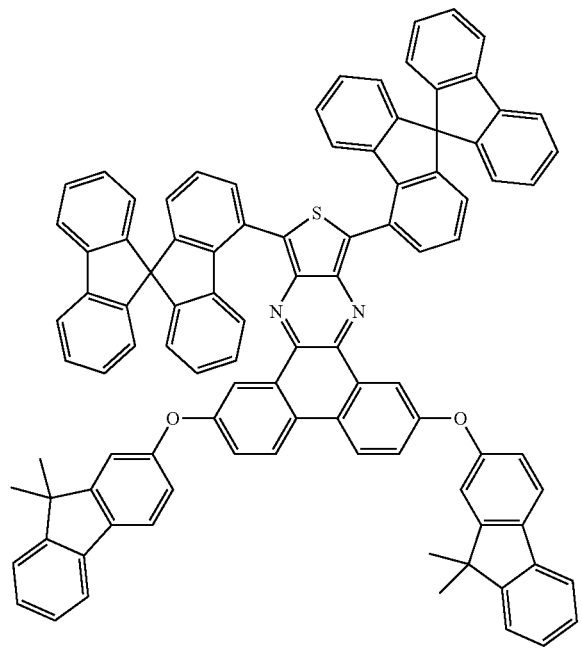
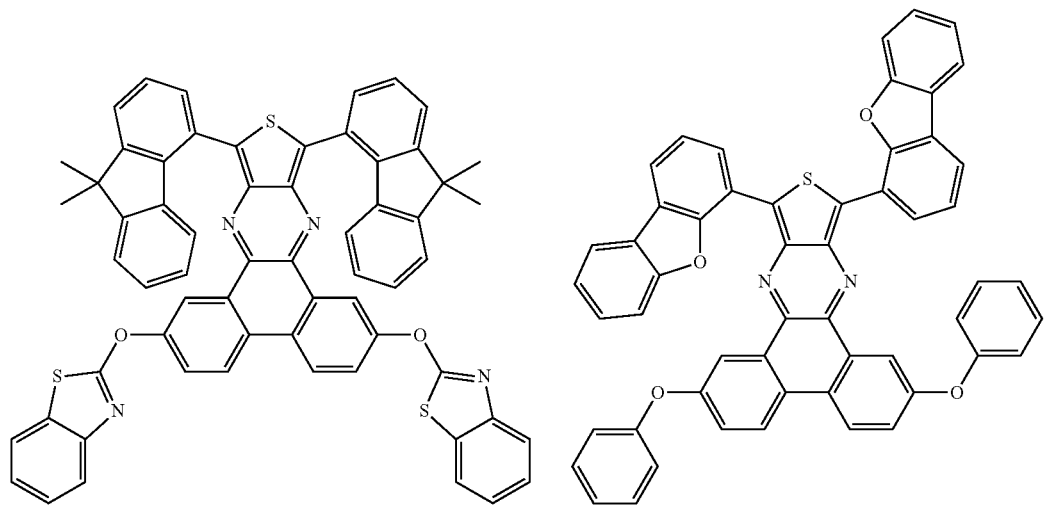
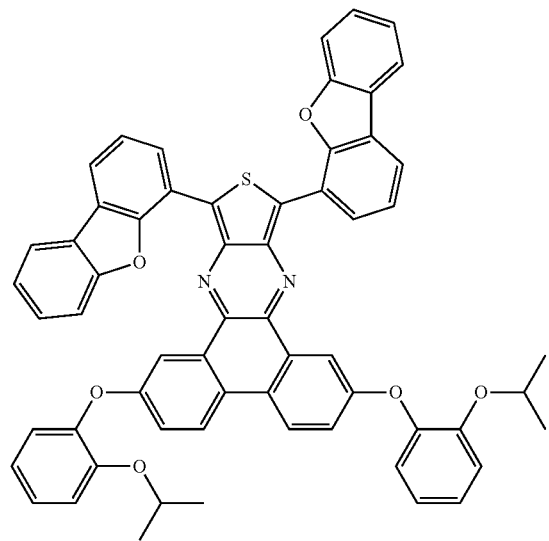
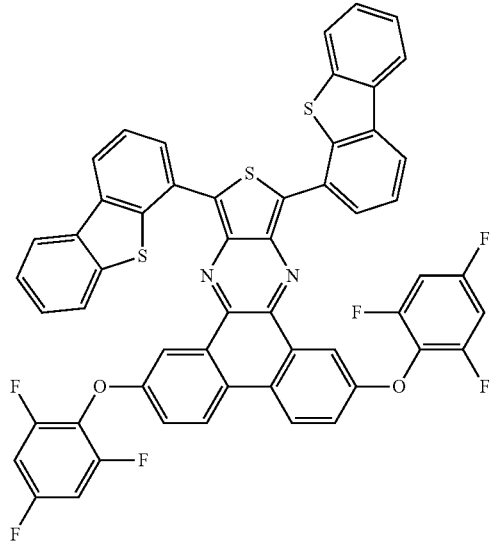

395 396
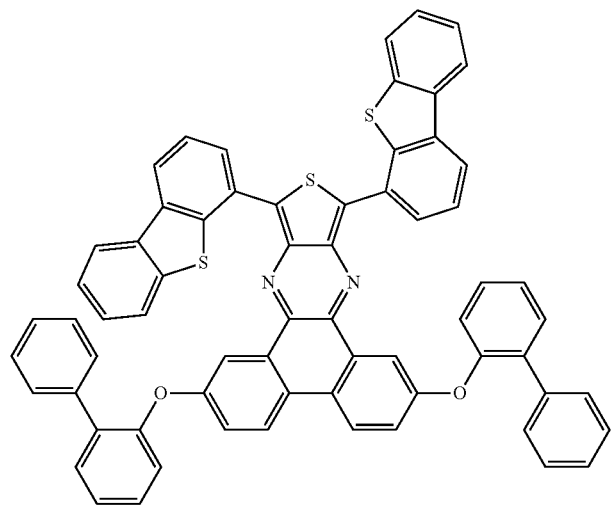
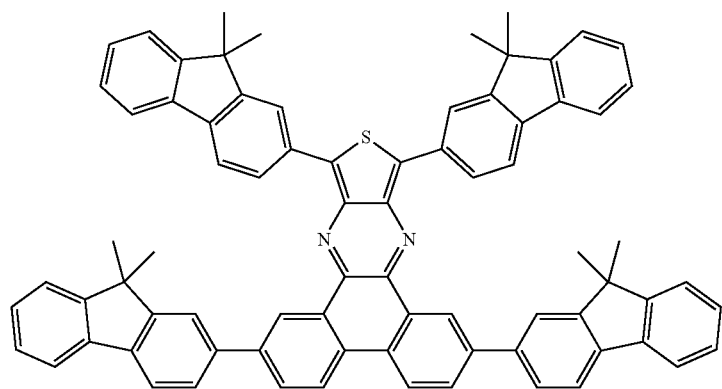
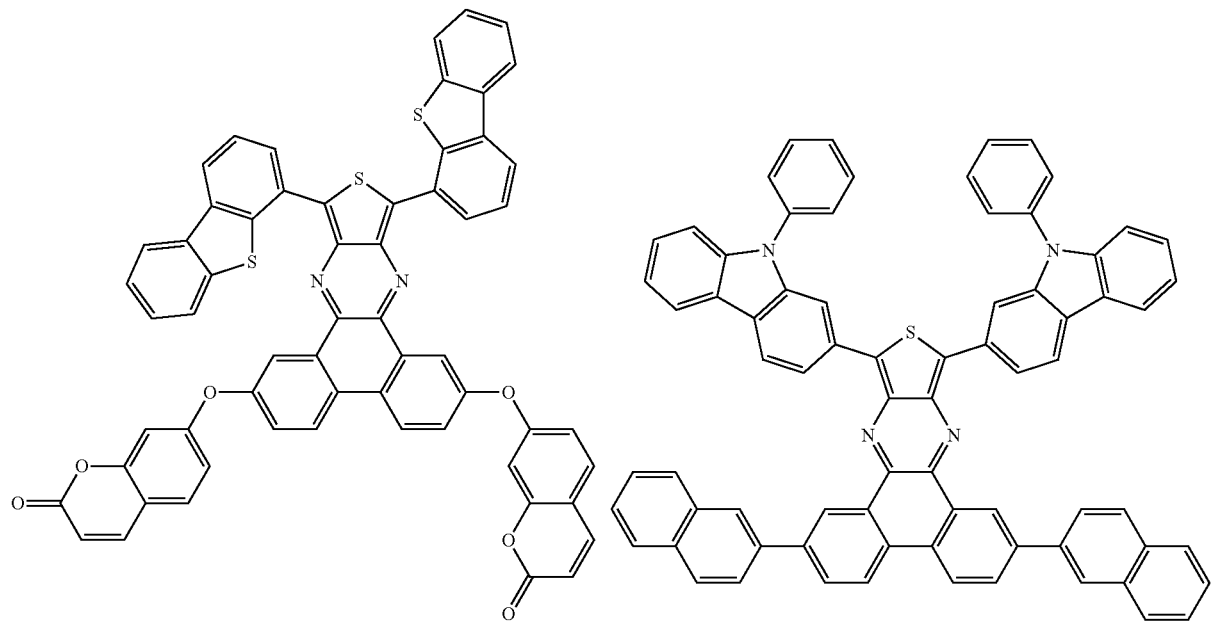

-continued
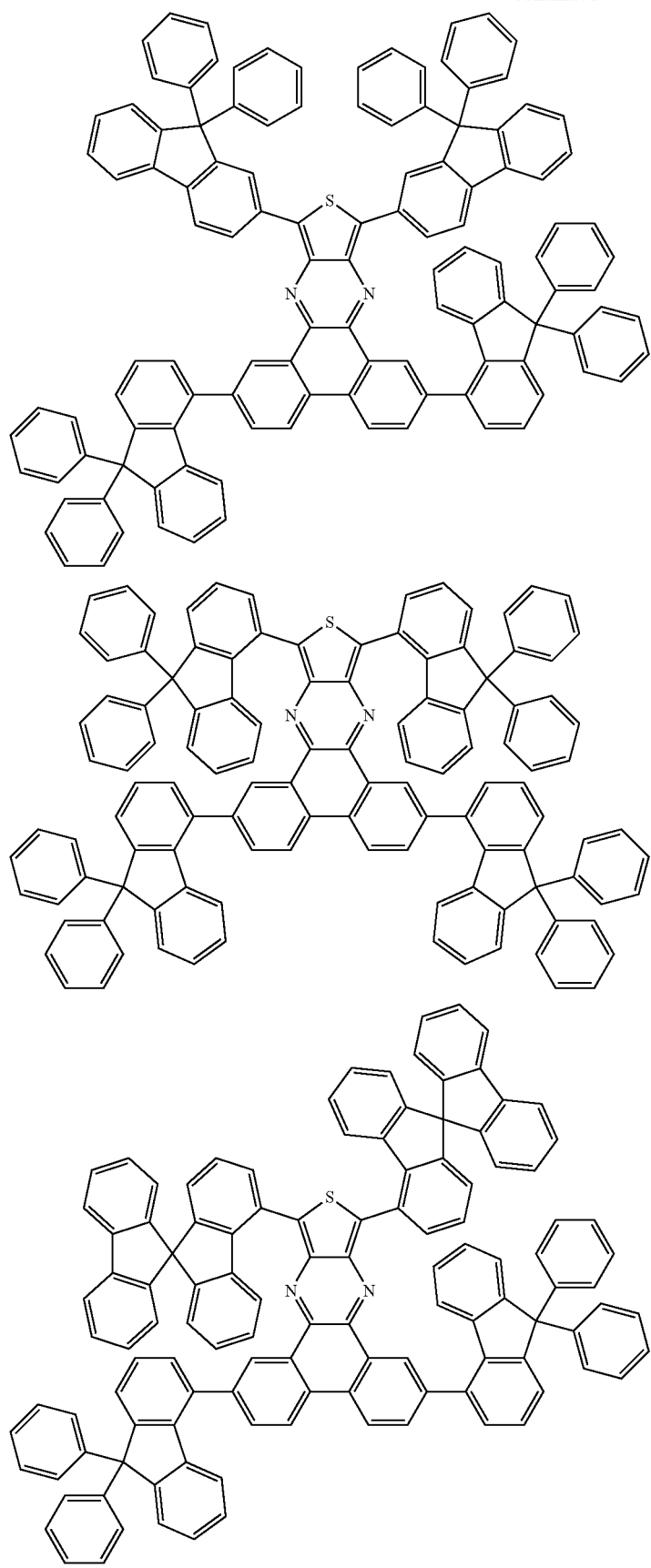

-continued
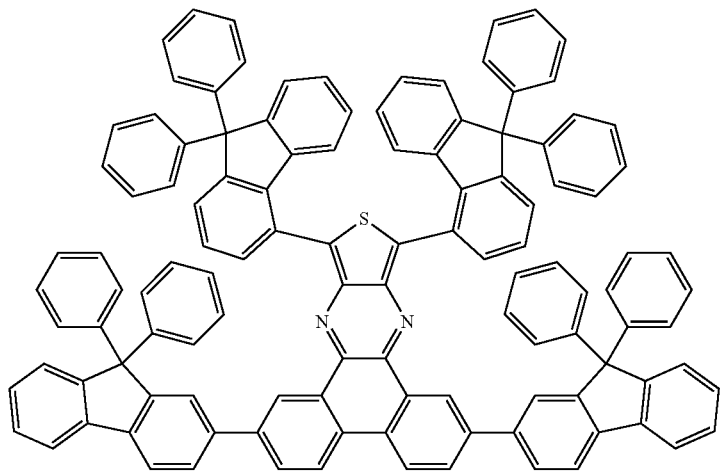
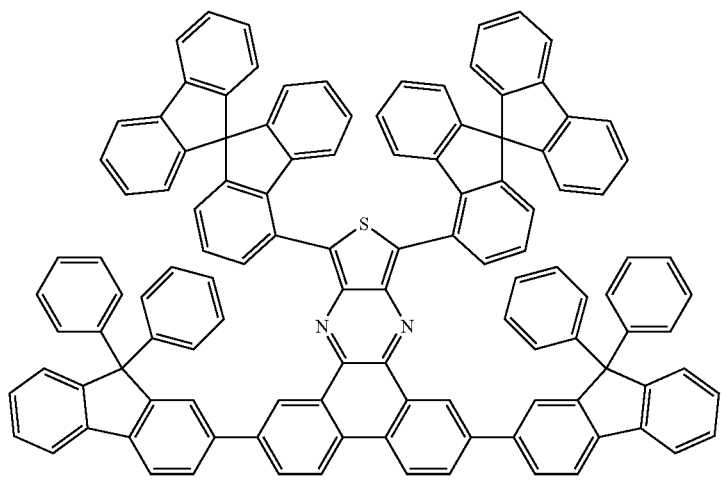
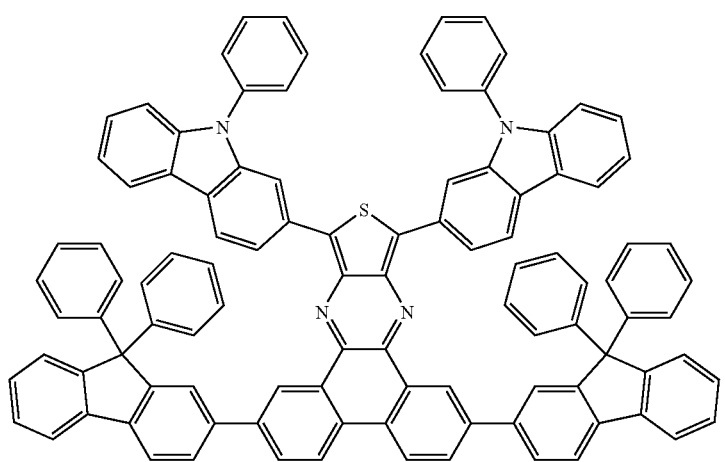

-continued
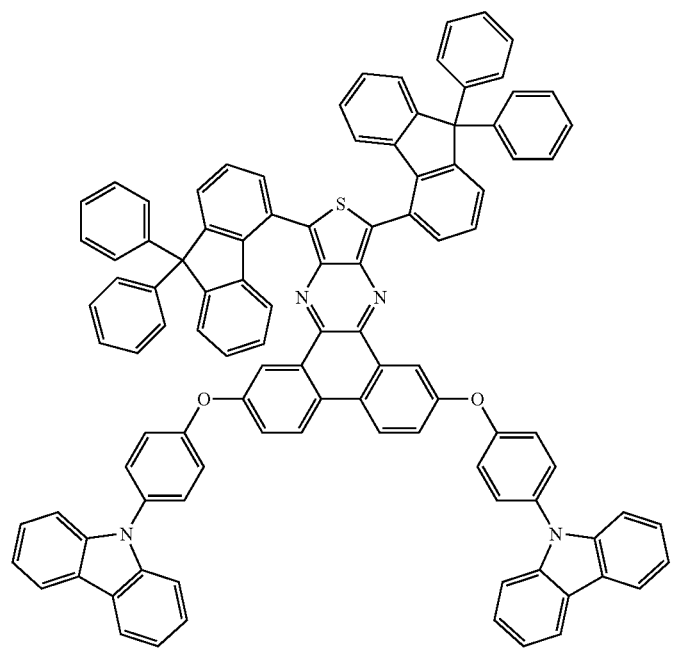
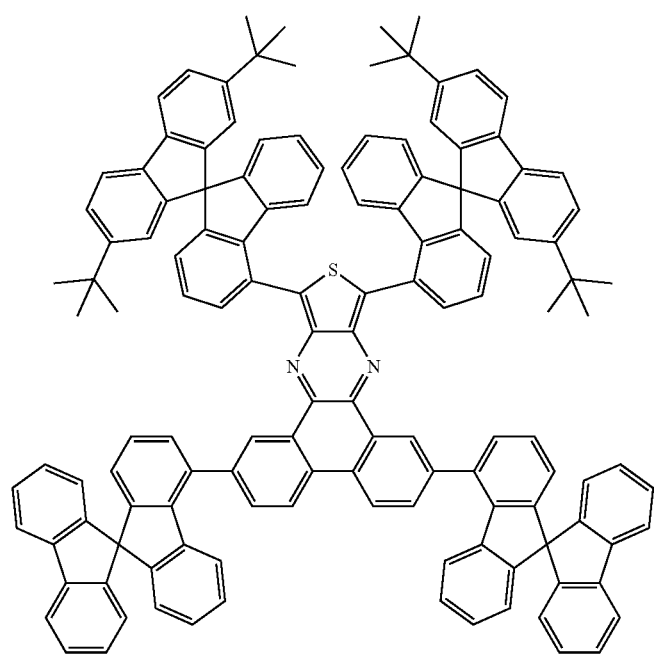

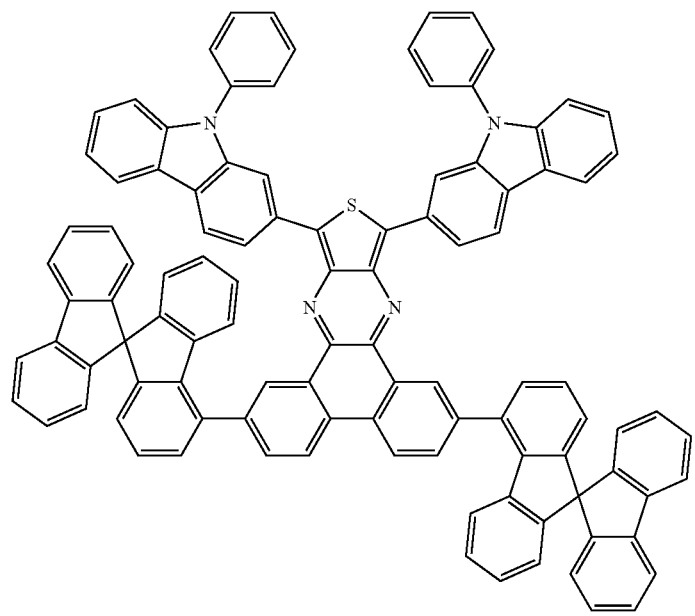
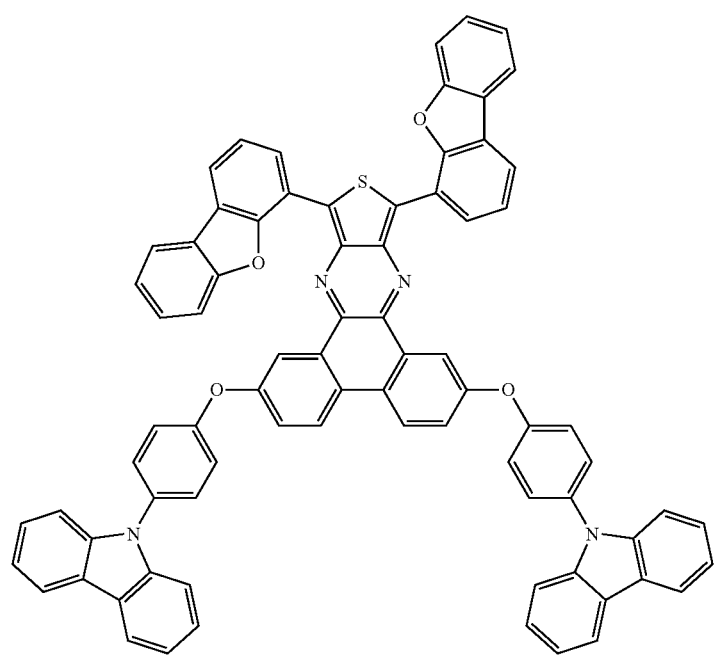

-continued
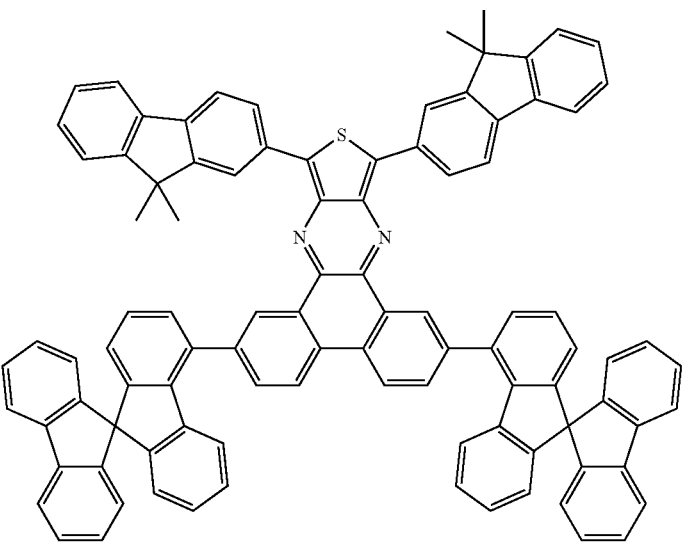
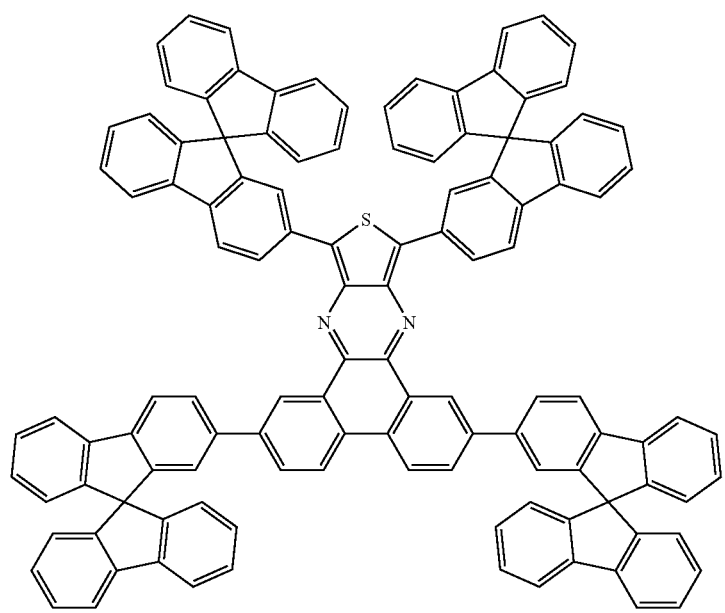

-continued
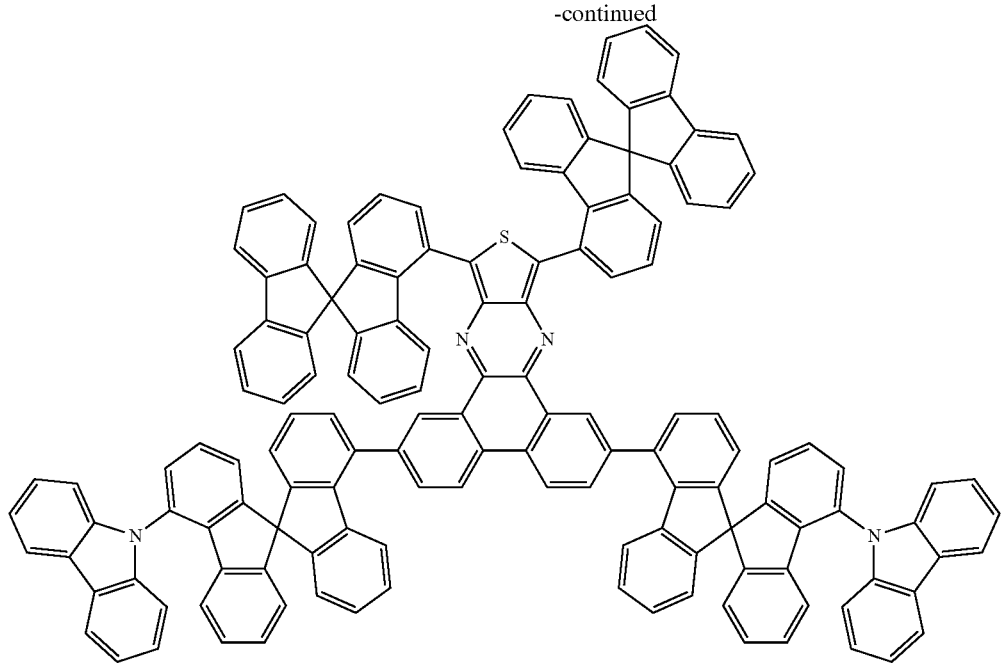
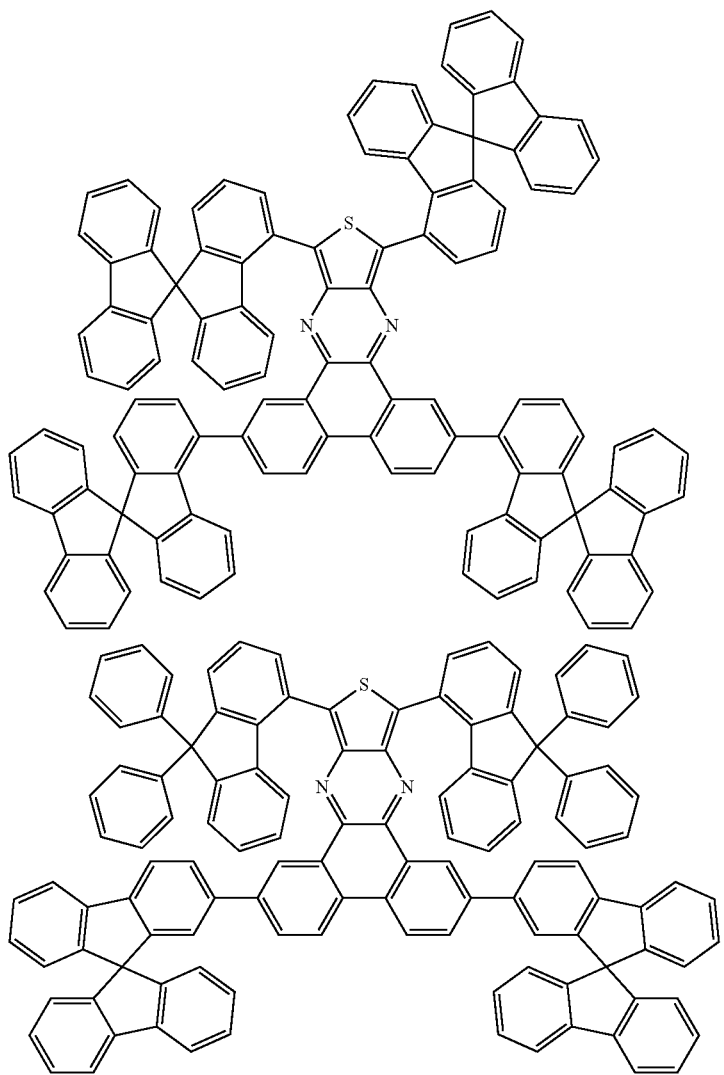

409            410
-continued
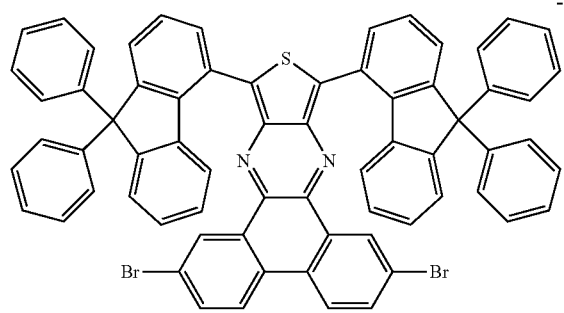 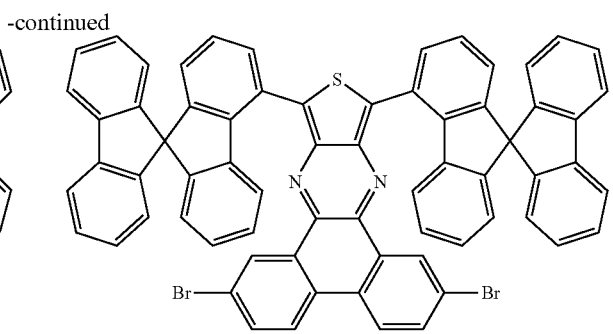
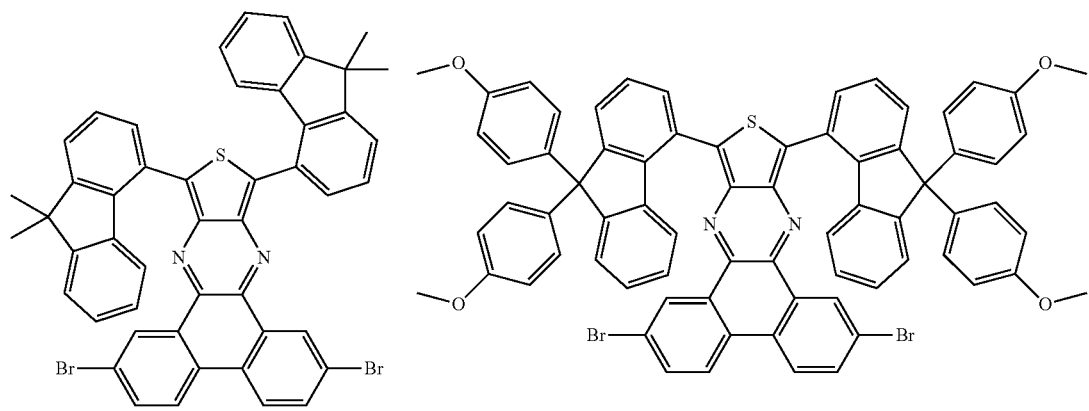
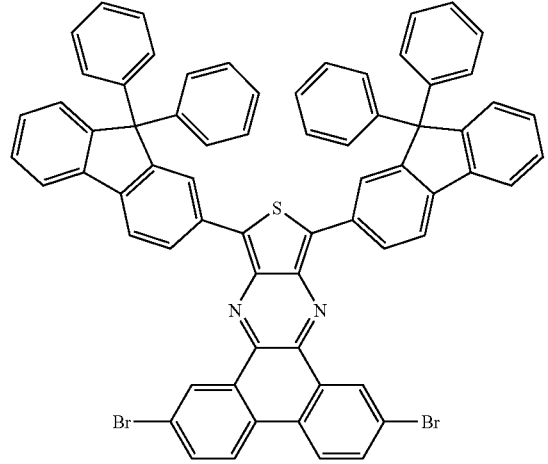 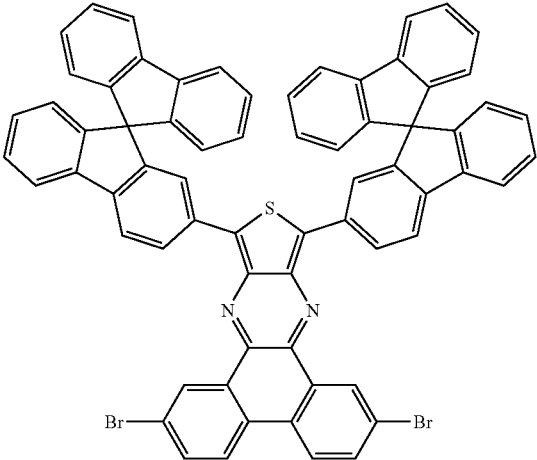
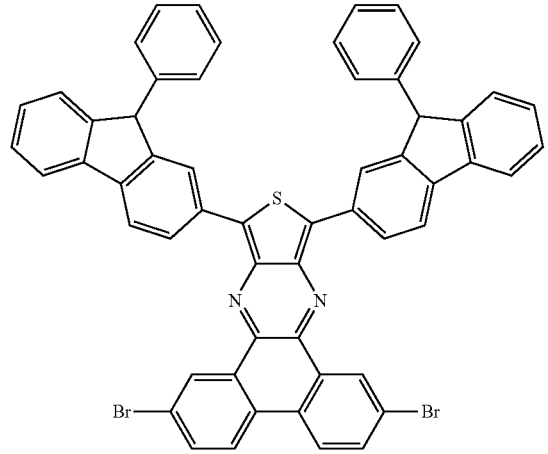 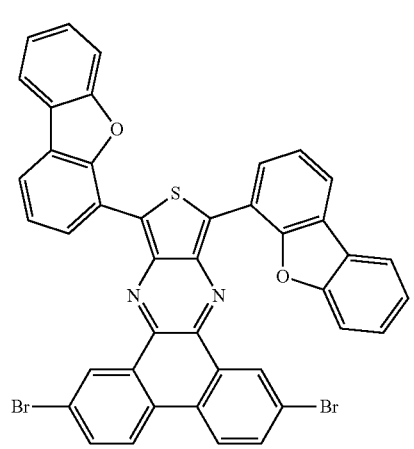

411
412
-continued
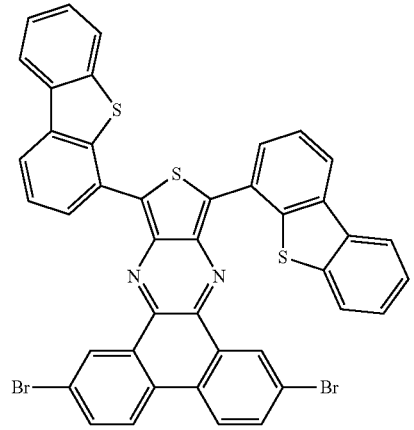
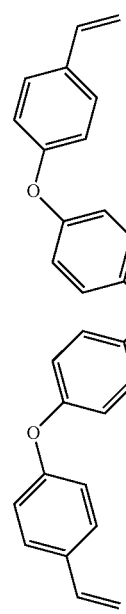
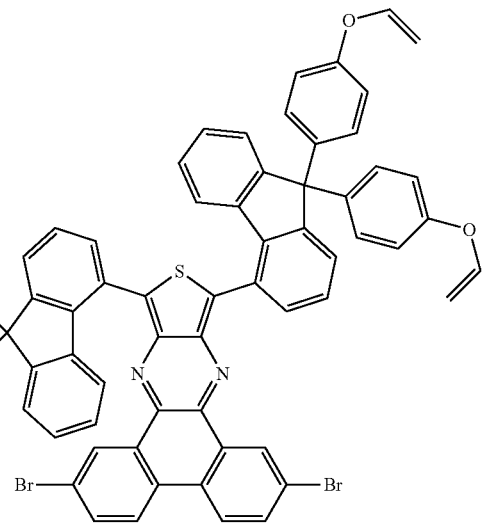
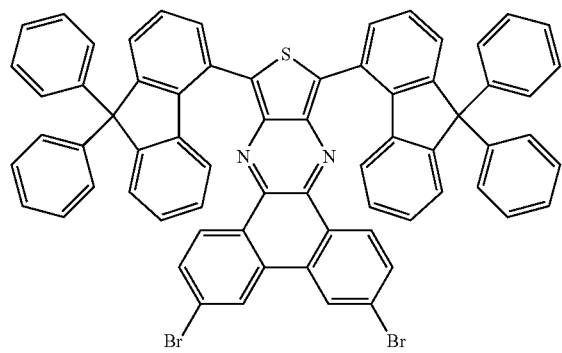
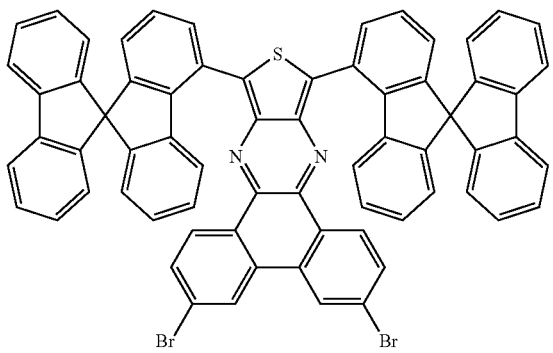
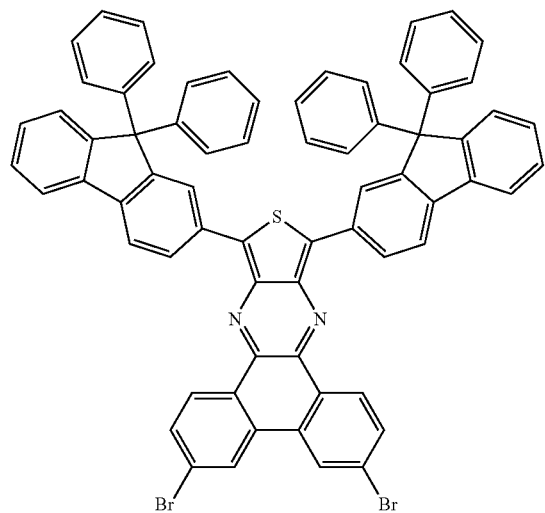
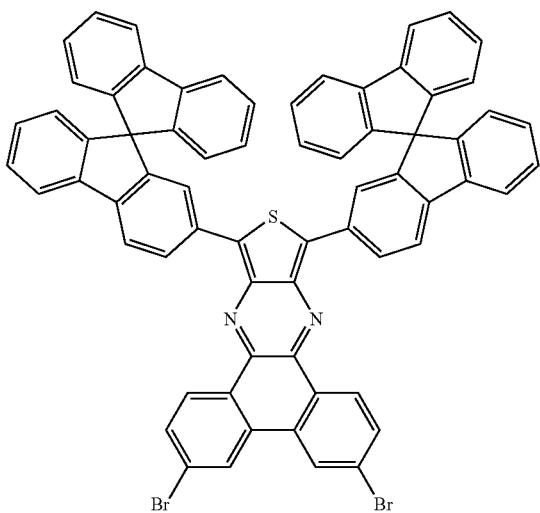

413
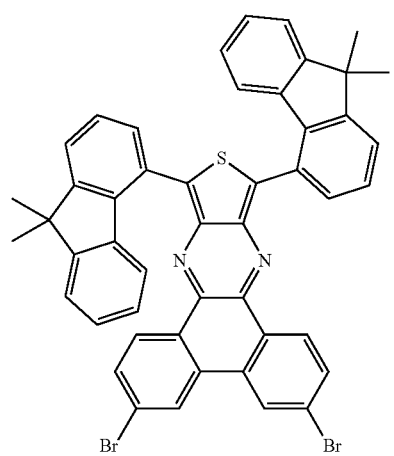
414
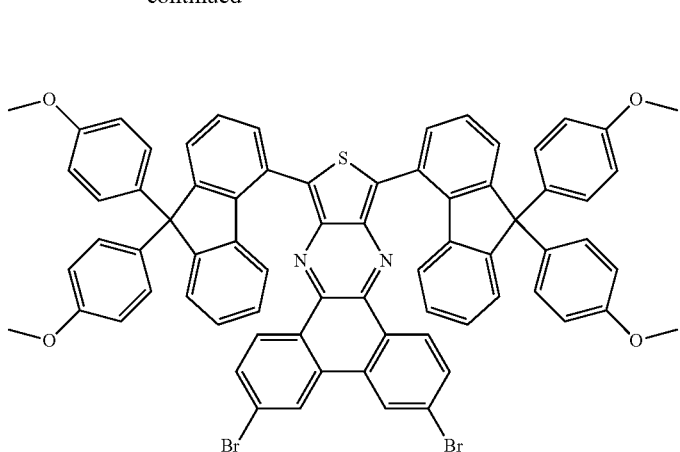
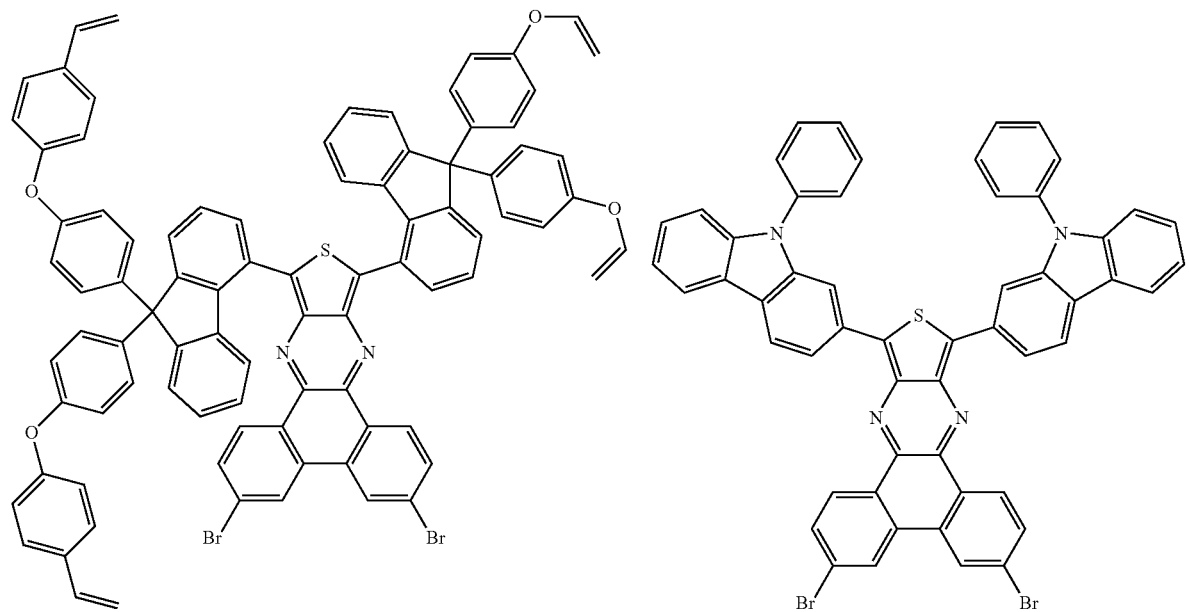
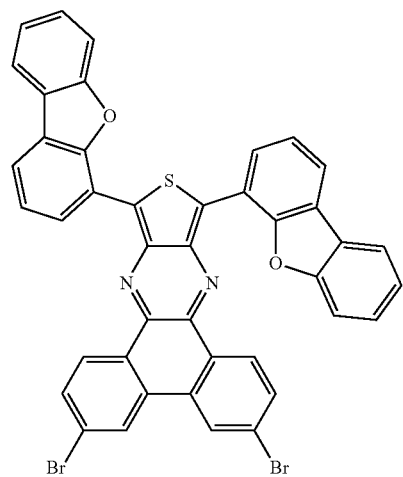
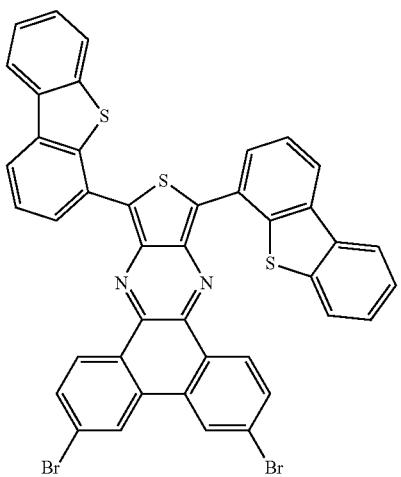

415
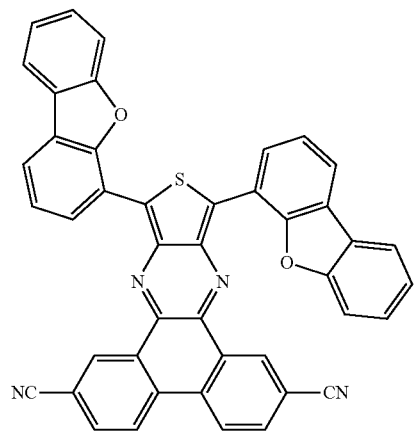
416
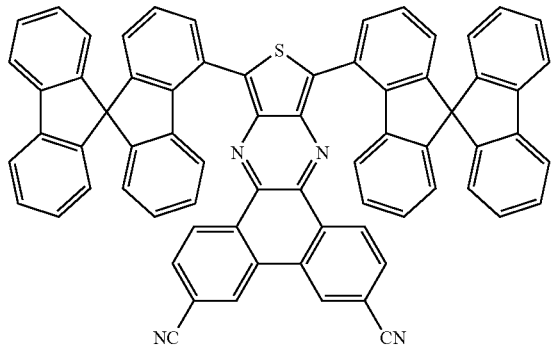
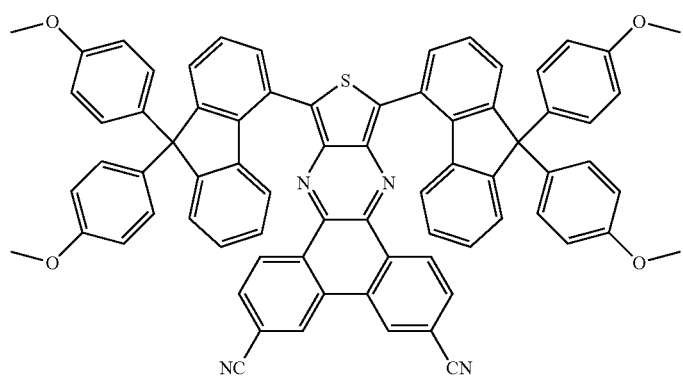
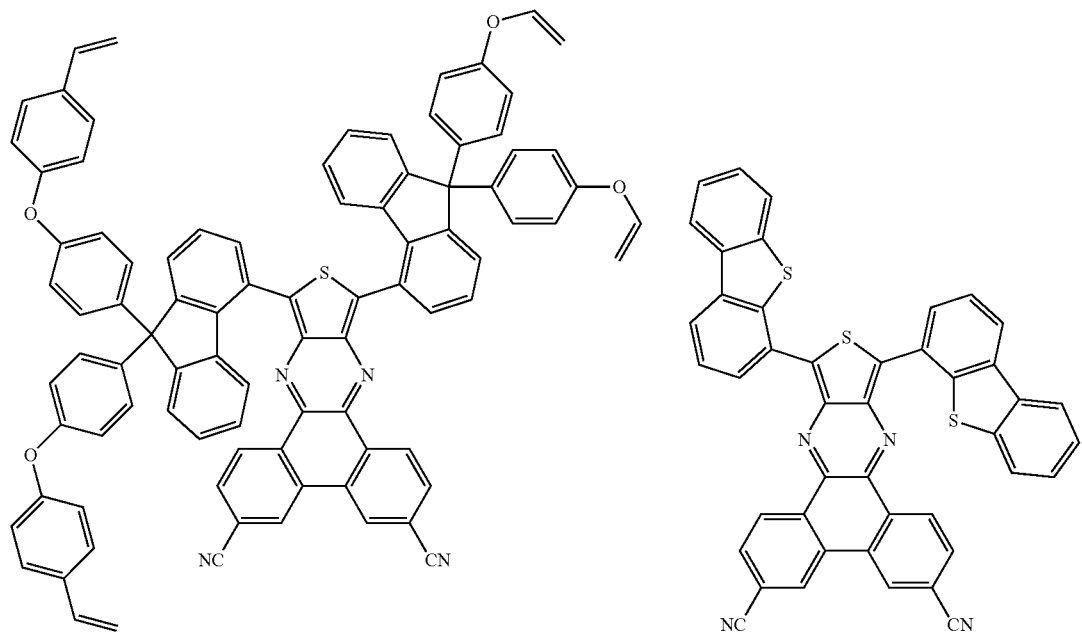

417
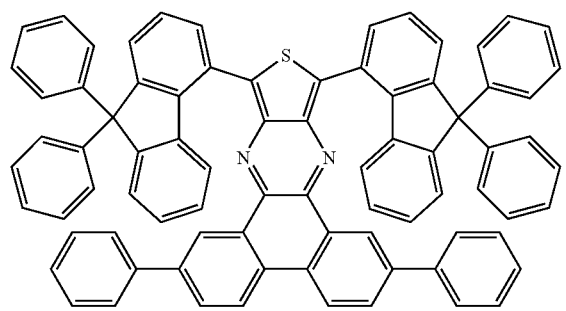
418
-continued
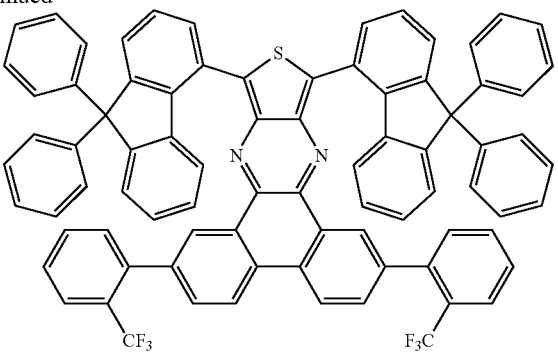
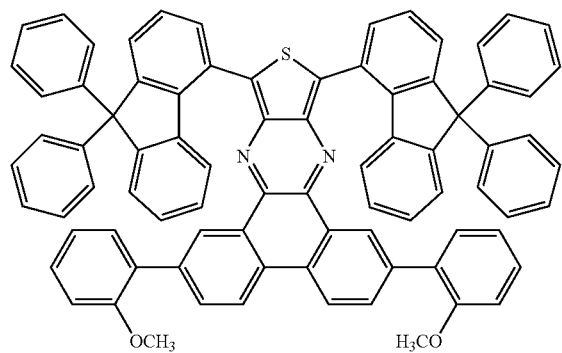
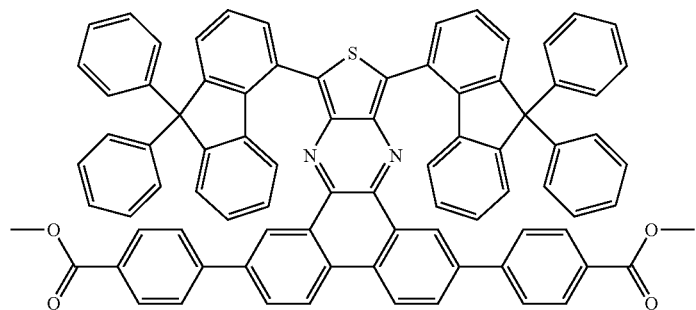
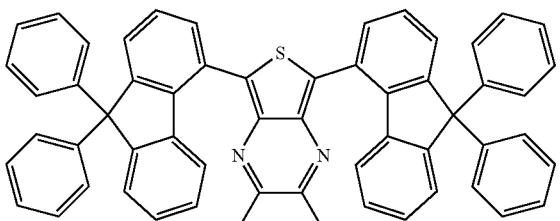
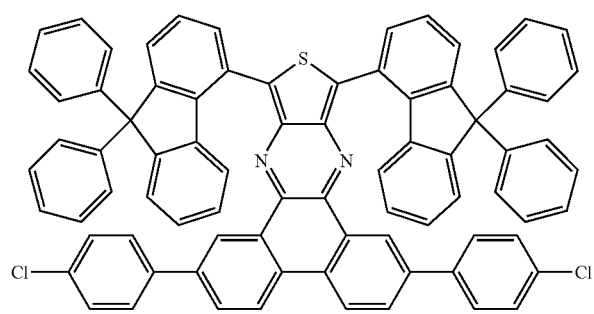
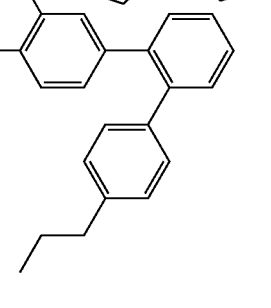

-continued
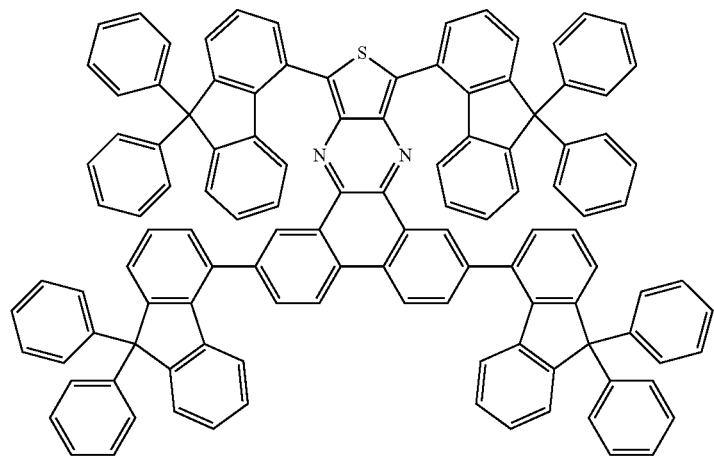
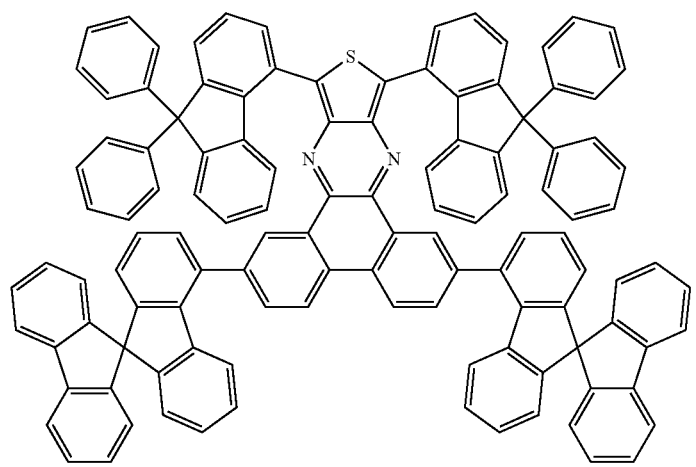
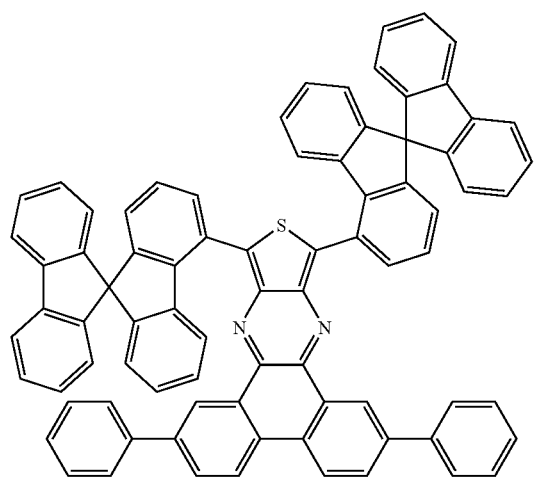

-continued
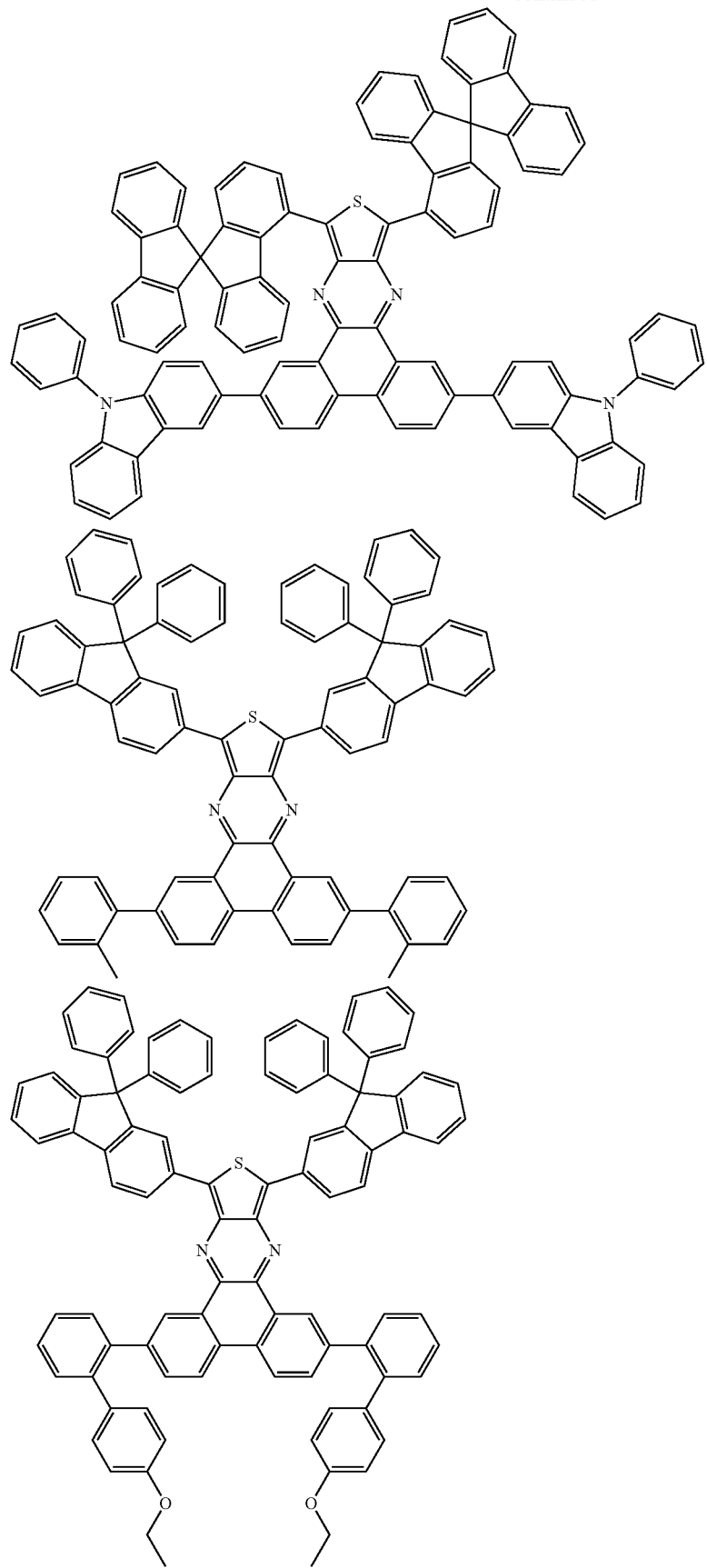

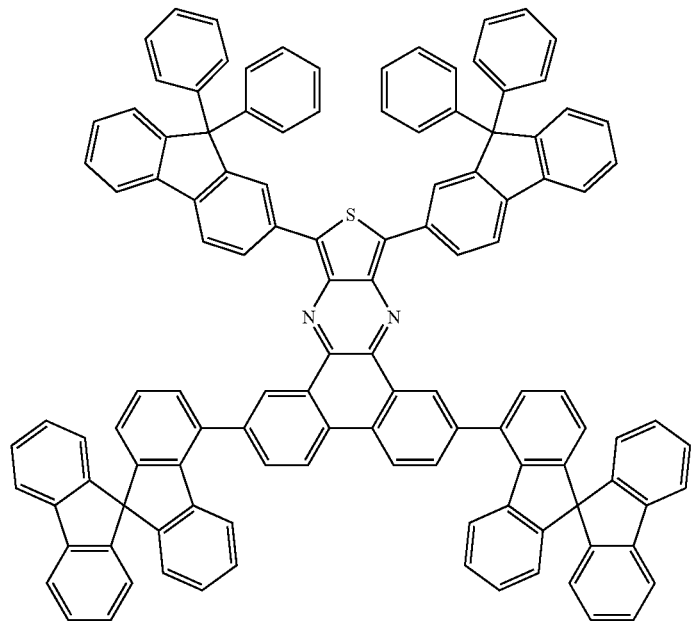
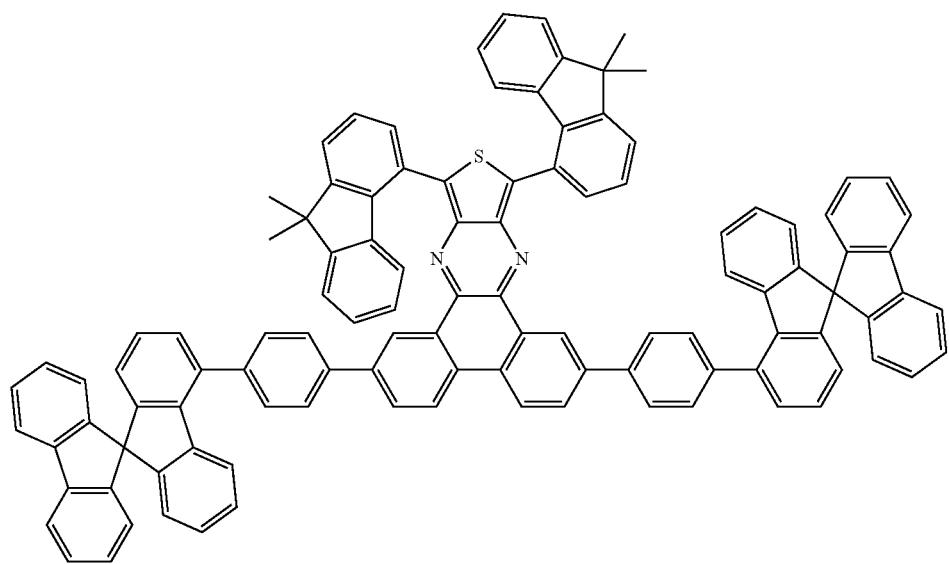

425 426
-continued
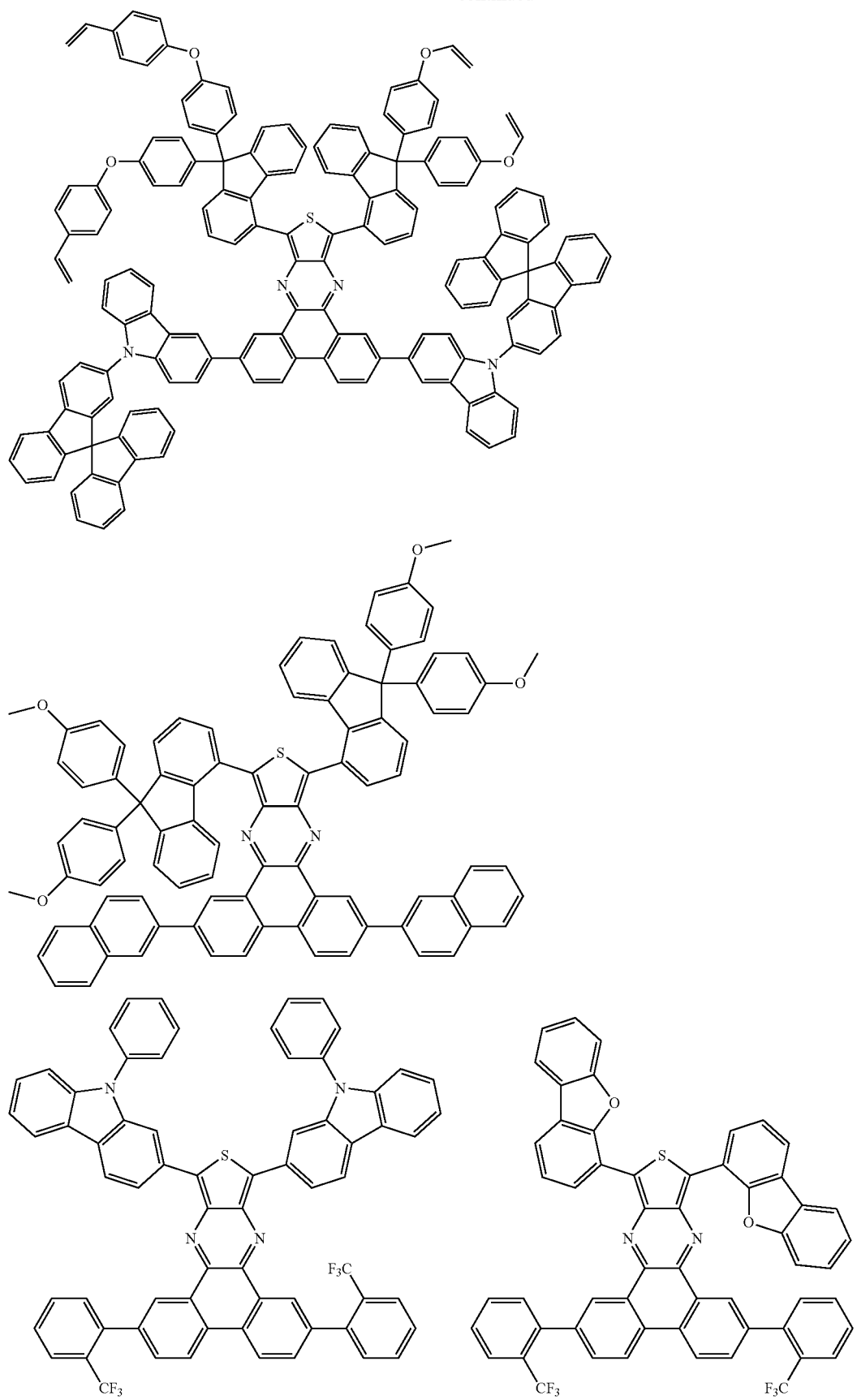

-continued
| 427 | 428 |
|---|---|
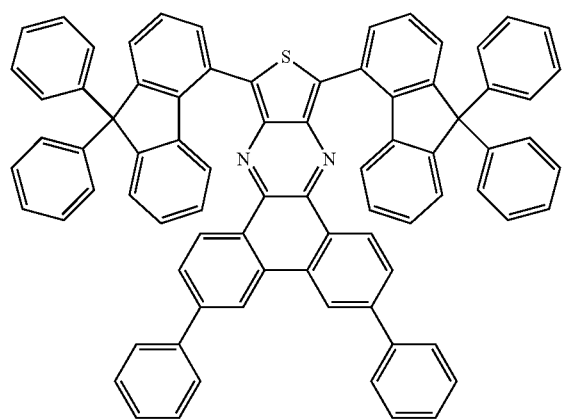
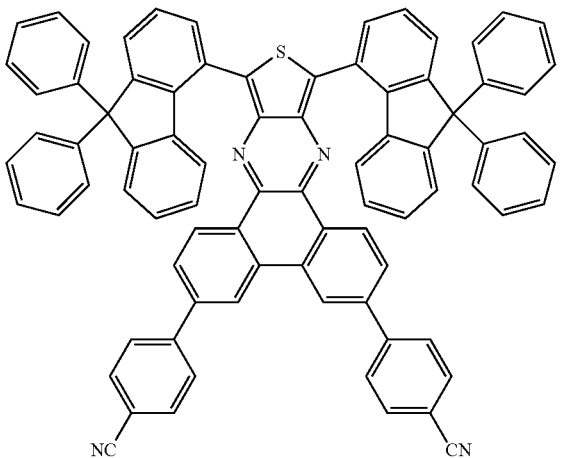
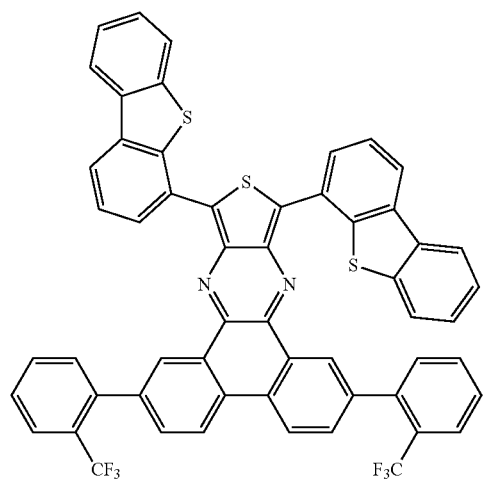
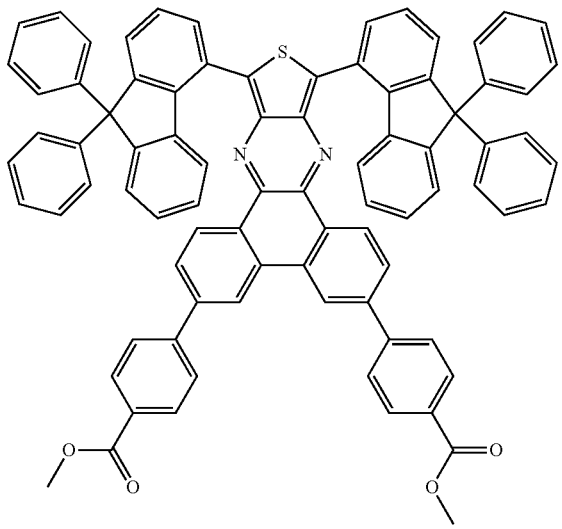
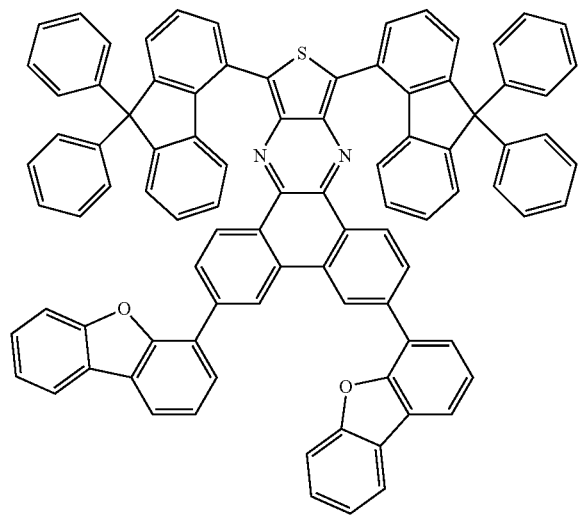

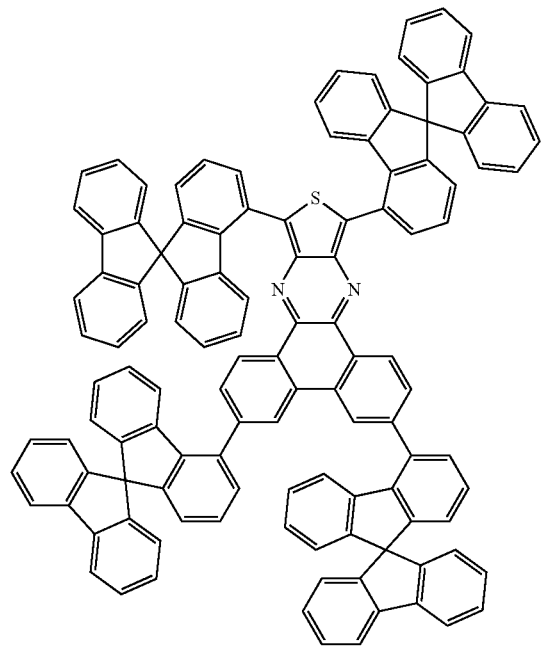
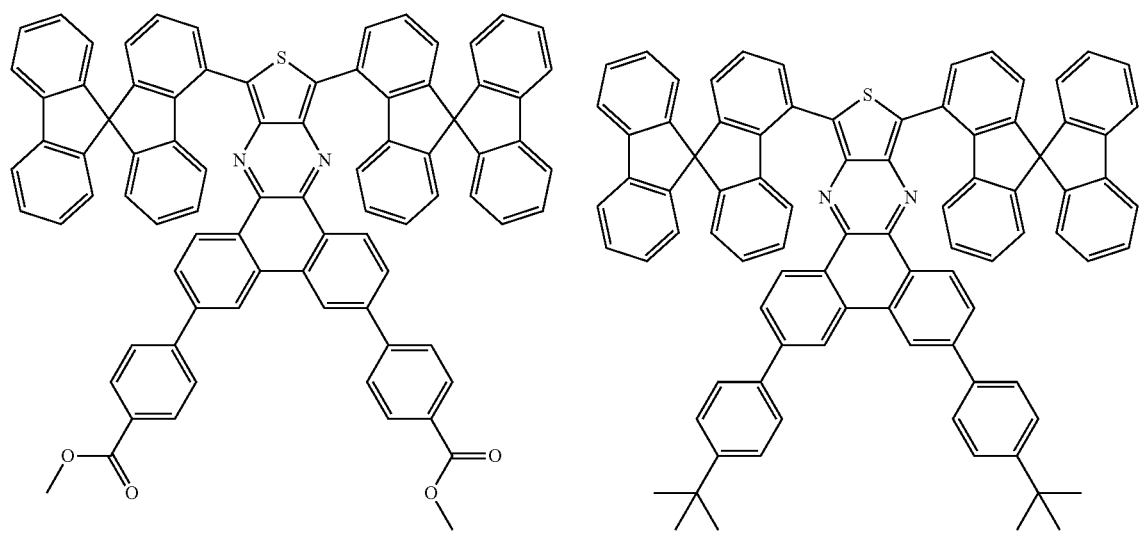

-continued

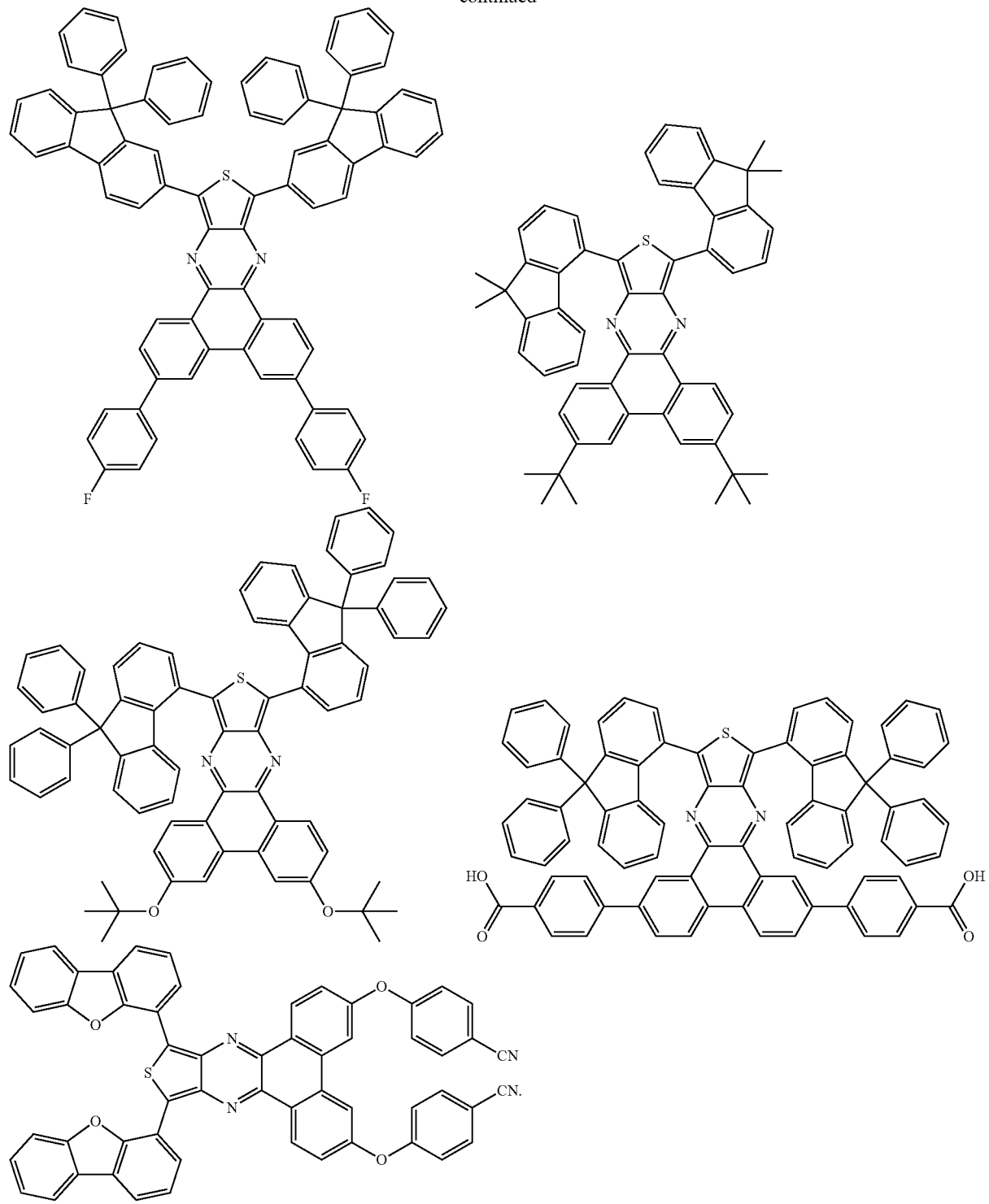

17. A color conversion film comprising:
   a resin matrix; and
   the compound according to claim 16, the compound being dispersed in the resin matrix.

18. The color conversion film of claim 17, comprising the compound in amount of 0.001 to 20 wt % based on the total weight of the color conversion film.

19. The color conversion film of claim 17, wherein the resin matrix is a thermoplastic polymer or a thermosetting polymer.

* * * * *